US009845327B2

(12) United States Patent
Krainc et al.

(10) Patent No.: US 9,845,327 B2
(45) Date of Patent: Dec. 19, 2017

(54) TREATMENT OF PROTEINOPATHIES

(75) Inventors: Dmitri Krainc, Boston, MA (US); Joseph R. Mazzulli, Boston, MA (US)

(73) Assignee: THE GENERAL HOSPITAL CORPORATION, Boston, MA (US)

( * ) Notice: Subject to any disclaimer, the term of this patent is extended or adjusted under 35 U.S.C. 154(b) by 317 days.

(21) Appl. No.: 14/127,546

(22) PCT Filed: Jun. 22, 2012

(86) PCT No.: PCT/US2012/043732
§ 371 (c)(1),
(2), (4) Date: Jun. 16, 2014

(87) PCT Pub. No.: WO2012/177997
PCT Pub. Date: Dec. 27, 2012

(65) Prior Publication Data
US 2014/0288093 A1   Sep. 25, 2014

Related U.S. Application Data

(60) Provisional application No. 61/499,930, filed on Jun. 22, 2011.

(51) Int. Cl.
| *A61K 31/519* | (2006.01) |
| *C07D 487/04* | (2006.01) |
| *G01N 33/50* | (2006.01) |
| *G01N 33/573* | (2006.01) |
| *C12Q 1/34* | (2006.01) |
| *C12Q 1/44* | (2006.01) |

(52) U.S. Cl.
CPC ............. *C07D 487/04* (2013.01); *C12Q 1/34* (2013.01); *C12Q 1/44* (2013.01); *G01N 33/5008* (2013.01); *G01N 33/573* (2013.01); *G01N 2333/924* (2013.01); *G01N 2500/10* (2013.01)

(58) Field of Classification Search
CPC .......... C07D 487/04; C12Q 1/34; C12Q 1/44; G01N 2333/924; G01N 2500/10; G01N 33/5008; G01N 33/573
USPC ...................................................... 514/259.3
See application file for complete search history.

(56) References Cited

U.S. PATENT DOCUMENTS

| 9,353,117 B2 * | 5/2016 | Marugan .............. C07D 487/04 |
| 2010/0113358 A1 | 5/2010 | Tezapsidis et al. |

FOREIGN PATENT DOCUMENTS

| CN | 101117330 A | 2/2008 |
| CN | 101541172 A | 9/2009 |
| EA | 013752 B1 | 6/2010 |
| JP | 2009541489 A | 11/2009 |
| WO | 2004089471 A2 | 10/2004 |
| WO | 2006020581 A2 | 2/2006 |
| WO | 2006/133446 A2 | 12/2006 |
| WO | 2007012061 A2 | 1/2007 |
| WO | 2007/150064 A2 | 12/2007 |
| WO | 2007140212 A2 | 12/2007 |
| WO | 2008144773 A1 | 11/2008 |
| WO | 2012061597 A1 | 5/2012 |
| WO | 2012078855 A1 | 6/2012 |

OTHER PUBLICATIONS

Patnaik et al., "Discovery, Structure-Activity Relationship, and Biological Evaluation of Noninhibitory Small Molecule Chaperones of Glucocerebrosidase", (Web Publication Date) May 30, 2012; J. Med. Chem., 55(12), pp. 5734-5748.*
Witte et al., "Ultrasensitive in situ visualization of active glucocerebrosidase molecules", 2010, Nature Chemical Biology, 6(12), pp. 907-913.*
Shelkovnikova et al., "Proteinopathies, Neurodegenerative Disorders with Protein Aggregation Based Pathology", May 2012, Molecular Biology, 46(3), pp. 362-374.*
Ashe et al., "Iminosugar-Based Inhibitors of Glucosylceramide Synthase Increase Brain Glycosphingolipids and Survival in a Mouse Model of Sandhoff Disease", PLoS One, 6(6):e21758 (2011).
Auluck et al., "Chaperone Suppression of Alpha-Synuclein Toxicity in a Drosophila Model for Parkinson's Disease", Science, 295(5556):865-868 (2002).
Chua et al., "Rabs, SNAREs and α-synuclein—Membrane trafficking defects in synucleinopathies", Brain Res Rev., 67(1-2):268-81 (2011).
Giasson et al., "A Panel of Epitope-Specific Antibodies Detects Protein Domains Distributed Throughout Human Alpha-Synuclein in Lewy Bodies of Parkinson's Disease", J. Neurosci. Res., 59:528-533 (2000).
Giasson et al., "Initiation and Synergistic Fibrillization of Tau and Alpha-Synuclein", Science, 300(5619):636-640 (2003).
Ivleva et al., "Estimation and comparison of lysosomal and cytoplasmic pH of human fibroblasts from healthy donors and patients with lysosomal storage diseases", Biomed. Sci., 2:398-402 (1991).
Kishimoto et al., "Saposins: structure, function, distribution, and molecular genetics", J. Lipid Res., 33(9):1255-1267 (1992).
Laferla, "Calcium Dyshomeostasis and Intracellular Signalling in Alzheimer's Disease", Nat. Rev. Neurosci., 3:862-872 (2002).
Larsen et al., "Property-based design of a glucosylceramide synthase inhibitor that reduces glucosylceramide in the brain", J. Lipid Res., 53:282-291 (2012).
Li et al., "Plasma alpha-synuclein is decreased in subjects with Parkinson's disease", Exp. Neurol., 204(2):583-588 (2007).

(Continued)

*Primary Examiner* — My-Chau T Tran
(74) *Attorney, Agent, or Firm* — Nixon Peabody LLP; David S. Resnick; Candace M. Summerford

(57) ABSTRACT

The present disclosure provides technologies relating to lysosomal activation. The disclosure provides several strategies for increasing level and/or activity of lysosomal enzyme, and furthermore demonstrates the surprising applicability of such strategies in the treatment and/or prophylaxis of certain proteinopathies. Among other things, the present invention provides methods and compositions for the treatment and/or prophylaxis of proteinopathies other than lysosomal storage diseases through lysosomal activation. In particular, the present disclosure provides methods and compositions for the treatment and/or prophylaxis of neurodegenerative proteinopathies, and in particular those associated with accumulation of α-synuclein. The present disclosure specifically provides methods and compositions for the treatment and/or prophylaxis of Parkinson's disease.

2 Claims, 49 Drawing Sheets

(56) References Cited

OTHER PUBLICATIONS

Lill et al., "Comprehensive Research Synopsis and Systematic Meta-Analyses in Parkinson's Disease Genetics: The PDGene Database", PLoS Genet., 8(3):e1002548 (2012).
Manning-Bog et al., "Alpha-synuclein-glucocerebrosidase interactions in pharmacological Gaucher models: A biological link between Gaucher disease and parkinsonism", NeuroToxicology, 30:1127-1132 (2009).
Martinez et al., "GM1 Specifically Interacts with Alpha-Synuclein and Inhibits Fibrillation", Biochemistry, 46(7):1868-1877 (2007).
Marugan et al., "Non-iminosugar glucocerebrosidase small molecule chaperones", Medchemcomm., 3(1):56-60 (2012).
Mu et al., "Partial Restoration of Mutant Enzyme Homeostasis in Three Distinct Lysosomal Storage Disease Cell Lines by Altering Calcium Homeostasis", PLoS Biology, 6(2):e26 (0253-0265) (2008).
Richards et al., "Discovery and Characterization of an Inhibitor of Glucosylceramide Synthase", J. Med. Chem., 55:4322-4335 (2012).
Sidransky, "Gaucher disease and parkinsonism", Mol. Genet. Metab., 84(4):302-304 (2005).
Sidransky et al., "Multicenter Analysis of Glucocerebrosidase Mutations in Parkinson's Disease", N. Engl. J. Med., 361(17):1651-1661 (2009).
Spillantini et al., "Alpha-Synuclein in Lewy bodies", Nature, 388(6645):839-840 (1997).
Suzuki et al., "Neuronal and glial accumulation of alpha- and beta-synucleins in human lipidoses", Acta Neuropathol, 114(5):481-489 (2007).
Tang et al., "Derivatives of oxoisoaporphine alkaloids: A novel class of selective acetylcholinesterase inhibitors", Bioorg. Med. Chem. Lett., 17(13):3765-3768 (2007).
Tayebi et al., "Gaucher Disease and Parkinsonism: A Phenotypic and Genotypic Characterization", Mol. Genet. Metab., 73(4):313-321 (2001).
Vanier et al., "Recent Advances in Elucidating Niemann-Pick C Disease", Brian Pathology, 8:163-174 (1998).
Castro-Obregon, S., Nature Education, 3(9):49 (2010). "The Discovery of Lysosomes and Autophagy."
Clark et al., PLoS One, 5(8):e12333 (2010). "Oral N-acetyl-cysteine attenuates loss of dopaminergic terminals in alpha-synuclein overexpressing mice."
Cookson, M. R., Molecular Neurodegeneration, 4:9 (2009). "Alpha-Synuclein and neuronal cell death."
"Proteostasis Therapeutics Exclusively Licenses Discoveries Related to Unfolded Protein Response from Ron Laboratory at New York University." Proteostasis Therapeutics Website, (2010). (Retrieved online Aug. 31, 2012). Retrieved from Internet: <URL:http://www.proteostasis.com/news_events/pr_2010_01_07.php>.
Tatti et al., Autophagy 7(1):94-95 (2011). "Autophagy in Gaucher Disease Due to Saposin C Deficiency."
Winslow et al., J. Cell Biol. 190(6):1023-1037 (2010). "Alpha-Synuclein Impairs Macroautophagy: Implications for Parkinson's Disease."
Almeida, "Glucocerebrosidase Involvement in Parkinson Disease and Other Synucleinopathies" Frontiers in Neurology 3:1-6 (2012).
Banerjee et al., "Mitochondrial dysfunction in the limelight of Parkinson's disease pathogenesis." Biochimica et Biophysica Acta 1792:651-663(2009).
Brady et al., "The metabolism of glucocerebrosides." J. Biol. Chem. 240:39-43 (1965).
Buckley et al., "Regulation of neuronal function by protein trafficking: a role for the endosomal pathway." J Physiol 525.1:11-19 (2000).
Clark et al., "Improved pharmacological chaperones for the treatment of neuronopathic Gaucher and Parkinson's disease" Molecular Genetics and Metabolism 102:S12 (2011).
Cooper et al., "Alpha-synuclein blocks ER-Golgi traffic and Rab1 rescues neuron loss in Parkinson's models." Science, 313(5785):324-328 (2006).
Dawson et al., "Genetic animal models of Parkinson's disease." Neuron 66:646-661 (2010).
Desplats et al., "Glycolipid and ganglioside metabolism imbalances in Huntington's disease." Neurobiol Dis. 27(3):265-277 (2007).
Devine et al., "Parkinson's disease and alpha-synuclein expression" Movement Disorders 26(12):2160-2168 (2011).
El-Agnaf et al., "Detection of oligomeric forms of alpha-synuclein protein in human plasma as a potential biomarker for Parkinson's disease." The FASEB J. 20:419-425 (2006).
Futerman et al., "The cell biology of lysosomal storage disorders." Nat Rev Mol Cell Biol 5:554-565 (2004).
Giasson et al., "A hydrophobic stretch of 12 amino acid residues in the middle of alpha-synuclein is essential for filament assembly." J. Biol. Chem. 276(4):2380-2386 (2001).
Goker-Alpan et al., "Parkinsonism among Gaucher disease carriers." J. Med. Genet. 41:937-940 (2004).
Goker-Alpan et al., "Glucocerebrosidase mutations are an important risk factor for Lewy body disorders." Neurology 67:908-910 (2006).
Goldin et al., "High Throughput Screening for Small Molecule Therapy for Gaucher Disease Using Patient Tissue as the Source of Mutant Glucocerebrosidase" 7(1):e29861 (2012).
Grosshans et al., "Rabs and their effectors: achieving specificity in membrane traffic." PNAS 103(32):11821-11827 (2006).
Hardy et al., "Respond to Beyond Frequencies and Coefficients." Am. J. Epidemiol. 164(2):126-127 (2006).
Helms et al., "Lipids as targeting signals: lipid rafts and intracellular trafficking." Traffic 5(4):247-254 (2004).
Hodara et al., "Functional consequences of alpha-synuclein tyrosine nitration: diminished binding to lipid vesicles and increased fibril formation." J. Biol. Chem 279(46):47746-47753 (2004).
Lachmann et al., "Treatment with miglustat reverses the lipid-trafficking defect in Niemann-Pick disease type C." Neurobiol Dis 16(3):654-658 (2004).
Lee, "The fine structure of the cerebroside occurring in Gaucher's disease." PNAS 61(2):484-489 (1968).
Lee et al., "The plasma alpha-synuclein levels in patients with Parkinson's disease and multiple system atrophy." J. Neural Transm 113(10):1435-1439 (2006).
Lee et al., "Autophagy, mitochondria and oxidative stress: cross-talk and redox signalling." Biochem J 441:523-540 (2012).
Maroteaux et al., "Synuclein: a neuron-specific protein localized to the nucleus and presynaptic nerve terminal." J. Neurosci. 8(8):2804-2815 (1988).
Marugan et al., "Evaluation of quinazoline analogues as glucocerebrosidase inhibitors with chaperone activity." J. Med. Chem. 54(4):1033-1058 (2011).
Mazzulli et al., "Gaucher Disease Glucocerebrosidase and alpha-Synuclein Form a Bidirectional Pathogenic Loop in Synucleinopathies," Cell 146(1):37-52 (2011).
Morimoto et al., "Distribution of saposin proteins (sphingolipid activator proteins) in lysosomal storage and other diseases." PNAS 87(9):3493-3497 (1990).
Mukhopadhyay et al., "Proteomic analysis of endocytic vesicles: Rab1a regulates motility of earlly endocyic vesicles," J. Cell Sci 124(Pt. 5):765-775 (2011).
Neumann et al., "Glucocerebrosidase mutations in clinical and pathologically proven Parkinson's disease." Brain 132:1783-1794 (2009).
Ong et al., "Endoplasmic reticulum Ca2+ increases enhance mutant glucocerebrosidase proteostasis." Nat Chem Biol. 6(6):424-432 (2010).
Pagano et al., "Membrane traffic in sphingolipid storage diseases." Traffic 1(11):807-815 (2000).
Patnaik et al., "Discovery, Structure-Activity Relationship, and Biological Evaluation of Noninhibitory Small Molecule Chaperones of Glucocerebrosidase" Journal of Medicinal Chemistry 55(12):5734-5748 (2012).
Petersen et al., "Calcium signalling: past, present and future." Cell Calcium 38(3-4):161-169 (2005).
Sillence et al., "Glucosylceramide modulates membrane traffic along the endocytic pathway." J. Lipid Res 43(11):1837-1845 (2002).

(56) References Cited

OTHER PUBLICATIONS

Sun et al., "Gaucher disease mouse models: point mutations at the acid beta-glucosidase locus combined with low-level prosaposin expression lead to disease variants." J. Lipid Res. 46:2102-2113 (2005).
Tropak et al., "Identification of pharmacological chaperones for Gaucher disease and characterization of their effects on beta-glucocerebrosidase by hydrogen/deuterium exchange mass spectrometry." Chem Bio Chem 9(16):2650-2662 (2008).
Tsika et al., "Distinct region-specific alpha-synuclein oligomers in A53T transgenic mice: implications for neurodegeneration." J. Neurosci 30:3409-3418 (2010).
Xu et al., "Viable mouse models of acid beta-glucosidase deficiency: the defect in Gaucher disease." Am. J. Pathol. 163(5):2093-2101 (2003).
Xu et al., "Accumulation and distribution of alpha-synuclein and ubiquitin in the CNS of Gaucher disease mouse models." Mol. Genet. Metab. 102:436-447 (2011).
Zheng et al., "Three classes of glucocerebrosidase inhibitors identified by quantitative high-throughput screening are chaperone leads for Gaucher disease." PNAS 104(32):13192-13197 (2007).

\* cited by examiner

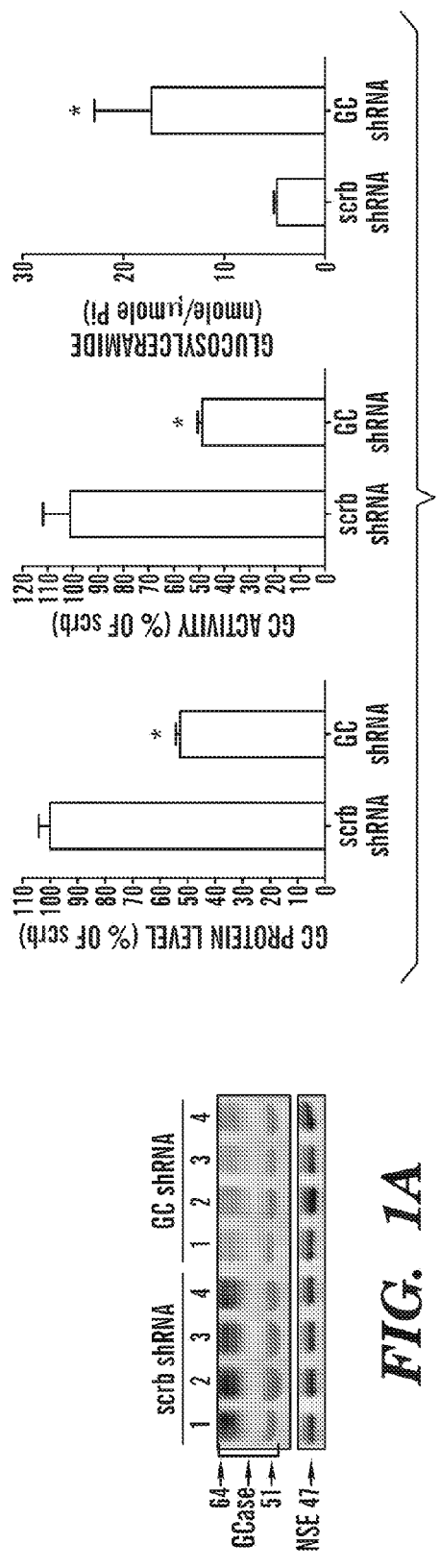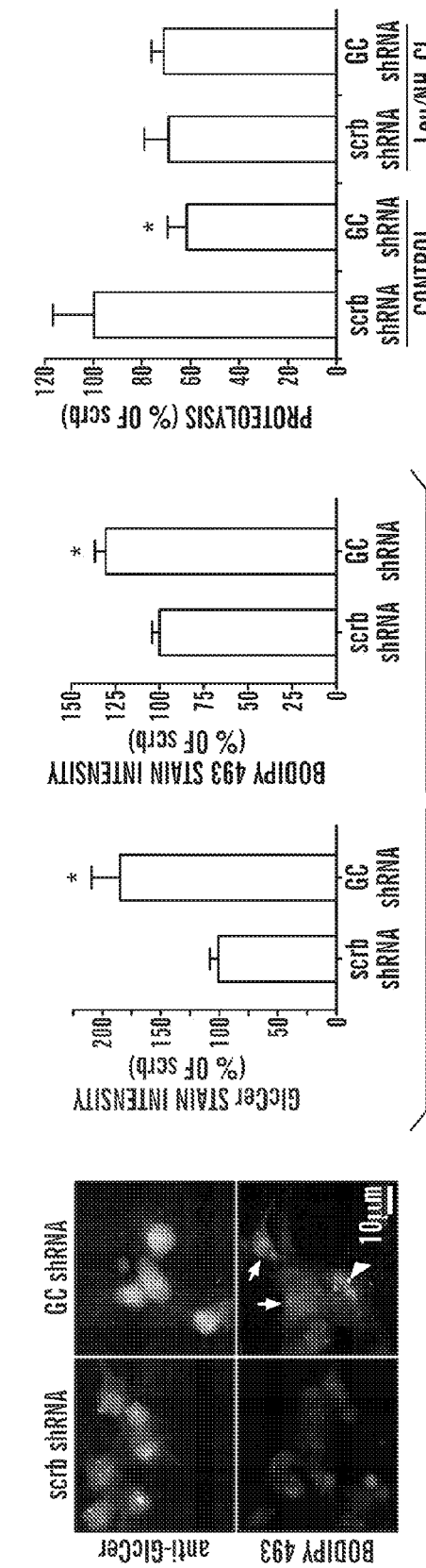

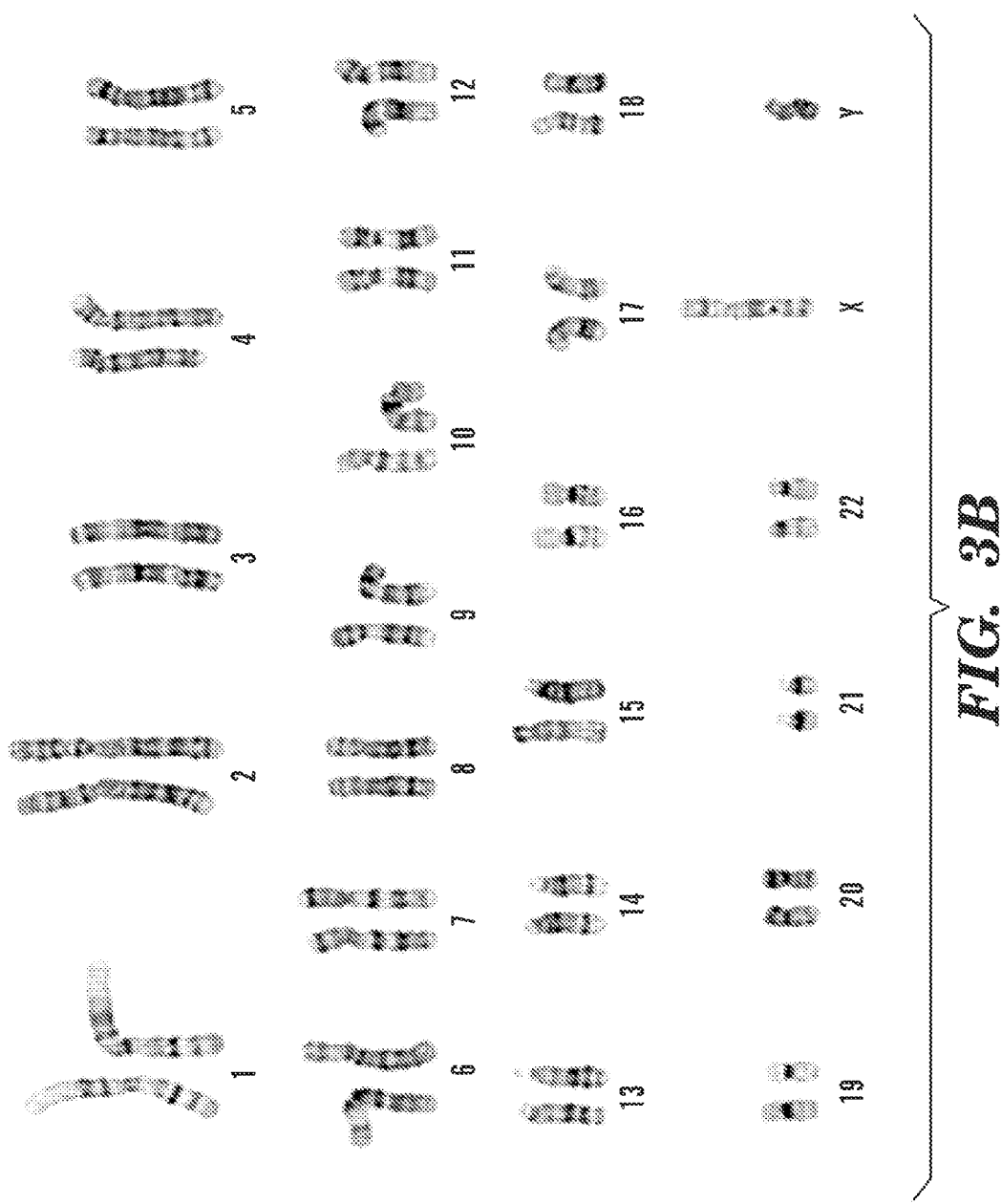

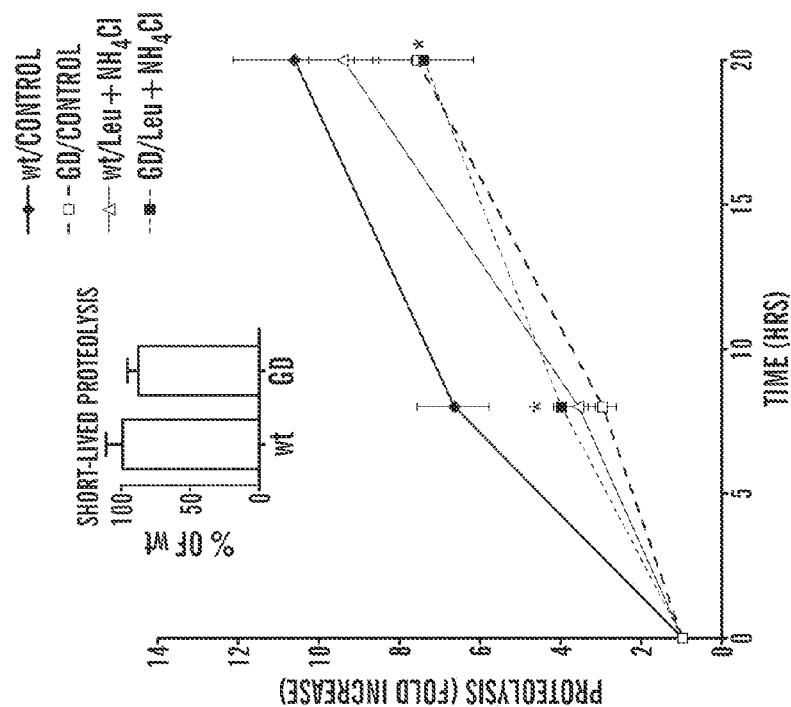
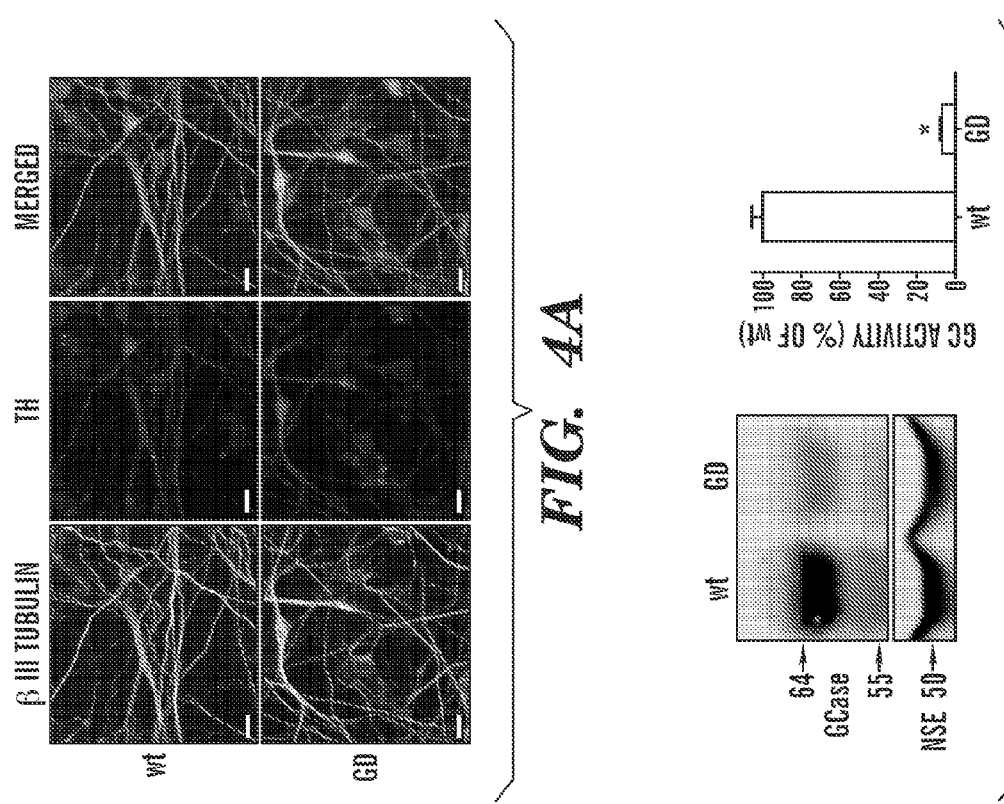
FIG. 4A
FIG. 4B
FIG. 4C

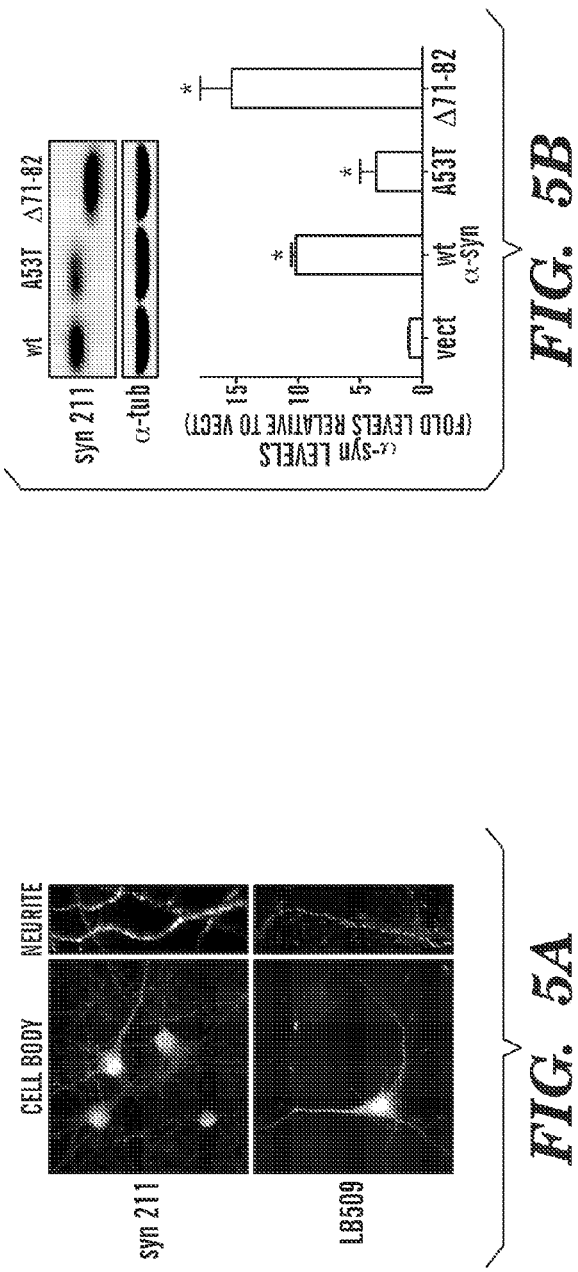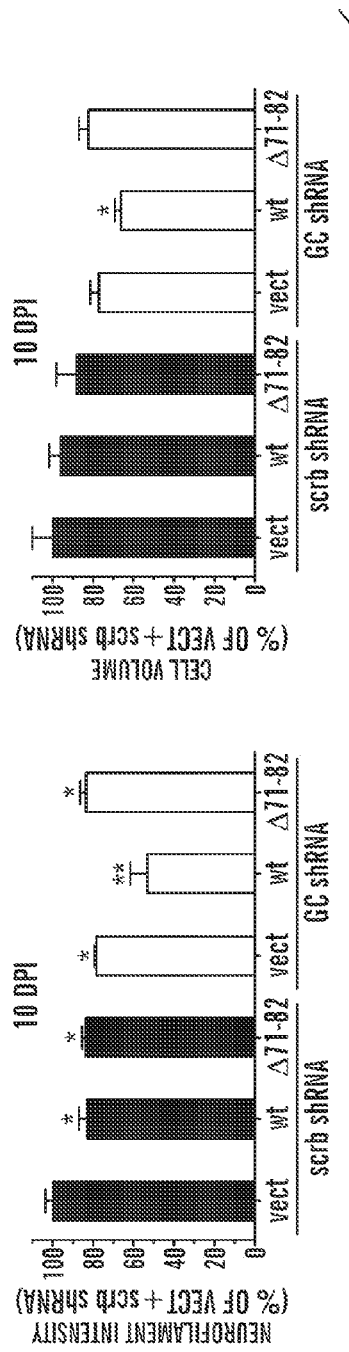
FIG. 5A
FIG. 5B
FIG. 5C

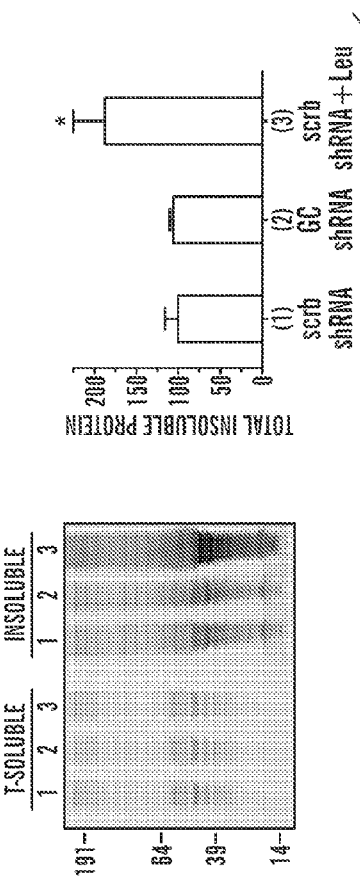
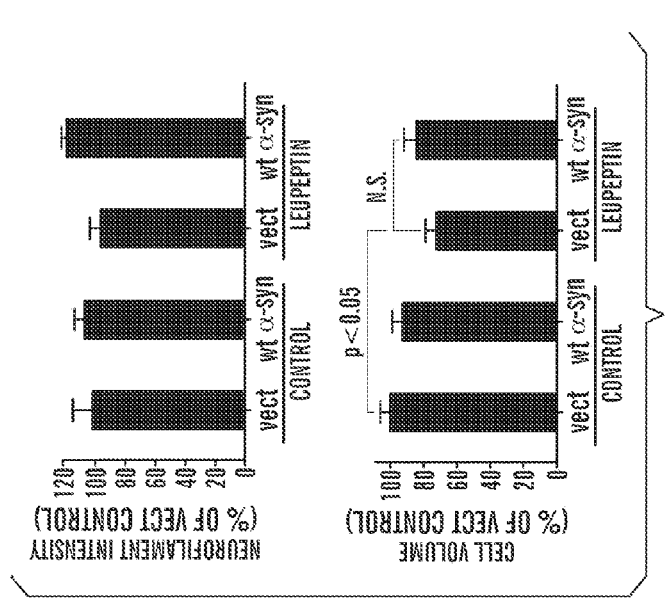
FIG. 5D  FIG. 5E  FIG. 5F  FIG. 5G

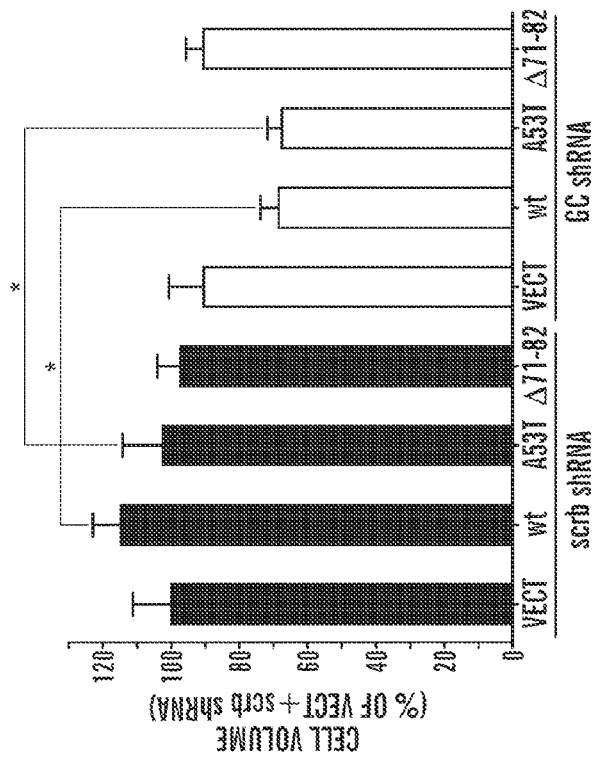
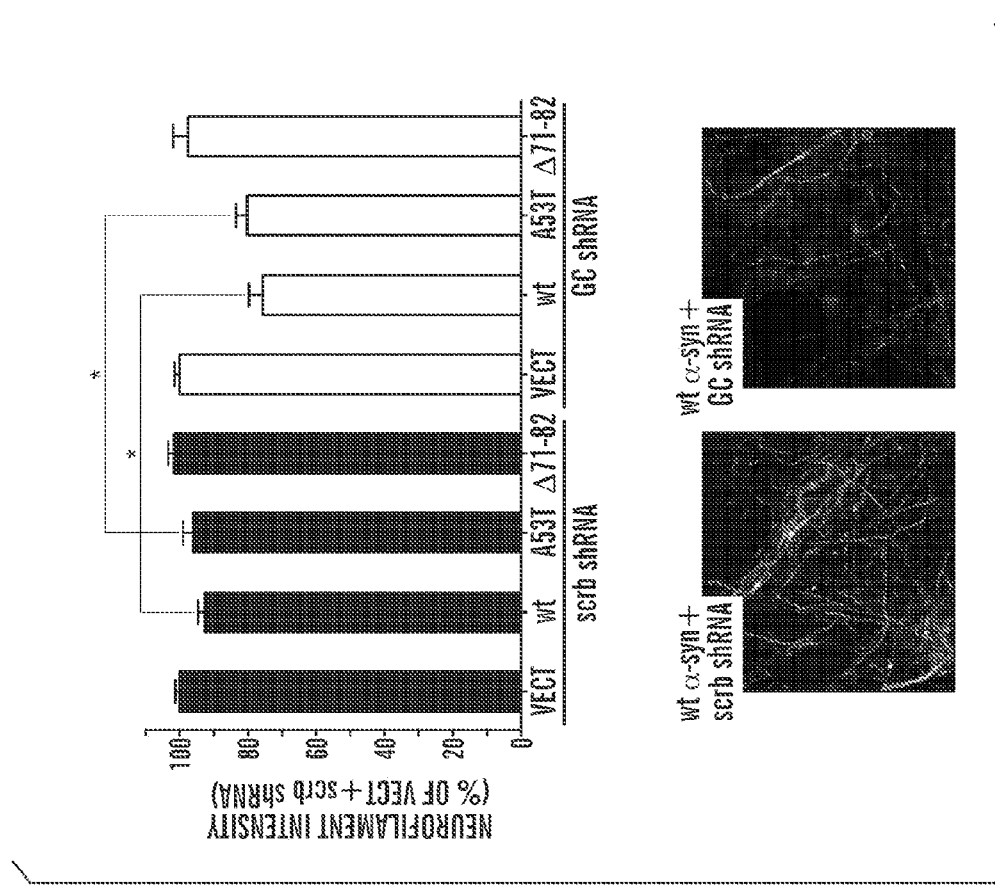
FIG. 6A
FIG. 6B

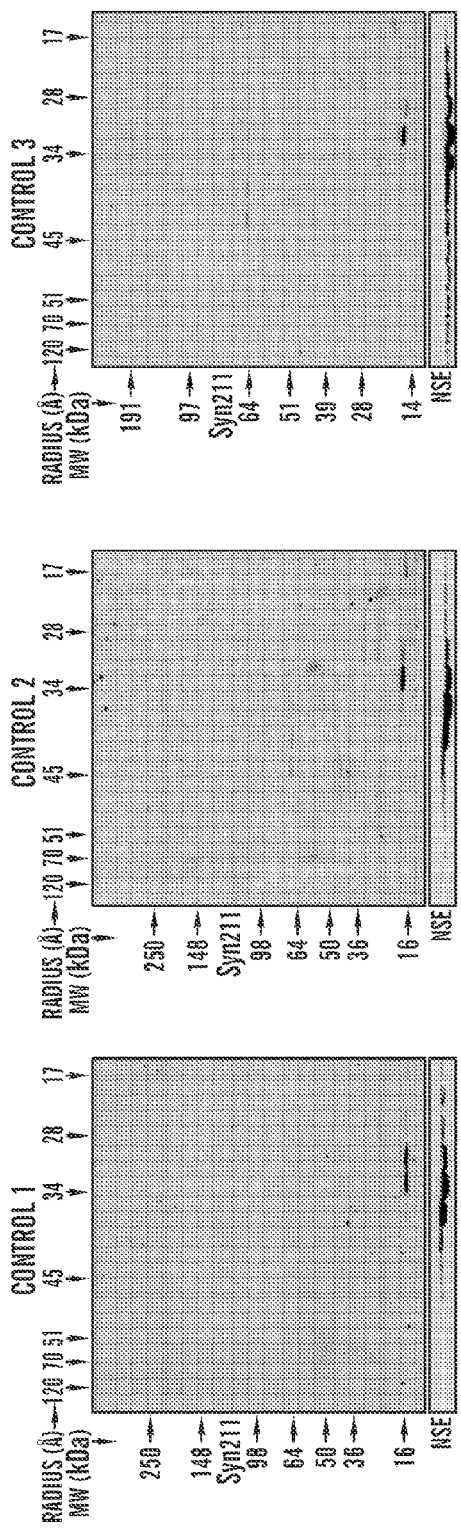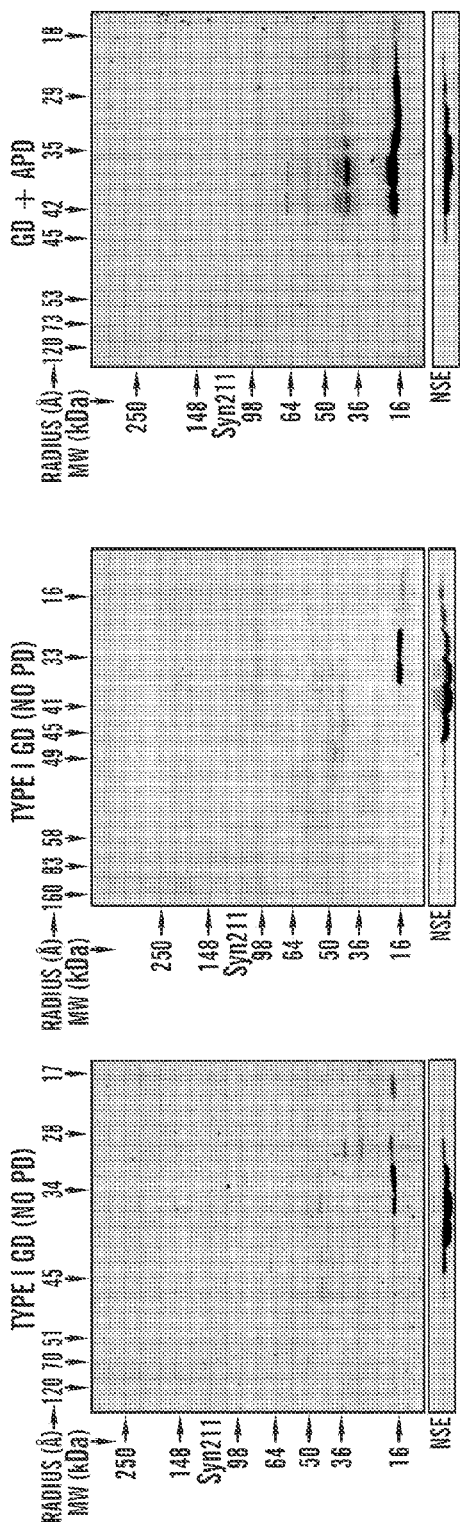

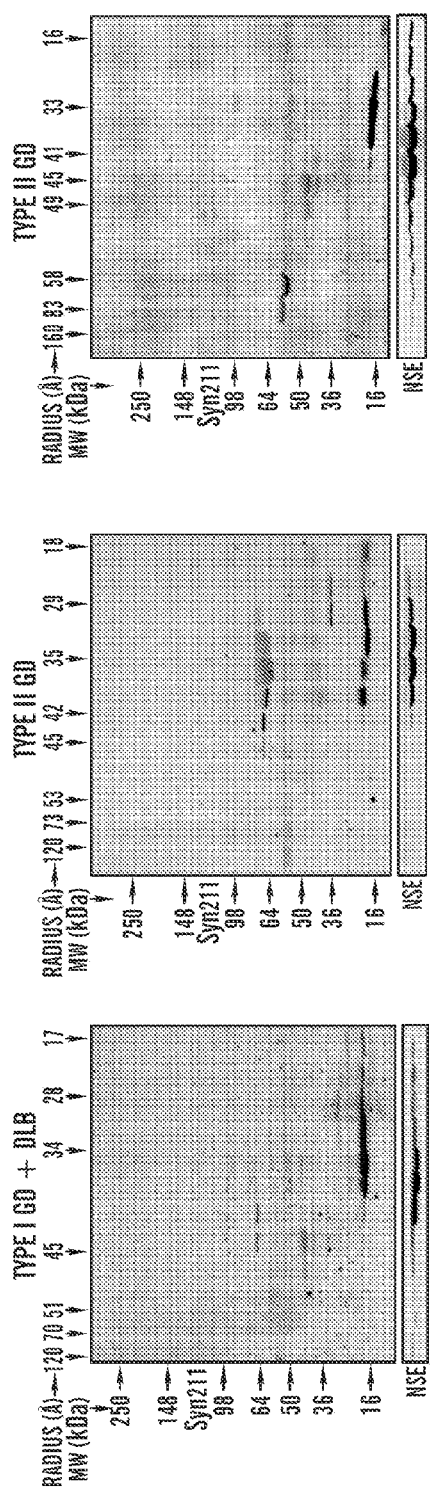

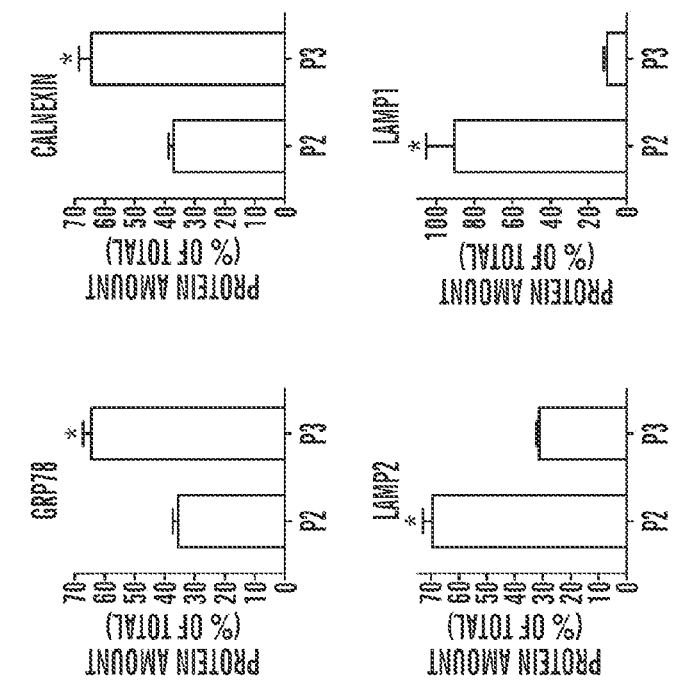
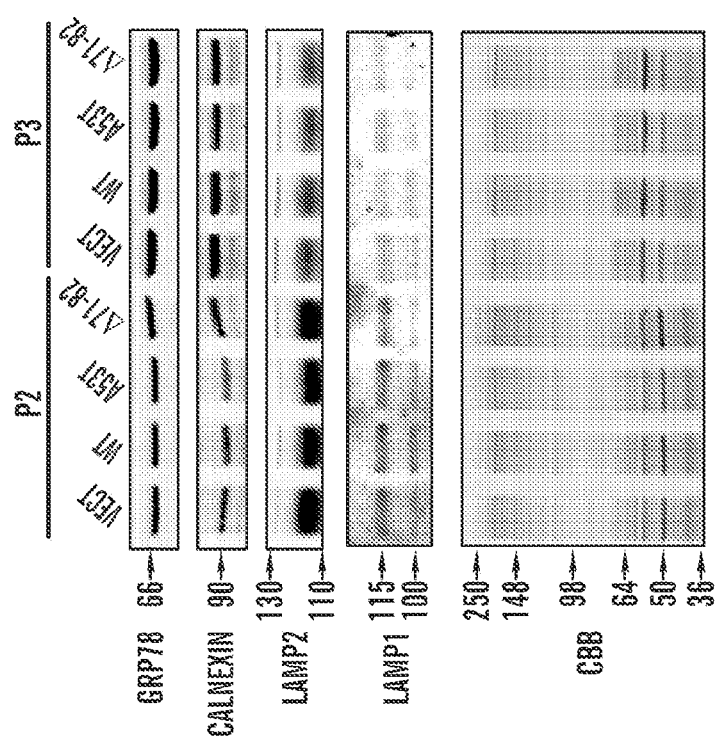
FIG. 14B
FIG. 14A

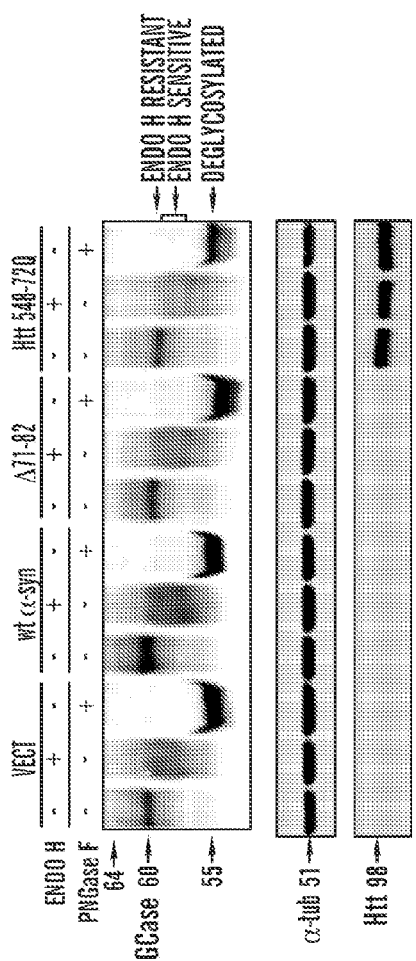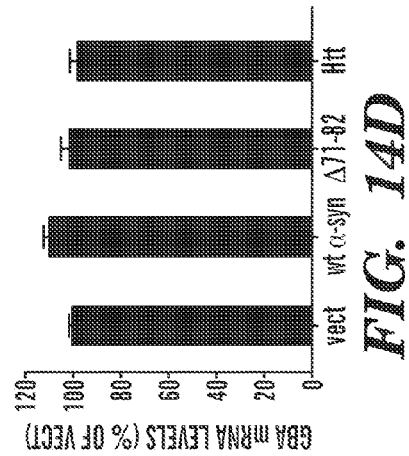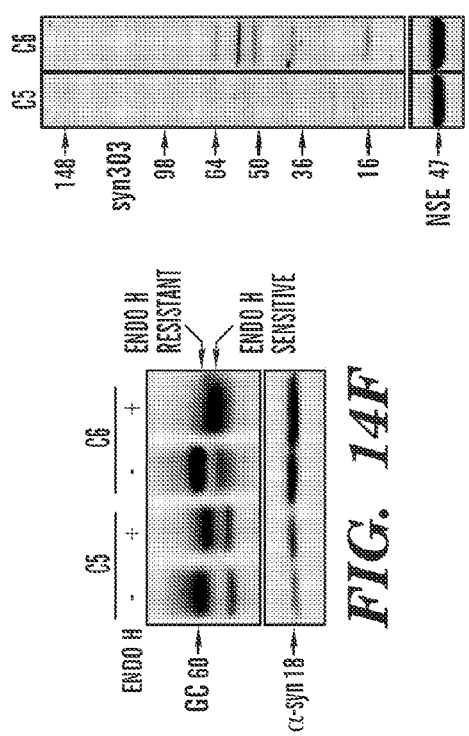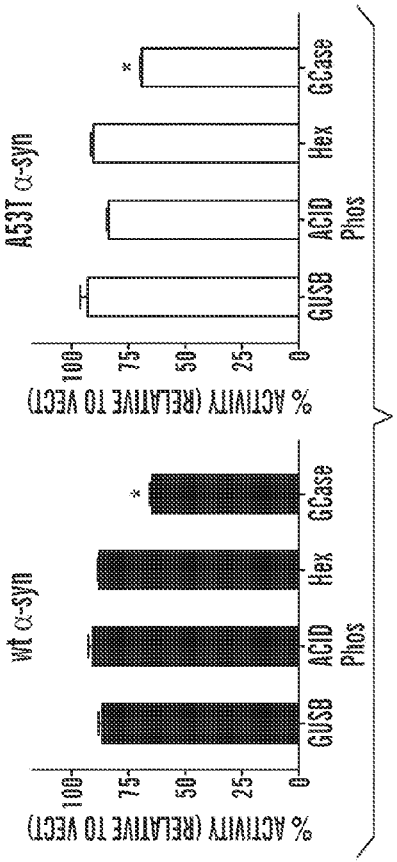
FIG. 14C
FIG. 14D
FIG. 14E
FIG. 14F
FIG. 14G

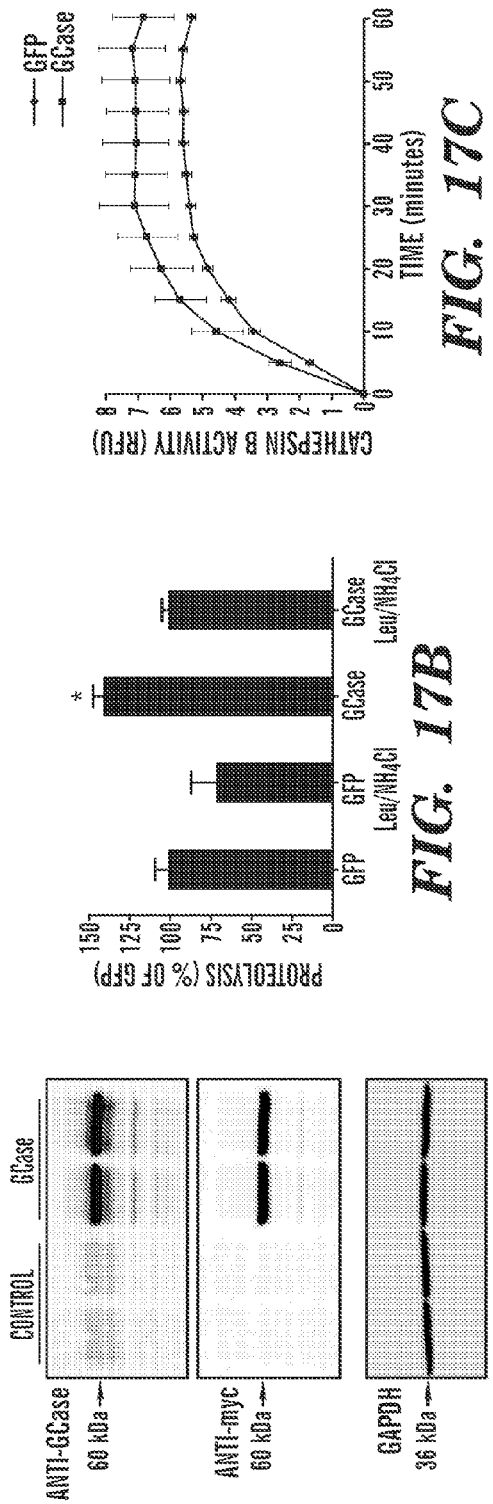
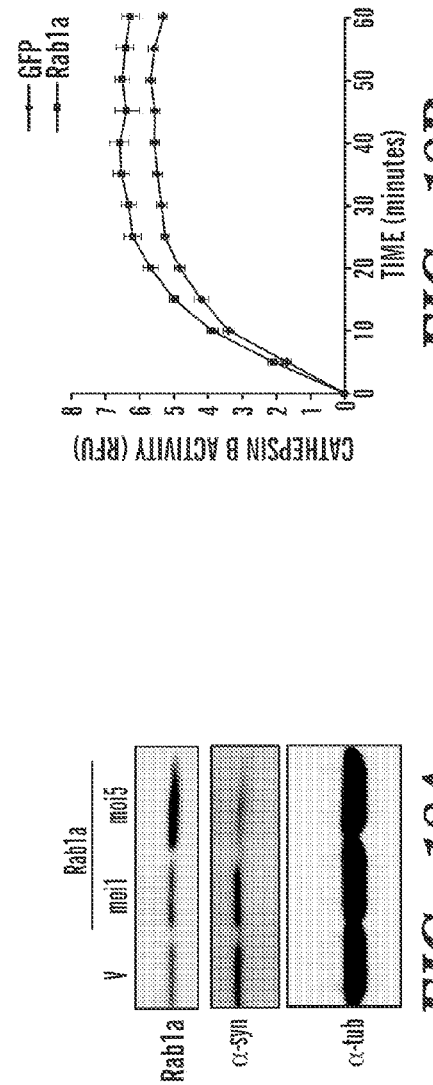

SEQUENCE LISTING

<160> NUMBER OF SEQ ID NOS: 50

<210> SEQ ID NO 1
<211> LENGTH: 677
<212> TYPE: PRT
<213> ORGANISM: Homo sapiens

<400> SEQUENCE: 1

```
Met Pro Gly Phe Leu Val Arg Ile Leu Leu Leu Leu Val Leu Leu
1               5                   10                  15

Leu Leu Gly Pro Thr Arg Gly Leu Arg Asn Ala Thr Gln Arg Met Phe
                20                  25                  30

Glu Ile Asp Tyr Ser Arg Asp Ser Phe Leu Lys Asp Gly Gln Pro Phe
            35                  40                  45

Arg Tyr Ile Ser Gly Ser Ile His Tyr Ser Arg Val Pro Arg Phe Tyr
        50                  55                  60

Trp Lys Asp Arg Leu Leu Lys Met Lys Met Ala Gly Leu Asn Ala Ile
65                  70                  75                  80

Gln Thr Tyr Val Pro Trp Asn Phe His Glu Pro Trp Pro Gly Gln Tyr
                85                  90                  95

Gln Phe Ser Glu Asp His Asp Val Glu Tyr Phe Leu Arg Leu Ala His
            100                 105                 110

Glu Leu Gly Leu Leu Val Ile Leu Arg Pro Gly Pro Tyr Ile Cys Ala
        115                 120                 125

Glu Trp Glu Met Gly Gly Leu Pro Ala Trp Leu Leu Glu Lys Glu Ser
    130                 135                 140

Ile Leu Leu Arg Ser Ser Asp Pro Asp Tyr Leu Ala Ala Val Asp Lys
145                 150                 155                 160

Trp Leu Gly Val Leu Leu Pro Lys Met Lys Pro Leu Leu Tyr Gln Asn
                165                 170                 175

Gly Gly Pro Val Ile Thr Val Gln Val Glu Asn Glu Tyr Gly Ser Tyr
            180                 185                 190

Phe Ala Cys Asp Phe Asp Tyr Leu Arg Phe Leu Gln Lys Arg Phe Arg
        195                 200                 205

His His Leu Gly Asp Asp Val Val Leu Phe Thr Thr Asp Gly Ala His
    210                 215                 220
```

-continued

```
Lys Thr Phe Leu Lys Cys Gly Ala Leu Gln Gly Leu Tyr Thr Thr Val
225                 230                 235                 240

Asp Phe Gly Thr Gly Ser Asn Ile Thr Asp Ala Phe Leu Ser Gln Arg
            245                 250                 255

Lys Cys Glu Pro Lys Gly Pro Leu Ile Asn Ser Glu Phe Tyr Thr Gly
            260                 265                 270

Trp Leu Asp His Trp Gly Gln Pro His Ser Thr Ile Lys Thr Glu Ala
            275                 280                 285

Val Ala Ser Ser Leu Tyr Asp Ile Leu Ala Arg Gly Ala Ser Val Asn
        290                 295                 300

Leu Tyr Met Phe Ile Gly Gly Thr Asn Phe Ala Tyr Trp Asn Gly Ala
305                 310                 315                 320

Asn Ser Pro Tyr Ala Ala Gln Pro Thr Ser Tyr Asp Tyr Asp Ala Pro
                325                 330                 335

Leu Ser Glu Ala Gly Asp Leu Thr Glu Lys Tyr Phe Ala Leu Arg Asn
                340                 345                 350

Ile Ile Gln Lys Phe Glu Lys Val Pro Glu Gly Pro Ile Pro Pro Ser
                355                 360                 365

Thr Pro Lys Phe Ala Tyr Gly Lys Val Thr Leu Glu Lys Leu Lys Thr
            370                 375                 380

Val Gly Ala Ala Leu Asp Ile Leu Cys Pro Ser Gly Pro Ile Lys Ser
385                 390                 395                 400

Leu Tyr Pro Leu Thr Phe Ile Gln Val Lys Gln His Tyr Gly Phe Val
                405                 410                 415

Leu Tyr Arg Thr Thr Leu Pro Gln Asp Cys Ser Asn Pro Ala Pro Leu
                420                 425                 430

Ser Ser Pro Leu Asn Gly Val His Asp Arg Ala Tyr Val Ala Val Asp
            435                 440                 445

Gly Ile Pro Gln Gly Val Leu Glu Arg Asn Asn Val Ile Thr Leu Asn
            450                 455                 460

Ile Thr Gly Lys Ala Gly Ala Thr Leu Asp Leu Leu Val Glu Asn Met
465                 470                 475                 480

Gly Arg Val Asn Tyr Gly Ala Tyr Ile Asn Asp Phe Lys Gly Leu Val
                485                 490                 495

Ser Asn Leu Thr Leu Ser Ser Asn Ile Leu Thr Asp Trp Thr Ile Phe
            500                 505                 510

Pro Leu Asp Thr Glu Asp Ala Val Arg Ser His Leu Gly Gly Trp Gly
            515                 520                 525

His Arg Asp Ser Gly His His Asp Glu Ala Trp Ala His Asn Ser Ser
            530                 535                 540

Asn Tyr Thr Leu Pro Ala Phe Tyr Met Gly Asn Phe Ser Ile Pro Ser
545                 550                 555                 560

Gly Ile Pro Asp Leu Pro Gln Asp Thr Phe Ile Gln Phe Pro Gly Trp
                565                 570                 575

Thr Lys Gly Gln Val Trp Ile Asn Gly Phe Asn Leu Gly Arg Tyr Trp
            580                 585                 590

Pro Ala Arg Gly Pro Gln Leu Thr Leu Phe Val Pro Gln His Ile Leu
            595                 600                 605

Met Thr Ser Ala Pro Asn Thr Ile Thr Val Leu Glu Leu Glu Trp Ala
            610                 615                 620

Pro Cys Ser Ser Asp Asp Pro Glu Leu Cys Ala Val Thr Phe Val Asp
625                 630                 635                 640
```

```
Arg Pro Val Ile Gly Ser Ser Val Thr Tyr Asp His Pro Ser Lys Pro
                645                 650                 655

Val Glu Lys Arg Leu Met Pro Pro Pro Gln Lys Asn Lys Asp Ser
        660                 665                 670

Trp Leu Asp His Val
        675

<210> SEQ ID NO 2
<211> LENGTH: 546
<212> TYPE: PRT
<213> ORGANISM: Homo sapiens

<400> SEQUENCE: 2

Met Pro Gly Phe Leu Val Arg Ile Leu Pro Leu Leu Val Leu Leu
1               5                   10                  15

Leu Leu Gly Pro Thr Arg Gly Leu Arg Asn Ala Thr Gln Arg Met Phe
                20                  25                  30

Glu Ile Asp Tyr Ser Arg Asp Ser Phe Leu Lys Asp Gly Gln Pro Phe
            35                  40                  45

Arg Tyr Ile Ser Gly Ser Ile His Tyr Ser Arg Val Pro Arg Phe Tyr
        50                  55                  60

Trp Lys Asp Arg Leu Leu Lys Met Lys Met Ala Gly Leu Asn Ala Ile
65                  70                  75                  80

Gln Thr Leu Pro Gly Ser Cys Gly Gln Val Val Gly Ser Pro Ser Ala
                85                  90                  95

Gln Asp Glu Ala Ser Pro Leu Ser Glu Trp Arg Ala Ser Tyr Asn Ser
            100                 105                 110

Ala Gly Ser Asn Ile Thr Asp Ala Phe Leu Ser Gln Arg Lys Cys Glu
        115                 120                 125

Pro Lys Gly Pro Leu Ile Asn Ser Glu Phe Tyr Thr Gly Trp Leu Asp
    130                 135                 140

His Trp Gly Gln Pro His Ser Thr Ile Lys Thr Glu Ala Val Ala Ser
145                 150                 155                 160

Ser Leu Tyr Asp Ile Leu Ala Arg Gly Ala Ser Val Asn Leu Tyr Met
                165                 170                 175

Phe Ile Gly Gly Thr Asn Phe Ala Tyr Trp Asn Gly Ala Asn Ser Pro
            180                 185                 190

Tyr Ala Ala Gln Pro Thr Ser Tyr Asp Tyr Asp Ala Pro Leu Ser Glu
        195                 200                 205

Ala Gly Asp Leu Thr Glu Lys Tyr Phe Ala Leu Arg Asn Ile Ile Gln
    210                 215                 220

Lys Phe Glu Lys Val Pro Glu Gly Pro Ile Pro Pro Ser Thr Pro Lys
225                 230                 235                 240

Phe Ala Tyr Gly Lys Val Thr Leu Glu Lys Leu Lys Thr Val Gly Ala
                245                 250                 255

Ala Leu Asp Ile Leu Cys Pro Ser Gly Pro Ile Lys Ser Leu Tyr Pro
            260                 265                 270

Leu Thr Phe Ile Gln Val Lys Gln His Tyr Gly Phe Val Leu Tyr Arg
        275                 280                 285

Thr Thr Leu Pro Gln Asp Cys Ser Asn Pro Ala Pro Leu Ser Ser Pro
    290                 295                 300

Leu Asn Gly Val His Asp Arg Ala Tyr Val Ala Val Asp Gly Ile Pro
305                 310                 315                 320

Gln Gly Val Leu Glu Arg Asn Asn Val Ile Thr Leu Asn Ile Thr Gly
                325                 330                 335
```

```
Lys Ala Gly Ala Thr Leu Asp Leu Leu Val Glu Asn Met Gly Arg Val
            340                 345                 350

Asn Tyr Gly Ala Tyr Ile Asn Asp Phe Lys Gly Leu Val Ser Asn Leu
        355                 360                 365

Thr Leu Ser Ser Asn Ile Leu Thr Asp Trp Thr Ile Phe Pro Leu Asp
    370                 375                 380

Thr Glu Asp Ala Val Arg Ser His Leu Gly Gly Trp Gly His Arg Asp
385                 390                 395                 400

Ser Gly His His Asp Glu Ala Trp Ala His Asn Ser Ser Asn Tyr Thr
            405                 410                 415

Leu Pro Ala Phe Tyr Met Gly Asn Phe Ser Ile Pro Ser Gly Ile Pro
        420                 425                 430

Asp Leu Pro Gln Asp Thr Phe Ile Gln Phe Pro Gly Trp Thr Lys Gly
    435                 440                 445

Gln Val Trp Ile Asn Gly Phe Asn Leu Gly Arg Tyr Trp Pro Ala Arg
450                 455                 460

Gly Pro Gln Leu Thr Leu Phe Val Pro Gln His Ile Leu Met Thr Ser
465                 470                 475                 480

Ala Pro Asn Thr Ile Thr Val Leu Glu Leu Glu Trp Ala Pro Cys Ser
            485                 490                 495

Ser Asp Asp Pro Glu Leu Cys Ala Val Thr Phe Val Asp Arg Pro Val
        500                 505                 510

Ile Gly Ser Ser Val Thr Tyr Asp His Pro Ser Lys Pro Val Glu Lys
    515                 520                 525

Arg Leu Met Pro Pro Pro Gln Lys Asn Lys Asp Ser Trp Leu Asp
    530                 535                 540

His Val
545

<210> SEQ ID NO 3
<211> LENGTH: 647
<212> TYPE: PRT
<213> ORGANISM: Homo sapiens

<400> SEQUENCE: 3

Met Phe Glu Ile Asp Tyr Ser Arg Asp Ser Phe Leu Lys Asp Gly Gln
1               5                   10                  15

Pro Phe Arg Tyr Ile Ser Gly Ser Ile His Tyr Ser Arg Val Pro Arg
            20                  25                  30

Phe Tyr Trp Lys Asp Arg Leu Leu Lys Met Lys Met Ala Gly Leu Asn
        35                  40                  45

Ala Ile Gln Thr Tyr Val Pro Trp Asn Phe His Glu Pro Trp Pro Gly
    50                  55                  60

Gln Tyr Gln Phe Ser Glu Asp His Asp Val Glu Tyr Phe Leu Arg Leu
65                  70                  75                  80

Ala His Glu Leu Gly Leu Leu Val Ile Leu Arg Pro Gly Pro Tyr Ile
            85                  90                  95

Cys Ala Glu Trp Glu Met Gly Gly Leu Pro Ala Trp Leu Leu Glu Lys
        100                 105                 110

Glu Ser Ile Leu Leu Arg Ser Ser Asp Pro Asp Tyr Leu Ala Ala Val
    115                 120                 125

Asp Lys Trp Leu Gly Val Leu Leu Pro Lys Met Lys Pro Leu Leu Tyr
    130                 135                 140

Gln Asn Gly Gly Pro Val Ile Thr Val Gln Val Glu Asn Glu Tyr Gly
```

```
            145                 150                 155                 160
        Ser Tyr Phe Ala Cys Asp Phe Asp Tyr Leu Arg Phe Leu Gln Lys Arg
                        165                 170                 175

Phe Arg His His Leu Gly Asp Asp Val Val Leu Phe Thr Thr Asp Gly
                        180                 185                 190

Ala His Lys Thr Phe Leu Lys Cys Gly Ala Leu Gln Gly Leu Tyr Thr
                        195                 200                 205

Thr Val Asp Phe Gly Thr Gly Ser Asn Ile Thr Asp Ala Phe Leu Ser
                210                 215                 220

Gln Arg Lys Cys Glu Pro Lys Gly Pro Leu Ile Asn Ser Glu Phe Tyr
        225                 230                 235                 240

Thr Gly Trp Leu Asp His Trp Gly Gln Pro His Ser Thr Ile Lys Thr
                        245                 250                 255

Glu Ala Val Ala Ser Ser Leu Tyr Asp Ile Leu Ala Arg Gly Ala Ser
                        260                 265                 270

Val Asn Leu Tyr Met Phe Ile Gly Gly Thr Asn Phe Ala Tyr Trp Asn
                275                 280                 285

Gly Ala Asn Ser Pro Tyr Ala Ala Gln Pro Thr Ser Tyr Asp Tyr Asp
                290                 295                 300

Ala Pro Leu Ser Glu Ala Gly Asp Leu Thr Glu Lys Tyr Phe Ala Leu
        305                 310                 315                 320

Arg Asn Ile Ile Gln Lys Phe Glu Lys Val Pro Glu Gly Pro Ile Pro
                        325                 330                 335

Pro Ser Thr Pro Lys Phe Ala Tyr Gly Lys Val Thr Leu Glu Lys Leu
                        340                 345                 350

Lys Thr Val Gly Ala Ala Leu Asp Ile Leu Cys Pro Ser Gly Pro Ile
                        355                 360                 365

Lys Ser Leu Tyr Pro Leu Thr Phe Ile Gln Val Lys Gln His Tyr Gly
                370                 375                 380

Phe Val Leu Tyr Arg Thr Thr Leu Pro Gln Asp Cys Ser Asn Pro Ala
        385                 390                 395                 400

Pro Leu Ser Ser Pro Leu Asn Gly Val His Asp Arg Ala Tyr Val Ala
                        405                 410                 415

Val Asp Gly Ile Pro Gln Gly Val Leu Glu Arg Asn Asn Val Ile Thr
                        420                 425                 430

Leu Asn Ile Thr Gly Lys Ala Gly Ala Thr Leu Asp Leu Leu Val Glu
                        435                 440                 445

Asn Met Gly Arg Val Asn Tyr Gly Ala Tyr Ile Asn Asp Phe Lys Gly
                450                 455                 460

Leu Val Ser Asn Leu Thr Leu Ser Ser Asn Ile Leu Thr Asp Trp Thr
        465                 470                 475                 480

Ile Phe Pro Leu Asp Thr Glu Asp Ala Val Arg Ser His Leu Gly Gly
                        485                 490                 495

Trp Gly His Arg Asp Ser Gly His His Asp Glu Ala Trp Ala His Asn
                        500                 505                 510

Ser Ser Asn Tyr Thr Leu Pro Ala Phe Tyr Met Gly Asn Phe Ser Ile
                        515                 520                 525

Pro Ser Gly Ile Pro Asp Leu Pro Gln Asp Thr Phe Ile Gln Phe Pro
                530                 535                 540

Gly Trp Thr Lys Gly Gln Val Trp Ile Asn Gly Phe Asn Leu Gly Arg
        545                 550                 555                 560

Tyr Trp Pro Ala Arg Gly Pro Gln Leu Thr Leu Phe Val Pro Gln His
                        565                 570                 575
```

```
Ile Leu Met Thr Ser Ala Pro Asn Thr Ile Thr Val Leu Glu Leu Glu
            580                 585                 590

Trp Ala Pro Cys Ser Ser Asp Asp Pro Glu Leu Cys Ala Val Thr Phe
        595                 600                 605

Val Asp Arg Pro Val Ile Gly Ser Ser Val Thr Tyr Asp His Pro Ser
610                 615                 620

Lys Pro Val Glu Lys Arg Leu Met Pro Pro Pro Gln Lys Asn Lys
625                 630                 635                 640

Asp Ser Trp Leu Asp His Val
                645

<210> SEQ ID NO 4
<211> LENGTH: 536
<212> TYPE: PRT
<213> ORGANISM: Homo sapiens

<400> SEQUENCE: 4

Met Glu Phe Ser Ser Pro Ser Arg Glu Glu Cys Pro Lys Pro Leu Ser
1               5                   10                  15

Arg Val Ser Ile Met Ala Gly Ser Leu Thr Gly Leu Leu Leu Leu Gln
            20                  25                  30

Ala Val Ser Trp Ala Ser Gly Ala Arg Pro Cys Ile Pro Lys Ser Phe
        35                  40                  45

Gly Tyr Ser Ser Val Val Cys Val Cys Asn Ala Thr Tyr Cys Asp Ser
    50                  55                  60

Phe Asp Pro Pro Thr Phe Pro Ala Leu Gly Thr Phe Ser Arg Tyr Glu
65                  70                  75                  80

Ser Thr Arg Ser Gly Arg Arg Met Glu Leu Ser Met Gly Pro Ile Gln
            85                  90                  95

Ala Asn His Thr Gly Thr Gly Leu Leu Leu Thr Leu Gln Pro Glu Gln
            100                 105                 110

Lys Phe Gln Lys Val Lys Gly Phe Gly Gly Ala Met Thr Asp Ala Ala
        115                 120                 125

Ala Leu Asn Ile Leu Ala Leu Ser Pro Pro Ala Gln Asn Leu Leu Leu
    130                 135                 140

Lys Ser Tyr Phe Ser Glu Glu Gly Ile Gly Tyr Asn Ile Ile Arg Val
145                 150                 155                 160

Pro Met Ala Ser Cys Asp Phe Ser Ile Arg Thr Tyr Thr Tyr Ala Asp
                165                 170                 175

Thr Pro Asp Asp Phe Gln Leu His Asn Phe Ser Leu Pro Glu Glu Asp
            180                 185                 190

Thr Lys Leu Lys Ile Pro Leu Ile His Arg Ala Leu Gln Leu Ala Gln
        195                 200                 205

Arg Pro Val Ser Leu Leu Ala Ser Pro Trp Thr Ser Pro Thr Trp Leu
    210                 215                 220

Lys Thr Asn Gly Ala Val Asn Gly Lys Gly Ser Leu Lys Gly Gln Pro
225                 230                 235                 240

Gly Asp Ile Tyr His Gln Thr Trp Ala Arg Tyr Phe Val Lys Phe Leu
                245                 250                 255

Asp Ala Tyr Ala Glu His Lys Leu Gln Phe Trp Ala Val Thr Ala Glu
            260                 265                 270

Asn Glu Pro Ser Ala Gly Leu Leu Ser Gly Tyr Pro Phe Gln Cys Leu
        275                 280                 285

Gly Phe Thr Pro Glu His Gln Arg Asp Phe Ile Ala Arg Asp Leu Gly
```

```
                    290                 295                 300
Pro Thr Leu Ala Asn Ser Thr His His Asn Val Arg Leu Leu Met Leu
305                 310                 315                 320

Asp Asp Gln Arg Leu Leu Pro His Trp Ala Lys Val Val Leu Thr
                325                 330                 335

Asp Pro Glu Ala Ala Lys Tyr Val His Gly Ile Ala Val His Trp Tyr
                340                 345                 350

Leu Asp Phe Leu Ala Pro Ala Lys Ala Thr Leu Gly Glu Thr His Arg
            355                 360                 365

Leu Phe Pro Asn Thr Met Leu Phe Ala Ser Glu Ala Cys Val Gly Ser
        370                 375                 380

Lys Phe Trp Glu Gln Ser Val Arg Leu Gly Ser Trp Asp Arg Gly Met
385                 390                 395                 400

Gln Tyr Ser His Ser Ile Ile Thr Asn Leu Leu Tyr His Val Val Gly
                405                 410                 415

Trp Thr Asp Trp Asn Leu Ala Leu Asn Pro Glu Gly Gly Pro Asn Trp
                420                 425                 430

Val Arg Asn Phe Val Asp Ser Pro Ile Ile Val Asp Ile Thr Lys Asp
                435                 440                 445

Thr Phe Tyr Lys Gln Pro Met Phe Tyr His Leu Gly His Phe Ser Lys
            450                 455                 460

Phe Ile Pro Glu Gly Ser Gln Arg Val Gly Leu Val Ala Ser Gln Lys
465                 470                 475                 480

Asn Asp Leu Asp Ala Val Ala Leu Met His Pro Asp Gly Ser Ala Val
                485                 490                 495

Val Val Val Leu Asn Arg Ser Ser Lys Asp Val Pro Leu Thr Ile Lys
                500                 505                 510

Asp Pro Ala Val Gly Phe Leu Glu Thr Ile Ser Pro Gly Tyr Ser Ile
            515                 520                 525

His Thr Tyr Leu Trp Arg Arg Gln
    530                 535

<210> SEQ ID NO 5
<211> LENGTH: 927
<212> TYPE: PRT
<213> ORGANISM: Homo sapiens

<400> SEQUENCE: 5

Met Gly Thr Gln Asp Pro Gly Asn Met Gly Thr Gly Val Pro Ala Ser
1               5                   10                  15

Glu Gln Ile Ser Cys Ala Lys Glu Asp Pro Gln Val Tyr Cys Pro Glu
                20                  25                  30

Glu Thr Gly Gly Thr Lys Asp Val Gln Val Thr Asp Cys Lys Ser Pro
            35                  40                  45

Glu Asp Ser Arg Pro Pro Lys Glu Thr Asp Cys Cys Asn Pro Glu Asp
        50                  55                  60

Ser Gly Gln Leu Met Val Ser Tyr Glu Gly Lys Ala Met Gly Tyr Gln
65                  70                  75                  80

Val Pro Pro Phe Gly Trp Arg Ile Cys Leu Ala His Glu Phe Thr Glu
                85                  90                  95

Lys Arg Lys Pro Phe Gln Ala Asn Asn Val Ser Leu Ser Asn Met Ile
                100                 105                 110

Lys His Ile Gly Met Gly Leu Arg Tyr Leu Gln Trp Trp Tyr Arg Lys
            115                 120                 125
```

-continued

```
Thr His Val Glu Lys Lys Thr Pro Phe Ile Asp Met Ile Asn Ser Val
130                 135                 140

Pro Leu Arg Gln Ile Tyr Gly Cys Pro Leu Gly Gly Ile Gly Gly Gly
145                 150                 155                 160

Thr Ile Thr Arg Gly Trp Arg Gly Gln Phe Cys Arg Trp Gln Leu Asn
                165                 170                 175

Pro Gly Met Tyr Gln His Arg Thr Val Ile Ala Asp Gln Phe Thr Val
            180                 185                 190

Cys Leu Arg Arg Glu Gly Gln Thr Val Tyr Gln Gln Val Leu Ser Leu
        195                 200                 205

Glu Arg Pro Ser Val Leu Arg Ser Trp Asn Trp Gly Leu Cys Gly Tyr
210                 215                 220

Phe Ala Phe Tyr His Ala Leu Tyr Pro Arg Ala Trp Thr Val Tyr Gln
225                 230                 235                 240

Leu Pro Gly Gln Asn Val Thr Leu Thr Cys Arg Gln Ile Thr Pro Ile
                245                 250                 255

Leu Pro His Asp Tyr Gln Asp Ser Ser Leu Pro Val Gly Val Phe Val
            260                 265                 270

Trp Asp Val Glu Asn Glu Gly Asp Glu Ala Leu Asp Val Ser Ile Met
        275                 280                 285

Phe Ser Met Arg Asn Gly Leu Gly Gly Asp Asp Ala Pro Gly Gly
290                 295                 300

Leu Trp Asn Glu Pro Phe Cys Leu Glu Arg Ser Gly Glu Thr Val Arg
305                 310                 315                 320

Gly Leu Leu Leu His His Pro Thr Leu Pro Asn Pro Tyr Thr Met Ala
                325                 330                 335

Val Ala Ala Arg Val Thr Ala Ala Thr Thr Val Thr His Ile Thr Ala
            340                 345                 350

Phe Asp Pro Asp Ser Thr Gly Gln Gln Val Trp Gln Asp Leu Leu Gln
        355                 360                 365

Asp Gly Gln Leu Asp Ser Pro Thr Gly Gln Ser Thr Pro Thr Gln Lys
370                 375                 380

Gly Val Gly Ile Ala Gly Ala Val Cys Val Ser Ser Lys Leu Arg Pro
385                 390                 395                 400

Arg Gly Gln Cys Arg Leu Glu Phe Ser Leu Ala Trp Asp Met Pro Arg
                405                 410                 415

Ile Met Phe Gly Ala Lys Gly Gln Val His Tyr Arg Tyr Thr Arg
            420                 425                 430

Phe Phe Gly Gln Asp Gly Asp Ala Ala Pro Ala Leu Ser His Tyr Ala
        435                 440                 445

Leu Cys Arg Tyr Ala Glu Trp Glu Glu Arg Ile Ser Ala Trp Gln Ser
450                 455                 460

Pro Val Leu Asp Asp Arg Ser Leu Pro Ala Trp Tyr Lys Ser Ala Leu
465                 470                 475                 480

Phe Asn Glu Leu Tyr Phe Leu Ala Asp Gly Gly Thr Val Trp Leu Glu
                485                 490                 495

Val Leu Glu Asp Ser Leu Pro Glu Glu Leu Gly Arg Asn Met Cys His
            500                 505                 510

Leu Arg Pro Thr Leu Arg Asp Tyr Gly Arg Phe Gly Tyr Leu Glu Gly
        515                 520                 525

Gln Glu Tyr Arg Met Tyr Asn Thr Tyr Asp Val His Phe Tyr Ala Ser
530                 535                 540

Phe Ala Leu Ile Met Leu Trp Pro Lys Leu Glu Leu Ser Leu Gln Tyr
```

```
                545                 550                 555                 560
Asp Met Ala Leu Ala Thr Leu Arg Glu Asp Leu Thr Arg Arg Tyr
                        565                 570                 575
Leu Met Ser Gly Val Met Ala Pro Val Lys Arg Arg Asn Val Ile Pro
                580                 585                 590
His Asp Ile Gly Asp Pro Asp Glu Pro Trp Leu Arg Val Asn Ala
                595                 600                 605
Tyr Leu Ile His Asp Thr Ala Asp Trp Lys Asp Leu Asn Leu Lys Phe
            610                 615                 620
Val Leu Gln Val Tyr Arg Asp Tyr Tyr Leu Thr Gly Asp Gln Asn Phe
625                 630                 635                 640
Leu Lys Asp Met Trp Pro Val Cys Leu Ala Val Met Glu Ser Glu Met
                        645                 650                 655
Lys Phe Asp Lys Asp His Asp Gly Leu Ile Glu Asn Gly Gly Tyr Ala
                660                 665                 670
Asp Gln Thr Tyr Asp Gly Trp Val Thr Thr Gly Pro Ser Ala Tyr Cys
            675                 680                 685
Gly Gly Leu Trp Leu Ala Ala Val Ala Val Met Val Gln Met Ala Ala
        690                 695                 700
Leu Cys Gly Ala Gln Asp Ile Gln Asp Lys Phe Ser Ser Ile Leu Ser
705                 710                 715                 720
Arg Gly Gln Glu Ala Tyr Glu Arg Leu Leu Trp Asn Gly Arg Tyr Tyr
                        725                 730                 735
Asn Tyr Asp Ser Ser Ser Arg Pro Gln Ser Arg Ser Val Met Ser Asp
                740                 745                 750
Gln Cys Ala Gly Gln Trp Phe Leu Lys Ala Cys Gly Leu Gly Glu Gly
            755                 760                 765
Asp Thr Glu Val Phe Pro Thr Gln His Val Val Arg Ala Leu Gln Thr
        770                 775                 780
Ile Phe Glu Leu Asn Val Gln Ala Phe Ala Gly Gly Ala Met Gly Ala
785                 790                 795                 800
Val Asn Gly Met Gln Pro His Gly Val Pro Asp Lys Ser Ser Val Gln
                        805                 810                 815
Ser Asp Glu Val Trp Val Gly Val Tyr Gly Leu Ala Ala Thr Met
                820                 825                 830
Ile Gln Glu Gly Leu Thr Trp Glu Gly Phe Gln Thr Ala Glu Gly Cys
            835                 840                 845
Tyr Arg Thr Val Trp Glu Arg Leu Gly Leu Ala Phe Gln Thr Pro Glu
850                 855                 860
Ala Tyr Cys Gln Gln Arg Val Phe Arg Ser Leu Ala Tyr Met Arg Pro
865                 870                 875                 880
Leu Ser Ile Trp Ala Met Gln Leu Ala Leu Gln Gln Gln His Lys
                        885                 890                 895
Lys Ala Ser Trp Pro Lys Val Lys Gln Gly Thr Gly Leu Arg Thr Gly
                900                 905                 910
Pro Met Phe Gly Pro Lys Glu Ala Met Ala Asn Leu Ser Pro Glu
            915                 920                 925

<210> SEQ ID NO 6
<211> LENGTH: 394
<212> TYPE: PRT
<213> ORGANISM: Homo sapiens

<400> SEQUENCE: 6
```

Met Ala Leu Leu Asp Leu Ala Leu Glu Gly Met Ala Val Phe Gly Phe
1               5                   10                  15

Val Leu Phe Leu Val Leu Trp Leu Met His Phe Met Ala Ile Ile Tyr
            20                  25                  30

Thr Arg Leu His Leu Asn Lys Lys Ala Thr Asp Lys Gln Pro Tyr Ser
            35                  40                  45

Lys Leu Pro Gly Val Ser Leu Leu Lys Pro Leu Lys Gly Val Asp Pro
50                  55                  60

Asn Leu Ile Asn Asn Leu Glu Thr Phe Phe Glu Leu Asp Tyr Pro Lys
65                  70                  75                  80

Tyr Glu Val Leu Leu Cys Val Gln Asp His Asp Pro Ala Ile Asp
                85                  90                  95

Val Cys Lys Lys Leu Leu Gly Lys Tyr Pro Asn Val Asp Ala Arg Leu
            100                 105                 110

Phe Ile Gly Gly Lys Lys Val Gly Ile Asn Pro Lys Ile Asn Asn Leu
            115                 120                 125

Met Pro Gly Tyr Glu Val Ala Lys Tyr Asp Leu Ile Trp Ile Cys Asp
130                 135                 140

Ser Gly Ile Arg Val Ile Pro Asp Thr Leu Thr Asp Met Val Asn Gln
145                 150                 155                 160

Met Thr Glu Lys Val Gly Leu Val His Gly Leu Pro Tyr Val Ala Asp
            165                 170                 175

Arg Gln Gly Phe Ala Ala Thr Leu Glu Gln Val Tyr Phe Gly Thr Ser
            180                 185                 190

His Pro Arg Tyr Tyr Ile Ser Ala Asn Val Thr Gly Phe Lys Cys Val
            195                 200                 205

Thr Gly Met Ser Cys Leu Met Arg Lys Asp Val Leu Asp Gln Ala Gly
210                 215                 220

Gly Leu Ile Ala Phe Ala Gln Tyr Ile Ala Glu Asp Tyr Phe Met Ala
225                 230                 235                 240

Lys Ala Ile Ala Asp Arg Gly Trp Arg Phe Ala Met Ser Thr Gln Val
            245                 250                 255

Ala Met Gln Asn Ser Gly Ser Tyr Ser Ile Ser Gln Phe Gln Ser Arg
            260                 265                 270

Met Ile Arg Trp Thr Lys Leu Arg Ile Asn Met Leu Pro Ala Thr Ile
            275                 280                 285

Ile Cys Glu Pro Ile Ser Glu Cys Phe Val Ala Ser Leu Ile Ile Gly
            290                 295                 300

Trp Ala His His Val Phe Arg Trp Asp Ile Met Val Phe Met
305                 310                 315                 320

Cys His Cys Leu Ala Trp Phe Ile Phe Asp Tyr Ile Gln Leu Arg Gly
            325                 330                 335

Val Gln Gly Gly Thr Leu Cys Phe Ser Lys Leu Asp Tyr Ala Val Ala
            340                 345                 350

Trp Phe Ile Arg Glu Ser Met Thr Ile Tyr Ile Phe Leu Ser Ala Leu
            355                 360                 365

Trp Asp Pro Thr Ile Ser Trp Arg Thr Gly Arg Tyr Arg Leu Arg Cys
370                 375                 380

Gly Gly Thr Ala Glu Glu Ile Leu Asp Val
385                 390

<210> SEQ ID NO 7
<211> LENGTH: 556
<212> TYPE: PRT

-continued

<213> ORGANISM: Homo sapiens

<400> SEQUENCE: 7

Met Glu Leu Cys Gly Leu Gly Leu Pro Arg Pro Pro Met Leu Leu Ala
1               5                   10                  15

Leu Leu Leu Ala Thr Leu Leu Ala Ala Met Leu Ala Leu Leu Thr Gln
                20                  25                  30

Val Ala Leu Val Val Gln Val Ala Glu Ala Ala Arg Ala Pro Ser Val
            35                  40                  45

Ser Ala Lys Pro Gly Pro Ala Leu Trp Pro Leu Pro Leu Ser Val Lys
    50                  55                  60

Met Thr Pro Asn Leu Leu His Leu Ala Pro Glu Asn Phe Tyr Ile Ser
65                  70                  75                  80

His Ser Pro Asn Ser Thr Ala Gly Pro Ser Cys Thr Leu Leu Glu Glu
                85                  90                  95

Ala Phe Arg Arg Tyr His Gly Tyr Ile Phe Gly Phe Tyr Lys Trp His
            100                 105                 110

His Glu Pro Ala Glu Phe Gln Ala Lys Thr Gln Val Gln Gln Leu Leu
        115                 120                 125

Val Ser Ile Thr Leu Gln Ser Glu Cys Asp Ala Phe Pro Asn Ile Ser
    130                 135                 140

Ser Asp Glu Ser Tyr Thr Leu Leu Val Lys Glu Pro Val Ala Val Leu
145                 150                 155                 160

Lys Ala Asn Arg Val Trp Gly Ala Leu Arg Gly Leu Glu Thr Phe Ser
                165                 170                 175

Gln Leu Val Tyr Gln Asp Ser Tyr Gly Thr Phe Thr Ile Asn Glu Ser
            180                 185                 190

Thr Ile Ile Asp Ser Pro Arg Phe Ser His Arg Gly Ile Leu Ile Asp
        195                 200                 205

Thr Ser Arg His Tyr Leu Pro Val Lys Ile Ile Leu Lys Thr Leu Asp
    210                 215                 220

Ala Met Ala Phe Asn Lys Phe Asn Val Leu His Trp His Ile Val Asp
225                 230                 235                 240

Asp Gln Ser Phe Pro Tyr Gln Ser Ile Thr Phe Pro Glu Leu Ser Asn
                245                 250                 255

Lys Gly Ser Tyr Ser Leu Ser His Val Tyr Thr Pro Asn Asp Val Arg
            260                 265                 270

Met Val Ile Glu Tyr Ala Arg Leu Arg Gly Ile Arg Val Leu Pro Glu
        275                 280                 285

Phe Asp Thr Pro Gly His Thr Leu Ser Trp Gly Lys Gly Gln Lys Asp
    290                 295                 300

Leu Leu Thr Pro Cys Tyr Ser Arg Gln Asn Lys Leu Asp Ser Phe Gly
305                 310                 315                 320

Pro Ile Asn Pro Thr Leu Asn Thr Thr Tyr Ser Phe Leu Thr Thr Phe
                325                 330                 335

Phe Lys Glu Ile Ser Glu Val Phe Pro Asp Gln Phe Ile His Leu Gly
            340                 345                 350

Gly Asp Glu Val Glu Phe Lys Cys Trp Glu Ser Asn Pro Lys Ile Gln
        355                 360                 365

Asp Phe Met Arg Gln Lys Gly Phe Gly Thr Asp Phe Lys Lys Leu Glu
    370                 375                 380

Ser Phe Tyr Ile Gln Lys Val Leu Asp Ile Ile Ala Thr Ile Asn Lys
385                 390                 395                 400

```
Gly Ser Ile Val Trp Gln Glu Val Phe Asp Asp Lys Ala Lys Leu Ala
                405                 410                 415

Pro Gly Thr Ile Val Glu Val Trp Lys Asp Ser Ala Tyr Pro Glu Glu
            420                 425                 430

Leu Ser Arg Val Thr Ala Ser Gly Phe Pro Val Ile Leu Ser Ala Pro
        435                 440                 445

Trp Tyr Leu Asp Leu Ile Ser Tyr Gly Gln Asp Trp Arg Lys Tyr Tyr
    450                 455                 460

Lys Val Glu Pro Leu Asp Phe Gly Gly Thr Gln Lys Gln Lys Gln Leu
465                 470                 475                 480

Phe Ile Gly Gly Glu Ala Cys Leu Trp Gly Glu Tyr Val Asp Ala Thr
                485                 490                 495

Asn Leu Thr Pro Arg Leu Trp Pro Arg Ala Ser Ala Val Gly Glu Arg
            500                 505                 510

Leu Trp Ser Ser Lys Asp Val Arg Asp Met Asp Asp Ala Tyr Asp Arg
        515                 520                 525

Leu Thr Arg His Arg Cys Arg Met Val Glu Arg Gly Ile Ala Ala Gln
    530                 535                 540

Pro Leu Tyr Ala Gly Tyr Cys Asn His Glu Asn Met
545                 550                 555

<210> SEQ ID NO 8
<211> LENGTH: 529
<212> TYPE: PRT
<213> ORGANISM: Homo sapiens

<400> SEQUENCE: 8

Met Thr Ser Ser Arg Leu Trp Phe Ser Leu Leu Ala Ala Phe
1               5                   10                  15

Ala Gly Arg Ala Thr Ala Leu Trp Pro Trp Pro Gln Asn Phe Gln Thr
                20                  25                  30

Ser Asp Gln Arg Tyr Val Leu Tyr Pro Asn Asn Phe Gln Phe Gln Tyr
            35                  40                  45

Asp Val Ser Ser Ala Ala Gln Pro Gly Cys Ser Val Leu Asp Glu Ala
        50                  55                  60

Phe Gln Arg Tyr Arg Asp Leu Leu Phe Gly Ser Gly Ser Trp Pro Arg
65                  70                  75                  80

Pro Tyr Leu Thr Gly Lys Arg His Thr Leu Glu Lys Asn Val Leu Val
                85                  90                  95

Val Ser Val Val Thr Pro Gly Cys Asn Gln Leu Pro Thr Leu Glu Ser
                100                 105                 110

Val Glu Asn Tyr Thr Leu Thr Ile Asn Asp Asp Gln Cys Leu Leu Leu
            115                 120                 125

Ser Glu Thr Val Trp Gly Ala Leu Arg Gly Leu Glu Thr Phe Ser Gln
        130                 135                 140

Leu Val Trp Lys Ser Ala Glu Gly Thr Phe Phe Ile Asn Lys Thr Glu
145                 150                 155                 160

Ile Glu Asp Phe Pro Arg Phe Pro His Arg Gly Leu Leu Leu Asp Thr
                165                 170                 175

Ser Arg His Tyr Leu Pro Leu Ser Ile Leu Asp Thr Leu Asp Val
            180                 185                 190

Met Ala Tyr Asn Lys Leu Asn Val Phe His Trp His Leu Val Asp Asp
        195                 200                 205

Pro Ser Phe Pro Tyr Glu Ser Phe Thr Phe Pro Glu Leu Met Arg Lys
210                 215                 220
```

```
Gly Ser Tyr Asn Pro Val Thr His Ile Tyr Thr Ala Gln Asp Val Lys
225                 230                 235                 240

Glu Val Ile Glu Tyr Ala Arg Leu Arg Gly Ile Arg Val Leu Ala Glu
            245                 250                 255

Phe Asp Thr Pro Gly His Thr Leu Ser Trp Gly Pro Gly Ile Pro Gly
            260                 265                 270

Leu Leu Thr Pro Cys Tyr Ser Gly Ser Glu Pro Ser Gly Thr Phe Gly
            275                 280                 285

Pro Val Asn Pro Ser Leu Asn Asn Thr Tyr Glu Phe Met Ser Thr Phe
            290                 295                 300

Phe Leu Glu Val Ser Ser Val Phe Pro Asp Phe Tyr Leu His Leu Gly
305                 310                 315                 320

Gly Asp Glu Val Asp Phe Thr Cys Trp Lys Ser Asn Pro Glu Ile Gln
                325                 330                 335

Asp Phe Met Arg Lys Lys Gly Phe Gly Glu Asp Phe Lys Gln Leu Glu
                340                 345                 350

Ser Phe Tyr Ile Gln Thr Leu Leu Asp Ile Val Ser Ser Tyr Gly Lys
                355                 360                 365

Gly Tyr Val Val Trp Gln Glu Val Phe Asp Asn Lys Val Lys Ile Gln
370                 375                 380

Pro Asp Thr Ile Ile Gln Val Trp Arg Glu Asp Ile Pro Val Asn Tyr
385                 390                 395                 400

Met Lys Glu Leu Glu Leu Val Thr Lys Ala Gly Phe Arg Ala Leu Leu
                405                 410                 415

Ser Ala Pro Trp Tyr Leu Asn Arg Ile Ser Tyr Gly Pro Asp Trp Lys
                420                 425                 430

Asp Phe Tyr Ile Val Glu Pro Leu Ala Phe Glu Gly Thr Pro Glu Gln
                435                 440                 445

Lys Ala Leu Val Ile Gly Gly Glu Ala Cys Met Trp Gly Glu Tyr Val
450                 455                 460

Asp Asn Thr Asn Leu Val Pro Arg Leu Trp Pro Arg Ala Gly Ala Val
465                 470                 475                 480

Ala Glu Arg Leu Trp Ser Asn Lys Leu Thr Ser Asp Leu Thr Phe Ala
                485                 490                 495

Tyr Glu Arg Leu Ser His Phe Arg Cys Glu Leu Leu Arg Arg Gly Val
                500                 505                 510

Gln Ala Gln Pro Leu Asn Val Gly Phe Cys Glu Gln Glu Phe Glu Gln
                515                 520                 525

Thr

<210> SEQ ID NO 9
<211> LENGTH: 550
<212> TYPE: PRT
<213> ORGANISM: Homo sapiens

<400> SEQUENCE: 9

Met Pro Pro Arg Thr Gly Arg Gly Leu Leu Trp Leu Gly Leu Val
1               5                   10                  15

Leu Ser Ser Val Cys Val Ala Leu Gly Ser Glu Thr Gln Ala Asn Ser
                20                  25                  30

Thr Thr Asp Ala Leu Asn Val Leu Leu Ile Ile Val Asp Asp Leu Arg
                35                  40                  45

Pro Ser Leu Gly Cys Tyr Gly Asp Lys Leu Val Arg Ser Pro Asn Ile
                50                  55                  60
```

```
Asp Gln Leu Ala Ser His Ser Leu Leu Phe Gln Asn Ala Phe Ala Gln
 65                  70                  75                  80

Gln Ala Val Cys Ala Pro Ser Arg Val Ser Phe Leu Thr Gly Arg Arg
                 85                  90                  95

Pro Asp Thr Thr Arg Leu Tyr Asp Phe Asn Ser Tyr Trp Arg Val His
            100                 105                 110

Ala Gly Asn Phe Ser Thr Ile Pro Gln Tyr Phe Lys Glu Asn Gly Tyr
        115                 120                 125

Val Thr Met Ser Val Gly Lys Val Phe His Pro Gly Ile Ser Ser Asn
    130                 135                 140

His Thr Asp Asp Ser Pro Tyr Ser Trp Ser Phe Pro Tyr His Pro
145                 150                 155                 160

Ser Ser Glu Lys Tyr Glu Asn Thr Lys Thr Cys Arg Gly Pro Asp Gly
                165                 170                 175

Glu Leu His Ala Asn Leu Leu Cys Pro Val Asp Val Leu Asp Val Pro
            180                 185                 190

Glu Gly Thr Leu Pro Asp Lys Gln Ser Thr Glu Gln Ala Ile Gln Leu
        195                 200                 205

Leu Glu Lys Met Lys Thr Ser Ala Ser Pro Phe Phe Leu Ala Val Gly
    210                 215                 220

Tyr His Lys Pro His Ile Pro Phe Arg Tyr Pro Lys Glu Phe Gln Lys
225                 230                 235                 240

Leu Tyr Pro Leu Glu Asn Ile Thr Leu Ala Pro Asp Pro Glu Val Pro
                245                 250                 255

Asp Gly Leu Pro Pro Val Ala Tyr Asn Pro Trp Met Asp Ile Arg Gln
            260                 265                 270

Arg Glu Asp Val Gln Ala Leu Asn Ile Ser Val Pro Tyr Gly Pro Ile
        275                 280                 285

Pro Val Asp Phe Gln Arg Lys Ile Arg Gln Ser Tyr Phe Ala Ser Val
    290                 295                 300

Ser Tyr Leu Asp Thr Gln Val Gly Arg Leu Leu Ser Ala Leu Asp Asp
305                 310                 315                 320

Leu Gln Leu Ala Asn Ser Thr Ile Ile Ala Phe Thr Ser Asp His Gly
                325                 330                 335

Trp Ala Leu Gly Glu His Gly Glu Trp Ala Lys Tyr Ser Asn Phe Asp
            340                 345                 350

Val Ala Thr His Val Pro Leu Ile Phe Tyr Val Pro Gly Arg Thr Ala
        355                 360                 365

Ser Leu Pro Glu Ala Gly Glu Lys Leu Phe Pro Tyr Leu Asp Pro Phe
    370                 375                 380

Asp Ser Ala Ser Gln Leu Met Glu Pro Gly Arg Gln Ser Met Asp Leu
385                 390                 395                 400

Val Glu Leu Val Ser Leu Phe Pro Thr Leu Ala Gly Leu Ala Gly Leu
                405                 410                 415

Gln Val Pro Pro Arg Cys Pro Val Pro Ser Phe His Val Glu Leu Cys
            420                 425                 430

Arg Glu Gly Lys Asn Leu Leu Lys His Phe Arg Phe Arg Asp Leu Glu
        435                 440                 445

Glu Asp Pro Tyr Leu Pro Gly Asn Pro Arg Glu Leu Ile Ala Tyr Ser
    450                 455                 460

Gln Tyr Pro Arg Pro Ser Asp Ile Pro Gln Trp Asn Ser Asp Lys Pro
465                 470                 475                 480
```

-continued

Ser Leu Lys Asp Ile Lys Ile Met Gly Tyr Ser Ile Arg Thr Ile Asp
            485                 490                 495

Tyr Arg Tyr Thr Val Trp Val Gly Phe Asn Pro Asp Glu Phe Leu Ala
            500                 505                 510

Asn Phe Ser Asp Ile His Ala Gly Glu Leu Tyr Phe Val Asp Ser Asp
            515                 520                 525

Pro Leu Gln Asp His Asn Met Tyr Asn Asp Ser Gln Gly Gly Asp Leu
            530                 535                 540

Phe Gln Leu Leu Met Pro
545                 550

<210> SEQ ID NO 10
<211> LENGTH: 629
<212> TYPE: PRT
<213> ORGANISM: Homo sapiens

<400> SEQUENCE: 10

Met Pro Arg Tyr Gly Ala Ser Leu Arg Gln Ser Cys Pro Arg Ser Gly
1               5                   10                  15

Arg Glu Gln Gly Gln Asp Gly Thr Ala Gly Ala Pro Gly Leu Leu Trp
            20                  25                  30

Met Gly Leu Val Leu Ala Leu Ala Leu Ala Leu Ala Leu Ala Leu Ser
            35                  40                  45

Asp Ser Arg Val Leu Trp Ala Pro Ala Glu Ala His Pro Leu Ser Pro
        50                  55                  60

Gln Gly His Pro Ala Arg Leu His Arg Ile Val Pro Arg Leu Arg Asp
65                  70                  75                  80

Val Phe Gly Trp Gly Asn Leu Thr Cys Pro Ile Cys Lys Gly Leu Phe
                85                  90                  95

Thr Ala Ile Asn Leu Gly Leu Lys Lys Glu Pro Asn Val Ala Arg Val
            100                 105                 110

Gly Ser Val Ala Ile Lys Leu Cys Asn Leu Leu Lys Ile Ala Pro Pro
            115                 120                 125

Ala Val Cys Gln Ser Ile Val His Leu Phe Glu Asp Asp Met Val Glu
        130                 135                 140

Val Trp Arg Arg Ser Val Leu Ser Pro Ser Glu Ala Cys Gly Leu Leu
145                 150                 155                 160

Leu Gly Ser Thr Cys Gly His Trp Asp Ile Phe Ser Ser Trp Asn Ile
                165                 170                 175

Ser Leu Pro Thr Val Pro Lys Pro Pro Lys Pro Ser Pro Pro
            180                 185                 190

Ala Pro Gly Ala Pro Val Ser Arg Ile Leu Phe Leu Thr Asp Leu His
            195                 200                 205

Trp Asp His Asp Tyr Leu Glu Gly Thr Asp Pro Asp Cys Ala Asp Pro
210                 215                 220

Leu Cys Cys Arg Arg Gly Ser Gly Leu Pro Pro Ala Ser Arg Pro Gly
225                 230                 235                 240

Ala Gly Tyr Trp Gly Glu Tyr Ser Lys Cys Asp Leu Pro Leu Arg Thr
                245                 250                 255

Leu Glu Ser Leu Leu Ser Gly Leu Gly Pro Ala Gly Pro Phe Asp Met
            260                 265                 270

Val Tyr Trp Thr Gly Asp Ile Pro Ala His Asp Val Trp His Gln Thr
        275                 280                 285

Arg Gln Asp Gln Leu Arg Ala Leu Thr Thr Val Thr Ala Leu Val Arg
    290                 295                 300

```
Lys Phe Leu Gly Pro Val Pro Val Tyr Pro Ala Val Gly Asn His Glu
305                 310                 315                 320

Ser Thr Pro Val Asn Ser Phe Pro Pro Phe Ile Glu Gly Asn His
            325                 330                 335

Ser Ser Arg Trp Leu Tyr Glu Ala Met Ala Lys Ala Trp Glu Pro Trp
            340                 345                 350

Leu Pro Ala Glu Ala Leu Arg Thr Leu Arg Ile Gly Gly Phe Tyr Ala
            355                 360                 365

Leu Ser Pro Tyr Pro Gly Leu Arg Leu Ile Ser Leu Asn Met Asn Phe
    370                 375                 380

Cys Ser Arg Glu Asn Phe Trp Leu Leu Ile Asn Ser Thr Asp Pro Ala
385                 390                 395                 400

Gly Gln Leu Gln Trp Leu Val Gly Glu Leu Gln Ala Ala Glu Asp Arg
            405                 410                 415

Gly Asp Lys Val His Ile Ile Gly His Ile Pro Pro Gly His Cys Leu
            420                 425                 430

Lys Ser Trp Ser Trp Asn Tyr Tyr Arg Ile Val Ala Arg Tyr Glu Asn
            435                 440                 445

Thr Leu Ala Ala Gln Phe Phe Gly His Thr His Val Asp Glu Phe Glu
    450                 455                 460

Val Phe Tyr Asp Glu Glu Thr Leu Ser Arg Pro Leu Ala Val Ala Phe
465                 470                 475                 480

Leu Ala Pro Ser Ala Thr Thr Tyr Ile Gly Leu Asn Pro Gly Tyr Arg
            485                 490                 495

Val Tyr Gln Ile Asp Gly Asn Tyr Ser Gly Ser Ser His Val Val Leu
            500                 505                 510

Asp His Glu Thr Tyr Ile Leu Asn Leu Thr Gln Ala Asn Ile Pro Gly
            515                 520                 525

Ala Ile Pro His Trp Gln Leu Leu Tyr Arg Ala Arg Glu Thr Tyr Gly
            530                 535                 540

Leu Pro Asn Thr Leu Pro Thr Ala Trp His Asn Leu Val Tyr Arg Met
545                 550                 555                 560

Arg Gly Asp Met Gln Leu Phe Gln Thr Phe Trp Phe Leu Tyr His Lys
            565                 570                 575

Gly His Pro Pro Ser Glu Pro Cys Gly Thr Pro Cys Arg Leu Ala Thr
            580                 585                 590

Leu Cys Ala Gln Leu Ser Ala Arg Ala Asp Ser Pro Ala Leu Cys Arg
            595                 600                 605

His Leu Met Pro Asp Gly Ser Leu Pro Glu Ala Gln Ser Leu Trp Pro
            610                 615                 620

Arg Pro Leu Phe Cys
625

<210> SEQ ID NO 11
<211> LENGTH: 685
<212> TYPE: PRT
<213> ORGANISM: Homo sapiens

<400> SEQUENCE: 11

Met Ala Glu Trp Leu Leu Ser Ala Ser Trp Gln Arg Arg Ala Lys Ala
1               5                   10                  15

Met Thr Ala Ala Ala Gly Ser Ala Gly Arg Ala Ala Val Pro Leu Leu
            20                  25                  30

Leu Cys Ala Leu Leu Ala Pro Gly Gly Ala Tyr Val Leu Asp Asp Ser
```

```
              35                  40                  45
Asp Gly Leu Gly Arg Glu Phe Asp Gly Ile Gly Ala Val Ser Gly Gly
 50                  55                  60

Gly Ala Thr Ser Arg Leu Leu Val Asn Tyr Pro Glu Pro Tyr Arg Ser
 65                  70                  75                  80

Gln Ile Leu Asp Tyr Leu Phe Lys Pro Asn Phe Gly Ala Ser Leu His
                 85                  90                  95

Ile Leu Lys Val Glu Ile Gly Gly Asp Gly Gln Thr Thr Asp Gly Thr
                100                 105                 110

Glu Pro Ser His Met His Tyr Ala Leu Asp Glu Asn Tyr Phe Arg Gly
                115                 120                 125

Tyr Glu Trp Trp Leu Met Lys Glu Ala Lys Lys Arg Asn Pro Asn Ile
            130                 135                 140

Thr Leu Ile Gly Leu Pro Trp Ser Phe Pro Gly Trp Leu Gly Lys Gly
145                 150                 155                 160

Phe Asp Trp Pro Tyr Val Asn Leu Gln Leu Thr Ala Tyr Tyr Val Val
                165                 170                 175

Thr Trp Ile Val Gly Ala Lys Arg Tyr His Asp Leu Asp Ile Asp Tyr
            180                 185                 190

Ile Gly Ile Trp Asn Glu Arg Ser Tyr Asn Ala Asn Tyr Ile Lys Ile
        195                 200                 205

Leu Arg Lys Met Leu Asn Tyr Gln Gly Leu Gln Arg Val Lys Ile Ile
210                 215                 220

Ala Ser Asp Asn Leu Trp Glu Ser Ile Ser Ala Ser Met Leu Leu Asp
225                 230                 235                 240

Ala Glu Leu Phe Lys Val Val Asp Val Ile Gly Ala His Tyr Pro Gly
                245                 250                 255

Thr His Ser Ala Lys Asp Ala Lys Leu Thr Gly Lys Lys Leu Trp Ser
            260                 265                 270

Ser Glu Asp Phe Ser Thr Leu Asn Ser Asp Met Gly Ala Gly Cys Trp
        275                 280                 285

Gly Arg Ile Leu Asn Gln Asn Tyr Ile Asn Gly Tyr Met Thr Ser Thr
290                 295                 300

Ile Ala Trp Asn Leu Val Ala Ser Tyr Tyr Glu Gln Leu Pro Tyr Gly
305                 310                 315                 320

Arg Cys Gly Leu Met Thr Ala Gln Glu Pro Trp Ser Gly His Tyr Val
                325                 330                 335

Val Glu Ser Pro Val Trp Val Ser Ala His Thr Thr Gln Phe Thr Gln
            340                 345                 350

Pro Gly Trp Tyr Tyr Leu Lys Thr Val Gly His Leu Glu Lys Gly Gly
        355                 360                 365

Ser Tyr Val Ala Leu Thr Asp Gly Leu Gly Asn Leu Thr Ile Ile Ile
    370                 375                 380

Glu Thr Met Ser His Lys His Ser Lys Cys Ile Arg Pro Phe Leu Pro
385                 390                 395                 400

Tyr Phe Asn Val Ser Gln Gln Phe Ala Thr Phe Val Leu Lys Gly Ser
                405                 410                 415

Phe Ser Glu Ile Pro Glu Leu Gln Val Trp Tyr Thr Lys Leu Gly Lys
            420                 425                 430

Thr Ser Glu Arg Phe Leu Phe Lys Gln Leu Asp Ser Leu Trp Leu Leu
        435                 440                 445

Asp Ser Asp Gly Ser Phe Thr Leu Ser Leu His Glu Asp Glu Leu Phe
450                 455                 460
```

Thr Leu Thr Thr Leu Thr Thr Gly Arg Lys Gly Ser Tyr Pro Leu Pro
465                 470                 475                 480

Pro Lys Ser Gln Pro Phe Pro Ser Thr Tyr Lys Asp Asp Phe Asn Val
            485                 490                 495

Asp Tyr Pro Phe Phe Ser Glu Ala Pro Asn Phe Ala Asp Gln Thr Gly
            500                 505                 510

Val Phe Glu Tyr Phe Thr Asn Ile Glu Asp Pro Gly Glu His His Phe
            515                 520                 525

Thr Leu Arg Gln Val Leu Asn Gln Arg Pro Ile Thr Trp Ala Ala Asp
            530                 535                 540

Ala Ser Asn Thr Ile Ser Ile Ile Gly Asp Tyr Asn Trp Thr Asn Leu
545                 550                 555                 560

Thr Ile Lys Cys Asp Val Tyr Ile Glu Thr Pro Asp Thr Gly Gly Val
            565                 570                 575

Phe Ile Ala Gly Arg Val Asn Lys Gly Gly Ile Leu Ile Arg Ser Ala
            580                 585                 590

Arg Gly Ile Phe Phe Trp Ile Phe Ala Asn Gly Ser Tyr Arg Val Thr
            595                 600                 605

Gly Asp Leu Ala Gly Trp Ile Ile Tyr Ala Leu Gly Arg Val Glu Val
610                 615                 620

Thr Ala Lys Lys Trp Tyr Thr Leu Thr Leu Thr Ile Lys Gly His Phe
625                 630                 635                 640

Ala Ser Gly Met Leu Asn Asp Lys Ser Leu Trp Thr Asp Ile Pro Val
            645                 650                 655

Asn Phe Pro Lys Asn Gly Trp Ala Ala Ile Gly Thr His Ser Phe Glu
            660                 665                 670

Phe Ala Gln Phe Asp Asn Phe Leu Val Glu Ala Thr Arg
            675                 680                 685

<210> SEQ ID NO 12
<211> LENGTH: 395
<212> TYPE: PRT
<213> ORGANISM: Homo sapiens

<400> SEQUENCE: 12

Met Pro Gly Arg Ser Cys Val Ala Leu Val Leu Leu Ala Ala Ala Val
1               5                   10                  15

Ser Cys Ala Val Ala Gln His Ala Pro Pro Trp Thr Glu Asp Cys Arg
            20                  25                  30

Lys Ser Thr Tyr Pro Pro Ser Gly Pro Thr Tyr Arg Gly Ala Val Pro
        35                  40                  45

Trp Tyr Thr Ile Asn Leu Asp Leu Pro Pro Tyr Lys Arg Trp His Glu
    50                  55                  60

Leu Met Leu Asp Lys Ala Pro Val Leu Lys Val Ile Val Asn Ser Leu
65                  70                  75                  80

Lys Asn Met Ile Asn Thr Phe Val Pro Ser Gly Lys Ile Met Gln Val
                85                  90                  95

Val Asp Glu Lys Leu Pro Gly Leu Leu Gly Asn Phe Pro Gly Pro Phe
            100                 105                 110

Glu Glu Glu Met Lys Gly Ile Ala Ala Val Thr Asp Ile Pro Leu Gly
            115                 120                 125

Glu Ile Ile Ser Phe Asn Ile Phe Tyr Glu Leu Phe Thr Ile Cys Thr
            130                 135                 140

Ser Ile Val Ala Glu Asp Lys Lys Gly His Leu Ile His Gly Arg Asn

```
                145                 150                 155                 160
Met Asp Phe Gly Val Phe Leu Gly Trp Asn Ile Asn Asn Asp Thr Trp
                    165                 170                 175

Val Ile Thr Glu Gln Leu Lys Pro Leu Thr Val Asn Leu Asp Phe Gln
                    180                 185                 190

Arg Asn Asn Lys Thr Val Phe Lys Ala Ser Ser Phe Ala Gly Tyr Val
                    195                 200                 205

Gly Met Leu Thr Gly Phe Lys Pro Gly Leu Phe Ser Leu Thr Leu Asn
                    210                 215                 220

Glu Arg Phe Ser Ile Asn Gly Gly Tyr Leu Gly Ile Leu Glu Trp Ile
225                 230                 235                 240

Leu Gly Lys Lys Asp Val Met Trp Ile Gly Phe Leu Thr Arg Thr Val
                    245                 250                 255

Leu Glu Asn Ser Thr Ser Tyr Glu Glu Ala Lys Asn Leu Leu Thr Lys
                    260                 265                 270

Thr Lys Ile Leu Ala Pro Ala Tyr Phe Ile Leu Gly Gly Asn Gln Ser
                    275                 280                 285

Gly Glu Gly Cys Val Ile Thr Arg Asp Arg Lys Glu Ser Leu Asp Val
                    290                 295                 300

Tyr Glu Leu Asp Ala Lys Gln Gly Arg Trp Tyr Val Val Gln Thr Asn
305                 310                 315                 320

Tyr Asp Arg Trp Lys His Pro Phe Phe Leu Asp Arg Arg Thr Pro
                    325                 330                 335

Ala Lys Met Cys Leu Asn Arg Thr Ser Gln Glu Asn Ile Ser Phe Glu
                    340                 345                 350

Thr Met Tyr Asp Val Leu Ser Thr Lys Pro Val Leu Asn Lys Leu Thr
                    355                 360                 365

Val Tyr Thr Thr Leu Ile Asp Val Thr Lys Gly Gln Phe Glu Thr Tyr
                    370                 375                 380

Leu Arg Asp Cys Pro Asp Pro Cys Ile Gly Trp
385                 390                 395

<210> SEQ ID NO 13
<211> LENGTH: 205
<212> TYPE: PRT
<213> ORGANISM: Homo sapiens

<400> SEQUENCE: 13

Met Ser Ser Met Asn Pro Glu Tyr Asp Tyr Leu Phe Lys Leu Leu Leu
1                   5                   10                  15

Ile Gly Asp Ser Gly Val Gly Lys Ser Cys Leu Leu Leu Arg Phe Ala
                    20                  25                  30

Asp Asp Thr Tyr Thr Glu Ser Tyr Ile Ser Thr Ile Gly Val Asp Phe
                    35                  40                  45

Lys Ile Arg Thr Ile Glu Leu Asp Gly Lys Thr Ile Lys Leu Gln Ile
                    50                  55                  60

Trp Asp Thr Ala Gly Gln Glu Arg Phe Arg Thr Ile Thr Ser Ser Tyr
65                  70                  75                  80

Tyr Arg Gly Ala His Gly Ile Ile Val Val Tyr Asp Val Thr Asp Gln
                    85                  90                  95

Glu Ser Phe Asn Asn Val Lys Gln Trp Leu Gln Glu Ile Asp Arg Tyr
                    100                 105                 110

Ala Ser Glu Asn Val Asn Lys Leu Leu Val Gly Asn Lys Cys Asp Leu
                    115                 120                 125
```

```
Thr Thr Lys Lys Val Val Asp Tyr Thr Thr Ala Lys Glu Phe Ala Asp
    130                 135                 140

Ser Leu Gly Ile Pro Phe Leu Glu Thr Ser Ala Lys Asn Ala Thr Asn
145                 150                 155                 160

Val Glu Gln Ser Phe Met Thr Met Ala Ala Glu Ile Lys Lys Arg Met
                165                 170                 175

Gly Pro Gly Ala Thr Gly Gly Ala Glu Lys Ser Asn Val Lys Ile
                180                 185                 190

Gln Ser Thr Pro Val Lys Gln Ser Gly Gly Gly Cys Cys
                195                 200                 205
```

<210> SEQ ID NO 14
<211> LENGTH: 618
<212> TYPE: DNA
<213> ORGANISM: Homo sapiens

<400> SEQUENCE: 14

```
atgtccagca tgaatcccga atatgattat ttattcaagt tacttctgat tggcgactca    60
ggggttggaa agtcttgcct tcttcttagg tttgcagatg atacatatac agaaagctac   120
atcagcacaa ttggtgtgga tttcaaaata agaactatag agttagacgg gaaaacaatc   180
aagcttcaaa tatgggacac agcaggccag gaaagatttc gaacaatcac ctccagttat   240
tacagaggag cccatggcat catagttgtg tatgatgtga cagatcagga gtccttcaat   300
aatgttaaac agtggctgca ggaaatagat cgttatgcca gtgaaaatgt caacaaattg   360
ttggtaggga caaatgtga tctgaccaca aagaaagtag tagactacac aacagcgaag   420
gaatttgctg attcccttgg aattccgttt ttggaaacca gtgctaagaa tgcaacgaat   480
gtagaacagt ctttcatgac gatggcagct gagattaaaa agcgaatggg tcccggagca   540
acagctggtg gtgctgagaa gtccaatgtt aaaattcaga gcactccagt caagcagtca   600
ggtggaggtt gctgctaa                                                 618
```

<210> SEQ ID NO 15
<211> LENGTH: 208
<212> TYPE: PRT
<213> ORGANISM: Homo sapiens

<400> SEQUENCE: 15

```
Met Ser Thr Gly Gly Asp Phe Gly Asn Pro Leu Arg Lys Phe Lys Leu
1               5                   10                  15

Val Phe Leu Gly Glu Gln Ser Val Gly Lys Thr Ser Leu Ile Thr Arg
                20                  25                  30

Phe Met Tyr Asp Ser Phe Asp Asn Thr Tyr Gln Ala Thr Ile Gly Ile
            35                  40                  45

Asp Phe Leu Ser Lys Thr Met Tyr Leu Glu Asp Arg Thr Val Arg Leu
    50                  55                  60

Gln Leu Trp Asp Thr Ala Gly Gln Glu Arg Phe Arg Ser Leu Ile Pro
65                  70                  75                  80

Ser Tyr Ile Arg Asp Ser Thr Val Ala Val Val Tyr Asp Ile Thr
                85                  90                  95

Asn Val Asn Ser Phe Gln Gln Thr Thr Lys Trp Ile Asp Val Arg
                100                 105                 110

Thr Glu Arg Gly Ser Asp Val Ile Ile Met Leu Val Gly Asn Lys Thr
                115                 120                 125

Asp Leu Ala Asp Lys Arg Gln Val Ser Ile Glu Glu Gly Glu Arg Lys
                130                 135                 140
```

```
Ala Lys Glu Leu Asn Val Met Phe Ile Glu Thr Ser Ala Lys Ala Gly
145                 150                 155                 160

Tyr Asn Val Lys Gln Leu Phe Arg Arg Val Ala Ala Leu Pro Gly
                165                 170                 175

Met Glu Ser Thr Gln Asp Arg Ser Arg Glu Asp Met Ile Asp Ile Lys
            180                 185                 190

Leu Glu Lys Pro Gln Glu Gln Pro Val Ser Glu Gly Gly Cys Ser Cys
        195                 200                 205

<210> SEQ ID NO 16
<211> LENGTH: 216
<212> TYPE: PRT
<213> ORGANISM: Homo sapiens

<400> SEQUENCE: 16

Met Gly Thr Arg Asp Asp Glu Tyr Asp Tyr Leu Phe Lys Val Val Leu
1               5                   10                  15

Ile Gly Asp Ser Gly Val Gly Lys Ser Asn Leu Leu Ser Arg Phe Thr
            20                  25                  30

Arg Asn Glu Phe Asn Leu Glu Ser Lys Ser Thr Ile Gly Val Glu Phe
        35                  40                  45

Ala Thr Arg Ser Ile Gln Val Asp Gly Lys Thr Ile Lys Ala Gln Ile
    50                  55                  60

Trp Asp Thr Ala Gly Gln Glu Arg Tyr Arg Ala Ile Thr Ser Ala Tyr
65                  70                  75                  80

Tyr Arg Gly Ala Val Gly Ala Leu Leu Val Tyr Asp Ile Ala Lys His
                85                  90                  95

Leu Thr Tyr Glu Asn Val Glu Arg Trp Leu Lys Glu Leu Arg Asp His
            100                 105                 110

Ala Asp Ser Asn Ile Val Ile Met Leu Val Gly Asn Lys Ser Asp Leu
        115                 120                 125

Arg His Leu Arg Ala Val Pro Thr Asp Glu Ala Arg Ala Phe Ala Glu
    130                 135                 140

Lys Asn Gly Leu Ser Phe Ile Glu Thr Ser Ala Leu Asp Ser Thr Asn
145                 150                 155                 160

Val Glu Ala Ala Phe Gln Thr Ile Leu Thr Glu Ile Tyr Arg Ile Val
                165                 170                 175

Ser Gln Lys Gln Met Ser Asp Arg Arg Glu Asn Asp Met Ser Pro Ser
            180                 185                 190

Asn Asn Val Val Pro Ile His Val Pro Pro Thr Thr Glu Asn Lys Pro
        195                 200                 205

Lys Val Gln Cys Cys Gln Asn Ile
    210                 215

<210> SEQ ID NO 17
<211> LENGTH: 524
<212> TYPE: PRT
<213> ORGANISM: Homo sapiens

<400> SEQUENCE: 17

Met Tyr Ala Leu Phe Leu Leu Ala Ser Leu Leu Gly Ala Ala Leu Ala
1               5                   10                  15

Gly Pro Val Leu Gly Leu Lys Glu Cys Thr Arg Gly Ser Ala Val Trp
            20                  25                  30

Cys Gln Asn Val Lys Thr Ala Ser Asp Cys Gly Ala Val Lys His Cys
        35                  40                  45
```

```
Leu Gln Thr Val Trp Asn Lys Pro Thr Val Lys Ser Leu Pro Cys Asp
 50                  55                  60
Ile Cys Lys Asp Val Val Thr Ala Ala Gly Asp Met Leu Lys Asp Asn
 65                  70                  75                  80
Ala Thr Glu Glu Glu Ile Leu Val Tyr Leu Glu Lys Thr Cys Asp Trp
                 85                  90                  95
Leu Pro Lys Pro Asn Met Ser Ala Ser Cys Lys Glu Ile Val Asp Ser
                100                 105                 110
Tyr Leu Pro Val Ile Leu Asp Ile Ile Lys Gly Glu Met Ser Arg Pro
                115                 120                 125
Gly Glu Val Cys Ser Ala Leu Asn Leu Cys Glu Ser Leu Gln Lys His
                130                 135                 140
Leu Ala Glu Leu Asn His Gln Lys Gln Leu Glu Ser Asn Lys Ile Pro
145                 150                 155                 160
Glu Leu Asp Met Thr Glu Val Val Ala Pro Phe Met Ala Asn Ile Pro
                165                 170                 175
Leu Leu Leu Tyr Pro Gln Asp Gly Pro Arg Ser Lys Pro Gln Pro Lys
                180                 185                 190
Asp Asn Gly Asp Val Cys Gln Asp Cys Ile Gln Met Val Thr Asp Ile
                195                 200                 205
Gln Thr Ala Val Arg Thr Asn Ser Thr Phe Val Gln Ala Leu Val Glu
210                 215                 220
His Val Lys Glu Glu Cys Asp Arg Leu Gly Pro Gly Met Ala Asp Ile
225                 230                 235                 240
Cys Lys Asn Tyr Ile Ser Gln Tyr Ser Glu Ile Ala Ile Gln Met Met
                245                 250                 255
Met His Met Gln Pro Lys Glu Ile Cys Ala Leu Val Gly Phe Cys Asp
                260                 265                 270
Glu Val Lys Glu Met Pro Met Gln Thr Leu Val Pro Ala Lys Val Ala
                275                 280                 285
Ser Lys Asn Val Ile Pro Ala Leu Glu Leu Val Glu Pro Ile Lys Lys
                290                 295                 300
His Glu Val Pro Ala Lys Ser Asp Val Tyr Cys Glu Val Cys Glu Phe
305                 310                 315                 320
Leu Val Lys Glu Val Thr Lys Leu Ile Asp Asn Asn Lys Thr Glu Lys
                325                 330                 335
Glu Ile Leu Asp Ala Phe Asp Lys Met Cys Ser Lys Leu Pro Lys Ser
                340                 345                 350
Leu Ser Glu Glu Cys Gln Glu Val Val Asp Thr Tyr Gly Ser Ser Ile
                355                 360                 365
Leu Ser Ile Leu Leu Glu Glu Val Ser Pro Glu Leu Val Cys Ser Met
                370                 375                 380
Leu His Leu Cys Ser Gly Thr Arg Leu Pro Ala Leu Thr Val His Val
385                 390                 395                 400
Thr Gln Pro Lys Asp Gly Gly Phe Cys Glu Val Cys Lys Lys Leu Val
                405                 410                 415
Gly Tyr Leu Asp Arg Asn Leu Glu Lys Asn Ser Thr Lys Gln Glu Ile
                420                 425                 430
Leu Ala Ala Leu Glu Lys Gly Cys Ser Phe Leu Pro Asp Pro Tyr Gln
                435                 440                 445
Lys Gln Cys Asp Gln Phe Val Ala Glu Tyr Glu Pro Val Leu Ile Glu
450                 455                 460
```

Ile Leu Val Glu Val Met Asp Pro Ser Phe Val Cys Leu Lys Ile Gly
465                 470                 475                 480

Ala Cys Pro Ser Ala His Lys Pro Leu Leu Gly Thr Glu Lys Cys Ile
            485                 490                 495

Trp Gly Pro Ser Tyr Trp Cys Gln Asn Thr Glu Thr Ala Ala Gln Cys
        500                 505                 510

Asn Ala Val Glu His Cys Lys Arg His Val Trp Asn
        515                 520

<210> SEQ ID NO 18
<211> LENGTH: 81
<212> TYPE: PRT
<213> ORGANISM: Homo sapiens

<400> SEQUENCE: 18

Ser Asp Val Tyr Cys Glu Val Cys Glu Phe Leu Val Lys Glu Val Thr
1               5                   10                  15

Lys Leu Ile Asp Asn Asn Lys Thr Glu Lys Glu Ile Leu Asp Ala Phe
            20                  25                  30

Asp Lys Met Cys Ser Lys Leu Pro Lys Ser Leu Ser Glu Glu Cys Gln
        35                  40                  45

Glu Val Val Asp Thr Tyr Gly Ser Ser Ile Leu Ser Ile Leu Leu Glu
    50                  55                  60

Glu Val Ser Pro Glu Leu Val Cys Ser Met Leu His Leu Cys Ser Gly
65                  70                  75                  80

Thr

<210> SEQ ID NO 19
<211> LENGTH: 332
<212> TYPE: PRT
<213> ORGANISM: Homo sapiens

<400> SEQUENCE: 19

Met Leu Leu Leu Ala Ala Ala Phe Leu Val Ala Phe Val Leu Leu Leu
1               5                   10                  15

Tyr Met Val Ser Pro Leu Ile Ser Pro Lys Pro Leu Ala Leu Pro Gly
            20                  25                  30

Ala His Val Val Thr Gly Gly Ser Ser Gly Ile Gly Lys Cys Ile
        35                  40                  45

Ala Ile Glu Cys Tyr Lys Gln Gly Ala Phe Ile Thr Leu Val Ala Arg
    50                  55                  60

Asn Glu Asp Lys Leu Leu Gln Ala Lys Lys Glu Ile Glu Met His Ser
65                  70                  75                  80

Ile Asn Asp Lys Gln Val Val Leu Cys Ile Ser Val Asp Val Ser Gln
            85                  90                  95

Asp Tyr Asn Gln Val Glu Asn Val Ile Lys Gln Ala Gln Glu Lys Leu
        100                 105                 110

Gly Pro Val Asp Met Leu Val Asn Cys Ala Gly Met Ala Val Ser Gly
    115                 120                 125

Lys Phe Glu Asp Leu Glu Val Ser Thr Phe Glu Arg Leu Met Ser Ile
130                 135                 140

Asn Tyr Leu Gly Ser Val Tyr Pro Ser Arg Ala Val Ile Thr Thr Met
145                 150                 155                 160

Lys Glu Arg Arg Val Gly Arg Ile Val Phe Val Ser Ser Gln Ala Gly
            165                 170                 175

Gln Leu Gly Leu Phe Gly Phe Thr Ala Tyr Ser Ala Ser Lys Phe Ala

```
                180             185             190
Ile Arg Gly Leu Ala Glu Ala Leu Gln Met Glu Val Lys Pro Tyr Asn
            195             200             205
Val Tyr Ile Thr Val Ala Tyr Pro Pro Asp Thr Asp Thr Pro Gly Phe
            210             215             220
Ala Glu Glu Asn Arg Thr Lys Pro Leu Glu Thr Arg Leu Ile Ser Glu
225             230             235             240
Thr Thr Ser Val Cys Lys Pro Glu Gln Val Ala Lys Gln Ile Val Lys
                245             250             255
Asp Ala Ile Gln Gly Asn Phe Asn Ser Ser Leu Gly Ser Asp Gly Tyr
            260             265             270
Met Leu Ser Ala Leu Thr Cys Gly Met Ala Pro Val Thr Ser Ile Thr
            275             280             285
Glu Gly Leu Gln Gln Val Val Thr Met Gly Leu Phe Arg Thr Ile Ala
            290             295             300
Leu Phe Tyr Leu Gly Ser Phe Asp Ser Ile Val Arg Arg Cys Met Met
305             310             315             320
Gln Arg Glu Lys Ser Glu Asn Ala Asp Lys Thr Ala
                325             330

<210> SEQ ID NO 20
<211> LENGTH: 365
<212> TYPE: PRT
<213> ORGANISM: Homo sapiens

<400> SEQUENCE: 20

Met Asp Ile Ile Glu Thr Ala Lys Leu Glu Glu His Leu Glu Asn Gln
1               5                   10                  15
Pro Ser Asp Pro Thr Asn Thr Tyr Ala Arg Pro Ala Glu Pro Val Glu
                20                  25                  30
Glu Glu Asn Lys Asn Gly Asn Gly Lys Pro Lys Ser Leu Ser Ser Gly
            35                  40                  45
Leu Arg Lys Gly Thr Lys Lys Tyr Pro Asp Tyr Ile Gln Ile Ala Met
    50                  55                  60
Pro Thr Glu Ser Arg Asn Lys Phe Pro Leu Glu Trp Trp Lys Thr Gly
65                  70                  75                  80
Ile Ala Phe Ile Tyr Ala Val Phe Asn Leu Val Leu Thr Thr Val Met
                85                  90                  95
Ile Thr Val Val His Glu Arg Val Pro Pro Lys Glu Leu Ser Pro Pro
                100             105             110
Leu Pro Asp Lys Phe Phe Asp Tyr Ile Asp Arg Val Lys Trp Ala Phe
            115             120             125
Ser Val Ser Glu Ile Asn Gly Ile Ile Leu Val Gly Leu Trp Ile Thr
130             135             140
Gln Trp Leu Phe Leu Arg Tyr Lys Ser Ile Val Gly Arg Arg Phe Cys
145             150             155             160
Phe Ile Ile Gly Thr Leu Tyr Leu Tyr Arg Cys Ile Thr Met Tyr Val
                165             170             175
Thr Thr Leu Pro Val Pro Gly Met His Phe Gln Cys Ala Pro Lys Leu
            180             185             190
Asn Gly Asp Ser Gln Ala Lys Val Gln Arg Ile Leu Arg Leu Ile Ser
            195             200             205
Gly Gly Gly Leu Ser Ile Thr Gly Ser His Ile Leu Cys Gly Asp Phe
        210             215             220
```

-continued

Leu Phe Ser Gly His Thr Val Thr Leu Thr Leu Thr Tyr Leu Phe Ile
225                 230                 235                 240

Lys Glu Tyr Ser Pro Arg His Phe Trp Trp Tyr His Leu Ile Cys Trp
            245                 250                 255

Leu Leu Ser Ala Ala Gly Ile Ile Cys Ile Leu Val Ala His Glu His
        260                 265                 270

Tyr Thr Ile Asp Val Ile Ile Ala Tyr Tyr Ile Thr Thr Arg Leu Phe
    275                 280                 285

Trp Trp Tyr His Ser Met Ala Asn Glu Lys Asn Leu Lys Val Ser Ser
290                 295                 300

Gln Thr Asn Phe Leu Ser Arg Ala Trp Trp Phe Pro Ile Phe Tyr Phe
305                 310                 315                 320

Phe Glu Lys Asn Val Gln Gly Ser Ile Pro Cys Cys Phe Ser Trp Pro
            325                 330                 335

Leu Ser Trp Pro Pro Gly Cys Phe Lys Ser Ser Cys Lys Lys Tyr Ser
        340                 345                 350

Arg Val Gln Lys Ile Gly Glu Asp Asn Glu Lys Ser Thr
    355                 360                 365

<210> SEQ ID NO 21
<211> LENGTH: 541
<212> TYPE: PRT
<213> ORGANISM: Homo sapiens

<400> SEQUENCE: 21

Met Lys Ser Tyr Thr Pro Tyr Phe Ile Leu Leu Trp Ser Ala Val Gly
1               5                   10                  15

Ile Ala Lys Ala Ala Lys Ile Ile Val Pro Pro Ile Met Phe Glu
                20                  25                  30

Ser His Met Tyr Ile Phe Lys Thr Leu Ala Ser Ala Leu His Glu Arg
            35                  40                  45

Gly His His Thr Val Phe Leu Leu Ser Glu Gly Arg Asp Ile Ala Pro
        50                  55                  60

Ser Asn His Tyr Ser Leu Gln Arg Tyr Pro Gly Ile Phe Asn Ser Thr
65                  70                  75                  80

Thr Ser Asp Ala Phe Leu Gln Ser Lys Met Arg Asn Ile Phe Ser Gly
                85                  90                  95

Arg Leu Thr Ala Ile Glu Leu Phe Asp Ile Leu Asp His Tyr Thr Lys
            100                 105                 110

Asn Cys Asp Leu Met Val Gly Asn His Ala Leu Ile Gln Gly Leu Lys
        115                 120                 125

Lys Glu Lys Phe Asp Leu Leu Leu Val Asp Pro Asn Asp Met Cys Gly
130                 135                 140

Phe Val Ile Ala His Leu Leu Gly Val Lys Tyr Ala Val Phe Ser Thr
145                 150                 155                 160

Gly Leu Trp Tyr Pro Ala Glu Val Gly Ala Pro Ala Pro Leu Ala Tyr
                165                 170                 175

Val Pro Glu Phe Asn Ser Leu Leu Thr Asp Arg Met Asn Leu Leu Gln
            180                 185                 190

Arg Met Lys Asn Thr Gly Val Tyr Leu Ile Ser Arg Leu Gly Val Ser
        195                 200                 205

Phe Leu Val Leu Pro Lys Tyr Glu Arg Ile Met Gln Lys Tyr Asn Leu
    210                 215                 220

Leu Pro Glu Lys Ser Met Tyr Asp Leu Val His Gly Ser Ser Leu Trp
225                 230                 235                 240

```
Met Leu Cys Thr Asp Val Ala Leu Glu Phe Pro Arg Pro Thr Leu Pro
                245                 250                 255

Asn Val Val Tyr Val Gly Gly Ile Leu Thr Lys Pro Ala Ser Pro Leu
            260                 265                 270

Pro Glu Asp Leu Gln Arg Trp Val Asn Gly Ala Asn Glu His Gly Phe
        275                 280                 285

Val Leu Val Ser Phe Gly Ala Gly Val Lys Tyr Leu Ser Glu Asp Ile
    290                 295                 300

Ala Asn Lys Leu Ala Gly Ala Leu Gly Arg Leu Pro Gln Lys Val Ile
305                 310                 315                 320

Trp Arg Phe Ser Gly Pro Lys Pro Lys Asn Leu Gly Asn Asn Thr Lys
                325                 330                 335

Leu Ile Glu Trp Leu Pro Gln Asn Asp Leu Leu Gly His Ser Lys Ile
            340                 345                 350

Lys Ala Phe Leu Ser His Gly Gly Leu Asn Ser Ile Phe Glu Thr Ile
        355                 360                 365

Tyr His Gly Val Pro Val Val Gly Ile Pro Leu Phe Gly Asp His Tyr
    370                 375                 380

Asp Thr Met Thr Arg Val Gln Ala Lys Gly Met Gly Ile Leu Leu Glu
385                 390                 395                 400

Trp Lys Thr Val Thr Glu Lys Glu Leu Tyr Glu Ala Leu Val Lys Val
                405                 410                 415

Ile Asn Asn Pro Ser Tyr Arg Gln Arg Ala Gln Lys Leu Ser Glu Ile
            420                 425                 430

His Lys Asp Gln Pro Gly His Pro Val Asn Arg Thr Ile Tyr Trp Ile
        435                 440                 445

Asp Tyr Ile Ile Arg His Asn Gly Ala His His Leu Arg Ala Ala Val
    450                 455                 460

His Gln Ile Ser Phe Cys Gln Tyr Phe Leu Leu Asp Ile Ala Phe Val
465                 470                 475                 480

Leu Leu Leu Gly Ala Ala Leu Leu Tyr Phe Leu Leu Ser Trp Val Thr
                485                 490                 495

Lys Phe Ile Tyr Arg Lys Ile Lys Ser Leu Trp Ser Arg Asn Lys His
            500                 505                 510

Ser Thr Val Asn Gly His Tyr His Asn Gly Ile Leu Asn Gly Lys Tyr
        515                 520                 525

Lys Arg Asn Gly His Ile Lys His Glu Lys Lys Val Lys
530                 535                 540

<210> SEQ ID NO 22
<211> LENGTH: 140
<212> TYPE: PRT
<213> ORGANISM: Homo sapiens

<400> SEQUENCE: 22

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
```

```
                65                  70                  75                  80
Thr Val Glu Gly Ala Gly Ser Ile Ala Ala Thr Gly Phe Val Lys
                    85                  90                  95
Lys Asp Gln Leu Gly Lys Asn Glu Glu Gly Ala Pro Gln Glu Gly Ile
                100                 105                 110
Leu Glu Asp Met Pro Val Asp Pro Asp Asn Glu Ala Tyr Glu Met Pro
                115                 120                 125
Ser Glu Glu Gly Tyr Gln Asp Tyr Glu Pro Glu Ala
                130                 135                 140

<210> SEQ ID NO 23
<211> LENGTH: 134
<212> TYPE: PRT
<213> ORGANISM: Homo sapiens

<400> SEQUENCE: 23

Met Asp Val Phe Met Lys Gly Leu Ser Met Ala Lys Glu Gly Val Val
1               5                   10                  15
Ala Ala Ala Glu Lys Thr Lys Gln Gly Val Thr Glu Ala Ala Glu Lys
                20                  25                  30
Thr Lys Glu Gly Val Leu Tyr Val Gly Ser Lys Thr Arg Glu Gly Val
            35                  40                  45
Val Gln Gly Val Ala Ser Val Ala Glu Lys Thr Lys Glu Gln Ala Ser
        50                  55                  60
His Leu Gly Gly Ala Val Phe Ser Gly Ala Gly Asn Ile Ala Ala Ala
65                  70                  75                  80
Thr Gly Leu Val Lys Arg Glu Glu Phe Pro Thr Asp Leu Lys Pro Glu
                85                  90                  95
Glu Val Ala Gln Glu Ala Ala Glu Glu Pro Leu Ile Glu Pro Leu Met
                100                 105                 110
Glu Pro Glu Gly Glu Ser Tyr Glu Asp Pro Pro Gln Glu Glu Tyr Gln
            115                 120                 125
Glu Tyr Glu Pro Glu Ala
            130

<210> SEQ ID NO 24
<211> LENGTH: 127
<212> TYPE: PRT
<213> ORGANISM: Homo sapiens

<400> SEQUENCE: 24

Met Asp Val Phe Lys Lys Gly Phe Ser Ile Ala Lys Glu Gly Val Val
1               5                   10                  15
Asp Ala Val Glu Lys Thr Lys Gln Gly Val Thr Glu Ala Ala Glu Lys
                20                  25                  30
Thr Lys Glu Gly Val Met Tyr Val Gly Ala Lys Thr Lys Glu Asn Val
            35                  40                  45
Val Gln Ser Val Thr Ser Val Ala Glu Lys Thr Lys Glu Gln Ala Asn
        50                  55                  60
Ala Val Ser Glu Ala Val Val Ser Ser Val Asn Thr Val Ala Thr Lys
65                  70                  75                  80
Thr Val Glu Glu Ala Glu Asn Ile Ala Val Thr Ser Gly Val Val Arg
                85                  90                  95
Lys Glu Asp Leu Arg Pro Ser Ala Pro Gln Gln Glu Gly Glu Ala Ser
                100                 105                 110
Lys Glu Lys Glu Glu Val Ala Glu Glu Ala Gln Ser Gly Gly Asp
```

-continued

<210> SEQ ID NO 25
<211> LENGTH: 952
<212> TYPE: PRT
<213> ORGANISM: Homo sapiens

<400> SEQUENCE: 25

```
Met Gly Val Arg His Pro Pro Cys Ser His Arg Leu Leu Ala Val Cys
1               5                   10                  15

Ala Leu Val Ser Leu Ala Thr Ala Ala Leu Leu Gly His Ile Leu Leu
            20                  25                  30

His Asp Phe Leu Leu Val Pro Arg Glu Leu Ser Gly Ser Ser Pro Val
        35                  40                  45

Leu Glu Glu Thr His Pro Ala His Gln Gln Gly Ala Ser Arg Pro Gly
    50                  55                  60

Pro Arg Asp Ala Gln Ala His Pro Gly Arg Pro Arg Ala Val Pro Thr
65                  70                  75                  80

Gln Cys Asp Val Pro Pro Asn Ser Arg Phe Asp Cys Ala Pro Asp Lys
                85                  90                  95

Ala Ile Thr Gln Glu Gln Cys Glu Ala Arg Gly Cys Cys Tyr Ile Pro
            100                 105                 110

Ala Lys Gln Gly Leu Gln Gly Ala Gln Met Gly Gln Pro Trp Cys Phe
        115                 120                 125

Phe Pro Pro Ser Tyr Pro Ser Tyr Lys Leu Glu Asn Leu Ser Ser Ser
    130                 135                 140

Glu Met Gly Tyr Thr Ala Thr Leu Thr Arg Thr Thr Pro Thr Phe Phe
145                 150                 155                 160

Pro Lys Asp Ile Leu Thr Leu Arg Leu Asp Val Met Met Glu Thr Glu
                165                 170                 175

Asn Arg Leu His Phe Thr Ile Lys Asp Pro Ala Asn Arg Arg Tyr Glu
            180                 185                 190

Val Pro Leu Glu Thr Pro Arg Val His Ser Arg Ala Pro Ser Pro Leu
        195                 200                 205

Tyr Ser Val Glu Phe Ser Glu Glu Pro Phe Gly Val Ile Val His Arg
    210                 215                 220

Gln Leu Asp Gly Arg Val Leu Leu Asn Thr Thr Val Ala Pro Leu Phe
225                 230                 235                 240

Phe Ala Asp Gln Phe Leu Gln Leu Ser Thr Ser Leu Pro Ser Gln Tyr
                245                 250                 255

Ile Thr Gly Leu Ala Glu His Leu Ser Pro Leu Met Leu Ser Thr Ser
            260                 265                 270

Trp Thr Arg Ile Thr Leu Trp Asn Arg Asp Leu Ala Pro Thr Pro Gly
        275                 280                 285

Ala Asn Leu Tyr Gly Ser His Pro Phe Tyr Leu Ala Leu Glu Asp Gly
    290                 295                 300

Gly Ser Ala His Gly Val Phe Leu Leu Asn Ser Asn Ala Met Asp Val
305                 310                 315                 320

Val Leu Gln Pro Ser Pro Ala Leu Ser Trp Arg Ser Thr Gly Gly Ile
                325                 330                 335

Leu Asp Val Tyr Ile Phe Leu Gly Pro Glu Pro Lys Ser Val Val Gln
            340                 345                 350

Gln Tyr Leu Asp Val Val Gly Tyr Pro Phe Met Pro Pro Tyr Trp Gly
        355                 360                 365
```

```
Leu Gly Phe His Leu Cys Arg Trp Gly Tyr Ser Ser Thr Ala Ile Thr
370                 375                 380

Arg Gln Val Val Glu Asn Met Thr Arg Ala His Phe Pro Leu Asp Val
385                 390                 395                 400

Gln Trp Asn Asp Leu Asp Tyr Met Asp Ser Arg Arg Asp Phe Thr Phe
                405                 410                 415

Asn Lys Asp Gly Phe Arg Asp Phe Pro Ala Met Val Gln Glu Leu His
                420                 425                 430

Gln Gly Gly Arg Arg Tyr Met Met Ile Val Asp Pro Ala Ile Ser Ser
            435                 440                 445

Ser Gly Pro Ala Gly Ser Tyr Arg Pro Tyr Asp Glu Gly Leu Arg Arg
450                 455                 460

Gly Val Phe Ile Thr Asn Glu Thr Gly Gln Pro Leu Ile Gly Lys Val
465                 470                 475                 480

Trp Pro Gly Ser Thr Ala Phe Pro Asp Phe Thr Asn Pro Thr Ala Leu
                485                 490                 495

Ala Trp Trp Glu Asp Met Val Ala Glu Phe His Asp Gln Val Pro Phe
                500                 505                 510

Asp Gly Met Trp Ile Asp Met Asn Glu Pro Ser Asn Phe Ile Arg Gly
                515                 520                 525

Ser Glu Asp Gly Cys Pro Asn Asn Glu Leu Glu Asn Pro Pro Tyr Val
530                 535                 540

Pro Gly Val Val Gly Gly Thr Leu Gln Ala Ala Thr Ile Cys Ala Ser
545                 550                 555                 560

Ser His Gln Phe Leu Ser Thr His Tyr Asn Leu His Asn Leu Tyr Gly
                565                 570                 575

Leu Thr Glu Ala Ile Ala Ser His Arg Ala Leu Val Lys Ala Arg Gly
                580                 585                 590

Thr Arg Pro Phe Val Ile Ser Arg Ser Thr Phe Ala Gly His Gly Arg
                595                 600                 605

Tyr Ala Gly His Trp Thr Gly Asp Val Trp Ser Ser Trp Glu Gln Leu
610                 615                 620

Ala Ser Ser Val Pro Glu Ile Leu Gln Phe Asn Leu Leu Gly Val Pro
625                 630                 635                 640

Leu Val Gly Ala Asp Val Cys Gly Phe Leu Gly Asn Thr Ser Glu Glu
                645                 650                 655

Leu Cys Val Arg Trp Thr Gln Leu Gly Ala Phe Tyr Pro Phe Met Arg
                660                 665                 670

Asn His Asn Ser Leu Leu Ser Leu Pro Gln Glu Pro Tyr Ser Phe Ser
                675                 680                 685

Glu Pro Ala Gln Gln Ala Met Arg Lys Ala Leu Thr Leu Arg Tyr Ala
690                 695                 700

Leu Leu Pro His Leu Tyr Thr Leu Phe His Gln Ala His Val Ala Gly
705                 710                 715                 720

Glu Thr Val Ala Arg Pro Leu Phe Leu Glu Phe Pro Lys Asp Ser Ser
                725                 730                 735

Thr Trp Thr Val Asp His Gln Leu Leu Trp Gly Glu Ala Leu Leu Ile
                740                 745                 750

Thr Pro Val Leu Gln Ala Gly Lys Ala Glu Val Thr Gly Tyr Phe Pro
                755                 760                 765

Leu Gly Thr Trp Tyr Asp Leu Gln Thr Val Pro Ile Glu Ala Leu Gly
770                 775                 780

Ser Leu Pro Pro Pro Pro Ala Ala Pro Arg Glu Pro Ala Ile His Ser
```

```
                785                 790                 795                 800
        Glu Gly Gln Trp Val Thr Leu Pro Ala Pro Leu Asp Thr Ile Asn Val
                        805                 810                 815

His Leu Arg Ala Gly Tyr Ile Ile Pro Leu Gln Gly Pro Gly Leu Thr
                        820                 825                 830

Thr Thr Glu Ser Arg Gln Gln Pro Met Ala Leu Ala Val Ala Leu Thr
                        835                 840                 845

Lys Gly Gly Glu Ala Arg Gly Glu Leu Phe Trp Asp Asp Gly Glu Ser
        850                 855                 860

Leu Glu Val Leu Glu Arg Gly Ala Tyr Thr Gln Val Ile Phe Leu Ala
        865                 870                 875                 880

Arg Asn Asn Thr Ile Val Asn Glu Leu Val Arg Val Thr Ser Glu Gly
                        885                 890                 895

Ala Gly Leu Gln Leu Gln Lys Val Thr Val Leu Gly Val Ala Thr Ala
                        900                 905                 910

Pro Gln Gln Val Leu Ser Asn Gly Val Pro Val Ser Asn Phe Thr Tyr
                        915                 920                 925

Ser Pro Asp Thr Lys Val Leu Asp Ile Cys Val Ser Leu Leu Met Gly
                        930                 935                 940

Glu Gln Phe Leu Val Ser Trp Cys
        945                 950

<210> SEQ ID NO 26
<211> LENGTH: 749
<212> TYPE: PRT
<213> ORGANISM: Homo sapiens

<400> SEQUENCE: 26

Ala Pro Ser Pro Leu Tyr Ser Val Glu Phe Ser Glu Glu Pro Phe Gly
        1               5                   10                  15

Val Ile Val His Arg Gln Leu Asp Gly Arg Val Leu Leu Asn Thr Thr
                        20                  25                  30

Val Ala Pro Leu Phe Phe Ala Asp Gln Phe Leu Gln Leu Ser Thr Ser
                        35                  40                  45

Leu Pro Ser Gln Tyr Ile Thr Gly Leu Ala Glu His Leu Ser Pro Leu
        50                  55                  60

Met Leu Ser Thr Ser Trp Thr Arg Ile Thr Leu Trp Asn Arg Asp Leu
        65                  70                  75                  80

Ala Pro Thr Pro Gly Ala Asn Leu Tyr Gly Ser His Pro Phe Tyr Leu
                        85                  90                  95

Ala Leu Glu Asp Gly Gly Ser Ala His Gly Val Phe Leu Leu Asn Ser
                        100                 105                 110

Asn Ala Met Asp Val Val Leu Gln Pro Ser Pro Ala Leu Ser Trp Arg
                        115                 120                 125

Ser Thr Gly Gly Ile Leu Asp Val Tyr Ile Phe Leu Gly Pro Glu Pro
        130                 135                 140

Lys Ser Val Val Gln Gln Tyr Leu Asp Val Val Gly Tyr Pro Phe Met
        145                 150                 155                 160

Pro Pro Tyr Trp Gly Leu Gly Phe His Leu Cys Arg Trp Gly Tyr Ser
                        165                 170                 175

Ser Thr Ala Ile Thr Arg Gln Val Val Glu Asn Met Thr Arg Ala His
                        180                 185                 190

Phe Pro Leu Asp Val Gln Trp Asn Asp Leu Asp Tyr Met Asp Ser Arg
                        195                 200                 205
```

-continued

Arg Asp Phe Thr Phe Asn Lys Asp Gly Phe Arg Asp Phe Pro Ala Met
210                 215                 220

Val Gln Glu Leu His Gln Gly Gly Arg Tyr Met Met Ile Val Asp
225                 230                 235                 240

Pro Ala Ile Ser Ser Gly Pro Ala Gly Ser Tyr Arg Pro Tyr Asp
                245                 250                 255

Glu Gly Leu Arg Arg Gly Val Phe Ile Thr Asn Glu Thr Gly Gln Pro
            260                 265                 270

Leu Ile Gly Lys Val Trp Pro Gly Ser Thr Ala Phe Pro Asp Phe Thr
                275                 280                 285

Asn Pro Thr Ala Leu Ala Trp Trp Glu Asp Met Val Ala Glu Phe His
290                 295                 300

Asp Gln Val Pro Phe Asp Gly Met Trp Ile Asp Met Asn Glu Pro Ser
305                 310                 315                 320

Asn Phe Ile Arg Gly Ser Glu Asp Gly Cys Pro Asn Asn Glu Leu Glu
                325                 330                 335

Asn Pro Pro Tyr Val Pro Gly Val Val Gly Gly Thr Leu Gln Ala Ala
                340                 345                 350

Thr Ile Cys Ala Ser Ser His Gln Phe Leu Ser Thr His Tyr Asn Leu
                355                 360                 365

His Asn Leu Tyr Gly Leu Thr Glu Ala Ile Ala Ser His Arg Ala Leu
370                 375                 380

Val Lys Ala Arg Gly Thr Arg Pro Phe Val Ile Ser Arg Ser Thr Phe
385                 390                 395                 400

Ala Gly His Gly Arg Tyr Ala Gly His Trp Thr Gly Asp Val Trp Ser
                405                 410                 415

Ser Trp Glu Gln Leu Ala Ser Ser Val Pro Glu Ile Leu Gln Phe Asn
                420                 425                 430

Leu Leu Gly Val Pro Leu Val Gly Ala Asp Val Cys Gly Phe Leu Gly
                435                 440                 445

Asn Thr Ser Glu Glu Leu Cys Val Arg Trp Thr Gln Leu Gly Ala Phe
450                 455                 460

Tyr Pro Phe Met Arg Asn His Asn Ser Leu Leu Ser Leu Pro Gln Glu
465                 470                 475                 480

Pro Tyr Ser Phe Ser Glu Pro Ala Gln Gln Ala Met Arg Lys Ala Leu
                485                 490                 495

Thr Leu Arg Tyr Ala Leu Leu Pro His Leu Tyr Thr Leu Phe His Gln
                500                 505                 510

Ala His Val Ala Gly Glu Thr Val Ala Arg Pro Leu Phe Leu Glu Phe
                515                 520                 525

Pro Lys Asp Ser Ser Thr Trp Thr Val Asp His Gln Leu Leu Trp Gly
530                 535                 540

Glu Ala Leu Leu Ile Thr Pro Val Leu Gln Ala Gly Lys Ala Glu Val
545                 550                 555                 560

Thr Gly Tyr Phe Pro Leu Gly Thr Trp Tyr Asp Leu Gln Thr Val Pro
                565                 570                 575

Ile Glu Ala Leu Gly Ser Leu Pro Pro Pro Ala Ala Pro Arg Glu
                580                 585                 590

Pro Ala Ile His Ser Glu Gly Gln Trp Val Thr Leu Pro Ala Pro Leu
                595                 600                 605

Asp Thr Ile Asn Val His Leu Arg Ala Gly Tyr Ile Ile Pro Leu Gln
610                 615                 620

Gly Pro Gly Leu Thr Thr Thr Glu Ser Arg Gln Gln Pro Met Ala Leu

```
                625                 630                 635                 640
Ala Val Ala Leu Thr Lys Gly Gly Glu Ala Arg Gly Glu Leu Phe Trp
                    645                 650                 655

Asp Asp Gly Glu Ser Leu Glu Val Leu Glu Arg Gly Ala Tyr Thr Gln
                660                 665                 670

Val Ile Phe Leu Ala Arg Asn Asn Thr Ile Val Asn Glu Leu Val Arg
            675                 680                 685

Val Thr Ser Glu Gly Ala Gly Leu Gln Leu Gln Lys Val Thr Val Leu
        690                 695                 700

Gly Val Ala Thr Ala Pro Gln Gln Val Leu Ser Asn Gly Val Pro Val
705                 710                 715                 720

Ser Asn Phe Thr Tyr Ser Pro Asp Thr Lys Val Leu Asp Ile Cys Val
                    725                 730                 735

Ser Leu Leu Met Gly Glu Gln Phe Leu Val Ser Trp Cys
                740                 745
```

<210> SEQ ID NO 27
<211> LENGTH: 536
<212> TYPE: PRT
<213> ORGANISM: Homo sapiens

<400> SEQUENCE: 27

```
Met Glu Phe Ser Ser Pro Ser Arg Glu Glu Cys Pro Lys Pro Leu Ser
1               5                   10                  15

Arg Val Ser Ile Met Ala Gly Ser Leu Thr Gly Leu Leu Leu Leu Gln
            20                  25                  30

Ala Val Ser Trp Ala Ser Gly Ala Arg Pro Cys Ile Pro Lys Ser Phe
        35                  40                  45

Gly Tyr Ser Ser Val Val Cys Val Cys Asn Ala Thr Tyr Cys Asp Ser
    50                  55                  60

Phe Asp Pro Pro Thr Phe Pro Ala Leu Gly Thr Phe Ser Arg Tyr Glu
65                  70                  75                  80

Ser Thr Arg Ser Gly Arg Arg Met Glu Leu Ser Met Gly Pro Ile Gln
                85                  90                  95

Ala Asn His Thr Gly Thr Gly Leu Leu Leu Thr Leu Gln Pro Glu Gln
            100                 105                 110

Lys Phe Gln Lys Val Lys Gly Phe Gly Gly Ala Met Thr Asp Ala Ala
        115                 120                 125

Ala Leu Asn Ile Leu Ala Leu Ser Pro Pro Ala Gln Asn Leu Leu Leu
    130                 135                 140

Lys Ser Tyr Phe Ser Glu Gly Ile Gly Tyr Asn Ile Ile Arg Val
145                 150                 155                 160

Pro Met Ala Ser Cys Asp Phe Ser Ile Arg Thr Tyr Thr Tyr Ala Asp
                165                 170                 175

Thr Pro Asp Asp Phe Gln Leu His Asn Phe Ser Leu Pro Glu Glu Asp
            180                 185                 190

Thr Lys Leu Lys Ile Pro Leu Ile His Arg Ala Leu Gln Leu Ala Gln
        195                 200                 205

Arg Pro Val Ser Leu Leu Ala Ser Pro Trp Thr Ser Pro Thr Trp Leu
    210                 215                 220

Lys Thr Asn Gly Ala Val Asn Gly Lys Gly Ser Leu Lys Gly Gln Pro
225                 230                 235                 240

Gly Asp Ile Tyr His Gln Thr Trp Ala Arg Tyr Phe Val Lys Phe Leu
                245                 250                 255
```

```
Asp Ala Tyr Ala Glu His Lys Leu Gln Phe Trp Ala Val Thr Ala Glu
            260                 265                 270

Asn Glu Pro Ser Ala Gly Leu Leu Ser Gly Tyr Pro Phe Gln Cys Leu
        275                 280                 285

Gly Phe Thr Pro Glu His Gln Arg Asp Phe Ile Ala Arg Asp Leu Gly
    290                 295                 300

Pro Thr Leu Ala Asn Ser Thr His His Asn Val Arg Leu Leu Met Leu
305                 310                 315                 320

Asp Asp Gln Arg Leu Leu Pro His Trp Ala Lys Val Val Leu Thr
                325                 330                 335

Asp Pro Glu Ala Ala Lys Tyr Val His Gly Ile Ala Val His Trp Tyr
                340                 345                 350

Leu Asp Phe Leu Ala Pro Ala Lys Ala Thr Leu Gly Glu Thr His Arg
                355                 360                 365

Leu Phe Pro Asn Thr Met Leu Phe Ala Ser Glu Ala Cys Val Gly Ser
370                 375                 380

Lys Phe Trp Glu Gln Ser Val Arg Leu Gly Ser Trp Asp Arg Gly Met
385                 390                 395                 400

Gln Tyr Ser His Ser Ile Ile Thr Asn Leu Leu Tyr His Val Val Gly
                405                 410                 415

Trp Thr Asp Trp Asn Leu Ala Leu Asn Pro Glu Gly Gly Pro Asn Trp
                420                 425                 430

Val Arg Asn Phe Val Asp Ser Pro Ile Ile Val Asp Ile Thr Lys Asp
                435                 440                 445

Thr Phe Tyr Lys Gln Pro Met Phe Tyr His Leu Gly His Phe Ser Lys
                450                 455                 460

Phe Ile Pro Glu Gly Ser Gln Arg Val Gly Leu Val Ala Ser Gln Lys
465                 470                 475                 480

Asn Asp Leu Asp Ala Val Ala Leu Met His Pro Asp Gly Ser Ala Val
                485                 490                 495

Val Val Val Leu Asn Arg Ser Ser Lys Asp Val Pro Leu Thr Ile Lys
                500                 505                 510

Asp Pro Ala Val Gly Phe Leu Glu Thr Ile Ser Pro Gly Tyr Ser Ile
                515                 520                 525

His Thr Tyr Leu Trp Arg Arg Gln
                530                 535

<210> SEQ ID NO 28
<211> LENGTH: 429
<212> TYPE: PRT
<213> ORGANISM: Homo sapiens

<400> SEQUENCE: 28

Met Gln Leu Arg Asn Pro Glu Leu His Leu Gly Cys Ala Leu Ala Leu
1               5                   10                  15

Arg Phe Leu Ala Leu Val Ser Trp Asp Ile Pro Gly Ala Arg Ala Leu
                20                  25                  30

Asp Asn Gly Leu Ala Arg Thr Pro Thr Met Gly Trp Leu His Trp Glu
            35                  40                  45

Arg Phe Met Cys Asn Leu Asp Cys Gln Glu Glu Pro Asp Ser Cys Ile
        50                  55                  60

Ser Glu Lys Leu Phe Met Glu Met Ala Glu Leu Met Val Ser Glu Gly
65              70                  75                  80

Trp Lys Asp Ala Gly Tyr Glu Tyr Leu Cys Ile Asp Asp Cys Trp Met
                85                  90                  95
```

Ala Pro Gln Arg Asp Ser Glu Gly Arg Leu Gln Ala Asp Pro Gln Arg
            100                 105                 110

Phe Pro His Gly Ile Arg Gln Leu Ala Asn Tyr Val His Ser Lys Gly
        115                 120                 125

Leu Lys Leu Gly Ile Tyr Ala Asp Val Gly Asn Lys Thr Cys Ala Gly
130                 135                 140

Phe Pro Gly Ser Phe Gly Tyr Tyr Asp Ile Asp Ala Gln Thr Phe Ala
145                 150                 155                 160

Asp Trp Gly Val Asp Leu Leu Lys Phe Asp Gly Cys Tyr Cys Asp Ser
                165                 170                 175

Leu Glu Asn Leu Ala Asp Gly Tyr Lys His Met Ser Leu Ala Leu Asn
            180                 185                 190

Arg Thr Gly Arg Ser Ile Val Tyr Ser Cys Glu Trp Pro Leu Tyr Met
        195                 200                 205

Trp Pro Phe Gln Lys Pro Asn Tyr Thr Glu Ile Arg Gln Tyr Cys Asn
210                 215                 220

His Trp Arg Asn Phe Ala Asp Ile Asp Asp Ser Trp Lys Ser Ile Lys
225                 230                 235                 240

Ser Ile Leu Asp Trp Thr Ser Phe Asn Gln Glu Arg Ile Val Asp Val
                245                 250                 255

Ala Gly Pro Gly Gly Trp Asn Asp Pro Asp Met Leu Val Ile Gly Asn
            260                 265                 270

Phe Gly Leu Ser Trp Asn Gln Gln Val Thr Gln Met Ala Leu Trp Ala
        275                 280                 285

Ile Met Ala Ala Pro Leu Phe Met Ser Asn Asp Leu Arg His Ile Ser
290                 295                 300

Pro Gln Ala Lys Ala Leu Leu Gln Asp Lys Asp Val Ile Ala Ile Asn
305                 310                 315                 320

Gln Asp Pro Leu Gly Lys Gln Gly Tyr Gln Leu Arg Gln Gly Asp Asn
                325                 330                 335

Phe Glu Val Trp Glu Arg Pro Leu Ser Gly Leu Ala Trp Ala Val Ala
            340                 345                 350

Met Ile Asn Arg Gln Glu Ile Gly Gly Pro Arg Ser Tyr Thr Ile Ala
        355                 360                 365

Val Ala Ser Leu Gly Lys Gly Val Ala Cys Asn Pro Ala Cys Phe Ile
370                 375                 380

Thr Gln Leu Leu Pro Val Lys Arg Lys Leu Gly Phe Tyr Glu Trp Thr
385                 390                 395                 400

Ser Arg Leu Arg Ser His Ile Asn Pro Thr Gly Thr Val Leu Leu Gln
                405                 410                 415

Leu Glu Asn Thr Met Gln Met Ser Leu Lys Asp Leu Leu
            420                 425

<210> SEQ ID NO 29
<211> LENGTH: 677
<212> TYPE: PRT
<213> ORGANISM: Homo sapiens

<400> SEQUENCE: 29

Met Pro Gly Phe Leu Val Arg Ile Leu Leu Leu Leu Val Leu Leu
1               5                   10                  15

Leu Leu Gly Pro Thr Arg Gly Leu Arg Asn Ala Thr Gln Arg Met Phe
            20                  25                  30

Glu Ile Asp Tyr Ser Arg Asp Ser Phe Leu Lys Asp Gly Gln Pro Phe

-continued

```
            35                  40                  45
Arg Tyr Ile Ser Gly Ser Ile His Tyr Ser Arg Val Pro Arg Phe Tyr
 50                  55                  60
Trp Lys Asp Arg Leu Leu Lys Met Lys Met Ala Gly Leu Asn Ala Ile
 65                  70                  75                  80
Gln Thr Tyr Val Pro Trp Asn Phe His Glu Pro Trp Pro Gly Gln Tyr
                 85                  90                  95
Gln Phe Ser Glu Asp His Asp Val Glu Tyr Phe Leu Arg Leu Ala His
                100                 105                 110
Glu Leu Gly Leu Leu Val Ile Leu Arg Pro Gly Pro Tyr Ile Cys Ala
                115                 120                 125
Glu Trp Glu Met Gly Gly Leu Pro Ala Trp Leu Leu Glu Lys Glu Ser
                130                 135                 140
Ile Leu Leu Arg Ser Ser Asp Pro Asp Tyr Leu Ala Ala Val Asp Lys
145                 150                 155                 160
Trp Leu Gly Val Leu Leu Pro Lys Met Lys Pro Leu Leu Tyr Gln Asn
                165                 170                 175
Gly Gly Pro Val Ile Thr Val Gln Val Glu Asn Glu Tyr Gly Ser Tyr
                180                 185                 190
Phe Ala Cys Asp Phe Asp Tyr Leu Arg Phe Leu Gln Lys Arg Phe Arg
                195                 200                 205
His His Leu Gly Asp Asp Val Val Leu Phe Thr Thr Asp Gly Ala His
                210                 215                 220
Lys Thr Phe Leu Lys Cys Gly Ala Leu Gln Gly Leu Tyr Thr Thr Val
225                 230                 235                 240
Asp Phe Gly Thr Gly Ser Asn Ile Thr Asp Ala Phe Leu Ser Gln Arg
                245                 250                 255
Lys Cys Glu Pro Lys Gly Pro Leu Ile Asn Ser Glu Phe Tyr Thr Gly
                260                 265                 270
Trp Leu Asp His Trp Gly Gln Pro His Ser Thr Ile Lys Thr Glu Ala
                275                 280                 285
Val Ala Ser Ser Leu Tyr Asp Ile Leu Ala Arg Gly Ala Ser Val Asn
                290                 295                 300
Leu Tyr Met Phe Ile Gly Gly Thr Asn Phe Ala Tyr Trp Asn Gly Ala
305                 310                 315                 320
Asn Ser Pro Tyr Ala Ala Gln Pro Thr Ser Tyr Asp Tyr Asp Ala Pro
                325                 330                 335
Leu Ser Glu Ala Gly Asp Leu Thr Glu Lys Tyr Phe Ala Leu Arg Asn
                340                 345                 350
Ile Ile Gln Lys Phe Glu Lys Val Pro Glu Gly Pro Ile Pro Pro Ser
                355                 360                 365
Thr Pro Lys Phe Ala Tyr Gly Lys Val Thr Leu Glu Lys Leu Lys Thr
                370                 375                 380
Val Gly Ala Ala Leu Asp Ile Leu Cys Pro Ser Gly Pro Ile Lys Ser
385                 390                 395                 400
Leu Tyr Pro Leu Thr Phe Ile Gln Val Lys Gln His Tyr Gly Phe Val
                405                 410                 415
Leu Tyr Arg Thr Thr Leu Pro Gln Asp Cys Ser Asn Pro Ala Pro Leu
                420                 425                 430
Ser Ser Pro Leu Asn Gly Val His Asp Arg Ala Tyr Val Ala Val Asp
                435                 440                 445
Gly Ile Pro Gln Gly Val Leu Glu Arg Asn Asn Val Ile Thr Leu Asn
                450                 455                 460
```

```
Ile Thr Gly Lys Ala Gly Ala Thr Leu Asp Leu Leu Val Glu Asn Met
465                 470                 475                 480

Gly Arg Val Asn Tyr Gly Ala Tyr Ile Asn Asp Phe Lys Gly Leu Val
                485                 490                 495

Ser Asn Leu Thr Leu Ser Ser Asn Ile Leu Thr Asp Trp Thr Ile Phe
            500                 505                 510

Pro Leu Asp Thr Glu Asp Ala Val Arg Ser His Leu Gly Gly Trp Gly
            515                 520                 525

His Arg Asp Ser Gly His His Asp Glu Ala Trp Ala His Asn Ser Ser
530                 535                 540

Asn Tyr Thr Leu Pro Ala Phe Tyr Met Gly Asn Phe Ser Ile Pro Ser
545                 550                 555                 560

Gly Ile Pro Asp Leu Pro Gln Asp Thr Phe Ile Gln Phe Pro Gly Trp
                565                 570                 575

Thr Lys Gly Gln Val Trp Ile Asn Gly Phe Asn Leu Gly Arg Tyr Trp
            580                 585                 590

Pro Ala Arg Gly Pro Gln Leu Thr Leu Phe Val Pro Gln His Ile Leu
            595                 600                 605

Met Thr Ser Ala Pro Asn Thr Ile Thr Val Leu Glu Leu Glu Trp Ala
610                 615                 620

Pro Cys Ser Ser Asp Asp Pro Glu Leu Cys Ala Val Thr Phe Val Asp
625                 630                 635                 640

Arg Pro Val Ile Gly Ser Ser Val Thr Tyr Asp His Pro Ser Lys Pro
                645                 650                 655

Val Glu Lys Arg Leu Met Pro Pro Pro Gln Lys Asn Lys Asp Ser
            660                 665                 670

Trp Leu Asp His Val
            675

<210> SEQ ID NO 30
<211> LENGTH: 669
<212> TYPE: PRT
<213> ORGANISM: Homo sapiens

<400> SEQUENCE: 30

Met Thr Ala Ala Ala Gly Ser Ala Gly Arg Ala Ala Val Pro Leu Leu
1               5                   10                  15

Leu Cys Ala Leu Leu Ala Pro Gly Gly Ala Tyr Val Leu Asp Asp Ser
                20                  25                  30

Asp Gly Leu Gly Arg Glu Phe Asp Gly Ile Gly Ala Val Ser Gly Gly
            35                  40                  45

Gly Ala Thr Ser Arg Leu Leu Val Asn Tyr Pro Glu Pro Tyr Arg Ser
50                  55                  60

Gln Ile Leu Asp Tyr Leu Phe Lys Pro Asn Phe Gly Ala Ser Leu His
65                  70                  75                  80

Ile Leu Lys Val Glu Ile Gly Gly Asp Gly Gln Thr Thr Asp Gly Thr
                85                  90                  95

Glu Pro Ser His Met His Tyr Ala Leu Asp Glu Asn Tyr Phe Arg Gly
            100                 105                 110

Tyr Glu Trp Trp Leu Met Lys Glu Ala Lys Lys Arg Asn Pro Asn Ile
            115                 120                 125

Thr Leu Ile Gly Leu Pro Trp Ser Phe Pro Gly Trp Leu Gly Lys Gly
            130                 135                 140

Phe Asp Trp Pro Tyr Val Asn Leu Gln Leu Thr Ala Tyr Tyr Val Val
```

```
            145                 150                 155                 160
        Thr Trp Ile Val Gly Ala Lys Arg Tyr His Asp Leu Asp Ile Asp Tyr
                        165                 170                 175
        Ile Gly Ile Trp Asn Glu Arg Ser Tyr Asn Ala Asn Tyr Ile Lys Ile
                        180                 185                 190
        Leu Arg Lys Met Leu Asn Tyr Gln Gly Leu Gln Arg Val Lys Ile Ile
                        195                 200                 205
        Ala Ser Asp Asn Leu Trp Glu Ser Ile Ser Ala Ser Met Leu Leu Asp
                        210                 215                 220
        Ala Glu Leu Phe Lys Val Val Asp Val Ile Gly Ala His Tyr Pro Gly
        225                 230                 235                 240
        Thr His Ser Ala Lys Asp Ala Lys Leu Thr Gly Lys Lys Leu Trp Ser
                        245                 250                 255
        Ser Glu Asp Phe Ser Thr Leu Asn Ser Asp Met Gly Ala Gly Cys Trp
                        260                 265                 270
        Gly Arg Ile Leu Asn Gln Asn Tyr Ile Asn Gly Tyr Met Thr Ser Thr
                        275                 280                 285
        Ile Ala Trp Asn Leu Val Ala Ser Tyr Tyr Glu Gln Leu Pro Tyr Gly
                        290                 295                 300
        Arg Cys Gly Leu Met Thr Ala Gln Glu Pro Trp Ser Gly His Tyr Val
        305                 310                 315                 320
        Val Glu Ser Pro Val Trp Val Ser Ala His Thr Thr Gln Phe Thr Gln
                        325                 330                 335
        Pro Gly Trp Tyr Tyr Leu Lys Thr Val Gly His Leu Glu Lys Gly Gly
                        340                 345                 350
        Ser Tyr Val Ala Leu Thr Asp Gly Leu Gly Asn Leu Thr Ile Ile Ile
                        355                 360                 365
        Glu Thr Met Ser His Lys His Ser Lys Cys Ile Arg Pro Phe Leu Pro
                        370                 375                 380
        Tyr Phe Asn Val Ser Gln Gln Phe Ala Thr Phe Val Leu Lys Gly Ser
        385                 390                 395                 400
        Phe Ser Glu Ile Pro Glu Leu Gln Val Trp Tyr Thr Lys Leu Gly Lys
                        405                 410                 415
        Thr Ser Glu Arg Phe Leu Phe Lys Gln Leu Asp Ser Leu Trp Leu Leu
                        420                 425                 430
        Asp Ser Asp Gly Ser Phe Thr Leu Ser Leu His Glu Asp Glu Leu Phe
                        435                 440                 445
        Thr Leu Thr Thr Leu Thr Thr Gly Arg Lys Gly Ser Tyr Pro Leu Pro
                        450                 455                 460
        Pro Lys Ser Gln Pro Phe Pro Ser Thr Tyr Lys Asp Asp Phe Asn Val
        465                 470                 475                 480
        Asp Tyr Pro Phe Phe Ser Glu Ala Pro Asn Phe Ala Asp Gln Thr Gly
                        485                 490                 495
        Val Phe Glu Tyr Phe Thr Asn Ile Glu Asp Pro Gly Glu His His Phe
                        500                 505                 510
        Thr Leu Arg Gln Val Leu Asn Gln Arg Pro Ile Thr Trp Ala Ala Asp
                        515                 520                 525
        Ala Ser Asn Thr Ile Ser Ile Gly Asp Tyr Asn Trp Thr Asn Leu
                        530                 535                 540
        Thr Ile Lys Cys Asp Val Tyr Ile Glu Thr Pro Asp Thr Gly Val
        545                 550                 555                 560
        Phe Ile Ala Gly Arg Val Asn Lys Gly Gly Ile Leu Ile Arg Ser Ala
                        565                 570                 575
```

Arg Gly Ile Phe Phe Trp Ile Phe Ala Asn Gly Ser Tyr Arg Val Thr
            580                 585                 590

Gly Asp Leu Ala Gly Trp Ile Tyr Ala Leu Gly Arg Val Glu Val
            595                 600                 605

Thr Ala Lys Lys Trp Tyr Thr Leu Thr Leu Thr Ile Lys Gly His Phe
610                 615                 620

Ala Ser Gly Met Leu Asn Asp Lys Ser Leu Trp Thr Asp Ile Pro Val
625                 630                 635                 640

Asn Phe Pro Lys Asn Gly Trp Ala Ala Ile Gly Thr His Ser Phe Glu
            645                 650                 655

Phe Ala Gln Phe Asp Asn Phe Leu Val Glu Ala Thr Arg
            660                 665

<210> SEQ ID NO 31
<211> LENGTH: 988
<212> TYPE: PRT
<213> ORGANISM: Homo sapiens

<400> SEQUENCE: 31

Met Ser Arg Ala Leu Arg Pro Leu Pro Leu Cys Phe Phe Leu
1               5                   10                  15

Leu Leu Leu Ala Ala Gly Ala Arg Ala Gly Gly Tyr Glu Thr Cys
            20                  25                  30

Pro Thr Val Gln Pro Asn Met Leu Asn Val His Leu Leu Pro His Thr
            35                  40                  45

His Asp Asp Val Gly Trp Leu Lys Thr Val Asp Gln Tyr Phe Tyr Gly
50                  55                  60

Ile Lys Asn Asp Ile Gln His Ala Gly Val Gln Tyr Ile Leu Asp Ser
65                  70                  75                  80

Val Ile Ser Ala Leu Leu Ala Asp Pro Thr Arg Arg Phe Ile Tyr Val
            85                  90                  95

Glu Ile Ala Phe Phe Ser Arg Trp Trp His Gln Thr Asn Ala Thr
            100                 105                 110

Gln Glu Val Val Arg Asp Leu Val Arg Gln Gly Arg Leu Glu Phe Ala
            115                 120                 125

Asn Gly Gly Trp Val Met Asn Asp Glu Ala Ala Thr His Tyr Gly Ala
            130                 135                 140

Ile Val Asp Gln Met Thr Leu Gly Leu Arg Phe Leu Glu Asp Thr Phe
145                 150                 155                 160

Gly Asn Asp Gly Arg Pro Arg Val Ala Trp His Ile Asp Pro Phe Gly
            165                 170                 175

His Ser Arg Glu Gln Ala Ser Leu Phe Ala Gln Met Gly Phe Asp Gly
            180                 185                 190

Phe Phe Phe Gly Arg Leu Asp Tyr Gln Asp Lys Trp Val Arg Met Gln
            195                 200                 205

Lys Leu Glu Met Glu Gln Val Trp Arg Ala Ser Thr Ser Leu Lys Pro
            210                 215                 220

Pro Thr Ala Asp Leu Phe Thr Gly Val Leu Pro Asn Gly Tyr Asn Pro
225                 230                 235                 240

Pro Arg Asn Leu Cys Trp Asp Val Leu Cys Val Asp Gln Pro Leu Val
            245                 250                 255

Glu Asp Pro Arg Ser Pro Glu Tyr Asn Ala Lys Glu Leu Val Asp Tyr
            260                 265                 270

Phe Leu Asn Val Ala Thr Ala Gln Gly Arg Tyr Tyr Arg Thr Asn His

```
            275                 280                 285
Ile Val Met Thr Met Gly Ser Asp Phe Gln Tyr Glu Asn Ala Asn Met
290                 295                 300
Trp Phe Lys Asn Leu Asp Lys Leu Ile Gln Leu Val Asn Ala Gln Gln
305                 310                 315                 320
Ala Lys Gly Ser Ser Val His Val Leu Tyr Ser Thr Pro Ala Cys Tyr
            325                 330                 335
Leu Trp Glu Leu Asn Lys Ala Asn Leu Thr Trp Ser Val Lys His Asp
            340                 345                 350
Asp Phe Phe Pro Tyr Ala Asp Gly His His Gln Phe Trp Thr Gly Tyr
            355                 360                 365
Phe Ser Ser Arg Pro Ala Leu Lys Arg Tyr Glu Arg Leu Ser Tyr Asn
            370                 375                 380
Phe Leu Gln Val Cys Asn Gln Leu Glu Ala Leu Val Gly Leu Ala Ala
385                 390                 395                 400
Asn Val Gly Pro Tyr Gly Ser Gly Asp Ser Ala Pro Leu Asn Glu Ala
            405                 410                 415
Met Ala Val Leu Gln His His Asp Ala Val Ser Gly Thr Ser Arg Gln
            420                 425                 430
His Val Ala Asn Asp Tyr Ala Arg Gln Leu Ala Ala Gly Trp Gly Pro
            435                 440                 445
Cys Glu Val Leu Leu Ser Asn Ala Leu Ala Arg Leu Arg Gly Phe Lys
450                 455                 460
Asp His Phe Thr Phe Cys Gln Gln Leu Asn Ile Ser Ile Cys Pro Leu
465                 470                 475                 480
Ser Gln Thr Ala Ala Arg Phe Gln Val Ile Val Tyr Asn Pro Leu Gly
            485                 490                 495
Arg Lys Val Asn Trp Met Val Arg Leu Pro Val Ser Glu Gly Val Phe
            500                 505                 510
Val Val Lys Asp Pro Asn Gly Arg Thr Val Pro Ser Asp Val Val Ile
            515                 520                 525
Phe Pro Ser Ser Asp Ser Gln Ala His Pro Pro Glu Leu Leu Phe Ser
            530                 535                 540
Ala Ser Leu Pro Ala Leu Gly Phe Ser Thr Tyr Ser Val Ala Gln Val
545                 550                 555                 560
Pro Arg Trp Lys Pro Gln Ala Arg Ala Pro Gln Pro Ile Pro Arg Arg
            565                 570                 575
Ser Trp Ser Pro Ala Leu Thr Ile Glu Asn Glu His Ile Arg Ala Thr
            580                 585                 590
Phe Asp Pro Asp Thr Gly Leu Leu Met Glu Ile Met Asn Met Asn Gln
            595                 600                 605
Gln Leu Leu Leu Pro Val Arg Gln Thr Phe Phe Trp Tyr Asn Ala Ser
            610                 615                 620
Ile Gly Asp Asn Glu Ser Asp Gln Ala Ser Gly Ala Tyr Ile Phe Arg
625                 630                 635                 640
Pro Asn Gln Gln Lys Pro Leu Pro Val Ser Arg Trp Ala Gln Ile His
            645                 650                 655
Leu Val Lys Thr Pro Leu Val Gln Glu Val His Gln Asn Phe Ser Ala
            660                 665                 670
Trp Cys Ser Gln Val Val Arg Leu Tyr Pro Gly Gln Arg His Leu Glu
            675                 680                 685
Leu Glu Trp Ser Val Gly Pro Ile Pro Val Gly Asp Thr Trp Gly Lys
            690                 695                 700
```

```
Glu Val Ile Ser Arg Phe Asp Thr Pro Leu Glu Thr Lys Gly Arg Phe
705                 710                 715                 720

Tyr Thr Asp Ser Asn Gly Arg Glu Ile Leu Glu Arg Arg Arg Asp Tyr
                725                 730                 735

Arg Pro Thr Trp Lys Leu Asn Gln Thr Glu Pro Val Ala Gly Asn Tyr
            740                 745                 750

Tyr Pro Val Asn Thr Arg Ile Tyr Ile Thr Asp Gly Asn Met Gln Leu
        755                 760                 765

Thr Val Leu Thr Asp Arg Ser Gln Gly Gly Ser Ser Leu Arg Asp Gly
    770                 775                 780

Ser Leu Glu Leu Met Val His Arg Arg Leu Lys Asp Asp Gly Arg
785                 790                 795                 800

Gly Val Ser Glu Pro Leu Met Glu Asn Gly Ser Gly Ala Trp Val Arg
                805                 810                 815

Gly Arg His Leu Val Leu Leu Asp Thr Ala Gln Ala Ala Ala Gly
                820                 825                 830

His Arg Leu Leu Ala Glu Gln Glu Val Leu Ala Pro Gln Val Val Leu
                835                 840                 845

Ala Pro Gly Gly Gly Ala Ala Tyr Asn Leu Gly Ala Pro Pro Arg Thr
850                 855                 860

Gln Phe Ser Gly Leu Arg Arg Asp Leu Pro Pro Ser Val His Leu Leu
865                 870                 875                 880

Thr Leu Ala Ser Trp Gly Pro Glu Met Val Leu Leu Arg Leu Glu His
                885                 890                 895

Gln Phe Ala Val Gly Glu Asp Ser Gly Arg Asn Leu Ser Ala Pro Val
                900                 905                 910

Thr Leu Asn Leu Arg Asp Leu Phe Ser Thr Phe Thr Ile Thr Arg Leu
                915                 920                 925

Gln Glu Thr Thr Leu Val Ala Asn Gln Leu Arg Glu Ala Ala Ser Arg
930                 935                 940

Leu Lys Trp Thr Thr Asn Thr Gly Pro Thr Pro His Gln Thr Pro Tyr
945                 950                 955                 960

Gln Leu Asp Pro Ala Asn Ile Thr Leu Glu Pro Met Glu Ile Arg Thr
                965                 970                 975

Phe Leu Ala Ser Val Gln Trp Lys Glu Val Asp Gly
            980                 985
```

<210> SEQ ID NO 32
<211> LENGTH: 879
<212> TYPE: PRT
<213> ORGANISM: Homo sapiens
<220> FEATURE:
<221> NAME/KEY: MOD_RES
<222> LOCATION: (160)..(160)
<223> OTHER INFORMATION: Any amino acid
<220> FEATURE:
<221> NAME/KEY: MOD_RES
<222> LOCATION: (253)..(253)
<223> OTHER INFORMATION: Any amino acid

<400> SEQUENCE: 32

```
Met Arg Leu His Leu Leu Leu Leu Ala Leu Cys Gly Ala Gly Thr
1               5                   10                  15

Thr Ala Ala Glu Leu Ser Tyr Ser Leu Arg Gly Asn Trp Ser Ile Cys
                20                  25                  30

Asn Gly Asn Gly Ser Leu Glu Leu Pro Gly Ala Val Pro Gly Cys Val
            35                  40                  45
```

-continued

```
His Ser Ala Leu Phe Gln Gln Gly Leu Ile Gln Asp Ser Tyr Tyr Arg
         50                  55                  60

Phe Asn Asp Leu Asn His Arg Trp Val Ser Leu Asp Asn Trp Thr Tyr
 65                  70                  75                  80

Ser Lys Glu Phe Lys Ile Pro Phe Glu Ile Ser Lys Trp Gln Lys Val
                 85                  90                  95

Asn Leu Ile Leu Glu Gly Val Asp Thr Val Ser Lys Ile Leu Phe Asn
            100                 105                 110

Glu Val Thr Ile Gly Glu Thr Asp Asn Met Phe Asn Arg Tyr Ser Phe
            115                 120                 125

Asp Ile Thr Asn Val Val Arg Asp Val Asn Ser Ile Glu Leu Arg Phe
        130                 135                 140

Gln Ser Ala Val Leu Tyr Ala Ala Gln Gln Ser Lys Ala His Thr Xaa
145                 150                 155                 160

Tyr Gln Val Pro Pro Asp Cys Pro Pro Leu Val Gln Lys Gly Glu Cys
                165                 170                 175

His Val Asn Phe Val Arg Lys Glu Gln Cys Ser Phe Ser Trp Asp Trp
            180                 185                 190

Gly Pro Ser Phe Pro Thr Gln Gly Ile Trp Lys Asp Val Arg Ile Glu
        195                 200                 205

Ala Tyr Asn Ile Cys His Leu Asn Tyr Phe Thr Phe Ser Pro Ile Tyr
    210                 215                 220

Asp Lys Ser Ala Gln Glu Trp Asn Leu Glu Ile Glu Ser Thr Phe Asp
225                 230                 235                 240

Val Val Ser Ser Lys Pro Val Gly Gly Gln Val Ile Xaa Ala Ile Pro
                245                 250                 255

Lys Leu Gln Thr Gln Thr Tyr Ser Ile Glu Leu Gln Pro Gly Lys
            260                 265                 270

Arg Ile Val Glu Leu Phe Val Asn Ile Ser Lys Asn Ile Thr Val Glu
        275                 280                 285

Thr Trp Trp Pro His Gly His Gly Asn Gln Thr Gly Tyr Asn Met Thr
    290                 295                 300

Val Leu Phe Glu Leu Asp Gly Gly Leu Asn Ile Glu Lys Ser Ala Lys
305                 310                 315                 320

Val Tyr Phe Arg Thr Val Glu Leu Ile Glu Glu Pro Ile Lys Gly Ser
                325                 330                 335

Pro Gly Leu Ser Phe Tyr Phe Lys Ile Asn Gly Phe Pro Ile Phe Leu
            340                 345                 350

Lys Gly Ser Asn Trp Ile Pro Ala Asp Ser Phe Gln Asp Arg Val Thr
        355                 360                 365

Ser Glu Leu Leu Arg Leu Leu Leu Gln Ser Val Val Asp Ala Asn Met
    370                 375                 380

Asn Thr Leu Arg Val Trp Gly Gly Gly Ile Tyr Glu Gln Asp Glu Phe
385                 390                 395                 400

Tyr Glu Leu Cys Asp Glu Leu Gly Ile Met Val Trp Gln Asp Phe Met
                405                 410                 415

Phe Ala Cys Ala Leu Tyr Pro Thr Asp Gln Gly Phe Leu Asp Ser Val
            420                 425                 430

Thr Ala Glu Val Ala Tyr Gln Ile Lys Arg Leu Lys Ser His Pro Ser
        435                 440                 445

Ile Ile Ile Trp Ser Gly Asn Asn Glu Asn Glu Glu Ala Leu Met Met
    450                 455                 460
```

```
Asn Trp Tyr His Ile Ser Phe Thr Asp Arg Pro Ile Tyr Ile Lys Asp
465                 470                 475                 480

Tyr Val Thr Leu Tyr Val Lys Asn Ile Arg Glu Leu Val Leu Ala Gly
            485                 490                 495

Asp Lys Ser Arg Pro Phe Ile Thr Ser Ser Pro Thr Asn Gly Ala Glu
        500                 505                 510

Thr Val Ala Glu Ala Trp Val Ser Gln Asn Pro Asn Ser Asn Tyr Phe
    515                 520                 525

Gly Asp Val His Phe Tyr Asp Tyr Ile Ser Asp Cys Trp Asn Trp Lys
530                 535                 540

Val Phe Pro Lys Ala Arg Phe Ala Ser Glu Tyr Gly Tyr Gln Ser Trp
545                 550                 555                 560

Pro Ser Phe Ser Thr Leu Glu Lys Val Ser Ser Thr Glu Asp Trp Ser
                565                 570                 575

Phe Asn Ser Lys Phe Ser Leu His Arg Gln His His Glu Gly Gly Asn
                580                 585                 590

Lys Gln Met Leu Tyr Gln Ala Gly Leu His Phe Lys Leu Pro Gln Ser
        595                 600                 605

Thr Asp Pro Leu Arg Thr Phe Lys Asp Thr Ile Tyr Leu Thr Gln Val
610                 615                 620

Met Gln Ala Gln Cys Val Lys Thr Glu Thr Glu Phe Tyr Arg Arg Ser
625                 630                 635                 640

Arg Ser Glu Ile Val Asp Gln Gln Gly His Thr Met Gly Ala Leu Tyr
                645                 650                 655

Trp Gln Leu Asn Asp Ile Trp Gln Ala Pro Ser Trp Ala Ser Leu Glu
                660                 665                 670

Tyr Gly Gly Lys Trp Lys Met Leu His Tyr Phe Ala Gln Asn Phe Phe
            675                 680                 685

Ala Pro Leu Leu Pro Val Gly Phe Glu Asn Glu Asn Thr Phe Tyr Ile
        690                 695                 700

Tyr Gly Val Ser Asp Leu His Ser Asp Tyr Ser Met Thr Leu Ser Val
705                 710                 715                 720

Arg Val His Thr Trp Ser Ser Leu Glu Pro Val Cys Ser Arg Val Thr
                725                 730                 735

Glu Arg Phe Val Met Lys Gly Gly Glu Ala Val Cys Leu Tyr Glu Glu
            740                 745                 750

Pro Val Ser Glu Leu Leu Arg Arg Cys Gly Asn Cys Thr Arg Glu Ser
        755                 760                 765

Cys Val Val Ser Phe Tyr Leu Ser Ala Asp His Glu Leu Leu Ser Pro
770                 775                 780

Thr Asn Tyr His Phe Leu Ser Ser Pro Lys Glu Ala Val Gly Leu Cys
785                 790                 795                 800

Lys Ala Gln Ile Thr Ala Ile Ile Ser Gln Gln Gly Asp Ile Phe Val
                805                 810                 815

Phe Asp Leu Glu Thr Ser Ala Val Ala Pro Phe Val Trp Leu Asp Val
            820                 825                 830

Gly Ser Ile Pro Gly Arg Phe Ser Asp Asn Gly Phe Leu Met Thr Glu
        835                 840                 845

Lys Thr Arg Thr Ile Leu Phe Tyr Pro Trp Glu Pro Thr Ser Lys Asn
        850                 855                 860

Glu Leu Glu Gln Ser Phe His Val Thr Ser Leu Thr Asp Ile Tyr
865                 870                 875
```

<210> SEQ ID NO 33
<211> LENGTH: 466
<212> TYPE: PRT
<213> ORGANISM: Homo sapiens

<400> SEQUENCE: 33

```
Met Arg Ala Pro Gly Met Arg Ser Arg Pro Ala Gly Pro Ala Leu Leu
1               5                   10                  15

Leu Leu Leu Leu Phe Leu Gly Ala Ala Glu Ser Val Arg Arg Ala Gln
            20                  25                  30

Pro Pro Arg Arg Tyr Thr Pro Asp Trp Pro Ser Leu Asp Ser Arg Pro
        35                  40                  45

Leu Pro Ala Trp Phe Asp Glu Ala Lys Phe Gly Val Phe Ile His Trp
50                  55                  60

Gly Val Phe Ser Val Pro Ala Trp Gly Ser Glu Trp Phe Trp Trp His
65                  70                  75                  80

Trp Gln Gly Glu Gly Arg Pro Gln Tyr Gln Arg Phe Met Arg Asp Asn
                85                  90                  95

Tyr Pro Pro Gly Phe Ser Tyr Ala Asp Phe Gly Pro Gln Phe Thr Ala
            100                 105                 110

Arg Phe Phe His Pro Glu Glu Trp Ala Asp Leu Phe Gln Ala Ala Gly
        115                 120                 125

Ala Lys Tyr Val Val Leu Thr Thr Lys His His Glu Gly Phe Thr Asn
130                 135                 140

Trp Pro Ser Pro Val Ser Trp Asn Trp Asn Ser Lys Asp Val Gly Pro
145                 150                 155                 160

His Arg Asp Leu Val Gly Glu Leu Gly Thr Ala Leu Arg Lys Arg Asn
                165                 170                 175

Ile Arg Tyr Gly Leu Tyr His Ser Leu Leu Glu Trp Phe His Pro Leu
            180                 185                 190

Tyr Leu Leu Asp Lys Lys Asn Gly Phe Lys Thr Gln His Phe Val Ser
        195                 200                 205

Ala Lys Thr Met Pro Glu Leu Tyr Asp Leu Val Asn Ser Tyr Lys Pro
210                 215                 220

Asp Leu Ile Trp Ser Asp Gly Glu Trp Glu Cys Pro Asp Thr Tyr Trp
225                 230                 235                 240

Asn Ser Thr Asn Phe Leu Ser Trp Leu Tyr Asn Asp Ser Pro Val Lys
                245                 250                 255

Asp Glu Val Val Val Asn Asp Arg Trp Gly Gln Asn Cys Ser Cys His
            260                 265                 270

His Gly Gly Tyr Tyr Asn Cys Glu Asp Lys Phe Lys Pro Gln Ser Leu
        275                 280                 285

Pro Asp His Lys Trp Glu Met Cys Thr Ser Ile Asp Lys Phe Ser Trp
290                 295                 300

Gly Tyr Arg Arg Asp Met Ala Leu Ser Asp Val Thr Glu Glu Ser Glu
305                 310                 315                 320

Ile Ile Ser Glu Leu Val Gln Thr Val Ser Leu Gly Gly Asn Tyr Leu
                325                 330                 335

Leu Asn Ile Gly Pro Thr Lys Asp Gly Leu Ile Val Pro Ile Phe Gln
            340                 345                 350

Glu Arg Leu Leu Ala Val Gly Lys Trp Leu Ser Ile Asn Gly Glu Ala
        355                 360                 365

Ile Tyr Ala Ser Lys Pro Trp Arg Val Gln Trp Glu Lys Asn Thr Thr
370                 375                 380
```

```
Ser Val Trp Tyr Thr Ser Lys Gly Ser Ala Val Tyr Ala Ile Phe Leu
385                 390                 395                 400

His Trp Pro Glu Asn Gly Val Leu Asn Leu Glu Ser Pro Ile Thr Thr
                405                 410                 415

Ser Thr Thr Lys Ile Thr Met Leu Gly Ile Gln Gly Asp Leu Lys Trp
            420                 425                 430

Ser Thr Asp Pro Asp Lys Gly Leu Phe Ile Ser Leu Pro Gln Leu Pro
        435                 440                 445

Pro Ser Ala Val Pro Ala Glu Phe Ala Trp Thr Ile Lys Leu Thr Gly
    450                 455                 460

Val Lys
465

<210> SEQ ID NO 34
<211> LENGTH: 743
<212> TYPE: PRT
<213> ORGANISM: Homo sapiens

<400> SEQUENCE: 34

Met Glu Ala Val Ala Val Ala Ala Ala Val Gly Val Leu Leu Leu Ala
1               5                   10                  15

Gly Ala Gly Gly Ala Ala Gly Asp Glu Ala Arg Glu Ala Ala Ala Val
            20                  25                  30

Arg Ala Leu Val Ala Arg Leu Leu Gly Pro Gly Pro Ala Ala Asp Phe
        35                  40                  45

Ser Val Ser Val Glu Arg Ala Leu Ala Ala Lys Pro Gly Leu Asp Thr
    50                  55                  60

Tyr Ser Leu Gly Gly Gly Gly Ala Ala Arg Val Arg Val Arg Gly Ser
65                  70                  75                  80

Thr Gly Val Ala Ala Ala Ala Gly Leu His Arg Tyr Leu Arg Asp Phe
                85                  90                  95

Cys Gly Cys His Val Ala Trp Ser Gly Ser Gln Leu Arg Leu Pro Arg
            100                 105                 110

Pro Leu Pro Ala Val Pro Gly Glu Leu Thr Glu Ala Thr Pro Asn Arg
        115                 120                 125

Tyr Arg Tyr Tyr Gln Asn Val Cys Thr Gln Ser Tyr Ser Phe Val Trp
    130                 135                 140

Trp Asp Trp Ala Arg Trp Glu Arg Glu Ile Asp Trp Met Ala Leu Asn
145                 150                 155                 160

Gly Ile Asn Leu Ala Leu Ala Trp Ser Gly Gln Glu Ala Ile Trp Gln
                165                 170                 175

Arg Val Tyr Leu Ala Leu Gly Leu Thr Gln Ala Glu Ile Asn Glu Phe
            180                 185                 190

Phe Thr Gly Pro Ala Phe Leu Ala Trp Gly Arg Met Gly Asn Leu His
        195                 200                 205

Thr Trp Asp Gly Pro Leu Pro Pro Ser Trp His Ile Lys Gln Leu Tyr
    210                 215                 220

Leu Gln His Arg Val Leu Asp Gln Met Arg Ser Phe Gly Met Thr Pro
225                 230                 235                 240

Val Leu Pro Ala Phe Ala Gly His Val Pro Glu Ala Val Thr Arg Val
                245                 250                 255

Phe Pro Gln Val Asn Val Thr Lys Met Gly Ser Trp Gly His Phe Asn
            260                 265                 270

Cys Ser Tyr Ser Cys Ser Phe Leu Leu Ala Pro Glu Asp Pro Ile Phe
        275                 280                 285
```

```
Pro Ile Ile Gly Ser Leu Phe Leu Arg Glu Leu Ile Lys Glu Phe Gly
    290                 295                 300
Thr Asp His Ile Tyr Gly Ala Asp Thr Phe Asn Glu Met Gln Pro Pro
305                 310                 315                 320
Ser Ser Glu Pro Ser Tyr Leu Ala Ala Thr Thr Ala Val Tyr Glu
                325                 330                 335
Ala Met Thr Ala Val Asp Thr Glu Ala Val Trp Leu Leu Gln Gly Trp
            340                 345                 350
Leu Phe Gln His Gln Pro Gln Phe Trp Gly Pro Ala Gln Ile Arg Ala
        355                 360                 365
Val Leu Gly Ala Val Pro Arg Gly Arg Leu Leu Val Leu Asp Leu Phe
    370                 375                 380
Ala Glu Ser Gln Pro Val Tyr Thr Arg Thr Ala Ser Phe Gln Gly Gln
385                 390                 395                 400
Pro Phe Ile Trp Cys Met Leu His Asn Phe Gly Gly Asn His Gly Leu
                405                 410                 415
Phe Gly Ala Leu Glu Ala Val Asn Gly Gly Pro Glu Ala Ala Arg Leu
            420                 425                 430
Phe Pro Asn Ser Thr Met Val Gly Thr Gly Met Ala Pro Glu Gly Ile
        435                 440                 445
Ser Gln Asn Glu Val Val Tyr Ser Leu Met Ala Glu Leu Gly Trp Arg
    450                 455                 460
Lys Asp Pro Val Pro Asp Leu Ala Ala Trp Val Thr Ser Phe Ala Ala
465                 470                 475                 480
Arg Arg Tyr Gly Val Ser His Pro Asp Ala Gly Ala Ala Trp Arg Leu
                485                 490                 495
Leu Leu Arg Ser Val Tyr Asn Cys Ser Gly Glu Ala Cys Arg Gly His
            500                 505                 510
Asn Arg Ser Pro Leu Val Arg Arg Pro Ser Leu Gln Met Asn Thr Ser
        515                 520                 525
Ile Trp Tyr Asn Arg Ser Asp Val Phe Glu Ala Trp Arg Leu Leu Leu
    530                 535                 540
Thr Ser Ala Pro Ser Leu Ala Thr Ser Pro Ala Phe Arg Tyr Asp Leu
545                 550                 555                 560
Leu Asp Leu Thr Arg Gln Ala Val Gln Glu Leu Val Ser Leu Tyr Tyr
                565                 570                 575
Glu Glu Ala Arg Ser Ala Tyr Leu Ser Lys Glu Leu Ala Ser Leu Leu
            580                 585                 590
Arg Ala Gly Gly Val Leu Ala Tyr Glu Leu Leu Pro Ala Leu Asp Glu
        595                 600                 605
Val Leu Ala Ser Asp Ser Arg Phe Leu Leu Gly Ser Trp Leu Glu Gln
    610                 615                 620
Ala Arg Ala Ala Ala Val Ser Glu Ala Glu Ala Asp Phe Tyr Glu Gln
625                 630                 635                 640
Asn Ser Arg Tyr Gln Leu Thr Leu Trp Gly Pro Glu Gly Asn Ile Leu
                645                 650                 655
Asp Tyr Ala Asn Lys Gln Leu Ala Gly Leu Val Ala Asn Tyr Tyr Thr
            660                 665                 670
Pro Arg Trp Arg Leu Phe Leu Glu Ala Leu Val Asp Ser Val Ala Gln
        675                 680                 685
Gly Ile Pro Phe Gln Gln His Gln Phe Asp Lys Asn Val Phe Gln Leu
    690                 695                 700
```

```
Glu Gln Ala Phe Val Leu Ser Lys Gln Arg Tyr Pro Ser Gln Pro Arg
705                 710                 715                 720

Gly Asp Thr Val Asp Leu Ala Lys Lys Ile Phe Leu Lys Tyr Tyr Pro
                725                 730                 735

Gly Trp Val Ala Gly Ser Trp
            740

<210> SEQ ID NO 35
<211> LENGTH: 411
<212> TYPE: PRT
<213> ORGANISM: Homo sapiens

<400> SEQUENCE: 35

Met Leu Leu Lys Thr Val Leu Leu Gly His Val Ala Gln Val Leu
1               5                   10                  15

Met Leu Asp Asn Gly Leu Leu Gln Thr Pro Met Gly Trp Leu Ala
                20                  25                  30

Trp Glu Arg Phe Arg Cys Asn Ile Asn Cys Asp Glu Asp Pro Lys Asn
                35                  40                  45

Cys Ile Ser Glu Gln Leu Phe Met Glu Met Ala Asp Arg Met Ala Gln
50                  55                  60

Asp Gly Trp Arg Asp Met Gly Tyr Thr Tyr Leu Asn Ile Asp Asp Cys
65                  70                  75                  80

Trp Ile Gly Gly Arg Asp Ala Ser Gly Arg Leu Met Pro Asp Pro Lys
                85                  90                  95

Arg Phe Pro His Gly Ile Pro Phe Leu Ala Asp Tyr Val His Ser Leu
                100                 105                 110

Gly Leu Lys Leu Gly Ile Tyr Ala Asp Met Gly Asn Phe Thr Cys Met
                115                 120                 125

Gly Tyr Pro Gly Thr Thr Leu Asp Lys Val Val Gln Asp Ala Gln Thr
130                 135                 140

Phe Ala Glu Trp Lys Val Asp Met Leu Lys Leu Asp Gly Cys Phe Ser
145                 150                 155                 160

Thr Pro Glu Glu Arg Ala Gln Gly Tyr Pro Lys Met Ala Ala Ala Leu
                165                 170                 175

Asn Ala Thr Gly Arg Pro Ile Ala Phe Ser Cys Ser Trp Pro Ala Tyr
                180                 185                 190

Glu Gly Gly Leu Pro Pro Arg Val Asn Tyr Ser Leu Leu Ala Asp Ile
                195                 200                 205

Cys Asn Leu Trp Arg Asn Tyr Asp Asp Ile Gln Asp Ser Trp Trp Ser
210                 215                 220

Val Leu Ser Ile Leu Asn Trp Phe Val Glu His Gln Asp Ile Leu Gln
225                 230                 235                 240

Pro Val Ala Gly Pro Gly His Trp Asn Asp Pro Asp Met Leu Leu Ile
                245                 250                 255

Gly Asn Phe Gly Leu Ser Leu Glu Gln Ser Arg Ala Gln Met Ala Leu
                260                 265                 270

Trp Thr Val Leu Ala Ala Pro Leu Leu Met Ser Thr Asp Leu Arg Thr
                275                 280                 285

Ile Ser Ala Gln Asn Met Asp Ile Leu Gln Asn Pro Leu Met Ile Lys
                290                 295                 300

Ile Asn Gln Asp Pro Leu Gly Ile Gln Gly Arg Arg Ile His Lys Glu
305                 310                 315                 320

Lys Ser Leu Ile Glu Val Tyr Met Arg Pro Leu Ser Asn Lys Ala Ser
                325                 330                 335
```

```
Ala Leu Val Phe Phe Ser Cys Arg Thr Asp Met Pro Tyr Arg Tyr His
            340                 345                 350

Ser Ser Leu Gly Gln Leu Asn Phe Thr Gly Ser Val Ile Tyr Glu Ala
            355                 360                 365

Gln Asp Val Tyr Ser Gly Asp Ile Ile Ser Gly Leu Arg Asp Glu Thr
370                 375                 380

Asn Phe Thr Val Ile Ile Asn Pro Ser Gly Val Val Met Trp Tyr Leu
385                 390                 395                 400

Tyr Pro Ile Lys Asn Leu Glu Met Ser Gln Gln
                405                 410

<210> SEQ ID NO 36
<211> LENGTH: 529
<212> TYPE: PRT
<213> ORGANISM: Homo sapiens

<400> SEQUENCE: 36

Met Thr Ser Ser Arg Leu Trp Phe Ser Leu Leu Leu Ala Ala Ala Phe
1               5                   10                  15

Ala Gly Arg Ala Thr Ala Leu Trp Pro Trp Pro Gln Asn Phe Gln Thr
            20                  25                  30

Ser Asp Gln Arg Tyr Val Leu Tyr Pro Asn Asn Phe Gln Phe Gln Tyr
        35                  40                  45

Asp Val Ser Ser Ala Ala Gln Pro Gly Cys Ser Val Leu Asp Glu Ala
    50                  55                  60

Phe Gln Arg Tyr Arg Asp Leu Leu Phe Gly Ser Gly Ser Trp Pro Arg
65                  70                  75                  80

Pro Tyr Leu Thr Gly Lys Arg His Thr Leu Glu Lys Asn Val Leu Val
                85                  90                  95

Val Ser Val Val Thr Pro Gly Cys Asn Gln Leu Pro Thr Leu Glu Ser
            100                 105                 110

Val Glu Asn Tyr Thr Leu Thr Ile Asn Asp Asp Gln Cys Leu Leu Leu
        115                 120                 125

Ser Glu Thr Val Trp Gly Ala Leu Arg Gly Leu Glu Thr Phe Ser Gln
    130                 135                 140

Leu Val Trp Lys Ser Ala Glu Gly Thr Phe Phe Ile Asn Lys Thr Glu
145                 150                 155                 160

Ile Glu Asp Phe Pro Arg Phe Pro His Arg Gly Leu Leu Leu Asp Thr
                165                 170                 175

Ser Arg His Tyr Leu Pro Leu Ser Ser Ile Leu Asp Thr Leu Asp Val
            180                 185                 190

Met Ala Tyr Asn Lys Leu Asn Val Phe His Trp His Leu Val Asp Asp
        195                 200                 205

Pro Ser Phe Pro Tyr Glu Ser Phe Thr Phe Pro Glu Leu Met Arg Lys
    210                 215                 220

Gly Ser Tyr Asn Pro Val Thr His Ile Tyr Thr Ala Gln Asp Val Lys
225                 230                 235                 240

Glu Val Ile Glu Tyr Ala Arg Leu Arg Gly Ile Arg Val Leu Ala Glu
                245                 250                 255

Phe Asp Thr Pro Gly His Thr Leu Ser Trp Gly Pro Gly Ile Pro Gly
            260                 265                 270

Leu Leu Thr Pro Cys Tyr Ser Gly Ser Glu Pro Ser Gly Thr Phe Gly
        275                 280                 285

Pro Val Asn Pro Ser Leu Asn Asn Thr Tyr Glu Phe Met Ser Thr Phe
```

```
            290                 295                 300
Phe Leu Glu Val Ser Ser Val Phe Pro Asp Phe Tyr Leu His Leu Gly
305                 310                 315                 320

Gly Asp Glu Val Asp Phe Thr Cys Trp Lys Ser Asn Pro Glu Ile Gln
                325                 330                 335

Asp Phe Met Arg Lys Lys Gly Phe Gly Glu Asp Phe Lys Gln Leu Glu
                340                 345                 350

Ser Phe Tyr Ile Gln Thr Leu Leu Asp Ile Val Ser Ser Tyr Gly Lys
            355                 360                 365

Gly Tyr Val Val Trp Gln Glu Val Phe Asp Asn Lys Val Lys Ile Gln
        370                 375                 380

Pro Asp Thr Ile Ile Gln Val Trp Arg Glu Asp Ile Pro Val Asn Tyr
385                 390                 395                 400

Met Lys Glu Leu Glu Leu Val Thr Lys Ala Gly Phe Arg Ala Leu Leu
                405                 410                 415

Ser Ala Pro Trp Tyr Leu Asn Arg Ile Ser Tyr Gly Pro Asp Trp Lys
                420                 425                 430

Asp Phe Tyr Ile Val Glu Pro Leu Ala Phe Glu Gly Thr Pro Glu Gln
            435                 440                 445

Lys Ala Leu Val Ile Gly Gly Glu Ala Cys Met Trp Gly Glu Tyr Val
        450                 455                 460

Asp Asn Thr Asn Leu Val Pro Arg Leu Trp Pro Arg Ala Gly Ala Val
465                 470                 475                 480

Ala Glu Arg Leu Trp Ser Asn Lys Leu Thr Ser Asp Leu Thr Phe Ala
                485                 490                 495

Tyr Glu Arg Leu Ser His Phe Arg Cys Glu Leu Leu Arg Arg Gly Val
                500                 505                 510

Gln Ala Gln Pro Leu Asn Val Gly Phe Cys Glu Gln Glu Phe Glu Gln
            515                 520                 525

Thr

<210> SEQ ID NO 37
<211> LENGTH: 556
<212> TYPE: PRT
<213> ORGANISM: Homo sapiens

<400> SEQUENCE: 37

Met Glu Leu Cys Gly Leu Gly Leu Pro Arg Pro Pro Met Leu Leu Ala
1               5                   10                  15

Leu Leu Leu Ala Thr Leu Ala Ala Met Leu Ala Leu Leu Thr Gln
            20                  25                  30

Val Ala Leu Val Val Gln Val Ala Glu Ala Ala Arg Ala Pro Ser Val
        35                  40                  45

Ser Ala Lys Pro Gly Pro Ala Leu Trp Pro Leu Pro Leu Ser Val Lys
    50                  55                  60

Met Thr Pro Asn Leu Leu His Leu Ala Pro Glu Asn Phe Tyr Ile Ser
65                  70                  75                  80

His Ser Pro Asn Ser Thr Ala Gly Pro Ser Cys Thr Leu Leu Glu Glu
                85                  90                  95

Ala Phe Arg Arg Tyr His Gly Tyr Ile Phe Gly Phe Tyr Lys Trp His
                100                 105                 110

His Glu Pro Ala Glu Phe Gln Ala Lys Thr Gln Val Gln Gln Leu Leu
            115                 120                 125

Val Ser Ile Thr Leu Gln Ser Glu Cys Asp Ala Phe Pro Asn Ile Ser
```

```
            130                 135                 140
Ser Asp Glu Ser Tyr Thr Leu Leu Val Lys Glu Pro Val Ala Val Leu
145                 150                 155                 160

Lys Ala Asn Arg Val Trp Gly Ala Leu Arg Gly Leu Glu Thr Phe Ser
                165                 170                 175

Gln Leu Val Tyr Gln Asp Ser Tyr Gly Thr Phe Thr Ile Asn Glu Ser
                180                 185                 190

Thr Ile Ile Asp Ser Pro Arg Phe Ser His Arg Gly Ile Leu Ile Asp
                195                 200                 205

Thr Ser Arg His Tyr Leu Pro Val Lys Ile Ile Leu Lys Thr Leu Asp
            210                 215                 220

Ala Met Ala Phe Asn Lys Phe Asn Val Leu His Trp His Ile Val Asp
225                 230                 235                 240

Asp Gln Ser Phe Pro Tyr Gln Ser Ile Thr Phe Pro Glu Leu Ser Asn
                245                 250                 255

Lys Gly Ser Tyr Ser Leu Ser His Val Tyr Thr Pro Asn Asp Val Arg
                260                 265                 270

Met Val Ile Glu Tyr Ala Arg Leu Arg Gly Ile Arg Val Leu Pro Glu
            275                 280                 285

Phe Asp Thr Pro Gly His Thr Leu Ser Trp Gly Lys Gly Gln Lys Asp
290                 295                 300

Leu Leu Thr Pro Cys Tyr Ser Arg Gln Asn Lys Leu Asp Ser Phe Gly
305                 310                 315                 320

Pro Ile Asn Pro Thr Leu Asn Thr Thr Tyr Ser Phe Leu Thr Thr Phe
                325                 330                 335

Phe Lys Glu Ile Ser Glu Val Phe Pro Asp Gln Phe Ile His Leu Gly
                340                 345                 350

Gly Asp Glu Val Glu Phe Lys Cys Trp Glu Ser Asn Pro Lys Ile Gln
            355                 360                 365

Asp Phe Met Arg Gln Lys Gly Phe Gly Thr Asp Phe Lys Lys Leu Glu
            370                 375                 380

Ser Phe Tyr Ile Gln Lys Val Leu Asp Ile Ile Ala Thr Ile Asn Lys
385                 390                 395                 400

Gly Ser Ile Val Trp Gln Glu Val Phe Asp Asp Lys Ala Lys Leu Ala
                405                 410                 415

Pro Gly Thr Ile Val Glu Val Trp Lys Asp Ser Ala Tyr Pro Glu Glu
                420                 425                 430

Leu Ser Arg Val Thr Ala Ser Gly Phe Pro Val Ile Leu Ser Ala Pro
            435                 440                 445

Trp Tyr Leu Asp Leu Ile Ser Tyr Gly Gln Asp Trp Arg Lys Tyr Tyr
                450                 455                 460

Lys Val Glu Pro Leu Asp Phe Gly Gly Thr Gln Lys Gln Lys Gln Leu
465                 470                 475                 480

Phe Ile Gly Gly Glu Ala Cys Leu Trp Gly Glu Tyr Val Asp Ala Thr
                485                 490                 495

Asn Leu Thr Pro Arg Leu Trp Pro Arg Ala Ser Ala Val Gly Glu Arg
                500                 505                 510

Leu Trp Ser Ser Lys Asp Val Arg Asp Met Asp Asp Ala Tyr Asp Arg
            515                 520                 525

Leu Thr Arg His Arg Cys Arg Met Val Glu Arg Gly Ile Ala Ala Gln
            530                 535                 540

Pro Leu Tyr Ala Gly Tyr Cys Asn His Glu Asn Met
545                 550                 555
```

<210> SEQ ID NO 38
<211> LENGTH: 653
<212> TYPE: PRT
<213> ORGANISM: Homo sapiens

<400> SEQUENCE: 38

```
Met Arg Pro Leu Arg Pro Arg Ala Ala Leu Ala Leu Leu Ala Ser
1               5                   10                  15

Leu Leu Ala Ala Pro Pro Val Ala Pro Ala Glu Ala Pro His Leu Val
            20                  25                  30

His Val Asp Ala Arg Ala Leu Trp Pro Leu Arg Arg Phe Trp Arg
            35                  40                  45

Ser Thr Gly Phe Cys Pro Pro Leu Pro His Ser Gln Ala Asp Gln Tyr
50                  55                  60

Val Leu Ser Trp Asp Gln Gln Leu Asn Leu Ala Tyr Val Gly Ala Val
65                  70                  75                  80

Pro His Arg Gly Ile Lys Gln Val Arg Thr His Trp Leu Leu Glu Leu
                85                  90                  95

Val Thr Thr Arg Gly Ser Thr Gly Arg Gly Leu Ser Tyr Asn Phe Thr
            100                 105                 110

His Leu Asp Gly Tyr Leu Asp Leu Leu Arg Glu Asn Gln Leu Leu Pro
            115                 120                 125

Gly Phe Glu Leu Met Gly Ser Ala Ser Gly His Phe Thr Asp Phe Glu
        130                 135                 140

Asp Lys Gln Gln Val Phe Glu Trp Lys Asp Leu Val Ser Ser Leu Ala
145                 150                 155                 160

Arg Arg Tyr Ile Gly Arg Tyr Gly Leu Ala His Val Ser Lys Trp Asn
                165                 170                 175

Phe Glu Thr Trp Asn Glu Pro Asp His His Asp Phe Asp Asn Val Ser
            180                 185                 190

Met Thr Met Gln Gly Phe Leu Asn Tyr Tyr Asp Ala Cys Ser Glu Gly
        195                 200                 205

Leu Arg Ala Ala Ser Pro Ala Leu Arg Leu Gly Gly Pro Gly Asp Ser
210                 215                 220

Phe His Thr Pro Pro Arg Ser Pro Leu Ser Trp Gly Leu Leu Arg His
225                 230                 235                 240

Cys His Asp Gly Thr Asn Phe Phe Thr Gly Glu Ala Gly Val Arg Leu
                245                 250                 255

Asp Tyr Ile Ser Leu His Arg Lys Gly Ala Arg Ser Ser Ile Ser Ile
            260                 265                 270

Leu Glu Gln Glu Lys Val Val Ala Gln Gln Ile Arg Gln Leu Phe Pro
        275                 280                 285

Lys Phe Ala Asp Thr Pro Ile Tyr Asn Asp Glu Ala Asp Pro Leu Val
290                 295                 300

Gly Trp Ser Leu Pro Gln Pro Trp Arg Ala Asp Val Thr Tyr Ala Ala
305                 310                 315                 320

Met Val Val Lys Val Ile Ala Gln His Gln Asn Leu Leu Leu Ala Asn
                325                 330                 335

Thr Thr Ser Ala Phe Pro Tyr Ala Leu Leu Ser Asn Asp Asn Ala Phe
            340                 345                 350

Leu Ser Tyr His Pro His Pro Phe Ala Gln Arg Thr Leu Thr Ala Arg
        355                 360                 365

Phe Gln Val Asn Asn Thr Arg Pro Pro His Val Gln Leu Leu Arg Lys
```

```
            370                 375                 380
Pro Val Leu Thr Ala Met Gly Leu Ala Leu Leu Asp Glu Glu Gln
385                 390                 395                 400

Leu Trp Ala Glu Val Ser Gln Ala Gly Thr Val Leu Asp Ser Asn His
                405                 410                 415

Thr Val Gly Val Leu Ala Ser Ala His Arg Pro Gln Gly Pro Ala Asp
                420                 425                 430

Ala Trp Arg Ala Ala Val Leu Ile Tyr Ala Ser Asp Asp Thr Arg Ala
                435                 440                 445

His Pro Asn Arg Ser Val Ala Val Thr Leu Arg Leu Arg Gly Val Pro
    450                 455                 460

Pro Gly Pro Gly Leu Val Tyr Val Thr Arg Tyr Leu Asp Asn Gly Leu
465                 470                 475                 480

Cys Ser Pro Asp Gly Glu Trp Arg Arg Leu Gly Arg Pro Val Phe Pro
                    485                 490                 495

Thr Ala Glu Gln Phe Arg Arg Met Arg Ala Ala Glu Asp Pro Val Ala
                500                 505                 510

Ala Ala Pro Arg Pro Leu Pro Ala Gly Gly Arg Leu Thr Leu Arg Pro
                515                 520                 525

Ala Leu Arg Leu Pro Ser Leu Leu Val His Val Cys Ala Arg Pro
530                 535                 540

Glu Lys Pro Pro Gly Gln Val Thr Arg Leu Arg Ala Leu Pro Leu Thr
545                 550                 555                 560

Gln Gly Gln Leu Val Leu Val Trp Ser Asp Glu His Val Gly Ser Lys
                565                 570                 575

Cys Leu Trp Thr Tyr Glu Ile Gln Phe Ser Gln Asp Gly Lys Ala Tyr
                580                 585                 590

Thr Pro Val Ser Arg Lys Pro Ser Thr Phe Asn Leu Phe Val Phe Ser
                595                 600                 605

Pro Asp Thr Gly Ala Val Ser Gly Ser Tyr Arg Val Arg Ala Leu Asp
                610                 615                 620

Tyr Trp Ala Arg Pro Gly Pro Phe Ser Asp Pro Val Pro Tyr Leu Glu
625                 630                 635                 640

Val Pro Val Pro Arg Gly Pro Pro Ser Pro Gly Asn Pro
                    645                 650

<210> SEQ ID NO 39
<211> LENGTH: 651
<212> TYPE: PRT
<213> ORGANISM: Homo sapiens

<400> SEQUENCE: 39

Met Ala Arg Gly Ser Ala Val Trp Ala Ala Leu Gly Pro Leu Leu
1               5                   10                  15

Trp Gly Cys Ala Leu Gly Leu Gln Gly Gly Met Leu Tyr Pro Gln Glu
                20                  25                  30

Ser Pro Ser Arg Glu Cys Lys Glu Leu Asp Gly Leu Trp Ser Phe Arg
                35                  40                  45

Ala Asp Phe Ser Asp Asn Arg Arg Arg Gly Phe Glu Glu Gln Trp Tyr
    50                  55                  60

Arg Arg Pro Leu Trp Glu Ser Gly Pro Thr Val Asp Met Pro Val Pro
65              70                  75                  80

Ser Ser Phe Asn Asp Ile Ser Gln Asp Trp Arg Leu Arg His Phe Val
                85                  90                  95
```

-continued

```
Gly Trp Val Trp Tyr Glu Arg Glu Val Ile Leu Pro Glu Arg Trp Thr
                100                 105                 110
Gln Asp Leu Arg Thr Arg Val Val Leu Arg Ile Gly Ser Ala His Ser
            115                 120                 125
Tyr Ala Ile Val Trp Val Asn Gly Val Asp Thr Leu Glu His Glu Gly
        130                 135                 140
Gly Tyr Leu Pro Phe Glu Ala Asp Ile Ser Asn Leu Val Gln Val Gly
145                 150                 155                 160
Pro Leu Pro Ser Arg Leu Arg Ile Thr Ile Ala Ile Asn Asn Thr Leu
                165                 170                 175
Thr Pro Thr Thr Leu Pro Pro Gly Thr Ile Gln Tyr Leu Thr Asp Thr
            180                 185                 190
Ser Lys Tyr Pro Lys Gly Tyr Phe Val Gln Asn Thr Tyr Phe Asp Phe
        195                 200                 205
Phe Asn Tyr Ala Gly Leu Gln Arg Ser Val Leu Leu Tyr Thr Thr Pro
210                 215                 220
Thr Thr Tyr Ile Asp Asp Ile Thr Val Thr Thr Ser Val Glu Gln Asp
225                 230                 235                 240
Ser Gly Leu Val Asn Tyr Gln Ile Ser Val Lys Gly Ser Asn Leu Phe
                245                 250                 255
Lys Leu Glu Val Arg Leu Leu Asp Ala Glu Asn Lys Val Val Ala Asn
            260                 265                 270
Gly Thr Gly Thr Gln Gly Gln Leu Lys Val Pro Gly Val Ser Leu Trp
        275                 280                 285
Trp Pro Tyr Leu Met His Glu Arg Pro Ala Tyr Leu Tyr Ser Leu Glu
290                 295                 300
Val Gln Leu Thr Ala Gln Thr Ser Leu Gly Pro Val Ser Asp Phe Tyr
305                 310                 315                 320
Thr Leu Pro Val Gly Ile Arg Thr Val Ala Val Thr Lys Ser Gln Phe
                325                 330                 335
Leu Ile Asn Gly Lys Pro Phe Tyr Phe His Gly Val Asn Lys His Glu
            340                 345                 350
Asp Ala Asp Ile Arg Gly Lys Gly Phe Asp Trp Pro Leu Leu Val Lys
        355                 360                 365
Asp Phe Asn Leu Leu Arg Trp Leu Gly Ala Asn Ala Phe Arg Thr Ser
370                 375                 380
His Tyr Pro Tyr Ala Glu Glu Val Met Gln Met Cys Asp Arg Tyr Gly
385                 390                 395                 400
Ile Val Val Ile Asp Glu Cys Pro Gly Val Gly Leu Ala Leu Pro Gln
                405                 410                 415
Phe Phe Asn Asn Val Ser Leu His His Met Gln Val Met Glu Glu
            420                 425                 430
Val Val Arg Arg Asp Lys Asn His Pro Ala Val Val Met Trp Ser Val
        435                 440                 445
Ala Asn Glu Pro Ala Ser His Leu Glu Ser Ala Gly Tyr Tyr Leu Lys
450                 455                 460
Met Val Ile Ala His Thr Lys Ser Leu Asp Pro Ser Arg Pro Val Thr
465                 470                 475                 480
Phe Val Ser Asn Ser Asn Tyr Ala Ala Asp Lys Gly Ala Pro Tyr Val
                485                 490                 495
Asp Val Ile Cys Leu Asn Ser Tyr Tyr Ser Trp Tyr His Asp Tyr Gly
            500                 505                 510
His Leu Glu Leu Ile Gln Leu Gln Leu Ala Thr Gln Phe Glu Asn Trp
```

```
            515                 520                 525
Tyr Lys Lys Tyr Gln Lys Pro Ile Ile Gln Ser Glu Tyr Gly Ala Glu
        530                 535                 540

Thr Ile Ala Gly Phe His Gln Asp Pro Leu Met Phe Thr Glu Glu
545                 550                 555                 560

Tyr Gln Lys Ser Leu Leu Glu Gln Tyr His Leu Gly Leu Asp Gln Lys
                565                 570                 575

Arg Arg Lys Tyr Val Val Gly Glu Leu Ile Trp Asn Phe Ala Asp Phe
            580                 585                 590

Met Thr Glu Gln Ser Pro Thr Arg Val Leu Gly Asn Lys Lys Gly Ile
        595                 600                 605

Phe Thr Arg Gln Arg Gln Pro Lys Ser Ala Ala Phe Leu Leu Arg Glu
    610                 615                 620

Arg Tyr Trp Lys Ile Ala Asn Glu Thr Arg Tyr Pro His Ser Val Ala
625                 630                 635                 640

Lys Ser Gln Cys Leu Glu Asn Ser Leu Phe Thr
                645                 650

<210> SEQ ID NO 40
<211> LENGTH: 415
<212> TYPE: PRT
<213> ORGANISM: Homo sapiens

<400> SEQUENCE: 40

Met Thr Gly Glu Arg Pro Ser Thr Ala Leu Pro Asp Arg Arg Trp Gly
1               5                   10                  15

Pro Arg Ile Leu Gly Phe Trp Gly Gly Cys Arg Val Trp Val Phe Ala
            20                  25                  30

Ala Ile Phe Leu Leu Leu Ser Leu Ala Ala Ser Trp Ser Lys Ala Glu
        35                  40                  45

Asn Asp Phe Gly Leu Val Gln Pro Leu Val Thr Met Glu Gln Leu Leu
    50                  55                  60

Trp Val Ser Gly Arg Gln Ile Gly Ser Val Asp Thr Phe Arg Ile Pro
65                  70                  75                  80

Leu Ile Thr Ala Thr Pro Arg Gly Thr Leu Leu Ala Phe Ala Glu Ala
                85                  90                  95

Arg Lys Met Ser Ser Ser Asp Glu Gly Ala Lys Phe Ile Ala Leu Arg
            100                 105                 110

Arg Ser Met Asp Gln Gly Ser Thr Trp Ser Pro Thr Ala Phe Ile Val
        115                 120                 125

Asn Asp Gly Asp Val Pro Asp Gly Leu Asn Leu Gly Ala Val Val Ser
    130                 135                 140

Asp Val Glu Thr Gly Val Val Phe Leu Phe Tyr Ser Leu Cys Ala His
145                 150                 155                 160

Lys Ala Gly Cys Gln Val Ala Ser Thr Met Leu Val Trp Ser Lys Asp
                165                 170                 175

Asp Gly Val Ser Trp Ser Thr Pro Arg Asn Leu Ser Leu Asp Ile Gly
            180                 185                 190

Thr Glu Val Phe Ala Pro Gly Pro Gly Ser Gly Ile Gln Lys Gln Arg
        195                 200                 205

Glu Pro Arg Lys Gly Arg Leu Ile Val Cys Gly His Gly Thr Leu Glu
    210                 215                 220

Arg Asp Gly Val Phe Cys Leu Leu Ser Asp Asp His Gly Ala Ser Trp
225                 230                 235                 240
```

```
Arg Tyr Gly Ser Gly Val Ser Gly Ile Pro Tyr Gly Gln Pro Lys Gln
                245                 250                 255

Glu Asn Asp Phe Asn Pro Asp Glu Cys Gln Pro Tyr Glu Leu Pro Asp
            260                 265                 270

Gly Ser Val Val Ile Asn Ala Arg Asn Gln Asn Asn Tyr His Cys His
        275                 280                 285

Cys Arg Ile Val Leu Arg Ser Tyr Asp Ala Cys Asp Thr Leu Arg Pro
    290                 295                 300

Arg Asp Val Thr Phe Asp Pro Glu Leu Val Asp Pro Val Val Ala Ala
305                 310                 315                 320

Gly Ala Val Val Thr Ser Ser Gly Ile Val Phe Phe Ser Asn Pro Ala
                325                 330                 335

His Pro Glu Phe Arg Val Asn Leu Thr Leu Arg Trp Ser Phe Ser Asn
            340                 345                 350

Gly Thr Ser Trp Arg Lys Glu Thr Val Gln Leu Trp Pro Gly Pro Ser
        355                 360                 365

Gly Tyr Ser Ser Leu Ala Thr Leu Glu Gly Ser Met Asp Gly Glu Glu
    370                 375                 380

Gln Ala Pro Gln Leu Tyr Val Leu Tyr Glu Lys Gly Arg Asn His Tyr
385                 390                 395                 400

Thr Glu Ser Ile Ser Val Ala Lys Ile Ser Val Tyr Gly Thr Leu
                405                 410                 415

<210> SEQ ID NO 41
<211> LENGTH: 550
<212> TYPE: PRT
<213> ORGANISM: Homo sapiens

<400> SEQUENCE: 41

Met Pro Pro Arg Thr Gly Arg Gly Leu Leu Trp Leu Gly Leu Val
1               5                   10                  15

Leu Ser Ser Val Cys Val Ala Leu Gly Ser Glu Thr Gln Ala Asn Ser
                20                  25                  30

Thr Thr Asp Ala Leu Asn Val Leu Leu Ile Ile Val Asp Asp Leu Arg
            35                  40                  45

Pro Ser Leu Gly Cys Tyr Gly Asp Lys Leu Val Arg Ser Pro Asn Ile
        50                  55                  60

Asp Gln Leu Ala Ser His Ser Leu Leu Phe Gln Asn Ala Phe Ala Gln
65                  70                  75                  80

Gln Ala Val Cys Ala Pro Ser Arg Val Ser Phe Leu Thr Gly Arg Arg
                85                  90                  95

Pro Asp Thr Thr Arg Leu Tyr Asp Phe Asn Ser Tyr Trp Arg Val His
            100                 105                 110

Ala Gly Asn Phe Ser Thr Ile Pro Gln Tyr Phe Lys Glu Asn Gly Tyr
        115                 120                 125

Val Thr Met Ser Val Gly Lys Val Phe His Pro Gly Ile Ser Ser Asn
    130                 135                 140

His Thr Asp Asp Ser Pro Tyr Ser Trp Ser Phe Pro Pro Tyr His Pro
145                 150                 155                 160

Ser Ser Glu Lys Tyr Glu Asn Thr Lys Thr Cys Arg Gly Pro Asp Gly
                165                 170                 175

Glu Leu His Ala Asn Leu Leu Cys Pro Val Asp Val Leu Asp Val Pro
            180                 185                 190

Glu Gly Thr Leu Pro Asp Lys Gln Ser Thr Glu Gln Ala Ile Gln Leu
        195                 200                 205
```

Leu Glu Lys Met Lys Thr Ser Ala Ser Pro Phe Phe Leu Ala Val Gly
210                 215                 220

Tyr His Lys Pro His Ile Pro Phe Arg Tyr Pro Lys Glu Phe Gln Lys
225                 230                 235                 240

Leu Tyr Pro Leu Glu Asn Ile Thr Leu Ala Pro Asp Pro Glu Val Pro
            245                 250                 255

Asp Gly Leu Pro Pro Val Ala Tyr Asn Pro Trp Met Asp Ile Arg Gln
        260                 265                 270

Arg Glu Asp Val Gln Ala Leu Asn Ile Ser Val Pro Tyr Gly Pro Ile
    275                 280                 285

Pro Val Asp Phe Gln Arg Lys Ile Arg Gln Ser Tyr Phe Ala Ser Val
290                 295                 300

Ser Tyr Leu Asp Thr Gln Val Gly Arg Leu Leu Ser Ala Leu Asp Asp
305                 310                 315                 320

Leu Gln Leu Ala Asn Ser Thr Ile Ile Ala Phe Thr Ser Asp His Gly
                325                 330                 335

Trp Ala Leu Gly Glu His Gly Glu Trp Ala Lys Tyr Ser Asn Phe Asp
            340                 345                 350

Val Ala Thr His Val Pro Leu Ile Phe Tyr Val Pro Gly Arg Thr Ala
        355                 360                 365

Ser Leu Pro Glu Ala Gly Glu Lys Leu Phe Pro Tyr Leu Asp Pro Phe
    370                 375                 380

Asp Ser Ala Ser Gln Leu Met Glu Pro Gly Arg Gln Ser Met Asp Leu
385                 390                 395                 400

Val Glu Leu Val Ser Leu Phe Pro Thr Leu Ala Gly Leu Ala Gly Leu
                405                 410                 415

Gln Val Pro Pro Arg Cys Pro Val Pro Ser Phe His Val Glu Leu Cys
            420                 425                 430

Arg Glu Gly Lys Asn Leu Leu Lys His Phe Arg Phe Arg Asp Leu Glu
        435                 440                 445

Glu Asp Pro Tyr Leu Pro Gly Asn Pro Arg Glu Leu Ile Ala Tyr Ser
    450                 455                 460

Gln Tyr Pro Arg Pro Ser Asp Ile Pro Gln Trp Asn Ser Asp Lys Pro
465                 470                 475                 480

Ser Leu Lys Asp Ile Lys Ile Met Gly Tyr Ser Ile Arg Thr Ile Asp
                485                 490                 495

Tyr Arg Tyr Thr Val Trp Val Gly Phe Asn Pro Asp Glu Phe Leu Ala
            500                 505                 510

Asn Phe Ser Asp Ile His Ala Gly Glu Leu Tyr Phe Val Asp Ser Asp
        515                 520                 525

Pro Leu Gln Asp His Asn Met Tyr Asn Asp Ser Gln Gly Gly Asp Leu
    530                 535                 540

Phe Gln Leu Leu Met Pro
545                 550

<210> SEQ ID NO 42
<211> LENGTH: 629
<212> TYPE: PRT
<213> ORGANISM: Homo sapiens

<400> SEQUENCE: 42

Met Pro Arg Tyr Gly Ala Ser Leu Arg Gln Ser Cys Pro Arg Ser Gly
1               5                   10                  15

Arg Glu Gln Gly Gln Asp Gly Thr Ala Gly Ala Pro Gly Leu Leu Trp

```
            20                  25                  30
Met Gly Leu Val Leu Ala Leu Ala Leu Ala Leu Ala Leu Ser
            35                  40                  45

Asp Ser Arg Val Leu Trp Ala Pro Ala Glu Ala His Pro Leu Ser Pro
50                  55                  60

Gln Gly His Pro Ala Arg Leu His Arg Ile Val Pro Arg Leu Arg Asp
65                  70                  75                  80

Val Phe Gly Trp Gly Asn Leu Thr Cys Pro Ile Cys Lys Gly Leu Phe
                85                  90                  95

Thr Ala Ile Asn Leu Gly Leu Lys Lys Glu Pro Asn Val Ala Arg Val
                100                 105                 110

Gly Ser Val Ala Ile Lys Leu Cys Asn Leu Leu Lys Ile Ala Pro Pro
                115                 120                 125

Ala Val Cys Gln Ser Ile Val His Leu Phe Glu Asp Asp Met Val Glu
                130                 135                 140

Val Trp Arg Arg Ser Val Leu Ser Pro Ser Glu Ala Cys Gly Leu Leu
145                 150                 155                 160

Leu Gly Ser Thr Cys Gly His Trp Asp Ile Phe Ser Ser Trp Asn Ile
                165                 170                 175

Ser Leu Pro Thr Val Pro Lys Pro Pro Lys Pro Ser Pro Pro
                180                 185                 190

Ala Pro Gly Ala Pro Val Ser Arg Ile Leu Phe Leu Thr Asp Leu His
                195                 200                 205

Trp Asp His Asp Tyr Leu Glu Gly Thr Asp Pro Asp Cys Ala Asp Pro
                210                 215                 220

Leu Cys Cys Arg Arg Gly Ser Gly Leu Pro Pro Ala Ser Arg Pro Gly
225                 230                 235                 240

Ala Gly Tyr Trp Gly Glu Tyr Ser Lys Cys Asp Leu Pro Leu Arg Thr
                245                 250                 255

Leu Glu Ser Leu Leu Ser Gly Leu Gly Pro Ala Gly Pro Phe Asp Met
                260                 265                 270

Val Tyr Trp Thr Gly Asp Ile Pro Ala His Asp Val Trp His Gln Thr
                275                 280                 285

Arg Gln Asp Gln Leu Arg Ala Leu Thr Thr Val Thr Ala Leu Val Arg
                290                 295                 300

Lys Phe Leu Gly Pro Val Pro Val Tyr Pro Ala Val Gly Asn His Glu
305                 310                 315                 320

Ser Ile Pro Val Asn Ser Phe Pro Pro Phe Ile Glu Gly Asn His
                325                 330                 335

Ser Ser Arg Trp Leu Tyr Glu Ala Met Ala Lys Ala Trp Glu Pro Trp
                340                 345                 350

Leu Pro Ala Glu Ala Leu Arg Thr Leu Arg Ile Gly Gly Phe Tyr Ala
                355                 360                 365

Leu Ser Pro Tyr Pro Gly Leu Arg Leu Ile Ser Leu Asn Met Asn Phe
                370                 375                 380

Cys Ser Arg Glu Asn Phe Trp Leu Leu Ile Asn Ser Thr Asp Pro Ala
385                 390                 395                 400

Gly Gln Leu Gln Trp Leu Val Gly Glu Leu Gln Ala Ala Glu Asp Arg
                405                 410                 415

Gly Asp Lys Val His Ile Ile Gly His Ile Pro Pro Gly His Cys Leu
                420                 425                 430

Lys Ser Trp Ser Trp Asn Tyr Tyr Arg Ile Val Ala Arg Tyr Glu Asn
                435                 440                 445
```

```
Thr Leu Ala Ala Gln Phe Phe Gly His Thr His Val Asp Glu Phe Glu
    450                 455                 460
Val Phe Tyr Asp Glu Glu Thr Leu Ser Arg Pro Leu Ala Val Ala Phe
465                 470                 475                 480
Leu Ala Pro Ser Ala Thr Thr Tyr Ile Gly Leu Asn Pro Gly Tyr Arg
                485                 490                 495
Val Tyr Gln Ile Asp Gly Asn Tyr Ser Arg Ser His Val Val Leu
            500                 505                 510
Asp His Glu Thr Tyr Ile Leu Asn Leu Thr Gln Ala Asn Ile Pro Gly
            515                 520                 525
Ala Ile Pro His Trp Gln Leu Leu Tyr Arg Ala Arg Glu Thr Tyr Gly
        530                 535                 540
Leu Pro Asn Thr Leu Pro Thr Ala Trp His Asn Leu Val Tyr Arg Met
545                 550                 555                 560
Arg Gly Asp Met Gln Leu Phe Gln Thr Phe Trp Phe Leu Tyr His Lys
                565                 570                 575
Gly His Pro Pro Ser Glu Pro Cys Gly Thr Pro Cys Arg Leu Ala Thr
            580                 585                 590
Leu Cys Ala Gln Leu Ser Ala Arg Ala Asp Ser Pro Ala Leu Cys Arg
        595                 600                 605
His Leu Met Pro Asp Gly Ser Leu Pro Glu Ala Gln Ser Leu Trp Pro
610                 615                 620
Arg Pro Leu Phe Cys
625

<210> SEQ ID NO 43
<211> LENGTH: 6
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 43

Lys Thr Lys Glu Gly Val
1               5

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
cgacttccag ttatccaact t                                           21

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ggcagctgga aagacaaaag                                             20

<210> SEQ ID NO 46
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
cagctccctc cactgtcttc                                                   20

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
gccaggctca tcggattctt c                                                 21

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
cacggggtca agagagtcac                                                   20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
agccatgtac gtagccatcc                                                   20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
ctctcagctg tggtggtgaa                                                   20
```

TREATMENT OF PROTEINOPATHIES

CROSS-REFERENCE TO RELATED APPLICATIONS

This Application is a 35 U.S.C. §371 National Phase Entry Application of International Application No. PCT/US2012/043732 filed Jun. 22, 2012, which designates the U.S., and which claims benefit under 35 U.S.C. §119(e) of U.S. Provisional Application No. 61/499,930, filed on Jun. 22, 2011, the contents of each of which are herein incorporated by reference in their entirety.

FEDERAL FUNDING

This invention was made with Government support under grants RO1NS051303 and F32NS066730 awarded by the National Institute of Health. The Government has certain rights in the invention.

SEQUENCE LISTING

The instant application contains a Sequence Listing which has been submitted in ASCII format via EFS-Web and is hereby incorporated by reference in its entirety. Said ASCII copy, created on Dec. 18, 2013, is named 32587298.txt and is 188,009 bytes in size.

BACKGROUND

Proteinopathies are diseases, disorders, and/or conditions associated with abnormalities in the production, folding, aggregation, metabolism, or degradation of proteins. Typically, proteinopathies are associated with and/or characterized by accumulation of one or more particular proteins into aggregates. Protein aggregates are observed in a variety of different types of diseases, disorders, and/or conditions, including cognitive impairment disorders, proliferative diseases, inflammatory diseases, cardiovascular diseases, immunologic diseases, ocular diseases, mitochondrial diseases, neurodegenerative diseases, and lysosomal storage diseases.

SUMMARY

The present invention encompasses the finding that activation of lysosomal enzymes, through increased levels and/or increased activity, can provide effective treatment for, and even prophylaxis of, certain proteinopathies. For example, the present invention provides novel insights into lysosomal activity and its effects on protein aggregation, and demonstrates that biochemical pathways linked to lysosomal function regulate levels of protein aggregation in various contexts, specifically including various cell cultures (including both neuronal and non-neuronal cultures), mammalian organisms (e.g., mice), and human brain. The present invention specifically encompasses the insight that, in some instances, increased trafficking of lysosomal enzymes can provide effective treatment (and/or prophylaxis) of certain proteinopathies.

The present invention provides the specific and surprising finding that, in some embodiments, increasing level and/or activity of lysosomal enzymes can provide effective treatment of, and in some embodiments prophylaxis of, proteinopathies other than lysosomal storage diseases. The present invention teaches particularly that increasing level and/or activity of lysosomal enzymes can provide effective treatment of, and in some embodiments prophylaxis of, certain neurodegenerative diseases, disorders, and/or conditions. In some particular embodiments, the present invention demonstrates that increasing level and/or activity of lysosomal enzymes can provide effective treatment of, and in some embodiments prophylaxis of, Parkinson's Disease.

The present invention encompasses the particular finding that increasing level and/or activity of lysosomal enzyme, glucocerebrosidase (GCase), can provide effective treatment, and even prophylaxis of, certain proteinopathies.

The present invention encompasses the particular finding that increasing lysosomal degradation capacity can provide effective treatment for, and even prophylaxis of, certain proteinopathies.

The present invention provides the specific finding that activating GCase activity in brain cells reduces α-synuclein levels in those cells. In accordance with the present invention, activation of GCase at a level that will reduce glucosylceramide (GlcCer) substrate levels may deplete or reverse aggregates (e.g., α-synuclein aggregates) that have already formed, and also prevent there ability to disseminate from cell-to-cell. The present invention further specifically provides a variety of approaches for lowering glucosylceramide levels, including, for example, increasing levels and/or activity of glucocerebrosidase (GCase) polypeptide and/or reducing GCase substrate levels by inhibition of glucosylceramide synthase.

In some embodiments, levels and/or activity of GCase polypeptide is increased by small molecules. In some embodiments, the small molecules bind directly to GCase polypeptide. In some embodiments, the small molecules bind at a site apart for the GCase polypeptide's catalytic or active site.

In some embodiments, GCase polypeptide is wild-type. In some embodiments, GCase polypeptide is mutant.

The present invention provides specific finding that gangliosides influence stabilization and enhancement of α-synuclein aggregates. In accordance with the present invention, activation of sphingolipid metabolizing enzymes (e.g., β-hexosaminidase or β-galactosidase isoform 1) at a level that will reduce sphingolipid substrate levels may deplete or reverse aggregates (e.g., α-synuclein aggregates) that have already formed, and also prevent there ability to disseminate from cell-to-cell.

In some particular embodiments, saposin polypeptides are useful in the treatment of proteinopathies.

The present invention further encompasses the finding that, at least in some embodiments, existence and/or degree of protein aggregate accumulation in a proteinopathy may be impacted by activity of $Ca^{2+}$ signaling pathway. In some particular embodiments, existence and/or degree of protein aggregate accumulation is affected by $Ca^{2+}$ channel-mediated signaling. In some embodiments, therefore, the present invention provides methods and reagents for treating gain of function proteinopathic diseases, disorders, and/or conditions with agents that block $Ca^{2+}$ channels; in some embodiments, such agents affect protein folding of one or more lysosomal enzymes, and therefore affect level and/or activity of such enzymes in the lysosome.

The present invention further encompasses the demonstration that, at least in some embodiments, existence or extent of aggregate accumulation may be affected by oxidative stress and/or may not be affected by level and/or activity of at least a particular lysosomal enzyme (e.g., GCase). In some embodiments, therefore, the present invention provides methods and reagents for treating lysosomal storage diseases with agents that affect oxidative stress, as an alternative to or in addition to agents that affect level and/or activity of one or more lysosomal enzymes (e.g., in the lysosome).

Still further, the present invention encompasses the demonstration that, at least on some embodiments, existence and/or degree of protein aggregate accumulation in a proteinopathy may be impacted by activity of protein trafficking pathways. In some particular embodiments, existence and/or degree of protein aggregate accumulation is affected by trafficking of one or more lysosomal enzymes. In some embodiments, therefore, the present invention provides methods and reagents for treating lysosomal storage diseases with agents that affect protein trafficking; in some embodiments, such agents affect protein trafficking of one or more lysosomal enzymes, and therefore affect level and/or activity of such enzymes in the lysosome.

The present invention provides the specific finding that improving lysosomal function through improved trafficking of lysosomal enzymes from the endoplasmic reticulum to the golgi apparatus then finally to the endosome-lysosome system through enhancement of Rab function and/or activation of GCase, results in enhancement of lysosomal proteolysis. In some embodiments, lysosomal proteolysis is enhanced by enhancement of proteolytic activity of acid hydrolases (enzymes that are commonly located in the lysosomes and have optimum enzymatic activity at acidic pHs, e.g., nucleases, proteases, glycosidases, lipases, phosphatases, sulfatases, phospholipases, and all lysosomal enzymes). In some embodiments, lysosomal proteolysis is enhanced by enhancement of the absolute number of lysosomal vesicles. In some embodiments, lysosomal proteolysis is enhanced by enhancement of the amount of acid hydrolases per lysosomal compartment. In some embodiments, lysosomal proteolysis is enhanced by enhancement of the exocytosis of cellular storage materials. The present invention teaches particularly that increasing trafficking of lysosomal enzymes can provide effective treatment of, and in some embodiments prophylaxis of, certain neurodegenerative diseases, disorders, and/or conditions.

In some particular embodiments, Rab1a polypeptide is useful in the treatment of lysosomal storage diseases as well as other types of proteinopathies.

In some particular embodiments, antioxidants are useful in the treatment of lysosomal storage diseases as well as other types of proteinopathies.

BRIEF DESCRIPTION OF THE DRAWINGS

The Figures of the Drawing are for illustration purposes only, not for limitation.

FIGS. 1A-1G show that GCase polypeptide knockdown (KD) results in compromised lysosomal degradation and causes accumulation of α-synuclein. (FIG. 1A) KD of GCase polypeptide in cortical neurons by GCase polypeptide shRNA is shown by western blot. Neural specific enolase (NSE) was used as a loading control. Four replicates are shown. Scrb, scrambled shRNA. (FIG. 1B) Left: GCase polypeptide levels (n=6, *p<0.01). Middle: Enzymatic activity of GCase polypeptide (n=6, *p<0.01). Right: Intracellular GlcCer quantification by MS (Pi, phosphate) (n=3, *p<0.05). (FIG. 1C) GlcCer immunofluorescence (top) and neutral lipids were visualized by BODIPY 493 fluorescence (bottom). Nuclei were visualized with DAPI. The arrows indicate cells with increased diffuse staining, whereas the arrowhead indicates a cell with punctated lipid accumulations. (FIG. 1D) Fluorescent intensity shown in (FIG. 1C) was quantified and normalized to DAPI (n=3, *p<0.05). (FIG. 1E) Proteolysis of long-lived proteins in neurons assessed at 8 hr. Lysosomal inhibitors leupeptin (leu) and ammonium chloride ($NH_4Cl$) were used (n=4, *p<0.05). (FIG. 1F) Western blot of endogenous α-synuclein (mAb syn202) and Tau. Four replicates are shown. Protein and mRNA levels are shown under the blots (n=4, *p<0.05). α-Tub was used as a loading control. (FIG. 1G) α-synuclein analysis in inducible H4 cells. Expression was turned off by doxycycline (DOX) and protein clearance was measured by western blot with mAb syn211. Quantifications are shown below (n=6, *p<0.05). GCase polypeptide KD is shown by western blot and α-tub was used as a loading control. Molecular weight (MW) is indicated in kDa. For all analyses, values are the mean±standard error of the mean (SEM).

(FIG. 2A) Lysates from transduced primary neurons were digested with endoglycosidase H (endo H) or PNGase. Nonspecific band (N.S.) is noted. N.T., not transduced. (FIG. 2B) Radioactive pulse-chase was performed in N2a cells as described in FIG. 1E. Leupeptin (leu), ammonium chloride ($NH_4Cl$) (n=3, values are the mean±SEM, *p<0.05). (FIG. 2C) Primary neurons were infected with scrb or GCase polypeptide shRNA constructs, and the levels of lysosomal proteins were determined by western blot. Right: Western blots were quantified by densitometry (n=3, values are the mean±SEM. *p<0.05). M, MW marker. Three separate experiments are shown. Protein MW is indicated in kilodaltons (kDa). (FIG. 2D) Measurement of sphingolipids upon GCase polypeptide knock-down in neurons by LC/MS/MS analysis. Cer, ceramide; Sph 1-P, sphingosine-1-phosphate; Sph, sphingosine; dh Sph 1-P, dihydrosphingosine-1-phosphate; dh Sph, dihydrosphingosine; dhC16-Cer, dihydroceramide. (n=3, values are the mean±SEM). (FIG. 2E) β-Hexosaminidase (Hex) activity measurements in transduced neurons (n=3, values are the mean±SEM). (FIG. 2F) Ganglioside GM1 levels and staining pattern were assessed by cholera toxin subunit B-conjugated to Alexa Fluoro 488. Nuclei were visualized by DAPI. Puncta number and area were quantified in the graphs below (n=3, values are the mean±SEM). N.T., nontransduced. Scale bar=10 μm. (FIG. 2G) Neurons were infected with scrb or GCase polypeptide shRNA constructs and cellular distribution patterns of LAMP1 were assessed by immunocytochemistry. Quantification of LAMP1 puncta size is shown in the graph (n=3, values are the mean±SEM, *p<0.05). Scale bars (top and middle)=10 μm, bottom=2 μm.

FIGS. 3A-3B show the generation of induced pluripotent stem cells from Gaucher disease patient fibroblasts. (FIG. 3A) Induced pluripotent stem (iPS) cells were analyzed for pluripotency markers Oct4, Tra-1-60, SSEA-4, and nanog by immunofluorescence analysis. Nuclei were visualized by DAPI. Scale bars=30 μm. (FIG. 3B) G-banding karyotype analysis of GD iPS cells showing normal chromosomal number, size, and genomic structure.

FIGS. 4A-4F show the compromised proteolysis of long-lived proteins and specific accumulation of endogenous α-synuclein in human GD dopaminergic neurons. (FIG. 4A) Immunofluorescence analysis of WT and GD neurons generated from iPS cells with the neuronal marker β III tubulin and catecholaminergic marker tyrosine hydroxylase (TH). Nuclei were visualized by DAPI. Scale bars=10 μm. (FIG. 4B) Western blot analysis of GCase polypeptide. NSE was used as a loading control. Bottom, quantification of GCase polypeptide activity (n=3, *p<0.05). (FIG. 4C) Long-lived protein degradation was assessed (n=4, *p<0.05). Inset, proteolysis of short-lived proteins (15 min post-chase).

(FIG. 4D) α-synuclein immunofluorescence analysis using mAb LB509, β III tubulin. Scale bar=30 µm. (FIG. 4E) Western blot of T-sol lysates from iPS neurons. Htt, huntingtin; CBB, Coomassie brilliant blue. (FIG. 4F) Western blot from FIG. 4E was quantified by densitometry.

FIGS. 5A-5I show the expression of human α-synuclein in primary cortical neurons and the effect of lysosomal inhibition with leupeptin treatment or GCase polypeptide knockdown. Neurons were infected with WT α-synuclein-expressing lentiviral vectors at moi 3 and analyzed at 7 days post-infection (dp). (FIG. 5A) Immunostaining analysis using mAb's specific for human α-synuclein, syn211 and LB509, reveals the typical punctated pattern expected for synaptic enrichment in neuronal extensions. Approximately 60%-70% of cells were transduced. (FIG. 5B) WT, A53T, and Δ71-82 α-synuclein were expressed in primary neurons at moi 3 and analyzed by western blot. α-tub was used as a loading control. Bottom: α-synuclein protein levels were measured by densitometry using mAb syn202 which detects both mouse and human α-synuclein. Values represent the level of α-synuclein overexpression relative to endogenous mouse protein (n=3, values are the mean±SEM. *p<0.05). (FIG. 5C) Neurotoxicity was assessed in neurons infected at moi 3, 10 dpi, by neurofilament immunostaining (top), or neuronal volume analysis (bottom) (n=4, values are the mean±SEM, *p<0.05 compared to vect+scrb shRNA condition, **p<0.05 compared to all conditions tested. (FIG. 5D) Top: Neurotoxicity assessment by neurofilament immunostaining in either empty vector (vect) or WT α-synuclein infected cells with or without leupeptin treatment (n=8). Bottom: Toxicity assessment by cell volume analysis (n=4, values are the mean±SEM, N.S., not significant). (FIG. 5E) Western blot of LC3-II upon GCase polypeptide knockdown or leupeptin treatment. NSE was used as a loading control. MW is indicated in kDa. (FIG. 5F) Neurons were analyzed by immunostaining for α-synuclein with mAb syn211 and pAb LC3 at 7 dpi and fluorescence intensity from the images, representing total α-synuclein (soluble and insoluble), was quantified (n=3, *p<0.05). (FIG. 5G) Total protein solubility was assessed upon scrb shRNA (1) GCase polypeptide knockdown (2) or scrb shRNA+leupeptin treatment (3) by sequential extraction in Triton X-100 (T-sol), then 2% SDS (T-insol). Fractions were analyzed by SDS-PAGE followed by Coomassie brilliant blue (CBB) staining to visualize total proteins. The MW is indicated in kDa. Right: Insoluble protein levels were quantified by densitometry (n=3, *p<0.05). (FIG. 5H) Immunostaining analysis of α-synuclein and LAMP1. Scale bars=10 µm in each image. Right top: Percentage of cells with condensed nuclei was quantified. Only α-synuclein-positive neurons were counted (n=3). Right middle: Percentage of neurons with α-synuclein/LAMP1 colocalized puncta was quantified (n=3, *p<0.05, compared to scrb shRNA, *p<0.05 compared to scrb and GC shRNA). Right bottom: Percentage of neurons with α-synuclein/LAMP1 colocalized puncta that also contained a condensed nucleus was quantified. (FIG. 5I) Subcellular fractionation of neuronal lysates expressing human WT α-synuclein followed by western blot analysis of Triton X-100-soluble (left) and T-insoluble (right) extracts. LAMP 2 was used to validate lysosomal enrichment in the P2 fraction, and the cytosolic protein NSE was found enriched in the supernatant fraction (S) as expected. CBB was used as a loading control. Right: Densitometric quantification of α-synuclein levels in each fraction (n=3). For each quantification, values are the mean±SEM. One-way ANOVA with Tukey's post-hoc test was used. N.S.=not significant. Please see discussion in Example 4.

FIGS. 6A-6H demonstrate that GCase polypeptide depletion enhances α-synuclein-mediated neurotoxicity through aggregation-dependent mechanisms. Neurons expressing human α-synuclein proteins and GCase polypeptide shRNA were analyzed at 7 dpi. (FIG. 6A) Neurofilament immunostaining was used to monitor neurite degeneration. Representative neurofilament immuno-fluorescence staining in WT α-synuclein expressing neurons is shown below. Nuclei were visualized by DAPI. Scale bars=10 µm. (FIG. 6B) Neurotoxicity was assessed by neuronal volume analysis. (for FIG. 6A and FIG. 6B: n=8, *p<0.001.) (FIG. 6C) Protein levels of human WT, A53T, and Δ71-82 α-synuclein (T-sol) by western blot. α-tub was used as a loading control. Quantification is shown below (n=6, *p<0.01). (FIG. 6D) α-synuclein western blot of T-sol fractions (leu, leupeptin; NT, not transduced). NSE was used as a loading control. (FIG. 6E) Western blot of T-insoluble α-synuclein. Quantification is shown below. The brackets show the signal used for quantification (n=3, *p<0.05, **p<0.01 compared to scrb control). (FIGS. 6F-6H) Native SEC/western blot analysis of T-sol lysates (Å, radius in angstroms). NSE was used as a loading control. Oligomeric α-synuclein (Void→64 Å) was quantified (fold change: scrb shRNA=1±0.5; GC shRNA=19.5±6.0) (n=3, values are the mean±SEM, *p<0.05). MW is indicated in kDa for each blot. For all quantifications, values are the mean±SEM.

(FIG. 7A) Purified α-synuclein was incubated with mixtures of PC and GlcCer at pH 5.0, 37° C. and amyloid formation was assessed by thioflavin T fluorescence (relative fluorescence units [RFU], n=4, *p<0.01). (FIG. 7B) Analysis of 100,000×g soluble α-synuclein at 1 and 5 hr by SEC (115-38 Å and 36-27 Å fractions), then SDS-PAGE/western blot (syn211). The MW is indicated in kDa. (FIG. 7C) Soluble oligomers were quantified by densitometry (n=3, "p<0.05). (FIG. 7D) ANS fluorescence of α-synuclein species formed after 1 hr (n=4, *p<0.01). (FIG. 7E) Centrifugal sedimentation analysis at 28 hr (s, supernatant; p, pellet). α-synuclein was detected with Coomassie brilliant blue staining. Pelletable α-synuclein was quantified in the graph below (n=3). Amyloid was measured from the same reactions by thioflavin T (n=4,*p<0.01). (FIG. 7F) EM analysis of α-synuclein aggregates showing a mixture of fibrillar (i-ii) and amorphous (iv-v) structures at 24 hr. Panels ii-v show immuno-EM analysis using mAb syn505. Scale bars: 100 nm for i-iii; 500 nm for iv and v. (FIG. 7G) Immuno-EM analysis with syn505 of α-synuclein+PC25/GlcCer75 reactions at 15 hr. GlcCer lipid tubules are ~50 nm in width. Scale bars: 100 nm for i and iii; 500 nm for ii. (FIG. 7H) Immuno-EM analysis with syn505 of α-synuclein+PC25/GlcCer75 reactions at 24 hr showing fibrillar structures of 10-14 nm in width with twisted (i) or straight (ii) morphologies that appear to extend from GlcCer tubules. Scale bars: 100 nm. (FIG. 7I) Immuno-EM analysis of GlcCer lipid dispersions alone. Scale bar: 100 nm. For each graph in (FIG. 7A) and (FIG. 7C)—(FIG. 7E), values are the mean±SEM.

(FIG. 8A) Amyloid formation was assessed at 36 hr at pH 5.0, 37° C. (2 mg/ml in 0.1 M sodium acetate buffer) or pH 7.4, 37° C. (2 mg/ml in 0.1 M sodium phosphate buffer). Values are expressed as fold-change relative to the control reaction of each pH condition. PC50%/polyethylene glycol (PEG) 50% was used in the pH 5.0 condition as a control. (n=6, *p<0.05). (FIG. 8B) Kinetic analysis of fibril formation at pH 7.4, 37° C. in the presence of GlcCer containing lipid dispersions. (n=6). (FIG. 8C) 100,000×g soluble α-synuclein/lipid reactions at pH 5.0 were analyzed by native gel electrophoresis/western blot. The marker indicates the apparent MW in kilodaltons according to globular protein standards (native mark, Invitrogen). (FIG. 8D) Densitometric quantification of the oligomer:monomer ratio detected by native gel/western blot analysis. The band migrating at ~50 kDa was quantified as the monomeric form (purified α-synuclein migrates at a higher than expected MW in native gel systems because of its elongated, non-globular structure) (n=3, *p<0.01). (FIG. 8E) Levels of 100,000×g α-synuclein soluble oligomers were determined after 3 and 15 hr incubation at pH 5.0 in the presence of PC25/lactosylceramide 75 (LacCer), PC25/galactosylceramide 75 (GalCer), PC25/Glucosylsphingosine75 (GluSph) by SDS-PAGE. GlcCer was used as a control (n=3, *p<0.05). (FIG. 8F) Sedimentation analysis of α-synuclein/lipid reactions at pH 5.0 after 3 and 15 hr incubations. S, supenatant; P, pellet. No soluble α-synuclein (oligomers or monomers) was detected at 15 hr since it was completely converted into the pelletable fraction (P). Values are the mean±SEM for all quantifications.

(FIG. 9A) LC/MS analysis of sphingolipids in cortex of 4L/PS-NA mice. Lactosylceramide and ceramide levels of 12-week-old 4L/PS-NA mice (values are the mean±SEM, n=3, *p<0.05) (n=3 mice). (FIG. 9B) Gangliosides were analyzed by thin layer chromatography (TLC). (FIG. 9C) Accumulation of α-synuclein in GD mice expressing D409H GCase polypeptide. Cortex from 42-week-old D409H homozygous mice and age-matched WT mice were analyzed for α-synuclein accumulations by immunofluorescence. Nuclei were visualized by DAPI. (FIG. 9D) Sequential extraction analysis of cortical tissue obtained from 42-week-old D409H mice. Left, T-sol levels of α-synuclein were measured in 42-week-old D409H mice with syn202, SNL-1, and syn505. NSE was used as a loading control. Right, T-insoluble α-synuclein was determined with syn202 and syn505. Vimentin (Vim) was used as a loading control. Bottom graph: The levels of T-insoluble α-synuclein were quantified by densitometry and normalized to Vim. Values are the mean±SEM from three separate mice (n=3, *p<0.05). MW markers are indicated in kDa. (FIG. 9E) GCase polypeptide knockdown in *C. elegans* enhances α-synuclein accumulation in vivo. α-synuclein aggregates are monitored in the body-wall muscles of worms expressing a human α-synuclein:GFP fusion protein (top) (Hamamichi et al., PNAS 105(2): 728-733, 2008). As previously shown, coexpression of the molecular chaperone-like protein, TOR-2 (worm ortholog of human torsinA), completely abolished α-synuclein:GFP aggregation (middle). Knockdown of a worm GCase polypeptide ortholog (C33C12.8) in α-synuclein:GFP+TOR-2 worms increased the amount of α-synuclein punctate structures (bottom).

(FIG. 10A) H & E stain of the substantia nigra (SN) and cortex (Ctx). The arrows indicate eosinophilic spheroids. Scale bars=50 μm. (FIG. 10B) Immunofluorescence of α-synuclein in SN and Ctx. Nuclei were visualized by DAPI. Scale bars=20 μm. (FIG. 10C) Costaining of α-synuclein and neuronal marker NeuN. Scale bars=20 μm. (FIG. 10D) Left: Quantification of neuronal spheroids. ND, not detected. Middle: Quantification of neuronal number by NeuN immunostaining. Right: Quantification of α-synuclein aggregates by immunostaining. (FIG. 10E) Sequential extraction analysis of Ctx. pAb SNL-1 and mAb syn202 detect total endogenous α-synuclein, whereas syn505 detects oxidized/nitrated and misfolded α-synuclein. NSE and α-tub were used as loading controls. (FIG. 10F) Quantification of T-sol monomers (18 kDa, left), T-sol oligomers (>18 kDa, middle), and T-insoluble α-synuclein (total lane, right). (FIG. 10G) Native SEC/SDS-PAGE/western blot of T-sol fractions. Radius, Å. (FIG. 10H) Chromatographic profile obtained by syn202 densitometry. The values are representative of independent SEC analyses from three mice. The MW is indicated in kDa for each blot. For all quantifications, values are the mean±SEM.

FIGS. 11A-11L show that accumulation of T-sol α-synuclein oligomers occurs in GD brain. Native SEC followed by SDS-PAGE/western blot of human cortical lysates (T-sol). Radius is in Å (horizontal), apparent MW is in kDa (vertical). Monomeric α-synuclein elutes at 34 Å. (FIGS. 11A-11C) Healthy controls. (FIGS. 11D and 11E) Type I non-neuronopathic GD. (FIG. 11F) Atypical Parkinson's disease (APD). (FIG. 11G) dementia with Lewy bodies (DLB). (FIGS. 11H and 11I) Analysis of cortical material obtained from infants with type II acute neuronopathic GD. (FIG. 11J) Cortical lysates from a 3-year old child with neuronopathic type III GD. (FIG. 11K) DLB with a heterozygous mutation in GBA1. (FIG. 11L) Analysis of the 45 Å-sized fraction with syn303, which preferentially detects pathological oligomeric α-synuclein. Bands migrating at 18, 44, and 75 kDa were detected with both syn303 and syn211 (arrows).

(FIG. 12A) GCase polypeptide activity was determined in whole-cell homogenate of cortical samples. The data were grouped according to the presence of GCase polypeptide mutations, and also neuropathological differences (with or without synucleinopathy). (FIG. 12B) The GCase polypeptide activity in the P2 fraction of heterozygous GCase polypeptide mutant carriers and WT brain reveals a more dramatic decrease in activity (50%) compared to whole cell measurements. (FIG. 12C) α-synuclein oligomers were quantified by densitometric analysis of SEC/SDS-PAGE/western blot analysis with mAb syn211 (representative examples shown in FIGS. 11A-11L; some GD heterozygote blots are not shown in FIGS. 11A-11L but quantified and presented in the graph). Fractions corresponding to 36 Å-sized particles up to the column void volume were quantified as oligomeric α-synuclein, while 35-28 Å-sized fractions were counted as the monomeric form. (FIG. 12D) Quantification of the 45 Å-sized fractions with mAb syn303. Representative examples are shown in FIG. 11L. Some samples could not be analyzed by syn303 due to sample limitation. (FIG. 12E) Western blot of GCase polypeptide in the same samples analyzed and presented in FIGS. 11A-11L. T-sol lysates were treated with endo H to reveal levels of the mature GCase polypeptide forms. NSE was used as a loading control. MW is indicated in kDa. The lines in panels A-D represent the mean values.

(FIG. 13A) Inducible H4 cells expressing human WT α-synuclein were analyzed by western blot for post-ER and ER GCase polypeptide (n=6, *p<0.01). α-tub was used as a loading control. (FIG. 13B) Post-ER/ER GCase polypeptide in cortical neurons expressing human WT, A53T, or Δ71-82 α-synuclein. α-synuclein levels were determined by syn211 (human-specific) and syn202 (human and mouse). NSE was used as a loading control. (FIG. 13C) GCase polypeptide activity in cortical neurons of P2 and P3 fractions (n=6, *p<0.01, compared to vect). (FIG. 13D) Analysis of GCase polypeptide in cortex of 65- to 80-year-old controls. Samples 1, 2, 4, 6="high α-synuclein"; samples 3, 5="low α-synuclein". Quantification of α-synuclein protein and post-ER/ER GCase polypeptide levels is graphed below the blots (*p<0.01). (FIG. 13E) GCase polypeptide western blot of PD brain lysates. α-Tub and CBB were used as loading controls. GCase polypeptide levels were quantified below (n=3 [control] or 6 [PD], *p=0.02). Bottom: GCase polypeptide activity in P2 and P3 fractions (n=3-6, *p=0.04). MW for each blot is indicated in kDa. (FIG. 13F) Pathogenic positive feedback mechanism of α-synuclein and GCase polypeptide depletion in the lysosome. (1) Lysosomal Glc-Cer accumulation accelerates and stabilizes soluble α-synuclein oligomers (bold arrow), which eventually convert into amyloid fibrils (thin arrow). (2) Accumulation of α-synuclein blocks the ER-Golgi trafficking of GCase polypeptide. (3) Decrease of GCase polypeptide in the lysosome further amplifies GlcCer accumulation and stabilization of soluble α-synuclein oligomers and results in a stronger inhibition of GCase polypeptide ER-Golgi trafficking with each pathogenic cycle. For all quantifications, values are the mean±SEM.

FIGS. 14A-14H demonstrate the modulation of lysosomal GCase polypeptide maturation and activity by α-synuclein expression in primary neurons and human brain. (FIG. 14A) Enrichment of lysosomal or microsomal organelles by subcellular centrifugal fractionation. Western blot analysis of neuronal cultures infected at moi 3 with empty vector (vect), WT, A53T, or Δ71-82 α-synuclein expressing lentivirus and harvested at dpi 7. Antibodies against GRP78 and calnexin were used to validate microsome enrichment, while antibodies against LAMP1 and 2 were used to validate lysosomal enrichment. Coomassie brilliant blue (CBB) is used as a loading control. MW is indicated along the left side of the blot in kDa. (FIG. 14B) Western blots were quantified by densitometric analysis (n=3, *p<0.05). (FIG. 14C) Accumulation and retention of ER GCase polypeptide upon expression of human WT α-synuclein in primary cultures. Endo H and PNGase F/GCase polypeptide western blot analysis of T-sol neuronal lysates transduced to express WT or Δ71-82 α-synuclein. Vect and N-terminal truncated polyQ expanded huntingtin protein (Htt 548-72Q) were used as controls. Endo H sensitive GCase polypeptide immunoreactive smears migrating below 60 kDa indicated the levels of ER-localized GCase polypeptide. PNGase F was used to determine the migration of deglycosylated GCase polypeptide. α-Tub was used as a loading control. (FIG. 14D) Quantification of GCase polypeptide mRNA levels by real-time PCR from infected neuronal cultures. (FIG. 14E) The activity of various lysosomal hydrolases including β-glucuronidase (GUSB), acid phosphatase, hexosaminidase A/B/S (Hex), and GCase polypeptide, was determined in the P2 fractions of neuronal cultures infected with WT or A53T α-synuclein by 4-methylumbelliferyl-substrate cleavage (n=3, *p<0.05). (FIG. 14F) Analysis of GCase polypeptide and activity levels of healthy control brains with variable levels of α-synuclein. Control human brain samples 5 and 6 from FIG. 13D were treated with endo H and analyzed by GCase polypeptide western blot. α-synuclein levels shown below with syn211. (FIG. 14G) Western blot analysis of the SEC fraction corresponding to 45 Å using mAb syn303. NSE was used as a loading control. The MW is in kDa. Syn303 detected elevated levels of the bands corresponding to 18, 44 kDa, and other HMW species. (FIG. 14H) Left: Whole-cell GCase polypeptide activity of "high" and "low" containing α-synuclein samples. GCase polypeptide activity was measured in P2 (middle) and P3 (right) fractions of C5 and C6 (values are the mean of three repeated-measurements ±SEM, *p<0.05). For quantification in (FIG. 14B), (FIG. 14D), and (FIG. 14E), values are the mean±SEM.

(FIG. 15A) Western blot analysis of GCase polypeptide. Neural specific enolase (NSE) was used as a loading control. (FIG. 15B) Densitometric analysis of GCase polypeptide levels normalized to NSE (% of Veh, n=3, values are the mean±SEM, *p<0.05). (FIG. 15C) Proteolysis rate was determined by radioactive pulse-chase. Rates were determined by measurements at 0, 8, and 20 hrs after chasing and expressed as fold increase in protein degradation per hour. (n=4, values are the mean±SEM, *p<0.05).

FIGS. 17A-17C demonstrate that GCase polypeptide overexpression increases lysosomal proteolysis in non-neuronal cells. Hela cells were transfected with GFP or myc-GCase polypeptide expression constructs. (FIG. 17A) Overexpression levels were determined by western blot using anti-GCase polypeptide or myc antibodies. GAPDH was used as a loading control. Two replicates shown. (FIG. 17B) Proteolysis of long-lived proteins was determined in transfected Hela cells by radioactive pulse-chase after 36 hrs. Lysosomal inhibitors leupeptin (Leu) and ammonium chloride ($NH_4Cl$) were used to determine the amount of lysosomal proteolysis in each condition. (FIG. 17C) Cathepsin B activity was determined in living Hela cells transfected with GFP or GCase polypeptide using an artificial substrate that fluoresces upon cleavage. Activity was determined by measurement of relative fluorescence units (RFU) between 0 and 60 minutes after substrate washout. For (FIG. 17B) and (FIG. 17C) n=4, values are the mean±SEM, *p<0.05.

FIGS. 18A-18B show the reduction of α-synuclein and enhancement of lysosomal function by Rab1a polypeptide overexpression. (FIG. 18A) Human iPS dopamine neurons from a PD patient were transduced with Rab1a polypeptide expressing lentivirus. Overexpression of Rab1a polypeptide was confirmed at moi 5 by western blot. α-synuclein levels were determined by western blot using mAb syn211. α-tubulin was used as a loading control. (FIG. 18B) Cathepsin B activity was assessed in transfected hela cells as described in FIGS. 17A-17C.

(FIG. 19A) Treatment of iPS neurons generated from an unaffected healthy control with the GCase polypeptide allosteric activator reduces α-synuclein levels. α-synuclein was detected with mAb syn211, and tubulin (tub) and huntingtin (htt) were used as loading controls. Right, α-synuclein levels were quantified by densitometry n=3, values are the mean±SEM, *p<0.05. (FIG. 19B) Neurons generated from a PD patient were treated and analyzed as described in (FIG. 19A).

(FIG. 20A) Neurons from a PD patient were treated with PBS (veh), IFG, n-acetyl-cysteine (NAC), or both IFG+NAC and GCase polypeptide maturation was determined by western blot. β iii tubulin was used as a loading control. (FIG. 20B) The amount of post-ER GCase polypeptide was quantified by densitometry and normalized to tub n=4, values are the mean±SEM, *p<0.05 compared to veh and IFG, **p<0.05 compared to veh, IFG, and NAC.

DEFINITIONS

Figure 1F:
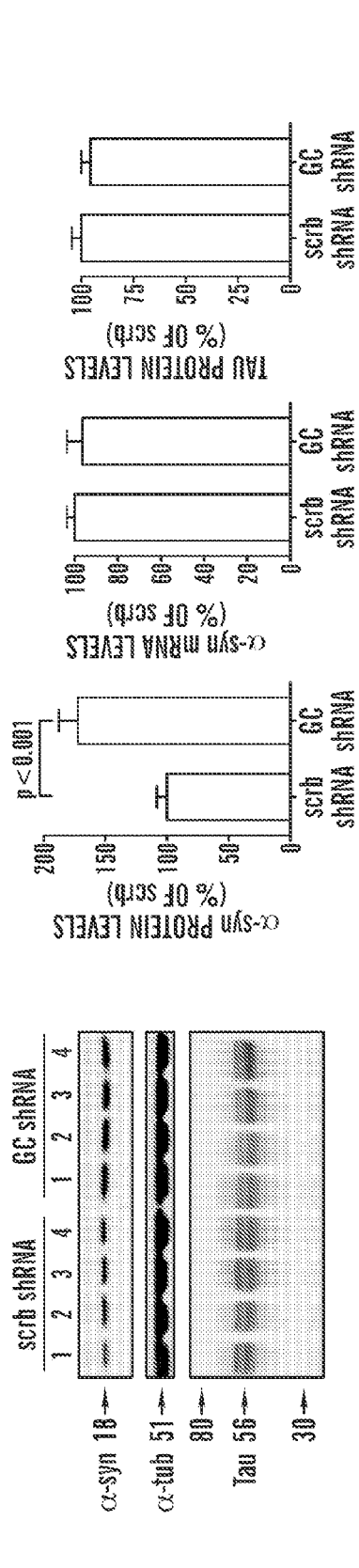

In order for the present invention to be more readily understood, certain terms are first defined below; those of ordinary skill in the art will appreciate and understand the use and scope of these terms as defined below and/or otherwise used herein.

Activating agent: The term "activating agent", as used herein, refers to an agent that increases level and/or activity of a target entity as compared with its level and/or activity under comparable conditions absent the activating agent. For example, an activating agent can increase level and/or activity of a target entity by at least about 5%, including at least about 10%, at least about 15%, at least about 20%, at least about 30%, at least about 40%, at least about 50%, at least about 60%, at least about 70%, at least about 80%, at least about 90%, at least about 95% or more, as compared with its level and/or activity under comparable conditions absent the activating agent. In some embodiments, an activating agent increases level and/or activity of its target entity to a point within a predetermined range of a reference level and/or activity. In some embodiments, a reference level and/or activity is the level and/or activity observed with a wild type version of the target entity in its natural context. In some embodiments, an activating agent binds directly to its target. In some embodiments, an activating agent binds indirectly (i.e., by binding with a physically distinct entity that binds to the target). In some embodiments, an activating agent does not interact physically, either directly or indirectly, with its target, but increases level and/or activity of the target through other action (e.g., binding to a regulatory site in a nucleic acid that increases expression of the target; activation or inhibition of an enzyme that modifies the target and alters its activity, etc). In some embodiments, an activating agent stabilizes and/or increases half-life of its target entity. In some embodiments, an activating agent stabilizes its target entity in a particular three-dimensional conformation. In some embodiments, an activating agent competes with an inhibitor for binding to its target entity. In some embodiments, an activating agent prevents or reduces aggregation of the target entity. In some embodiments, an activating agent stabilizes interaction of its target entity with another entity (e.g., a substrate protein, RNA, or DNA, a small molecule, peptide, or carbohydrate). In some embodiments, an activating agent binds to a target entity and increases the interaction of that target entity with another entity as compared with its interaction under comparable conditions absent the activating agent. In some embodiments, an activating agent-mediated increase in interaction of a target entity with another entity increases level and/or activity of that target entity as compared with its level and/or activity under comparable conditions absent the activating agent. In some embodiments, an activating agent binds to a target entity and decreases interaction of that target entity with another entity as compared with its interaction under comparable conditions absent the activating agent. In some embodiments, an activating agent-mediated decrease in interaction of the target entity with another entity increases level and/or activity of that target entity as compared with its level and/or activity under comparable conditions absent the activating agent. In general, an activating agent may be or comprise a compound of any chemical class (e.g., a small molecule, metal, nucleic acid, polypeptide, lipid and/or carbohydrate). In some embodiments, an activating agent is or comprises an antibody or antibody mimic. In some embodiments, an activating agent is or comprises a nucleic acid agent (e.g., an antisense oligonucleotide, a siRNA, a shRNA, etc) or mimic thereof. In some embodiments, an activating agent is or comprises a small molecule. In some embodiments, an activating agent is or comprises a naturally-occurring compound (e.g., small molecule). In some embodiments, an activating agent has a chemical structure that is generated and/or modified by the hand of man. In general, an activating agent increases level or activity of one or more target entities present in and/or produced by a cell or organism. In some embodiments, a target entity is or comprises a polypeptide. In some embodiments, a target entity is or comprises a nucleic acid (e.g., a nucleic acid that encodes or regulates [e.g., by altering expression and/or activity of] a polypeptide). In some embodiments, a target entity is or comprises a carbohydrate. In some embodiments, a target entity is or comprises a lipid. In some embodiments, a target entity is or comprises an enzyme. In some embodiments, a target entity is or comprises a lysosomal enzyme. In some embodiments, a target entity is or comprises a polypeptide involved in cellular trafficking.

Amyloidopathy: As used herein, the term "amyloidopathy" or "amyloidopathic" refers to diseases, disorders, and/or conditions that are associated with or characterized by pathological accumulation of the any disease-linked protein exhibiting amyloid conformation (i.e., β-pleated sheet), including but not limited to Alzheimer's disease, vascular dementia, and cognitive impairment.

Antioxidant: As used herein, the term "antioxidant" refers to an entity, e.g., small molecule, polypeptide, nucleic acid, saccharide, lipid, inorganic agent (e.g., metal, mineral, etc), or combinations thereof that inhibits the oxidation, nitration, or nitrosylation of another entity.

β-galactosidase polypeptide: As used herein, the term "β-galactosidase polypeptide" or "beta-gal polypeptide" refers to a polypeptide that is a β-galactosidase enzyme. Those of ordinary skill in the art will appreciate that β-galactosidase is a hydrolase enzyme that catalyzes hydrolysis of β-glycosidic bond formed between a galactose and its organic moiety. β-galactosidase enzyme has different subcellular locations, i.e., β-galactosidase isoform 1 localized in lysosome and β-galactosidase isoform 2 localized in perinuclear region of the cytoplasm. Substrates of β-galactosidase enzyme include ganglioside $G_{M1}$, lactosylceramides, lactose, and various glycoproteins. Representative known β-galactosidase polypeptides include those listed below in Table 1.

In some embodiments, the β-galactosidase polypeptide is a β-galactosidase polypeptide homolog. The term "β-galactosidase polypeptide homolog" comprises a polypeptide whose amino acid sequence includes at least one sequence element comprising conserved residues found in polypeptides of Table 1; in some such embodiments, such sequence element comprises at least 3, 4, 5, 6, 7, 8, 9, 10 or more residues whose identity and relative position is preserved. In some embodiments, such sequence element comprises at least 3, 4, 5, 6, 7, 8, 9, 10 or more consecutive residues. Alternatively or additionally, in some embodiments, a "β-galactosidase polypeptide homolog" is or comprises a polypeptide whose amino acid sequence shows at least 50%, 55%, 60%, 65%, 70%, 75%, 80%, 85%, 90%, 95%, 96%, 97%, 98%, 99% or greater overall sequence identity with one or more polypeptides in Table 1 and/or shares at least one characteristic sequence element with one or more polypeptides in Table 1. In some embodiments, such a characteristic sequence element includes one or more catalytic residues and/or one or more conserved residues found in polypeptides of Table 1.

Calcium channel blocker: The term "calcium channel blocker" refers to an agent that blocks voltage-dependent calcium channels. Synonyms of the term "calcium channel blocker" are calcium channel antagonists, calcium channel inhibitors and calcium entry blockers and these terms are used interchangeably herein. Exemplary calcium channel blockers include, but are not limited to amlodipine, felodipine, isradipine, lacidipine, nicardipine, nifedipine, niguldipine, niludipine, nimodipine, nisoldipine, nitrendipine, nivaldipine, ryosidine, anipamil, diltiazem, fendiline, flunarizine, gallopamil, mibefradil, prenylamine, tiapamil, verapamil, perhexyline maleate, fendiline, prenylamine, and derivatives of any of thereof.

Characteristic sequence element: The term "characteristic sequence element" refers to a distinctive core sequence or structural element that is found in all members of a family of polypeptides, small molecule, or nucleic acids, and therefore can be used by those of ordinary skill in the art to define members of the family.

Combination therapy: The term "combination therapy" refers to those situations in which two or more different pharmaceutical agents are administered in overlapping regimens so that the subject is simultaneously exposed to both agents.

Comparable: The term "comparable" is used herein to describe two (or more) sets of conditions or circumstances that are sufficiently similar to one another to permit comparison of results obtained or phenomena observed. In some embodiments, comparable sets of conditions or circumstances are characterized by a plurality of substantially identical features and one or a small number of varied features. Those of ordinary skill in the art will appreciate that sets of conditions are comparable to one another when characterized by a sufficient number and type of substantially identical features to warrant a reasonable conclusion that differences in results obtained or phenomena observed under the different sets of conditions or circumstances are caused by or indicative of the variation in those features that are varied.

Dosing regimen: As used herein, a "dosing regimen" or "therapeutic regimen" refers to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regime comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount.

Enzyme replacement therapy: The term "enzyme replacement therapy", as used herein, refers to the administration of an enzyme to a subject that shows, prior to such administration, a reduced level of activity of the enzyme as compared with that observed, on average, across a population of normal individuals of the same species (e.g., humans).

Equivalent dosage: The term "equivalent dosage" is used herein to compare dosages of different pharmaceutically active agents that effect the same biological result. Dosages of two different agents are considered to be "equivalent" to one another in accordance with the present invention if they achieve a comparable level or extent of the biological result. In some embodiments, equivalent dosages of different pharmaceutical agents for use in accordance with the present invention are determined using in vitro and/or in vivo assays as described herein. In some embodiments, one or more lysosomal activating agents for use in accordance with the present invention is utilized at a dose equivalent to a dose of a reference lysosomal activating agent; in some such embodiments, the reference lysosomal activating agent for such purpose is selected from the group consisting of small molecule allosteric activators (e.g., pyrazolpyrimidines), imminosugars (e.g., isofagomine), antioxidants (e.g., n-acetyl-cysteine), and regulators of cellular trafficking (e.g., Rab1a polypeptide).

Gain of function disease: The term "gain of function disease" typically refers to a disease characterized by increased aggregation-associated proteotoxicity. In such diseases, aggregation exceeds clearance inside and/or outside of the cell. Gain of function diseases are often associated with aging and are also referred to as gain of toxic function diseases. Exemplary gain of function diseases include, but are not limited to neurodegenerative diseases associated with aggregation of polyglutamine repeats in proteins or repeats at other amino acids such as alanine, Lewy body diseases, and other disorders associated with α-synuclein aggregation, amyotrophic lateral sclerosis, transthyretin-associated aggregation diseases, Alzheimer's disease, age-associated macular degeneration, inclusion body myositosis, and prion diseases. Neurodegenerative diseases associated with aggregation of polyglutamine include, but are not limited to, Huntington's disease, dentatorubral and pallidoluysian atrophy, several forms of spino-cerebellar ataxia, and spinal and bulbar muscular atrophy. Alzheimer's disease is characterized by the formation of two types of aggregates: intracellular and extracellular aggregates of Aβ peptide and intracellular aggregates of the microtubule associated protein tau. Transthyretin-associated aggregation diseases include, for example, senile systemic amyloidoses, familial amyloidotic neuropathy, and familial amyloid cardiomyopathy. Lewy body diseases are characterized by an aggregation of α-synuclein protein and include, for example, Parkinson's disease. Prion diseases (also known as transmissible spongiform encephalopathies) are characterized by aggregation of prion proteins. Exemplary human prion diseases are Creutzfeldt-Jakob Disease (CJD), Variant Creutzfeldt-Jakob Disease, Gerstmann-Straussler-Scheinker Syndrome. Fatal Familial Insomnia and Kuru.

Gene therapy: The term "gene therapy", as used herein, refers to the administration to a subject (e.g., a human subject) of a nucleic acid (or a nucleic acid derived from the nucleic acid as, for example, by reverse transcription) encoding a polypeptide. In many embodiments, such administration is performed so that the polypeptide is expressed in or by cells of the subject after the administration. Nucleic acids may be incorporated into the genome of the cell or remain permanently in the cell as an episome (a genetic particle of certain cells that can exist either autonomously in the cytoplasm or as part of a chromosome). Gene therapy also encompasses delivery of nucleic acids that do not integrate or remain permanently in the cell to which they are delivered.

Glucocerebrosidase polypeptide: As used herein, the term "glucocerebrosidase polypeptide" refers to a polypeptide that is a β-glucocerebrosidase enzyme. Those of ordinary skill in the art will appreciate that a glucocerebrosidase is naturally found localized in the lysosome, where it hydrolyses the β-glucosidic linkage of glucosylceramide. This naturally occurring glucocerebrosidase enzyme is also known as acid β-glucosidase, alglucerase, β-glucocerebrosidase, D-glucosyl-N-acylsphingosine glucosylhydrolase, GBA1, Glcm_human, Gluc, glucocerebrosidase β-glucosidase, glucosphingosine glucosylhydrolase, glucosylceramidase, glucosylceramide β-glucosidase, or imiglucerase. Representative known glucocerebrosidase polypeptides include those listed below in Table 2.

In some embodiments, glucocerebrosidase polypeptide can be a gluocerebrosidase polypeptide homolog. The term "glucocerebrosidase polypeptide homolog" comprises a polypeptide whose amino acid sequence includes at least one sequence element comprising conserved residues found in polypeptides of Table 2; in some such embodiments, such sequence element comprises at least 3, 4, 5, 6, 7, 8, 9, 10 or more residues whose identity and relative position is preserved. In some embodiments, such sequence element comprises at least 3, 4, 5, 6, 7, 8, 9, 10 or more consecutive residues. Alternatively or additionally, in some embodiments, a "glucocerebrosidase polypeptide homolog" is or comprises a polypeptide whose amino acid sequence shows at least 50%, 55%, 60%, 65%, 70%, 75%, 80%, 85%, 90%, 95%, 96%, 97%, 98%, 99% or greater overall sequence identity with one or more polypeptides in Table 2 and/or shares at least one characteristic sequence element with one or more polypeptides in Table 2. In some embodiments, such a characteristic sequence element includes one or more catalytic residues and/or one or more conserved residues found in polypeptides of Table 2.

Glucosylceramide synthase polypeptide: As used herein, the term "glucosylceramide synthase polypeptide" refers to a polypeptide that shares at least one characteristic sequence element and/or overall sequence identity with a glucosyltransferase enzyme involved in the production of glucosylceramide-based glycosphingolipids, and similarly shows glycosyltransferase activity. In nature, glucosylceramide synthase regulates the production of glycosphingolipid conjugates called gangliosides (such as $G_{M3}$) via glucosyl transfer to ceramide. Representative known glucosylceramide synthase polypeptides include those listed below in Table 3. In some embodiments, a glucosylceramide synthase polypeptide is or comprises a polypeptide whose amino acid sequence includes at least one element comprising conserved residues found in polypeptides of Table 3.

In some embodiments, the glucosylceramide synthase polypeptide can be a glucosylceramide synthase polypeptide homolog. The term "glucosylceramide synthase polypeptide homolog" comprises a polypeptide whose amino acid sequence includes at least one sequence element comprising conserved residues found in polypeptides of Table 3; in some such embodiments, such sequence element comprises at least 3, 4, 5, 6, 7, 8, 9, 10 or more residues whose identity and relative position is preserved. In some embodiments, such sequence element comprises at least 3, 4, 5, 6, 7, 8, 9, 10 or more consecutive residues. Alternatively or additionally, in some embodiments, a "glucosylceramide synthase polypeptide homolog" is or comprises a polypeptide whose amino acid sequence shows at least 50%, 55%, 60%, 65%, 70%, 75%, 80%, 85%, 90%, 95%, 96%, 97%, 98%, 99% or greater overall sequence identity with one or more polypeptides in Table 3 and/or shares at least one characteristic sequence element with one or more polypeptides in Table 3. In some embodiments, such a characteristic sequence element includes one or more catalytic residues and/or one or more conserved residues found in polypeptides of Table 3.

Hexosaminidase polypeptide: As used herein, the term "hexosaminidase polypeptide" or "β-hexosaminidase polypeptide" refers to a polypeptide that is a β-hexosaminidase enzyme. Those of ordinary skill in the art will appreciate that β-hexosaminidase enzyme participates in hydrolysis of terminal N-acetyl-D-hexosamine residues in N-acetyl-β-D-hexosaminides. β-hexosaminidase enzyme and the cofactor $G_{M2}$ activator protein catalyze the degradation of the $G_{M2}$ gangliosides and other molecules containing terminal N-acetyl hexosamines. Lysosomal β-hexosaminidase enzymes are dimeric in structure and three active dimeric isozymes are produced through the combination of α- and β-subunits (encoded by HEXA and HEXB genes, respectively). Hexosaminidase isozyme A can hydrolyze $G_{M2}$ ganglioside in vivo and has an α/β heterodimer subunit composition. Hexosaminidase isozyme B has a β/β homodimer subunit composition and hexosaminidase isozyme S has an α/α homodimer subunit composition. Representative known hexosaminidase polypeptides include those listed below in Table 4.

In some embodiments, the hexosaminidase polypeptide can be a hexosaminidase polypeptide homolog. The term "hexosaminidase polypeptide homolog" comprises a polypeptide whose amino acid sequence includes at least one sequence element comprising conserved residues found in polypeptides of Table 4; in some such embodiments, such sequence element comprises at least 3, 4, 5, 6, 7, 8, 9, 10 or more residues whose identity and relative position is preserved. In some embodiments, such sequence element comprises at least 3, 4, 5, 6, 7, 8, 9, 10 or more consecutive residues. Alternatively or additionally, in some embodiments, a "hexosaminidase polypeptide homolog" is or comprises a polypeptide whose amino acid sequence shows at least 50%, 55%, 60%, 65%, 70%, 75%, 80%, 85%, 90%, 95%, 96%, 97%, 98%, 99% or greater overall sequence identity with one or more polypeptides in Table 4 and/or shares at least one characteristic sequence element with one or more polypeptides in Table 4. In some embodiments, such a characteristic sequence element includes one or more catalytic residues and/or one or more conserved residues found in polypeptides of Table 4.

Improve, increase, or reduce: As used herein, the terms "improve," "increase" or "reduce," or grammatical equivalents, indicate values that are relative to a reference measurement. In some embodiments, a reference measurement is one that was taken under comparable conditions. In some embodiments, a reference measurement is or comprises a historical value. In some embodiments, a reference measurement is or comprises a measurement in the same individual at a different time (e.g., prior to initiation of a particular treatment or event). In some embodiments, a reference measurement is or comprises a measurement in a control individual (or multiple control individuals); in some such embodiments, a "control" individual is one who a) has not been exposed to a particular treatment or event, and/or b) displays a different (as compared with the test individual) susceptibility to or affliction with a proteinopathy, but optionally shares one or more features such as race, age (e.g., approximate, for example within a range), weight (e.g., approximate, for example within a range), height (e.g., approximate, for example within a range), temperament, geographic residence, eating habits, exercise habits, etc with a test individual. In some embodiments, a reference measurement is a measurement taken in a different setting (for example, in a setting in which such treatment or event does not occur or has not occurred).

Loss of function disease: The term "loss of function disease" typically refers to a disease characterized by by inefficient folding of a protein resulting in excessive degradation of the protein. Exemplary loss of function diseases include, but are not limited to cystic fibrosis, lysosomal storage diseases, and Von Hippel-Lindau (VHL) Disease. In cystic fibrosis, the mutated or defective enzyme is the cystic fibrosis transmembrane conductance regulator (CFTR). One of the most common mutations of this protein is ΔF508 which is a deletion (Δ) of three nucleotides resulting in a loss of the amino acid phenylalanine (F) at the 508 position on the protein.

Lysosomal enzyme: As used herein, the term "lysosomal enzyme" refers to an enzyme that functions in the lysosome. Some examples of lysosomal enzymes include, but are not limited to α-galactosidase A; β-glucosidase; α-glucosidase; β-hexosaminidase A; β-hexosaminidase B; α-L-iduronidase; β-galactosidase; β-glucuronidase; α-glucuronidase; α-fucosidase; sulfatases; acid ceramidases; NPC 1; acid sphingomyelinase; cathepsins (A, D, H, S, Z); H(+)-ATPases; sialidase; β-galactocerebrosidase; arylsulfatase; iduronate-2-sulfatase; heparan N-sulfatase; α-N-acetylglucosaminidase; α-glucosaminide N-acetyltransferase; N-acetylglucosamine-6-sulfate sulfatase; N-acetylgalactosamine-6-sulfate sulfatase; arylsulfatase B; acid α-mannosidase; acid β-mannosidase; acid α-L-fucosidase; α-N-acetylneuraminidase; β-N-acetylglucosaminidase; and α-N-acetylgalactosaminidase. Representative known lysosomal enzymes include those listed below in Table 5. In some embodiments, a lysosomal enzyme can be a lysosomal enzyme homolog. A "lysosomal enzyme homolog" is or comprises a polypeptide whose amino acid sequence includes at least one sequence element comprising conserved residues found in polypeptides of Table 5; in some such embodiments, such sequence element comprises at least 3, 4, 5, 6, 7, 8, 9, 10 or more residues whose identity and relative position is preserved. In some embodiments, such sequence element comprises at least 3, 4, 5, 6, 7, 8, 9, 10 or more consecutive residues. Alternatively or additionally, in some embodiments, a "lysosomal enzyme homolog" is or comprises a polypeptide whose amino acid sequence shows at least 50%, 55%, 60%, 65%, 70%, 75%, 80%, 85%, 90%, 95%, 96%, 97%, 98%, 99% or greater overall sequence identity with one or more polypeptides in Table 5 and/or shares at least one characteristic sequence element with one or more polypeptides in Table 5. In some embodiments, such a characteristic sequence element includes one or more catalytic residues and/or one or more conserved residues found in polypeptides of Table 5.

Lysosomal storage diseases: As used herein, the term "lysosomal storage diseases" refers to a group of genetic disorders that result from deficiency in at least one of the enzymes (e.g., acid hydrolases) that are required to break macromolecules down to peptides, amino acids, monosaccharides, nucleic acids and fatty acids in lysosomes. Lysosomal storage diseases may result from non-lysosomal proteins that may or may not have enzymatic activity such as: a deficiency in a protein involved in trafficking an acid hydrolase to the lysosome such as lysosomal integral membrane protein 2 (LIMP2); deficiency of an ER-resident protein involved in post-translational modifications of acid hydrolases such as that found in multiple sulfatase deficiency (MSD); deficiency in a protein found in the Golgi apparatus that is involved in trafficking acid hydrolases and other lysosomal proteins to the lysosomal compartment such as N-acetylglucosamine-1-phosphotransferase which is deficient in Inclusion cell disease (1-cell disease); deficiency in an acid hydrolase cofactor such as sphingolipid activator proteins (saposin A, B, C, D); deficiency of a membrane fusion protein such as ceroid lipofuscinosis neuronal proteins (CLN1-9) that cause neuronal ceroid lipofuscinosis (NCL); deficiency of proteins involved in transporting substrates or metabolites of acid hydrolases to and from the lysosome such as Niemann-Pick type C protein, a cholesterol transporter, that is deficient in Niemann-Pick type C(NPC); and deficiency in lysosomal receptor or transport proteins which import substrates of acid hydrolases into the lysosomal lumen such as LAMP2 Å that is deficient in Dannon's disease. As a result, individuals suffering from lysosomal storage diseases have accumulated materials in lysosomes. Representative lysosomal storage diseases include those listed below in Table 10.

Mutant: As used herein, the term "mutant" refers to an entity that shows significant structural identity with a reference entity but differs structurally from the reference entity in the presence or level of one or more chemical moieties as compared with the reference entity. In many embodiments, a mutant also differs functionally from its reference entity. In general, whether a particular entity is properly considered to be a "mutant" of a reference entity is based on its degree of structural identity with the reference entity. As will be appreciated by those skilled in the art, any biological or chemical reference entity has certain characteristic structural elements. A mutant, by definition, is a distinct chemical entity that shares one or more such characteristic structural elements. To give but a few examples, a small molecule may have a characteristic core structural element (e.g., a macrocycle core) and/or one or more characteristic pendent moieties so that a mutant of the small molecule is one that shares the core structural element and the characteristic pendent moieties but differs in other pendent moieties and/or in types of bonds present (single vs double, E vs Z, etc) within the core, a polypeptide may have a characteristic sequence element comprised of a plurality of amino acids having designated positions relative to one another in linear or three-dimensional space and/or contributing to a particular biological function, a nucleic acid may have a characteristic sequence element comprised of a plurality of nucleotide residues having designated positions relative to on another in linear or three-dimensional space. For example, a mutant polypeptide may differ from a reference polypeptide as a result of one or more differences in amino acid sequence and/or one or more differences in chemical moieties (e.g., carbohydrates, lipids, etc) covalently attached to the polypeptide backbone. In some embodiments, a mutant polypeptide shows an overall sequence identity with a reference polypeptide that is at least 85%, 86%, 87%, 88%, 89%, 90%, 91%, 92%, 93%, 94%, 95%, 96%, 97%, or 99%. Alternatively or additionally, in some embodiments, a mutant polypeptide does not share at least one characteristic sequence element with a reference polypeptide. In some embodiments, the reference polypeptide has one or more biological activities. In some embodiments, a mutant polypeptide shares one or more of the biological activities of the reference polypeptide. In some embodiments, a mutant polypeptide lacks one or more of the biological activities of the reference polypeptide. In some embodiments, a mutant polypeptide shows a reduced level of one or more biological activities as compared with the reference polypeptide.

Pharmaceutical composition: As used herein, the term "pharmaceutical composition" refers to an active agent, formulated together with one or more pharmaceutically acceptable carriers. In some embodiments, active agent is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Pharmaceutically acceptable: As used herein, the phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable carrier: As used herein, the term "pharmaceutically acceptable carrier" means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Pharmaceutically acceptable salt: The term "pharmaceutically acceptable salt", as used herein, refers to salts of such compounds that are appropriate for use in pharmaceutical contexts, i.e., salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). In some embodiments, pharmaceutically acceptable salt include, but are not limited to, nontoxic acid addition salts, which are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. In some embodiments, pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. In some embodiments, pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

Polypeptide: In general, a "polypeptide" is a string of at least two residues (e.g., amino acids) linked to one another by peptide bonds. In some embodiments, a polypeptide includes one or more moieties other than such residues. For example, in some embodiments, a polypeptide comprises one or more glycan moieties attached to its residues (e.g., is a glycopeptide). In some embodiments, a polypeptide comprises one or more polyethylene glycol moieties (i.e., is pegylated). In some embodiments, a polypeptide comprises one or more polypeptide chain linked by one or more disulfide bonds or associated by other means. In some embodiments, a polypeptide includes amino acid residues. In some embodiments, a polypeptide includes one or more residues that are not amino acids. In some embodiments, a polypeptide includes one or more residues that is an amino acid that does not occur in nature.

Pharmacological chaperone: As used herein, the term "pharmacological chaperone" refers to a molecule, such as small molecule, polypeptide, nucleic acid, lipid, or carbohydrate that specifically binds to a protein and has one or more of the following effects: enhancing the formation of a stable molecular conformation of the protein; inducing trafficking of the protein from the ER to another cellular location, preferably a native cellular location, i.e., preventing ER-associated degradation of the protein; preventing aggregation of misfolded proteins; and/or restoring or enhancing at least partial wild-type function and/or activity of the protein. For example, in some embodiments, a pharmacological chaperone acts on one or more lysosomal enzymes. In some such embodiments, a pharmacological chaperone is an entity that binds to a lysosomal enzyme so that its proper folding, trafficking, non-aggregation, and/or activity is increased relative to that observed absent the pharmacological chaperone.

Proteinopathy: As used herein, the term "proteinopathy" or "proteinopathic" refers to a disease, disorder, and/or condition associated with the pathogenic aggregation and/or accumulation of one or more types of proteins, for example, but not limited to α-synuclein, β-amyloid, and/or tau proteins. In some embodiments, a proteinopathy is characterized by an anomaly in one or more of protein production, folding, aggregation, metabolism, or degradation (e.g. autophagy), transportation, etc. In some embodiments, proteinopathies are neurodegenerative diseases. In some embodiments, proteinopathies are inflammatory diseases. In some embodiments, proteinopathies are cardiovascular diseases. In some embodiments, proteinopathies are proliferative diseases. Specific pathologies such as synucleinopathies, tauopathies, amyloidopathies, TDP-43 proteinopathies and others are examples of proteinopathies. Exemplary proteins implicated in proteinopathies include: α-synuclein in the case of Parkinson's disease, Lewy body disease, and other synucleinopathies; tau and β-amyloid in the case of Alzheimer's disease and certain other neurodegenerative diseases; SOD1 and TDP-43 in the case of amyotrophic lateral sclerosis; huntingtin in the case of Huntington's disease; rhodopsin in the case of retinitis pigmentosa; and proteins involved in lysosomal storage diseases.

Proteostasis: The term "proteostasis", or "protein homeostasis", refers to the concentration, conformation, binding interactions, e.g., quaternary structure, and location of proteins making up the proteome. Proteostasis is influenced by the chemistry of protein folding/misfolding and by numerous regulated networks of interacting and competing biological pathways that influence protein synthesis, folding, conformation, binding interactions, trafficking, disaggregation and degradation. In some embodiments, proteostasis is controlled, for example, by altering level and/or activity of one or more nucleic acids or proteins. In some embodiments, proteostasis is controlled through transcriptional and/or translational changes.

Rab polypeptide: As used herein, the term "Rab polypeptide" refers to a polypeptide that shares a characteristic sequence element and/or overall degree of sequence identity with a member of the Rab family of small guanosine triphosphates (GTPases) that regulate multiple steps of vesicle trafficking and membrane fusion, including but not limited to vesicles of the endosome-lysosome system, synaptic vesicles of neurons, exocytosis of cellular storage materials, and the transport of newly synthesized proteins from endoplasmic reticulum to the Golgi apparatus and within Golgi compartments. An example of Rab polypeptide is Rab1a polypeptide. Table 6 provides nucleic acid sequence encoding Rab1a polypeptide. Table 6 provides representative examples of Rab polypeptide sequences.

In some embodiments, a Rab polypeptide is a Rab polypeptide homolog. The term "Rab polypeptide homolog" comprises a polypeptide whose amino acid sequence includes at least one sequence element comprising conserved residues found in polypeptides of Table 6; in some such embodiments, such sequence element comprises at least 3, 4, 5, 6, 7, 8, 9, 10 or more residues whose identity and relative position is preserved. In some embodiments, such sequence element comprises at least 3, 4, 5, 6, 7, 8, 9, 10 or more consecutive residues. Alternatively or additionally, in some embodiments, a "Rab polypeptide homolog" is or comprises a polypeptide whose amino acid sequence shows at least 50%, 55%, 60%, 65%, 70%, 75%, 80%, 85%, 90%, 95%, 96%, 97%, 98%, 99% or greater overall sequence identity with one or more polypeptides in Table 6 and/or shares at least one characteristic sequence element with one or more polypeptides in Table 6. In some embodiments, such a characteristic sequence element includes one or more catalytic residues and/or one or more conserved residues found in polypeptides of Table 6.

Sample: As used herein, the term "sample" refers to a biological sample obtained or derived from a source of interest, as described herein. In some embodiments, a source of interest comprises an organism, such as an animal or human. In some embodiments, a biological sample comprises biological tissue or fluid. In some embodiments, a biological sample is or comprises bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; feces, other body fluids, secretions, and/or excretions; and/or cells therefrom, etc. In some embodiments, a biological sample is or comprises cells obtained from an individual. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to techniques such as amplification or reverse transcription of mRNA, isolation and/or purification of certain components, etc.

Saposin polypeptide: As used herein, the term "saposin" refers to a polypeptide that shares at least one characteristic sequence element and/or overall sequence identity with a saposin protein domain. Saposins are small heat-stable lysosomal proteins that serve as activators of various lysosomal lipid-degrading enzymes by isolating the lipid substrate form the membrane surroundings and making it more accessible to the soluble degradative enzymes. Saposins are synthesized as a single precursor molecule, prosaposin, which contains four saposin-B domains (four each of SapB1 and SapB2), yielding the active saposins after proteolytic cleavage (saposin A, B, C, and D), and two saposin-A domains (SapA) that are removed in the activation process. Representative known saposin polypeptides include those listed below in Table 7.

In some embodiments, saposin polypeptide is a saposin polypeptide homolog. The term "saposin polypeptide homolog" is or comprises a polypeptide whose amino acid sequence includes at least one sequence element comprising conserved residues found in polypeptides of Table 7; in some such embodiments, such sequence element comprises at least 3, 4, 5, 6, 7, 8, 9, 10 or more residues whose identity and relative position is preserved. In some embodiments, such sequence element comprises at least 3, 4, 5, 6, 7, 8, 9, 10 or more consecutive residues. Alternatively or additionally, in some embodiments, a "saposin polypeptide homolog" is or comprises a polypeptide whose amino acid sequence shows at least 50%, 55%, 60%, 65%, 70%, 75%, 80%, 85%, 90%, 95%, 96%, 97%, 98%, 99% or greater overall sequence identity with one or more polypeptides in Table 7 and/or shares at least one characteristic sequence element with one or more polypeptides in Table 7. In some embodiments, such a characteristic sequence element includes one or more catalytic residues and/or one or more conserved residues found in polypeptides of Table 7.

Small molecule: As used herein, the term "small molecule" includes any chemical or other moiety whose molecular weight is less than about 5000 daltons (Da). In some embodiments, small molecules have molecular weights below about 2500, about 1000, or about 500 daltons. In some embodiments, small molecules are not polymers. In some embodiments, small molecules are not peptides. In some embodiments, small molecules are not nucleic acids. In some embodiments, small molecules have biological activity and/or act to affect biological processes. In some embodiments, small molecules are natural products. In some embodiments, small molecules are not natural products (e.g., were first prepared by chemical synthesis).

Sphingolipid metabolizing enzyme: As used herein, the term "sphingolipid metabolizing enzyme" refers to enzymes that control synthesis and degradation of sphingolipids. These enzymes co-ordinate interconversion of sphigolipid metabolites (e.g., ceramide, sphingosine, diacyglycerol, or sphingosine-1-phosphate). Exemplary sphingolipid metabolizing enzymes include, but are not limited to serine palmitoyltransferase, 3-ketodihydrosphingosine reductase, ceramide galactosyltransferase, glucosylceramide synthase, sphingomyelin synthase, and/or various lysosomal enzymes such as β-hexosaminidase, β-galactosidase. Representative known sphingolipid metabolizing enzymes include those listed below in Table 8. In some embodiments, a sphingolipid metabolizing enzyme can be a sphingolipid metabolizing enzyme homolog. A "sphingolipid metabolizing enzyme homolog" is or comprises a polypeptide whose amino acid sequence includes at least one sequence element comprising conserved residues found in polypeptides of Table 8; in some such embodiments, such sequence element comprises at least 3, 4, 5, 6, 7, 8, 9, 10 or more residues whose identity and relative position is preserved. In some embodiments, such sequence element comprises at least 3, 4, 5, 6, 7, 8, 9, 10 or more consecutive residues. Alternatively or additionally, in some embodiments, a "sphingolipid metabolizing enzyme homolog" is or comprises a polypeptide whose amino acid sequence shows at least 50%, 55%, 60%, 65%, 70%, 75%, 80%, 85%, 90%, 95%, 96%, 97%, 98%, 99% or greater overall sequence identity with one or more polypeptides in Table 8 and/or shares at least one characteristic sequence element with one or more polypeptides in Table 8. In some embodiments, such a characteristic sequence element includes one or more catalytic residues and/or one or more conserved residues found in polypeptides of Table 8.

Stability: As used herein, the term "stability" refers to inducing or stabilizing a lysosomal enzyme in its wild-type or functionally identical conformation. The term functionally identical used herein means that while there may be minor variations in the conformation as almost all proteins exhibit some conformational flexibility in their physiological state, conformational flexibility does not result in protein aggregation, elimination through the endoplasmic reticulum-associated degradation pathway, impairment of protein function, and/or improper transport within the cell. Stabilization can be determined by any one of: increased enzyme half-life in the cell; increased levels of the enzyme in the lysosome; or increased hydrolytic activity as measured in cellular lysates using an artificial substrate.

Subject: As used herein, the term "subject", "individual" or "patient" refers to any organism upon which embodiments of the invention may be used or administered, e.g., for experimental, diagnostic, prophylactic, and/or therapeutic purposes. Typical subjects include animals (e.g., mammals such as mice, rats, rabbits, non-human primates, and humans; insects; worms; etc.). A human includes pre and post natal forms. In some embodiments, subject carries mutant allele for the lysosomal enzyme targeted by the administered lysosomal activating agent.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Suffering from: An individual who is "suffering from" a disease, disorder, and/or condition (e.g., stroke) has been diagnosed with and/or exhibits one or more symptoms of the disease, disorder, and/or condition.

Susceptible to: An individual who is "susceptible to" a disease, disorder, and/or condition (e.g., any disease, disorder, and/or condition, including, but not limited to, any disease, disorder, and/or condition described herein) is at risk for developing the disease, disorder, and/or condition. In some embodiments, an individual who is susceptible to a disease, disorder, and/or condition does not display any symptoms of the disease, disorder, and/or condition. In some embodiments, an individual who is susceptible to a disease, disorder, and/or condition has not been diagnosed with the disease, disorder, and/or condition. In some embodiments, an individual who is susceptible to a disease, disorder, and/or condition is an individual who has been exposed to conditions associated with development of the disease, disorder, and/or condition (e.g., the individual has been exposed to an infectious agent; the individual has been exposed to an environmental hazard thought to cause the disease, disorder, and/or condition; etc.). In some embodiments, a risk of developing a disease, disorder, and/or condition is a population-based risk (e.g., an individual carries a gene and/or allele associated with the disease, disorder, and/or condition).

Synucleinopathy: As used herein, the term "synucleinopathy" or "α-synucleinopathy" refers to diseases, disorders, and/or conditions that are associated with or characterized by pathological accumulation of the protein α-synuclein, including but not limited to Parkinson's disease, Lewy body disease, multiple system atrophy, Hallervorden-Spatz disease, and frontotemporal dementia.

Tauopathy: As used herein, the term "tauopathy" or "tauopathic" refers to diseases, disorders, and/or conditions that are associated with or characterized by pathological accumulation of the tau protein, including but not limited to Alzheimer's disease, frontotemporal dementia, and progressive supranuclear palsy.

Therapeutic agent: As used herein, the phrase "therapeutic agent" refers to any agent that elicits a desired pharmacological effect when administered to an organism. In some embodiments, an agent is considered to be a therapeutic agent if it demonstrates a statistically significant effect across an appropriate population. In some embodiments, the appropriate population may be a population of model organisms. In some embodiments, an appropriate population may be defined by various criteria, such as a certain age group, gender, genetic background, preexisting clinical conditions, etc. In some embodiments, a therapeutic agent is any substance that can be used to alleviate, ameliorate, relieve, inhibit, delay onset of, reduce severity of, and/or reduce incidence of one or more symptoms or features of a disease, disorder, and/or condition.

Therapeutically effective amount: The term "therapeutically effective amount", as used herein, refers to an amount of a therapeutic agent whose administration, when viewed in a relevant population, correlates with or is reasonably expected to correlate with achievement of a particular therapeutic effect. The therapeutic effect may be objective (i.e., measurable by some test or marker) or subjective (i.e., subject gives an indication of or feels an effect). In some embodiments, a therapeutically effective amount of a substance is an amount that is sufficient, when administered to a subject suffering from or susceptible to a disease, disorder, and/or condition, to treat, diagnose, prevent, and/or delay and/or alleviate one or more symptoms of the disease, disorder, and/or condition. In some embodiments, therapeutically effective amount is the amount that increases post-ER forms of lysosomal enzymes in target cells. In some embodiments, therapeutically effective amount is the amount that increases lysosomal proteolysis in target cells. In some embodiments, therapeutically effective amount is the amount that reduces sphingolipid levels in target cells. In some embodiments, therapeutically effective amount is the amount that reduces glucosylceramide levels in target cells. In some embodiments, therapeutically effective amount is the amount that reduces α-synuclein levels in target cells. Disease progression can be monitored by clinical observations, laboratory and neuroimaging investigations apparent to a person skilled in the art. A therapeutically effective amount is commonly administered in a dosing regimen that may comprise multiple unit doses. For any particular therapeutic agent, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific fusion protein employed; the duration of the treatment; and like factors as is well known in the medical arts. Furthermore, an effective amount may be administered via a single dose or via multiple doses within a treatment regimen. In some embodiments, individual doses or compositions are considered to contain a "therapeutically effective amount" when they contain an amount effective as a dose in the context of a treatment regimen. Those of ordinary skill in the art will appreciate that a dose or amount may be considered to be effective if it is or has been demonstrated to show statistically significant effectiveness when administered to a population of patients; a particular result need not be achieved in a particular individual patient in order for an amount to be considered to be therapeutically effective as described herein.

Trafficking: As used herein, the term "trafficking" refers to movement of a polypeptide or vesicle through the endoplasmic reticulum to a predetermined location within the cell, cell membrane, or into the extracellular environment. In some specific embodiments, the term as used herein refers to the movement of a polypeptide (e.g., a lysosomal enzyme) through the ER and/or into the lysosome.

Treatment: As used herein, the term "treatment" (also "treat" or "treating") refers to any administration of a pharmaceutical agent that alleviates, ameliorates, relieves, inhibits, reduces severity of and/or reduces incidence of at least one symptom or feature of a particular disease, disorder, and/or condition. Treatment includes prevention of worsening of the disease condition, i.e., halting the development of additional symptoms from the time the subject is diagnosed with the disease based on some symptoms. Treatment in the context of this application may also be defined as reduction in alpha-synuclein levels in the subject. In some embodiments, treatment is therapeutic in that it is administered to a subject who displays at least one sign or symptom of a disease, disorder, and/or condition.

Prophylaxis: As used herein, the term "prophylaxis" refers to administration of the pharmaceutical agent that delays onset of at least one symptom from exhibiting in a subject, wherein the subject has not exhibited prior signs or symptoms of the relevant disease, disorder, and/or condition.

Unit dose: The expression "unit dose" as used herein refers to an amount administered as a single dose and/or in a physically discrete unit of a pharmaceutical composition. In many embodiments, a unit dose contains a predetermined quantity of an active agent. In some embodiments, a unit dose contains an entire single dose of the agent. In some embodiments, more than one unit dose is administered to achieve a total single dose. In some embodiments, administration of multiple unit doses is required, or expected to be required, in order to achieve an intended effect. A unit dose may be, for example, a volume of liquid (e.g., an acceptable carrier) containing a predetermined quantity of one or more therapeutic agents, a predetermined amount of one or more therapeutic agents in solid form, a sustained release formulation or drug delivery device containing a predetermined amount of one or more therapeutic agents, etc. It will be appreciated that a unit dose may be present in a formulation that includes any of a variety of components in addition to the therapeutic agent(s). For example, acceptable carriers (e.g., pharmaceutically acceptable carriers), diluents, stabilizers, buffers, preservatives, etc., may be included as described infra. It will be appreciated by those skilled in the art, in many embodiments, a total appropriate daily dosage of a particular therapeutic agent may comprise a portion, or a plurality, of unit doses, and may be decided, for example, by the attending physician within the scope of sound medical judgment. In some embodiments, the specific effective dose level for any particular subject or organism may depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs and/ or additional therapies used in combination or coincidental with specific compound(s) employed, and like factors well known in the medical arts.

Wild-type: As used herein, the term "wild-type" has its art-understood meaning that refers to an entity having a structure and/or activity as found in nature in a "normal" (as contrasted with mutant, diseased, altered, etc) state or context. Those of ordinary skill in the art will appreciate that wild type genes and polypeptides often exist in multiple different forms (e.g., alleles).

Definitions for Small Molecule Chemical Compound Structures

Small molecule chemical compound structures are described herein using standard nomenclature. Unless defined otherwise, all technical and scientific terms used herein have the same meaning as is commonly understood by one of skill in the art to which this invention belongs.

Unless otherwise indicated (i.e., by implication or statement), it is understood that any particular small molecule compound depicted or described herein may be comprised of any available or appropriate isotope of the atoms that comprise the compound. As is understood by those skilled in the art, isotopes are atoms having the same atomic number but different mass numbers. By way of general example, and without limitation, isotopes of hydrogen include tritium and deuterium; isotopes of carbon include $^{11}C$, $^{13}C$, and $^{14}C$.

The term "substituted" means that any one or more hydrogens on the designated atom or group is replaced with a selection from the indicated group, provided that the designated atom's normal valence is not exceeded. When the substituent is oxo (i.e., =O), then 2 hydrogens on the atom are replaced. When aromatic moieties are substituted by an oxo group, the aromatic ring is replaced by the corresponding partially unsaturated ring. For example a pyridyl group substituted by oxo is a pyridone. In certain embodiments, particular substituents and/or variables are permissible only if such combinations result in stable compounds or useful synthetic intermediates. A stable compound or stable structure is one that is sufficiently robust to survive the environment(s) to which it is exposed in practice of the present invention. For example, in some embodiments, a compound or structure is stable if it is sufficiently robust to be isolated and/or purified. In some embodiments, a compound or structure is stable if it is sufficiently robust to be compounded into a pharmaceutical composition. In some embodiments, a compound or structure is stable if it is sufficiently robust to be utilized in a functional assay as described herein.

Suitable groups that may be present on an "optionally substituted" position include, but are not limited to, e.g., halogen, cyano, hydroxyl, amino, nitro, oxo, azido, alkanoyl (such as a $C_2$-$C_6$ alkanoyl group such as acyl or the like); carboxamido; alkylcarboxamide; alkyl groups, alkoxy groups, alkylthio groups including those having one or more thioether linkages, alkylsulfinyl groups including those having one or more sulfinyl linkages, alkylsulfonyl groups including those having one or more sulfonyl linkages, mono- and diaminoalkyl groups including groups having one or more N atoms, all of the foregoing optional alkyl substituents may have one or more methylene group replaced by an oxygen or —NH—, and have from about 1 to about 8, from about 1 to about 6, or from 1 to about 4 carbon atoms, cycloalkyl; phenyl; phenylalkyl with benzyl being an exemplary phenylalkyl group, phenylalkoxy with benzyloxy being an exemplary phenylalkoxy group.

A dash ("-") that is not between two letters or symbols is used to indicate a point of attachment for a substituent.

"Alkyl" includes both branched and straight chain saturated aliphatic hydrocarbon groups, having the specified number of carbon atoms. The term $C_1$-$C_2$ alkyl means an alkyl group having from 1 to about 2 carbon atoms, e.g., methyl and ethyl, respectively.

"Alkylene" is a straight or branched saturated bivalent carbon chain having the indicated number of carbon atoms.

"Alkylester" is an alkyl group as defined above attached through an ester linkage. The ester linkage may be in either orientation, e.g., a group of the formula —O(C=O) alkyl or a group of the formula —(C=O)O alkyl.

"Alkanoyl" is an alkyl group as defined above, attached through a keto (—(C=O)—) bridge. Alkanoyl groups have the indicated number of carbon atoms, with the carbon of the keto group being included in the numbered carbon atoms. For example a $C_2$ alkanoyl group is an acetyl group having the formula $CH_3$(C=O)—.

"Alkylsulfonyl" is a group of the formula alkyl —($SO_2$)—, where the alkyl group is an alkyl group as defined above having the defined number of carbon atoms. An exemplary alkylsulfonyl group is methylsulfonyl.

"Alkylthio" indicates an alkyl group as defined above attached through a sulfur linkage, i.e. a group of the formula alkyl —S—. Examples include ethylthio and pentylthio.

"Alkoxy" means an alkyl group, as defined above, with the indicated number of carbon atoms attached via an oxygen bridge.

"Cycloalkyl" is a saturated hydrocarbon ring group, having the specified number of carbon atoms, usually from 3 to about 7 carbon atoms. Examples of cycloalkyl groups include cyclopropyl, cyclobutyl, cyclopentyl, or cyclohexyl as well as bridged or caged saturated ring groups such as norborane or adamantane.

A "mono- or bicyclic carbocycle" is a 3 to 8 membered saturated, partially unsaturated, or aromatic ring containing only carbon ring atoms or a 6 to 11 membered saturated, partially unsaturated, or aromatic bicyclic carbocyclic ring system containing only carbon ring atoms. Unless otherwise indicated, the carbocyclic group may be attached to its pendant group at any carbon atom that results in a stable structure. When indicated the carbocyclic rings described herein may be substituted on any available ring carbon if the resulting compound is stable. Carbocyclic groups include, cycloalkyl groups, such as cyclopropyl and cyclohexyl; cycloalkenyl groups, such as cyclohexenyl, bridged cycloalkyl groups; and aryl groups, such as phenyl.

"Halo" or "halogen" means fluoro, chloro, bromo, or iodo.

"Heterocycloalkyl" is a saturated cyclic group having the indicated number of ring atoms containing from 1 to about 3 heteroatoms chosen from N, O, and S, with remaining ring atoms being carbon. Examples of heterocycloalkyl groups include, tetrahydrofuranyl and pyrrolidinyl groups.

"Mono- or bicyclic heterocycle" is a 5- to 8-membered saturated, partially unsaturated, or aromatic ring containing from 1 to about 4 heteroatoms chosen from N, O, and S, with remaining ring atoms being carbon, or a 7 to 11 membered bicyclic saturated, partially unsaturated, or aromatic heterocylic ring system, each containing at least 1 heteroatom in the multiple ring system chosen from N, O, and S and containing up to about 4 heteroatoms independently chosen from N, O, and S in each ring of the multiple ring system. Unless otherwise indicated, the heterocyclic ring may be attached to the group it substitutes at any heteroatom or carbon atom that results in a stable structure. When indicated the heterocyclic rings described herein may be substituted on carbon or on a nitrogen atom if the resulting compound is stable. A nitrogen atom in the heterocycle may optionally be quaternized. It is preferred that the total number of heteroatoms in a heterocyclic groups is not more than 4 and that the total number of S and O atoms in a heterocyclic group is not more than 2, more preferably not more than 1. Examples of heterocyclic groups include, pyridyl, indolyl, pyrimidinyl, pyridizinyl, pyrazinyl, imidazolyl, oxazolyl, furanyl, thiophenyl, thiazolyl, triazolyl, tetrazolyl, isoxazolyl, quinolinyl, pyrrolyl, pyrazolyl, benz[b]thiophenyl, isoquinolinyl, quinazolinyl, quinoxalinyl, thienyl, isoindolyl, dihydroisoindolyl, 5,6,7,8-tetrahydroisoquinoline, pyridinyl, pyrimidinyl, furanyl, thienyl, pyrrolyl, pyrazolyl, pyrrolidinyl, morpholinyl, piperazinyl, piperidinyl, and pyrrolidinyl.

"Mono- and/or di-alkylamino" means secondary or tertiary alkyl amino groups, wherein the alkyl groups are as defined above and have the indicated number of carbon atoms. The point of attachment of the alkylamino group is on the nitrogen. The alkyl groups are independently chosen. Examples of mono- and di-alkylamino groups include ethylamino, dimethylamino, and methyl-propyl-amino.

"Mono- or di-alkylcarboxamide" is a group of the formula —(C═O)Nalkyl$_1$alkyl$_2$, where the alkyl$_1$ and alkyl$_2$ groups are independently chosen alkyl groups as defined herein, attached through a carboxamide linkage. The carboxamide linkage may be in either orientation, e.g., —NH(C═O)— or —(C═O)NH—.

"Haloalkyl" means both branched and straight-chain alkyl groups having the specified number of carbon atoms, substituted with 1 or more halogen atoms, generally up to the maximum allowable number of halogen atoms. Examples of haloalkyl include, but are not limited to, trifluoromethyl, difluoromethyl, 2-fluoroethyl, and penta-fluoroethyl.

"Haloalkoxy" indicates a haloalkyl group as defined above attached through an oxygen bridge (oxygen of an alcohol radical).

The term "chiral" refers to molecules, which have the property of non-superimposability of the mirror image partner.

"Stereoisomers" are compounds, which have identical chemical constitution, but differ with regard to the arrangement of the atoms or groups in space.

A "diastereomer" is a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis, crystallization in the presence of a resolving agent, or chromatography, using, for example a chiral HPLC column.

"Enantiomers" refer to two stereoisomers of a compound, which are non-superimposable mirror images of one another. A 50:50 mixture of enantiomers is referred to as a racemic mixture or a racemate, which may occur where there has been no stereoselection or stereospecificity in a chemical reaction or process.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., Stereochemistry of Organic Compounds (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory.

A "racemic mixture" or "racemate" is an equimolar (or 50:50) mixture of two enantiomeric species, devoid of optical activity. A racemic mixture may occur where there has been no stereoselection or stereospecificity in a chemical reaction or process.

TABLE 1

Representative amino acid sequences for β-galactosidase polypeptides.

| Name | Exemplary Sequence | Genbank Accession number |
|---|---|---|
| β-galactosidase, isoform 1 (Homo sapiens) | MPGFLVRILLLLLVLLLLGPTRGLRNATQRMFEIDYSR DSFLKDGQPFRYISGSIHYSRVPRFYWKDRLL KMKMAGLNAIQTYVPWNFHEPWPGQYQFSEDHDVEY FLRLAHELGLLVILRPGPYICAEWEMGGLPAWLL EKESILLRSSDPDYLAAVDKWLGVLLPKMKPLLYQNG GPVITVQVENEYGSYFACDFDYLRFLQKRFRHH LGDDVVLFTTDGAHKTFLKCGALQGLYTTVDFGTGSN ITDAFLSQRKCEPKGPLINSEFYTGWLDHWGQPHSTIKT EAVASSLYDILARGASVNLYMFIGGTNFAYWNGANSP YAAQPTSYDYDAPLSEAGDLTEKYFALRNIIQKFEKVP EGPIPPSTPKFAYGKVTLEKLKTVGAALDILCPSGPIKSL YPLTFIQVKQHYGFVLYRTTLPQDCSNPAPLSSPLNGV HDRAYVAVDGIPQGVLERNNVITLNITGKAGATLDLLV ENMGRVNYGAYINDFKGLVSNLTLSSNILTDWTIFPLD TEDAVRSHLGGWGHRDSGHHDEAWAHNSSNYTLPAF | AAA51823.1 |

TABLE 1 -continued

Representative amino acid sequences for β-galactosidase polypeptides.

| Name | Exemplary Sequence | Genbank Accession number |
|---|---|---|
| | YMGNFSIPSGIPDLPQDTFIQFPGWTKGQVWINGFNLG RYWPARGPQLTLFVPQHILMTSAPNTITVLELEWAPCS SDDPELCAVTFVDRPVIGSSVTYDHPSKPVEKRLMPPPP QKNKDSWLDHV (SEQ ID NO. 1) | |
| β-galactosidase, isoform 2 (Homo sapiens) | MPGFLVRILPLLLVLLLLGPTRGLRNATQRMFEIDYSRD SFLKDGQPFRYISGSIHYSRVPRFYWKDRLLKMKMAG LNAIQTLPGSCGQVVGSPSAQDEASPLSEWRASYNSAG SNITDAFLSQRKCEPKGPLINSEFYTGWLDHWGQPHSTI KTEAVASSLYDILARGASVNLYMFIGGTNFAYWNGAN SPYAAQPTSYDYDAPLSEAGDLTEKYFALRNIIQKFEK VPEGPIPPSTPKFAYGKVTLEKLKTVGAALDILCPSGPIK SLYPLTFIQVKQHYGFVLYRTTLPQDCSNPAPLSSPLNG VHDRAYVAVDGIPQGVLERNNVITLNITGKAGATLDLL VENMGRVNYGAYINDFKGLVSNLTLSSNILTDWTIFPL DTEDAVRSHLGGWGHRDSGHHDEAWAHNSSNYTLPA FYMGNFSIPSGIPDLPQDTFIQFPGWTKGQVWINGFNLG RYWPARGPQLTLFVPQHILMTSAPNTITVLELEWAPCS SDDPELCAVTFVDRPVIGSSVTYDHPSKPVEKRLMPPPP QKNKDSWLDHV (SEQ ID NO. 2) | NP_001129074.1 |
| β-galactosidase, isoform 3 (Homo sapiens) | MFEIDYSRDSFLKDGQPFRYISGSIHYSRVPRFYWKDRL LKMKMAGLNAIQTYVPWNFHEPWPGQYQFSEDHDVE YFLRLAHELGLLVILRPGPYICAEWEMGGLPAWLLEKE SILLRSSDPDYLAAVDKWLGVLLPKMKPLLYQNGGPVI TVQVENEYGSYFACDFDYLRFLQKRFRHHLGDDVVLF TTDGAHKTFLKCGALQGLYTTVDFGTGSNITDAFLSQR KCEPKGPLINSEFYTGWLDHWGQPHSTIKTEAVASSLY DILARGASVNLYMFIGGTNFAYWNGANSPYAAQPTS YDYDAPLSEAGDLTEKYFALRNIIQKFEKVPEGPIPPSTP KFAYGKVTLEKLKTVGAALDILCPSGPIKSLYPLTFIQV KQHYGFVLYRTTLPQDCSNPAPLSSPLNGVHDRAYVA VDGIPQGVLERNNVITLNITGKAGATLDLLVENMGRV NYGAYINDFKGLVSNLTLSSNILTDWTIFPLDTEDAVRS HLGGWGHRDSGHHDEAWAHNSSNYTLPAFYMGNFSI PSGIPDLPQDTFIQFPGWTKGQVWINGFNLGRYWPARG PQLTLFVPQHILMTSAPNTITVLELEWAPCSSDDPELCA VTFVDRPVIGSSVTYDHPSKPVEKRLMPPPPQKNKDSW LDHV (SEQ ID NO. 3) | NP_001073279.1 |

TABLE 2

Representative amino acid sequences for β-glucocerebrosidase polypeptides.

| Name | Exemplary Sequence | Genbank Accession number |
|---|---|---|
| Lysosomal β-glucocerebrosidase, GBA1 (Homo sapiens) | MEFSSPSREECPKPLSRVSIMAGSLTGLLLLQAVSWAS GARPCIPKSFGYSSVVCVCNATYCDSFDPPTFPALGTFS RYESTRSGRRMELSMGPIQANHTGTGLLLTLQPEQKFQ KVKGFGGAMTDAAALNILALSPPAQNLLLKSYFSEEGI GYNIIRVPMASCDFSIRTYTYADTPDDFQLHNFSLPEED TKLKIPLIHRALQLAQRPVSLLASPWTSPTWLKTNGAV NGKGSLKGQPGDIYHQTWARYFVKFLDAYAEHKLQF WAVTAENEPSAGLLSGYPFQCLGFTPEHQRDFIARDLG PTLANSTHHNVRLLMLDDQRLLLPHWAKVVLTDPEAA KYVHGIAVHWYLDFLAPAKATLGETHRLFPNTMLFAS EACVGSKFWEQSVRLGSWDRGMQYSHSIITNLLYHVV GWTDWNLALNPEGGPNWVRNFVDSPIIVDITKDTFYK QPMFYHLGHFSKFIPEGSQRVGLVASQKNDLDAVALM HPDGSAVVVLNRSSKDVPLTIKDPAVGFLETISPGYSI HTYLWRRQ (SEQ ID NO. 4) | AAH03356.1 |

TABLE 2 -continued

Representative amino acid sequences for β-glucocerebrosidase polypeptides.

| Name | Exemplary Sequence | Genbank Accession number |
|---|---|---|
| Non-lysosomal β-glucocerebrosidase GBA2 (Homo sapiens) | MGTQDPGNMGTGVPASEQISCAKEDPQVYCPEETGGT KDVQVTDCKSPEDSRPPKETDCCNPEDSGQLMVSYEG KAMGYQVPPFGWRICLAHEFTEKRKPFQANNVSLSNM IKHIGMGLRYLQWWYRKTHVEKKTPFIDMINSVPLRQI YGCPLGGIGGGTITRGWRGQFCRWQLNPGMYQHRTVI ADQFTVCLRREGQTVYQQVLSLERPSVLRSWNWGLCG YFAFYHALYPRAWTVYQLPGQNVTLTCRQITPILPHDY QDSSLPVGVFVWDVENEGDEALDVSIMFSMRNGLGGG DDAPGGLWNEPFCLERSGETVRGLLLHHPTLPNPYTM AVAARVTAATTVTHITAFDPDSTGQQVWQDLLQDGQL DSPTGQSTPTQKGVGIAGAVCVSSKLRPRGQCRLEFSL AWDMPRIMFGAKGQVHYRRYTRFFGQDGDAAPALSH YALCRYAEWEERISAWQSPVLDDRSLPAWYKSAL FNELYFLADGGTVWLEVLEDSLPEELGRNMCHLRPTL RDYGRFGYLEGQEYRMYNTYDVHFYASFALIMLWPK LELSLQYDMALATLREDLTRRRYLMSGVMAPVKRRN VIPHDIGDPDDEPWLRVNAYLIHDTADWKDLNLKFVL QVYRDYYLTGDQNFLKDMWPVCLAVMESEMKFDK DHDGLIENGGYADQTYDGWVTTGPSAYCGGLWLAAV AVMVQMAALCGAQDIQDKFSSILSRGQEAYERLLWNG RYYNYDSSSRPQSRSVMSDQCAGQWFLKACGLGEGD TEVFPTQHVVRALQTIFELNVQAFAGGAMGAVNGMQP HGVPDKSSVQSDEVWVGVVYGLAATMIQEGLTWE GFQTAEGCYRTVWERLGLAFQTPEAYCQQRVFRSLAY MRPLSIWAMQLALQQQQHKKASWPKVKQGTGLRTGP MFGPKEAMANLSPE (SEQ ID NO. 5) | NP_065995.1 |

TABLE 3

Representative amino acid sequences for glucosylceramide synthase polypeptide.

| Name | Exemplary Sequence | Genbank Accession number |
|---|---|---|
| glucosylceramide synthase (Homo sapiens) | MALLDLALEGMAVFGFVLFLVLWLMHFMAIIYTRLHL NKKATDKQPYSKLPGVSLLKPLKGVDPNLINNLETFFE LDYPKYEVLLCVQDHDDPAIDVCKKLLGKYPNVDARL FIGGKKVGINPKINNLMPGYEVAKYDLIWICDSGIRVIP DTLTDMVNQMTEKVGLVHGLPYVADRQGFAATLEQV YFGTSHPRYYISANVTGFKCVTGMSCLMRKDVLDQAG GLIAFAQYIAEDYFMAKAIADRGWRFAMSTQVAMQNS GSYSISQFQSRMIRWTKLRINMLPATIICEPISECFVASLI IGWAAHHVFRWDIMVFFMCHCLAWFIFDYIQLRGVQG GTLCFSKLDYAVAWFIRESMTIYIFLSALWDPTISWRTG RYRLRCGGTAEEILDV (SEQ ID NO. 6) | NP_003349.1 |

TABLE 4

Representative amino acid sequences for hexosaminidase polypeptides.

| Name | Exemplary Sequence | Genbank Accession number |
|---|---|---|
| β-hexosaminidase, β-subunit (Homo sapiens) | MELCGLGLPRPPMLLALLLATLLAAMLALLTQVALVV QVAEAARAPSVSAKPGPALWPLPLSVKMTPNLL HLAPENFYISHSPNSTAGPSCTLLEEAFRRYHGYIFGFY KWHHEPAEFQAKTQVQQLLVSITLQSECDAF PNISSDESYTLLVKEPVAVLKANRVWGALRGLETFSQL VYQDSYGTFTINESTIIDSPRFSHRGILIDTS RHYLPVKIILKTLDAMAFNKFNVLHWHIVDDQSFPYQS ITFPELSNKGSYSLSHVYTPNDVRMVIEYARL RGIRVLPEFDTPGHTLSWGKGQKDLLTPCYSRQNKLDS FGPINPTLNTTYSFLTTFFKEISEVFPDQFIH LGGDEVEFKCWESNPKIQDFMRQKGFGTDFKKLESFYI QKVLDIIATINKGSIVWQEVFDDKAKLAPGTI | NP_000512.1 |

TABLE 4 -continued

Representative amino acid sequences for hexosaminidase polypeptides.

| Name | Exemplary Sequence | Genbank Accession number |
|---|---|---|
| | VEVWKDSAYPEELSRVTASGFPVILSAPWYLDLISYGQ DWRKYYKVEPLDFGGTQKQKQLFIGGEACLWG EYVDATNLTPRLWPRASAVGERLWSSKDVRDMDDAY DRLTRHRCRMVERGIAAQPLYAGYCNHENM (SEQ ID NO. 7) | |
| β-hexosaminidase, α-subunit (Homo sapiens) | MTSSRLWFSLLLAAAFAGRATALWPWPQNFQTSDQRY VLYPNNFQFQYDVSSAAQPGCSVLDEAFQRYRDLLFG SGSWPRPYLTGKRHTLEKNVLVVSVVTPGCNQLPTLES VENYTLTINDDQCLLLSETVWGALRGLETFSQLVWKS AEGTFFINKTEIEDFPRFPHRGLLLDTSRHYLPLSSILDT LDVMAYNKLNVFHWHLVDDPSFPYESFTFPELMRKGS YNPVTHIYTAQDVKEVIEYARLRGIRVLAEFDTPGHTL SWGPGIPGLLTPCYSGSEPSGTFGPVNPSLNNTYEFMST FFLEVSSVFPDFYLHLGGDEVDFTCWKSNPEIQDFMRK KGFGEDFKQLESFYIQTLLDIVSSYGKGYVVWQEVFDN KVKIQPDTIIQVWREDIPVNYMKELELVTKAGFRALLS APWYLNRISYGPDWKDFYIVEPLAFEGTPEQKALVIGG EACMWGEYVDNTNLVPRLWPRAGAVAERLWSNKLT SDLTFAYERLSHFRCELLRRGVQAQPLNVGFCEQEFEQ T (SEQ ID NO. 8) | NP_000511.2 |

TABLE 5

Representative amino acid sequences for lysosomal enzymes.

| Name | Exemplary Sequence | Genbank Accession number |
|---|---|---|
| iduronate-2-sulfatase (Homo sapiens) | MPPPRTGRGLLWLGLVLSSVCVALGSETQANSTTDAL NVLLIIVDDLRPSLGCYGDKLVRSPNIDQLASHSLLFQN AFAQQAVCAPSRVSFLTGRRPDTTRLYDFNSYWRVHA GNFSTIPQYFKENGYVTMSVGKVFHPGISSNHTDDSPY SWSFPPYHPSSEKYENTKTCRGPDGELHANLLCPVDVL DVPEGTLPDKQSTEQAIQLLEKMKTSASPEFLAVGYHK PHIPFRYPKEFQKLYPLENITLAPDPEVPDGLPPVAYNP WMDIRQREDVQALNISVPYGPIPVDFQRKIRQSYFASV SYLDTQVGRLLSALDDLQLANSTIIAFTSDHGWALGEH GEWAKYSNFDVATHVPLIFYVPGRTASLPEAGEKLFPY LDPFDSASQLMEPGRQSMDLVELVSLFPTLAGLAGLQV PPRCPVPSFHVELCREGKNLLKHFRFRDLEEDPYLPGNP RELIAYSQYPRPSDIPQWNSDKPSLKDIKIMGYSIRTIDY RYTVWVGFNPDEFLANFSDIHAGELYFVDSDPLQDHN MYNDSQGGDLFQLLMP (SEQ ID NO. 9) | NP_000193.1 |
| Acid sphingomyelinase (Homo sapiens) | MPRYGASLRQSCPRSGREQGQDGTAGAPGLLWMGLV LALALALALALSDSRVLWAPAEAHPLSPQGHPARLHRI VPRLRDVFGWGNLTCPICKGLFTAINLGLKKEPNVARV GSVAIKLCNLLKIAPPAVCQSIVHLFEDDMVEVWRRSV LSPSEACGLLLGSTCGHWDIFSSWNISLPTVPKPPPKPPS PPAPGAPVSRILFLTDLHWDHDYLEGTDPDCADPLCCR RGSGLPPASRPGAGYWGEYSKCDLPLRTLESLLSGLGP AGPFDMVYWTGDIPAHDVWHQTRQDQLRALTTVTAL VRKFLGPVPVYPAVGNHESTPVNSFPPPPFIEGNHSSRWL YEAMAKAWEPWLPAEALRTLRIGGFYALSPYPGLRLIS LNMNFCSRENFWLLINSTDPAGQLQWLVGELQAAEDR GDKVHIIGHIPPGHCLKSWSWNYYRIVARYENTLAAQF FGHTHVDEFEVFYDEETLSRPLAVAFLAPSATTYIGLNP GYRVYQIDGNYSGSSHVVLDHETYILNLTQANIPGAIP HWQLLYRARETYGLPNTLPTAWHNLVYRMRGDMQLF QTFWFLYHKGHPPSEPCGTPCRLATLCAQLSARADSPA LCRHLMPDGSLPEAQSLWPRPLFC (SEQ ID NO. 10) | P17405 |
| Galactosylceramidase (Homo sapiens) | MAEWLLSASWQRRAKAMTAAAGSAGRAAVPLLLCAL LAPGGAYVLDDSDGLGREFDGIGAVSGGGATSRLLVN YPEPYRSQILDYLFKPNFGASLHILKVEIGGDGQTTSAT EPSHMHYALDENYFRGYEWWLMKEAKKRNPNITLIGL PWSFPGWLGKGFDWPYVNLQLTAYYVVTWIVGAKRY HDLDIDYIGIWNERSYNANYIKILRKMLNYQGLQRVKII ASDNLWESISASMLLDAELFKVVDVIGAHYPGTHSAK | P54803 |

TABLE 5 -continued

Representative amino acid sequences for lysosomal enzymes.

| Name | Exemplary Sequence | Genbank Accession number |
|---|---|---|
| | DAKLTGKKLWSSEDFSTLNSDMGAGCWGRILNQNYIN GYMTSTIAWNLVASYYEQLPYGRCGLMTAQEPWSGH YVVESPVWVSAHTTQFTQPGWYYLKTVGHLEKGGSY VALTDGLGNLTIIIETMSHKHSKCIRPFLPYFNVSQQFA TFVLKGSFSEIPELQVWYTKLGKTSERFLFKQLDSLWL LDSDGSFTLSLHEDELFTLTTLTTGRKGSYPLPPKSQPFP STYKDDFNVDYPFFSEAPNFADQTGVFEYFTNIEDPGE HHFTLRQVLNQRPITWAADASNTISIIGDYNWTNLTIKC DVYIETPDTGGVFIAGRVNKGGILIRSARGIFFWIFANGS YRVTGDLAGWIIYALGRVEVTAKKWYTLTLTIKGHFA SGMLNDKSLWTDIPVNFPKNGWAAIGTHSFEFAQFDN FLVEATR (SEQ ID NO. 11) | |
| Acid Ceramidase (Homo sapiens) | MPGRSCVALVLLAAAVSCAVAQHAPPWTEDCRKSTYP PSGPTYRGAVPWYTINLDLPPYKRWHELMLDKAPVLK VIVNSLKNMINTFVPSGKIMQVVDEKLPGLLGNFPGPF EEEMKGIAAVTDIPLGEIISFNIFYELFTICTSIVAEDKKG HLIHGRNMDFGVFLGWNINNDTWVITEQLKPLTVNLD FQRNNKTVFKASSFAGYVGMLTGFKPGLFSLTLNERFS INGGYLGILEWILGKKDVMWIGFLTRTVLENSTSYEEA KNLLTKTKILAPAYFILGGNQSGEGCVITRDRKESLDV YELDAKQGRWYVVQTNYDRWKHPFFLDDRRTPAKM CLNRTSQENISLLTMYDVLSTKPVLNKLTVYTTLIDVT KGQFLTYLRDCPDPCIGW (SEQ ID NO. 12) | NP_808592.2 |

TABLE 6

Representative sequences for Rab polypeptides.

| Name | Exemplary Sequence | Genbank Accession number |
|---|---|---|
| Rab1a (Homo sapiens) | MSSMNPEYDYLFKLLLIGDSGVGKSCLLLRFADDTYTE SYISTIGVDFKIRTIELDGKTIKLQIWDTAGQERFRTITSS YYRGAHGIIVVYDVTDQESFNNVKQWLQEIDRYASEN VNKLLVGNKCDLTTKKVVDYTTAKEFADSLGIPFLETS AKNATNVEQSFMTMAAEIKKRMGPGATAGGAEKSNV KIQSTPVKQSGGGCC (SEQ ID NO. 13) | NP_004152.1 |
| Rab1a (Homo sapiens) Nucleotide sequence | ATGTCCAGCATGAATCCCGAATATGATTATTTATTCA AGTTACTTCTGATTGGCGACTCAGGGGTTGGAAAGT CTTGCCTTCTTCTTAGGTTTGCAGATGATACATATAC AGAAAGCTACATCAGCACAATTGGTGTGGATTTCAA AATAAGAACTATAGAGTTAGACGGGAAAACAATCA AGCTTCAAATATGGGACACAGCAGGCCAGGAAAGA TTTCGAACAATCACCTCCAGTTATTACAGAGGAGCC CATGGCATCATAGTTGTGTATGATGTGACAGATCAG GAGTCCTTCAATAATGTTAAACAGTGGCTGCAGGAA ATAGATCGTTATGCCAGTGAAAATGTCAACAAATTG TTGGTAGGGAACAAATGTGATCTGACCACAAAGAA GTAGTAGACTACACAACAGCGAAGGAATTTGCTGAT TCCCTTGGAATTCCGTTTTTGGAAACCAGTGCTAAGA ATGCAACGAATGTAGAACAGTCTTTCATGACGATGG CAGCTGAGATTAAAAAGCGAATGGGTCCCGGAGCA ACAGCTGGTGGTGCTGAGAAGTCCAATGTTAAAATT CAGAGCACTCCAGTCAAGCAGTCAGGTGGAGGTTGC TGCTAA (SEQ ID NO. 14) | NM_004161.4 |
| Rab6a (Homo sapiens) | MSTGGDFGNPLRKFKLVFLGEQSVGKTSLITRFMYDSF DNTYQATIGIDFLSKTMYLEDRTVRLQLWDTAGQERF RSLIPSYIRDSTVAVVVYDITNVNSFQQTTKWIDDVRTE RGSDVIIMLVGNKTDLADKRQVSIEEGERKAKELNVM FIETSAKAGYNVKQLFRRVAAALPGMESTQDRSREDMI DIKLEKPQEQPVSEGGCSC (SEQ ID NO. 15) | NP_942599.1 |
| Rab11a (Homo sapiens) | MGTRDDEYDYLFKVVLIGDSGVGKSNLLSRFTRNEFN LESKSTIGVEFATRSIQVDGKTIKAQIWDTAGQERYRAI TSAYYRGAVGALLVYDIAKHLTYENVERWLKELRDH ADSNIVIMLVGNKSDLRHLRAVPTDEARAFAEKNGLSF | NP_004654.1 |

TABLE 6 -continued

Representative sequences for Rab polypeptides.

| Name | Exemplary Sequence | Genbank Accession number |
|---|---|---|
| | IETSALDSTNVEAAFQTILTEIYRIVSQKQMSDRRENDM SPSNNVVPIHVPPTTENKPKVQCCQNI (SEQ ID NO. 16) | |

TABLE 7

Representative amino acid sequences for saposin polypeptides.

| Name | Exemplary Sequence | Genbank Accession number |
|---|---|---|
| Proactivator polypeptide isoform a preprotein (Homo sapiens) | MYALFLLASLLGAALAGPVLGLKECTRGSAVWCQNV KTASDCGAVKHCLQTVWNKPTVKSLPCDICKDVVTAA GDMLKDNATEEEILVYLEKTCDWLPKPNMSASCKEIV DSYLPVILDIIKGEMSRPGEVCSALNLCESLQKHLAELN HQKQLESNKIPELDMTEVVAPFMANIPLLLYPQDGPRS KPQPKDNGDVCQDCIQMVTDIQTAVRTNSTFVQALVE HVKEECDRLGPGMADICKNYISQYSEIAIQMMMHMQP KEICALVGFCDEVKEMPMQTLVPAKVASKNVIPALEL VEPIKKHEVPAKSDVYCEVCEFLVKEVTKLIDNNKTEK EILDAFDKMCSKLPKSLSEECQEVVDTYGSSILSILLEEV SPELVCSMLHLCSGTRLPALTVHVTQPKDGGFCEVCK KLVGYLDRNLEKNSTKQEILAALEKGCSFLPDPYQKQC DQFVAEYEPVLIEILVEVMDPSFVCLKIGACPSAHKPLL GTEKCIWGPSYWCQNTETAAQCNAVEHCKRHVWN (SEQ ID NO. 17) | NP_002769.1 |
| Saposin C (Homo sapiens) | SDVYCEVCEFLVKEVTKLIDNNKTEKEILDAFDKMCSK LPKSLSEECQEVVDTYGSSILSILLEEVSPELVCSMLHLC SGT (SEQ ID NO. 18) | P07602 |

TABLE 8

Representative amino acid sequences for sphingolipid metabolizing enzymes.

| Name | Exemplary Sequence | Genbank Accession number |
|---|---|---|
| 3-keto-dihydrosphingosine reductase (Homo sapiens) | MLLLAAAFLVAFVLLLYMVSPLISPKPLALPGAHVVVT GGSSGIGKCIAIECYKQGAFITLVARNEDKLLQAKKEIE MHSINDKQVVLCISVDVSQDYNQVENVIKQAQEKLGP VDMLVNCAGMAVSGKFEDLEVSTFERLMSINYLGSVY PSRAVITTMKERRVGRIVFVSSQAGQLGLFGFTAYSAS KFAIRGLAEALQMEVKPYNVYITVAYPPDTDTPGFAEE NRTKPLETRLISETTSVCKPEQVAKQIVKDAIQGNFNSS LGSDGYMLSALTCGMAPVTSITEGLQQVVTMGLF RTIALFYLGSFDSIVRRCMMQREKSENADKTA (SEQ ID NO. 19) | NP_002026.1 |
| sphingomyelin synthase (Homo sapiens) | MDIIETAKLEEHLENQPSDPTNTYARPAEPVEEENKNG NGKPKSLSSGLRKGTKKYPDYIQIAMPTESRNKFPLEW WKTGIAFIYAVFNLVLTTVMITVVHERVPPKELSPPLPD KFFDYIDRVKWAFSVSEINGIILVGLWITQWLFLRYKSI VGRRFCFIIGTLYLYRCITMYVTTLPVPGMHFQCAPKL NGDSQAKVQRILRLISGGGLSITGSHILCGDFLFSGHTV TLTLTYLFIKEYSPRHFWWYHLICWLLSAAGIICILVAH EHYTIDVIIAYYITTRLFWWYHSMANEKNLKVSSQTNF LSRAWWFPIFYFFLKNVQGSIPCCFSWPLSWPPGCFKSS CKKYSRVQKIGEDNEKST (SEQ ID NO. 20) | NP_001129729.1 |
| ceramide galactosyltransferase (Homo sapiens) | MKSYTPYFILLWSAVGIAKAAKIIIVPPIMFESHMYIFKT LASALHERGHHTVFLLSEGRDIAPSNHYSLQRYPGIFNS TTSDAFLQSKMRNIFSGRLTAIELFDILDHYTKNCDLM VGNHALIQGLKKEKFDLLLVDPNDMCGFVIAHLLGVK YAVFSTGLWYPAEVGAPAPLAYVPEFNSLLTDRMNLL QRMKNTGVYLISRLGVSFLVLPKYERIMQKYNLLPEKS MYDLVHGSSLWMLCTDVALEFPRPTLPNVVYVGGILT KPASPLPEDLQRWVNGANEHGFVLVSFGAGVKYLSED | Q16880.2 |

TABLE 8 -continued

Representative amino acid sequences for sphingolipid metabolizing enzymes.

| Name | Exemplary Sequence | Genbank Accession number |
|---|---|---|
| | IANKLAGALGRLPQKVIWRFSGPKPKNLGNNTKLIEWL<br>PQNDLLGHSKIKAFLSHGGLNSIFETIYHGVPVVGIPLF<br>GDHYDTMTRVQAKGMGILLEWKTVTEKELYEALVKV<br>INNPSYRQRAQKLSEIHKDQPGHPVNRTIYWIDYIIRHN<br>GAHHLRAAVHQISFCQYFLLDIAFVLLLGAALLYFLLS<br>WVTKFIYRKIKSLWSRNKHSTVNGHYHNGILNGKYKR<br>NGHIKHEKKVK (SEQ ID NO. 21) | |

DETAILED DESCRIPTION OF CERTAIN EMBODIMENTS

The present invention provides methods and compositions relating to treatment (whether therapeutic or prophylactic) of proteinopathic diseases, disorders, and/or conditions and/or to identification and/or characterization of agents useful for such treatment. In particular, the present invention provides methods of administering one or more therapeutic agents that activate lysosomal enzymes in an individual diagnosed with, at risk of, or suspected of having a proteinopathic disease, disorder, and/or condition. In particular, the invention provides methods of increasing levels and/or functional activity of lysosomal enzymes for effective treatment and/or prophylaxis of certain proteinopathies. Specifically, in some embodiments the invention provides methods that achieve increased trafficking of lysosomal enzymes, thereby providing effective treatment and/or prophylaxis of certain proteinopathies.

In some embodiments, the invention provides methods for using a lysosomal activating agent (e.g., an agent that increases trafficking of a lysosomal enzyme), and/or an antioxidant either alone or in combination with each other for the effective treatment and/or prophylaxis of proteinopathies. In particular, in some embodiments the invention provides methods that achieve increased activity of protein trafficking pathways for effective treatment and/or prophylaxis of certain proteinopathies. Specifically, among other things, the invention provides methods for using agents that affect protein trafficking, and therefore affect level and/or activity of lysosomal enzymes in the lysosome. In particular, in certain embodiments, the invention provides methods for lowering glucosylceramide levels resulting in reduction of α-synuclein accumulation or aggregation in cells.

Provided methods and compositions are useful in medicine. Provided methods and compositions are particularly useful in the treatment and/or prophylaxis of proteinopathies. Provided methods and compositions are surprisingly useful in treatment and/or prophylaxis of proteinopathies other than lysosomal storage diseases. Provided methods and compositions are surprisingly useful in treatment and/or prophylaxis of neurodegenerative proteinopathies. Provided methods and compositions additionally permit identification and/or characterization of new agents, combinations of agents, and/or therapeutic regimens that are useful in medicine, in treatment and/or prophylaxis of proteinopathies, in treatment and/or prophylaxis of proteinopathies other than lysosomal storage diseases, and/or in treatment and/or prophylaxis of neurodegenerative proteinopathies.

Proteinopathies

The term proteinopathy refers to diseases, disorders, and/or conditions that is associated with the pathogenic accumulation and/or aggregation of one or more types of proteins. In some embodiments, a proteinopathy may involve pathological alterations in one or more of protein production, folding, metabolism, degradation (e.g., autophagic, lysosomal, proteosomal), transportation or trafficking, secretion, etc. Autophagy may include microautophagy, macroautophagy, chaperone-mediated autophagy, mitophagy, pexophagy.

In some embodiments, a proteinopathy may involve efficiency of transport or the ability of a protein to be transported out of the endoplasmic reticulum to its native location within cell, cell membrane, or into the extracellular environment. For example, the native location of a lysosomal enzyme is the lysosome. The regular trafficking pathway for a protein comprises of: endoplasmic reticulum→Golgi apparatus→endosomes→lysosomes, but mutant proteins and/or certain wild-type proteins whose folding and trafficking may be incomplete would be unstable in the endoplasmic reticulum and their trafficking along the normal transport pathway would be retarded.

In some embodiments, a proteinopathy may involve regulatory intracellular signaling pathways. For example, in some embodiments, temporal cellular proteostasis adaptation is necessary, due to the presence of an ever-changing proteome during development and the presence of new proteins and the accumulation of misfolded proteins upon aging. Because the fidelity of the proteome is challenged during development and aging, and by exposure to pathogens that demand high protein folding and trafficking capacity, cells utilize stress sensors and inducible pathways to respond to a loss of proteostatic control. These include the heat shock response (HSR) pathway that regulates cytoplasmic proteostasis, unfolded protein response (UPR) pathway that helps maintain exocytic pathway proteostasis, the calcium ion ($Ca^{2+}$) signaling pathway, and/or pathways associated with organismal longevity including, insulin/insulin growth factor receptor signaling pathway and pathways associated with dietary restriction as well as processes associated with the mitochondrial electron transport chain process.

HSR pathway refers to enhanced expression of heat shock proteins (chaperone/cochaperone/folding enzymes) in the cytosol that can have an effect on proteostasis of proteins folded and trafficked within the secretory pathway as a soluble lumenal enzyme. Cytosolic factors including chaperones are likely essential for adapting the secretory pathway to be more folding and trafficking permissive (Bush et al., J Biol Chem 272: 9086, 1997; Liao et al., J Cell Biochem 99: 1085, 2006; Westerheide et al., J Biol Chem 279: 56053, 2004).

UPR pathway refers to a stress sensing mechanism in the endoplasmic reticulum (ER) wherein the ER responds to the accumulation of unfolded proteins in its lumen by activating up to three integrated arms of intracellular signaling pathways, e.g., UPR-associated stress sensors, IRE1, ATF6, and PERK, collectively referred to as the unfolded protein response, that regulate the expression of numerous genes that function within the secretory pathway (Ron et al., Nat Rev Mol Cell Biol 8: 519, 2007; Schroeder et al., Ann Rev Biochem 74: 739, 2005). UPR associated chaperones include, but are not limited to BiP, GRP94, and calreticulin.

The $Ca^{2+}$ ion is a universal and important signaling ion in the cell. $Ca^{2+}$ signaling affects numerous cellular functions by diverse pathways, and is a primary regulator of endoplasmic reticulum (ER) function (Berridge et al., Nat Rev Mol Cell Biol 4: 517, 2003; Burdakov et al., Cell Calcium 38: 303, 2005; Gorlach et al., Antioxid Redox Signal 8: 1391, 2006). $Ca^{2+}$ homeostasis is also modulated by the activity of ER calcium receptors. ER calcium receptors include, for example, ryanodine receptors (RyR), inositol 3-phosphate receptors (IP3R) and sarcoplasmic/endoplasmic calcium (SERCA) pump proteins. RyR and IP3R mediate efflux of calcium from the ER whereas SERCA pump proteins mediate influx of calcium into the ER. There are three RyR subtypes, RyR1, RyR2 and RyR3. Emerging evidence indicates that calcium signaling may influence proteinopathic diseases, diorders, and/or conditions (Futerman et al., Nat Rev Mol Cell Biol 5: 554, 2004; LaFerla, Nat Rev Neurosci 3: 862, 2002; Petersen et al., Cell Calcium 38: 161, 2005). This hypothesis is supported by observations that manipulation of calcium homeostasis by SERCA pump inhibitors, such as thapsigargin enhances folding and trafficking of the ΔF508 cystic fibrosis transmembrane conductance regulator (CFTR) and curcumin (Egan et al., Nat Med 8: 485, 2002; Egan et al., Science 304: 600, 2004).

In some embodiments, the present invention provides methods directed to increased lysosomal degradation in a cell of a subject suffering from a proteinopathic disease, disorder, and/or condition by administering at least one lysosomal activating agent that can increase the level and/or activity of both wild-type and mutant lysosomal enzymes.

In some embodiments, the present invention provides a method directed to reducing the level of α-synuclein levels in a cell of a subject comprising administering to the subject an α-synuclein level reducing amount of agent capable of activating GCase activity, such as a Rab1a polypeptide or a homolog thereof capable of activating GCase activity. In some embodiments, the subject is first diagnosed as having increased level of α-synuclein prior to administering the agent capavle of activating GCase activity. In some embodiments, the subject is at increased risk of having increased α-synuclein levels.

In some embodiments, proteinopathy may involve lipid accumulation. For example, pathological accumulations of lactosylceramide, glucosylceramide (GlcCer), $G_{M2}$-ganglioside, and asialo-$G_{M2}$ are found in Nieman-Pick Type C disease, which is a lysosomal cholesterol storage disease that is not associated with deficient acid sphingomyelinase due to missense mutaions in the gene encoding the enzyme (Vanier et al., Brian Pathology 8: 163-74, 1998). Without wishing to be bound by any particular theory, Applicants note that a variety of mechanisms have been proposed to explain this accumulation including, for example, defective lipid trafficking. A healthy endosomal trafficking system is critical to neuronal function (Buckley et al., J Physiol 525: 11, 2000). Disruption of glycosphingolipid metabolism, including GlcCer, impairs cellular trafficking and causes cholesterol sequestration and accumulation (Pagano et al., Traffic 1(11): 807, 2000; Sillence et al., J Lipid Res 43(11): 1837, 2002; Helms et al., Traffic 5(4): 247-54, 2004).

Accumulated glycolipids form "lipid rafts" that can sequester proteins important in maintaining normal trafficking in the endosomal system. Moreover, the defective trafficking of lipids observed in fibroblasts from Niemann-Pick Type C cells can be reversed by treatment with a potent inhibitor of glycosphingolipid biosynthesis (Lachmann et al., Neurobiol Dis. 16(3): 654, 2004), further underscoring the involvement of GlcCer and other lipids in the pathology of this disease. For example, inhibition of glucosylceramide synthase, the enzyme that catalyzes the first step in the biosynthesis of glycosphingolipids delay onset of a proteinopathic disease, disorder, and/or condition through the following potential mechanisms: substrate reduction; lessen the extent of aggregation of a protein (e.g., α-synuclein); act as an anti-inflammatory agent; or inhibit non-lysosomal GCase resulting in altered levels of neuronal glycosphingolipids.

Further, association with lipid rafts is required for normal localization of α-synuclein to its native cellular location, the synapses (Fortin et al., J Neurosci 24(30): 6715-23, 2004). Mutations associated with the pathology of Parkinson's disease disrupt this association. Thus, changes in lipid raft composition that also disrupt this association could contribute to Parkinson's disease by impairing normal localization and distribution of α-synuclein.

In some embodiments, the present invention provides methods directed to reducing lipid accumulation caused by a proteinopathic disease, disorder and/or condition in a cell of a subject by administering at least one lysosomal activating agent to the subject. The present invention specifically provides methods directed to reducing GlcCer accumulation by administering at least one lysosomal activating agent.

Exemplary proteins whose aggregation is observed in certain proteinopathies include α-synuclein (synucleinopathies such as Parkinson's diseases (PD) and Lewy body disease), tau proteins (tauopathies such as Alzheimer's Disease), amyloid beta proteins (amyloidopathies such as vascular dementia, cognitive impairment, and Alzheimer's Disease), SOD1 (SOD1 proteinopathies such as amyotrophic lateral sclerosis), TDP-43 (TDP-43 proteinopathies such as amyotrophic lateral sclerosis), huntingtin (Huntington's disease), rhodopsin (retinitis pigmentosa) and/or a number of proteins (e.g., glucosylceramide) in the case of the diseases collectively known as lysosomal storage disease. It will be appreciated by those of ordinary skill in the art that certain diseases, disorders, and/or conditions are associated with misfolding and/or aggregation of more than one different protein.

In some embodiments, the present invention provides methods for reducing α-synuclein levels in the cell of a subject by administering at least one lysosomal activating agent.

Protein aggregates are observed in a variety of different types of disorders, diseases, and/or conditions, including cognitive impairment disorders, proliferative diseases, inflammatory diseases, cardiovascular diseases, immunologic diseases, ocular diseases, mitochondrial diseases, neurodegenerative diseases, and lysosomal storage diseases. Some embodiments of the present invention are applicable to all proteinopathies. Some embodiments of the present invention are applicable to proteinopathies other than lysosomal storage diseases.

A. Neurodegenerative Diseases

The present invention provides methods and compositions related to neurodegenerative diseases. Many neurodegenerative diseases are linked to intracellular and/or extracellular accumulation of specific protein aggregates. In many cases, it is thought that the protein aggregates exert toxic effects on the brain, and contribute to disease pathology.

Neurodegenerative proteinopathies are typically associated with aggregates in the following structures: cytosol, e.g., PD and Huntington's disease; nucleus, e.g., spinocerebellar ataxia type 1 (SCA1); endoplasmic reticulum (ER), e.g., familial encephalopathy with neuroserpin inclusion bodies; extracellular proteins, e.g., amyloid beta in Alzheimer's disease (AD).

Mitochondrial dysfunction and oxidative stress can also play a role in neurodegenerative disease pathogenesis (Lin et al., Nature 443: 787, 2006).

1. Synucleinopathies

The present invention provides methods and compositions related to synucleinopathies. Synucleinopathies are a diverse group of neurodegenerative proteinopathies that share common pathological lesions composed of aggregates of conformational and posttranslational modification of the protein α-synuclein in certain populations of neurons and glia.

PD is a neurodegenerative movement disorder characterized by the accumulation of the pre-synaptic α-synuclein protein in the form of Lewy body inclusions (Spillantini et al., Nature 388(6645); 839, 1997). Other neurodegenerative disorders characterized by α-synuclein accumulation include, multiple systems atrophy, dementia with Lewy bodies, and Lewy body mutant of Alzheimer's disease. Pathological α-synuclein is also recognized as a subset of the proteinacious lesions detected in neurodegeneration with brain iron accumulate type I, amyotrophic lateral sclerosis/Parkinson's dementia complex of Guam, and familial AD.

Certain evidence links that α-synuclein interacts and accelerates the aggregation of tau, another aggregation-prone protein of the central nervous system that is found in neurofibrillary tangles that characterize sporadic AD (Giasson et al., Sci. Aging Knowl. Environ. 18: orb, 2003). Several mutations in α-synuclein, all which stabilize and accelerate protein aggregation, have been found in rare familial forms of PD (Hardy et al., Am. J. Epidmeiol. 164(2): 126, 2006). Several in vivo and cell culture models have demonstrated that overexpression and aggregation of α-synuclein cause neurotoxicity (Dawson et al., Neuron 66: 646, 2010).

Synucleins are small proteins (123 to 143 amino acids) and the primary structure is usually divided into three distinct domains: an amphipahtic N-terminal region characterized by negative imperfect repeats of the consensus sequence KTKEGV. This sequence results in all synucleins having in common a highly conserved α-helical lipid-binding motif; a central hydrophobic region which includes the non-Aβ component of Alzheimer's disease amyloid plaque (NAC) region involved in protein aggregation; and a highly acidic and proline-rich C-terminal region that has no distinct structural propensity.

Human synuclein family members include α-synuclein, β-synuclein, and γ-synuclein and all synuclein genes are relatively well conserved both within and between species (Cookson M R, Molecular Neurodegeneration 4(9): 1750, 2009). The most recently cloned synuclein protein, synoretin has a close homology to γ-synuclein, and is predominantly expressed in the retina. Table 9 provides representative examples of known α-synuclein, β-synuclein, and γ-synuclein sequences.

TABLE 9

Representative amino acid sequences of α-, β-, and γ-synuclein.

| Name | Exemplary Sequence | Genbank Accession number |
| --- | --- | --- |
| α-synuclein (Homo sapiens) | MDVFMKGLSKAKEGVVAAAEKTKQGVAEAAGKTKEGVLYV GSKTKEGVVHGVATVAEKTKEQVTNVGGAVVTGVTAVAQKT VEGAGSIAAATGFVKKDQLGKNEEGAPQEGILEDMPVDPDNEA YEMPSEEGYQDYEPEA (SEQ ID NO. 22) | AAL15443.1 |
| β-synuclein (Homo sapiens) | MDVFMKGLSMAKEGVVAAAEKTKQGVTEAAEKTKEGVLYV GSKTREGVVQGVASVAEKTKEQASHLGGAVFSGAGNIAAATG LVKREEFPTDLKPEEVAQEAAEEPLIEPLMEPEGESYEDPPQEEY QEYEPEA (SEQ ID NO. 23) | AAH02902.1 |
| γ-synuclein (Homo sapiens) | MDVFKKGFSIAKEGVVDAVEKTKQGVTEAAEKTKEGVMYVG AKTKENVVQSVTSVAEKTKEQANAVSEAVVSSVNTVATKTVE EAENIAVTSGVVRKEDLRPSAPQQEGEASKEKEEVAEEAQSGG D (SEQ ID NO. 24) | AAL05870.1 |

α-synuclein, also referred to as non-amyloid component of senile plaques precursor protein (NACP), SYN 1 or synelfin, is a heat-stable, "natively unfolded" protein of poorly defined function. It is predominantly expressed in the central nervous system (CNS) neurons where it is localized to presynaptic terminals. Electron microscopy analysis have suggested that α-synuclein is localized in close proximity to synaptic vesicles at axonal termini, pointing to a role for α-synuclein in neurotransmission or synaptic organization. Further, biochemical analysis have revealed that a small fraction of α-synuclein may be associated with vesicular membranes, but most α-synuclein is cytosolic.

Genetic and histopathological evidence supports the idea that α-synuclein is the major component of several proteinaceous inclusions characteristic of specific neurodegenerative diseases. Pathological synuclein aggregations are restricted to the α-synuclein isoforms, as β- and γ-synucleins have not been detected in these inclusions. The presence of α-synuclein positive aggregates is disease specific. Lewy bodies, neuronal fibrous cytoplasmic inclusions that are histopathological hallmarks of PD and DLBD are strongly labeled with antibodies to α-synuclein. Dystrophic ubiquitin-positive neurites associated with PD pathology, termed Lewy neurites (LN) and CA2/CA3 ubiquitin neurites are also α-synuclein positive. Furthermore, pale bodies, putative precursors of LBs, thread-like structures in the perikarya of slightly swollen neurons and glial silver positive inclusions in the midbrains of patients with LB diseases are also immunoreactive for α-synuclein. α-synuclein is likely the major component of glial cell inclusions (GCIs) and neuronal cytoplasmic inclusions in MSA and brain iron accumulation type 1 (PANK1). α-synuclein immunoreactivity is present in some dystrophic neurites in senile plaques in Alzheimer's Disease (AD) and in the cord and cortex in ALS. α-synuclein immunoreactivity is prominent in transgenic and toxin-induced mouse models of PD, AD, ALS, and HD.

Further evidence supports the notion that α-synuclein is the actual building block of the fibrillary components of LBs, LNs, and GCIs. Immunoelectron microscopic studies have demonstrated that these fibrils are intensely labeled with α-synuclein antibodies in situ. Sarcosyl-insoluble α-synuclein filaments with straight and twisted morphologies can also be observed in extracts of DLBD and MSA brains. Moreover, α-synuclein can assemble in vitro into elongated homopolymers with similar widths as sarcosyl-insoluble fibrils or filaments visualized in situ. Polymerization is associated with a concomitant change in secondary structure from random coil to anti-parallel β-sheet structure consistent with the Thioflavine-S reactivity of these filaments. Furthermore, the PD-association with α-synuclein mutation, A53T, may accelerate this process, as recombinant A53T α-synuclein has a greater propensity to polymerize than wild-type α-synuclein. This mutation also affects the ultrastructure of the polymers; the filaments are slightly wider and are more twisted in appearance, as if assembled from two protofilaments. The A30P mutation may also modestly increase the propensity of α-synuclein to polymerize, but the pathological effects of this mutation also may be related to its reduced binding to vesicles. Interestingly, carboxylterminally truncated α-synuclein may be more prone to form filaments than the full-length protein.

Current treatment options for synucleinopathic diseases include symptomatic medications such as carbidopa-levodopa, anticholinergics, and monoamine oxidase inhibitors, with widely variable benefit. Even for the best responders, i.e., patients with idiopathic Parkinson's disease, an initial good response to levodopa is typically overshadowed by drug-induced complications such as motor fluctuations and debilitating dyskinesia, following the first five to seven years of therapy. For the rest of the disorders, the current medications offer marginal symptomatic benefit. Given the severe debilitating nature of these disorders and their prevalence, there is a clear need in the art for novel approaches towards treating and managing synucleinopathies.

The present invention provides, among other things, the surprising insight that synucleinopathies can be effectively treated by activating lysosomal activity. In some embodiments, the present invention provides methods of reducing both soluble and insoluble α-synuclein toxicity in a cell by administering a lysosomal activating agent. In some embodiments, the present invention provides a method of reducing the accumulation of α-synuclein in a cell, the method comprising administering to a cell a therapeutically effective amount of a provided lysosomal activating agent. In some embodiments, the present invention provides a method of reducing α-synuclein toxicity and/or accumulation in a cell, the method comprising administering to a cell a therapeutically effective amount of a provided lysosomal activating agent in combination with one or more of another therapeutic agent. In some embodiments, the cell is a neuronal cell. In some embodiments, the cell is a non-neuronal cell. In some embodiments, the cell expresses α-synuclein. In certain embodiments, the synucleinopathy is Parkinson's disease, diffuse Lewy body disease, and/or multiple system atrophy disorder.

Parkinson's Disease

In some embodiments, the present invention specifically provides methods related to PD, a synucleinopathy. PD is a neurodegenerative disorder characterized by bradykinesia, rigidity, tremor, and postural instability. The pathologic hallmark of PD is loss of neurons in the substantia nigra pars compacta (SNpc) and the appearance of Lewy bodies in remaining neurons. It appears that more than about 50% of the cells in the SNpc need to be lost before motor symptoms appear. Associated symptoms often include small handwriting (micrographia), seborrhea, orthostatic hypotension, urinary difficulties, constipation and other gastrointestinal dysfunction, sleep disorders, depression and other neuropsychiatric phenomena, dementia, and smelling disturbances (occurs early). Patients with Parkinsonism have greater mortality, about two times compared to general population without PD. This is attributed to greater frailty or reduced mobility.

Diagnosis of PD is mainly clinical and is based on the clinical findings listed above. Parkinsonism, refers to any combination of two of bradykinesia, rigidity, and/or tremor. PD is the most common cause of parkinsonism. Other causes of parkinsonism are side effects of drugs, mainly the major tranquilizers, such as Haldol, strokes involving the basal ganglia, and other neurodegenerative disorders, such as DLBD, progressive supranuclear palsy (PSP), frontotemporal dementia (FTD), MSA, and Huntington's disease. The pathological hallmark of PD is the Lewy body, an intracytoplasmatic inclusion body typically seen in affected neurons of the substantia nigra and to a variable extent, in the cortex. Recently, α-synuclein has been identified as the main component of Lewy bodies in sporadic Parkinsonism.

Although parkinsonism can be clearly traced to viruses, stroke, or toxins in a few individuals, in many cases, the etiology of Parkinson's disease is unknown. Environmental influences which may contribute to PD may include drinking well water, farming and industrial exposure to heavy metals (e.g., iron, zinc, copper, mercury, magnesium and manganese), alkylated phosphates, and orthonal chlorines. Paraquat (a herbicide) has also been associated with increased prevalence of Parkinsonism including PD. Cigarette smoking is associated with a decreased incidence of PD. The current consensus is that PD may either be caused by an uncommon toxin combined with high genetic susceptibility or a common toxin combined with relatively low genetic susceptibility.

Some subjects that are at risk of developing PD can be identified for example by genetic analysis. There is good evidence for certain genetic factors being associated with PD. Large pedigrees of autosomal dominantly inherited PDs have been reported. For example, a mutation in α-synuclein is responsible for one pedigree and triplication of the SNCA gene (the gene coding for α-synuclein) is associated with PD in others.

Diffuse Lewy Body Disease and Rapid Eye Movement Sleep Disorder

In some embodiments, present invention specifically provides methods related to DLBD, a synucleinopathy. DLBD is the second most common cause of neurodegenerative dementia on older people, it effects 7% of the general population older than 65 years and 30% of those aged over 80 years. It is part of a range of clinical presentations that share a neurotic pathology based on normal aggregation of the synaptic protein α-synuclein. DLBD has many of the clinical and pathological characteristics of the dementia that occurs during the course of PD. In addition to other clinical and neurologic diagnostic criteria, a "one year rule" can been used to separate DLBD from PD. According to this rule, onset of dementia within 12 months of Parkinsonism qualifies as DLBD, whereas more than 12 months of Parkinsonism before onset of dementia qualifies as PD. The central features of DLBD include progressive cognitive decline of sufficient magnitude to interfere with normal social and occupational function. Prominent or persistent memory impairment does not necessarily occur in the early stages, but it is evident with progression in most cases. Deficits on tests of attention and of frontal cortical skills and visual spatial ability can be especially prominent core diagnostic features, two of which are essential for diagnosis of probable and one for possible DLBD are fluctuating cognition with pronounced variations in attention and alertness, recurrent visual hallucinations that are typically well-formed and detailed, and spontaneous features of Parkinsonism. In addition, there can be some supportive features, such as repeated falls, syncope, transient loss of consciousness, neuroleptic sensitivity, systematized delusions, hallucinations and other modalities, REM sleep behavior disorder, and depression. Patients with DLBD do better than those with Alzheimer's Disease in tests of verbal memory, but worse on visual performance tests. This profile can be maintained across the range of severity of the disease, but can be harder to recognize in the later stages owing to global difficulties. DLBD typically presents with recurring episodes of confusion on a background of progressive deterioration. Patients with DLBD show a combination of cortical and subcortical neuropsychological impairments with substantial attention deficits and prominent frontal subcortical and visual spatial dysfunction. These help differentiate this disorder from Alzheimer's disease.

Rapid eye movement (REM), sleep behavior disorder is a parasomnia manifested by vivid and frightening dreams associated with simple or complex motor behavior during REM sleep. This disorder is frequently associated with the synucleinopathies, DLBD, PD, and MSA, but it rarely occurs in amyloidopathies and tauopathies. The neuropsychological pattern of impairment in REM sleep behavior disorder/dementia is similar to that reported in DLBD and qualitatively different from that reported in Alzheimer's disease. Neuropathological studies of REM sleep behavior disorder associated with neurodegenerative disorder have shown Lewy body disease or multiple system atrophy. REM sleep wakefulness disassociations (REM sleep behavior disorder, daytime hypersomnolence, hallucinations, cataplexy) characteristic of narcolepsy can explain several features of DLBD, as well as PD. Sleep disorders could contribute to the fluctuations typical of DLBD, and their treatment can improve fluctuations and quality of life. Subjects at risk of developing DLBD can be identified. Repeated falls, syncope, transient loss of consciousness, and depression are common in older people with cognitive impairment and can serve as (a red flag) to a possible diagnosis of DLBD. By contrast, narcoleptic sensitivity in REM sleep behavior disorder can be highly predictive of DLBD. Their detection depends on the clinicians having a high index of suspicion and asking appropriate screening questions.

Clinical diagnosis of synucleinopathic subjects that are affected by or at risk of developing LBD can be supported by neuroimaging investigations. Changes associated with DLBD include preservation of hippocampal, and medial temporal lobe volume on magnetic resonance imaging (MRI) and occipital hypoperfusion on single-photon emission computed tomography (SPECT). Other features, such as generalized atrophy, white matter changes, and rates of progression of whole brain atrophy are not helpful in differential diagnosis. Dopamine transporter loss in the caudate and putamen, a marker of nigrostriatal degeneration, can be detected by dopamenergic SPECT and can prove helpful in clinical differential diagnosis. A sensitivity of 83% and specificity of 100% has been reported for an abnormal scan with an autopsy diagnosis of DLBD.

Consensus criteria for diagnosing DLBD include ubiquitin immunohistochemistry for Lewy body identification and staging into three categories; brain stem predominant, limbic, or neocortical, depending on the numbers and distribution of Lewy bodies. The recently-developed α-synuclein immunohistochemistry can visualize more Lewy bodies and is also better at indicating previously under recognized neurotic pathology, termed Lewy neurites. Use of antibodies to α-synuclein moves the diagnostic rating for many DLBD cases from brain stem and limbic groups into the neocortical group.

In most patients with DLBD, there are no genetic mutations in the α-synuclein or other Parkinson's disease-associated genes. Pathological up-regulation of normal, wild-type α-synuclein due to increased mRNA expression is a possible mechanism, or Lewy bodies may form because α-synuclein becomes insoluble or more able to aggregate. Another possibility is that α-synuclein is abnormally processed, for example, by a dysfunctional proteasome system and that toxic "proto fibrils" are therefore produced. Sequestering of these toxic fibrils into Lewy bodies could reflect an effort by the neurons to combat biological stress inside the cell, rather than their simply being neurodegenerative debris.

Target symptoms for the accurate diagnosis of DLBD can include extrapyramidal motor features, cognitive impairment, neuropsychiatric features (including hallucinations, depression, sleep disorder, and associated behavioral disturbances), or autonomic dysfunction.

Methods of the invention can be used in combination with one or more other medications for treating DLBD. For example, the lowest acceptable doses of levodopa can be used to treat DLBD. D2-receptor antagonists, particularly traditional neuroleptic agents, can provoke severe sensitivity reactions in DLBD subjects with an increase in mortality of two to three times. Cholinesterase inhibitors discussed above are also used in the treatment of DLBD.

Multiple System Atrophy

The present invention specifically provides methods related to MSA. MSA is a neurodegenerative disease marked by a combination of symptoms; affecting movement, cognition, autonomic and other body functions, hence the label "multiple system atrophy". The cause of MSA is unknown. Symptoms of MSA vary in distribution of onset and severity from person to person. Because of this, the nomenclature initially included three distinct terms: Shy-Drager syndrome, striatonigral degeneration (SD), and olivopontocerebellar atrophy (OPCA).

In Shy-Drager syndrome, the most prominent symptoms are those involving the autonomic system; blood pressure, urinary function, and other functions not involving conscious control. Striatonigral degeneration causes Parkinsonism symptoms, such as slowed movements and rigidity, while OPCA principally affects balance, coordination and speech. The symptoms for MSA can also include orthostatic hypertension, male impotence, urinary difficulties, constipation, speech and swallowing difficulties, and blurred vision.

The initial diagnosis of MSA is usually made by carefully interviewing the patient and performing a physical examination. Several types of brain imaging, including computer tomography, scans, MRI, and positron emission tomography (PET), can be used as corroborative studies. An incomplete and relatively poor response to dopamine replacement therapy, such as Sinemet, may be a clue that the presentation of bradykinesia and rigidity (parkinsonism) is not due to PD. A characteristic involvement of multiple brain systems with prominent autonomic dysfunction is a defining feature of MSA and one that at autopsy confirms the diagnosis. Patients with MSA can have the presence of glial cytoplasmic inclusions in certain types of brain cells, as well. Prototypic Lewy bodies are not present in MSA. However, α-synuclein staining by immunohistochemistry is prominent. In comparison to Parkinson's, in addition to the poor response to Sinemet, there are a few other observations that are strongly suggested for MSA, such as postural instability, low blood pressure on standing (orthostatic hypotension) and high blood pressure when lying down, urinary difficulties, impotence, constipation, speech and swallowing difficulties out of proportion to slowness and rigidity.

Methods of the present invention can be used in combination with one or more alternative medications for treating MSA. Typically, the drugs that can be used to treat various symptoms of MSA become less effective as the disease progresses. Levodopa and dopamine agonists used to treat PD are sometimes effective for the slowness and rigidity of MSA. Orthostatic hypertension can be improved with cortisone, midodrine, or other drugs that raise blood pressure. Male impotence may be treated with penile implants or drugs. Incontinence may be treated with medication or catheterization. Constipation may improve with increased dietary fiber or laxatives.

2. Amyloidopathies

Amyloid precursor protein (APP) serves a variety of physiological functions, including modulation of synaptic function, facilitation of neuronal growth and survival, protection against oxidative stress, and surveillance against neuroactive compounds, toxins and pathogens. Two catabolic pathways have been described for processing of APP: the non-amyloidogenic and amyloidogenic cascade. The non-amyloidogenic pathway leads to formation of extracellular soluble N-terminal part of APP generated by α-secretase mediated cleavage. The amyloidogenic pathway results in the formation of the amyloid beta (Aβ) peptide by successive β-secretase and γ-secretase cleavages. Aβ is thought to be intrinsically unstructured, meaning that it cannot acquire a unique tertiary fold but rather populates a set of structures. The Aβ extracellular form is Aβ1-40, while the intraneuronal Aβ corresponds to Aβ1-42. Activation of the γ-secretase pathway in a pathological condition such as AD results in the accumulation of Aβ. This accumulation of Aβ resulting in diseases that are grouped under amyloidopathies.

The present invention provides methods related to amyloidopathies. For example, in some embodiments, the present invention provides a method of reducing amyloid beta toxicity in a cell, the method comprising administering to a cell a therapeutically effective amount of such a provided compound. In some embodiments, the present invention provides a method of reducing the accumulation of amyloid beta proteins in a cell, the method comprising administering to a cell a therapeutically effective amount of such a provided compound. In some embodiments, the cell is a neuronal cell. In some embodiments, the cell is a non-neuronal cell. In some embodiments, the cell expresses amyloid beta proteins. In certain embodiments, the amyloidopathy is Alzheimer's disease, vascular dementia, and/or cognitive impairment.

3. Tauopathies

Tauopathies are neurodegenerative disorders characterized by the presence of filamentous deposits, consisting of hyperphosphorylated tau protein, in neurons and glia. Abnormal tau phosphorylation and deposition in neurons and glial cells is one of the major features in tauopathies. The term tauopathy, was first used to describe a family with frontotemporal dementia (FTD) and abundant tau deposits. This term is now used to identify a group of diseases with widespread tau pathology in which tau accumulation appears to be directly associated with pathogenesis. Major neurodegenerative tauopathies includes sporadic and hereditary diseases characterized by filamentous tau deposits in brain and spinal cord.

In the majority of tauopathies, glial, and neuronal tau inclusions are the sole or predominant CNS lesions. Exemplary such tauopathies include amytrophic lateral sclerosis (ALS), parkinsonism, argyrophilic grain dementia, diffuse neurofibrillary tangles with calcification, frontotemporal dementia linked to chromosome 17, corticobasal degeneration, Pick's disease, progressive supranuclear palsy, progressive subcortical gliosis, and tangle only dementia.

Additionally, tauopathies characterize a large group of diseases, disorders and conditions in which significant filaments and aggregates of tau protein are found. Exemplary such diseases, disorders, and conditions include sporadic and/or familial Alzheimer's Disease, amyotrophic lateral sclerosis/parkinsonism-dementia complex (ALS-FTDP), argyrophilic grain dementia, dementia pugilistica, diffuse neurofibrillary tangles with calcification, Down syndrome, frontotemporal dementia, parkinsonism linked to chromosome 17 (FTDP-17), Gerstmann-Straussler-Scheinker disease, Hallervorden-Spatz disease, inclusion body myositis, Creutzfeld-Jakob disease (CJD), multiple system atrophy, Niemann-Pick disease (NPC), Pick's disease, prion protein cerebral amyloid angiopathy, progressive supranuclear palsy (PSP), subacute sclerosing panencephalitis, tangle-predominant Alzheimer's disease, corticobasal degeneration, (CBD), myotonic dystrophy, non-guanamian motor neuron disease with neurofibrillary tangles, postencephalitic parkinsonism, prion protein cerebral amyloid angiopathy, progressive subcortical gliosis, subacute sclerosing panencephalitis, and tangle-only dementia.

Neurodegenerative diseases where tau pathology is found in conjunction with other abnormal protein lesions may be considered secondary tauopathies. Examples include AD and certain diseases where prion protein, Bri, or α-synuclein are aggregated. Although tau is probably not the initial pathological factor, tau aggregates contribute to the final degeneration.

Tau deposits can also be found in several other neurodegenerative diseases in which tau pathology is evident in conjunction with other abnormal protein lesions protein. Abundant cytoplasmic inclusions consisting of aggregated hyperphosphorylated protein tau are a characteristic pathological observation in several neurodegenerative disorders such as AD, Pick's disease, frontotemporal dementia, cortico-basal degeneration, and progressive supranuclear palsy.

The present invention provides methods relevant to tauopathies. For example, in some embodiments, the present invention provides a method of reducing tau toxicity in a cell, the method comprising administering to a cell a therapeutically effective amount of such a provided compound. In some embodiments, the present invention provides a method of reducing the accumulation of tau proteins in a cell, the method comprising administering to a cell a therapeutically effective amount of such a provided compound. In some embodiments, the cell is a neuronal cell. In some embodiments, the cell is a non-neuronal cell. In some embodiments, the cell expresses tau proteins. In certain embodiments, the tauopathy is Alzheimer's disease.

Alzheimer's Disease

AD is the leading cause of dementia and cognitive impairment in the elderly and a leading cause of death in developing nations after cardiovascular disease, cancer, and stroke. Up to 70% of cases of dementia are due to AD, with vascular disease being the second most common cause. The frequency of AD among 60-year-olds is approximately 1%. The incidence of AD doubles approximately every 5 years. Forsyth, Phys. Ther. 78:1325, 1998; Evans et al., JAMA 262: 2551, 1989. AD afflicts an estimated four million people in the U.S. alone at a cost of $100 billion per year. Schumock, J. Health Syst. Pharm. 55(52):17, 1998; Hay & Ernst, Am. J. Public Health 77:1169, 1987.

Alzheimers Disease is characterized by the deterioration of mental faculties (e.g., memory loss, confusion, loss of visual/spatial comprehension) and associated with both amyloidopathies and tauopathies. The central role of the long form of amyloid β-peptide, in particular Aβ(1-42), in Alzheimer's disease has been established through a variety of histopathological, genetic and biochemical studies. Specifically, it has been found that deposition in the brain of Aβ(1-42) is an early and innate feature of all forms of Alzheimer's disease. This occurs before a diagnosis of Alzheimer's disease is possible and before the deposition of the shorter primary form of Aβ, Aβ(1-40). Further implication of Aβ(1-42) in disease etiology comes from the observation that mutations in presenilin (γ-secretase) genes associated with early onset familial forms of Alzheimer's disease uniformly result in increased levels of Aβ(1-42). Additional mutations in APP raise total Aβ and in some cases raise Aβ(1-42) alone. Although the various APP mutations may influence the type, quantity, and location of Aβ deposited, it has been found that the predominant and initial species deposited in the brain parenchyma is long Aβ. In early deposits of Aβ, when most deposited protein is in the form of amorphous or diffuse plaques, virtually all of the Aβ is of the long form. These initial deposits of Aβ(1-42) then are able to seed the further deposition of both long and short forms of Aβ. In transgenic animals expressing Aβ, deposits were associated with elevated levels of Aβ(1-42), and the pattern of deposition is similar to that seen in human disease with Aβ(1-42) being deposited early followed by deposition of Aβ(1-40). Similar patterns and timing of deposition are seen in Down's Syndrome patients in which Aβ expression is elevated and deposition is accelerated. The association of Alzheimer's Diseases with amyloid plaques means that Alzheimer's Diseases is considered to be an amyloidopathy. Alzheimer's Disease is also associated with accumulation of tau aggregates and therefore is a tauopathy.

Cognitive Impairment or Dementia

Cognitive impairment and dementia are highly prevalent neurological conditions associated with any of a variety of diseases, disorders, and/or conditions. Dementia is commonly defined as a progressive decline in cognitive function due to damage or disease in the body beyond what is expected from normal aging. Dementia is described as a loss of mental function, involving problems with memory, reasoning, attention, language, and problem solving. Higher level functions are typically affected first. Dementia interferes with a person's ability to function in normal daily life.

The cognitive impairment or dementia may stem from any etiology. Exemplary causes of cognitive impairment and dementia include neurodegenerative diseases, neurological diseases, psychiatric disorders, genetic diseases, infectious diseases, metabolic diseases, cardiovascular diseases, vascular diseases, aging, trauma, malnutrition, childhood diseases, chemotherapy, autoimmune diseases, ocular diseases, and inflammatory diseases. Particular diseases that are associated with cognitive impairment or dementia include, but are not limited to, atherosclerosis, stroke, cerebrovascular disease, vascular dementia, multi-infarct dementia, Parkinson's disease and Parkinson's disease dementia, Lewy body disease, Pick's disease, Alzheimer's disease, mild cognitive impairment, Huntington's disease, AIDS and AIDS-related dementia, brain neoplasms, brain lesions, epilepsy, multiple sclerosis, Down's syndrome, retinitis pigmentosa, wet and dry forms of age related macular degeneration, ocular hypertension, glaucoma, corneal dystrophies, Rett's syndrome, progressive supranuclear palsy, frontal lobe syndrome, schizophrenia, traumatic brain injury, post coronary artery by-pass graft surgery, cognitive impairment due to electroconvulsive shock therapy, cognitive impairment due to chemotherapy, cognitive impairment due to a history of drug abuse, attention deficit disorder (ADD), attention deficit hyperactivity disorder (ADHD), autism, dyslexia, depression, bipolar disorder, post-traumatic stress disorder, apathy, myasthenia gravis, cognitive impairment during waking hours due to sleep apnea, Tourette's syndrome, autoimmune vasculitis, systemic lupus erythematosus, polymyalgia rheumatica, hepatic conditions, metabolic diseases, Kufs' disease, adrenoleukodystrophy, metachromatic leukodystrophy, storage diseases, infectious vasculitis, syphillis, neurosyphillis, Lyme disease, complications from intracerebral hemorrhage, hypothyroidism, B12 deficiency, folic acid deficiency, niacin deficiency, thiamine deficiency, hydrocephalus, complications post anoxia, prion disease (Creutzfeldt-Jakob disease), Fragile X syndrome, phenylketonuria, malnutrition, neurofibromatosis, maple syrup urine disease, hypercalcemia, hypothyroidism, hypercalcemia, and hypoglycemia.

The degree of cognitive impairment may be assessed by a health care professional. A variety of standardized test are available for assessing cognition, including, but not limited to, the Mini-Mental Status Examination, the Dementia Symptom Assessment Scale, and the Alzheimer's Dementia Assessment Scale (ADAS). Such tests typically provide a measurable score of cognitive impairment. In certain embodiments, the cognitive impairment being treated or prevented is associated with Alzheimer's disease. In certain embodiments, the cognitive impairment is associated with a psychiatric disorder (e.g., schizophrenia). In certain embodiments, the cognitive impairment being treated or prevented is associated with a genetic disease. In certain embodiments, the cognitive impairment being treated or prevented is associated with an infectious disease (e.g., HIV, syphillis).

B. Lysosomal Storage Diseases

Lysosomal storage diseases represent a set of disorders, diseases, and/or conditions characterized by a defect in lysosomal activity. In many embodiments, lysosomal storage diseases result from a decrease in the level or activity of one or more lysosomal enzymes. Lysosomal activity disruptions involved in lysosomal storage diseases may interfere, for example, with degradation of lipids, proteins or organelles by the lysosome, with proper trafficking of molecules into or out of the lysosome, and/or with lysosome-mediated signaling. Many lysosomal storage diseases are associated with accumulation of aggregates of one or more proteins in the lysosome (particularly of one or more proteins that is a substrate for a relevant lysosomal enzyme); such lysosomal storage diseases may be considered to be proteinopathies in accordance with certain embodiments of the invention.

Insights provided by the present invention with respect to links between lysosomal activity and proteinopathies are therefore applicable, in some embodiments, to appropriate lysosomal storage diseases. The present invention therefore provides methods and reagents for the treatment and/or prophylaxis of such lysosomal storage diseases.

Many lysosomal storage diseases include neurological involvement which can be (though not always) progressive and degenerative; symptoms may include developmental delay, ataxia, visual problems, seizures, etc. The lysosome, when healthy, processes unwanted material into substances that can be utilized by cells. Lysosomal storage diseases typically result when one or more of the enzymes involved in this processing is or becomes defective or absent. Defect or absence of such an enzyme results in accumulation of unwanted material in cells, eventually damaging the cells. In many embodiments, lysosomal storage diseases are genetic diseases that show autosomal recessive inheritance; some (e.g., Fabry disease and Hunter syndrome) are X-linked.

Representative lysosomal storage diseases include, for example, Activator Deficiency/GM2 Gangliosidosis, Alpha-mannosidosis, Aspartylglucosaminuria, Cholesteryl ester storage disease, Chronic Hexosaminidase A Deficiency, Cystinosis, Danon disease, Fabry disease, Farber disease, Fucosidosis, Galactosialidosis, Gaucher Disease (e.g., Type I, Type II, Type III), GM1 gangliosidosis (e.g., Infantile, Late infantile/Juvenile, Adult/Chronic), I-Cell disease/Mucolipidosis II, Infantile Free Sialic Acid Storage Disease/ISSD, Juvenile Hexosaminidase A Deficiency, Krabbe disease (e.g., Infantile Onset, Late Onset), Metachromatic Leukodystrophy, Mucopolysaccharidoses disorders, Pseudo-Hurler polydystrophy/Mucolipidosis IIIA (e.g., MPSI Hurler Syndrome, MPSI Scheie Syndrome, MPS I Hurler-Scheie Syndrome, MPS II Hunter syndrome, Sanfilippo syndrome Type A/MPS III A, Sanfilippo syndrome Type B/MPS III B, Sanfilippo syndrome Type C/MPS III C, Sanfilippo syndrome Type D/MPS III D, Morquio Type A/MPS IVA, Morquio Type B/MPS IVB, MPS IX Hyaluronidase Deficiency, MPS VI Maroteaux-Lamy, MPS VII Sly Syndrome, Mucolipidosis I/Sialidosis, Mucolipidosis IIIC, Mucolipidosis type IV), Multiple sulfatase deficiency, Niemann-Pick Disease (e.g., Type A, Type B, Type C), Neuronal Ceroid Lipofuscinoses (e.g., CLN6 disease—Atypical Late Infantile, Late Onset mutant, Early Juvenile, Batten-Spielmeyer-Vogt/Juvenile NCL/CLN3 disease, Finnish Mutant Late Infantile CLN5, Jansky-Bielschowsky disease/Late infantile CLN2/TPP1 Disease, Kufs/Adult-onset NCL/CLN4 disease, Northern Epilepsy/mutant late infantile CLN8, Santavuori-Haltia/Infantile CLN1/PPT disease, Beta-mannosidosis), Pompe disease/Glycogen storage disease type II, Pycnodysostosis, Sandhoff disease/GM2 Gangliosidosis (e.g., Adult Onset, Infantile, Juvenile), Schindler disease, Salla disease/Sialic Acid Storage Disease, Tay-Sachs/GM2 gangliosidosis, Wolman disease, etc.

Lysosomal storage diseases can result from a number of defects, including a primary defect in a lysosomal enzyme's activity, e.g., as in Gaucher disease or Fabry disease, or a defect in the post-translational processing of a lysosomal enzyme e.g., as in Mucosuphatidosis, or a defect in the trafficking of a lysosomal enzyme e.g., as in Mucolipidosis type IIIA, or a defect in a lysosomal protein that is not an enzyme e.g., as in Danon disease, or a defect in a non-lysosomal protein e.g., as in a mutant of Late Infantile Neuronal Ceroid Lipofuscinosis. In lysosomal storage diseases, there is often an accumulation of certain lipids e.g., glucosylceramide or cholesterol, or of certain proteins e.g., subunit c of ATP synthase, or of certain damaged organelles or organelle fragments e.g., fragmented mitochondria. Drug-induced stimulation of a cellular phagic response may be of therapeutic benefit in lysosomal storage diseases; such phagic responses may include microautophagy, macroautophagy, chaperone-mediated autophagy, mitophagy, pexophagy.

Exemplary lysosomal enzymes, defects in which may result in or contribute to a lysosomal storage disease are listed in Table 10.

TABLE 10

| Lysosomal Storage Diseases and associated enzyme defects | | |
|---|---|---|
| Disease Name | Enzyme Defect | Substance Stored |
| A. Glycogenosis Disorders | | |
| Pompe Disease | Acid-α1,4-Glucosidase | Glycogen α1-4 linked Oligosaccharides |
| B. Glycolipidosis Disorders | | |
| GM1 Gangliodsidosis | β-Galactosidase | $GM_1$ Gangliosides |
| Tay-Sachs Disease | β-Hexosaminidase A | $GM_2$ Ganglioside |
| GM2 Gangliosidosis: AB Mutant | $GM_2$ Activator Protein | $GM_2$ Ganglioside |
| Sandhoff Disease | β-Hexosaminidase A&B | $GM_2$ Ganglioside |
| Fabry Disease | α-Galactosidase A | Globosides |
| Gaucher Disease | Glucocerebrosidase | Glucosylceramide |
| Metachromatic Leukodystrophy | Arylsulfatase A | Sulphatides |
| Krabbe Disease | Galactosylceramidase | Galactocerebroside |
| Niemann-Pick, Types A and B | Acid Sphingomyelinase | Sphingomyelin |
| Niemann-Pick, Type C | Cholesterol Esterification Defect | Sphingomyelin |

TABLE 10-continued

Lysosomal Storage Diseases and associated enzyme defects

| Disease Name | Enzyme Defect | Substance Stored |
|---|---|---|
| Niemann-Pick, Type D | Unknown | Sphingomyelin |
| Farber Disease | Acid Ceramidase | Ceramide |
| Wolman Disease | Acid Lipase | Cholesteryl Esters |
| C. Mucopolysaccharide Disorders | | |
| Hurler Syndrome (MPS IH) | α-L-Iduronidase | Heparan & Dermatan Sulfates |
| Scheie Syndrome (MPS IS) | α-L-Iduronidase | Heparan & Dermatan, Sulfates |
| Hurler-Scheie (MPS IH/S) | α-L-Iduronidase | Heparan & Dermatan Sulfates |
| Hunter Syndrome (MPS II) | Iduronate Sulfatase | Heparan & Dermatan Sulfates |
| Sanfilippo A (MPS IIIA) | Heparan N-Sulfatase | Heparan Sulfate |
| Sanfilippo B (MPS IIIB) | α-N-Acetylglucosaminidase | Heparan Sulfate |
| Sanfilippo C (MPS IIIC) | Acetyl-CoA-Glucosaminide Acetyltransferase | Heparan Sulfate |
| Sanfilippo D (MPS IIID) | N-Acetylglucosamine-6-Sulfatase | Heparan Sulfate |
| Morquio A (MPS IVA) | Galactosamine-6-Sulfatase | Keratan Sulfate |
| Morquio B (MPS IVB) | β-Galactosidase | Keratan Sulfate |
| Maroteaux-Lamy (MPS VI) | Arylsulfatase B | Dermatan Sulfate |
| Sly Syndrome (MPS VII) | β-Glucuronidase | |
| D. Oligosaccharide/Glycoprotein Disorders | | |
| α-Mannosidosis | α-Mannosidase | Mannose/Oligosaccharides |
| β-Mannosidosis | β-Mannosidase | Mannose/Oligosaccharides |
| Fucosidosis | α-L-Fucosidase | Fucosyl Oligosaccharides |
| Aspartylglucosaminuria | N-Aspartyl-β-Glucosaminidase | Aspartylglucosamine Asparagines |
| Sialidosis (Mucolipidosis I) | α-Neuraminidase | Sialyloligosaccharides |
| Galactosialidosis (Goldberg Syndrome) | Lysosomal Protective Protein Deficiency | Sialyloligosaccharides |
| Schindler Disease | α-N-Acetyl-Galactosaminidase | |
| E. Lysosomal Enzyme Transport Disorders | | |
| Mucolipidosis II (I-Cell Disease) | N-Acetylglucosamine-1-Phospho-transferase | Heparan Sulfate |
| Mucolipidosis III (Pseudo-Hurler Polydystrophy) | Same as ML II | |
| F. Lysosomal Membrane Transport Disorders | | |
| Cystinosis | Cystine Transport Protein | Free Cystine |
| Salla Disease | Sialic Acid Transport Protein | Free Sialic Acid and Glucuronic Acid |
| Infantile Sialic Acid Storage Disease | Sialic Acid Transport Protein | Free Sialic Acid and Glucuronic Acid |
| G. Other | | |
| Batten Disease (Juvenile Neuronal Ceroid Lipofuscinosis) | Unknown | Lipofuscins |
| Infantile Neuronal Ceroid Lipofuscinosis | Palmitoyl-Protein Thioesterase | Lipofuscins |
| Mucolipidosis IV | Unknown | Gangliosides & Hyaluronic Acid |
| Prosaposin | Saposins A, B, C or D | |

C. Other Proteinopathies

Other proteinopathies may include, for example, inflammatory diseases, disorders, and/or conditions; proliferative diseases, disorders, and/or conditions; cardiovascular diseases, disorders, and/or conditions; immunologic diseases, disorders, and/or conditions; ocular diseases, disorders, and/or conditions; and/or mitochondrial diseases, disorders, and/or conditions.

1. Inflammatory Disease

In general, inflammatory diseases, disorders, and/or conditions are characterized by intense episodes of inflammation that result in such symptoms as fever, rash, or joint swelling. The mammalian immune system provides a means for the recognition and elimination of foreign pathogens. While the immune system normally provides a line of defense against foreign pathogens, there are many instances where the immune response itself is involved in the progression of disease. Inflammatory diseases, disorders, and/or conditions are different from immune diseases, but also share a common characteristic in that both groups of disorders result from immune system attacking the body's own tissues, and also result in increased inflammation.

In certain embodiments, proteinopathic inflammatory diseases, disorders, and/or conditions may include one or more of inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitus, irritable bowel syndrome, ulcerative colitis, glomerulonephritis, dermatomyositis, scleroderma, vasculitis, allergic disorders including asthma such as bronchial, allergic, intrinsic, extrinsic and dust asthma, particularly chronic or inveterate asthma (e.g. late asthma airways hyper-responsiveness) and bronchitis, chronic obstructive pulmonary disease (COPD), multiple sclerosis, rheumatoid arthritis, disorders of the gastrointestinal tract, including, without limitation, Coeliac disease, proctitis, eosinophilic gastroenteritis, mastocytosis, pancreatitis, Crohn's disease, ulcerative colitis, food-related allergies which have effects remote from the gut, e.g. migraine, rhinitis and eczema. Conditions characterised by inflammation of the nasal mucus membrane, including acute rhinitis, allergic, atrophic thinitis and chronic rhinitis including rhinitis caseosa, hypertrophic rhinitis, rhinitis purulenta, rhinitis sicca and rhinitis medicamentosa; membranous rhinitis including croupous, fibrinous and pseudomembranous rhinitis and scrofoulous rhinitis, seasonal rhinitis including rhinitis nervosa (hay fever) and vasomotor rhinitis, sarcoidosis, farmer's lung and related diseases, fibroid lung and idiopathic interstitial pneumonia, acute pancreatitis, chronic pancreatitis, and adult respiratory distress syndrome, and/or acute inflammatory responses (such as acute respiratory distress syndrome and ischemia/reperfusion injury).

2. Proliferative and Immunologic Disease

In general, cell proliferative disorders, diseases, and/or conditions encompass a variety of conditions characterized by aberrant cell growth, preferably abnormally increased cellular proliferation. For example, proteionopathic cell proliferative diseases, disorders, and/or conditions include, but are not limited to, cancer, immune-mediated responses and diseases (e.g., transplant rejection, graft vs host disease, immune reaction to gene therapy, autoimmune diseases, pathogen-induced immune dysregulation, etc.), certain circulatory diseases, and certain neurodegenerative diseases.

In general, cancer is a group of diseases which are characterized by uncontrolled growth and spread of abnormal cells. Examples of such diseases are carcinomas, sarcomas, leukemias, lymphomas and the like.

For example, cancers include, but are not limited to leukemias and lymphomas such as cutaneous T-cell lymphomas (CTCL), peripheral T-cell lymphomas, lymphomas associated with human T-cell lymphotropic virus (HTLV) such as adult T-cell leukemia/lymphoma (ATLL), B-cell lymphoma, acute lymphocytic leukemia, acute nonlymphocytic leukemias, chronic lymphocytic leukemia, chronic myelogenous leukemia, acute myelogenous leukemia, Hodgkin's disease, non-Hodgkin's lymphomas, multiple myeloma, myelodysplastic syndrome, mesothelioma, common solid tumors of adults such as head and neck cancers (e.g., oral, laryngeal and esophageal), genitourinary cancers (e.g., prostate, bladder, renal, uterine, ovarian, testicular, rectal and colon), lung cancer, breast cancer, pancreatic cancer, melanoma and other skin cancers, stomach cancer, brain tumors, liver cancer and thyroid cancer, and/or childhood solid tumors such as brain tumors, neuroblastoma, retinoblastoma, Wilms' tumor, bone tumors, and soft-tissue sarcomas.

Examples of immune-mediated responses and diseases include, rejection following transplantation of synthetic or organic grafting materials, cells, organs or tissue to replace all or part of the function of tissues, such as heart, kidney, liver, bone marrow, skin, cornea, vessels, lung, pancreas, intestine, limb, muscle, nerve tissue, duodenum, small-bowel, pancreatic-islet-cell, including xenotransplants, etc.; treatment of graft-versus-host disease, autoimmune diseases, such as rheumatoid arthritis, systemic lupus erythematosus, thyroiditis, Hashimoto's thyroiditis, multiple sclerosis, myasthenia gravis, type I diabetes uveitis, juvenile-onset or recent-onset diabetes mellitus, uveitis, Graves' disease, psoriasis, atopic dermatitis, Crohn's disease, ulcerative colitis, vasculitis, auto-antibody mediated diseases, aplastic anemia, Evan's syndrome, autoimmune hemolytic anemia, and the like; and further to treatment of infectious diseases causing aberrant immune response and/or activation, such as traumatic or pathogen induced immune dysregulation, including for example, that which are caused by hepatitis B and C infections, HIV, *Staphylococcus aureus* infection, viral encephalitis, sepsis, parasitic diseases wherein damage is induced by an inflammatory response (e.g., leprosy). Other immune-mediated responses and diseases relate to graft vs host disease (especially with allogenic cells), rheumatoid arthritis, systemic lupus erythematosus, psoriasis, atopic dermatitis, Crohn's disease, ulcerative colitis and/or multiple sclerosis.

Examples also include, diseases caused or worsened by the host's own immune response. For example, autoimmune diseases such as multiple sclerosis, lupus erythematosus, psoriasis, pulmonary fibrosis, and rheumatoid arthritis and diseases in which the immune response contributes to pathogenesis such as atherosclerosis, inflammatory diseases, osteomyelitis, ulcerative colitis, Crohn's disease, and graft versus host disease (GVHD) often resulting in organ transplant rejection. Additional exemplary inflammatory disease states include fibromyalgia, osteoarthritis, sarcoidosis, systemic sclerosis, Sjogren's syndrome, inflammations of the skin (e.g., psoriasis), glomerulonephritis, proliferative retinopathy, restenosis, and chronic inflammations.

3. Cardiovascular Disease

Cardiovascular diseases, disorders, and/or conditions are a leading cause of deaths worldwide. Over 50 million Americans have heart and cardiovascular related problems. By the time that cardiovascular heart problems are usually detected, the disease is usually quite advanced, having progressed for decades, and often too advanced to allow successful prevention of major permanent disability.

In general, cardiovascular disease may be a disease which involves the heart and/or blood vessels, arteries, and occasionally veins. In some embodiments, the disease is a vascular disease. These problems are most commonly due to consequences of arterial disease, atherosclerosis, atheroma, but also can be related to infection, valvular and clotting problems. In some embodiments, the proteinopathic diseases, disorders, and/or conditions are related to circulatory diseases, such as arteriosclerosis, atherosclerosis, vasculitis, polyarteritis nodosa, and/or myocarditis.

Exemplary particular proteinopathic cardiovascular diseases, disorders, and/or conditions may include one or more of myocardial ischemia, myocardial infarction, vascular hyperplasia, cardiac hypertrophy, congestive heart failure, cardiomegaly, restenosis, atherosclerosis, hypertension, and/or angina pectoris.

In certain embodiments, the proteinopathic cardiovascular disease, disorder or condition is atherosclerosis, a coronary heart disease, an acute coronary symptom, unstable angina pectoris or acute myocardial infarction, stable angina pectoris, stroke, ischemic stroke, inflammation or autoimmune disease associated atherosclerosis or restenosis.

4. Mitochondrial Disease

In general, mitochondrial diseases, disorders, and/or conditions may be caused by mutations, acquired or inherited, in mitochondrial DNA or in nuclear genes that code for mitochondrial components. They may also be the result of acquired mitochondrial dysfunction due to adverse effects of drugs, infections, or other environmental causes.

Mitochondria generate most of the cell's supply of adenosine triphosphate (ATP), used as a source of chemical energy. In addition to supplying cellular energy, mitochondria are involved in a range of other processes, such as signaling, cellular differentiation, cell death, as well as the control of the cell cycle and cell growth (McBride et al., Curr. Biol. 16(14): R551, 2006). Given their entral role in cell metabolism, damage and subsequent dysfunction in mitochondria is an important factor in a wide range of human diseases and may play role in the aging process.

Mitochondrial DNA inheritance behaves differently from autosomal and sex-linked inheritance. Mitochondrial DNA, unlike nuclear DNA, is strictly inherited from the mother and each mitochondrial organelle typically contains multiple mtDNA copies. During cell division, the mitochondrial DNA copies segregate randomly between the two new mitochondria, and then those new mitochondria make more copies. As a result, if only a few of the mtDNA copies inherited from the mother are defective, mitochondrial division may cause most of the defective copies to end up in just one of the new mitochondria. Mitochondrial disease may become clinically apparent once the number of affected mitochondria reaches a certain level; this phenomenon is called 'threshold expression'. Mitochondrial DNA mutations occur frequently, due to the lack of the error checking capability that nuclear DNA has. This means that mitochondrial DNA disorders may occur spontaneously and relatively often. In addition, defects in enzymes that control mitochondrial DNA replication may cause mitochondrial DNA mutations.

Mitochondrial diseases include any clinically heterogeneous multisystem disease characterized by mutations of the brain-mitochondrial encephalopathies and/or muscle-mitochondrial myopathies due to alterations in the protein complexes of the electron transport chain of oxidative phosphorylation. In some embodiments, proteinopathic mitochondrial diseases may include one or more of Leber's hereditary optic atrophy, MERRF (Myoclonus Epilepsy with Ragged Red Fibers), MELAS (Mitochondrial Encephalopathy, Lactic Acidosis and Stroke-like episodes); Alper syndrome, Lowe syndrome, Luft syndrome, Menke's kinky hair syndrome, Zellweger syndrome, mitochondrial myopathy, and rhizomelic chondrodysplasia punctata.

Defects in nuclear genes lead to dysfunction of mitochondrial proteins. This is the case in Friedreich's ataxia, hereditary spastic paraplegia, and Wilson's disease (Chinnery et al., J. Neurol. Neurosurg. Psychiatr. 74(9): 1188, 2003). These diseases are inherited in a dominance relationship, as applies to most other genetic diseases. A variety of disorders can be caused by nuclear mutations of oxidative phosphorylation enzymes, such as coenzyme Q10 deficiency and Barth syndrome (Zeviani et al., Brian 127 (pt 10): 2153, 2004). Environmental influences may interact with hereditary predispositions and cause mitochondrial disease. For example, there may be a link between pesticide exposure and the later onset of Parkinson's disease (Gomez et al., Front Biosci. 12:1079, 2007).

Other pathologies with etiology involving mitochondrial dysfunction include schizophrenia, bipolar disorder, dementia, Alzheimer's disease, Parkinson's disease, epilepsy, stroke, cardiovascular disease, retinitis pigmentosa. A common thread thought to link these seemingly-unrelated conditions is cellular damage causing oxidative stress.

In some embodiments, the present invention provides treatment for, and/or prophylaxis of, diseases that are characterized by mitochondrial dysfunction and oxidative stress.

Lysosomal Enzymes

The lysosome is bound by a membrane and contains digestive enzymes, each of which can cleave a particular chemical bond found in natural materials. Most lysosomal enzymes work best in an acid environment, which is accomplished by a proton pump, built into the membrane surrounding the lysosome. Lysosomes digest materials taken into the cell from the outside (a process known as heterophagy) as well as other materials that originate in the cell's own cytoplasm (autophagy). The materials to be digested are ultimately incorporated into the same membrane-bounded compartments as the lysosomal enzymes. Selective degradative products can pass out of the lysosome by crossing the membrane, but the enzymes cannot. This sequestration, which protects the cell, persists because the admixture of the enzymes and the materials to digest takes place through fusion of membrane-bounded compartments.

As described herein, the present invention provides insights and technologies relevant to the treatment of proteinopathies by modulation of lysosomal function. In some embodiments, such modulation is achieved by increasing level and/or activity of one or more lysosomal enzymes. Representative such lysosomal enzymes include, for example, heparin sulfate sulfamidase, β-glucuronidase, β-galactosidase, β-mannosidase, hexoaminidases, β-Glucocerebrosidase, and others as listed in Table 5.

Some lysosomal enzymes (e.g., glucocerbrosidase) share a similar catalytic domain or active site consisting of an $(\alpha/\beta)_8$ barrel with conserved functional amino acids located at the C-terminal ends of six of the eight strands constituting the β-barrel (Durand P et al. Glycobiology 1997). The active-site of an enzyme is part of an enzyme where substrates bind and undergo a chemical reaction. The active site residues (amino acids or nucleotides) participate in recognition of the substrate and directly participate in the catalytic reaction mechanism. Several mutations reported to be responsible for lysosomal enzyme-mediated diseases (e.g., lysosomal storage diseases) are located within these conserved regions of the lysosomal enzyme catalytic domains.

1. Glucocerebrosidase Polypeptide

Naturally occurring glucocerebrosidase (GCase) encoded by the GBA or GBA1 gene is an enzyme that is active in the lysosomes where it hydrolysis the β-glucosidic linkage of the sphingolipid glucosylceramide (GlcCer) into a sugar (glucose) and a simpler fat molecule (ceramide). Representative GCase polypeptides are provided in Table 2.

Non-lysosomal GCase polypeptides are encoded by GBA2 and GBA3 genes. Cytosolic GCase polypeptide, in humans is encoded by GBA3 gene. Cytosolic GCase is a predominantly liver enzyme that efficiently hydrolyzes β-D-glucoside and β-D-galactoside, but not any known physiologic β-glycoside. GBA3 also has significant neutral glycosylceramidase activity, suggesting that it may be involved in a non-lysosomal catabolic pathway of glucosylceramide metabolism. GBA2 gene encodes a microsomal GCase polypeptide that catalyzes the hydrolysis of bile acid 3-O-glucosides as endogenous compounds. Subcellular localization of this protein in the liver indicated that the enzyme was mainly enriched in the microsomal fraction where it appeared to be confined to the endoplasmic reticulum. This putative transmembrane protein is thought to play a role in carbohydrate transport and metabolism.

In some embodiments, the present invention teaches that increasing level and/or activity of GBA2 and/or GBA3 proteins may also be useful in the treatment and/or prophylaxis of certain proteinopathies.

GCase polypeptide defects cause Gaucher's disease (GD). Based on the rate of clinical progression and involvement of the nervous system, three types of GD have been described (Grabowski, The Lancet 372(9645): 1263, 2008). Type I GD is classically defined as non-neuropathic and is typically characterized by hepatosplenomegaly, skeletal and hematopoietic system abnormalities. Phenotypic variation in type I GD has been observed, and a small subset of patients develop parkinsonism at variable ages throughout the course of the disease (Bultron et al., J. Inherit. Metab. Dis. 33: 167, 2010; Tayebi et al., Mol. Genet. Metab. 79: 104, 2003). Types II and III are differentiated from type I by neurodegeneration of the central nervous system with either rapid (type II) or chronic progression (type III); however these forms can also show some phenotypic variation. A common feature of all three types is accumulation of GlcCer in the affected tissues.

Recent studies have suggested a link between mutations in lysosomal enzymes and neurological disorders other than lysosomal storage diseases. For example, a clinical link between Gauche disease (GD) and parkinsonism (Sidransky et al., Mol. Genet. Metab. 84: 302, 2005) suggested that mutations in the glucocerebrosidase (GCase) gene (GBA1) and alterations in sphingolipid metabolism contribute to the pathogenesis of synucleinopathies. GD is a rare, autosomal recessive LSD that results from loss-of-function mutations in GCase polypeptide, that cleaves the β-glucosyl linkage of GlcCer (Brady et al., J. Biol. Chem. 240: 39, 1965).

Parkinsonism is often observed in a subset of adult onset type I GD patients (Neudorfer et al., QJM 89: 691, 1996; Sidransky et al., Mol. Genet. Metab. 84: 302, 2005; Tayebi et al., Mol. Genet. Metab., 2003). Neuropathological analysis of these patients has revealed the presence of α-synuclein-positive Lewy bodies (Wong et al., Mol. Genet. Metab. 82: 192, 2004). It has also been noted that patients with GD and parkinsonism frequently have relatives with parkinsonism that are heterozygous for GBA1 mutations (Goker-Alpan et al., J. Med. Genet. 41: 937, 2004). Several additional genetic studies in large patient cohorts demonstrated that patients with parkinsonism have an increased incidence of GBA1 mutations (Lill et al., The PDGene Database, Alzheimer Research Forum, 2008; Sidransky et al., N. Engl. J. Med. 361: 1651, 2009), making GBA1 the most common known genetic risk factor for PD to date. GBA1 mutations have also been identified in patients with the diagnosis of DLB (Goker-Alpan et al., Neurology 67: 908, 2006; Neumann et al., Brian 132: 1783, 2009). Also, inhibitors of GCase polypeptide function have been shown to modulate α-synuclein levels (Manning-Bog et al., Neurotoxicology 30: 1127, 2009).

The present invention demonstrates, among other things, that either expression of GD-linked mutations or depletion of lysosomal enzyme GCase causes the accumulation of α-synuclein and results in neurodegeneration (see, for example, Examples 1 and 2).

The present invention additionally demonstrates that GlcCer accumulation specifically affects the conformation and solubility of α-synuclein by stabilizing the levels of soluble intermediates (see, for example, Example 3).

The present invention also demonstrates that GlcCer has the ability to prolong the lag phase of fibril growth and stabilize oligomeric intermediates at acidic pH (see, for example, Example 4). After the lag phase, GlcCer accelerated amyloid formation and formed fibrils that appeared to extend from GlcCer lipid tubules.

Without wishing to be bound by any particular theory, the present invention proposes that GlcCer tubules provide a scaffold or platform for oligomeric intermediates to form that, once saturated proceed to rapid polymerization of fibrils. This ability may be a crucial step in pathogenesis, as the documentation of α-synuclein oligomers appears to be correlated with neurodegeneration in neuronal cultures, mouse models, and human neuropathic GD brain.

The present invention therefore demonstrates that GCase polypeptide loss-of-function mutations reduce lysosomal proteolysis in human dopamine neurons, and thus, suggesting GlcCer metabolism as a fundamental regulator of lysosomal activity.

In some embodiments, the present invention demonstrates that α-synuclein accumulation inhibits the lysosomal activity of GCase polypeptide, thus establishing a bidirectional positive feedback loop between α-synuclein and GCase polypeptide that comprises a self-propagating disease mechanism. According to the present invention, elevation and/or formation of α-synuclein assemblies further inhibit the lysosomal maturation and activity of normal or wild-type GCase polypeptide, resulting in additional GlcCer accumulation and augmented α-synuclein oligomer formation (see for example, Example 7). Thus, the present invention teaches that depletion of lysosomal GCase occurs not only in patients that carry mutations in GCase polypeptide, but also in patients with sporadic forms of PD and other synucleinopathies and/or proteinopathies.

In some embodiments, the present invention teaches that lowering GlcCer levels in cells, either by enhancing GCase polypeptide function or reducing substrate levels, will lead to reduction of α-synuclein levels in brain. This therapeutic strategy should break the pathogenic feedback loop and stop or possibly even reverse neurodegeneration. According to the present invention, enhancing the function of GCase polypeptide provides therapeutic benefit in all neurodegenerative disorders characterized by the accumulation of α-synuclein.

In some embodiments, the present invention demonstrates that overexpression of GCase polypeptide in non-neuronal Hela cells increased lysosomal proteolysis by approximately 40% (see for example, Example 8).

The present invention demonstrates, among other things, that allosteric agents result in GCase polypeptide activation. The present invention teaches that treatment of dopamine neurons from a PD patient with allosteric activating agents of GCase polypeptide increased lysosomal degradation capacity (see for example, Example 8).

Allosteric sites on an enzyme are sites that are physically distinct from its active site. Allosteric sites bind to molecules in the cellular environment (e.g., enzymes called coenzymes or other nonorganic matter called cofactors) to form weak, noncovalent bonds with these molecules, causing a change in the conformation of the enzyme. This change in conformation translates to the active site, which then affects the reaction rate of the enzyme. Allosteric interactions can both inhibit and activate enzymes.

Allosteric activating agents bind to allosteric sites and do not compete for the active site with the substrate.

In some embodiments of the invention, allosteric agents increase the stability of a lysosomal enzyme. In some embodiments the invention, allosteric agents increase the binding between a lysosomal enzyme and substrate. In some embodiments the invention, allosteric agents increase the trafficking of a lysosomal enzyme.

The present invention also teaches that treatment of PD dopamine neurons overexpressing α-synuclein with allosteric activating agents of GCase polypeptide results in dose-dependant decrease of α-synuclein. The present invention additionally demonstrates that the treatment with GCase polypeptide activator increased the levels of total wild-type GCase and the post-ER forms, indicating enhancement of flux to the lysosome (see for example, Example 10).

Without wishing to be bound by any particular theory, the present invention proposes that allosteric activating agents that do not interfere with the GCase enzyme active site provide methods of treating proteinopathic neurodegenerative disorders (e.g., associated with α-synuclein accumulation) by increasing levels and lysosomal trafficking of both mutant and/or wild-type GCase polypeptide.

The present invention therefore provides methods of treating proteinopathic neurodegenerative disorders (e.g., associated with α-synuclein accumulation) and other diseases characterized by neuronal and non-neuronal protein accumulation by increasing level and/or activity of GCase polypeptide and/or by reducing level and/or availability of a GCase polypeptide substrate such as GlcCer.

2. Sphingolipid Metabolizing Polypeptides

Sphingolipids represent a major class of lipids which are ubiquitous constituents of membranes in eukaryotes. Sphingolipids were considered to play primarily structural roles in membrane formation. However, intensive research on sphingolipid metabolism and function has revealed members of the sphingolipid family, including ceramide, sphingosine, sphingosine-1-phosphate, and ceramide-1-phosphate, as bioactive molecules playing roles from regulation of signal transduction pathways, through direction of protein sorting to the mediation of cell-to-cell interactions and recognition. Sphingolipids have also been reported to dynamically cluster with sterols to form lipid microdomains or rafts, which function as hubs for effective signal transduction and protein sorting (Bartke et al., Journal of Lipid Research S91-6, 2009).

Sphingolipid synthesis starts with the condensation of L-serine and palmitoyl coenzyme A (palmitoyl-CoA) to 3-ketosphinganine, and its reduction to sphinganine in the endoplasmic reticulum. Serine palmitoyltransferase (SPT), a membrane-associated heterodimer consisting of two gene products, long-chain base (LCB) 1 and LCB2, is the rate-limiting enzyme for the sphingolipid synthesis (Hanada, 2003). Ceramide is central molecule that serves as the precursor for all major sphingolipids, that is, sphingomyelin (SM), glucosylceramide, and more complex sphingolipids in eukaryotic cells, and sphingolipid metabolism involves different key enzymes (Hannun et al., Biochemistry 40: 4893, 2001; Gault et al., Adv Exp Med. Biol. 688: 1, 2010).

A complex group of lipids known as glycosphingolipids (GSL) contain dozens of different sphingolipid species differing by both the order and type of sugar residues attached to their headgroups.

Gangliosides are complex glycosphingolipids (ceramide and oligosaccharide) with one or more sialic acids (e.g., n-acetylneuraminic acid, NeuNAc) linked on the sugar chain. Structural diversity of gangliosides results from the variation in the composition and sequence of the sugar residues. In all gangliosides, the ceramide is linked through its C-1 to a β-glucosyl residue, which in turn is bound to a β-galactosyl residue. $G_{M1}$ (monosialotetrahexosylganglioside) conatins one sialic acid residue (monoasilo) and impacts neuronal plasticity and repair mechanisms, it also participates in the release of neurotrophins in the brain. $G_{M2}$ is the second monoasilo ganglioside that has been characterized.

Gangliosides are important constituents of cell-membranes and are associated with a plethora of biological functions, including cellular recognition and adhesion, signal transduction, growth regulation and differentiation. While they are present in most vertebrate cells and tissues, gangliosides are particularly abundant in the nervous system where they are expressed most frequently as components of the outer leaflet of the plasma membranes of neural and glial cells. Ganglioside metabolism abnormalities is associated with various neurodegenerative diseases. For example, imbalance of ganglioside levels can result in apoptosis and disruption in $Ca^{+2}$ signaling, both of which have been associated with Huntington's disease. (Desplats et al., Neurobiol Dis. 27(3): 265, 2007).

The present invention demonstrates, among other things, that gangliosides cause accumulation of α-synulcein in vitro (see, for example, Example 12).

The present invention additionally demonstrates that gangliosides stabilize and increase the formation of soluble α-synuclein oligomers.

Without wishing to be bound by any particular theory, the present invention proposes that lowering of ganglioside levels provides strategies treating proteinopathic neurodegenerative disorders (e.g., associated with α-synulcein accumulation) by enhancing activity and/or level of ganglioside metabolizing enzymes.

The present invention therefore provides methods and compositions for the treatment and/or prophylaxis of certain proteinopathic diseases, disorders, and/or conditions, and particularly neurodegenerative proteinopathic diseases, disorders, and/or conditions (e.g., associated with α-synuclein accumulation), as well as other diseases characterized by neuronal and non-neuronal protein accumulation by increasing level and/or activity of lysosomal sphingolipid metabolizing polypeptides such as β-hexosaminidase A/B/S and β-galactosidase isoform 1 polypeptides and/or by reducing level and/or availability of a sphingolipid metabolizing enzyme substrate including but not limited to ganglioside $G_{M1}$, $G_{M2}$, $G_{M3}$.

Membrane Trafficking

The present invention demonstrates that protein trafficking defects may contribute to protein accumulation in certain proteinopathies. Membrane trafficking is essential for transport of proteins and other macromolecules to various destinations inside and outside of the cell. Membrane trafficking also underlies the fundamental need for cells to maintain cellular homeostasis, as well as to meet specific demands during signal perception and transduction.

The pathways of membrane protein trafficking, starting from the endoplasmic reticulum (ER), are long, branched, and occasionally even bidirectional. The blueprint of membrane trafficking system is conserved among eukaryotes and comprises the ER, the Golgi apparatus, endosomes, and lytic compartments (e.g., lysosomes). Studies have shown that accumulation of proteins in pathologically high amounts, or mutant forms of proteins with enhanced membrane association and oligomerization can result in neuronal demise with manifestations of heightened oxidative stress, mitochondrial degeneration, defects in lipid metabolism, and impaired membrane trafficking (Chua et al., Brain Res Rev. 67(1-2): 268, 2011). Certain components of the eukaryotic membrane traffic machinery, including for example Rab polypeptides and soluble N-ethylmaleimide sensitive factor attachment protein receptors (SNAREs), have been suggested to play an important role in impairment of membrane trafficking.

The large Rab family of GTPases regulates lipid and protein traffic between intracellular membrane system of eukaryotic cells Like other GTPases, Rab polypeptides switch between conformations, an inactive form bound to guanosine diphosphate (GDP), and an active form bound to guanosine triphosphate (GTP). A GDP/GTP exchange factor (GEF) catalyzes the conversion from GDP-bound to GTP-bound forms, and GTP hydrolysis to GDP is catalyzed by GTPase-activating protein (GAP). Rab polypeptides are modified via the addition of a C-terminal lipid anchor by Rab geranylgeranyl transferase (RabGGT) with the aid of Rab escort protein (REP), thus enabling their membrane targeting and attachment. Conversely, Rab guanine nucleotide dissociation inhibitors (Rab GDIs) extract Rab-GDP from membranes and keep them cytosolic. Activated Rab polypeptides recruit a myriad of effector proteins to mediate vesicle/carrier transport. There are approximately 70 types of Rab polypeptides identified in humans.

Rab1a polypeptide has been identified through proteomics to be associated with both early and late endocytic vesicles (Mukopadhyay et al. J Cell Sci 124: 765, 2011). There are two isoforms of Rab1 polypeptide; Rab1a and Rab1b, which share 92% amino acid sequence homology and are thought to be functionally redundant in mammalian cells. Rab1 polypeptide has been established to function specifically at the ER-Golgi step of the secretory pathway (Duvernay et al., Cell Signal 17: 1457, 2005). Specifically, Rab1 polypeptide recruits the tethering factor p115 into a cis-SNARE complex that programs coat protein II (COPII) vesicles budding from the ER for fusion with the Golgi with the help of the cis-Golgi tethering protein GM130 complexed to GRASP65. Recently, a role of Rab1a polypeptide in early-endosome-to-Golgi trafficking has been reported and Rab1a polypeptide has been described as a component of transcytotic vesicles. Rab1a polypeptide has been shown to be important for transport of early endocytic vesicles along microtubules.

The present invention demonstrates that overexpression of Rab1a polypeptide in human PD dopamine neurons overexpressing α-synuclein, results in dramatic reduction of α-synuclein levels in the neurons (see for example, Example 9). The present invention additionally demonstrates that Rab1a polypeptide enhances lysosomal function by increase in cathepsin B activity.

Without wishing to be bound by any particular theory, the present invention proposes that stimulation of membrane trafficking or secretory pathway provide activation of lysosomal enzyme trafficking. The present invention also teaches that stimulation of lysosomal enzyme trafficking results in increased lysosomal function, which leads to reduction in α-synuclein levels in both neuronal and non-neuronal cells.

As demonstrated herein the present invention teaches that elevated α-synuclein results in disruption of lysosomal trafficking of GCase polypeptide, decreased GCase polypeptide activity and thus compromised lysosomal proteolysis. According to the present invention the GCase polypeptide activity not only contributes to toxicity in patients with GBA1 mutations, but also affect the development of more common sporadic forms of PD and synucleinopathies that do not have mutations in the GBA1 gene.

The invention also demonstrates that variation of α-synuclein in healthy control subjects can also alter ER-Golgi flux of GCase polypeptide, a property that may be potentiated by α-synuclein oligomerization. This fact is further demonstrated in the invention by normal GCase polypeptide activity in neurons expressing aggregation-incompetent Δ71-82-α-synuclein as well as the increased immuno-reactivity to syn303 in controls that contain higher levels of GCase polypeptide in ER.

The present invention therefore provides methods of treating proteinopathic neurodegenerative disorders (e.g., associated with α-synuclein accumulation) in subjects with wild-type GCase polypeptide by increasing intracellular lysosomal trafficking of normal GCase polypeptide through stimulation of membrane trafficking or secretory pathway.

Oxidative Stress

The present invention provides methods relevant to oxidative or nitrative stress resulting in proteinopathies. Impaired mitochondrial function, oxidative stress, accumulation of protein aggregates, and autophagic stress are common in many proteinopathies including, but not limited to, neurodegenerative diseases (Lee et al., Biochem. J. 441: 523, 2012).

Oxidative stress can lead to the non-specific post-translational modifications of proteins and contributes to protein aggregation. Since the brain uses 20% of the inspired oxygen and 90% of the consumed oxygen to produce energy during oxidative phosphorylation, it is not surprising that neuronal cells are particularly sensitive to oxidative stress. During oxidative phosphorylation, neurons in the brain are vulnerable to oxidative damage because of their high metabolic activity, low antioxidant capacity and non-replicative nature. The highly abundant mitochondria in brain cells are a major site of generation and action of reactive oxygen species (ROS)/reactive nitrogen species (RNS). Specific forms of ROS and RNS include hydrogen peroxide ($H_2O_2$), superoxide ($O_2.^-$), nitric oxide (NO), peroxynitrite ($ONOO^-$) and reactive lipid species (RLS). Lipid peroxidation is a consistent feature of neurodegenerative diseases and biologically active RLS, such as HNE (4-hydroxynonenal), accumulates in brains of individuals with Parkinson's or Alzheimer's disease. Other mechanisms of protein modification are NO-dependent. For example, NO reacts with $O_2.^-$ and generates $ONOO^-$, which is capable of initiating further protein oxidation and nitration. The nitrogen dioxide radical, formed biologically from the reaction of NO with oxygen or decomposition from $ONOO^-$, reacts with tyrosine residues, resulting in 3-nitrotyrosine formation. The addition of NO to thiol groups on proteins, S-nitrosation (also referred to as S-nitrosylation), has also been reported in neurodegenerative diseases. This adduct has been detected in a broad range of pathologies, including Parkinson's disease, which is associated with both nitrated α-synuclein and S-nitrosated parkin. Likewise, ONOO⁻-dependent modifications of proteins are widespread in brains of individuals with Alzheimer's disease. Studies have documented the presence of oxidized α-synuclein within Lewy bodies and neurites in brains of patients with various synucleinopathies (Gias son et al., J. Neurosci Res. 59(4): 528, 2000). Oxidative stress is inseparably linked to mitochondrial dysfunction, as mitochondria are both generators of and targets for reactive species. Mitochondrial dysfunction, which leads to increased oxidants, is linked to PD pathogenesis (Banerjee et al., Biochem. Biophys. Acta 1792: 651, 2009). Mitochondrial turnover is dependent on autophagy, which declines with age and is frequently dysfunctional in neurodegenerative diseases. Thus, there is a crosstalk between autophagy, redox signalling and mitochondrial dysfunction in neurodegenerative diseases.

The present invention demonstrates that oxidative stress may contribute to existence, nature and/or extent of protein aggregation in certain proteinopathies. For example, among other things, the present invention shows by size exclusion chromatography (SEC) analysis that postmortem GD and PD brain samples have elevated levels of a previously undocumented 36-45 Å-sized soluble oligomeric α-synuclein species whose presence and/or level correlates with a neurological phenotype (see, for example, Examples 5 and 6).

The present invention additionally demonstrates that the soluble α-synuclein oligomers prominently reacted with the monoclonal antibody (mAb) syn303 (see for example, Example 6), an antibody generated against oxidized/nitrated α-synuclein that preferentially detects pathological conformations of the protein that exhibit toxic properties (Tsika et al., J. Neurosci. 30: 3409, 2010).

The present invention also demonstrates that the pathological α-synuclein oligomers were also detected in infantile neuronopathic GD cases, and in a child with type III GD (see for example, Example 6), strongly suggesting that GBA1 mutations and specific alterations in the GlcCer metabolism pathway influence α-synuclein oligomerization that is not necessarily age dependent.

Without wishing to be bound by any particular theory, the present invention proposes that the absence of oligomeric α-synuclein in samples from type I GD without parkinsonism indicates that other factors, in addition to deficiency of GCase polypeptide, likely contribute to oligomerization of α-synuclein in neuronopathic GD. For example, oxidation and nitration of α-synuclein have been shown to impede clearance and stabilize α-synuclein oligomers in vitro (Hodara et al., J. Biol. Chem. 279: 47746, 2004), and chaperones have also been shown to abrogate α-synuclein toxicity and aggregation (Auluck et al., Science 295: 865, 2002).

In some embodiments, the present invention demonstrates increased levels of oxidized α-synuclein oligomers only in brains of patients with GD that also exhibited parkinsonism or neuronopathic forms of the disease.

The present invention demonstrates a 3-fold increase in amount of post endoplasmic reticulum (ER) or mature GCase polypeptide in PD neurons treated in combination with a chaperone for GCase polypeptide, isofagomine (IFG), and an antioxidant, n-acetyl-cysteine (NAC), compared to treatment with either alone.

Without wishing to be bound by any particular theory, the present invention proposes the use of antioxidants for increasing GCase polypeptide maturation for treatment of PD. The present invention also demonstrates that combining small-molecules that stabilize and activate GCase polypeptide in addition to antioxidants results in an efficient disruption of the pathogenic feedback loop initiated by α-synuclein accumulation.

The present invention therefore provides methods of treating proteinopathic neurodegenerative disorders (e.g., associated with α-synuclein accumulation) by increasing level and/or activity of GCase polypeptide using combination therapy. According to the present invention combination therapies targeting two or more critical pathways leading to proteinopathies provide a greater benefit compared to therapies that target each pathway alone. In some embodiments, the present invention teaches therapeutic targeting of two critical pathways leading to proteinopathies. In some embodiments, the present invention teaches therapeutic targeting of three critical pathways leading to proteinopathies. Without wishing to be bound by any theory, the present invention proposes therapeutic targeting of one or more of the following three critical pathways in treatment of proteinopathies: lysosomal enzyme activation (increase in level or function); enhancement of the membrane trafficking pathway; and/or antioxidant function. In some embodiments of the present invention, the lysosomal enzyme is GCase.

Calcium Ion-Mediated Signaling

The $Ca^{2+}$ ion is a universal and important signaling ion in the cell. $Ca^{2+}$ signaling affects numerous cellular functions by diverse pathways and is a primary regulator of ER function (Berridge et al., Nat Rev Mol Cell Biol. 4:517, 2003; Gorlach et al., Antioxid Redox Signal 8: 1391, 2006). Activation of $Ca^{2+}$ channels allows extracellular $Ca^{2+}$ to enter the cytosol, which subsequently induces further $Ca^{2+}$ ion release from the intracellular $Ca^{2+}$ stores, such as the ER, by activating RyRs, and/or the $Ca^{2+}$ ion channels within the ER membrane. Inhibiting this calcium-induced calcium release pathway minimizes depletion of the ER $Ca^{2+}$ store, a process that appears to up-regulate the expression of a subset of cytosolic and ER chaperones, possibly by activation of signaling pathways that mitigate cellular stress (e.g., HSR, UPR). Thus, blocking $Ca^{2+}$ channel activity enhances the capacity of the ER to fold misfolding-prone proteins, likely by modest up-regulation of a subset of molecular chaperones, including Bip and Hsp40.

ER $Ca^{2+}$ levels can be elevated by overexpressing the SERCA2b $Ca^{2+}$ influx pump or by inhibiting the RyR ER $Ca^{2+}$ efflux channels. This in turn can increase chaperone function and enhance the folding, trafficking, and function of mutated, misfolded, and degradation-prone lysosomal enzymes. For example, post-translational regulation of the calnexin folding pathway by an elevated ER calcium concentration can enhance the capacity of this chaperone system to fold mutant misfolding-prone enzymes, increasing the folded mutant lysosomal enzyme population that can engage the trafficking receptor at the expense of ER-associated degradation, increasing the lysosomal enzyme concentration and activity.

Calnexin (and calreticulin) is known to bind to glycoproteins through a lectin site with specificity for $Glc_1Man_9GlcNAc_2$ and/or through a polypeptide binding site that recognizes exposed hydrophobic surfaces in folding intermediates. Biochemical and X-ray crystallographic studies identify a single, ER-luminal, low-affinity $Ca^{2+}$ binding site ($K_d$~0.15±0.05 mM) on the N-terminal β-sandwich of calnexin that may serve a structural role. Occupancy of this Ca$^{2+}$ binding site enhances calnexin's binding to the oligosaccharide substructure of N-linked glycoproteins and its ability to suppress the aggregation of unglycosylated firefly luciferase, rationalizing why ER Ca$^{2+}$ increases seem to increase the affinity or specificity of the interaction between calnexin and partially folded lysosomal enzyme mutants. There is another putative moderate-affinity Ca$^{2+}$ binding site within the C-terminal domain of calnexin, but its cytoplasmic localization suggests that it is unlikely to influence the calnexin-lysosomal enzyme interaction. Calreticulin's function seems to be regulated analogously, as there is a putative Ca$^{2+}$ binding site on its ER luminal N-terminal domain (Schrag et al., Mol. Cell. 8: 633, 2001; Brockmeier et al., Biochemistry 45:12906, 2006; Corbett et al., J. Biol. Chem. 275: 27177, 2000).

Literature reports that manipulation of intracellular calcium homeostasis for treatment of loss of function diseases, disorders, and/or conditions, e.g., lysosomal storage diseases (Tong Ong et al., Nat Chem. Biol. 6: 424, 2010; Mu et al., PLoS Biology 6(2): e26, 2008) using small molecules shows enhancement in the folding, trafficking, and function of endogenous mutant lysosomal enzymes in multiple cell lines associated with different lysosomal storage diseases. These small molecules post-translationally regulate calnexin's function, and unlike unfolded protein response activators, this category of proteostasis regulators does not induce transcription of stress responsive genes. The small molecules therefore restore function by repairing, rather than replacing, the damaged enzyme through altering calcium homeostasis.

The present invention provides the insight that calcium channel blockers may provide effective treatment for, and/or prophylaxis of, certain proteinopathies. Without wishing to be bound by any particular theory, the present invention recognizes that calcium channel blockers may be useful to increase levels and/or activity of one or more lysosomal enzymes, and in particular of GCase. In contrast to the literature, the present invention particularly teaches that calcium channel blockers provide effective treatment for, and/or prophylaxis of, gain of function proteinopathies. Moreover, the present invention provides the particular insight that calcium channel blockers provide effective treatment for, and/or prophylaxis of, proteinopathic neurodegenerative diseases, disorders, or conditions, including particularly those associated with α-synuclein accumulation or aggregation.

Saposins Polypeptides

Saposin A, B, C, and D polypeptides are small heat-stable glycoproteins derived from a common precursor protein, prosaposin. These mature saposin polypeptides, as well as prosaposin polypeptide, activate several lysosomal hydrolases involved in the metabolism of various sphingolipids (Monmoto et al., PNAS 87(9): 3493, 1990; Kishimoto et al., The Journal Lipid Research 33:1255, 1992)

All four saposin polypeptides are structurally similar to one another including placement of six cysteines, a glycosylation site, and conserved prolines in identical positions. In spite of the structural similarities, the specificity and mode of activation of sphingolipid hydrolases differs among individual saposin polypeptides. Saposin polypeptides appear to be lysosomal proteins, exerting their action upon lysosomal hydrolases.

Prosaposin is a 70 kDa glycoprotein containing four domains, one for each saposin, placed in tandem. Prosaposin is proteolytically processed to saposins A, B, C and D, apparently within lysosomes. However, prosaposin also exists as an integral membrane protein not destined for lysosomal entry and exists uncleaved in many biological fluids such as seminal plasma, human milk, and cerebrospinal fluid, where it appears to have a different function.

The physiological significance of saposins is underlined by their accumulation in tissues of lysosomal storage disease patients and the occurrence of sphingolipidosis due to mutations in the prosaposin gene.

The present invention provides the insight that saposin polypeptides may provide effective treatment for, and/or prophylaxis of, certain proteinopathies. Without wishing to be bound by any particular theory, the present invention recognizes that saposin polypeptides may be useful to increase activity of one or more lysosomal enzymes, and in particular of GCase. Moreover, the present invention provides the particular insight that saposin polypeptides provide effective treatment for, and/or prophylaxis of, proteinopathic neurodegenerative diseases, disorders, or conditions, including particularly those associated with α-synuclein accumulation or aggregation.

Lysosomal Activating Agents

As described herein, the present invention provides methods and reagents for treating proteinopathies by activating lysosomal activity. In some such embodiments, activation is achieved by administration of one or more lysosomal activating agents. In some embodiments such lysosomal activating agents increase level and/or activity of one or more lysosomal components (e.g., of a lysosomal enzyme or activator thereof). In some embodiments such lysosomal activating agents decrease level and/or activity of one or more lysosomal components (e.g., an inhibitor or substrate of a lysosomal enzyme).

Substrate inhibition therapy, also referred to as substrate reduction or deprivation therapy, can be used as an alternative therapy for treatment of certain proteinopathic diseases. This strategy seeks to abate the accumulation of a substrate through inhibition of the enzyme that catalyzes the synthesis of the disease-inducing substrate. In some embodiments, the present invention provides lysosome activating agents that arrest accumulation of a proteinpathy-inducing substrate and allow decrease in overall levels of that substrate. In some such embodiments, lysosome activating agent reduce glycoshphingolipid biosynthetic pathway. For example, GlcCer synthesis is the first step in the glycosphingolipid biosynthetic pathway and by reducing GlcCer substrate synthesis, there could be an effect on the levels of more complex glycosphingolipids associated with various proteinopathic disease, disorder, and/or condition.

Those of ordinary skill in the art, reading the present disclosure, will immediately appreciate that any of a variety of chemical entities and agents are useful as lysosomal activating agents in accordance with the present invention. To give but a few examples, in some embodiments, lysosomal activating agents are or comprise small molecule agents. In some embodiments, lysosomal activating agents are or comprise polypeptide agents (e.g., enzymatic polypeptides, regulatory polypeptides, antibodies, etc). In some embodiments, lysosomal activating agents are or comprise nucleic acid agents. In some embodiments, lysosomal activating agents are or comprise carbohydrate agents. In some embodiments, lysosomal activating agents are or comprise lipid agents.

In some embodiments, lysosomal activating agents for use in accordance with the present invention are those that act as pharmacological chaperones, for example helping a misfolded enzyme to fold properly and/or to be trafficked from the endoplasmic reticulum to the lysosome. In some embodiments, lysosomal activating agents interact directly with a lysosomal enzyme.

In some embodiments, lysosomal activating agents interact directly with a lysosomal enzyme through the active site or substrate-binding site of that lysosomal enzyme. In some embodiments, lysosomal activating agents interact directly with a lysosomal enzyme but through a site other than the active site or substrate-binding site of that lysosomal enzyme. In some embodiments, lysosomal activating agents do not interact directly with a lysosomal enzyme. In some embodiments, lysosomal activating agents that do not interact directly with a lysosomal enzyme modulate protein proteostasis. In some embodiments, lysosomal activating agents that do not interact directly with a lysosomal enzyme modulate calcium homeostatsis. In some embodiments, lysosomal activating agents that do not interact directly with a lysosomal enzyme modulate the biological folding capacity of the ER. In some embodiments, lysosomal activating agents are calcium blockers. In some embodiments lysosomal activating agents, particularly those that interact directly with a lysosomal enzyme inhibit activity of the enzyme. In some embodiments, lysosomal activating agents, particularly those that interact directly with a lysosomal enzyme, do not inhibit activity of the enzyme. In some embodiments, lysosomal activating agents are allosteric activators of a lysosomal enzyme.

In some embodiments, lysosomal activating agents for use in accordance with the present invention increase level and/or activity of wild type lysosomal enzymes. Alternatively or additionally, in some embodiments, lysosomal activating agents for use in accordance with the present invention increase level and/or activity of mutant lysosomal enzymes. In some embodiments, a particular lysosomal activating agent for use in accordance with the present invention increases level and/or activity of both a wild type target lysosomal enzyme and one or more mutants of that target lysosomal enzyme.

Alternatively or additionally, in some embodiments, a lysosomal activating agent comprises a pharmacological chaperone for a lysosomal enzyme other than GCase. For example, Table 11 lists potential chaperones for certain lysosomal enzymes.

In some embodiments, the chaperones are administered to an individual who does not have any mutations in any of the lysosomal enzymes for which chaperones are administered. In some embodiments, the individual has mutations in any of the lysosomal enzymes for which chaperones are administered.

In some embodiments, a lysosomal activating agent for use in treatment of a particular disease, disorder, and/or condition is an agent not previously used for such disease, disorder, and/or condition.

TABLE 11

Lysosomal enzymes and corresponding pharmacological chaperones. (Exemplary amino acid sequences of the lysosomal enzymes referenced by SEQ ID NOs. are shown in the Sequence Listing)

| LYSOSOMAL ENZYME | SPECIFIC PHARMACOLOGICAL CHAPERONE |
|---|---|
| α-Glucosidase (e.g., GenBank Accession No. Y00839: SEQ ID NO. 25 or SEQ ID NO. 26) | 1-deoxynojirimycin (DNJ) α-homonojirimycin castanospermine |
| Acid β-Glucosidase (β-glucocerebrosidase) (e.g., GenBank Accession No. J03059: SEQ ID NO. 27) | isofagomine C-benzyl isofagomine and derivatives N-alkyl (C9-12)-DNJ Glucoimidazole (and derivatives) C-alkyl-IFG (and derivatives) N-alkyl-β-valeinamines Fluphenozine calystegines $A_3$, $B_1$, $B_2$, and $C_1$ |
| α-Galactosidase A (e.g., GenBank Accession No. NM000169: SEQ ID NO. 28) | 1-deoxygalactonojirimycin (DGJ) α-allo-homonojirimycin α-galacto-homonojirimycin β-1-C-butyl-deoxynojirimycin calystegines $A_2$ and $B_2$ N-methyl calystegines $A_2$ and $B_2$ |
| Acid β-Galactosidase (e.g., GenBank Accession No. M34423: SEQ ID NO. 29) | 4-epi-isofagomine 1-deoxygalactonojirimyicn |
| Galactocerebrosidase (Acid β-Galactosidase) (e.g., GenBank Accession No. D25283: SEQ ID NO. 30) | 4-epi-isofagomine 1-deoxygalactonojirimycin |
| Acid α-Mannosidase (e.g., GenBank Accession No. U68567: SEQ ID NO. 31) | 1-deoxymannojirimycin Swainsonine Mannostatin A |
| Acid β-Mannosidase (e.g., GenBank Accession No. U60337: SEQ ID NO. 32) | 2-hydroxy-isofagomine |
| Acid α-L-fucosidase (e.g., GenBank Accession No. NM000147: SEQ ID NO. 33) | 1-deoxyfuconojirimycin β-homofuconojirimycin 2,5-imino-1,2,5-trideoxy-L-glucol 2,5-deoxy-2,5-imino-D-fucitol 2,5-imino-1,2,5-trideoxy-D-altritol |
| α-N-Acetylglucosaminidase (e.g., GenBank Accession No. U40846: | 1,2-dideoxy 2-N-acetamido-nojirimycin |

TABLE 11-continued

Lysosomal enzymes and corresponding pharmacological chaperones. (Exemplary amino acid sequences of the lysosomal enzymes referenced by SEQ ID NOs. are shown in the Sequence Listing)

| LYSOSOMAL ENZYME | SPECIFIC PHARMACOLOGICAL CHAPERONE |
|---|---|
| SEQ ID NO. 34) | |
| α-N-Acetylgalactosaminidase (e.g., GenBank Accession No. M62783: SEQ ID NO. 35) | 1,2-dideoxy 2-N-acetamido-galactonojirimycin |
| β-Hexosaminidase A (e.g., GenBank Accession No. NM000520: SEQ ID NO. 36) | 2-N-acetylamino-isofagomine 1,2-dideoxy-2-acetamido-nojirimycin nagstatin |
| β-Hexosaminidase B (e.g., GenBank Accession No. NM000521: SEQ ID NO. 37) | 2-N-acetamido-isofagomine 1,2-dideoxy-2-acetamido-nojirimycin nagstatin |
| α-L-Iduronidase (e.g., GenBank Accession No. NM000203: SEQ ID NO. 38) | 1-deoxyiduronojirimycin 2-carboxy-3,4,5-trideoxypiperidine |
| B-Glucuronidase (e.g., GenBank Accession No. NM000181: SEQ ID NO. 39) | 6-carboxy-isofagomine 2-carboxy-3,4,5-trideoxypiperidine |
| Sialidase (e.g., GenBank Accession No. U84246: SEQ ID NO. 40) | 2,6-dideoxy-2,6, imino-sialic acid Siastatin B |
| Iduronate sulfatase (e.g., GenBank Accession No. AF011889: SEQ ID NO. 41) | 2,5-anhydromannito1-6-sulphate |
| Acid sphingomyelinase (e.g., GenBank Accession No. M59916: SEQ ID NO. 42) | desipramine, phosphatidylinositol-4,5-diphosphate |

1. Small Molecule Agents

In some embodiments, a lysosomal activating agent is a small molecule. In some embodiments, a small molecule lysosomal activating agent increases level and/or activity of a lysosomal enzyme (including by increasing trafficking) as compared with that observed absent the agent. In some embodiments, a small molecule lysosomal activating agent reduces level and/or activity of an inhibitor of a lysosomal enzyme (including by decreasing or otherwise interfering with trafficking), as compared with that observed absent the agent. Anything that activates enzyme or activates positive regulator or inhibits negative regulator (including substrate, e.g., agents that inhibit enzymes that catalyze synthesis of substrate).

In some embodiments, a small molecule lysosomal activating agent is or comprises a sugar, for example an iminosugar (e.g., isofagomine, N-butyl-deoxynojirimycin, N-nonyl-deoxynojirimycin, conduritol-β-epoxide).

In some such embodiments, a iminosugar-based lysosomal activating agent is or comprises compound AMP-DMP or Genz-529468, or an analog thereof, for example as set forth in Ashe et al., PLoS ONE 6(6): e21758, 2011.

In some embodiments, a small molecule lysosomal activating agent is or comprises of 1-phenyl-2-decanoylamino-3-morpholino-1-propanol (PDMP). In some such embodiments, a lyososmal activating agent is or comprises compound N-((1R,2R)-1-(2,3-dihydrobenzo[b][1,4]dioxin-6-yl)-1-hydroxy-3-(pyrrolidin-1yl)propan-2-yl)octanamide (Genz-112638), or an analog thereof, for example as set forth in McEachern et al., Mol. Genetics and Metabolism 91: 259, 2007. In some such embodiments, a lyososmal activating agent is or comprises compound 2-(2,3-dihydro-1H-inden-2-yl)-1-hydroxy-3-(pyrrolidin-1-yl)propan-2-yl)acetamide (CCG-203586), or an analog thereof, for example as set forth in Larsen et al., J. Lipid Res. 53: 282, 2012.

In some embodiments, a small molecule lysosomal activating agent is or comprises a non-iminosugar compound. In some such embodiments, a lyososmal activating agent is or comprises compound EXEL-0346, or an analog thereof, for example as set forth in Richards et al., J. Med. Chem. 55: 4322, 2012.

In some embodiments, a small molecule lysosomal activating agent is or comprises a non-iminosugar compound. In some such embodiments, a lyososmal activating agent is or comprises compound ML156, or an analog thereof, for example as set forth in Marugan et al., Med. Chem. Commun. 3: 56, 2011.

In some embodiments, a small molecule lysosomal activating agent is or comprises a non-iminosugar compound. In some such embodiments, a lyososmal activating agent is or comprises compound MLS000674724, NCGC00182292, NCGC00159568, NCGC00182186, NCGC00182510, or an analog thereof, for example as set forth in Goldin et al., PLoS ONE 7(1): e29861, 2012.

In some embodiments, a small molecule lysosomal activating agent is or comprises a non-iminosugar compound. In some such embodiments, a lyososmal activating agent is or comprises compounds N-(4-methyl-2-morpholinoquinolin-6-yl)cyclohexanecarboxamide, N-(5-ethyl-1,3,4-thiadiazol-2-yl)-4-(phenylsulfonamido)benzamide, and 2-(4-(5-chloro-2-methoxyphenylamino)-6-(pyrrolidin-1-yl)-1,3,5-triazin-2-ylamino)ethanol, or an analog thereof, for example as set forth in Zheng et al., PNAS 104: 32, 2007.

In some such embodiments, a lyososmal activating agent is or comprises compounds with N4-phenyl modifications of N2-(2-hydroxyl)ethyl-6-(pyrrolidin-1-yl)-1,3,5-triazine-2,4-diamines, or an analog thereof, for example as set forth in Huang et al., Biorg. Med. Chem. Lett. 17, 2007.

In some such embodiments, a lyososmal activating agent is or comprises compounds 5-((4-methylphenyl)thio)quinazoline-2,4-diamine and 5-(3,5-dichlorophenoxy)-N-(4-pyridinyl)-2-furamide, or an analog thereof, for example as set forth in Tropak et al., ChemBioChem 9(16): 2650, 2008 and/or compounds with a quinazoline core for example as set forth in Marugan et al., J. Med. Chem. 54(4): 1033, 2011.

In some such embodiments, a lyososmal activating agent is or comprises compounds 5-((4-methylphenyl)thio)quinazoline-2,4-diamine and 5-(3,5-dichlorophenoxy)-N-(4-pyridinyl)-2-furamide, or an analog thereof, for example as set forth in Tropak et al., ChemBioChem 9(16): 2650, 2008.

In some such embodiments, a lyosomal activating agent is or comprises compounds of Formula I or II, or an analog thereof, for example as set forth in WO 2012/061597.

In some particular embodiments, a small molecule lyosomal activating agent is or comprises a substituted pyrazolopyrimidines, for example as described in Patnaik et al., J. Med. Chem., 2012, and/or Marugan et al., WO 2012/078855 incorporated herein by reference in its entirety.

In some embodiments, such a small molecule lysosomal activating agent has the structure of Formula (I):

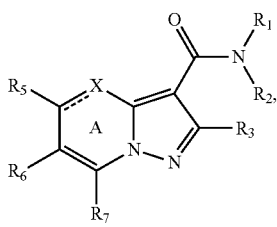

Formula (I)

wherein the ring

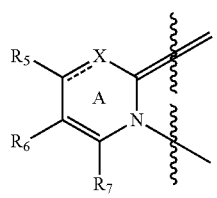

is a ring system of the formula

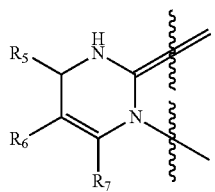

(i)

in which $R_5$ is an optionally substituted methylidene group and $R_6$ and $R_7$ carry the definitions set forth below, or

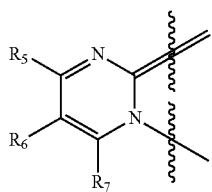

(ii)

in which $R_5$, $R_6$, and $R_7$ carry the definitions set forth below; $R_1$ is (mono- or bicyclic carbocycle) $C_0$-$C_4$ alkyl or (mono- or bicyclic heterocycle) $C_0$-$C_4$ alkyl, each of which is unsubstituted or substituted with one or more substituents independently chosen from halogen, hydroxyl, cyano, nitro, amino, —CHO, —COOH, $C_1$-$C_6$ alkyl, $C_1$-$C_6$ alkoxy, $C_2$-$C_6$ alkanoyl, mono- or di-$C_1$-$C_6$ alkylamino, mono- or di-$C_1$-$C_6$ alkylcarboxamide, $C_1$-$C_6$ alkylester, $C_1$-$C_6$ alkylthio, $C_1$-$C_6$ alkylsulfonyl, $C_1$-$C_2$ haloalkyl, and $C_1$-$C_2$ haloalkoxy, and with 0 or 1 substituents chosen from Y—Z— where Z is a covalent bond, $C_1$-$C_4$ alkylene, —S—, —O—, —NR—, —C(O)—, —NHC(O)—, or —C(O)NH—, where R is hydrogen or $C_1$-$C_4$ alkyl, and Y is phenyl or pyridyl, each of which is unsubstituted or substituted with 1 to 3 substituents independently chosen from halogen, hydroxyl, cyano, nitro, amino, $C_1$-$C_4$alkyl, $C_1$-$C_4$alkoxy, trifluoromethyl, difluoromethyl, and trifluoromethoxy; and $R_2$ is hydrogen, $C_1$-$C_6$ alkyl, $C_3$-$C_7$ cycloalkyl, (phenyl)$C_0$-$C_2$ alkyl; or $R_1$ and $R_2$ are joined to form a 5- to 7-membered heterocycloalkyl ring having 0 or 1 additional heteroatoms chosen from N, O, and S, which 5- to 7-membered heterocycloalkyl ring is optionally fused to a phenyl or pyridyl; which 5- to 7-membered heterocycloalkyl ring is unsubstituted or substituted with one or more substituents independently chosen from halogen, hydroxyl, $C_1$-$C_2$ alkyl, and $C_1$-$C_2$ alkoxy; $R_3$ is hydrogen or $C_1$-$C_2$ alkyl; $R_5$ is halogen, hydroxyl, amino, cyano, $C_1$-$C_4$ alkyl, $C_1$-$C_4$ alkoxy, difluoromethyl, trifluoromethyl, or phenyl; $R_6$ is hydrogen, halogen, hydroxyl, $C_1$-$C_4$ alkyl, or $C_1$-$C_4$ alkoxy; and $R_7$ is halogen, hydroxyl, amino, cyano, $C_1$-$C_4$ alkyl, $C_1$-$C_4$ alkoxy, difluoromethyl, or trifluoromethyl, or phenyl. In certain embodiments $R_1$ is not unsubstituted phenyl, dihydroindenyl, benzy[b][1,4]dioxolyl, benzo[d][1,3]dioxo1-5-yl, cyclohexyl, pyridyl, or phenyl substituted with 1 or 2 substituents independently chosen from chloro, fluoro, $C_1$-$C_4$ alkyl, C1-C2 alkoxy, acetyl, trifluoromethyl, when $R_6$ is hydrogen, $R_5$ and $R_7$ are both methyl, or when $R_6$ is hydrogen and one $R_5$ and $R_7$ is methyl and the other is phenyl; and $R_1$ is not 1-(4-fluorobenzyl)-1H-pyrazol-4-yl when $R_6$ is hydrogen and one $R_5$ and $R_7$ is methyl and the other is phenyl.

In some embodiments, small molecule lysosomal activating agents for use in accordance with the present invention have structures of Formulas II or III, which are subformulae of Formula I, and compounds in which the variables, e.g., $R_1$-$R_7$ carry the following definitions are also disclosed.

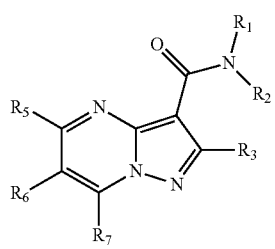

Formula II

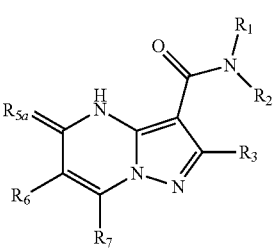

Formula III

In Formula III, $R_{5a}$ is $C_1$-$C_4$ alkylidene, $C_3$-$C_7$ cycloalkylidene, or 4- to 7-membered carbon attached heterocycloalkylidene, having 1 or 2 heteroatoms independently chosen from N, S, and O.

In certain embodiments of Formula III, $R_{5a}$ is methylidene or cyclopropylidene.

In certain embodiments of Formula I and II in which: $R_2$ is hydrogen or methyl; and $R_5$ is $C_1$-$C_4$ alkyl, difluoromethyl, or phenyl; $R_7$ is $C_1$-$C_4$ alkyl, difluoromethyl, or phenyl; and $R_5$ and $R_7$ are not both phenyl.

In certain embodiments of Formula I and II: $R_5$ and $R_7$ are both methyl; or one of $R_5$ and $R_7$ is methyl and the other is phenyl; or one of $R_5$ and $R_7$ is methyl and the other is difluoromethyl.

In certain embodiments of Formula I, II, and III: $R_1$ is (phenyl) $C_0$-$C_4$ alkyl, (pyridyl) $C_0$-$C_4$ alkyl, (pyrimidinyl) $C_0$-$C_4$ alkyl, ($C_3$-$C_7$ cycloalkyl) $C_0$-$C_4$ alkyl, (pyrazolyl) $C_0$-$C_2$ alkyl, (pyrrolyl) $C_0$-$C_2$ alkyl, (imidazolyl) $C_0$-$C_2$ alkyl, (thienyl) $C_0$-$C_2$ alkyl, (furanyl) $C_0$-$C_2$ alkyl, (oxazolyl) $C_0$-$C_2$ alkyl, (thiazolyl) $C_0$-$C_2$ alkyl, pyrrolidinyl, naphthyl, quinolinyl, isoquinolinyl, tetrahydronaphthyl, tetrahydroquinolinyl, tetrahydroisoquinolinyl, tetrahydrofuranyl, piperazinyl, morpholinyl, piperidinyl, thiomorpholinyl, dihydroindenyl, benzo[b][1,4]dioxinyl, or benzo[d][1,3]dioxolyl, each of which is unsubstituted or substituted with one or more substituents independently chosen from halogen, hydroxyl, cyano, nitro, amino, —CHO, —COOH, $C_1$-$C_6$alkyl, $C_1$-$C_6$ alkoxy, $C_2$-$C_6$ alkanoyl, mono- or di-$C_1$-$C_6$ alkylamino, mono- or di-$C_1$-$C_6$ alkylcarboxamide, $C_1$-$C_6$ alkylester, $C_1$-$C_6$ alkylthio, $C_1$-$C_6$ alkylsulfonyl, $C_1$-$C_2$ haloalkyl, and $C_1$-$C_2$haloalkoxy, and with 0 or 1 substituents chosen from Y—Z— where Z is a covalent bond, $C_1$-$C_4$ alkylene, —S—, —O—, —NR—, —C(O)—, —NHC(O)—, or —C(O)NH—, where R is hydrogen or $C_1$-$C_4$ alkyl, and Y is phenyl or pyridyl, each of which is unsubstituted or substituted with 1 to 3 substituents independently chosen from halogen, hydroxyl, cyano, nitro, amino, $C_1$-$C_4$ alkyl, and $C_1$-$C_4$ alkoxy.

In some embodiments of Formula I, II, and III: $R_1$ and $R_2$ are joined to form a 5- to 7-membered heterocycloalkyl ring having 0 or additional heteroatoms chosen from N, O, and S, which 5- to 7-membered heterocycloalkyl ring is optionally fused to a phenyl or pyridyl; which 5- to 7-membered heterocycloalkyl ring is unsubstituted or substituted with one or more substituents independently chosen from halogen, hydroxyl, $C_1$-$C_2$ alkyl, and $C_1$-$C_2$ alkoxy.

In some embodiments of Formula I, II, and III in which $R_1$ is (phenyl) $C_0$-$C_2$ alkyl, substituted with at least one substituent chosen from cyano, trifluoromethyl, $CH_3C(O)NH$—, orn $R_1$ is cyclohexyl, substituted with at least one trifluoromethyl, $C_3$-$C_6$ alkyl; or $R_1$ is dihydroindenyl, quinolinyl, or isoquinolinyl; each of which $R_1$ may be substituted with one or more substituents independently chosen from halogen, hydroxyl, cyano, nitro, amino, —CHO, —COOH, $C_1$-$C_4$ alkyl, $C_1$-$C_4$alkoxy, $C_2$-$C_4$ alkanoyl, mono- or di-$C_1$-$C_4$alkylamino, $C_1$-$C_2$haloalkyl, and $C_1$-$C_2$haloalkoxy.

In some embodiments of Formula I, II, and III in which: $R_2$ is hydrogen or methyl; and $R_7$ is $C_1$-$C_4$ alkyl, difluoromethyl, or phenyl. In some embodiments $R_7$ is difluoromethyl.

In some embodiments of Formula I, II, and III in which: $R_2$ is hydrogen or methyl; and $R_7$ is methyl or difluoromethyl; and $R_1$ is (phenyl) $C_0$-$C_2$ alkyl, (pyridyl) $C_0$-$C_2$ alkyl, (cyclohexyl) $C_0$-$C_2$ alkyl, pyrazolyl, furanylnaphthyl, quinolinyl, isoquinolinyl, tetrahydronaphthyl, tetrahydroquinolinyl, tetrahydroisoquinolinyl tetrahydrofuranyl, morpholinyl, piperidinyl, piperazinyl, thiomorpholinyl, dihydroindenyl, benzo[b][1,4]dioxinyl, or benzo[d][1,3]dioxolyl, each of which is unsubstituted or substituted with one or more substituents independently chosen from halogen, hydroxyl, cyano, nitro, amino, —CHO, —COOH, $C_1$-$C_4$ alkyl, $C_1$-$C_4$ alkoxy, $C_2$-$C_4$alkanoyl, mono- or di-$C_1$-$C_4$ alkylamino, mono- or di-$C_1$-$C_4$ alkylcarboxamide, $C_1$-$C_4$ alkylester, $C_1$-$C_2$ alkylsulfonyl, trifluoromethyl, trifluoromethoxy, and difluoromethyl, and with 0 or 1 substituents chosen from Y—Z— where Z is a covalent bond, $C_1$-$C_4$ alkylene, —S—, —O—, —NR—, —C(O)—, —NHC(O)—, or —C(O)NH—, where R is hydrogen or $C_1$-$C_4$ alkyl, and Y is phenyl or pyridyl, each of which is unsubstituted or substituted with 1 to 3 substituents independently chosen from halogen, hydroxyl, $C_1$-$C_2$ alkyl, and $C_1$-$C_2$ alkoxy.

Compounds of Formula I have the following tautomeric formulas:

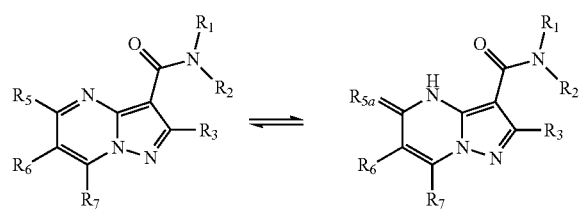

In some embodiments, compounds of Formulas I, II, and/or III may be utilized at doses within the range of about 0.1 mg to about 140 mg per kilogram of body weight per day (about 0.5 mg to about 7 g per subject per day). The amount of compound that may be combined with the carrier materials to produce a single dosage form will vary depending upon the patient treated and the particular mode of administration. Dosage unit forms will generally contain between from about 1 mg to about 500 mg of each active compound. In certain embodiments, 25 mg to 500 mg, or 25 mg to 200 mg of small molecule lysosomal activating agent of Formula I are provided daily to a patient. Frequency of dosage may also vary depending on the small molecule lysosomal activating agent used and the particular disease treated. However, for treatment of most diseases disorders, and/or conditions a dosage regimen of 4 times daily or less can be used and in certain embodiments, a dosage regimen of 1 or 2 times daily is used. In some embodiments, substituted pyrazolopyrimidine compounds are utilized at doses within the range of 10 ng/kg of body weight to about 100 mg/kg of body weight at a frequency of administration from once a day to once a month.

Small molecule lysosomal activating agents may contain one or more asymmetric elements such as stereogenic centers, stereogenic axes and the like, e.g., asymmetric carbon atoms, so that the compounds can exist in different stereoisomeric forms. Such compounds can be utilized in racemate or optically active form. In some embodiments, such compounds can be utilized as a stereoisomerically pure form. As will be appreciated by those skilled in the art, optically active forms can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column. For compounds with two or more asymmetric elements, compounds can be used as mixtures of diastereomers.

Those skilled in the art will appreciate that small molecule compounds often can be prepared in a variety of different forms (for example solvates, optical isomers, enantiomeric forms, polymorphs, free compound and salts). Any appropriate form may be utilized in accordance with the present invention.

Those of ordinary skill in the art will further appreciate that small molecule lysosomal activating agents may be provided in salt form. Examples of pharmaceutically acceptable salts include, but are not limited to, mineral or organic acid salts of basic residues such as amines; alkali or organic salts of acidic residues such as carboxylic acids; and the like. In some embodiments, pharmaceutically acceptable salts include conventional non-toxic salts and specifically include quaternary ammonium salts of a parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—(CH$_2$)n-COOH where n is 0-4, and the like. Lists of additional suitable salts may be found, e.g., in *Remington's Pharmaceutical Sciences*, 17th ed., Mack Publishing Company, Easton, Pa., p. 1418 (1985).

In some embodiments, a small molecule lysosomal activating agent is or comprises a calcium channel blocker, for example diltiazem and/or verapamil, or an analog thereof.

In some embodiments, a small molecule lysosomal activating agent is or comprises an inhibitor of RyR, for example dantrolene.

In some embodiments, a small molecule lysosomal activating agent is or comprises an antioxidant, for example n-acetyl-cysteine.

In some embodiments, small molecules that activate lysosomal GCase enzyme are particularly useful as lysosomal activating agents in accordance with the present invention. In some such embodiments, small molecules lysosomal activating agents bind to an allosteric site and activate lysosomal GCase enzyme.

2. Polypeptide Agents

In some embodiments, lysosomal activating agents for use in accordance with the present invention are or comprise polypeptides. In some such embodiments, lysosomal activating agents are or comprise antibodies or fragments thereof. In some such embodiments, lysosomal activating agents are enzymes (e.g., lysosomal enzymes). In some such embodiments, lysosomal activating agents are polypeptides that regulate level and/or activity of one or more lysosomal enzymes (including by affecting trafficking of such lysosomal enzymes).

In some embodiments, a lysosomal activating agent is or comprises a polypeptide that is and/or a nucleic acid that encodes a lysosomal enzyme. In some embodiments, a lysosomal activating agent is or comprises a polypeptide that is and/or a nucleic acid that encodes an enzyme whose activity decreases level of a substrate for a lysosomal enzyme; in some such embodiments, the lysosomal activating agent is or comprises a polypeptide that is and/or a nucleic acid that encodes a lysosomal enzyme. Those skilled in the art will appreciate that provision of lysosomal activating agents that are enzymes to subjects who lack or show a reduced level of activity for the relevant enzyme as compared with that level observed, on average, in a population of normal individuals, may be referred to, in some embodiments, as "enzyme replacement therapy". Those skilled in the art will appreciate that provision of a polypeptide lysosomal activating agent that is or comprises a polypeptide through administration of a nucleic acid encoding the polypeptide, so that level of the polypeptide is increased after such administration may be referred to as "gene therapy".

In some embodiments, a polypeptide lysosomal activating agent is or comprises a Rab polypeptide. Rab polypeptides constitute the largest branch of the Ras GTPase superfamily (Grosshans et al., PNAS 103(32): 11821, 2006). Rab polypeptides regulate each of the four major steps in membrane traffic (i.e.: vesicle budding, vesicle delivery, vesicle tethering, and fusion of the vesicle membrane with that of the target compartment) using the guanine nucleotide-dependent switch mechanism as explained above. These different activities of Rab polypeptides are regulated by a diverse collection of effector molecules that bind to specific Rabs in their GTP-bound state. Some non-limiting examples of known Rab effectors are listed in Tables 12 and 13.

TABLE 12

Yeast Rab polypeptide GTPase effectors.

| Rab GTPase | Rab Effector | Effector function |
|---|---|---|
| Sec4p | Exocyst (Sec15p) | Tethering complex; tethering of Golgi-derived vesicles to the plasma membrane (PM) |
| | Sro7p | SNARE-interacting protein; possible influence on PM SNARE function via its binding to t-SNARE Sec9p |
| Vps21p (Ypt51) | Vac1p | SM-family binding protein; required for late endosome (LE) to vacuole transport; possible influence on LE SNARE function via binding to SM-family protein Vps45p |
| Ypt1p | Sec34/35p (COG) | Tethering complex; tethering of ER-derived and intra-Golgi vesicles to the Golgi |
| | Uso1p | Coiled-coil tether; tethering of ER-derived vesicles to the Golgi; works in conjunction with the Sec34/35p complex |
| Ypt6p | GARP/VFT (Vps52p) | Tethering complex and SNARE-interacting factor; tethering of endosome-derived vesicles to the Golgi; binds to the target membrane (t)-SNARE Tlg1p |

TABLE 12-continued

Yeast Rab polypeptide GTPase effectors.

| Rab GTPase | Rab Effector | Effector function |
|---|---|---|
| Ypt7p | Class C VPS/HOPS | Tethering complex and SNARE-interacting factor; tethering of vacuolar and endosomal vesicles to vacuoles; contains SNARE-binding protein and Sec1/Mun18 (SM)-family member Vps33p |
| Ypt31/ 32p | Sec2p Rcy1p | RabGEF (of Sec4p); Rab cascade for efficient transition between vesicle formation and vesicle transport<br>SNARE-interacting protein and cargo adaptor; endosome to Golgi transport; possible influence on SNARE recycling via binding to, and regulation of, vesicle (v)-SNARE Snc1p |

TABLE 13

Mammalian Rab polypeptide GTPase effectors.

| Rab GTPase | Rab Effector | Effector function |
|---|---|---|
| Rab1a | p115, GM130<br>Giantin<br>Golgin-84<br>Iporin<br>MICAL-1,-2,-3 | Coiled-coil tethers; tethering of ER-derived and intra-Golgi vesicles to the Golgi<br>Possible recruitment of cis-Golgi tethering protein GM130<br>Cytoskeleton-interacting proteins; might link ER to Golgi and intra-Golgi transport to the intermediate filament network |
| Rab3 | Rabphilin-3<br>RIM1 & RIM2<br>Noc2 | Regulatory protein ($Ca^{2+}$- and lipid-binding); involved in docking and fusion of synaptic vesicles (exocytosis); plays a role in their endocytosis via interaction with Rabaptin5<br>Potential protein scaffolds; possible role in synaptic vesicle fusion; bind 14-3-3, which binds Rabphilin3<br>Potential negative regulation of regulated exocytosis, possibly via interactions with the cytoskeleton |
| Rab4 | Rabaptin4<br>Rabaptin5<br>Rabenosyn5<br>Rabip4<br>Rabip4'<br>CD2AP/CMS<br>RCP<br>Syntaxin4<br>KIF3 (kinesin II)<br>Dynein light chain-1 | Might stabilize Rab4 on endosomes; could act as linker between early endocytosis and recycling through its additional interaction with Rab5<br>Thought to link endocytosis to recycling via its additional interaction with Rab5 (more information see Rab5)<br>Appears to ensure fast recycling by linking endocytosis and recycling via its additional interaction with Rab5 (more information see Rab5)<br>Might regulate a retrograde [recycling endosome (RE) to early endosome (EE)] transport step<br>Appears to link endocytosis and recycling via its additional interaction with Rab5<br>Might regulate EE to LE transport; seems to control early endosome morphology through its binding to c-Cbl<br>Involved in protein recycling; could act as linker between recycling vesicles and the recycling endosome through its stronger binding to Rab11; Interaction in vivo is doubted<br>SNARE protein; t-SNARE for the fusion of GLUT4-positive vesicles to the PM<br>Motor protein; possibly required for transport of GLUT4-containing vesicles to the PM after insulin stimulation<br>Motor regulator; might be required for endocytic vesicle movement along microtubules |
| Rab5 | Rabaptin-5<br>EEA1<br>Rabenosyn-5<br>hVps34/p150<br>p85/p110β<br>Class C VPS/HOPS complex (hVps11)<br>Rabip4'<br>Rabankyrin-5<br>APPL1 and APPL2 | Increases GEF activity of Rabex-5 on Rab5 and, therefore, stabilizes active Rab5 on EE; thought to link endocytosis to recycling via its dual interaction with Rab4 and Rab5; its interaction with $\gamma_1$-adaptin and GGA might regulate fusion of Golgi-derived vesicles to endosomes<br>Interacts with Rab5-GEF Rabex5; functions in cooperation with Rabaptin5<br>Function not known<br>Coiled-coil tether and SNARE-interacting protein; tethering of EE membranes for homotypic EE fusion; possible influence on SNARE function via its interaction with t-SNAREs syntaxin 6 and syntaxin 13 |

TABLE 13-continued

Mammalian Rab polypeptide GTPase effectors.

| Rab GTPase | Rab Effector | Effector function |
|---|---|---|
|  | HAP40 | SM-family interacting protein; required for homotypic EE fusion and fusion of endocytic vesicles to the EE; possible influence on SNARE function via binding to SM-family homologue Vps45p |
|  |  | Produces PI(3)P at EE, which is required for the recruitment of diverse Rab5 effectors and for minus-end-directed motility of endosomes along microtubules p85α displays GAP activity toward Rab5 |
|  |  | Tethering complex and potential GEF (for Rab7); appears to facilitate EE to LE maturation by linking Rab5 function to Rab7 recruitment |
|  |  | Appears to link endocytosis and recycling (on the EE) via its additional interaction with Rab4 |
|  |  | Involved in macropinocytosis and homotypic, and to a smaller extent heterotypic, fusion events at the EE |
|  |  | Induce cell proliferation after transfer to the nucleus; released from EE membrane after GTP hydrolysis by Rab5 in combination with EGF signaling |
|  |  | Mediates the Rab5-dependent recruitment of Huntingtin onto EE; influences EE motility (possible switch between actin cytoskeleton and microtubules) |
| Rab6 | Rabkinesin6 (Rab6-KIFL, RB6K) Dynactin complex (p150$^{glued}$, BICD1, BICD2) TMF (ARA160) | Motor protein; kinesin-like protein required for Golgi dynamics and possibly for Golgi to ER transport Motor adaptor complex; recruitment of microtubule motor dynein onto Rab6-positive membranes (Golgi and Golgi-derived vesicles) Coiled-coil tether; Appears to be required for Golgi maintenance/organization |
| Rab7 | RILP Rabring7 ORP1L | Motor adaptor; might regulate LE to lysosome transport by recruitment of the dynein-dynactin complex required for fusion of phagosomes with LE or lysosomes Might play a role in LE to lysosome transport and in lysosomal acidification Appears to stabilize Rab7 on LE and might be involved in LE movement |
| Rab8 | Rab8ip Optineurin (FIP-2) | Potential stress-activated Ser/Thr kinase that could be involved in Golgi to PM transport Motor adaptor; recruitment of myosin-VI to Rab8-positive membranes (TGN and TGN-derived vesicles; required for the regulation of cell shape/polarity, partially via its interaction with Huntingtin |
| Rab9 | TIP47 p40 | Cargo adaptor; seems to regulate sorting of cargo into LE-derived vesicles Required for LE to Golgi transport; interacts with PIKfyve |
| Rab11 | Rabphilin11 (Rab11BP) FIP2 RCP, Exocyst (Sec15) Rip11 FIP3, FIP4 | Involved in recycling, colocalizes with Rab11 also along microtubules in HeLa cells Motor adaptor; involved in endocytosis and recycling; Possibly involved in actin-dependent recycling vesicle transport via its association with myosin-Vb Involved in recycling; could act as linker between incoming vesicles and the RE through its binding to Rab4 Tethering complex; tethering of vesicles to the plasma membrane Required for transport from RE to the apical membrane in polarized cells Required for cytokinesis; implicated in the delivery of RE's to the cleavage furrow; interact with the exocyst via Arf6 |
| Rab15 | REP15 | Might regulate exit from the RE |
| Rab27 | Melanophilin (exophilin3, Slac2-a) Granuphilin (exophilin2, Slp4) MyRIP (exophilin8, Slac2-c) Rabphilin-3 Noc2 | Motor adaptor; required for actin-dependent retention and transport of melanosomes at the melanocyte periphery via its interaction with myosin-Va SNARE-interacting protein and potential tethering factor; required for exocytosis of insulin-containing granules in pancreatic cells via its interaction with t-SNARE syntaxin1A Motor adaptor; regulates retinal melanosome transport via its interaction with myosin-VIIa Required for dense-core vesicle exocytosis (compare to Rab3) |

TABLE 13-continued

Mammalian Rab polypeptide GTPase effectors.

| Rab GTPase | Rab Effector | Effector function |
|---|---|---|
| | Munc13-4 | SNARE-interacting protein; positive influence on dense core granule exocytosis; possible function in SNARE regulation (SM-family member) Regulates melanosome distribution in meanocytes Functions are not clear |
| | Slp2-a | |
| | Slp1,3,5; Slac2-b | |
| Rab34 | RILP | Appears to regulate the intracellular localization and morphology of lysosomes |

In some particular embodiments, a polypeptide lysosomal activating agent comprises guanine nucleotide exchange factors. Some non-limiting examples of guanine nucleotide exchange factors are GEFs and/or GAPs.

Rab polypeptides also undergo a membrane insertion and extraction cycle, which is partially coupled to the nucleotide cycle. Membrane insertion requires the irreversible modification of two carboxyl-terminal cysteines with isoprenyl lipid (geranylgeranyl) moieties. A protein called GDP dissociation inhibitor (GDI) binds to prenylated Rab polypeptides in their GDP-bound form, masking their isoprenyl anchor and thereby maintaining the Rab polypeptide in the cytosol. Membrane attachment of Rab polypeptides therefore requires the function of a GDI displacement factor (GDF). Once dissociated from GDI the Rab polypeptides are available for GEF-stimulated GTP binding. The active, membrane-bound Rab polypeptides are then able to fulfill their various functions in membrane traffic by binding to their specific effectors. After inactivation by their specific GAPs, the GDP-bound Rab polypeptides can be extracted from the membrane by GDI and recycled back to the cytosol.

In some particular embodiments, a polypeptide lysosomal activating agent comprises GDIs and/or GDFs In some embodiments, a polypeptide lysosomal activating agent comprises an effector of Rab polypeptide.

In some particular embodiments, a polypeptide lysosomal activating agent is or comprises Rab1a polypeptide.

In some particular embodiments, a polypeptide lysosomal activating agent activates lysosomal hydrolases involved in the metabolism of various sphingolipids. In some such embodiments, the lysosomal activating agent is or comprises saposin polypeptide. In some such embodiments, the saposin polypeptide is or comprises saposin C polypeptide.

3. Nucleic Acid Agents

In some embodiments, lysosomal activating agents for use in accordance with the present invention are or comprise nucleic acids. In some such embodiments, lysosomal activating agents are or comprise RNA and/or DNA. In some such embodiments, lysosomal activating agents are or comprise RNAi agents (for example, miRNAs, siRNAs, shRNAs, antisense oligonucleotides, ribozymes), and/or gene therapy vectors.

RNA interference or RNAi refers to sequence-specific inhibition of gene expression and/or reduction in target RNA levels mediated by an at least partly double-stranded RNA, which RNA comprises a portion that is substantially complementary to a target RNA. Typically, at least part of the substantially complementary portion is within the double stranded region of the RNA. In some embodiments, RNAi can occur via selective intracellular degradation of RNA. In some embodiments, RNAi can occur by translational repression.

An RNAi agent is an RNA, optionally including one or more nucleotide analogs or modifications, having a structure characteristic of molecules that can mediate inhibition of gene expression through an RNAi mechanism. In some embodiments, RNAi agents mediate inhibition of gene expression by causing degradation of target transcripts. In some embodiments, RNAi agents mediate inhibition of gene expression by inhibiting translation of target transcripts. Generally, an RNAi agent includes a portion that is substantially complementary to a target RNA. In some embodiments, RNAi agents are at least partly double-stranded. In some embodiments, RNAi agents are single-stranded. In some embodiments, exemplary RNAi agents can include siRNA, shRNA, and/or miRNA. In some embodiments, RNAi agents may be composed entirely of natural RNA nucleotides (i.e., adenine, guanine, cytosine, and uracil). In some embodiments, RNAi agents may include one or more non-natural RNA nucleotides (e.g., nucleotide analogs, DNA nucleotides, etc.). Inclusion of non-natural RNA nucleic acid residues may be used to make the RNAi agent more resistant to cellular degradation than RNA. In some embodiments, the term "RNAi agent" may refer to any RNA, RNA derivative, and/or nucleic acid encoding an RNA that induces an RNAi effect (e.g., degradation of target RNA and/or inhibition of translation). In some embodiments, an RNAi agent may comprise a blunt-ended (i.e., without overhangs) dsRNA that can act as a Dicer substrate. For example, such an RNAi agent may comprise a blunt-ended dsRNA which is ≥25 base pairs length, which may optionally be chemically modified to abrogate an immune response.

The terms microRNA or miRNA refer to an RNAi agent that is approximately 21-23 nucleotides (nt) in length. miRNAs can range between 18-26 nucleotides in length. Typically, miRNAs are single-stranded. However, in some embodiments, miRNAs may be at least partially double-stranded. In certain embodiments, miRNAs may comprise an RNA duplex (referred to herein as a "duplex region") and may optionally further comprises one or two single-stranded overhangs. In some embodiments, an RNAi agents comprises a duplex region ranging from 15 to 29 bp in length and optionally further comprising one or two single-stranded overhangs. An miRNA may be formed from two RNA molecules that hybridize together, or may alternatively be generated from a single RNA molecule that includes a self-hybridizing portion. In general, free 5' ends of miRNA molecules have phosphate groups, and free 3' ends have hydroxyl groups. The duplex portion of an miRNA usually, but does not necessarily, comprise one or more bulges consisting of one or more unpaired nucleotides. One strand of an miRNA includes a portion that hybridizes with a target RNA. In certain embodiments of the invention, one strand of the miRNA is not precisely complementary with a region of the target RNA, meaning that the miRNA hybridizes to the target RNA with one or more mismatches. In other embodiments of the invention, one strand of the miRNA is precisely complementary with a region of the target RNA, meaning that the miRNA hybridizes to the target RNA with no mismatches. Typically, miRNAs are thought to mediate inhibition of gene expression by inhibiting translation of target transcripts. However, in some embodiments, miRNAs may mediate inhibition of gene expression by causing degradation of target transcripts.

The term "short, interfering RNA" (or "siRNA") refers to an RNAi agent comprising an RNA duplex (referred to herein as a "duplex region") that is approximately 19 basepairs (bp) in length and optionally further comprises one or two single-stranded overhangs. In some embodiments, an RNAi agents comprises a duplex region ranging from 15 to 29 bp in length and optionally further comprising one or two single-stranded overhangs. An siRNA may be formed from two RNA molecules that hybridize together, or may alternatively be generated from a single RNA molecule that includes a self-hybridizing portion. In general, free 5' ends of siRNA molecules have phosphate groups, and free 3' ends have hydroxyl groups. The duplex portion of an siRNA may, but typically does not, comprise one or more bulges consisting of one or more unpaired nucleotides. One strand of an siRNA includes a portion that hybridizes with a target RNA. In certain embodiments of the invention, one strand of the siRNA is precisely complementary with a region of the target RNA, meaning that the siRNA hybridizes to the target RNA without a single mismatch. In other embodiments of the invention one or more mismatches between the siRNA and the targeted portion of the target RNA may exist. In some embodiments of the invention in which perfect complementarity is not achieved, any mismatches are generally located at or near the siRNA termini. In some embodiments, siRNAs mediate inhibition of gene expression by causing degradation of target transcripts.

The term "short hairpin RNA" (or "shRNA") refers to an RNAi agent comprising an RNA having at least two complementary portions hybridized or capable of hybridizing to form a double-stranded (duplex) structure sufficiently long to mediate RNAi (typically at least approximately 19 bp in length), and at least one single-stranded portion, typically ranging between approximately 1 and 10 nucleotides (nt) in length that forms a loop. In some embodiments, an shRNA comprises a duplex portion ranging from 15 to 29 bp in length and at least one single-stranded portion, typically ranging between approximately 1 and 10 nt in length that forms a loop. The duplex portion may, but typically does not, comprise one or more bulges consisting of one or more unpaired nucleotides. In some embodiments, siRNAs mediate inhibition of gene expression by causing degradation of target transcripts. shRNAs are thought to be processed into siRNAs by the conserved cellular RNAi machinery. Thus shRNAs may be precursors of siRNAs. Regardless, siRNAs in general are capable of inhibiting expression of a target RNA, similar to siRNAs.

Certain nucleic acid molecules referred to as ribozymes or deoxyribozymes have been shown to catalyze the sequence-specific cleavage of RNA molecules. The cleavage site is determined by complementary pairing of nucleotides in the RNA or DNA enzyme with nucleotides in the target RNA. Thus, RNA and DNA enzymes can be designed to cleave to any RNA molecule, thereby increasing its rate of degradation (Cotten et al, EMBO J. 8: 3861, 1989; Usman et al., Nucl. Acids Mol. Biol. 10: 243, 1996; Usman, et al., Curr. Opin. Struct. Biol. 1: 527, 1996; Sun, et al., Pharmacol. Rev., 52: 325, 2000. See also e.g., Cotten et al, EMBO J. 8: 3861, 1989).

In some embodiments, nucleic acid lysosomal activating agents for use in accordance with the present invention have a nucleotide sequence that corresponds to or hybridizes with a portion of a polynucleotide that encodes a lysosomal enzyme. In some embodiments, nucleic acid lysosomal activating agents for use in accordance with the present invention have a nucleotide sequence that includes a binding site for a gene expression regulator that controls expression of a lysosomal enzyme or regulator thereof.

Pharmaceutical Compositions

As will be appreciated by those skilled in the art, lysosomal activating agents are typically utilized in accordance with the present invention as part of a pharmaceutical composition formulated for delivery by an appropriate route, and/or comprising a single unit dose of a lysosomal activating agent for use in a therapeutic regimen (e.g., that is correlated with a particular biological effect or result).

A pharmaceutical composition for use in accordance with the present invention may be formulated for a particular intended mode of administration and/or therapeutic application. Such compositions can include, depending on the formulation desired, one or more pharmaceutically-acceptable, non-toxic carriers or diluents, which are defined as vehicles commonly used to formulate pharmaceutical compositions for animal or human administration. Typically, a diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

In some embodiments, pharmaceutical compositions for use in accordance with the present invention comprise at least one lysosomal activating agent and at least one pharmaceutically acceptable excipient. Such pharmaceutical compositions may optionally comprise and/or be administered in combination with one or more additional therapeutically active substances. In some embodiments, provided pharmaceutical compositions are useful in medicine. In some embodiments, provided pharmaceutical compositions are useful as prophylactic agents in the treatment or prevention of proteionpathies. In some embodiments, provided pharmaceutical compositions are useful in therapeutic applications, for example in individuals suffering from PD. In some embodiments, pharmaceutical compositions are formulated for administration to humans.

As described herein, pharmaceutical compositions of the present invention may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream or foam; sublingually; ocularly; transdermally; or nasally, pulmonary and to other mucosal surfaces.

Pharmaceutically acceptable salts of lysosomal activating agents described herein include, conventional nontoxic salts or quaternary ammonium salts of a compound, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In certain embodiments, described lysosomal activating agents may contain one or more acidic functional groups and, thus, are capable of forming pharmaceutically-acceptable salts with pharmaceutically-acceptable bases. These salts can likewise be prepared in situ in the administration vehicle or the dosage form manufacturing process, or by separately reacting a purified compound (e.g., a small molecule Lysosomal activating agent) in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in certain embodiments of pharmaceutical compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations for use in accordance with the present invention include those suitable for oral, nasal, topical (including buccal and sublingual), rectal, vaginal and/or parenteral administration. The formulations may conveniently be presented in unit dosage form and may be prepared by any methods well known in the art of pharmacy.

The amount of active ingredient combined with a carrier material to produce a single dosage form can vary depending upon the host being treated, and the particular mode of administration. The amount of active ingredient that can be combined with a carrier material to produce a single dosage form will generally be that amount of the lysosomal activating agent, which produces a therapeutic effect when administered according to an appropriate therapeutic regimen. Generally, this amount will constitute a weight percent of the total pharmaceutical compositions that is within a range from about 1% to about 99% of active ingredient in the composition, preferably from about 5% to about 70%, most preferably from about 10% to about 30%.

In certain embodiments, a formulation as described herein comprises an excipient selected from the group consisting of cyclodextrins, liposomes, micelle forming agents, e.g., bile acids, and polymeric carriers, e.g., polyesters and polyanhydrides; and a lysosomal activating agent of the present invention. In certain embodiments, an aforementioned formulation renders orally bioavailable a described lysosomal activating agent of the present invention.

Pharmaceutical compositions may comprise a pharmaceutically acceptable excipient, which, as used herein, may be or comprise solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's The Science and Practice of Pharmacy, 21st Edition, A. R. Gennaro, (Lippincott, Williams & Wilkins, Baltimore, Md., 2006) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention.

Methods of preparing formulations or compositions comprising described lysosomal activating agents typically include a step of bringing into association a lysosomal activating agent of the present invention with a carrier and, optionally, one or more accessory ingredients. In many embodiments, formulations may be prepared by uniformly and intimately bringing into association a lysosomal activating agent of the present invention with liquid carriers, or finely divided solid carriers, or both, and then, if necessary, shaping a product.

Formulations described herein suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a lysosomal activating agent of the present invention as an active ingredient. Lysosomal activating agents described herein may also be administered as a bolus, electuary or paste.

In solid dosage forms for oral administration (capsules, tablets, pills, dragees, powders, granules and the like), an active ingredient is mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol, glycerol monostearate, and non-ionic surfactants; absorbents, such as kaolin and bentonite clay; lubricants, such as talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

Tablets may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made in a suitable machine in which a mixture of the powdered lysosomal activating agent is moistened with an inert liquid diluent.

Tablets and other solid dosage forms, such as dragees, capsules, pills and granules, may optionally be scored or prepared with coatings and shells, such as enteric coatings and other coatings well known in the pharmaceutical-formulating art. They may alternatively or additionally be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of lysosomal activating agents of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, oral compositions can also include adjuvants such as wetting agents, emulsifying and suspending agents, sweetening, flavoring, coloring, perfuming and preservative agents.

Suspensions, in addition to active lysosomal activating agents, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more lysosomal activating agents of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active lysosomal activating agent.

Dosage forms for topical or transdermal administration of a lysosomal activating agent of this invention include powders, sprays, ointments, pastes, creams, lotions, gels, solutions, patches, and inhalants. The active lysosomal activating agent may be mixed under sterile conditions with a pharmaceutically-acceptable carrier, and with any preservatives, buffers, or propellants which may be required.

Ointment, paste, cream and gel compositions may contain, in addition to an active lysosomal activating agent of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powder and spray compositions can contain, in addition to a lysosomal activating agent of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a lysosomal activating agent of the present invention to the body. Dissolving or dispersing the compound in the proper medium can make such dosage forms. Absorption enhancers can also be used to increase the flux of the lysosomal activating agent across the skin. Either providing a rate controlling membrane or dispersing the lysosomal activating agent in a polymer matrix or gel can control the rate of such flux.

Examples of suitable aqueous and nonaqueous carriers, which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Such compositions may also contain adjuvants such as preservatives, wetting agents, emulsifying agents and dispersing agents. Inclusion of one or more antibacterial and/or and antifungal agents, for example, paraben, chlorobutanol, phenol sorbic acid, and the like, may be desirable in certain embodiments. It may alternatively or additionally be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it may be desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the described lysosomal activating agents in biodegradable polymers such as polylactide-polyglycolide.

Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

In certain embodiments, a described lysosomal activating agent or pharmaceutical preparation is administered orally. In other embodiments, a described lysosomal activating agent or pharmaceutical preparation is administered intravenously. Alternative routs of administration include sublingual, intramuscular, and transdermal administrations.

When lysosomal activating agents described herein are administered as pharmaceuticals, to humans and animals, they can be given per se or as a pharmaceutical composition containing, for example, 0.1% to 99.5% (more preferably, 0.5% to 90%) of active ingredient in combination with a pharmaceutically acceptable carrier.

Preparations described herein may be given orally, parenterally, topically, or rectally. They are of course given in forms suitable for the relevant administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

Such lysosomal activating agents may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, lysosomal activating agents described herein which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of the invention may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular lysosomal activating agent of the present invention employed, or the ester, salt or amide thereof, the route of administration, the time of administration, the rate of excretion or metabolism of the particular lysosomal activating agent being employed, the duration of the treatment, other drugs, compounds and/or materials used in combination with the particular lysosomal activating agent employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of described compounds employed in the pharmaceutical composition at levels lower than that required to achieve the desired therapeutic effect and then gradually increasing the dosage until the desired effect is achieved.

In some embodiments, one or more described lysosomal activating agents, or pharmaceutical compositions thereof, is provided to a proteinopathic subject chronically. Chronic treatments include any form of repeated administration for an extended period of time, such as repeated administrations for one or more months, between a month and a year, one or more years, or longer. In many embodiments, chronic treatment involves administering one or more described lysosomal activating agents, or pharmaceutical compositions thereof, repeatedly over the life of the subject. Preferred chronic treatments involve regular administrations, for example one or more times a day, one or more times a week, or one or more times a month. In general, a suitable dose such as a daily dose of one or more described lysosomal activating agents, or pharmaceutical compositions thereof, will be that amount of the one or more described lysosomal activating agent that is the lowest dose effective to produce a therapeutic effect. Such an effective dose will generally depend upon the factors described above. Generally doses of the lysosomal activating agents of this invention for a patient, when used for the indicated effects, will range from about 0.0001 to about 100 mg per kg of body weight per day. Preferably, the daily dosage will range from 0.001 to 50 mg of compound per kg of body weight, and even more preferably from 0.01 to 10 mg of compound per kg of body weight. However, lower or higher doses can be used. In some embodiments, the dose administered to a subject may be modified as the physiology of the subject changes due to age, disease progression, weight, or other factors.

If desired, the effective daily dose of one or more described lysosomal activating agents may be administered as two, three, four, five, six, or more sub-doses administered separately at appropriate intervals throughout the day, optionally, in unit dosage forms.

While it is possible for a described lysosomal activating agent to be administered alone, it is preferable to administer a described compound as a pharmaceutical formulation (composition) as described above.

Described lysosomal activating agents may be formulated for administration in any convenient way for use in human or veterinary medicine, by analogy with other pharmaceuticals.

According to the invention, described lysosomal activating agent for treating neurological conditions or diseases can be formulated or administered using methods that help the lysosomal activating agents cross the blood-brain barrier (BBB). The vertebrate brain (and CNS) has a unique capillary system unlike that in any other organ in the body. The unique capillary system has morphologic characteristics which make up the blood-brain barrier (BBB). The blood-brain barrier acts as a system-wide cellular membrane that separates the brain interstitial space from the blood.

The unique morphologic characteristics of the brain capillaries that make up the BBB are: (a) epithelial-like high resistance tight junctions which literally cement all endothelia of brain capillaries together, and (b) scanty pinocytosis or transendothelial channels, which are abundant in endothelia of peripheral organs. Due to the unique characteristics of the blood-brain barrier, hydrophilic drugs and peptides that readily gain access to other tissues in the body are barred from entry into the brain or their rates of entry and/or accumulation in the brain are very low.

In one aspect of the invention, described lysosomal activating agents that cross the BBB are particularly useful for treating proteinopathies. In one embodiment, described compounds that cross the BBB are particularly useful for treating Parkinson's Disease (PD). Therefore it will be appreciated by a person of ordinary skill in the art that some of the lysosomal activating agent of the invention might readily cross the BBB. Alternatively, the lysosomal activating agents of the invention can be modified, for example, by the addition of various substituents that would make them less hydrophilic and allow them to more readily cross the BBB.

Various strategies have been developed for introducing those drugs into the brain which otherwise would not cross the blood-brain barrier. Widely used strategies involve invasive procedures where the drug is delivered directly into the brain. One such procedure is the implantation of a catheter into the ventricular system to bypass the blood-brain barrier and deliver the drug directly to the brain. These procedures have been used in the treatment of brain diseases which have a predilection for the meninges, e.g., leukemic involvement of the brain (see U.S. Pat. No. 4,902,505).

Although invasive procedures for the direct delivery of drugs to the brain ventricles have experienced some success, they are limited in that they may only distribute the drug to superficial areas of the brain tissues, and not to the structures deep within the brain. Further, the invasive procedures are potentially harmful to the patient.

Other approaches to circumventing the blood-brain barrier utilize pharmacologic-based procedures involving drug latentiation or the conversion of hydrophilic drugs into lipid-soluble drugs. The majority of the latentiation approaches involve blocking the hydroxyl, carboxyl and primary amine groups on the drug to make it more lipid-soluble and therefore more easily able to cross the blood-brain barrier.

Another approach to increasing the permeability of the BBB to drugs involves the intra-arterial infusion of hypertonic substances which transiently open the blood-brain barrier to allow passage of hydrophilic drugs. However, hypertonic substances are potentially toxic and may damage the blood-brain barrier.

Antibodies are another method for delivery of compositions of the invention. For example, an antibody that is reactive with a transferrin receptor present on a brain capillary endothelial cell, can be conjugated to a neuropharmaceutical agent to produce an antibody-neuropharmaceutical agent conjugate (see U.S. Pat. No. 5,004,697). Such methods are conducted under conditions whereby the antibody binds to the transferrin receptor on the brain capillary endothelial cell and the neuropharmaceutical agent is transferred across the blood brain barrier in a pharmaceutically active form. The uptake or transport of antibodies into the brain can also be greatly increased by cationizing the antibodies to form cationized antibodies having an isoelectric point of between about 8.0 to 11.0 (see U.S. Pat. No. 5,527,527).

A ligand-neuropharmaceutical agent fusion protein is another method useful for delivery of compositions to a host (see U.S. Pat. No. 5,977,307). The ligand is reactive with a brain capillary endothelial cell receptor. The method is conducted under conditions whereby the ligand binds to the receptor on a brain capillary endothelial cell and the neuropharmaceutical agent is transferred across the blood brain barrier in a pharmaceutically active form. In some embodiments, a ligand-neuropharmaceutical agent fusion protein, which has both ligand binding and neuropharmaceutical characteristics, can be produced as a contiguous protein by using genetic engineering techniques. Gene constructs can be prepared comprising DNA encoding the ligand fused to DNA encoding the protein, polypeptide or peptide to be delivered across the blood brain barrier. The ligand coding sequence and the agent coding sequence are inserted in the expression vectors in a suitable manner for proper expression of the desired fusion protein. The gene fusion is expressed as a contiguous protein molecule containing both a ligand portion and a neuropharmaceutical agent portion.

The permeability of the blood brain barrier can be increased by administering a blood brain barrier agonist, for example bradykinin (see U.S. Pat. No. 5,112,596), or polypeptides called receptor mediated permeabilizers (RMP) (see U.S. Pat. No. 5,268,164). Exogenous molecules can be administered to the host's bloodstream parenterally by subcutaneous, intravenous or intramuscular injection or by absorption through a bodily tissue, such as the digestive tract, the respiratory system or the skin. The form in which the molecule is administered (e.g., capsule, tablet, solution, emulsion) depends, at least in part, on the route by which it is administered. The administration of the exogenous molecule to the host's bloodstream and the intravenous injection of the agonist of blood-brain barrier permeability can occur simultaneously or sequentially in time. For example, a therapeutic drug can be administered orally in tablet form while the intravenous administration of an agonist of blood-brain barrier permeability is given later (e.g., between 30 minutes later and several hours later). This allows time for the drug to be absorbed in the gastrointestinal tract and taken up by the bloodstream before the agonist is given to increase the permeability of the blood-brain barrier to the drug. On the other hand, an agonist of blood-brain barrier permeability (e.g., bradykinin) can be administered before or at the same time as an intravenous injection of a drug. Thus, the term "co-administration" is used herein to mean that the agonist of blood-brain barrier and the exogenous molecule will be administered at times that will achieve significant concentrations in the blood for producing the simultaneous effects of increasing the permeability of the blood-brain barrier and allowing the maximum passage of the exogenous molecule from the blood to the cells of the central nervous system.

In some embodiments, a described lysosomal activating agent can be formulated as a prodrug with a fatty acid carrier (and optionally with another neuroactive drug). The prodrug is stable in the environment of both the stomach and the bloodstream and may be delivered by ingestion. The prodrug passes readily through the blood brain barrier. The prodrug preferably has a brain penetration index of at least two times the brain penetration index of the drug alone. Once in the central nervous system, the prodrug, which preferably is inactive, is hydrolyzed into the fatty acid carrier and a described compound or analog thereof (and optionally another drug). The carrier preferably is a normal component of the central nervous system and is inactive and harmless. The lysosomal activating agent and/or drug, once released from the fatty acid carrier, is active. Preferably, the fatty acid carrier is a partially-saturated straight chain molecule having between about 16 and 26 carbon atoms, and more preferably 20 and 24 carbon atoms. Examples of fatty acid carriers are provided in U.S. Pat. Nos. 4,939,174; 4,933,324; 5,994,932; 6,107,499; 6,258,836; and 6,407,137.

Administration of agents of the present invention may be for either prophylactic or therapeutic purposes. When provided prophylactically, the lysosomal activating agent is provided in advance of disease symptoms. The prophylactic administration of the agent serves to prevent or reduce the rate of onset of symptoms of for example, Parkinson's disease (including idiopathic Parkinson's disease (PD)), Diffuse Lewy Body Disease (DLBD) also known as Dementia with Lewy Bodies (DLB), Combined Alzheimer's and Parkinson disease and multiple system atrophy (MSA). When provided therapeutically, the lysosomal activating agent is provided at (or shortly after) the onset of the appearance of symptoms of actual disease. In some embodiments, the therapeutic administration of the lysosomal activating agent serves to reduce the severity and duration of the disease.

In some embodiments pharmaceutical compositions can include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes). Additionally, these carriers can function as immunostimulating agents (i.e., adjuvants).

For parenteral administration, lysosomal activating agents of the invention can be administered as injectable dosages of a solution or suspension of the substance in a physiologically acceptable diluent with a pharmaceutical carrier that can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions. Antibodies can be administered in the form of a depot injection or implant preparation which can be formulated in such a manner as to permit a sustained release of the active ingredient. An exemplary composition comprises monoclonal antibody at 5 mg/mL, formulated in aqueous buffer consisting of 50 mM L-histidine, 150 mM NaCl, adjusted to pH 6.0 with HCl. Compositions for parenteral administration are typically substantially sterile, substantially isotonic and manufactured under GMP conditions of the FDA or similar body.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above (see Langer, Science 249:1527, 1990) and Hanes, Advanced Drug Delivery Reviews 28: 97, 1997). The lysosomal activating agent s of this invention can be administered in the form of a depot injection or implant preparation which can be formulated in such a manner as to permit a sustained or pulsatile release of the active ingredient.

Additional formulations suitable for other modes of administration include oral, intranasal, and pulmonary formulations, suppositories, and transdermal applications. For suppositories, binders and carriers include, for example, polyalkylene glycols or triglycerides; such suppositories can be formed from mixtures containing the active ingredient in the range of 0.5% to 10%, preferably 1%-2%. Oral formulations include excipients, such as pharmaceutical grades of mannitol, lactose, starch, magnesium stearate, sodium saccharine, cellulose, and magnesium carbonate. These compositions take the form of solutions, suspensions, tablets, pills, capsules, sustained release formulations or powders and contain 10%-95% of active ingredient, preferably 25%-70%.

Topical application can result in transdermal or intradermal delivery. Topical administration can be facilitated by co-administration of the lysosomal activating agent with cholera toxin or detoxified derivatives or subunits thereof or other similar bacterial toxins (See Glenn et al., Nature 391:851, 1998). Co-administration can be achieved by using the components as a mixture or as linked molecules obtained by chemical crosslinking or expression as a fusion protein. Alternatively, transdermal delivery can be achieved using a skin path or using transferosomes (Paul et al., Eur. J. Immunol. 25: 3521, 1995; Cevc et al., Biochem. Biophys. Acta 1368: 201, 1998).

In some embodiments, pharmaceutical compositions are provided in a form that can be refrigerated and/or frozen. In some embodiments, pharmaceutical compositions are provided in a form that cannot be refrigerated and/or frozen. In some embodiments, reconstituted solutions and/or liquid dosage forms may be stored for a certain period of time after reconstitution (e.g., 2 hours, 12 hours, 24 hours, 2 days, 5 days, 7 days, 10 days, 2 weeks, a month, two months, or longer).

Liquid dosage forms and/or reconstituted solutions may comprise particulate matter and/or discoloration prior to administration. In some embodiments, a solution should not be used if discolored or cloudy and/or if particulate matter remains after filtration.

In some embodiments, inventive compositions are administered using a device that delivers a metered dosage of composition.

Suitable devices for use in delivering intradermal pharmaceutical compositions described herein include short needle devices such as those described in U.S. Pat. No. 4,886,499, U.S. Pat. No. 5,190,521, U.S. Pat. No. 5,328,483, U.S. Pat. No. 5,527,288, U.S. Pat. No. 4,270,537, U.S. Pat. No. 5,015,235, U.S. Pat. No. 5,141,496, U.S. Pat. No. 5,417,662. Intradermal compositions may also be administered by devices which limit the effective penetration length of a needle into the skin, such as those described in WO99/34850, incorporated herein by reference, and functional equivalents thereof. Also suitable are jet injection devices which deliver liquid compositions to the dermis via a liquid jet injector or via a needle which pierces the stratum corneum and produces a jet which reaches the dermis. Jet injection devices are described for example in U.S. Pat. No. 5,480,381, U.S. Pat. No. 5,599,302, U.S. Pat. No. 5,334,144, U.S. Pat. No. 5,993,412, U.S. Pat. No. 5,649,912, U.S. Pat. No. 5,569,189, U.S. Pat. No. 5,704,911, U.S. Pat. No. 5,383,851, U.S. Pat. No. 5,893,397, U.S. Pat. No. 5,466,220, U.S. Pat. No. 5,339,163, U.S. Pat. No. 5,312,335, U.S. Pat. No. 5,503,627, U.S. Pat. No. 5,064,413, U.S. Pat. No. 5,520,639, U.S. Pat. No. 4,596,556, U.S. Pat. No. 4,790,824, U.S. Pat. No. 4,941,880, U.S. Pat. No. 4,940,460, WO 97/37705 and WO 97/13537. Also suitable are ballistic powder/particle delivery devices which use compressed gas to accelerate compositions in powder form through the outer layers of the skin to the dermis. Additionally, conventional syringes may be used in the classical mantoux method of intradermal administration.

Pharmaceutical compositions in accordance with the present invention are provided in a formulation and/or format appropriate for the relevant active pharmaceutical agent and/or route of delivery. Established formats and formulations for particular classes of agents are known in the art.

For example, nucleic acid agents (e.g., gene therapy agents, RNAi agents, etc) may be provided in or with a nucleic acid vector system, and/or cationic polymers; various peptide molecular transporters including arginine-rich peptides, histidine-rich peptides, and cationic and neutral lipids; various non-cationic polymers; liposomes; carbohydrates; and surfactant materials (see, for example, US Publications 2002/0150626 and 2004/242518; and U.S. Pat. Nos. 5,574,142, 5,925,628, 6,383,814, 6,410,517, 7,101,995 and 7,109,173).

As used herein, "vector" refers to a nucleic acid molecule capable of mediating entry of (e.g., transferring, transporting, etc.) a second nucleic acid molecule into a cell. The transferred nucleic acid is generally linked to (e.g., inserted into) the vector nucleic acid molecule. A vector may include sequences that direct autonomous replication, or may include sequences sufficient to allow integration into cellular DNA. Useful vectors include, for example, plasmids (typically DNA molecules although RNA plasmids are known), cosmids, and viral vectors. As is well known in the art, the term "viral vector" may refer either to a nucleic acid molecule (e.g., a plasmid) that includes virus-derived nucleic acid elements that typically facilitate transfer or integration of the nucleic acid molecule (examples include retroviral or lentiviral vectors) or to a virus or viral particle that mediates nucleic acid transfer (examples include retroviruses or lentiviruses). As will be evident to one of ordinary skill in the art, viral vectors may include various viral components in addition to nucleic acid(s).

RNAi can be induced using a "RNAi-inducing vector", which refers to a vector whose presence within a cell results in production of one or more RNAs that self-hybridize or hybridize to each other to form an RNAi agent (e.g. siRNA, shRNA, and/or miRNA). In various embodiments of the invention this term encompasses plasmids, e.g., DNA vectors (whose sequence may comprise sequence elements derived from a virus), or viruses (other than naturally occurring viruses or plasmids that have not been modified by the hand of man), whose presence within a cell results in production of one or more RNAs that self-hybridize or hybridize to each other to form an RNAi agent. In general, the vector comprises a nucleic acid operably linked to expression signal(s) so that one or more RNAs that hybridize or self-hybridize to form an RNAi agent are transcribed when the vector is present within a cell. Thus the vector provides a template for intracellular synthesis of the RNA or RNAs or precursors thereof. For purposes of inducing RNAi, presence of a viral genome in a cell (e.g., following fusion of the viral envelope with the cell membrane) is considered sufficient to constitute presence of the virus within the cell. In addition, for purposes of inducing RNAi, a vector is considered to be present within a cell if it is introduced into the cell, enters the cell, or is inherited from a parental cell, regardless of whether it is subsequently modified or processed within the cell. An RNAi-inducing vector is considered to be targeted to a transcript if presence of the vector within a cell results in production of one or more RNAs that hybridize to each other or self-hybridize to form an RNAi agent that is targeted to the transcript, i.e., if presence of the vector within a cell results in production of one or more RNAi agents targeted to the transcript.

In some embodiments, pharmaceutical compositions for use in accordance with the present invention (e.g., in combination therapies) may comprise vaccine compositions. Vaccine compositions typically comprise one or more antigens and one or more adjuvants.

Combination Therapy

In some embodiments, combination therapy involves administration of two or more lysosomal activating agents.

In some embodiments, the present invention utilizes at least one lysosomal activating agent in combination with one or more other therapeutic agents, for example including medications that are currently used to treat proteinopathies, and/or to reduce one or more side-effects of the relevant proteinopathy and/or of one or more treatments therefor.

In some embodiments, a lysosomal activating agent and an additional therapeutic agent are administered together in a single pharmaceutical compositions; in some embodiments, a lysosomal activating agent and an additional therapeutic agent are administered in separate pharmaceutical compositions. In some embodiments, one or more individual dose(s) of lysosomal activating agent and other therapeutic agent is/are administered together; in some embodiments, lysosomal activating agents and other therapeutic agent are administered according to distinct therapeutic regimens.

In some embodiments, one or more individual doses of lysosomal activating agent, and/or of other therapeutic agent, is reduced in amount and/or frequency when the two agents are used in combination than when either is used alone in a reference therapeutic regimen correlated with some therapeutic benefit. Typically, a Lysosomal activating agent and/or another therapeutic agent will be used in accordance with the present invention at doses and/or exposures within the range of 50-100% of those utilized in such a reference therapeutic regimen (if one exists for the relevant agent).

As used herein, the term "combination," "combined," and related terms refers to the simultaneous or sequential administration of therapeutic agents in accordance with this invention.

Two or more agents are typically considered to be administered "in combination" when a patient or individual is simultaneously exposed to both agents. In many embodiments, two or more agents are considered to be administered "in combination" when a patient or individual simultaneously shows therapeutically relevant levels of the agents in a particular target tissue or sample (e.g., in brain, in serum, etc).

To give but a few non-limiting examples, when the proteinopathy of interest is PD, suitable agents for use in combination therapy in accordance with the present invention include, for example, levodopa, carbidopa, amantidine (SYMMETREL®), anticholinergics (trihexyphenidyl, benztropine mesylate, procyclidine, artane, cogentin), COMT (Catechol-O-methyl transferase), MAOI (monoamine oxidase inhibitors), peripheral decarboxylase inhibitors, dopamine receptor agonist, e.g., bromocriptidine (Parlodel), pergolide (Permax), ropinirol (Requip), pramipexole (Mirapex), Ergolide.

Where the proteinopathy of interest is DLBD suitable agents for use in combination therapy in accordance with the present invention include, for example, levodopa, D2-receptor antagonists, cholinesterase inhibitors.

Where the proteinopathy of interest is Niemann-Pick Type C disease suitable agents for use in combination therapy in accordance with the present invention include, for example, allopregnanolone, a low cholesterol diet, or cholesterol-lowering agents such as the statins (e.g., LIPITOR; approved for to reduce certain LDL levels and/or to reduce risk of stroke in certain populations, to be administered at doses within the range of 10-80 mg/day, with a recommended start dose of 10 or 20 mg once daily or 40 mg once daily if a large (>45%) LDL-C reduction is required, or 10 mg once daily for pediatric subjects), fibrates such as fenofibrate (LIPIDIL), niacin, ezetimibe (ZETIA), and/or binding resins such as cholestyramine (QUESTRAN).

In some embodiments, described compositions and formulations may be administered in combination with one or more treatments for Parkinson's Disease such as ACR-343, rotigotine (Schwarz), rotigotine patch (UCB), apomorphine (Amarin), apomorphine (Archimedes), AZD-3241 (Astra Zeneca), creatine (Avicena), AV-201 (Avigen), lisuride (Axxonis/Biovail), nebicapone (BIAL Group), apomorphine (Mylan), CERE-120 (Ceregene), melevodopa+carbidopa (Cita Neuropharmaceuticals), piclozotan (Daiichi), GM1 Ganglioside (Fidia Farmaceutici), Altropane (Harvard University), Fluoratec (Harvard University), fipamezole (Juvantia Pharma), istradefylline (Kyowa Hakko Kogyo), GPI-1485 (MGI GP), Neu-120 (Neurim Pharmaceuticals), NGN-9076 (NeuroGeneration Inc), NLX-P101 (Neurologix), AFQ-056 (Novartis), arundic acid (Ono/Merck & Co), COMT inhibitor (Orion), ProSavin (Oxford Biomedica), safinamide (Pharmacia & Upjohn), PYM-50028 (Phytopharm), PTX-200 (Phytix), 123I-iometopane (Research Triangle Institute), SYN-115 (Roche Holding), preladenant (Schering Plough), ST-1535 (Sigma-Tau Ind. Farm), ropinirole (SmithKline Beecham), pardoprunox (Solvay), SPN-803 (Supernus Pharmaceuticals), nitisinone (Syngenta), TAK-065 (Takeda), cell therapy (Titan Pharmaceuticals), PD gene therapy (University of Auckland/Weill Medical College), 18F-AV-133 (University of Michigan), mitoquinone/mitoquinol redox mixture (Antipodean Pharmaceuticals), 99m-Tc-tropantiol (University of Pennsylvania), apomorphine (Vectura), BIIB-014 (Vernalis Group), aplindore (Wyeth), and XP-21279 (XenoPort Inc), ABT-126 (Abbott Laboratories), pozanicline (Abbott Laboratories), MABT-5102A (AC Immune), Affitope AD-01 (AFFiRiS GmbH), Affitope AD-02 (AFFiRiS GmbH), davunetide (Allon Therapeutics Inc), nilvadipine derivative (Archer Pharmaceuticals), Anapsos (ASAC Pharmaceutical International AIE), ASP-2535 (Astellas Pharma Inc), ASP-2905 (Astellas Pharma Inc), 11C-AZD-2184 (AstraZeneca plc), 11C-AZD-2995 (AstraZeneca plc), 18F-AZD-4694 (AstraZeneca plc), AV-965 (Avera Pharmaceuticals Inc), AVN-101 (Avineuro Pharmaceuticals Inc), immune globulin intravenous (Baxter International Inc), EVP-6124 (Bayer AG), nimodipine (Bayer AG), BMS-708163 (Bristol-Myers Squibb Co), CERE-110 (Ceregene Inc), CLL-502 (CLL Pharma), CAD-106 (Cytos Biotechnology AG), mimopezil ((Debiopharm SA), DCB-AD1 (Development Centre for Biotechnology), EGb-761 ((Dr Willmar Schwabe GmbH & Co), E-2012 (Eisai Co Ltd), ACC-001 (Elan Corp plc), bapineuzumab (Elan Corp plc), ELND-006 (Elan Pharmaceuticals Inc), atomoxetine (Eli Lilly & Co), LY-2811376 (Eli Lilly & Co), LY-451395 (Eli Lilly & Co), m266 (Eli Lilly & Co), semagacestat (Eli Lilly & Co), solanezumab (Eli Lilly & Co), AZD-103 (Ellipsis Neurotherapeutics Inc), FGLL (ENKAM Pharmaceuticals A/S), EHT-0202 (ExonHit Therapeutics SA), celecoxib (GD Searle & Co), GSK-933776A (GlaxoSmithKline), rosiglitazone XR (GlaxoSmithKline plc), SB-742457 (GlaxoSmithKline), R-1578 (Hoffmann-La Roche AG), HF-0220 (Hunter-Fleming Ltd), oxiracetam (ISF Societa Per Azioni), KD-501 (Kwang Dong Pharmaceutical Co Ltd), NGX-267 (Life Science Research Israel), huperzine A (Mayo Foundation), Dimebon (Medivation Inc), MEM-1414 (Memory Pharmaceuticals Corp), MEM-3454 (Memory Pharmaceuticals Corp), MEM-63908 (Memory Pharmaceuticals Corp), MK-0249 (Merck & Co Inc), MK-0752 (Merck & Co Inc), simvastatin (Merck & Co Inc), V-950 (Merck & Co Inc), memantine (Merz & Co GmbH), neramexane (Merz & Co GmbH), Epadel (Mochida Pharmaceutical Co Ltd), 123I-MNI-330 (Molecular Neuroimaging Llc), gantenerumab (MorphoSys AG), $NIC_{5-15}$ (Mount Sinai School of Medicine), huperzine A (NeuroHitech Inc), OXIGON (New York University), NP-12 (Noscira SA), NP-61 (Noscira SA), rivastigmine (Novartis AG), ECT-AD (NsGene A/S), arundic acid (Ono Pharmaceutical Co Ltd), PF-3084014 (Pfizer Inc), PF-3654746 (Pfizer Inc), RQ-00000009 (Pfizer Inc), PYM-50028 (Phytopharm plc), Gero-46 (PN Gerolymatos SA), PBT-2 (Prana Biotechnology Ltd), PRX-03140 (Predix Pharmaceuticals Inc), Exebryl-1 (ProteoTech Inc), PF-4360365 (Rinat Neuroscience Corp), HuCAL anti-beta amyloid monoclonal antibodies (Roche AG), EVT-302 (Roche Holding AG), nilvadipine (Roskamp Institute), galantamine (Sanochemia Pharmazeutika AG), SAR-110894 (sanofi-aventis), INM-176 (Scigenic & Scigen Harvest), mimopezil (Shanghai Institute of Materia Medica of the Chinese Academy of Sciences), NEBO-178 (Stegram Pharmaceuticals), SUVN-502 (Suven Life Sciences), TAK-065 (Takeda Pharmaceutical), ispronicline (Targacept Inc), rasagiline (Teva Pharmaceutical Industries), T-817MA (Toyama Chemical), PF-4494700 (TransTech Pharma Inc), CX-717 (University of California), 18F-FDDNP (University of California Los Angeles), GTS-21 (University of Florida), 18F-AV-133 (University of Michigan), 18F-AV-45 (University of Michigan), tetrathiomolybdate (University of Michigan), 123I-IMPY (University of Pennsylvania), 18F-AV-1/ZK (University of Pennsylvania), 11C-6-Me-BTA-1 (University of Pittsburgh), 18F-6-OH-BTA-1 (University of Pittsburgh), MCD-386 (University of Toledo), leuprolide acetate implant (Voyager Pharmaceutical Corp), aleplasinin (Wyeth), begacestat (Wyeth), GSI-136 (Wyeth), NSA-789 (Wyeth), SAM-531 (Wyeth), CTS-21166 (Zapaq), and ZSET-1446 (Zenyaku Kogyo).

In some embodiments, described compositions and formulations may be administered in combination with one or more treatments for Alzheimer's disease such as ARICEPT and EXCELON.

In some embodiments, described compositions and formulations may be administered in combination with one or more treatments for motor neuronal disorders, such as AEOL-10150 (Aeolus Pharmaceuticals Inc), riluzole (Aventis Pharma AG), ALS-08 (Avicena Group Inc), creatine (Avicena Group Inc), arimoclomol (Biorex Research and Development Co), mecobalamin (Eisai Co Ltd), talampanel (Eli Lilly & Co), R-7010 (F Hoffmann-La Roche Ltd), edaravone (Mitsubishi-Tokyo Pharmaceuticals Inc), arundic acid (Ono Pharmaceutical Co Ltd), PYM-50018 (Phytopharm plc), RPI-MN (ReceptoPharm Inc), SB-509 (Sangamo BioSciences Inc), olesoxime (Trophos SA), sodium phenylbutyrate (Ucyclyd Pharma Inc), and R-pramipexole (University of Virginia).

In some embodiments, described compositions and formulations may be administered in combination with one or more calcium channel blockers, including rate-limiting agents such as verapamil and dilitiazem, and the dihydropyridine group of calcium channel blockers (Meredith et al., J of Hypertension 22: 1641, 2004). Other examples of calcium channel blockers are amlodipine, felodipine, isradipine, lacidipine, nicardipine, nifedipine, niguldipine, niludipine, nimodipine, nisoldipine, nitrendipine, nivaldipine, ryosidine, anipamil, fendiline, flunarizine, gallopamil, mibefradil, prenylamine, tiapamil, perhexyline maleate, fendiline and prenylamine and salts, esters, amides, prodrugs, or other derivatives of any of thereof.

In some embodiments, a lysosomal activating agent is used herein to treat PD and neurodegenerative diseases, disorders, and/or conditions other than lysosomal storage diseases in combination with one or more L-type $Ca^{2+}$ channel blocker.

In some embodiments, described compositions and formulations may be administered in combination with one or more inhibitors of one or more RyR including administration of a receptor antagonist and inhibiting the expression of the receptor, for example, by administering an antisense nucleic acid, or by using siRNA or shRNA. Exemplary RyR receptor antagonists are dantrolene, ryanodine, azumolene, calquestrin and procaine.

In some embodiments, a lysosomal activating agent is used herein to treat a particular disease, disorder, and/or condition in combination with one or more agents previously used to treat the disease, disorder, and/or condition. In some such embodiments, a lysosomal activating agent is used herein to treat a particular disease, disorder, and/or condition in combination with one or more agents approved for treatment of the disease, disorder, and/or condition.

In some embodiments, methods of the invention are utilized in combination with one or more surgical therapies. For example, surgical treatment is presently recommended for those who have failed medical management of PD. Unilateral thallamotomy can be used to reduce tremor. It is occasionally considered for patients with unilateral tremor not responding to medication. Bilateral procedures are typically not advised for treatment of PD. Unilateral deep brain stimulation of the thalamus for tremor may also be a benefit for tremor. Unilateral pallidotomy is an effective technique for reducing contralateral drug-induced dyskinesias. Gamma knife surgery—thalamotomy or pallidotomy—can be performed as a radiological alternative to conventional surgery. The currently preferred neurosurgical intervention for PD is, however, bilateral subthalamic nucleus stimulation. Neurotransplantation strategies remain experimental. In addition to surgery and medication, physical therapy in Parkinsonism maintains muscle tone, flexibility, and improves posture and gait.

When the proteinopathy of interest is inflammatory disease, disorder and/or condition, suitable agents for use in combination therapy in accordance with the present invention include, for example, anti-inflammatory agents, immunomodulators, immunosuppressive agents, and combinations thereof. Non-limiting examples of anti-inflammatory agents include steroids, non-steroidal anti-inflammatory agents (NSAIDS) (such as, for example, salicylates, fenoprofen, naproxen, piroxicam tolmetin, indomethacin, sulindac, meclofenamate, etc.), and disease modifying anti-rheumatoid drugs (DMARDS) (such as, for example, D-penicillamine, gold salts, hydroxychloroquine, azathioprine, methotrexate, cyclophosphamide, etc.).

In some embodiments, methods of the invention can be used in combination with substrate inhibitor of GCase polypeptide. To give but an example, for treatment of synucleinopathies such a substrate inhibitor of GCase polypeptide is N-butyl-deoxynojirimycin (ZAVESCA).

Determining Responses to Therapy

Subjects with specific proteinopathic diseases, disorders and/or conditions exhibit characteristic symptoms. For example, patients having Parkinson's disease experience tremor, rigidity, bradykinesia, and postural imbalance. Patients having Lewy Body Dementia experience strong psychotic symptoms (visual hallucinations) in addition to mental decline such as memory loss and an inability to carry out simple tasks. Observable improvements in symptoms with lysosomal activating agent therapy, or a delay of onset of certain symptoms in patients at risk of developing a disorder, or a delay in progression of the disorder will be evidence of a favorable response to the therapy.

Alternatively or additionally, measurable surrogate markers also may be useful for evaluating response to lysosomal activating agent therapy. For instance, some investigators have reported detecting higher levels of α-synuclein or oligomeric forms of α-synuclein in plasma of patients with Parkinson's disease (Lee et al., J Neural Transm. 113(10): 1435, 2006; El-Agnaf et al., FASEB J. 20: 419, 2006), while some have reported decreased plasma α-synuclein in Parkinson's patients compared with normal controls (Li et al., Exp Neurol. 204(2):583, 2007).

In some embodiments of the present invention, lysosomal degradation capacity or monitoring levels of α-synuclein in dopamine neurons from Parkinson's disease patients may be used as markers for determining or characterizing response to lysosomal activating agent therapy.

Assays for Identification and/or Characterization of Lysosomal Activating Agents Among other things, the present invention provides systems for identifying and/or characterizing lysosomal activating agents. As noted herein, in some embodiments, particularly useful lysosomal activating agents for use in accordance with the present invention are those that increase stability and/or trafficking of one or more lysosomal enzymes.

In some embodiments, particularly useful lysosomal activating agents for use in accordance with the present invention are those that increase stability and/or trafficking of one or more lysosomal enzymes in neuronal and/or non-neuronal cells.

In some embodiments, particularly useful lysosomal activating agents for use in accordance with the present invention are those that bind directly to a target lysosomal enzyme.

In some embodiments, particularly useful lysosomal activating agents for use in accordance with the present invention are those that do not significantly inhibit activity of their target lysosomal activating enzyme.

In some embodiments, particularly useful lysosomal activating agents for use in accordance with the present invention are those that increase level and/or activity of a wild-type lysosomal enzyme.

The present invention provides systems for identifying and/or characterizing such agents. In some embodiments, the present invention provides systems for identifying and/or characterizing an equivalent dose of a lysosomal activating agent of interest as compared with a reference lysosomal activating agent.

A variety of assays can be utilized in accordance with the present invention to identify and/or characterize lysosomal activating agents and/or to otherwise assess lysosomal activity. For example, assays that monitor protein trafficking, particularly of lysosomal enzymes and/or of proteins (e.g., lysosomal enzymes) to the lysosome may be employed. Alternatively or additionally, assays that monitor accumulation of proteins (e.g., as observed in proteinopathies) can be utilized; in some embodiments such assays are employed as indirect read-outs of lysosomal activity and/or of effects of one or more potential or known lysosomal activating agents.

To give but a few particular examples, in some embodiments, protein accumulation in the ER can be detected and/or visualized using techniques that detect perinuclear localization in tubulovesicular profiles that co-localize with ER resident proteins such as BiP. These proteins are also reduced or absent at their native location within the cell such as at the cell surface or in another cellular compartment such as the lysosome. Protein accumulation in the cytoplasm can be detected using similar co-localization methods with cytosolic proteins.

Exemplary methods for detecting and/or analyzing protein trafficking (e.g., of lysosomal enzymes) include, for example pulse-chase metabolic labeling (e.g. using radioactive or otherwise detectable labels) of proteins that are N- and O-glycosylated in the Golgi apparatus, for example combined with glycosidase treatment and immunoprecipitation to assess whether the proteins are undergoing full glycosylation in the Golgi, or whether they are being retained in the ER instead of trafficking to the Golgi for further glycosylation.

Sensitive methods for visually detecting cellular localization of proteins also include fluorescent microscopy (e.g., using fluorescent proteins and/or fluorescent antibodies). Appropriate fluorescent moieties for use in such approaches include, for example, polypeptide moieties (that can, for example, be fused with a protein to be detected) including, for example, appropriate moieties from green fluorescent protein (GFP), cyan fluorescent protein, yellow fluorescent protein (YFP), and/or red fluorescent protein; small molecule or other detectable fluorescent markers (e.g., dyes, quantum dots, etc.,) can also be employed. In some embodiments, dual labeling studies (e.g., in which both the lysosome and a protein of interest whose targeting to the lysosome is to be assessed) are particularly useful for co-localization studies. For a review of the use of fluorescent imaging in protein trafficking, see Watson et al., Adv Drug Deliv Rev. 57(1):43, 2005. For a description of the use of confocal microscopy for intracellular co-localization of proteins, see Miyashita et al., Methods Mol. Biol. 261:399, 2004.

Fluorescence correlation spectroscopy (FCS) is an ultra-sensitive and non-invasive detection method capable of single-molecule and real-time resolution (Vukojevic et al., Cell Mol Life Sci. 62(5): 535, 2005). Single-particle fluorescence imaging (SPFI) uses the high sensitivity of fluorescence to visualize individual molecules that have been selectively labeled with small fluorescent particles (Chemy et al., Biochem Soc Trans. 31(Pt 5): 1028, 2003). For localization of proteins within lipid rafts, see Latif et al., Endocrinology. 144(11): 4725, 2003). For a review of live cell imaging, see Hariguchi, Cell Struct Funct. 27(5):333, 2002). Fluorescence resonance energy transfer (FRET) microscopy is also used to study the structure and localization of proteins under physiological conditions (Periasamy, J Biomed Opt. 6(3): 287, 2001).

In some embodiments, techniques such as ELISA and/or western-blot analysis can be employed, for example to monitor protein trafficking and/or accumulation.

In some embodiments mass spectroscopy and/or chromatography (e.g., thin layer chromatography) techniques can be employed, for example to monitor lysosomal enzyme activity, for example by assessing levels of enzyme substrates or other relevant entities.

In some embodiments, techniques are employed that monitor oligomer formation, for example of a polypeptide that accumulates in a synucleinopathy. For example, α-synuclein accumulates in oligomeric form. Levels of α-synuclein monomers and/or particular oligomers (e.g., dimers and/or tetramers), and/or optionally ratios thereof, can be monitored in accordance with the present invention to assess lysosomal activity and/or effects of a putative or known lysosomal activating agent. In some embodiments, such techniques monitor oligomer levels in vivo, for example through use of brain slice assays.

In some embodiments, lysosomal activity and/or effects of putative or known lysosomal activating agents can be monitored by assessing morphological abnormalities in neurons (e.g., morphometric analysis). To give but a few examples, in one format, changes in neuron morphology in neurons transfected with tau-GFP included asymmetry, a reduction in the number of axons in the anterior and posterior projections abnormal axon bundling, axon blebbing, and reduced terminal arborisations. Alternatively or additionally, alterations in cell morphology including aggregation, cell size (cell area or cell density), polymegathism (variation of cell size such as coefficient of variation of mean cell area), pleomorphism (variation of cell shape such as percent of hexagonal cells or coefficient of variation of cell shape), cell perimeter, average cell side length, cell shape, and so forth can be assessed. For example, morphology can be evaluated using for instance quantitative morphometric analysis according to methods described in, Ventimiglia et al., J Neurosci Methods. 57:63, 1995 and Wu et al., Cerebral Cortex. 14: 543, 2004 (high-throughput analysis); optionally together with image analysis software such as Image Pro-Plus software.

Trafficking of proteins in cells occurs along pH gradients (i.e., ER pH about 7.0, Golgi pH about 6.2-7.0, trans-Golgi network pH about 6.0, early and late endosomes pH about 6.5, lysosomes pH about 4.5). Trafficking, lysosome/endosome morphologies, and luminal pHs are also disrupted in some proteinopathies (Ivleva et al., Biomed Sci. 2: 398, 1991; Futerman and van Meer, Nat Rev Mol Cell Biol. 5: 554, 2004), and elevated pH in the endosome has been shown to promote a reversal of vesicular trafficking from endosomes to Golgi. The growth rate of cells (e.g., wild-type, untreated patient cells and lysosomal activating agent treated patient cells) exposed to a range of pHs can be measured and compared using a fluorescent plate reader. Apoptosis and cell death assays can be utilized to assess pH-sensitivity on cell viability. Alternatively or additionally, lysosomal pH and pH effects on trafficking can be evaluated using a confocal microscope. pH-sensitive fluorescent probes that are endocytosed by the cells can be used to measure pH ranges in the lysosomes and endosomes (i.e., fluorescein is red at pH 5.0 and blue to green at pH 5.5 to 6.5). *Lysosome* morphology and pH can be compared in wild-type and lysosome activating agent treated and untreated patient cells. In some embodiments, this assay can be run in parallel with a plate reader assay to determine the pH-sensitivity. In some embodiments, trafficking of enzymes to the lysosome can be evaluated in cells at different pH's using the dual labeling experiments described above rates of endocytosis for cells (wild-type, chaperone treated and untreated patient cells) exposed to various pHs can be measured using Quantum dots or Dextran Blue. In some embodiments, assays describing the use of fluorescent lipid analogs (e.g., BODIPY-LacCer, -GM1 gangliosides etc.) are described in Pagano, Phil Trans R Soc Lond B. 358-885-91, 2003.

In some embodiments of the present invention, biochemical assays can be used to assess protein function and/or determine whether the proteins are functional, and to assess the effects of restoring function, effects of restoring or disrupting function. In some such embodiments, such assays are performed at one or more different points during trafficking (e.g., after release from the ER, after entrance into the lysosome, etc)

In many embodiments, protein activity assays are designed to measure the activity of a protein of interest in the presence or absence of a test agent. Details of such assays will depend on the specific protein whose activity is being assessed. For example, where the protein is an enzyme, intracellular enzyme activity assays using substrates are routine in the art can be used to assess enzyme activity. Ex vivo and in vivo evaluation of enzyme activity can be performed using normal animals and animal models of disease states.

Different assays have been used in the current disclosure to demonstrate that endogenous mutations in GCase polypeptide affect its lysosomal trafficking, which in turn affects lysosomal proteolysis leading to preferential accumulation of α-synuclein. See for example, Example 1, which describes: monitoring of levels of mature GCase polypeptide in lysosome by endoglycosidase H (endo H) treatment; monitoring of GCase activity by analysis of whole cell lysates; monitoring of cellular lipids by BODIPY 493 and immunostaining; monitoring of neurotoxicity by neurofilament (NF) immunostaining; and/or monitoring the affects of loss in GCase polypeptide function in lysosomal-mediated pathway by immunoflourescence analysis of LAMP1. Example 1 further describes assays for monitoring proteolysis of long lived proteins in neurons using neurons treated with lysosomal inhibitors ammonium chloride and leupeptin, and using radioactive pulse-chase experiments. Example 1 also described methods for monitoring accumulation of α-synuclein in primary and iPS neuronal cells by using immunoflourescence and western blot analysis.

The present disclosure describes the use of different assays to delineate mechanisms of α-synuclein-mediated neurotoxicity. See for example, Example 3, which describes monitoring of soluble high molecular weight oligomers of α-synuclein by using size exclusion chromatography, sodium dodecyl sulfate polyacrylamide gel electrophoresis (SDS-PAGE), western blot analysis, and immunostaining analysis.

The present disclosure describes the use of different assays to delineate lysosomal enzyme substrate (e.g., GlcCer)-mediated specific aggregation of proteins (e.g., α-synuclein). See for example, Example 4, which describes analysis of α-synuclein fibril formation with lipid dispersions mixtures of GlcCer under acidic conditions using electron microscopy (EM) and immuno EM, biochemical methods like centrifugal sedimentation analysis, native gel electrophoresis, and by using 8-anilino-1-napthalene sulfonate binding, a fluorescent dye used to detect aggregation-prone conformational intermediates (Stryer, J. Mol. Biol. 13: 482, 1965).

A variety of systems is available to monitor the accumulation of proteins (e.g., α-synuclein) in vivo. See for example, Example 5, which describes analysis of brain tissues from a GD mouse model using histopathology, immunoflourescence and co-staining with neuron specific marker to identify intraneuronal and extraneuronal α-synuclein accumulations. Example 5 also describes the use of a *C. elegans* model for demonstrating GCase depletion-mediated accumulation of α-synuclein in vivo. Further, Example 6 describes use of human postmortem brain samples obtained from patients with GD for analysis of co-relation between elevated levels of soluble oligomeric α-synuclein aggregation and neurodegeneration.

The present disclosure describes assays to demonstrate decreased trafficking and activity of wild-type lysosomal enzyme (e.g., GCase) as a result of aggregation/accumulation of proteins (e.g., α-synuclein) in proteinopathies (e.g., PD). See for example, Example 7, which describes monitoring intracellular trafficking of wild-type GCase lysosomal enzyme for in vitro and in vivo models that overexpress α-synuclein by assessing various glycosylated forms of GCase polypeptide using SDS-PAGE, western blot, measuring enzymatic activity in lysosomal and microsomal enriched fractions, and endo H treatment.

A variety of assays is available to identify candidate lysosomal activating agents that stabilize and/or increase trafficking of lysosomal enzymes resulting in the enhanced proteolytic activity of the enzyme. See for example, Example 8, which describes treatment followed by wash-out (to activate the lysosomal enzyme by removing the active-site binder) of neuronal cells with a lysosomal activating agent, i.e., GCase pharmacological chaperone activator (e.g., IFG) and monitoring the increase in levels of GCase polypeptide by western blot and densitometric analysis, and monitoring the increased proteolytic activity of GCase polypeptide by radioactive pulse chase experiments. Example 8 also describes an assay to identify lysosomal activating agents wherein GCase overexpression in a non-neuronal cell enhances lysosomal proteolysis (assessed by radioactive pulse-chase) as compared to control cells. Lysosomal inhibitors (e.g., leupeptin and ammonium chloride) completely reversed this effect indicating that GCase overexpression resulted in augmentation of primarily the lysosomal degradation pathway (as should a candidate lysosomal activating agent). Example 8 further describes an assay to identify a candidate lysosomal activating agent by measuring the effect of GCase overexpression on the activity of cathepsin B. In this assay GCase overexpression results in increased cathepsin B activity in degrading its substrate (as should a candidate lysosomal activating agent).

The present disclosure also describes assays that identify and/or characterize potential lysosomal activating agents that stimulate the secretory pathway for treatment of proteinopathies. See for example, Example 9, which describes the effect of overexpressing Rab1a polypeptide in human PD neuronal cells that overexpress α-synuclein resulting in lysosomal trafficking defects. Rab1a polypeptide overexpression results in significant reduction of α-synuclein (as should a candidate lysosomal activating agent). Similarly, Rab1a polypeptide-mediated enhancement of lysosomal function is seen in non-neuronal cells transfected with Rab1a polypeptide by monitoring cathepsin B activity.

The present disclosure additionally describes assays that identify and/or characterize potential lysosomal activating agents that bind to a allosteric site in a lysosomal enzyme. See for example, Examples 8 and 10, the later of which describes a dose-dependent decrease of α-synuclein in human PD neurons overexpressing α-synuclein after treatment with allosteric lysosomal activating agent. Such compounds do not require a washout step to activate the lysosomal enzyme.

The present disclosure also describes assays that demonstrate that certain candidate lysosomal activating agents show/achieve greater stabilization and activation of lysosomal enzyme when combined together. See for example, Example 11, which describes that GCase polypeptide maturation in PD neurons was increased more significantly when neurons were treated in combination with two lysosomal modulating agents than when treated with either agent alone.

The present disclosure also describes assays to test if a lysosomal activating agent physically interacts with lysosomal enzyme and/or for selection of candidate lysosomal activating agent for in vivo evaluation, see Example 13.

Those of skill in the art will appreciate that any of a variety of agents may be tested and/or studied in such provided assays to assess its characteristics and/or appropriateness as a lysosomal activating agent in accordance with the present invention. For example, agents of the chemical classes discussed above as lysosomal activating agents can be screened, tested, and/or confirmed as appropriate lysosomal activating agents for use in accordance with the present invention using such systems as described herein.

Some embodiments of the present invention may be defined in any of the following numbered paragraphs:

1. A method comprising steps of:
    administering to a subject suffering from or susceptible to a neurodegenerative proteinopathic disease, disorder, and/or condition, a pharmaceutical composition comprising:
    a lysosomal activating agent; and
    a pharmaceutically acceptable carrier,
    the lysosomal activating agent being administered in an amount and according to a dosing regimen that correlates with a predetermined therapeutic benefit when administered in accordance with a predetermined dosing regimen.
2. The method of paragraph 1, wherein the neurodegenerative proteinopathic disease, disorder, and/or condition is selected from the group consisting of:
    adrenoleukodystrophy, AIDS and AIDS-related dementia, Agryophilic grain disease, Alzheimer's disease, amyotrophic lateral sclerosis (Parkinsonism-dementia complex of Guam or Lytico-Bodig disease), aortic medial amyloid, apathy, atherosclerosis, attention deficit disorder (ADD), attention deficit hyperactivity disorder (ADHD), autism, autoimmune vasculitis, B12 deficiency, bipolar disorder, bovine spongiform encephalopathy, brain neoplasms, brain lesions, cardiac arrythmias, cerebrovascular disease, cerebral amyloid angiopathy (and Icelandic type), cognitive impairment due to electroconvulsive shock therapy, cognitive impairment due to chemotherapy, cognitive impairment due to a history of drug abuse, cognitive impairment during waking hours due to sleep apnea, complications post anoxia, complications from intracerebral hemorrhage, corticobasal degeneration, dementia with Lewy bodies, dementia pugilistica, dentatorubropallidouysian atrophy, depression, diabetes mellitus type 2, dialysis related amyloidosis, diffuse Lewy body disease, Down's syndrome, dyslexia, epilepsy, familial amyloid polyneuropathy, Finnish amyloidosis, folic acid deficiency, Fragile X syndrome, Fragile X associated tremor/ataxia syndrome, Fragile XE mental retardation, frontal lobe syndrome, frontotemporal dementia with Parkinsonism linked to chromosome 17, frontotemporal lobar degeneration, Friedrich's ataxia, ganglioglioma, hallervorden-spatz disease, hepatic conditions, hereditary non-neuropathic systemic amyloidosis, Huntington's disease, hypoglycemia, hypercalcemia, hypothyroidism, hydrocephalus, inclusion body myositis, infectious vasculitis, Kufs' disease, Kufor Rakeb disease, isolated atrial amyloidosis, lattice corneal dystrophy, lead enphalapathy, Lewy body disease, Lewy body mutant of Alzheimer's disease, Lipofuscinosis, Lyme disease, malnutrition, maple syrup urine disease, medullary carcinoma of the thyroid, meningioangiomatosis, metabolic diseases, mild cognitive impairment, multi-infarct dementia, multiple sclerosis, multiple system atrophy, myasthenia gravis, Myotonic dystrophy, neurofibromatosis, neurosyphillis, neurodegeneration with brain iron accumulation type I, niacin deficiency, Parkinson's disease and Parkinson's disease dementia, Pick's disease, phenylketonuria, polymyalgia rheumatica, post-traumatic stress disorder, prion disease (Creutzfeldt-Jakob disease), prolactinomas, post coronary artery by-pass graft surgery, progressive supranuclear palsy, protein and lipid accumulation due to normal aging, Rett's syndrome, Rheumatoid arthritis, schizophrenia, systemic lupus erythematosus, spinocerebellar ataxia (types 1-8, 10-14, 16-29), spinobulbar muscular atrophy (Kennedy's disease), sporadic inclusion body myositis, storage diseases, stroke, subacute sclerosing panencephalitis, syphillis, systemic AL amyloidosis, thiamine deficiency, traumatic brain injury, Tourette's syndrome, transmissible spongiform encephalopathy, Tuberous sclerosis, and vascular dementia.
3. The method of paragraph 1, wherein the neurodegenerative proteinopathic disease, disorder, and/or condition is synucleinopathic.
4. The method of paragraph 3, wherein the synucleinopathic disease, disorder, and/or condition is Parkinson's disease.
5. The method of paragraph 3, wherein the synucleinopathic disease, disorder, and/or condition is multiple system atrophy.
6. The method of paragraph 3, wherein the synucleinopathic disease, disorder, and/or condition is diffuse Lewy body disease.
7. The method of paragraph 3, wherein the synucleinopathic disease, disorder, and/or condition is dementia with Lewy bodies.
8. The method of paragraph 3, wherein the synucleinopathic disease, disorder, and/or condition is neurodegeneration with brain iron accumulation type I.
9. The method of paragraph 3, wherein the synucleinopathic disease, disorder, and/or condition is Parkinsonism-dementia complex of Guam.
10. The method of paragraph 1, wherein the neurodegenerative proteinopathic disease, disorder, and/or condition is amyloidopathic.
11. The method of paragraph 10, wherein the amyloidopathic disease, disorder, and/or condition is selected from the group consisting of:
    adrenoleukodystrophy, AIDS and AIDS-related dementia, Agryophilic grain disease, Alzheimer's disease, amyotrophic lateral sclerosis (Parkinsonism-dementia complex of Guam or Lytico-Bodig disease), aortic medial amyloid, apathy, atherosclerosis, attention deficit disorder (ADD), attention deficit hyperactivity disorder (ADHD), autism, autoimmune vasculitis, B12 deficiency, bipolar disorder, bovine spongiform encephalopathy, brain neoplasms, brain lesions, cardiac arrythmias, cerebrovascular disease, cerebral amyloid angiopathy (and Icelandic type), cognitive impairment due to electroconvulsive shock therapy, cognitive impairment due to chemotherapy, cognitive impairment due to a history of drug abuse, cognitive impairment during waking hours due to sleep apnea, complications post anoxia, complications from intracerebral hemorrhage, corticobasal degeneration, dementia with Lewy bodies, dementia pugilistica, dentatorubropallidouysian atrophy, depression, diabetes mellitus type 2, dialysis related amyloidosis, diffuse Lewy body disease, Down's syndrome, dyslexia, epilepsy, familial amyloid polyneuropathy, Finnish amyloidosis, folic acid deficiency, Fragile X syndrome, Fragile X associated tremor/ataxia syndrome, Fragile XE mental retardation, frontal lobe syndrome, frontotemporal dementia with Parkinsonism linked to chromosome 17, frontotemporal lobar degeneration, Friedrich's ataxia, ganglioglioma, hallervorden-spatz disease, hepatic conditions, hereditary non-neuropathic systemic amyloidosis, Huntington's disease, hypoglycemia, hypercalcemia, hypothyroidism, hydrocephalus, inclusion body myositis, infectious vasculitis, Kufs' disease, Kufor Rakeb disease, isolated atrial amyloidosis, lattice corneal dystrophy, lead enphalapathy, Lewy body disease, Lewy body mutant of Alzheimer's disease, Lipofuscinosis, Lyme disease, malnutrition, maple syrup urine disease, medullary carcinoma of the thyroid, meningioangiomatosis, metabolic diseases, mild cognitive impairment, multi-infarct dementia, multiple sclerosis, multiple system atrophy, myasthenia gravis, Myotonic dystrophy, neurofibromatosis, neurosyphillis, neurodegeneration with brain iron accumulation type I, niacin deficiency, Parkinson's disease and Parkinson's disease dementia, Pick's disease, phenylketonuria, polymyalgia rheumatica, post-traumatic stress disorder, prion disease (Creutzfeldt-Jakob disease), prolactinomas, post coronary artery by-pass graft surgery, progressive supranuclear palsy, protein and lipid accumulation due to normal aging, Rett's syndrome, Rheumatoid arthritis, schizophrenia, systemic lupus erythematosus, spinocerebellar ataxis (types 1-8, 10-14, 16-29), spinobulbar muscular atrophy (Kennedy's disease), sporadic inclusion body myositis, storage diseases, stroke, subacute sclerosing panencephalitis, syphillis, systemic AL amyloidosis, thiamine deficiency, traumatic brain injury, Tourette's syndrome, transmissible spongiform encephalopathy, Tuberous sclerosis, and vascular dementia.

12. The method of paragraph 10, wherein the amyloidopathic disease, disorder, and/or condition is Alzheimer's disease.

13. The method of paragraph 10, wherein the amyloidopathic disease, disorder, and/or condition is vascular dementia.

14. The method of paragraph 10, wherein the amyloidopathic disease, disorder, and/or condition is cognitive impairment.

15. The method of paragraph 1, wherein the neurodegenerative proteinopathic disease, disorder, and/or condition is taupathic.

16. The method of paragraph 15, wherein the taupathic disease, disorder, and/or condition is selected from the group consisting of:

adrenoleukodystrophy, AIDS and AIDS-related dementia, Agryophilic grain disease, Alzheimer's disease, amyotrophic lateral sclerosis (Parkinsonism-dementia complex of Guam or Lytico-Bodig disease), aortic medial amyloid, apathy, atherosclerosis, attention deficit disorder (ADD), attention deficit hyperactivity disorder (ADHD), autism, autoimmune vasculitis, B12 deficiency, bipolar disorder, bovine spongiform encephalopathy, brain neoplasms, brain lesions, cardiac arrythmias, cerebrovascular disease, cerebral amyloid angiopathy (and Icelandic type), cognitive impairment due to electroconvulsive shock therapy, cognitive impairment due to chemotherapy, cognitive impairment due to a history of drug abuse, cognitive impairment during waking hours due to sleep apnea, complications post anoxia, complications from intracerebral hemorrhage, corticobasal degeneration, dementia with Lewy bodies, dementia pugilistica, dentatorubropallidouysian atrophy, depression, diabetes mellitus type 2, dialysis related amyloidosis, diffuse Lewy body disease, Down's syndrome, dyslexia, epilepsy, familial amyloid polyneuropathy, Finnish amyloidosis, folic acid deficiency, Fragile X syndrome, Fragile X associated tremor/ataxia syndrome, Fragile XE mental retardation, frontal lobe syndrome, frontotemporal dementia with Parkinsonism linked to chromosome 17, frontotemporal lobar degeneration, Friedrich's ataxia, ganglioglioma, hallervorden-spatz disease, hepatic conditions, hereditary non-neuropathic systemic amyloidosis, Huntington's disease, hypoglycemia, hypercalcemia, hypothyroidism, hydrocephalus, inclusion body myositis, infectious vasculitis, Kufs' disease, Kufor Rakeb disease, isolated atrial amyloidosis, lattice corneal dystrophy, lead enphalapathy, Lewy body disease, Lewy body mutant of Alzheimer's disease, Lipofuscinosis, Lyme disease, malnutrition, maple syrup urine disease, medullary carcinoma of the thyroid, meningioangiomatosis, metabolic diseases, mild cognitive impairment, multi-infarct dementia, multiple sclerosis, multiple system atrophy, myasthenia gravis, Myotonic dystrophy, neurofibromatosis, neurosyphillis, neurodegeneration with brain iron accumulation type I, niacin deficiency, Parkinson's disease and Parkinson's disease dementia, Pick's disease, phenylketonuria, polymyalgia rheumatica, post-traumatic stress disorder, prion disease (Creutzfeldt-Jakob disease), prolactinomas, post coronary artery by-pass graft surgery, progressive supranuclear palsy, protein and lipid accumulation due to normal aging, Rett's syndrome, Rheumatoid arthritis, schizophrenia, systemic lupus erythematosus, spinocerebellar ataxis (types 1-8, 10-14, 16-29), spinobulbar muscular atrophy (Kennedy's disease), sporadic inclusion body myositis, storage diseases, stroke, subacute sclerosing panencephalitis, syphillis, systemic AL amyloidosis, thiamine deficiency, traumatic brain injury, Tourette's syndrome, transmissible spongiform encephalopathy, Tuberous sclerosis, and vascular dementia.

17. The method of paragraph 15, wherein the taupathic disease, disorder, and/or condition is Alzheimer's disease.

18. A method of reducing α-synuclein levels in a subject comprising steps of:
administering a pharmaceutical composition to the subject comprising:
a lysosomal activating agent; and
a pharmaceutically acceptable carrier,
the lysosomal activating agent being administered in an amount and according to a dosing regimen that correlates with a predetermined therapeutic benefit when administered in accordance with a predetermined dosing regimen.

19. The method of paragraph 18 further comprising a step of determining the α-synuclein levels in the individual prior to the step of administering and if the α-synuclein level is elevated compared to a reference value, then administering the lysosomal activating agent and a pharmaceutically acceptable carrier to the subject.

20. The method of paragraph 1, 18, or 19, wherein the lysosomal activating agent increases trafficking of at least one lysosomal enzyme.

21. The method of paragraph 1, 18, or 19, wherein the lysosomal activating agent increases stability of at least one lysosomal enzyme.

22. The method of paragraph 20 or 21, wherein the lysosomal activating agent increases level of the lysosomal enzyme in the lysosome.

23. The method of paragraph 21, wherein the lysosomal activating agent increases activity of the lysosomal enzyme in the lysosome.

24. The method of paragraph 21, wherein the lysosomal activating agent increases binding of the lysosomal enzyme to its substrate.
25. The method of paragraph 1, 18, 19, 20, or 21, wherein the lysosomal activating agent binds directly to the lysosomal enzyme.
26. The method of paragraph 1, 18, 19, 20, or 21, wherein the lysosomal activating agent does not bind directly to the lysosomal enzyme.
27. The method of paragraph 25, wherein the lysosomal activating agent binds at a site apart from the lysosomal enzyme's catalytic or active site.
28. The method of paragraph 25, wherein the lysosomal activating agent binds in a manner that does not compete with the lysosomal enzyme's substrate.
29. The method of paragraph 20 or 21, wherein the lysosomal enzyme is β-glucocerebrosidase.
30. The method of paragraph 29, wherein the β-glucocerebrosidase is wild-type.
31. The method of paragraph 29, wherein the β-glucocerebrosidase is mutant.
32. The method of paragraph 1, 18, 19, 20, or 21, wherein the lysosomal activating agent activates β-glucocerebrosidase.
33. The method of paragraph 20 or 21, wherein the lysosomal enzyme is β-hexosamindase A/B.
34. The method of paragraph 33, wherein the β-hexosamindase A/B is wild-type.
35. The method of paragraph 33, wherein the β-hexosamindase A/B is mutant.
36. The method of paragraph 1, 18, 19, 20, or 21, wherein the lysosomal activating agent activates β-hexosamindase A/B.
37. The method of paragraph 20 or 21, wherein the lysosomal enzyme is β-galactosidase isoform 1.
38. The method of paragraph 37, wherein β-galactosidase isoform 1 is wild-type.
39. The method of paragraph 37, wherein the β-galactosidase isoform 1 is mutant.
40. The method of paragraph 1, 18, 19, 20, or 21, wherein the lysosomal activating agent activates β-galactosidase isoform 1.
41. The method of paragraph 20, wherein the lysosomal activating agent is or comprises Rab1a polypeptide.
42. The method of paragraph 20, wherein the lysosomal activating agent is or comprises a nucleic acid encoding Rab1a polypeptide.
43. The method of paragraph 20, wherein the lysosomal activating agent activates Rab1a polypeptide.
44. The method of paragraph 20, wherein the lysosomal activating agent inhibits an inhibitor of Rab1a polypeptide.
45. The method of paragraph 21, wherein the lysosomal activating agent is or comprises saposin polypeptide.
46. The method of paragraph 45, wherein the lysosomal activating agent activates saposin polypeptide.
47. The method of paragraph 45, wherein the lysosomal activating agent inhibits an inhibitor of saposin polypeptide.
48. The method of paragraph 45, wherein the saposin polypeptide is or comprises saposin C.
49. The method of paragraph 1, 18, 19, 20, or 21, wherein the lysosomal activating agent is a small molecule.
50. The method of paragraph 49, wherein the small molecule binds directly to a target lysosomal enzyme.
51. The method of paragraph 49, wherein the small molecule binds to a target lysosomal enzyme in a manner that does not compete with the enzyme's substrate.
52. The method of paragraph 49, wherein the small molecule does not inhibit activity of the target lysosomal enzyme.
53. The method of paragraph 50, 51, or 52, wherein the lysosomal enzyme is β-glucocerebrosidase.
54. The method of paragraph 50, 51, or 52, wherein the lysosomal enzyme is O-hexosamindase A/B.
55. The method of paragraph 50, 51, or 52, wherein the lysosomal enzyme is β-galactosidase isoform 1.
56. The method of paragraph 49, wherein lysosomal activating agent is a compound having the formula:

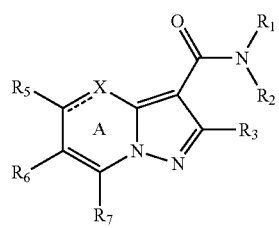

wherein the ring

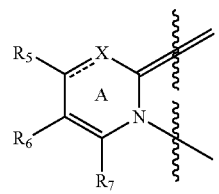

is a ring system of the formula

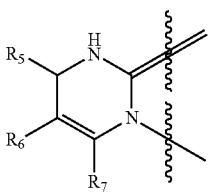

(i)

in which $R_5$ is an optionally substituted vinyl group and $R_6$ and $R_7$ carry the definitions set forth below, or

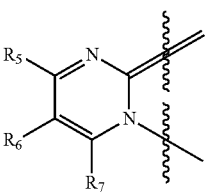

(ii)

in which $R_5$, $R_6$, and $R_7$ carry the definitions set forth below;
$R_1$ is (mono- or bicyclic carbocycle) $C_0$-$C_4$ alkyl or (mono- or bicyclic heterocycle) $C_0$-$C_4$ alkyl, each of which is unsubstituted or substituted with one or more substituents independently chosen from halogen, hydroxyl, cyano, nitro, amino, —CHO, —COOH, $C_1$-$C_6$ alkyl, $C_1$-$C_6$ alkoxy, $C_2$-$C_6$ alkanoyl, mono- or di-$C_1$-$C_6$ alkylamino, mono- or di-$C_1$-$C_6$ alkylcarboxamide, $C_1$-$C_6$ alkylester, $C_1$-$C_6$ alkylthio, $C_1$-$C_6$ alkylsulfonyl, $C_1$-$C_2$ haloalkyl, and $C_1$-$C_2$ haloalkoxy, and with 0 or 1 substituents chosen from Y—Z— where Z is a covalent bond, $C_1$-$C_4$ alkylene, $C_2$-$C_4$ alkenylene, $C_2$-$C_4$ alkynylene, —S—, —O—, —NR—, —C(O)—, —NHC(O)—, or —C(O)NH—, where R is hydrogen or $C_1$-$C_4$ alkyl, and Y is phenyl, pyrimidinyl, 5- or 6-membered heterocycloalkyl, or pyridyl, each of which is substituted with 0 to 3 substituents independently chosen from halogen, hydroxyl, cyano, nitro, amino, $C_1$-$C_4$alkyl, $C_1$-$C_4$alkoxy, mono- or di-$C_1$-$C_4$ alkylamino, trifluoromethyl, difluoromethyl, trifluoromethoxy, and phenyl; and $R_2$ is hydrogen, $C_1$-$C_6$ alkyl, $C_3$-$C_7$ cycloalkyl, (phenyl)$C_0$-$C_2$ alkyl; or $R_1$ and $R_2$ are joined to form a 5- to 7-membered heterocycloalkyl ring having 0 or 1 additional heteroatoms chosen from N, O, and S, which 5- to 7-membered heterocycloalkyl ring is optionally fused to a phenyl or pyridyl; which 5- to 7-membered heterocycloalkyl ring is unsubstituted or substituted with one or more substituents independently chosen from halogen, hydroxyl, $C_1$-$C_2$ alkyl, and $C_1$-$C_2$ alkoxy; $R_3$ is hydrogen or $C_1$-$C_2$ alkyl; $R_5$ is halogen, hydroxyl, amino, cyano, $C_1$-$C_4$ alkyl, $C_1$-$C_4$ alkoxy, difluoromethyl, trifluoromethyl, or phenyl; $R_6$ is halogen, hydroxyl, $C_1$-$C_4$ alkyl, or $C_1$-$C_4$ alkoxy; and $R_7$ is halogen, hydroxyl, amino, cyano, $C_1$-$C_4$ alkyl, $C_1$-$C_4$ alkoxy, difluoromethyl, or trifluoromethyl, or $R_7$ is phenyl or a 5- to 7-membered heterocycloalkyl ring having 1 or 2 heteroatoms chosen from N, O, and S, each of which $R_7$ is directly attached via a covalent bond or attached via a $C_1$-$C_4$ alkyl, $C_1$-$C_4$alkoxy, or $C_1$-$C_4$alkylamino, and each of which $R_7$ is unsubstituted or substituted with 1 to 3 substituents independently chosen from $C_1$-$C_4$ alkyl, (mono- or di-$C_1$-$C_2$ alkylamino)$C_0$-$C_4$ alkyl; or $R_6$ and $R_7$ are taken together to form a 5- or 6-membered carbocyclic ring with no additional points of unsaturation, which ring is unsubstituted or substituted with 1 to 3 substituents independently chosen from $C_1$-$C_2$ alkyl and $C_1$-$C_2$ alkoxy; wherein $R_1$ is not unsubstituted phenyl, dihydroindenyl, benzo[b][1,4]dioxolyl, benzo[d][1,3]dioxol-5-yl, cyclohexyl, pyridyl, or phenyl substituted with 1 or 2 substituents independently chosen from chloro, fluoro, $C_1$-$C_4$ alkyl, $C_1$-$C_2$ alkoxy, acetyl, trifluoromethyl, when $R_6$ is hydrogen, $R_5$ and $R_7$ are both methyl, or when $R_6$ is hydrogen and one $R_5$ and $R_7$ is methyl and the other is phenyl; and $R_1$ is not 1-(4-fluorobenzyl)-1H-pyrazol-4-yl when $R_6$ is hydrogen and one $R_5$ and $R_7$ is methyl and the other is phenyl, or pharmaceutically acceptable salt thereof.

57. The method of paragraph 1, 18, 19, 20, or 21, wherein the lysosomal activating agent is a pharmacological chaperone.

58. The method of paragraph 57, wherein the pharmacological chaperone binds directly to a target lysosomal enzyme.

59. The method of paragraph 57, wherein the pharmacological chaperone binds to a target lysosomal enzyme in a manner that does not compete with the enzyme's substrate.

60. The method of paragraph 57, wherein the pharmacological chaperone does not inhibit activity of the target lysosomal enzyme.

61. The method of paragraph 58, 59, or 60, wherein the lysosomal enzyme is β-glucocerebrosidase.

62. The method of paragraph 58, 59, or 60, wherein the lysosomal enzyme is O-hexosamindase A/B.

63. The method of paragraph 58, 59, or 60, wherein the lysosomal enzyme is β-galactosidase isoform 1.

64. The method of paragraph 57, wherein the pharmacological chaperone is isofagomine.

65. The method of paragraph 1, 18, 19, 20, or 21, wherein the lysosomal activating agent is a proteostasis regulator.

66. The method of paragraph 65, wherein the proteostasis regulator does not bind directly to a target lysosomal enzyme.

67. The method of paragraph 65, wherein the proteostasis regulator is a $Ca^{2+}$ channel blocker.

68. The method of paragraph 65, wherein the proteostasis regulator is an inhibitor of RyR.

69. The method of paragraph 67, wherein the $Ca^{2+}$ channel blocker is a small molecule.

70. The method of paragraph 69, wherein the small molecule is diltiazem.

71. The method of paragraph 69, wherein the small molecule is verapamil.

72. The method of paragraph 68, wherein the inhibitor of RyR is a small molecule.

73. The method of paragraph 72, wherein the small molecule is dantrolene.

74. The method of paragraph 1, 18, or 19, wherein the lysosomal activating agent is administered in a pharmaceutical composition formulated for oral delivery.

75. A method comprising steps of:
  administering to a subject suffering from or susceptible to a proteinopathic disease, disorder, and/or condition a combination of:
  a lysosomal activating agent; and
  at least one second therapeutic agent,
  wherein the lysosomal activating agent and at least one second therapeutic agent are administered in unit doses and in accordance with a therapeutic regimen correlated with a predetermined therapeutic benefit.

76. The method of paragraph 75, wherein the lysosomal activating agent is a compound according to paragraph 56, and the second therapeutic agent is used in the treatment of Parkinson's disease.

77. The method of paragraph 75, wherein the lysosomal activating agent is a Rab1a polypeptide, and the second therapeutic agent is used in the treatment of Parkinson's disease.

78. The method of paragraph 75, wherein the lysosomal activating agent is a nucleic acid encoding Rab1a polypeptide, and the second therapeutic agent is used in the treatment of Parkinson's disease.

79. The method of paragraph 75, wherein the lysosomal activating agent is a saposin C polypeptide, and the second therapeutic agent is used in the treatment of Parkinson's disease.

80. The method of paragraphs 76, 77, 78, or 79, wherein the second therapeutic agent used in the treatment of Parkinson's disease is selected from the group consisting of levodopa, carbidopa, amantidine, an anticholinergic, a Catechol-O-methyl transferase, a monoamine oxidase inhibitor, a peripheral decarboxylase inhibitor, bromocriptidine, pergolide, ropinirol, pramipexole, and Ergolide.

81. The method of paragraph 75, wherein the lysosomal activating agent is a Rab1a polypeptide, and the second therapeutic agent is used in the treatment of a lysosomal storage disease.

82. The method of paragraph 75, wherein the lysosomal activating agent is a nucleic acid encoding Rab1a polypeptide, and the second therapeutic agent is used in the treatment of a lysosomal storage disease.

83. The method of paragraph 81 or 82, wherein the second therapeutic agent used in the treatment of lysosomal storage disease is selected from the group consisting of allopregnanolone, a statin, fenofibrate, a niacin, ezetimibe, and cholestyramine.

84. The method of paragraph 75, wherein the second therapeutic agent is a lysosomal activating agent.

85. The method of paragraph 75 or 84, wherein the lysosomal activating agent is a small molecule, and the second therapeutic agent is a polypeptide lysosomal activating agent.

86. The method of paragraph 75 or 84, wherein the lysosomal activating agent is a small molecule, and the second therapeutic agent is an antioxidant lysosomal activating agent.

87. The method of paragraph 75 or 84, wherein the lysosomal activating agent is an antioxidant, and the second therapeutic agent is a polypeptide lysosomal activating agent.

88. The method of paragraph 85 or 86, wherein the small molecule is a compound according to paragraph 56.

89. The method of paragraph 85 or 86, wherein the small molecule is a pharmacological chaperone according to paragraph 64.

90. The method of paragraph 85 or 86, wherein the small molecule is an inhibitor of glucosylceramide synthase polypeptide.

91. The method of paragraph 90, wherein the inhibitor of glucosylceramide synthase polypeptide is selected from the group consisting of N-butyl-deoxynojirimycin, AMP-DMP, N-((1R,2R)-1-(2,3-dihydrobenzo[b][1,4]dioxin-6-yl)-1-hydroxy-3-(pyrrolidin-1yl)propan-2-yl)octanamide (Genz-112638), 2-(2,3-dihydro-1-H-inden-2-yl)-1-hydroxy-3-(pyrrolidin-1-yl)propan-2-yl)acetamide (CCG-203586), and EXEL-0346.

92. The method of paragraph 85 or 86, wherein the small molecule is a $Ca^{2+}$ channel blocker.

93. The method of paragraph 92, wherein the a $Ca^{2+}$ channel blocker is selected from the group consisting of dihydropyridine group of calcium channel blockers, amlodipine, felodipine, isradipine, lacidipine, nicardipine, nifedipine, niguldipine, niludipine, nimodipine, nisoldipine, nitrendipine, nivaldipine, ryosidine, anipamil, diltiazem, fendiline, flunarizine, gallopamil, mibefradil, prenylamine, tiapamil, verapamil, perhexyline maleate, fendiline, prenylamine, salts, esters, amides, and prodrugs.

94. The method of paragraph 85 or 86, wherein the small molecule is an inhibitor of RyR.

95. The method of paragraph 94, wherein the an inhibitor of RyR is selected from the group consisting of dantrolene, ryanodine, azumolene, calquestrin, and procaine.

96. The method of paragraph 85 or 86, wherein the polypeptide is a Rab1a polypeptide.

97. The method of paragraph 85 or 86, wherein the polypeptide is a saposin C polypeptide 98. The method of paragraph 75 or 84, further comprising at least one third lysosomal activating agent.

99. The method of paragraph 98, wherein the third lysosomal activating agent is selected from the group consisting of: compound according to paragraph 58, isofagomine, Rab1a polypeptide, nucleic acid encoding Rab1a polypeptide, saposin C polypeptide, antioxidant, compounds according to paragraph 93, compounds according to paragraph 95, and compounds according to paragraph 97.

100. The method of paragraph 86, 87, or 99, wherein the antioxidant is n-acetyl-cysteine.

101. The method of paragraph 75, 84, or 98, wherein at least one of the unit doses is less than a reference unit dose of the same agent when administered alone.

102. The method of paragraph 75, 84, or 98, wherein the therapeutic regimen includes doses administered less frequently than are doses in a reference therapeutic regimen in which the same agent is administered alone.

103. A method of reducing protein aggregation or accumulation toxicity in a cell, comprising steps of: administering to the cell a therapeutically effective amount of a lysosomal activating agent.

104. The method of paragraph 103, wherein the lysosomal activating agent is the compound according to paragraph 56.

105. The method of paragraph 103, wherein the lysosomal activating agent is the pharmacological chaperone according to paragraph 64.

106. The method of paragraph 103, wherein the lysosomal activating agent is the inhibitor of glucosylceramide synthase polypeptide according to paragraph 91.

107. The method of paragraph 103, wherein the lysosomal activating agent is the $Ca^{2+}$ channel blocker according to paragraph 93.

108. The method of paragraph 103, wherein the lysosomal activating agent is the inhibitor of RyR according to paragraph 95.

109. The method of paragraph 103, wherein the lysosomal activating agent is or comprises of Rab1a polypeptide.

110. The method of paragraph 103, wherein the lysosomal activating agent is a nucleic acid encoding Rab1a polypeptide.

111. The method of paragraph 103, wherein the lysosomal activating agent is an activator of Rab1a polypeptide.

112. The method of paragraph 103, wherein the lysosomal activating agent is an inhibitor of an inhibitor of Rab1a polypeptide.

113. The method of paragraph 103, wherein the lysosomal activating agent is or comprises of saposin C polypeptide.

114. The method of paragraph 103, wherein the lysosomal activating agent is an activator of saposin C polypeptide.

115. The method of paragraph 103, wherein the lysosomal activating agent is an inhibitor of an inhibitor of saposin C polypeptide.

116. The method of paragraph 103, wherein the lysosomal activating agent is an antioxidant.

117. The method of paragraph 116, wherein the antioxidant is n-acetyl-cysteine.

118. The method of paragraph 103, wherein administering comprises administering to a cell in a system.

119. The method of paragraph 118, wherein the system is in vitro system.

120. The method of paragraph 118, wherein the system comprises an organism.

121. The method of paragraph 103, wherein the cell is a neuronal cell.

122. The method of paragraph 103, wherein the cell is a non-neuronal cell.

123. The method of paragraph 103, wherein the cell expresses α-synuclein.

124. The method of paragraph 103, wherein the cell expresses amyloid.

125. The method of paragraph 103, wherein the cell expresses tau.
126. A method comprising steps of:
administering to a subject suffering from or susceptible to a non-lysosomal storage disease proteinopathies, a pharmaceutical composition comprising:
a lysosomal activating agent; and
a pharmaceutically acceptable carrier,
the lysosomal activating agent being administered in an amount and according to a dosing regimen that correlates with a predetermined therapeutic benefit when administered in accordance with a predetermined dosing regimen.
127. The method of paragraph 126, wherein the proteinopathic disease, disorder, and/or condition is a proliferative disease.
128. The method of paragraph 126, wherein the proteinopathic disease, disorder, and/or condition is an inflammatory disease.
129. The method of paragraph 126, wherein the proteinopathic disease, disorder, and/or condition is a cardiovascular disease.
130. A method comprising steps of:
administering to a subject suffering from or susceptible to a lysosomal storage disease, disorder, and/or condition, a pharmaceutical composition comprising:
a lysosomal activating agent; and
a pharmaceutically acceptable carrier,
the lysosomal activating agent being administered in an amount and according to a dosing regimen that correlates with a predetermined therapeutic benefit when administered in accordance with a predetermined dosing regimen.
131. The method of paragraph 130, wherein the lysosomal activating agent increases level and/or activity of a Rab1a polypeptide.
132. The method of paragraph 130, wherein the lysosomal activating agent is an antioxidant.
133. The method of paragraph 130, wherein the antioxidant is n-acetyl-cysteine.
134. The method of paragraph 130, wherein the lysosomal activating agent is a compound according to paragraph 56.
135. The method of paragraph 130, wherein the lysosomal activating agent is a pharmacological chaperone according to paragraph 64.
136. The method of paragraphs 130, wherein the lysosomal storage disease, disorder, and/or condition is selected from the group consisting of:
alpha-mannosidosis types I/II, aspartylglucosaminuria, Batten disease, Batten disease (late infantile), beta-mannosidosis, cardiac arrythmias, cystinosis, Danon disease, Fabry disease, Farber disease, Fucosidosis, Gaucher disease, GM1-gangliosidosis types I/II/III, GM2-gangliosidosis types I/II, galactosialidosis types I/II, Hunter syndrome, Hurler syndrome, Krabbe disease, Kufs' disease, I-cell disease, mucolipidosis type IV, Morquio syndrome, mucopolysaccharidosis type IX, multiple sulfatase deficiency, Maroteaux-Lamy syndrome, metachromatic leukodystropy, Niemann-Pick disease, Pompe disease, pseudo-Hurler polydystrophy, pycnodystosis, Sandhoff disease, Sanfilippo syndrome A, Sanfilippo syndrome B, Sanfilippo syndrome C, Sanfilippo syndrome D, Schindler disease, scheie syndrome, Sialuria, Salla disease, sialidosis types I/II, Sly syndrome, Tay-Sachs disease, Vogt-Spielmeyer disease, and Wolman disease.
137. The method of paragraph 130, wherein the lysosomal storage disease, disorder, and/or condition is Gauche disease.
138. A method of identifying and/or characterizing a lysosomal activating agent, the method comprising steps of:
providing a system comprising at least one lysosomal enzyme;
contacting the system with a test lysosomal activating agent;
determining level or activity of the lysosomal enzyme when the test lysosomal activating agent is present;
comparing the determined level or activity with a reference level or activity so that the test lysosomal activating agent is identified or characterized relative to the reference.
139. The method of paragraph 138, wherein the system comprises a lysosome.
140. The method of paragraph 138, wherein the system comprises a cell.
141. The method of paragraph 138, wherein the system comprises an organism.
142. The method of paragraph 138, wherein the system comprises a neuronal cell.
143. The method of paragraph 138, wherein the reference comprises a level or activity observed under otherwise comparable conditions when a reference lysosomal activating agent is present.
144. The method of paragraph 138, wherein the method further comprises a step of comparing the determined level or activity with that observed under otherwise comparable conditions when the reference lysosomal activating agent is absent.
145. The method of paragraph 144, wherein step of determining level or activity comprises determining extent of trafficking.
146. The method of paragraph 144, wherein step of determining level or activity comprises determining extent of type of aggregation.

EXAMPLES

The present invention will be better understood in connection with the following Examples. However, it should be understood that these examples are for illustrative purposes only and are not meant to limit the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1: Depletion of GCase Polypeptide Compromises Protein Degradation Capacity and Increases α-Synuclein Levels in Neurons Experiments in this Example illustrate that knockdown (KD) of GCase polypeptide in neurons leads to decreased lysosomal degradation capacity and consequently increased levels of α-synuclein protein. Furthermore, experiments in this Example also confirmed that endogenous mutations in GCase polypeptide affected lysosomal proteolysis and caused the preferential accumulation of α-synuclein.

Figure 2A:
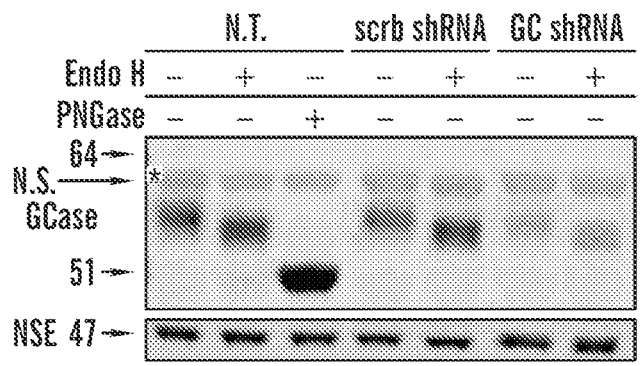
FIGS. 2A-2G demonstrate the specificity of the shRNA GCase polypeptide lenti-infection system and changes to lysosomal protein levels upon GCase polypeptide knockdown.

To test the biological effects of GCase polypeptide KD in neurons, shRNA-mediated KD of GCase polypeptide was achieved by lentiviral infection. This resulted in a 50% reduction in GCase polypeptide levels compared to non-transduced neurons or control scrambled (scrb) shRNA-infected neurons (FIGS. 1A and 1B). The level and activity of GCase polypeptide was monitored after shRNA treatment. The levels of mature lysosomal GCase polypeptide were analyzed by endoglycosidase H (endo H) treatment, an enzyme that cleaves high mannose moieties of endoplasmic reticulum (ER) proteins. This analysis revealed lower levels endo H-resistant GCase polypeptide upon infection with GCase polypeptide shRNA constructs, suggesting a depletion of the lysosomal form (FIG. 2A). Further analysis of whole cell lysates showed a decline in GCase polypeptide activity (FIG. 1B), increased cellular lipids were seen with BODIPY 493, and increased GlcCer was observed by immunoflourescence (FIGS. 1C and 1D). GlcCer accumulation was also validated by mass spectrometry, which revealed a 4-fold increase of GlcCer in GCase polypeptide-depleted neurons, whereas the levels of ceramide and other sphingolipids remained unchanged (FIG. 1B and FIG. 2D). Analysis of other lysosomal proteins and activity suggested that the constructs specifically decrease GCase polypeptide (FIGS. 2C-2F). Neurotoxicity upon GCase polypeptide KD was assessed by neurofilament (NF) immunostaining, a sensitive method that detects the degeneration of neuritis in cell culture before the occurrence of more severe nuclear toxicity (Zala et al., Neurobiol. Dis. 20:785, 2005). This analysis revealed no change in neurotoxicity when assessed at 7 days post-infection (dpi), suggesting that neurons have the ability to tolerate alterations in the GlcCer metabolizing pathway within this timeframe.

Figure 2B:
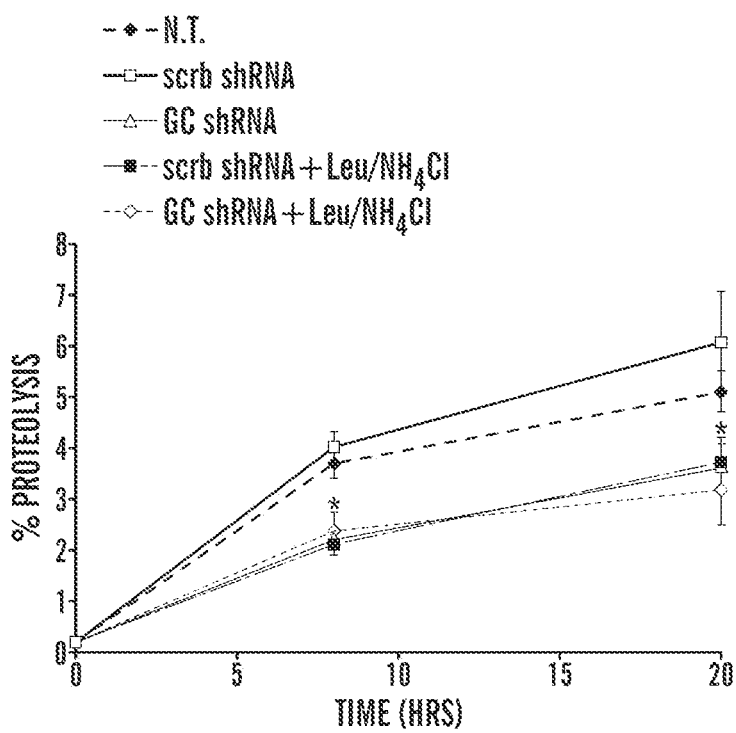
Figure 2C:
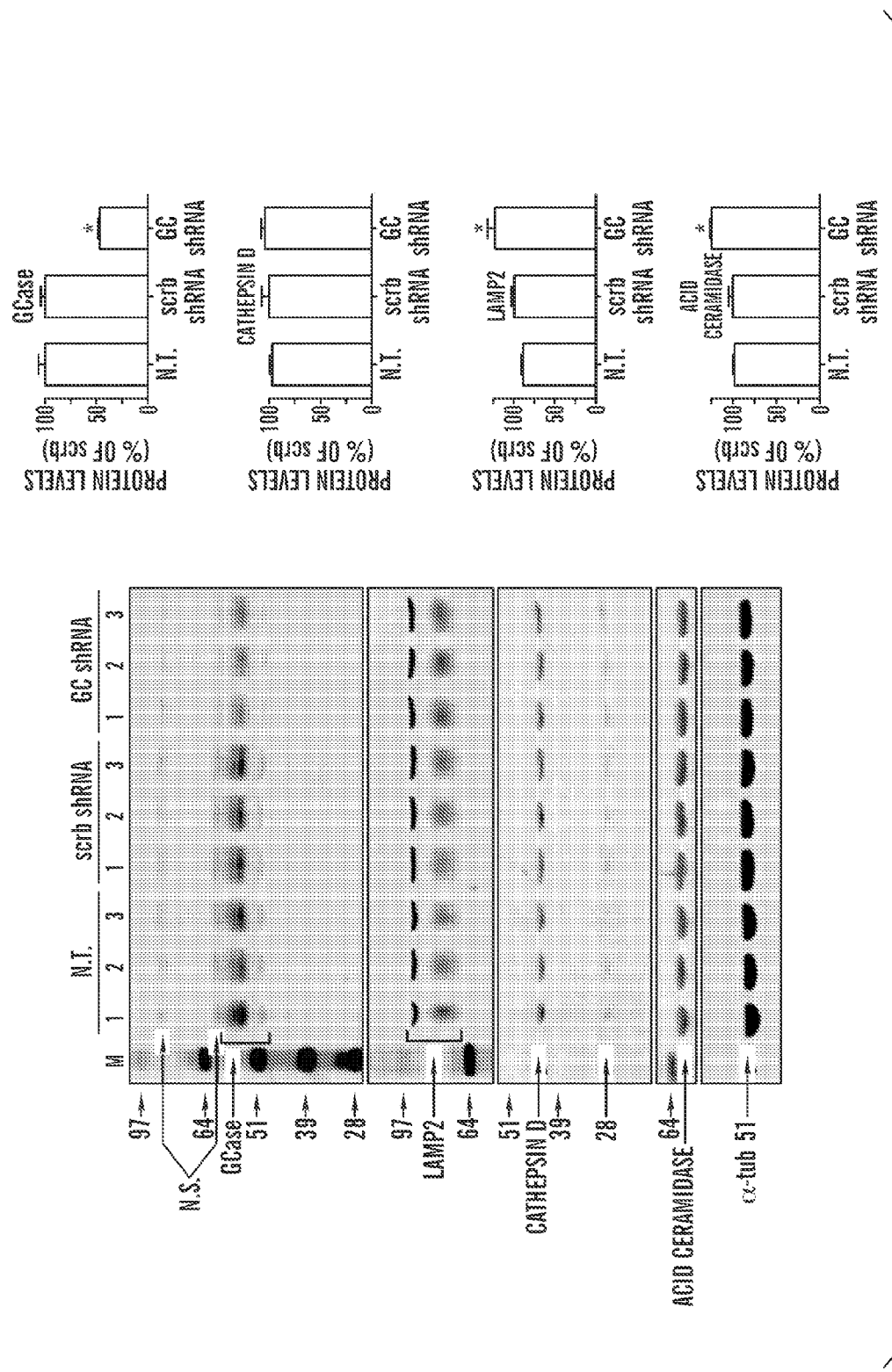
Figure 2D:
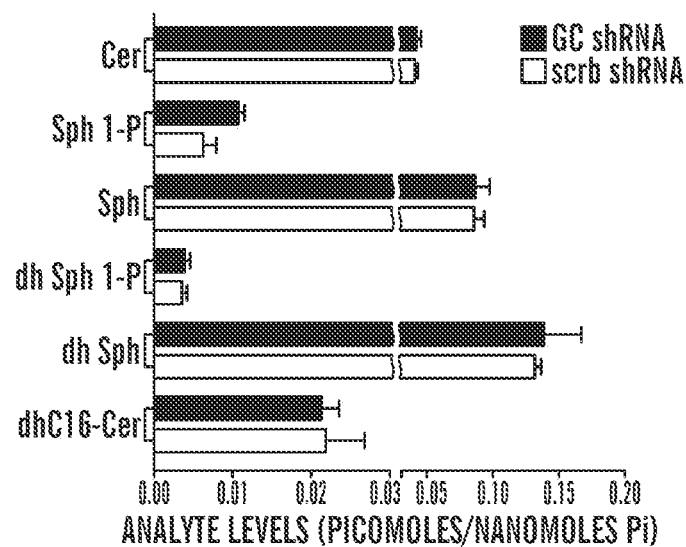
Figure 2E:
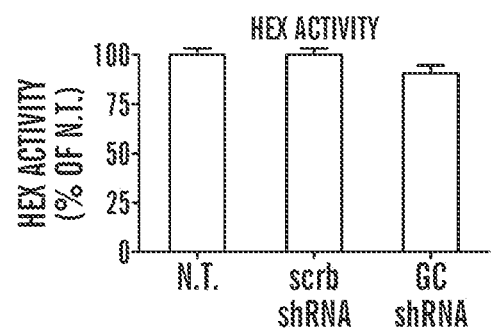
Figure 2F:
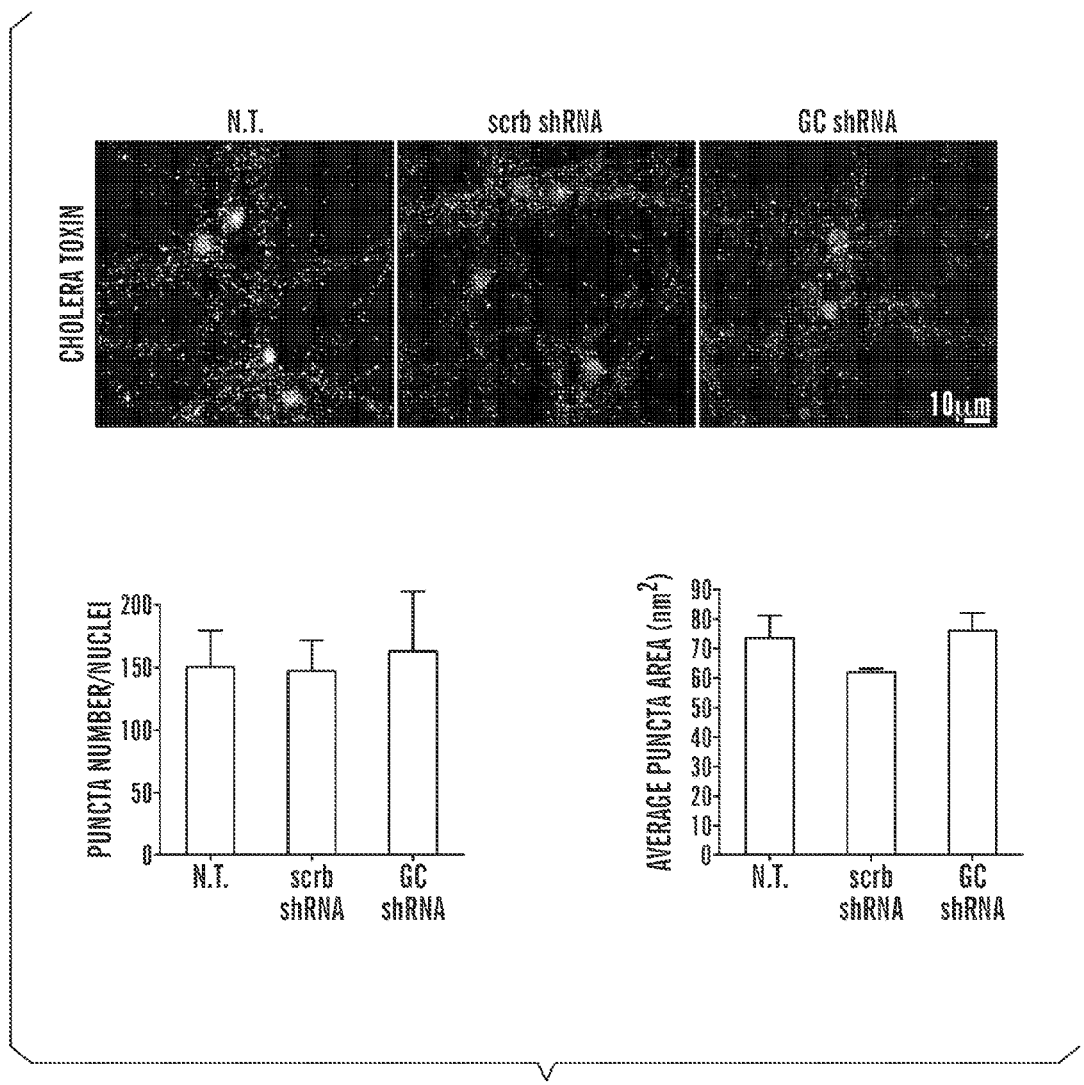
Figure 2G:
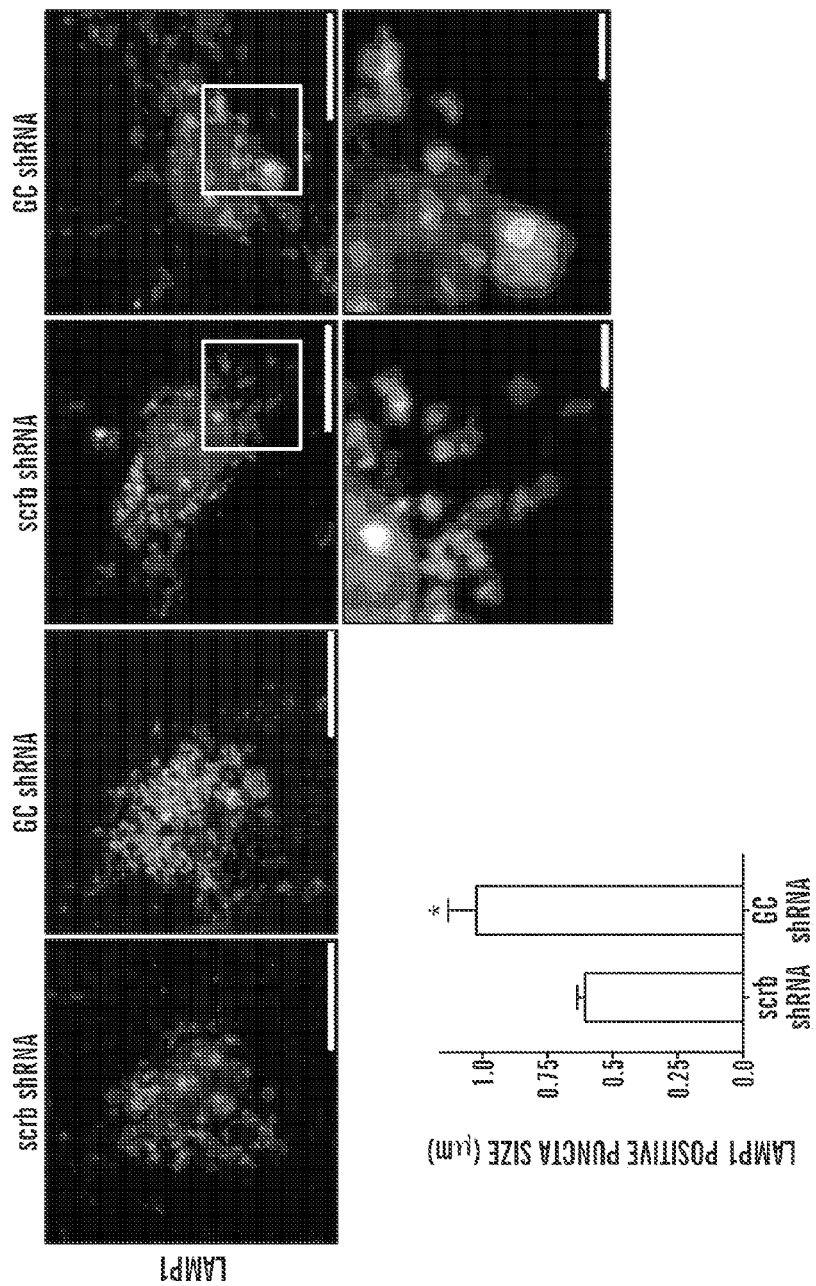

In this Example, proteolysis of long-lived proteins in living neurons was also analyzed and it was found that GCase polypeptide KD significantly reduced the rate of proteolysis of these proteins by 40% (FIG. 1E and FIG. 2B). In this Example, a test was conducted to determine whether GCase polypeptide KD affects a lysosomal degradation pathway. In this test, neurons were treated with the well-established lysosomal inhibitors ammonium chloride ($NH_4Cl$) and leupeptin. These compounds did not additively inhibit the proteolysis in GCase polypeptide shRNA-treated cells, indicating that GCase polypeptide KD affects a lysosomal-mediated pathway (FIG. 1E). This was also confirmed by immunoflourescence analysis of LAMP1, a lysosomal marker, which revealed accumulation and enlargement of LAMP1-positive puncta in neurons (FIG. 2G).

Figure 1G:
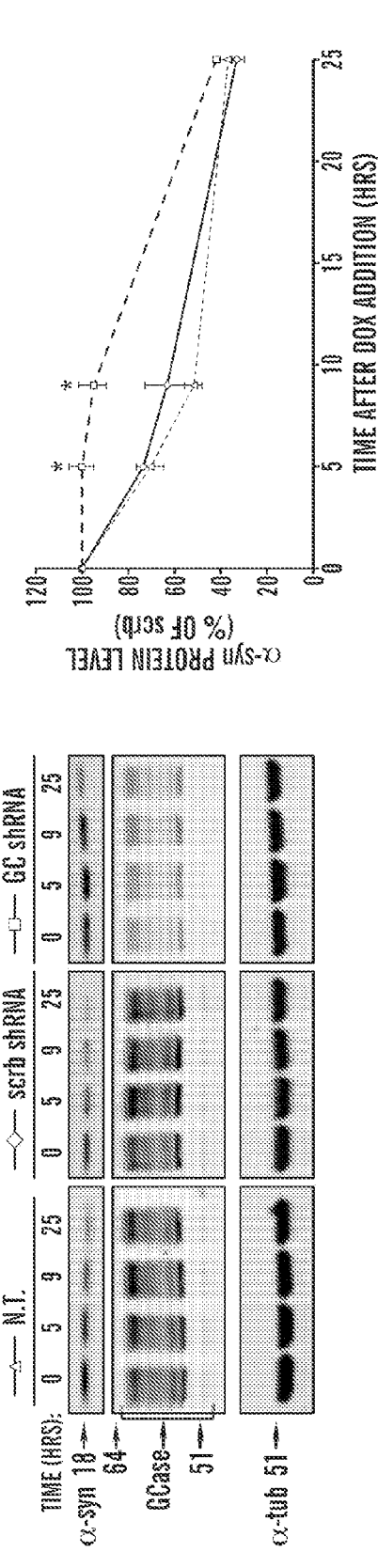

In this Example, it was demonstrated that the KD of GCase polypeptide increased the steady state levels of α-synuclein by 1.8-fold relative to controls, whereas the levels of another disease-associated aggregation-prone protein, tau, were not changed in this particular study (FIG. 1F). Also there was no change in mRNA levels of α-synuclein, which suggested that the observed increase in α-synuclein protein levels resulted from compromised protein degradation (FIG. 1F). In this Example, analysis of α-synuclein levels after KD of GCase polypeptide was also performed in a human neuroglioma cell line (H4), which expresses wild-type (WT) α-synuclein under the control of a tetracycline-inducible promoter ("tet-off"). α-synuclein expression was turned off by Dox to determine the α-synuclein degradation rate, which revealed that GCase polypeptide KD impeded the clearance of α-synuclein (FIG. 1G).

Figure 3A:
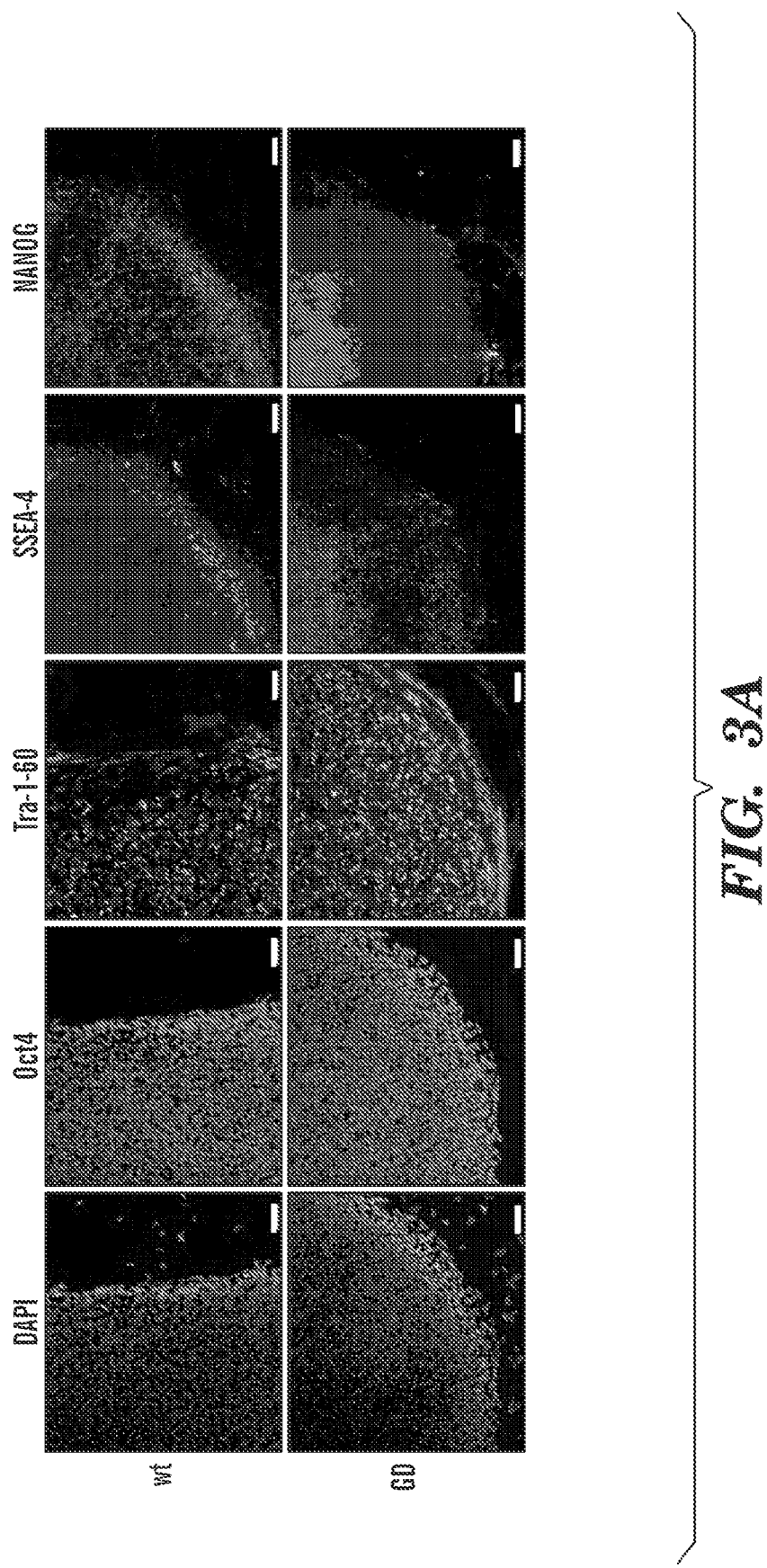
Figures 4D, 4E:
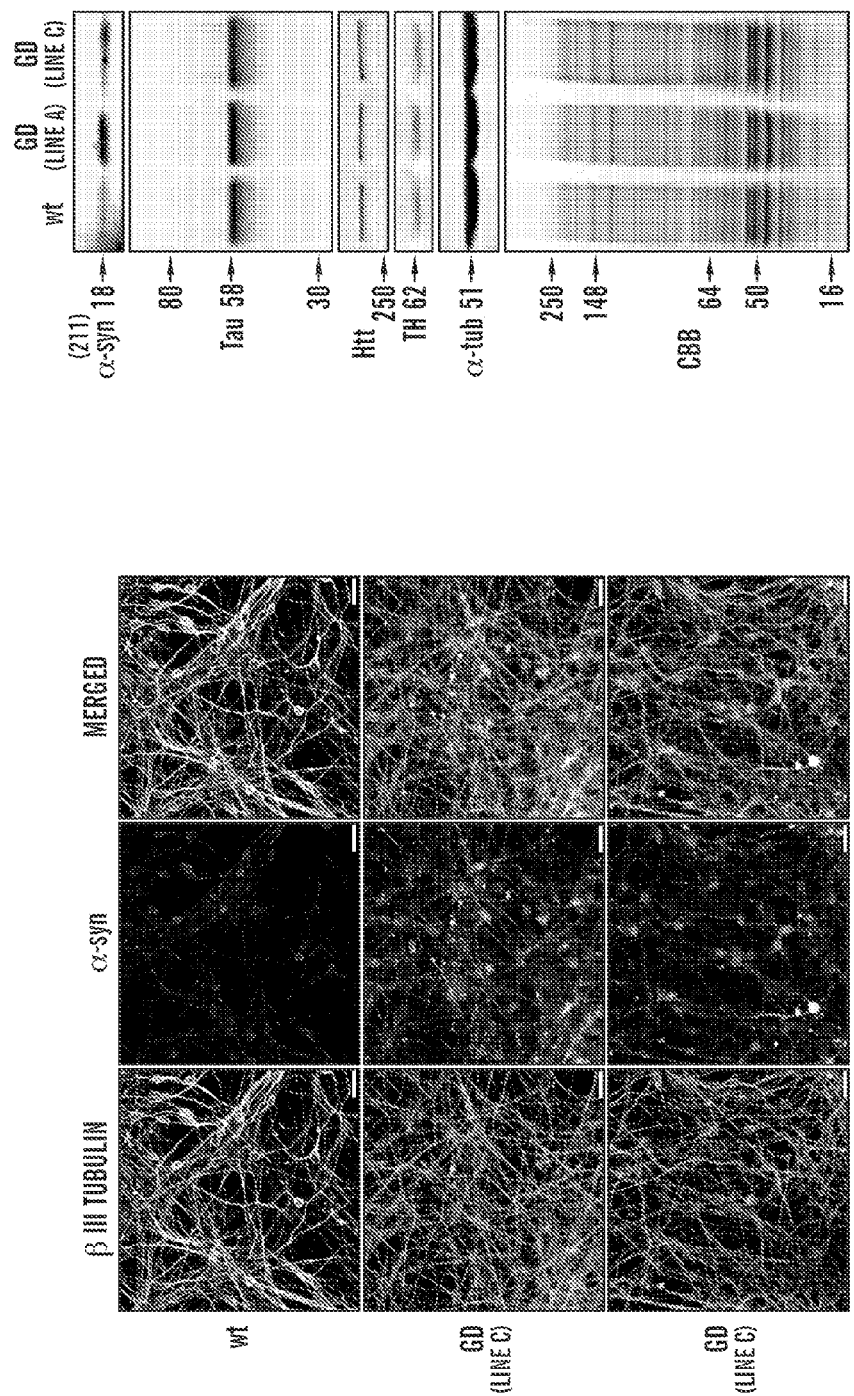
Figure 4F:
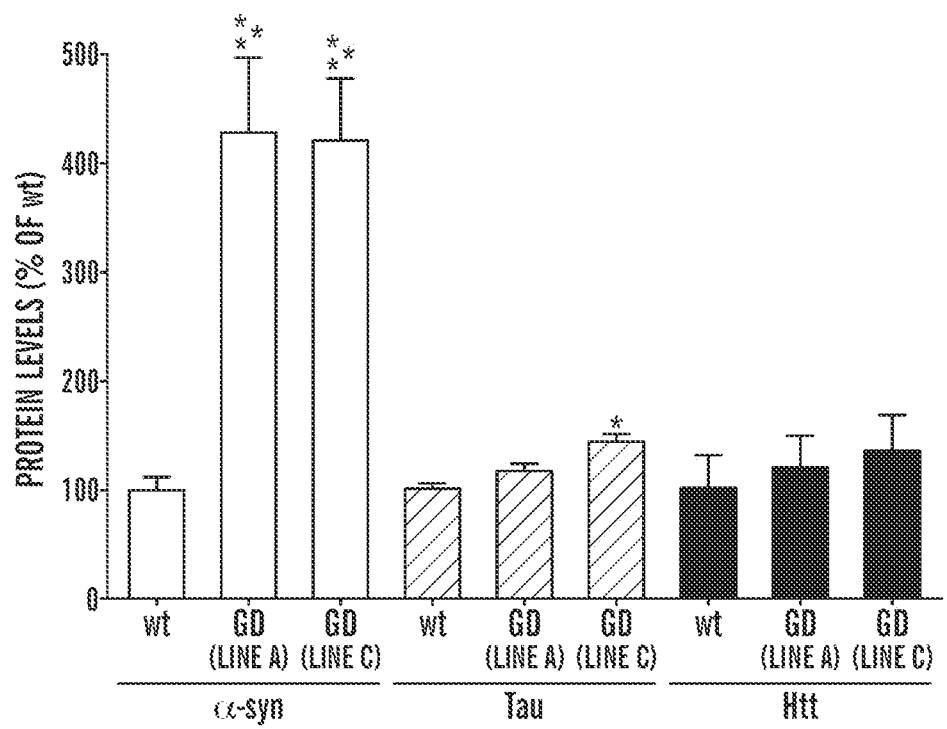

In this Example, to confirm the results obtained in primary cell culture from above, dopaminergic neurons were generated from induced pluripotent stem (iPS) cells derived from skin fibroblasts of a GD patient. Analysis of GD iPS cells revealed the expression of Oct4, Tra-1-60, SSEA-4, and nanog, indicating that GD iPS cells contain the essential pluripotency factors, as well as normal chromosomal number, size, and genomic structure (FIGS. 3A and 3B). Dopaminergic neurons were induced from iPS cells by a previously established protocol (Seibler et al., J. Neurosci. 31:5970, 2011) to yield ~80% of cells that expressed the neuron-specific β III tubulin, and ~10% that expressed the dopaminergic marker tyrosine hydroxylase (TH) (FIG. 4A). Genotyping analysis confirmed that GD, but not WT, iPS neurons harbored the expected mutations in GCase polypeptide (N370S/84GG insertion) and lower levels of GCase polypeptide and activity (FIG. 4B, Table 14). In addition, WT and GD cells did not contain other mutations previously shown to cause PD (Table 14). Radioactive pulse-chase experiments in GD iPS neurons revealed a decline in proteolysis of long-lived proteins compared to WT cells, and the addition of lysosomal inhibitors did not further affect proteolysis (FIG. 4C). Proteolysis measurement of short-lived proteins revealed no change compared to WT cells (FIG. 4C, inset). Immunofluorescence and western blot analysis revealed a dramatic increase in α-synuclein protein levels in GD iPS neurons compared to WT cells (FIGS. 4D and 4E). In this study, no changes were observed in the levels of huntingtin and only mild changes of tau in GD iPS neurons, indicating that GCase polypeptide mutations primarily affect α-synuclein levels (FIGS. 4E and 4F).

TABLE 14

Sequenom MassARRAY genotyping analysis of genomic DNA isolated from wt and GD neurons generated from iPS cells.

| SNP ID | Alleles (minor/major) | Gene | protein mutation | wt | GD |
|---|---|---|---|---|---|
| GBA--84GG | G/DEL | GBA1 | L84TER | DEL/DEL | G/DEL |
| GBA-N370S | G/A | GBA1 | N370S | A/A | A/G |
| rs2230288 | A/G | GBA1 | E326K | G/G | G/G |
| rs421016 | A/C/G/T | GBA1 | L444P | G/G | G/G |
| rs104893877 | A/G | SNCA | A53T | G/G | G/G |
| rs104893878 | C/G | SNCA | A30P | G/G | G/G |
| rs104893875 | A/G | SNCA | E46K | G/G | G/G |
| rs55774500 | A/C | PARKIN | A82E | C/C | C/C |
| rs5030732 | A/C | UCHL1 | S18Y | C/C | C/C |
| rs45539432 | T/C | PINK1 | Q456TER | C/C | C/C |
| PINK1 A344T | T/A | PINK1 | A344T | A/A | A/A |
| rs28938172 | C/T | PARK7/DJ1 | L166P | T/T | T/T |
| rs74315351 | A/G | PARK7/DJ1 | M261 | G/G | G/G |
| rs74315353 | C/G | PARK7/DJ1 | E64D | G/G | G/G |
| rs35801418 | G/A | LRRK2 | Y1669C | A/A | A/A |
| rs34778348 | A/G | LRRK2 | G2385R | G/G | G/G |

Example 2: Depletion of GCase Polypeptide Enhances α-Synuclein-Mediated Neurotoxicity Through Aggregation-Dependent Mechanisms Experiments in this Example demonstrate that GCase polypeptide KD promotes accumulation and neurotoxicity of α-synuclein through polymerization-dependent mechanisms.

Figure 5H:
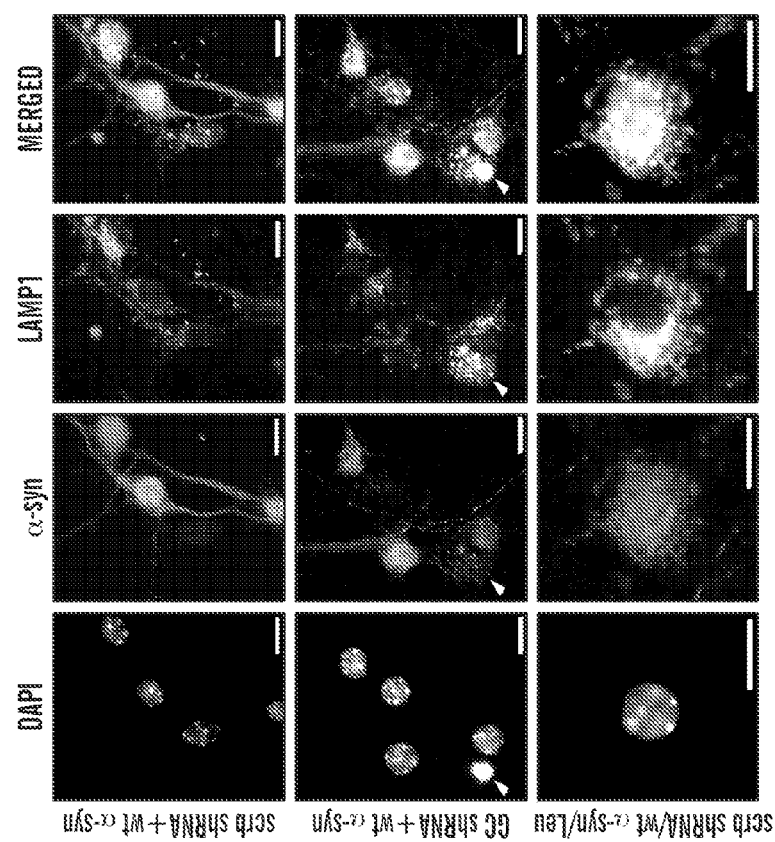
Figure 5H:
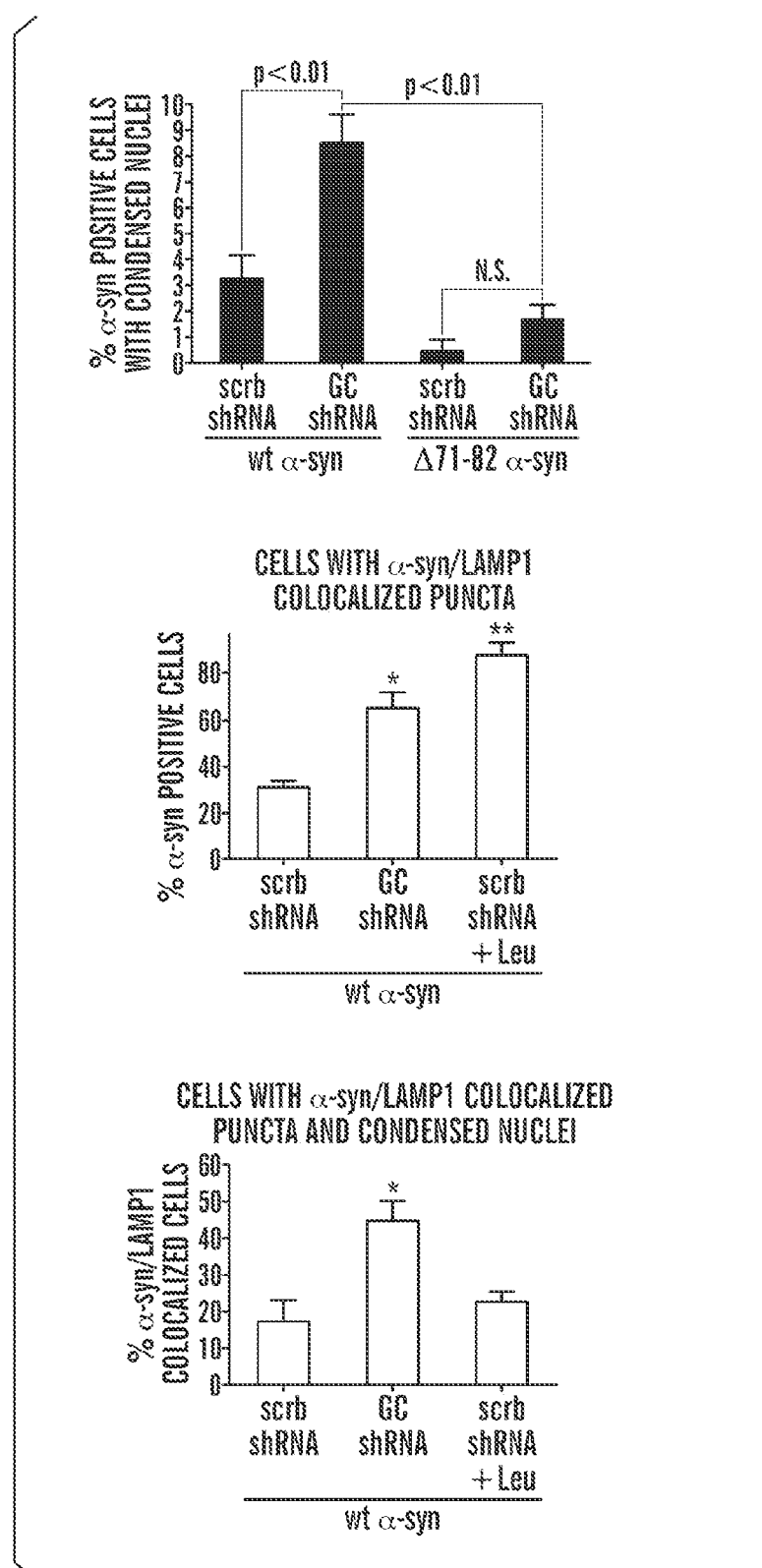
Figure 6D:
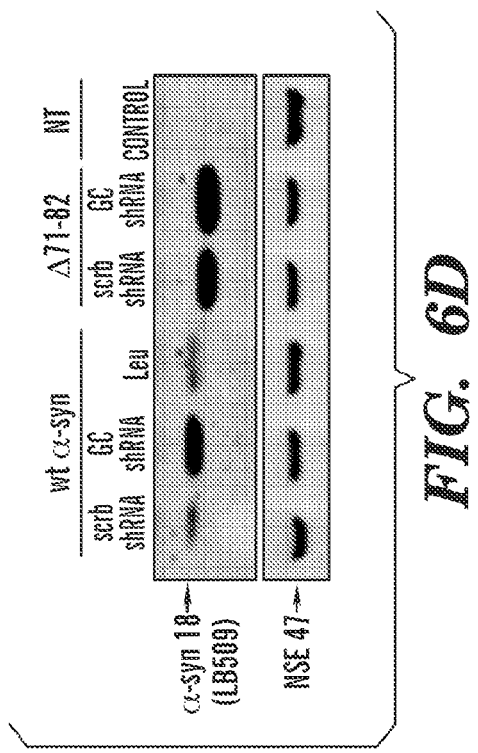
Figure 6C:
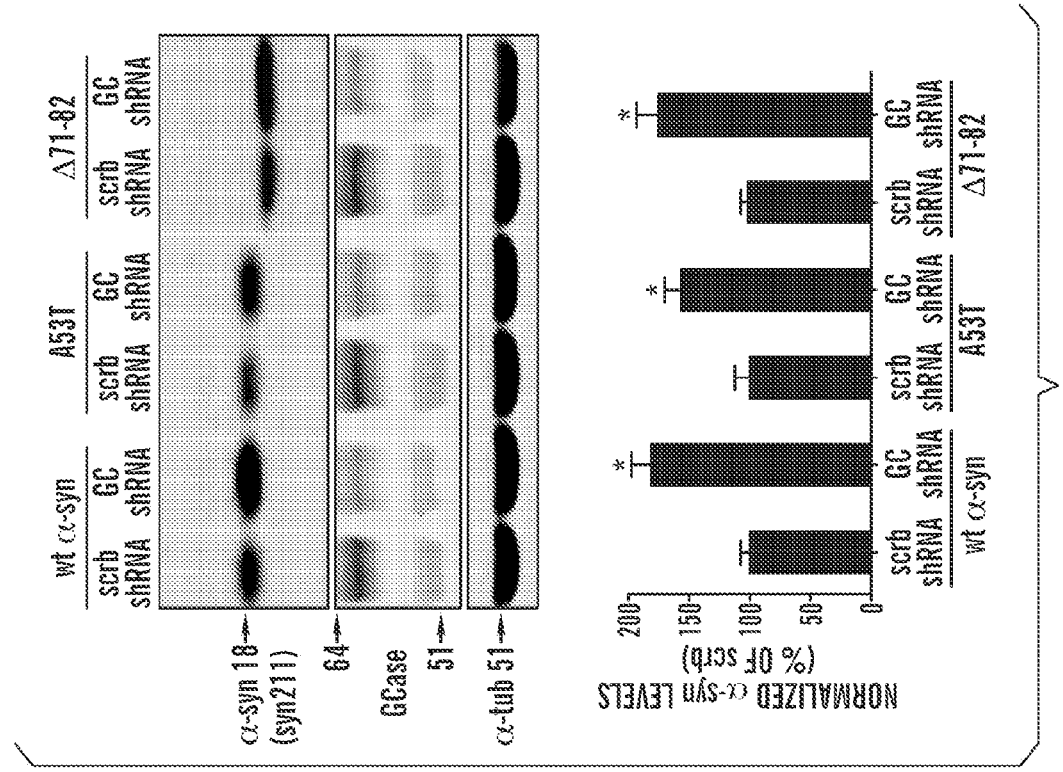

In this Example, human α-synuclein was overexpressed by lentiviral transduction. Immunostaining with human-specific anti-α-synuclein monoclonal antibodies (mAbs) syn211 and LB509 revealed the expected punctate staining pattern in neuronal extensions consistent with a synaptic enrichment of α-synuclein (FIG. 5A) (Maroteaux et al., J. Neurosci. 8: 2804, 1988). In this Example, to examine the contribution of α-synuclein misfolding to neurotoxicity, the PD-linked A53T α-synuclein mutant as well as an artificial fibrillization-incompetent mutant, Δ71-82 α-synuclein (Giasson et al., J. Biol. Chem. 276: 2380, 2001) were expressed in primary neurons and increased levels of all three mutants without neurotoxicity at 7 dpi (FIG. 6 and FIG. 5B) were observed. By contrast, expression of human WT α-synuclein with GCase polypeptide KD resulted in an ~25% decline in viability by NF intensity and neuronal volume measurements compared to controls (FIGS. 6A and 6B). Western blot analysis with mAb syn211 of Triton X-100 soluble (T-sol) lysates indicated that α-synuclein protein levels increased by 1.8-fold concomitantly with the enhanced toxicity (FIG. 6C). Importantly, KD of GCase polypeptide also enhanced the toxicity of titer-matched A53T α-synuclein-infected cells to the same extent as WT α-synuclein, whereas no toxicity was observed in Δ71-82 α-synuclein-expressing neurons (FIGS. 6A and 6B). Toxicity by WT α-synuclein expression/GCase polypeptide KD was further verified by measurement of condensed nuclei (FIG. 5H, right). In this Example, neuronal viability was also determined at later time points after infection (10 dpi) and it was found that toxicity was further enhanced in WT α-synuclein/GCase polypeptide-depleted cells (~50% viability assessed by NF intensity) (FIG. 5C). Because GCase polypeptide KD resulted in increased levels of A53T and Δ71-82 α-synuclein proteins to a similar extent as WT α-synuclein (FIG. 6C), the toxicity appears to depend on amino acids 71-82 of α-synuclein, a mostly hydrophobic region that is required for α-synuclein polymerization (Giasson et al., J. Biol. Chem. 276: 2380, 2001).

Example 3: Enhanced α-Synuclein-Mediated Neurotoxicity by GCase Polypeptide Depletion is Dependent on the Formation of Different α-Synuclein Species Experiments in this Example indicate that alterations in the GCase polypeptide-mediated GlcCer metabolic pathway influences the formation of toxic soluble and insoluble α-synuclein species, causing a stabilization of soluble high-molecular-weight (HMW) forms of α-synuclein.

Figure 6E:
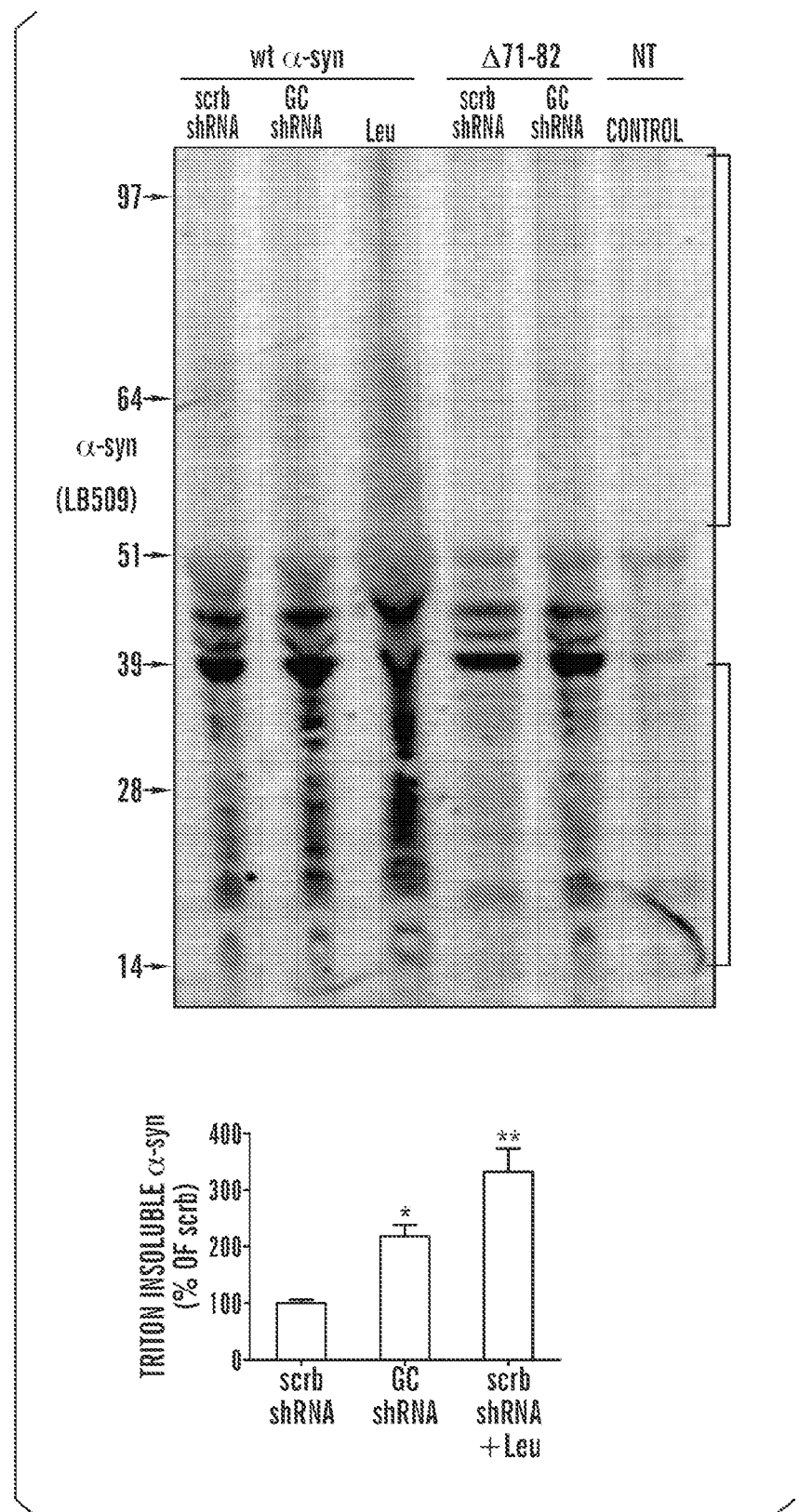
Figure 6F:
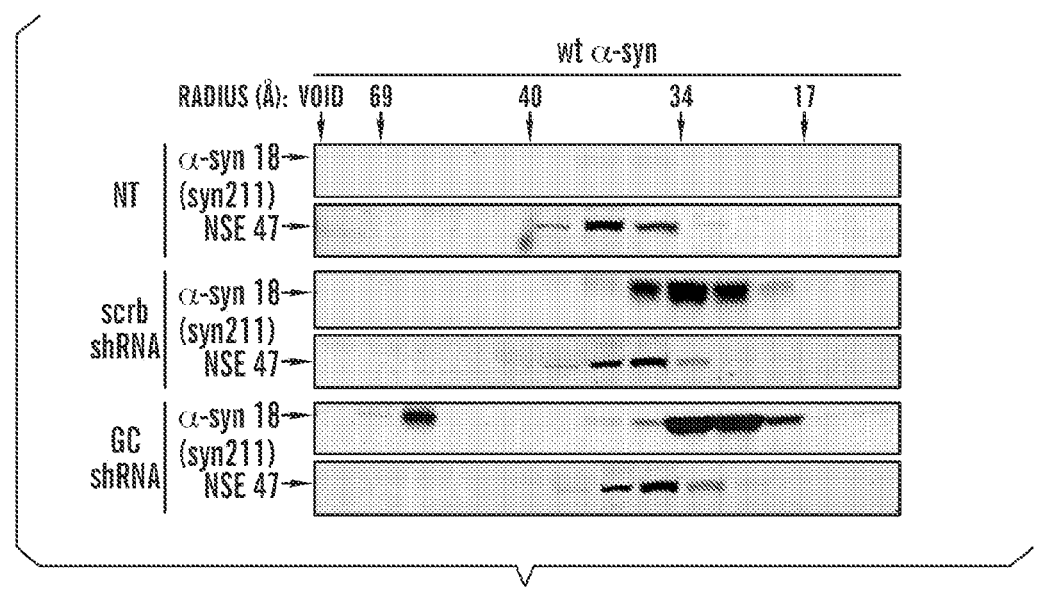
Figure 6G:
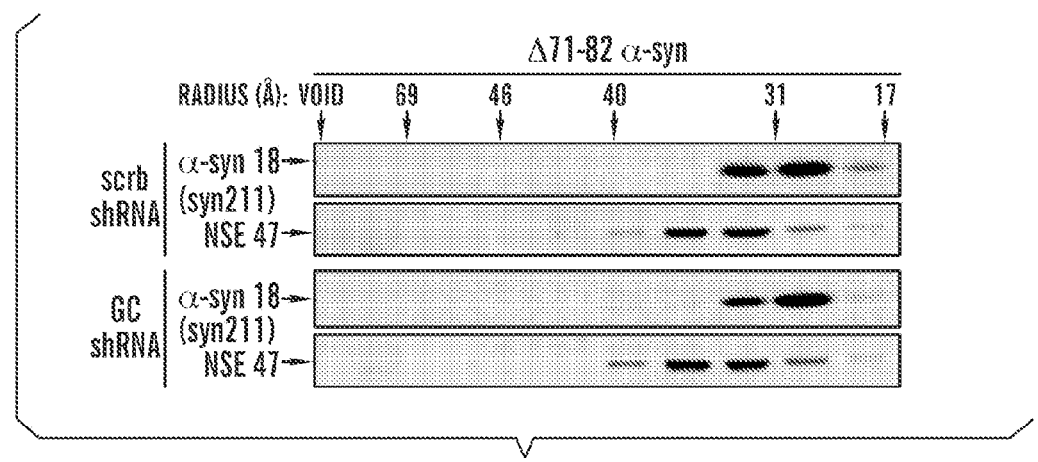
Figure 6H:
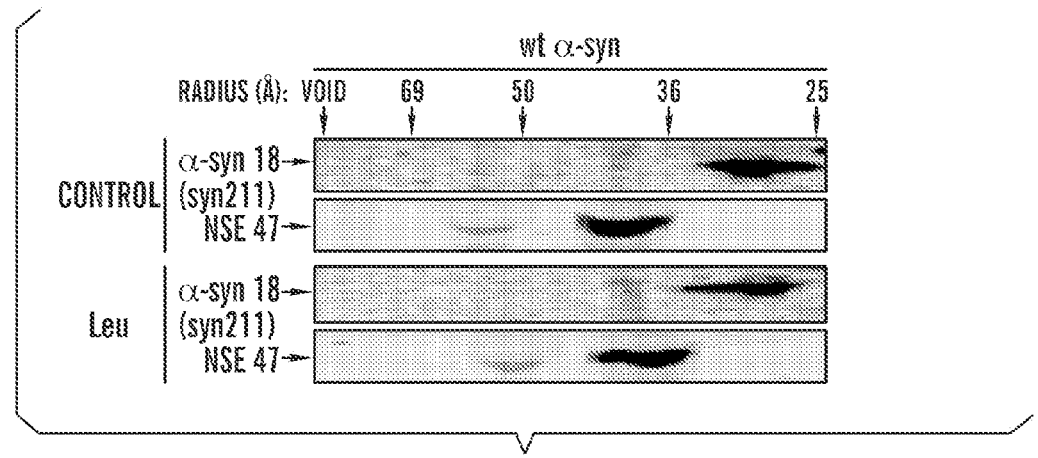

In this Example, it was directly determined whether GCase polypeptide KD affects α-synuclein polymerization in neurons. Lysates were sequentially extracted and separated into T-sol and -insoluble fractions followed by western blot with mAb LB509. This revealed an increase of T-sol monomeric α-synuclein (18 kDa), as well as T-insoluble α-synuclein species migrating between 14 and 39 kDa in size upon GCase polypeptide KD (FIGS. 6D and 6E). In this Example, the presence of T-sol oligomeric α-synuclein species was determined utilizing native size exclusion chromatography (SEC) followed by SDS-PAGE/western blot of the collected fractions. GCase polypeptide KD resulted in the formation of HMW assemblies with a molecular radius of 64-95 Å, in addition to the normal monomeric form eluting as a 31-34 Å sized particle (FIG. 6F). Interestingly, analysis of Δ71-82 α-synuclein-expressing neurons revealed no change in the elution profile upon GCase polypeptide KD (FIG. 6G), further indicating that GCase polypeptide KD induces the formation of a soluble HMW oligomeric α-synuclein that depends on the residues 71-82. These results further suggested that the ability of α-synuclein to form soluble oligomers and insoluble species is a critical determinant for neurotoxicity induced by GCase polypeptide KD.

As discussed above, the increased α-synuclein levels and toxicity that occur with GCase polypeptide depletion may result from generalized lysosomal inhibition or may be due to alterations in GlcCer lipid metabolism. To distinguish between these two possibilities, in this Example, the lysosomal protein degradation was inhibited with leupeptin in WT α-synuclein-expressing neurons and the neurotoxicity was assessed. It was found that leupeptin treatment did not enhance α-synuclein-mediated neurotoxicity (FIGS. 5D and 5H). Biochemical analysis revealed an increase of T-insoluble α-synuclein in leupeptin-treated cells but no change in the amount of soluble α-synuclein (FIGS. 6D and 6E). This was corroborated by immunostaining analysis, which showed an increase in the total α-synuclein immunostaining intensity in leupeptin-treated compared to control cells (FIG. 5F). SEC analysis also showed that soluble HMW α-synuclein were not detectable in neurons upon leupeptin treatment (FIG. 6H), consistent with their rapid consumption into insoluble species. Further in this Example, when comparing the increase of total α-synuclein (soluble and insoluble) by leupeptin treatment or GCase polypeptide KD, it was found that both approaches had similar effects (FIG. 5F). Western blot analysis also indicated a comparable increase in the levels of LC3-II, a well-established lysosomal substrate, by leupeptin or GCase polypeptide KD (FIG. 5E). Thus, despite similar effects on the total α-synuclein levels by leupeptin or GCase polypeptide KD, only GCase polypeptide KD increased the steady-state levels of soluble HMW α-synuclein. In this Example, sequential extraction followed by SDS-PAGE/Coomassie brilliant blue (CBB) staining was used to determine the effect of leupeptin treatment on the solubility of total cellular proteins. Interestingly, it was found that whereas leupeptin treatment increased the levels of total insoluble proteins by ~2-fold, GCase polypeptide KD had no effect (FIG. 5G). This Example indicates that GCase polypeptide KD preferentially affects the solubility of α-synuclein.

Example 4: GlcCer Influences the Aggregation of α-Synuclein In Vitro by Stabilizing Soluble Oligomeric Intermediates Experiments in this Example indicate that GlcCer selectively stabilizes the formation of soluble oligomeric intermediates on-pathway to forming amyloid fibrils and when the concentration of GlcCer is surpassed as the accumulation of these soluble on-pathway intermediates continues, it results in the rapid formation of thioT-positive amyloid fibrils.

In this Example, lipid dispersions made of mixtures of purified GlcCer and brain phosphatidylcholines (PCs) were incubated with α-synuclein at physiological conditions (pH 7.4, 37° C.). Electron microscopy (EM) analysis indicated the formation of tubules consisting of polymerized GlcCer (FIGS. 7G-7I), similar to those previously observed in Gaucher cells in patients and mouse models (Lee, PNAS 61: 484, 1968). The analysis of α-synuclein aggregation under physiological conditions showed that GlcCer had no effect on fibril formation (FIG. 8), consistent with previous observations (Martinez et al., Biochemistry 46:1868, 2007).

Figure 5I:
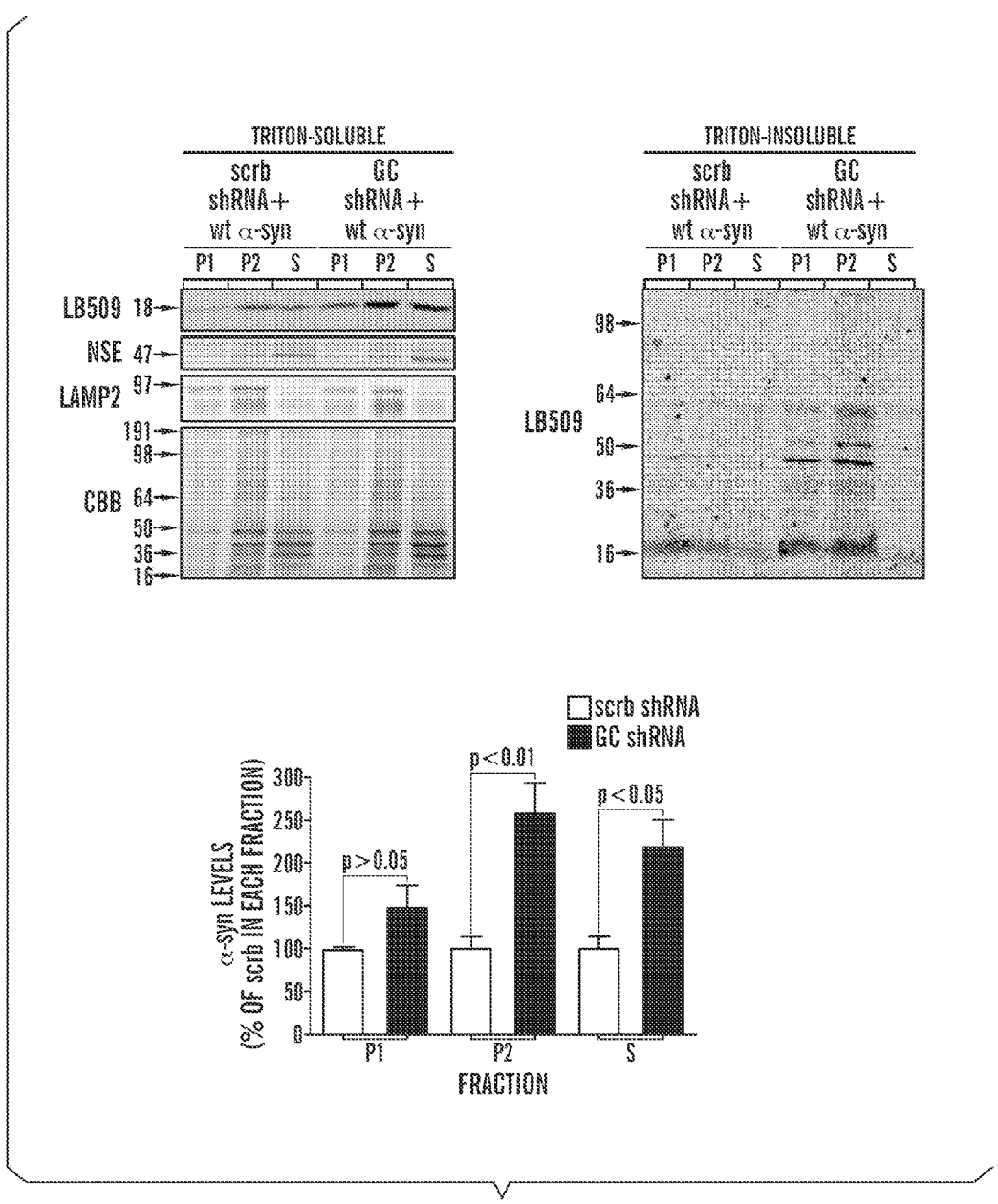

Next in this Example, the effect of GlcCer on α-synuclein fibril formation was assessed under acidic conditions (pH 5.0, 37° C.), to simulate a lysosome-like environment in vitro because the neuronal culture data had indicated increased colocalization of α-synuclein with LAMP1 upon GCase polypeptide KD (FIGS. 5H and 5I). The data in panels H and I had indicated that increased punctate α-synuclein structures colocalize with LAMP1, a lysosomal marker, upon GCase polypeptide knockdown (panel H). An increased frequency of condensed nuclei in WT α-synuclein/GC-depleted cells, compared to WT α-synuclein/scrb shRNA cells (panel H), was consistent with a decline in neuronal viability. Leupeptin-treated cells, although demonstrated a dramatic increase in the percentage of cells containing α-synuclein/LAMP1 colocalized puncta (~90%), and did not alter the percentage of cells with condensed nuclei compared to untreated control cells when assessed at 7 dpi (panel H). However, leupeptin treatment did result in neurotoxicity at later time points (>12 dpi). Subcellular fractionation of WT α-synuclein-expressing lysates indicated that lysosome-enriched fractions (P2) of GCase polypeptide depleted neurons contained more α-synuclein compared to scrb shRNA control infected cells; however increased soluble α-synuclein in the supernatant fraction was observed (panel I). The α-synuclein detected in P2 was in the form of a T-sol 18 kDa monomer (panel I, left), as well as T-insoluble monomer and multimers (panel I, right). The data thus demonstrated that GCase polypeptide knockdown enhanced the colocalization of α-synuclein with LAMP1 accumulated in the lysosome-enriched P2 fraction, and suggested that α-synuclein may accumulate within lysosomes of GCase polypeptide-depleted neurons.

Figure 7A:
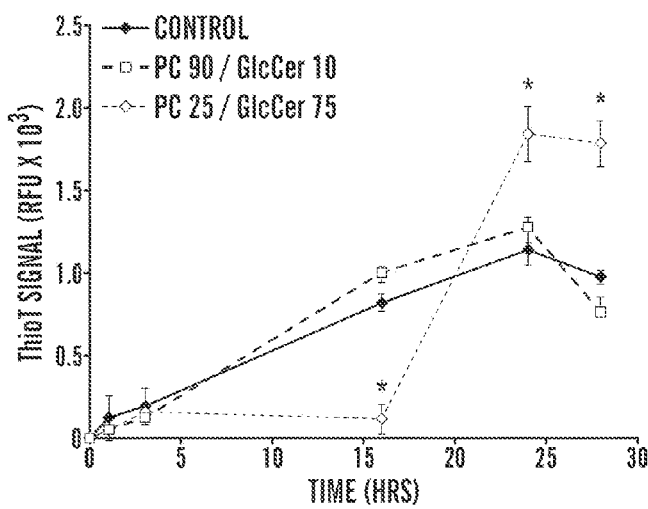
FIGS. 7A-7I show that GlcCer directly influences the in vivo fibril formation of recombinant α-synuclein and stabilizes soluble oligomeric species.
Figure 8A:
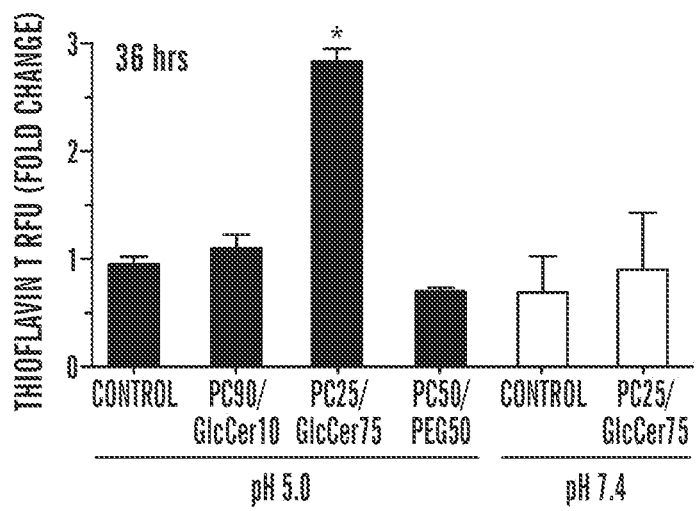
FIGS. 8A-8F demonstrate that GlcCer specifically affects the in vitro formation of α-synuclein fibrils and soluble oligomers in pH-dependent manner. Purified α-synuclein was incubated with lipid dispersions as described in FIGS. 7A-7I.
Figure 8B:
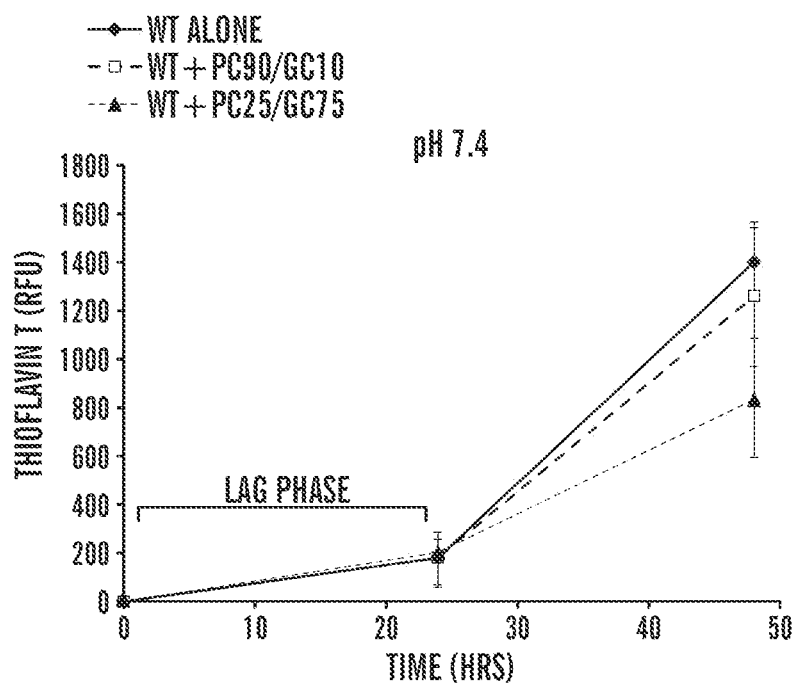

The experiments in this Example revealed that acidic reactions containing lipid dispersions made of 90% PC and 10% GlcCer (PC90/GlcCer10) did not significantly influence the fibril formation of α-synuclein compared to control reactions containing α-synuclein alone (FIG. 7A, FIG. 8A). However, increasing the amount of GlcCer to 75% while keeping the total lipid amount constant (PC25/GlcCer75) altered the kinetic profile of α-synuclein fibril formation by delaying the formation of insoluble thioT-positive α-synuclein fibrils, extending the lag time from 2 to 16 hr (FIG. 7A).

Figure 7B:
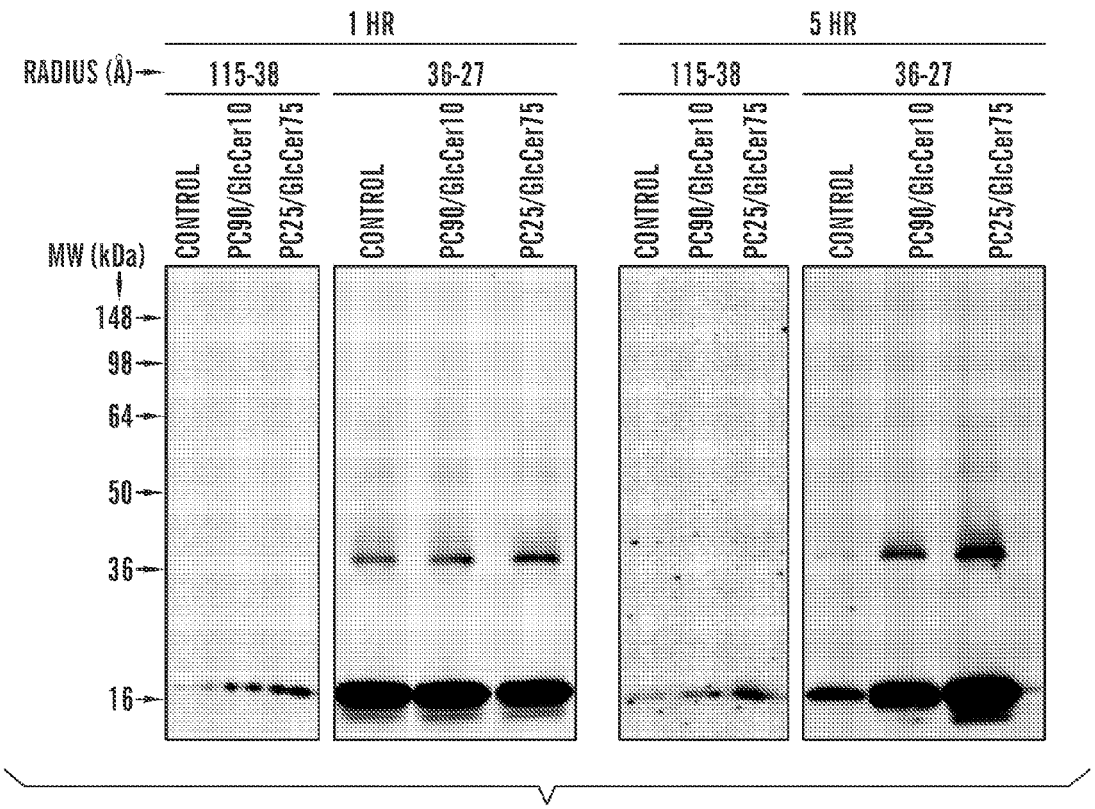
Figure 7C:
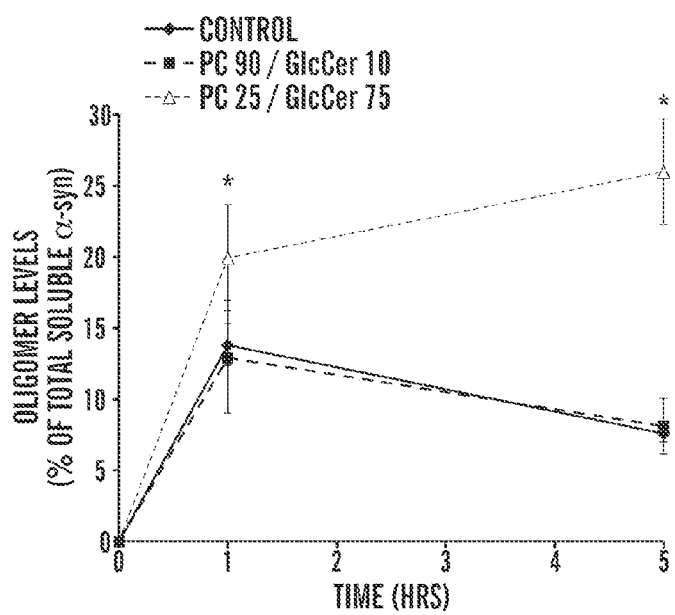
Figure 7D:
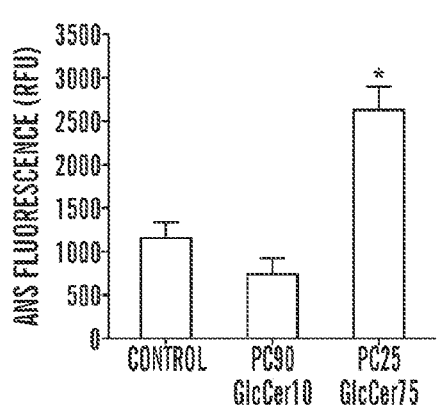
Figure 7E:
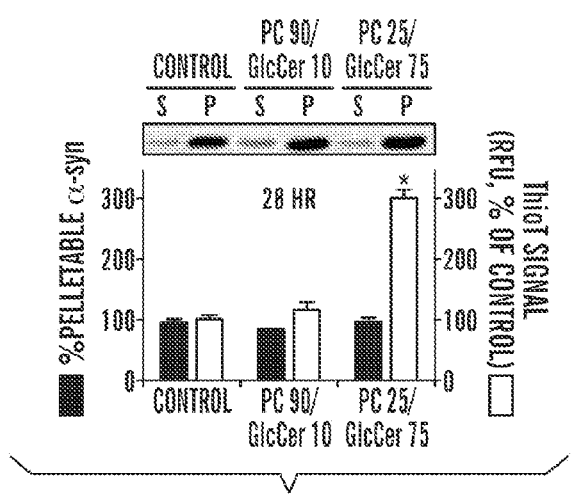
Figure 7G:
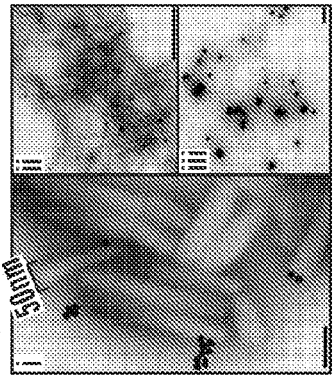
Figure 7I:
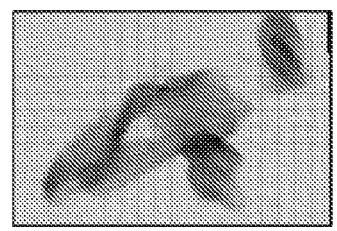
Figure 8C:
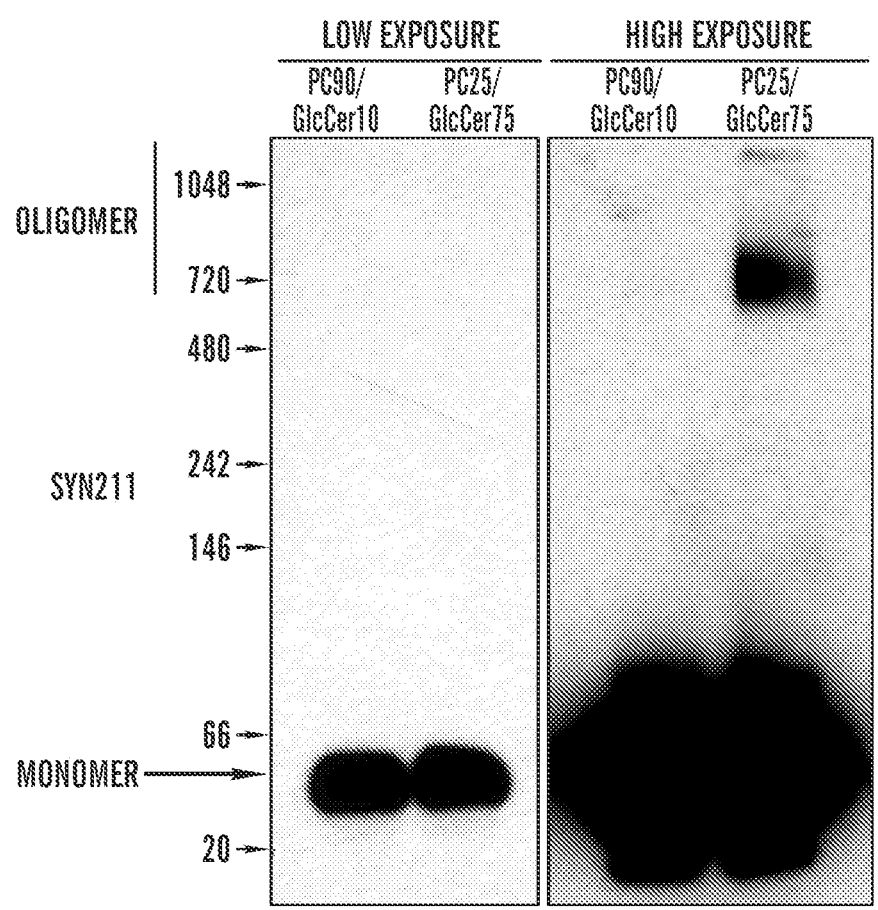
Figure 8D:
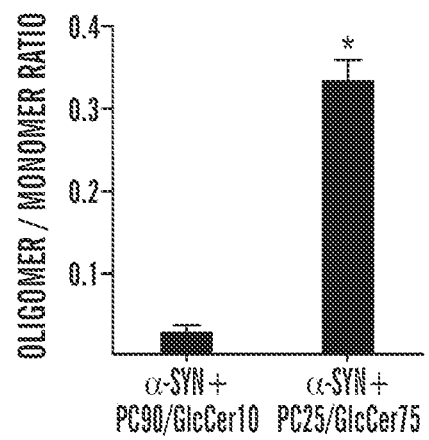
Figure 8E:
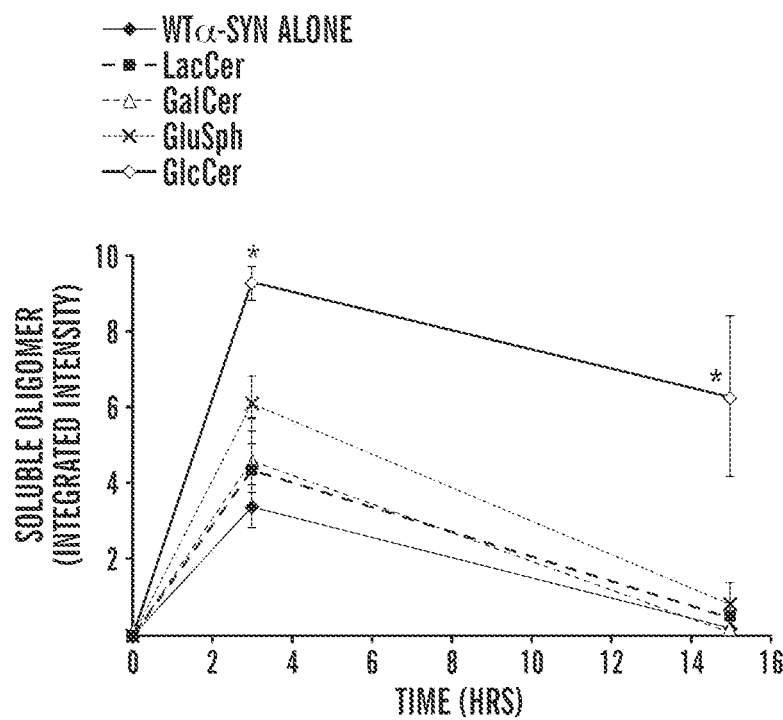
Figure 8F:
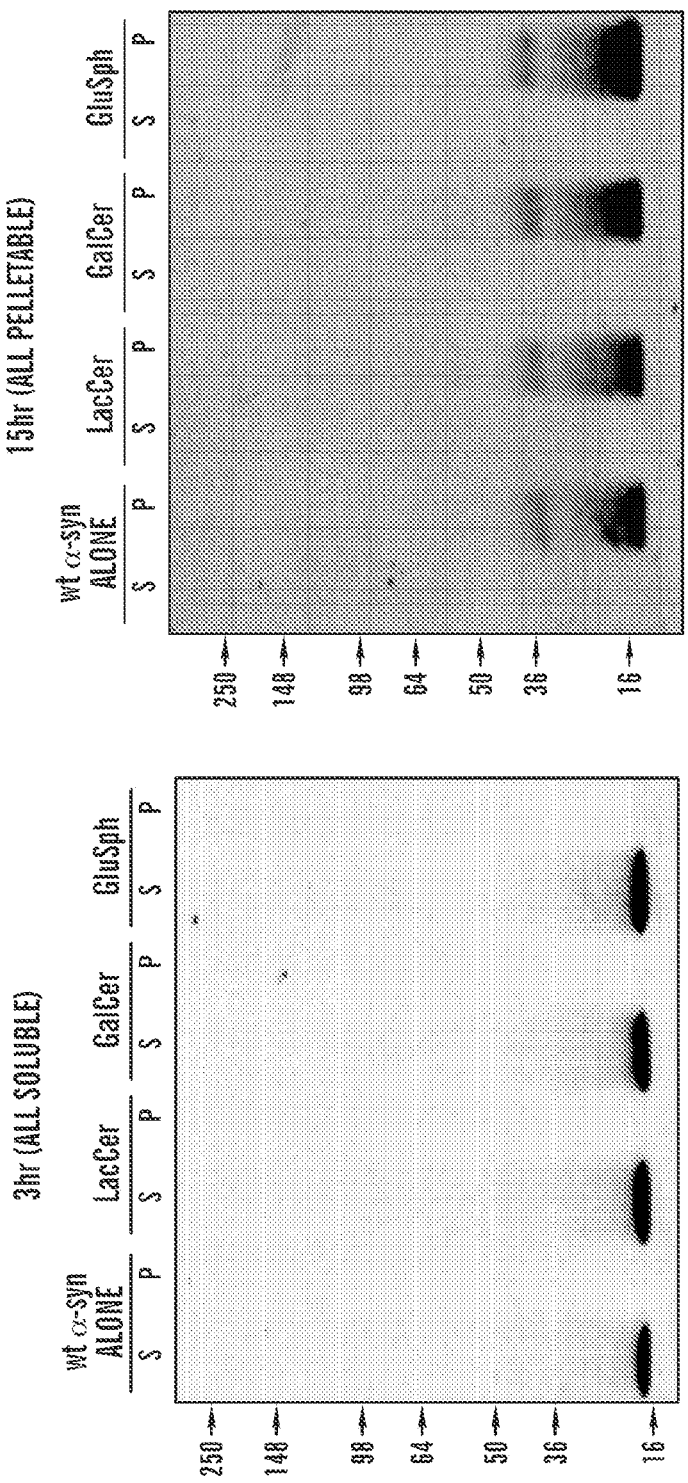

As discussed above, the biochemical data from cell culture experiments had suggested that GlcCer selectively increased soluble HMW forms of α-synuclein (FIG. 6). Therefore, in this Example it was hypothesized that the delay in fibril formation observed in vitro resulted from a kinetic stabilization of a soluble oligomeric intermediate species. To test this, the nature of the species that form during the lag phase (between 1 and 16 hr) of PC25/GlcCer75-containing reactions were characterized by analytic biochemical methods. Soluble portions of the reaction mixtures were obtained by centrifugation at 100,000×g and analyzed at 1 and 5 hr after the addition of lipids by SEC/SDS-PAGE. This revealed an increase in the amount of HMW oligomeric α-synuclein eluting between 115 and 38 Å, and migrating at 18 kDa by SDS-PAGE, in samples containing PC25/GlcCer75 lipid dispersions (FIG. 7B). Further, detected were increased amounts of soluble SDS and heat-stable dimers (36 kDa), trimers (54 kDa), and higher oligomeric species eluting as 36-27 Å-sized particles in PC25/GlcCer75-containing reactions compared to controls (FIG. 7B). The GlcCer-induced soluble oligomeric species appeared to increase between 1 and 5 hr, whereas oligomers and monomers in control reactions decreased, consistent with their consumption into insoluble fibrils (FIGS. 7B and 7C). Native gel electrophoresis also revealed an increase in the amount of 720-1048 kDa-sized α-synuclein species (FIGS. 8C and 8D). Further, in this Example it was found that other sphingolipids did not significantly alter the amounts of soluble oligomers, indicating a specific effect by GlcCer (FIGS. 8E and 8F). Immuno-EM with syn505 antibodies that preferentially detect misfolded α-synuclein demonstrated the formation of individual spherical structures of ~25-50 nm in diameter that occasionally appeared to coalesce to form larger amorphous structures (FIG. 7G, iii).

Syn505 also detected α-synuclein directly on GlcCer tubular structures (FIG. 7G, i and ii) but not on GlcCer-alone reactions (FIG. 7I), indicating an association of misfolded α-synuclein with GlcCer. α-synuclein-GlcCer reactions were further analyzed by 8-anilino-1-napthalene sulfonate (ANS) binding, a fluorescent dye used to detect aggregation-prone conformational intermediates (Stryer, 1965). Enhanced ANS fluorescence was observed in soluble α-synuclein samples incubated with PC25/GlcCer75 compared to control reactions, indicating that GlcCer addition results in a conformational alteration that increases solvent-exposed hydrophobic regions (FIG. 7D). Because hydrophobicity changes in proteins correlate with aggregation propensity, this observation indicates that GlcCer stabilizes the formation of a soluble assembly-competent intermediate species during the lag phase of the fibril formation reaction.

Figure 7F:
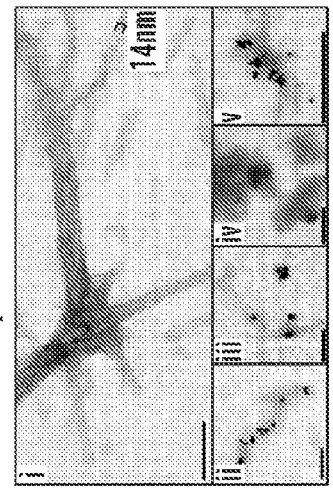
Figure 7H:
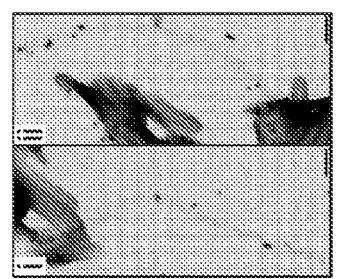

Further in this Example, inspection of the kinetic profile indicated that although GlcCer delayed the onset of fibril formation from 2 to 16 hr, it also accelerated fibril assembly once this phase was initiated (FIG. 7A). The fibril assembly phase PC25/GlcCer75-containing reactions occurred between 16 and 24 hr, compared to control reactions where the assembly occurred between 2 and 24 hr. Furthermore, the maximal thioT signal at the end stages of the reaction was 2- to 3-fold higher compared to control reactions (FIG. 7A). The aggregated species formed at the end stage of the fibril-forming reaction, after assembly was completed and equilibrium was reached (at 28 hr) were further analyzed. Centrifugal sedimentation analysis at 100,000×g, which detects both amyloid and non-amyloid aggregates in the pelletable (P) fractions, revealed that GlcCer had no effect on the amount of pelletable α-synuclein protein (FIG. 7E). In the same reaction mixtures used for sedimentation analysis, measurement of amyloidogenic α-synuclein with thioT revealed a 3-fold increase in the amount of amyloid detected in PC25/GlcCer75-containing reactions (FIG. 7E, bottom). Immuno-EM analysis of α-synuclein/GlcCer reactions at 24 hr confirmed the presence of ~14 nm wide fibrillar structures that appeared to extend from GlcCer tubules (FIG. 7H), whereas α-synuclein-alone reactions contained both fibrillar (FIG. 7F, i-iii) as well as amorphous aggregates (FIG. 7F, iv and v). Taken together, the data indicates that GlcCer selectively stabilizes the formation of soluble oligomeric intermediates on-pathway to forming amyloid fibrils. However, due to the continuous accumulation of these soluble on-pathway intermediates that occurs in vitro between 2 and 16 hr, the concentration of GlcCer is likely eventually surpassed and results in the rapid formation of thioT-positive amyloid fibrils.

Example 5: Accumulation of Soluble and Insoluble α-Synuclein Species Occurs in GD Mouse Experiments in this Example demonstrate that GCase polypeptide depletion promotes the formation of soluble oligomeric and insoluble α-synuclein in vivo, consistent with cell culture and in vitro data discussed above.

Figure 9A:
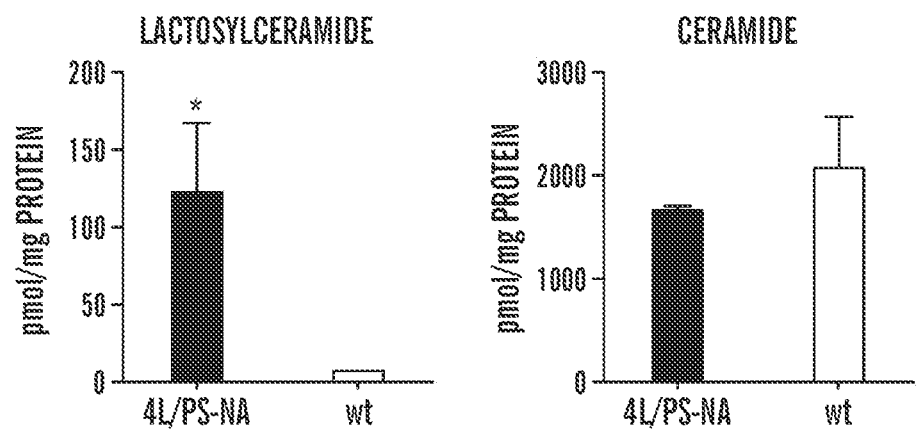
FIGS. 9A-9E show the accumulation of sphingolipids in a mouse GD model.
Figure 9B:
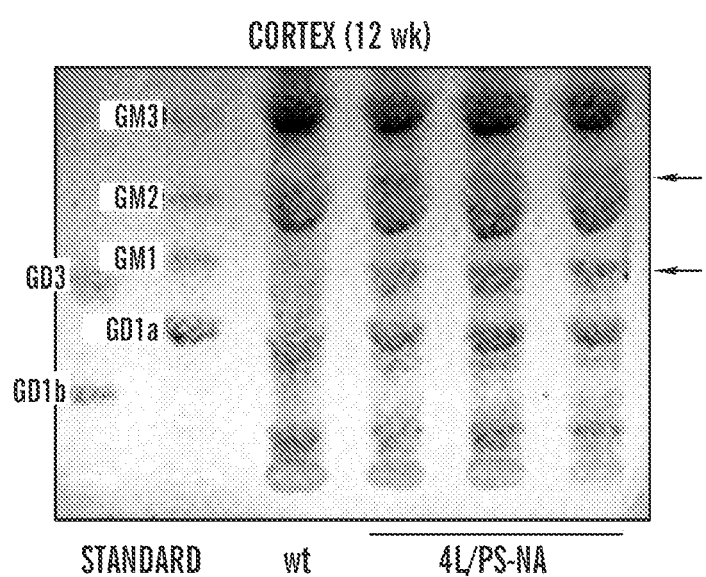
Figure 10B:
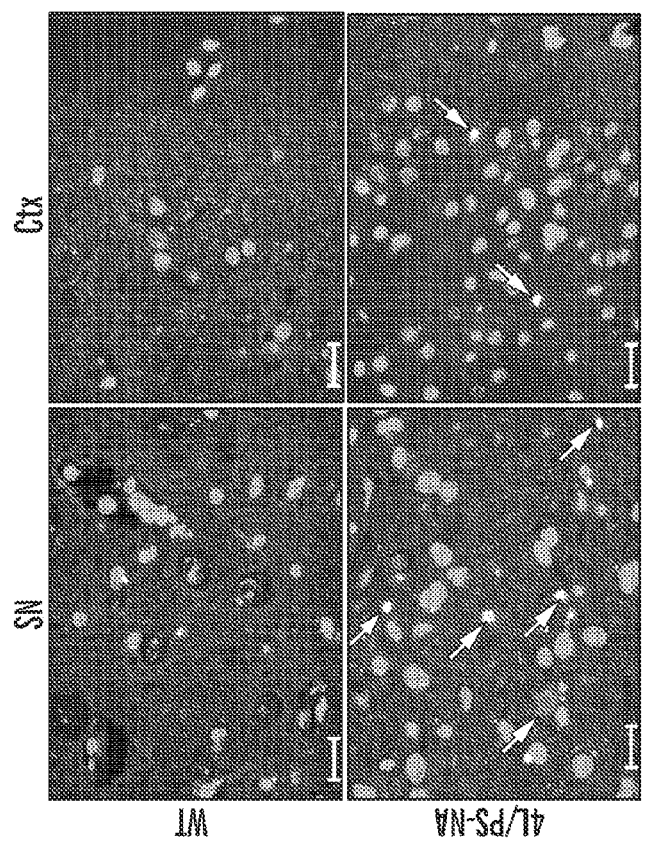
FIGS. 10A-10H show α-synuclein accumulation and soluble oligomer formation in GD mice. Analysis of 12-week-old GD mice (4L/PS-NA).
Figure 10A:
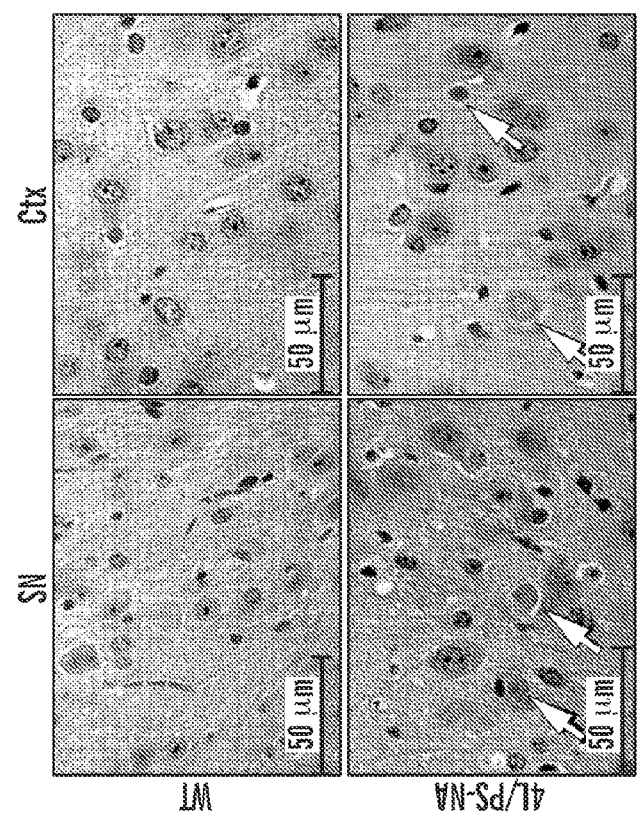
Figure 10C:
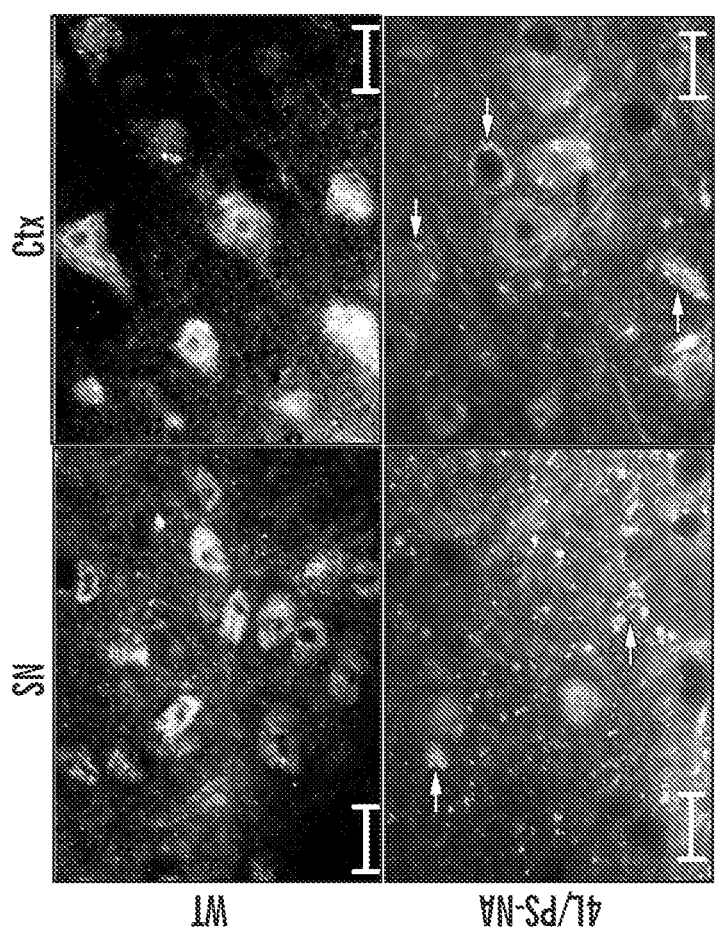
Figure 10D:
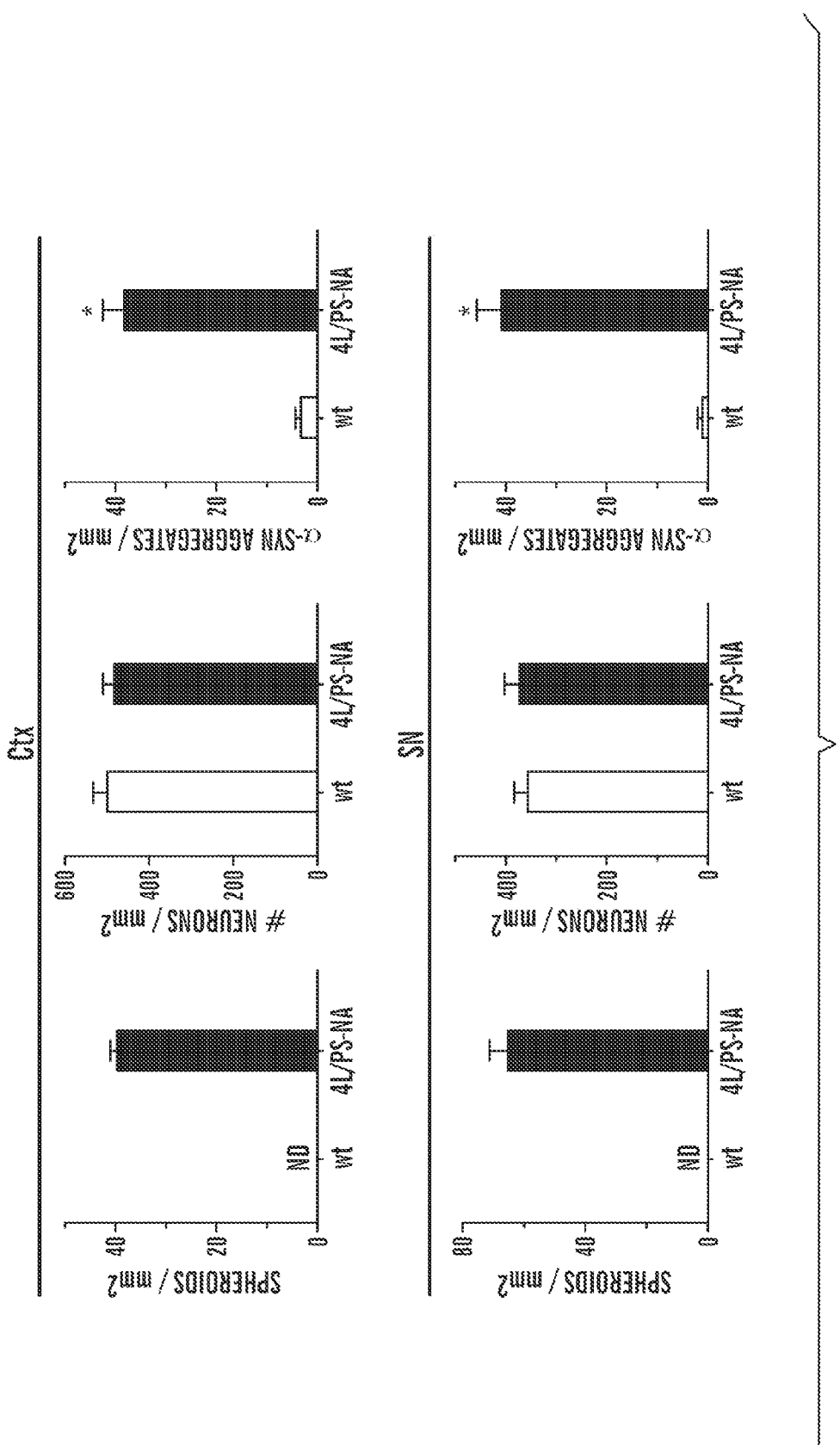

In this Example, brain tissues from a previously described GD mouse model (4L/PS-NA) were analyzed to determine whether endogenously expressed α-synuclein protein levels were elevated. Previous analysis of this mouse model indicated low levels of GCase polypeptide activity, neuronal accumulation of GlcCer, and severe neurological deterioration by 20 weeks of age (Sun et al., J. Lipid Res. 46: 2102, 2005). In addition to GlcCer, the levels of other sphingolipids were also determined showing an accumulation of lactosylceramide, GM2, and GD3, whereas ceramide levels remained unchanged (FIGS. 9A and 9B). The neuropathological analysis here revealed the presence of eosinophilic spheroids, suggesting the presence of degenerating neurons, in multiple brain regions including the substantia nigra (SN) and cortex (Ctx) in GD mice compared to WT mice that exhibited normal neuronal architecture (FIGS. 10A and 10D). These degenerative changes occurred concomitantly with increased levels of α-synuclein in these regions (FIG. 10B). Immunofluorescence analysis revealed the presence of α-synuclein accumulations in the form of punctated structures (<5 μm in diameter), whereas WT mice showed a normal neuropil staining pattern expected for α-synuclein (FIGS. 10B-10D). These changes were not restricted to the SN and Ctx, as α-synuclein accumulations were also observed in other neural regions including cerebellum, hippocampus, and brainstem (Xu et al., Mol. Genet. Metab. 102: 436, 2010).

Figure 9C:
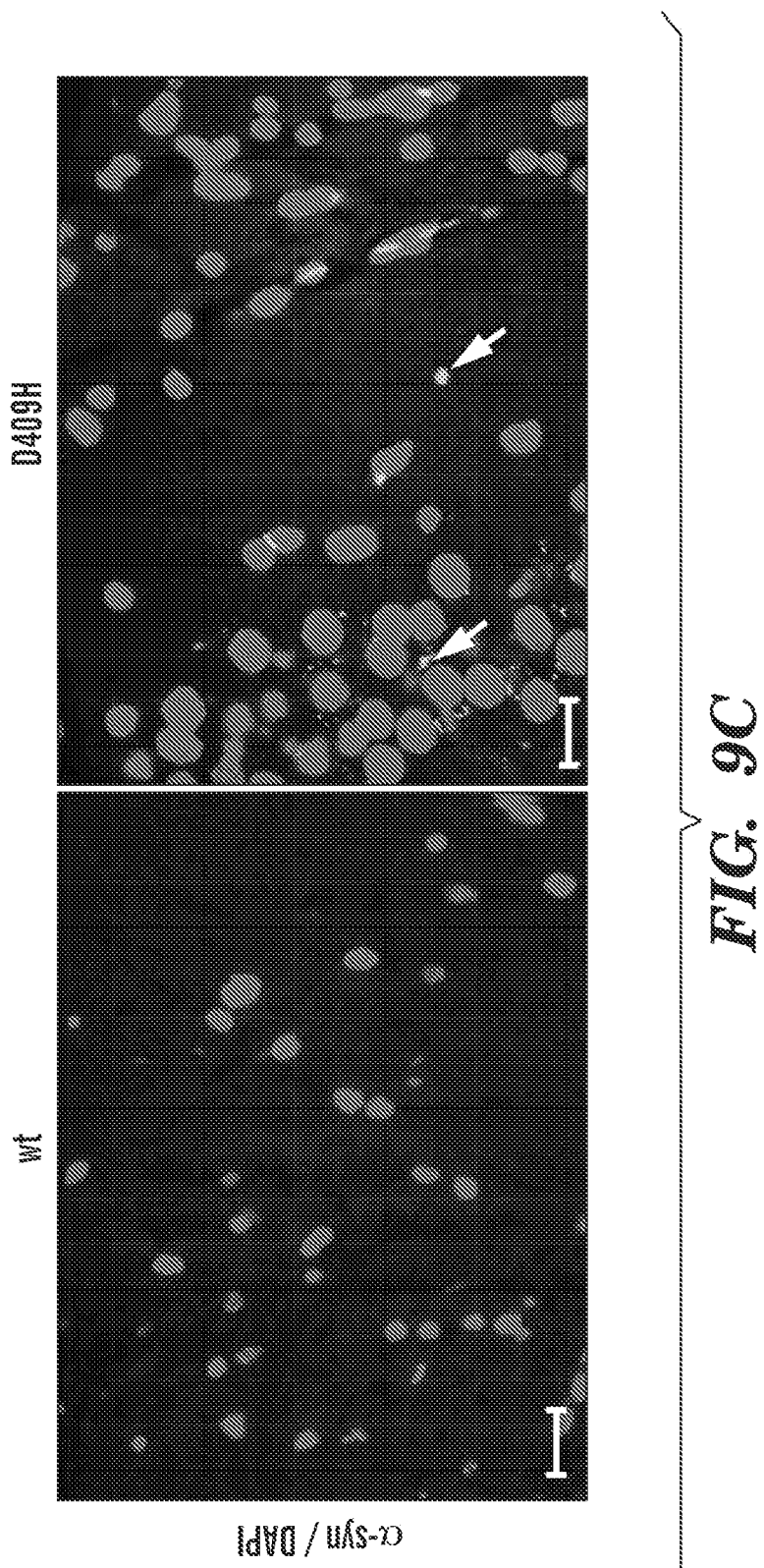
Figure 9D:
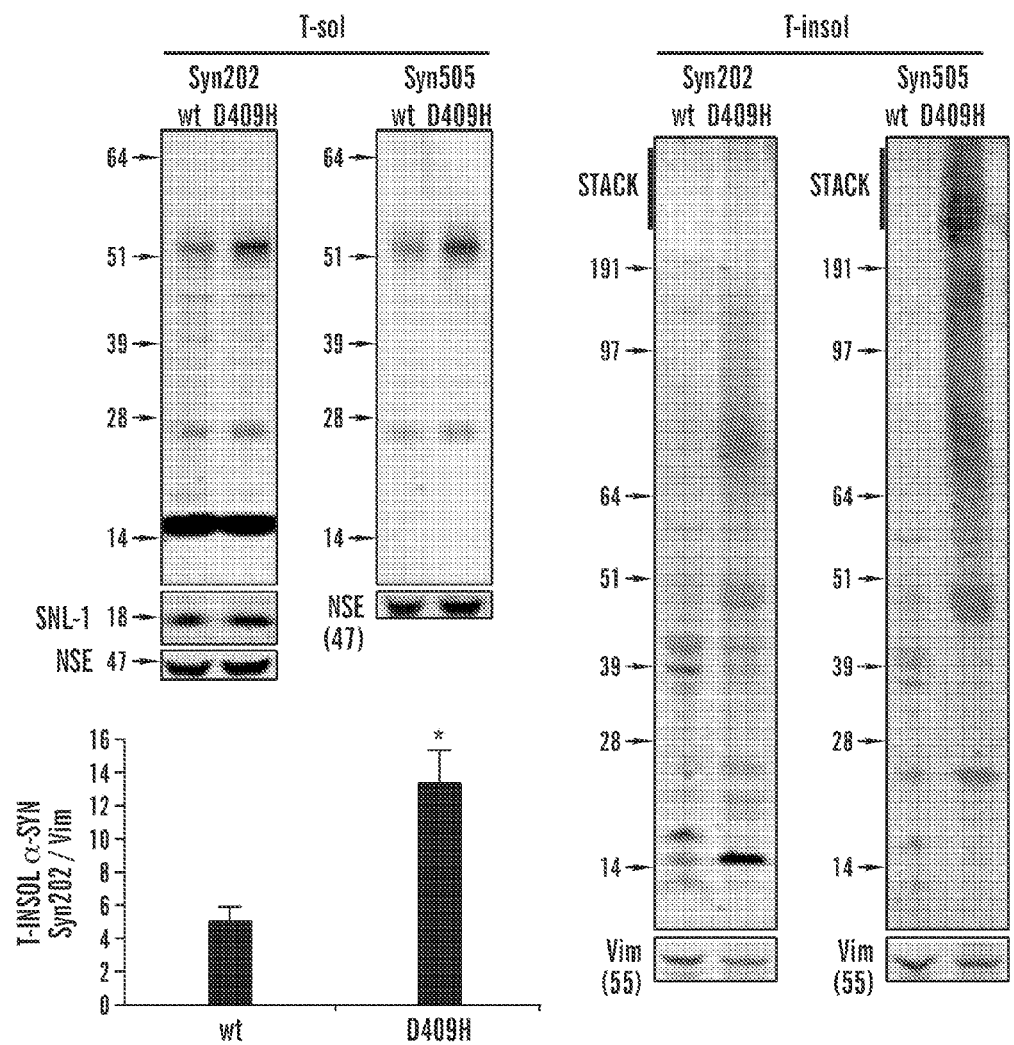
Figure 9E:
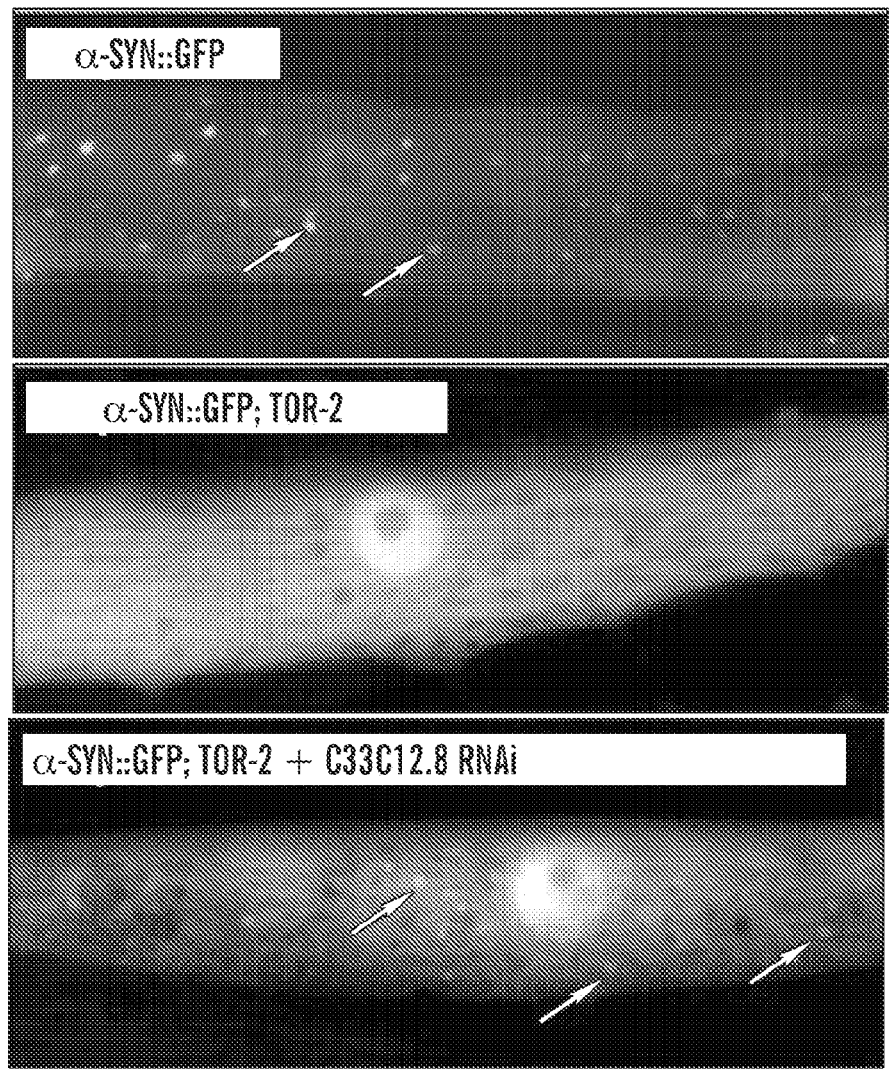
Figure 10E:
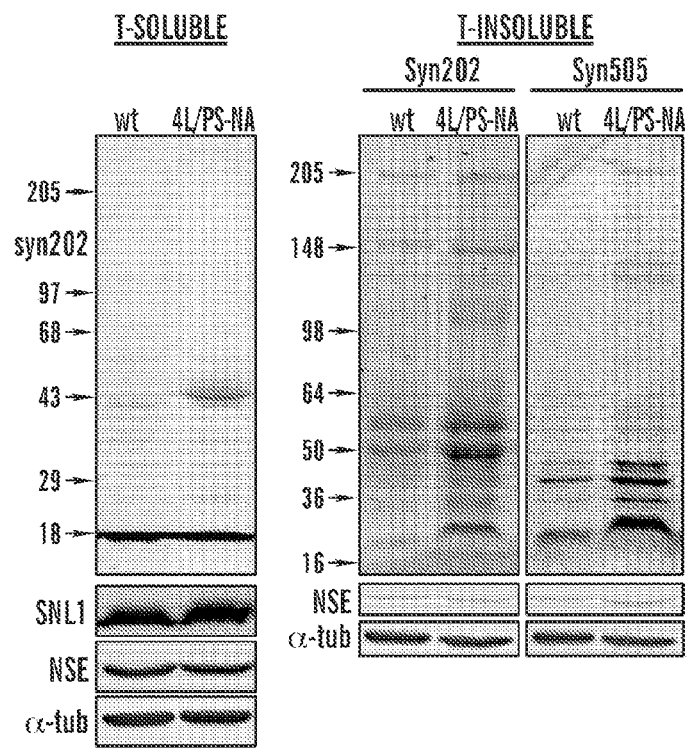
Figure 10F:
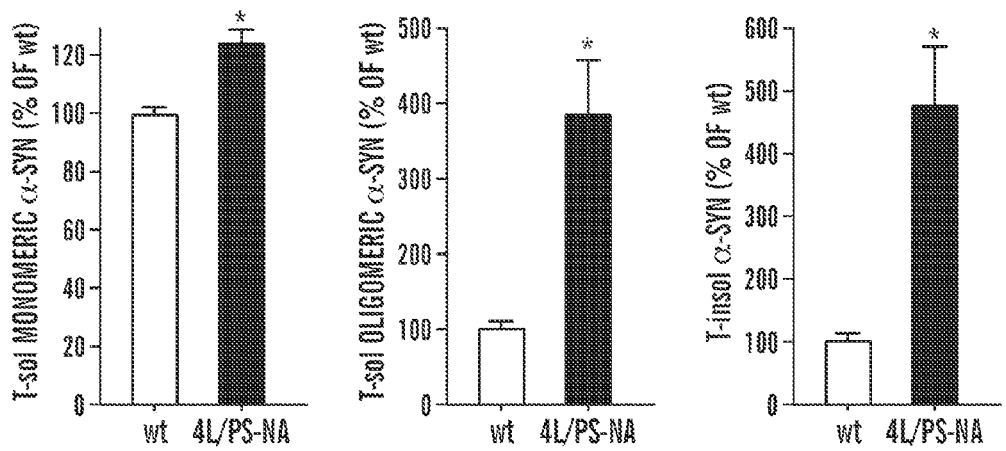
Figure 10G:
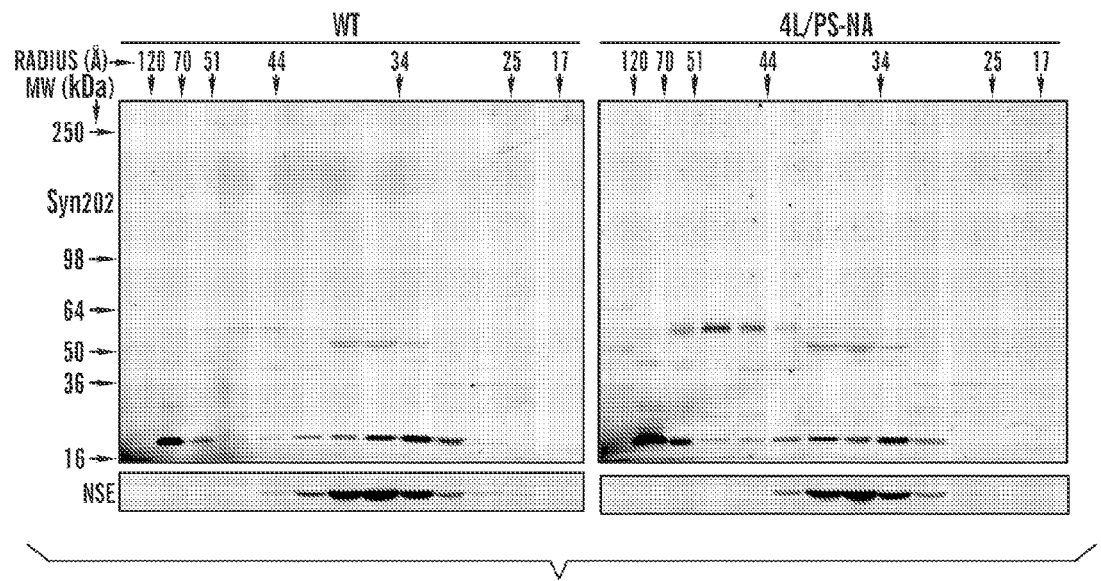
Figure 10H:
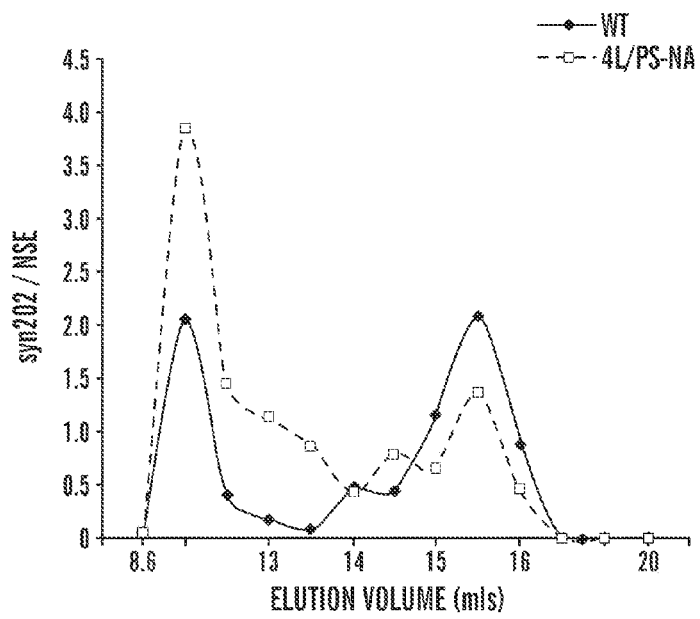

Additionally in this Example, both intraneuronal and extraneuronal α-synuclein accumulations were identified by co-staining with the neuron-specific marker NeuN (FIG. 10C), whereas quantitative analysis did not reveal significant neuronal loss (FIG. 10D). The solubility of α-synuclein was analyzed in 4L/PS-NA by sequential extraction in Triton X-100 buffer, then 2% SDS buffer. Both syn202 and SNL-1, antibodies that detect total α-synuclein, revealed increased levels of T-sol α-synuclein in 4L/PS-NA mice compared to WT mice (FIGS. 10E, left, and 10F). T-insoluble fractions showed the expected low levels of α-synuclein in WT mice and more aggregated α-synuclein in 4L/PS-NA mice as detected with both syn202 and syn505 (FIGS. 10E, right, and 10F). Analysis of T-sol levels by SEC showed increased levels of putative oligomeric forms (120-70 Å- and 51-44 Å-sized species), whereas monomers were similar to control mice (FIGS. 10G and 10H). Quantification of the soluble HMW α-synuclein revealed a 4-fold increase in 4L/PS-NA mice compared to control mice (FIGS. 10F and 10H). The analysis of α-synuclein was confirmed in another previously described and well-characterized GD mouse model, GCase polypeptide harboring the GD-linked D409H loss-of-function mutation (Xu et al., Am. J. Pathol. 163:2093, 2003). This revealed that D409H mice had similar increases in α-synuclein punctated structures as observed by immunostaining analysis (FIG. 9C) as well as higher levels of soluble oligomers and insoluble α-synuclein species (FIG. 9D). Finally, a well established *C. elegans* model was used to further demonstrate that depletion of GCase polypeptide causes the accumulation of α-synuclein in vivo (FIG. 9E).

Example 6: Elevated Levels of Soluble HMW α-Synuclein in GD Brain are Associated with Neurodegeneration Experiments in this Example suggest that GCase polypeptide deficiency promotes the formation of oligomeric α-synuclein, and the occurrence of these oligomers in type II and type III GD brain suggests that they may also play a role in the pathogenesis of age-dependent infantile GD forms. Data in this Example also demonstrates that toxic oligomeric α-synuclein is elevated in patients harboring GBA1 mutations and is preferentially associated with neuropathic forms of the disease.

As discussed above, the in vitro, cell culture, and GD animal model data suggested that GlcCer accumulation led to elevated levels of soluble α-synuclein oligomers. Therefore, in this Example the emphasis was on identifying these species in human postmortem brain samples obtained from patients with GD. T-sol fractions of cortical samples were analyzed by native SEC, followed by SDS-PAGE/western blot of the collected fractions using mAb syn211. Analysis of healthy controls without GBA1 mutations (Table 15) revealed the expected elution profile typically observed for monomeric human α-synuclein, eluting mainly as a 34 Å-sized particle by SEC and migrating at 18 kDa by SDS-PAGE (FIGS. 11A-11C). Analysis of cortical T-sol lysate from two pathologically and clinically confirmed non-neuronopathic type I GD patients revealed an α-synuclein elution profile that was similar to control (FIGS. 11D and 11E), although the total levels of monomeric α-synuclein were elevated (α-synuclein protein levels, % of control): control=100±12.6, GD type I (no PD)=*243±53, values are the mean±standard error of the mean (SEM), *p<0.05, n=3 controls, n=2 GD type I). When brain lysate from a previously documented GD patient diagnosed with atypical Parkinson's disease (APD) was analyzed (Tayebi et al., Mol. Genet. Metab. 73: 313, 2001), a dramatic increase in α-synuclein levels was observed (FIG. 11F). α-synuclein eluted as a 34 Å-sized particle and migrated at 18 kDa by SDS-PAGE similar to controls, but a substantial proportion (50% of the total T-sol) also eluted as a larger putative oligomeric species at 42-45 Å (or 110-140 kDa globular protein). The α-synuclein in this oligomeric fraction, when analyzed by denaturing SDS-PAGE, resolved as 22, 44, and 75 kDa heat-stable species (FIG. 11F). Data here demonstrated that elevated T-sol α-synuclein in the form of oligomeric species is present primarily in the GD/APD brain.

Figure 12A:
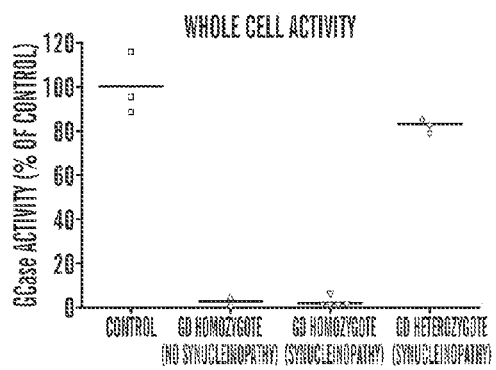
FIGS. 12A-12E show the quantification of GCase polypeptide activity, GCase protein levels, and α-synuclein oligomer levels in human GD brain. The samples analyzed here are the same as those presented in FIGS. 11A-11L and Table 15.
Figure 12B:
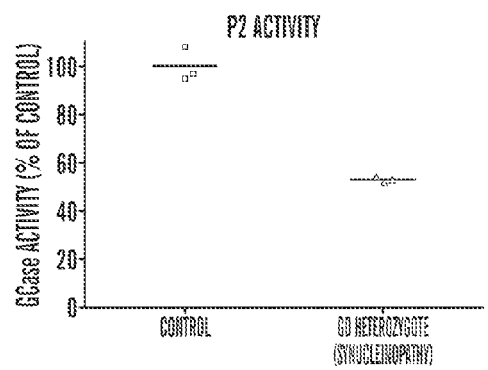
Figure 12C:
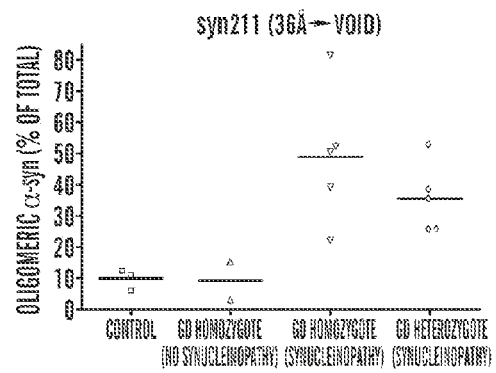
Figure 12D:
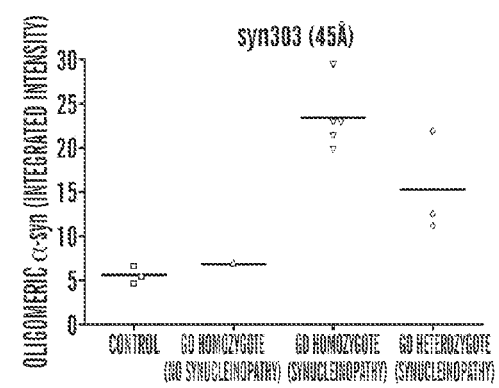
Figure 12E:
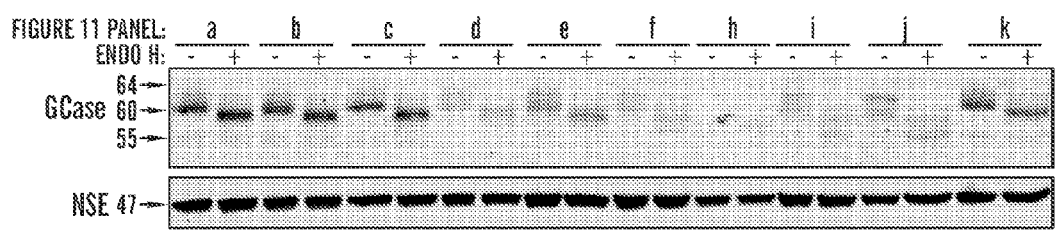

Further in this Example, elevated levels of α-synuclein oligomers were detected in patients that were homozygous or heterozygous for GCase polypeptide mutations (Table 15) with a diagnosis of Lewy body dementia (DLB) (FIGS. 11G and 11K). Analysis of postmortem brain lysate obtained from infants diagnosed with type II GD as well as a 3-year-old child diagnosed with type III GD also exhibited increased oligomeric α-synuclein eluting above 36 Å (FIGS. 11H-11J), although some variation between samples was observed. The levels of oligomeric α-synuclein detected with the syn211 mAb were quantified and it was found that both homozygote and heterozygote carriers of GBA1 mutations with a neuronopathic phenotype contained significantly higher levels of oligomers compared to controls (FIG. 12C). It was also verified that these GD samples contained lower GCase polypeptide and activity levels (FIGS. 12A, 12B, and 12E).

Also analyzed in this Example were the oligomeric fractions of size 45 Å. These were analyzed with mAb syn303, an antibody that preferentially detects pathological oligomeric α-synuclein (Duda et al., Ann. Neurol. 52: 205, 2002) and can distinguish potentially toxic from nontoxic α-synuclein species (Tsika et al., J. Neurosci. 30: 3409, 2010). We found that syn303 immunoreactivity was increased in all of the neuronopathic GD samples (FIG. 11L, FIG. 12D). In most of the cases, syn303 reacted with the 22, 44, and 75 kDa species that were also detected with syn211 (FIG. 11L).

TABLE 15

Clinical data of control and GD patients.

| FIG. 11 panel | Sex | Diagnosis | Age at onset | Age at death | GBA1 mutation | GC activity (% of control)* |
|---|---|---|---|---|---|---|
| a | M | control | none | 65 | wt/wt | 115.8 ± 3.8 |
| b | NA | control | none | NA | wt/wt | 88.5 ± 2.0 |
| c | M | control | none | 73 | wt/wt | 95.6 ± 2.8 |
| d | M | GD type1 (non-neuronopathic) | none | 87 | N370S/N370S | 4.5 ± 0.5 |
| e | M | GD type1 (non-neuronopathic) | none | 58 | N370S/c.208del C | 0.9 ± 0.5 |
| f | F | GD + atypical PD | 42 | 52 | D409H/L444P | 1.6 ± 0.9 |
| g | M | GD type 1 + DLB | 44 | 55 | N370S/N370S | 6 ± 0.6 |
| h | F | GD type 2 | NA | 1 month | IVS2 + 1G > A/F251L | 0.6 ± 0.3 |
| i | F | GD type 2 | NA | 6 months | IVS2 + 1/L444P | 0.8 ± 0.4 |
| j | M | GD type 3 | NA | 3 | L444P/L444P | 0.7 ± 1.4 |
| k | M | DLB | 54 | 75 | T267I + E326K/wt | WC = 82.2 ± 1.8, P2 = 52.9 ± 0.6 |

*3 repeated activity measurements were performed for each whole cell lysate (values are the mean ± SEM),
NA, not available;
WC, whole cell homogenate;
P2, lysosomal enriched fraction,
DLB, dementia with Lewy bodies.

Example 7: Overexpression of α-Synuclein Inhibits the Intracellular Trafficking of GCase Polypeptide Resulting in Decreased GCase Polypeptide Activity Experiments in this Example illustrate that normal variation of α-synuclein protein levels modulate the lysosomal maturation and activity of GCase polypeptide in vivo. Data in this Example also suggests that elevated levels of α-synuclein observed in PD and other synucleinopathies led to decreased lysosomal activity of normal GCase polypeptide that may in turn contribute to further propagation and stabilization of oligomeric α-synuclein.

Figure 13A:
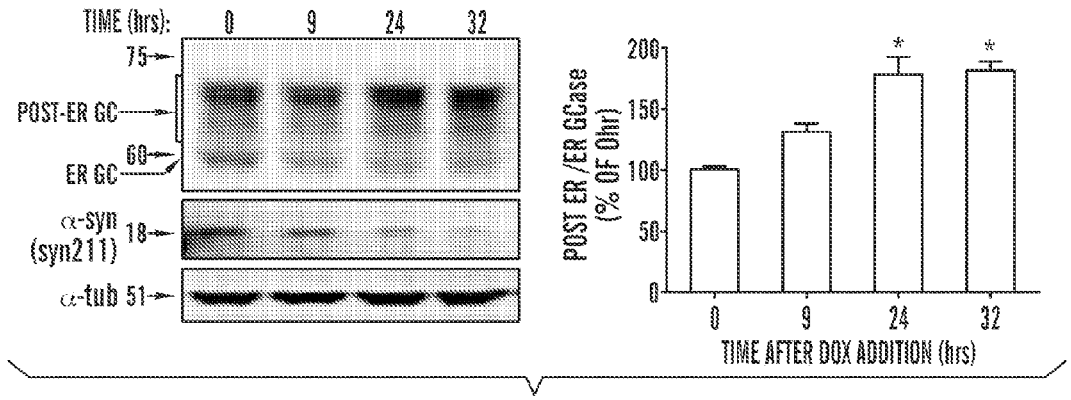
FIGS. 13A-13F demonstrate that elevated levels of α-synuclein inhibit the intracellular trafficking of GCase polypeptide and decrease lysosomal GCase polypeptide function.
Figure 13B:
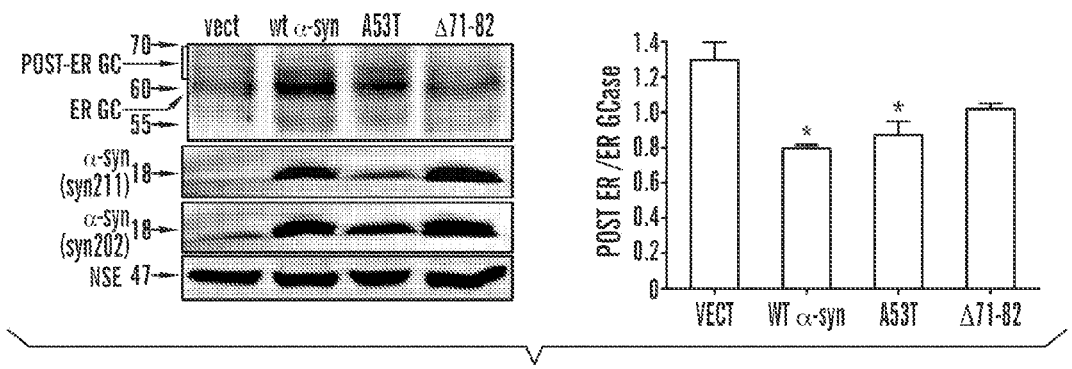
Figure 13C:
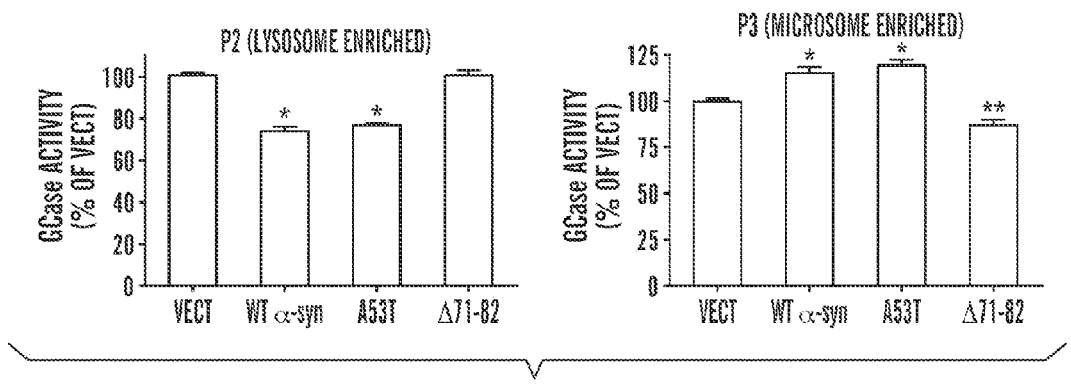

Most patients with idiopathic PD invariably have elevated levels of α-synuclein protein, but they do not harbor mutations in the GBA1 gene and thus are expected to have normal lysosomal function of GCase polypeptide. In this Example, α-synuclein was overexpressed in H4 cells and primary cortical neurons that express WT GCase polypeptide and the post-ER forms were measured to determine whether α-synuclein disrupts lysosomal maturation activity of GCase polypeptide. The intracellular trafficking of GCase polypeptide was assessed by SDS-PAGE/western blot, through molecular weight (MW) analysis of various GCase polypeptide forms that result from protein glycosylation. While the ER form of GCase polypeptide migrated at 60 kDa, the post-ER GCase polypeptide forms migrated above 60 kDa (Erickson et. al., 1985). Analysis of whole-cell lysates from inducible H4 cells showed that lowering α-synuclein expression levels by the addition of Dox for 24 or 32 hr resulted in a concomitant increase in the post-ER GCase polypeptide forms while decreasing the 60 kDa ER form (FIG. 13A). Similarly, overexpression of human WT and A53T α-synuclein in primary cortical neurons also altered the post-ER/ER GCase polypeptide ratio by causing an accumulation of the ER form, as well as a decrease in the post-ER forms migrating above 60 kDa (FIG. 13B). Titer-matched infection of WT and A53T α-synuclein containing plasmids resulted in almost equal alterations in the post-ER/ER GCase polypeptide ratio, despite the lower protein expression of A53T, indicating that A53T more potently inhibits GCase polypeptide trafficking compared to the WT protein (FIG. 13B). Interestingly, expression of Δ71-82 α-synuclein at levels that were slightly higher than WT α-synuclein caused only a mild alteration in the post-ER/ER GCase polypeptide ratio that was not significantly different compared to empty vector controls (FIG. 13B). To verify that alterations in GCase polypeptide glycoslyation patterns observed by western blot corresponded to lower lysosomal activity of GCase polypeptide, enzymatic activity was measured in lysosomal (P2) and microsomal (P3) enriched fractions (FIGS. 14A and 14B) of primary neuronal cultures. In P2 fractions, expression of both WT and A53T α-synuclein resulted in a significant decrease in GCase polypeptide activity and a concomitant increase in the P3 activity compared to controls (FIG. 13C). Conversely, the expression of Δ71-82 α-synuclein did not affect GCase polypeptide lysosomal activity (FIG. 13C). The results were validated by endo H treatment of lysates, which revealed higher levels of endo H-sensitive GCase polypeptide migrating below 60 kDa in endo H-treated samples of WT α-synuclein-expressing cells compared to control conditions (FIG. 14C). Additionally, the ability of another amyloid-forming protein, poly Q-expanded huntingtin fragment 548-72Q, to inhibit GCase polypeptide maturation was tested and no change was observed in this study (FIG. 14C). Further, it was confirmed that the accumulation of ER GCase polypeptide by α-synuclein occurred at the protein level, as measurement of GBA1 mRNA of α-synuclein-expressing neurons was not different compared to control conditions (FIG. 14D). The enzymatic activity of other lysosomal proteins in the P2 fraction of infected neurons revealed only minor alterations by α-synuclein expression, suggesting a preferential effect of α-synuclein on GCase polypeptide activity (FIG. 14E).

Figure 13D:
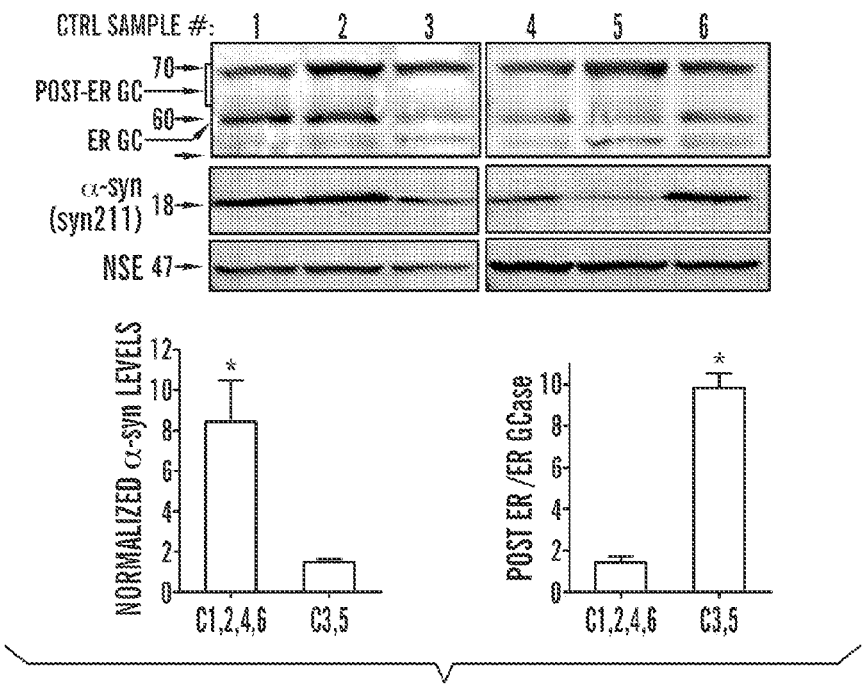
Figure 14H:
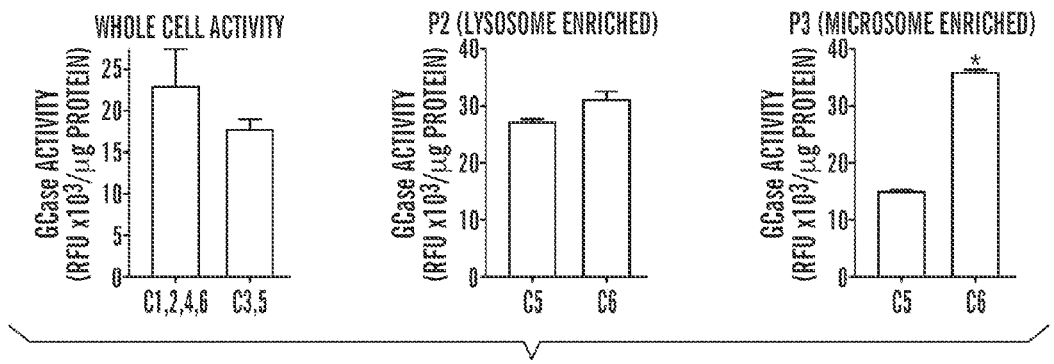

Further in this Example, it was determined whether GCase polypeptide glycosylation patterns are sensitive to α-synuclein protein levels in vivo by analyzing human cortical material by GCase polypeptide western blot. Upon analyzing brain tissue from several reportedly healthy controls without common GBA1 mutations and between the ages of 65 and 80 years of age (Table 16 and Table 17), a natural variability of α-synuclein expression levels was noticed between subjects. Control samples 1, 2, 4, and 6 were noted to have mid-to-high levels of α-synuclein relative to samples 3 and 5, which contained very low α-synuclein levels (FIG. 13D). When the GCase polypeptide glycosylation patterns were analyzed by western blot, a dramatic difference in the post-ER/ER GCase polypeptide ratio was observed that correlated with α-synuclein levels. While all samples appeared to have similar levels of post-ER GCase polypeptide, samples with low α-synuclein (samples 3 and 5) contained much less of the 60 kDa ER form (FIG. 13D). Endo H digestion also confirmed higher levels of ER-containing GCase polypeptide, which migrated below 60 kDa after endo H treatment (FIG. 14F). The GCase polypeptide activity levels in cortical tissue from whole-cell lysates of all low and high α-synuclein-containing samples were further analyzed and no difference in activity was observed (FIG. 14H, left). However, when P2 and P3 GCase polypeptide activity was determined, it was found that microsome-enriched P3 fractions of "high" α-synuclein samples contained significantly higher levels of activity whereas no change was observed in the P2 fraction (FIG. 14H). Western blot analysis with syn303 also revealed higher levels of oligomeric, oxidized α-synuclein in "high" α-synuclein sample C6 compared to C5 (FIG. 14G). These findings suggested that normal variation of α-synuclein protein levels modulate the lysosomal maturation and activity GCase polypeptide in vivo.

Figure 13E:
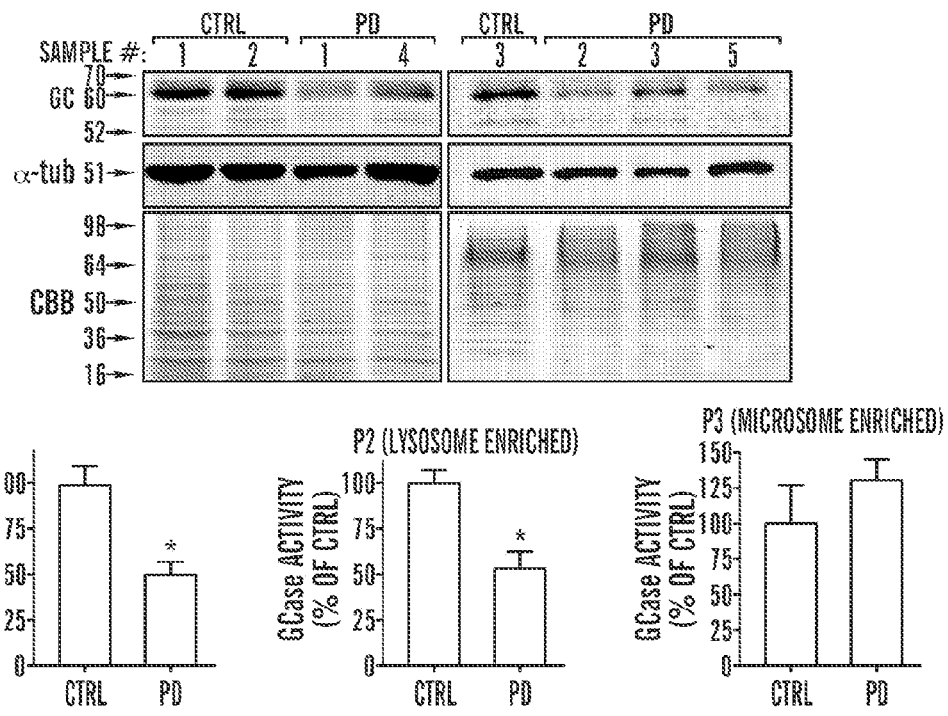
Figure 13F:
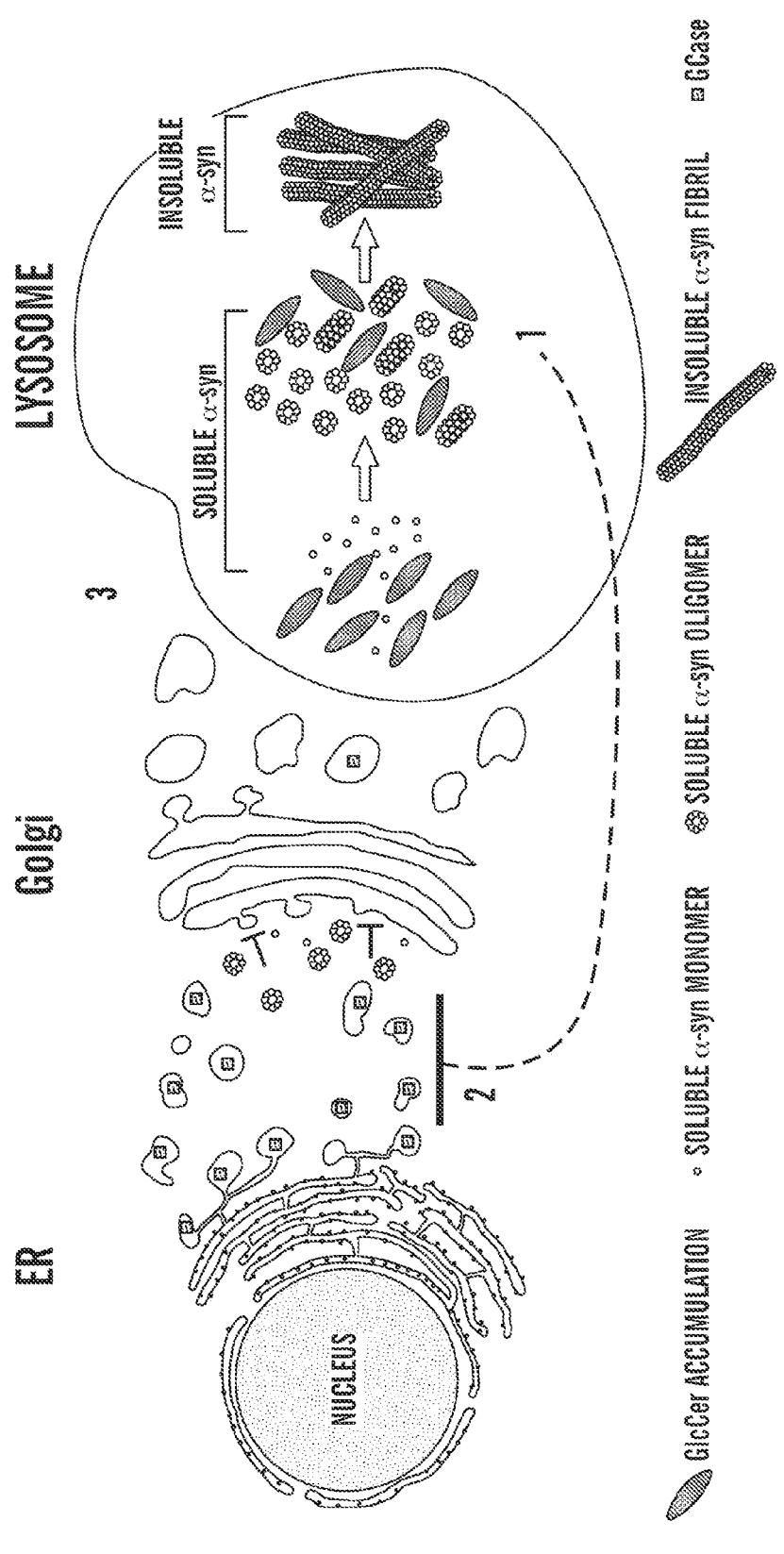

The observation in the data above that elevated α-synuclein levels affect GCase polypeptide trafficking in neurons led to the hypothesis that lysosomal GCase polypeptide function may be lowered in idiopathic PD brain. In this Example, it was further observed that there was an ~40% decline in the total GCase polypeptide levels in T-sol lysates from cingular cortex of PD brain when compared to age- and postmortem time-matched controls (FIG. 13E). In addition, there was an ~50% decline in GCase polypeptide activity in the P2 fraction relative to age-matched controls, whereas no change was observed in the P3 fraction (FIG. 13E, bottom). Genotyping analysis revealed that these patients did not harbor mutations in GBA1, with the exception of one sample that contained the heterozygous mutation N370S (Table 18). One sample, PD4, had lower than the expected 50% decline in GCase polypeptide activity (38% of control), possibly indicating additional inhibition of GCase polypeptide by α-synuclein accumulation (Table 18). Table 19 is related to FIG. 13.

TABLE 16

Clinical data of controls.

| | C1 | C2 | C3 | C4 | C5 | C6 |
|---|---|---|---|---|---|---|
| Race | c | NA | c | c | c | c |
| Age at death | 65 | NA | 76 | 80 | 79 | 73 |
| PMI | NA | NA | 24 | 54 | NA | 22 | c, Caucasian;
PMI, postmortem interval;
NA, not available

TABLE 17

Sequenom MassARRAY genotype analysis of controls.

| SNP ID | Alleles (minor/major) | Gene | Protein mutation | C1 | C2 | C3 | C4 | C5 | C6 |
|---|---|---|---|---|---|---|---|---|---|
| GBA--84GG | G/DEL | GBA1 | L84TER | DEL/DEL | DEL/DEL | DEL/DEL | DEL/DEL | DEL/DEL | DEL/DEL |
| GBA-N370S | G/A | GBA1 | N370S | A/A | A/A | A/A | A/A | A/A | A/A |
| rs2230288 | A/G | GBA1 | E326K | G/G | G/G | G/G | G/G | G/G | G/G |
| rs421016 | A/C/G/T | GBA1 | L444P | G/G | G/G | G/G | G/G | G/G | G/G |

TABLE 18

Sequenom MassARRAY genotype analysis of controls and PD samples.

| SNP ID | Alleles (minor/major) | Gene | Protein mutation | O.R. | Ctrl1 | Ctrl2 | Ctrl3 | PD1 | PD2 | PD3 | PD4 | PD5 | PD6 |
|---|---|---|---|---|---|---|---|---|---|---|---|---|---|
| GBA--84GG | G/DEL | GBA1 | L84TER | | DEL/DEL | DEL/DEL | DEL/DEL | DEL/DEL | DEL/DEL | DEL/DEL | DEL/DEL | DEL/DEL | DEL/DEL |
| GBA-N370S | G/A | GBA1 | N370S | 3.28 | A/A | A/A | A/A | A/A | A/A | A/A | G/A | A/A | A/A |
| rs2230288 | A/G | GBA1 | E326K | | G/G | G/G | G/G | G/G | G/G | G/G | G/G | G/G | G/G |
| rs421016 | A/C/G/T | GBA1 | L444P | | G/G | G/G | G/G | G/G | G/G | G/G | G/G | NC | G/G |
| rs104893877 | A/G | SNCA | A53T | | G/G | G/G | G/G | G/G | G/G | G/G | G/G | G/G | G/G |
| rs104893878 | C/G | SNCA | A30P | | G/G | G/G | G/G | G/G | G/G | G/G | G/G | G/G | G/G |
| rs104893875 | A/G | SNCA | E46K | | G/G | G/G | G/G | G/G | G/G | G/G | G/G | G/G | G/G |
| rs55774500 | A/C | PARKIN | A82E | | C/C | C/C | C/C | C/C | C/C | C/C | C/C | C/C | C/C |
| rs5030732 | A/C | UCHL1 | S18Y | | A/C | C/C | C/C | C/C | A/A | C/C | C/C | A/A | C/C |
| rs45539432 | T/C | PINK1 | Q456TER | | C/C | C/C | C/C | C/C | C/C | C/C | C/C | C/C | C/C |
| PINK1 A344T | T/A | PINK1 | A344T | | A/A | A/A | A/A | A/A | A/A | NC | A/A | A/A | A/A |
| rs28938172 | C/T | PARK7/DJ1 | L166P | | T/T | T/T | T/T | T/T | T/T | T/T | T/T | T/T | T/T |
| rs74315351 | A/G | PARK7/DJ1 | M26I | | G/G | G/G | G/G | G/G | G/G | G/G | G/G | G/G | G/G |
| rs74315353 | C/G | PARK7/DJ1 | E64D | | G/G | G/G | G/G | G/G | G/G | G/G | G/G | G/G | G/G |
| rs35801418 | G/A | LRRK2 | Y1669C | | A/A | A/A | A/A | A/A | A/A | A/A | A/A | A/A | A/A |
| rs34778348 | A/G | LRRK2 | G2385R | | G/G | G/G | G/G | G/G | G/G | G/G | G/G | G/G | G/G |

TABLE 18-continued

Sequenom MassARRAY genotype analysis of controls and PD samples.

| SNP ID | Alleles (minor/major) | Gene | Protein mutation | O.R. | Ctrl1 | Ctrl2 | Ctrl3 | PD1 | PD2 | PD3 | PD4 | PD5 | PD6 |
|---|---|---|---|---|---|---|---|---|---|---|---|---|---|
| rs356221 | T/A | SNCA | NA | 1.35 | T/A | T/A | T/A | A/A | T/A | A/A | T/A | T/T | T/A |
| rs356219 | G/A | SNCA | NA | 1.28 | A/A | G/A | G/A | A/A | G/A | G/G | G/A | G/A | G/A |
| rs2736990 | T/C | SNCA | NA | 1.27 | T/C | T/C | T/C | T/T | T/C | C/C | T/C | C/C | T/C |
| rs823128 | G/A | NUCKS1 | NA | 0.76 | G/A | A/A | A/A | A/A | A/A | G/A | A/A | A/A | A/A |
| rs11240572 | A/C | PM20D1 | NA | 0.75 | A/C | C/C | C/C | C/C | C/C | A/C | C/C | C/C | C/C |
| rs11012 | A/G | PLEKHM1 | NA | 0.77 | G/G | G/G | G/G | G/G | G/G | G/G | A/A | G/G | G/G |
| rs823156 | A/G | SLC41A1 | NA | 0.83 | A/G | G/G | A/A | A/G | A/A | A/G | A/A | A/A | A/A |
| rs1564282 | T/C | GAK | NA | 1.29 | C/C | C/C | C/C | C/C | C/C | C/C | T/C | T/C | C/C |
| rs4538475 | G/A | BST1 | NA | 0.88 | A/A | A/A | A/G | A/A | A/G | A/A | A/A | A/A | A/A |

O.R., odds ratio;
NC, no cell

TABLE 19

Clinical data of controls and PD patients.

|  | Ctrl1 | Ctrl2 | Ctrl3 | PD1 | PD2 | PD3 | PD4 | PD5 | PD6 |
|---|---|---|---|---|---|---|---|---|---|
| normalized GCase protein levels (% of control avg) | 120.9 | 89.8 | 89.3 | 67.3 | 35.1 | 38.3 | 53.9 | 33.1 | 72.2 |
| P2 GCase activity (% of control avg) | 85.1 | 109.5 | 105.4 | 26.3 | 46 | 76 | 38.5 | 64 | 75 |
| Diagnosis | Control | Control | Control | PD | PD | PD | PD | PD | PD |
| Race | c | c | c | c | c | c | c | c | c |
| Sex | m | f | f | m | m | m | m | m | m |
| Age at death (yrs) | 85 | 79 | 91 | 80 | 73 | 83 | 73 | 83 | 66 |
| PMI (hrs) | NA | NA | 19 | NA | 2 | NA | 24 | 18 | 24 | c, Caucasian;
m, male;
f, female;
PMI, post mortem interval;
NA, not available

Example 8: Activation of GCase Polypeptide as a Treatment of Neuronal and Non-Neuronal Proteinopathies Experiments in this Example demonstrate that enhancement of GCase polypeptide function, either by pharmacological chaperone treatment or GCase polypeptide overexpression, activated the lysosomal degradation pathway. The data in this Example therefore also suggests that activation of GCase polypeptide function could not only be therapeutically beneficial in diseases characterized by α-synuclein accumulation, but also other diseases characterized by neuronal and non-neuronal protein accumulation.

Figure 15A:
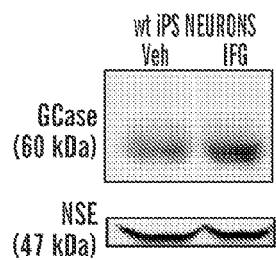
FIGS. 15A-15C show that GCase polypeptide activation increases proteolysis in human dopamine neurons. Neurons were treated with 100 μM IFG or vehicle control (veh) for 5 days followed by 1 day wash-out to remove IFG.
Figure 15B:
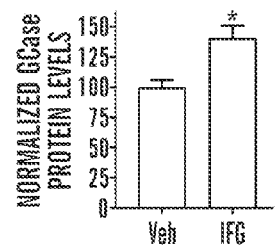
Figure 15C:
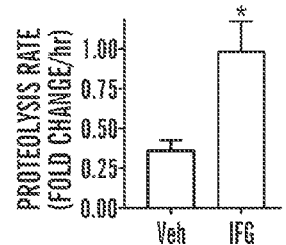

In this Example, human dopamine neurons generated from iPS cells of an unaffected control were treated with a pharmacological chaperone activator of GCase polypeptide, isofagomine (IFG). Through genotyping analysis it was validated that these cells do not harbor any of the most commonly found GBA1 mutations including, N370S, L444P, L84TER, and E326K. Treatment of wild-type neurons with 100 μM IFG for 5 days followed by 1 day wash-out increased the levels of GCase polypeptide (FIGS. 15A and 15B). This increase was likely due to the fact that wild-type GCase polypeptide was occasionally misfolded in the ER and degraded (about 30% of the total made in the ER), and IFG appeared to also stabilize the wild-type misfolded forms. Proteolysis rate was then determined by radioactive pulse-chase as described below, which revealed a 3-fold increase in IFG treated neurons compared to controls (FIG. 15C). This suggested that GCase polypeptide activity correlates with enhanced degradation capacity.

Figure 16A:
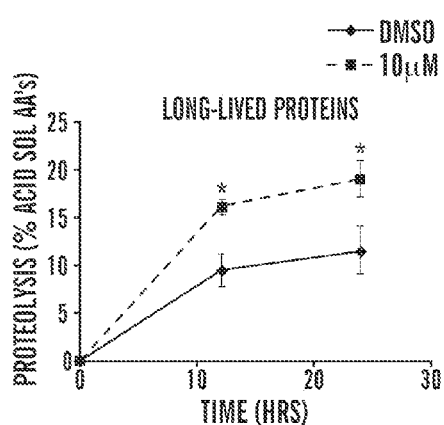
FIGS. 16A-16B demonstrate the enhancement of long-lived proteolysis by allosteric activation of GCase polypeptide in human midbrain iPS dopamine neurons from a PD patient. Neurons were treated with an allosteric activator of GCase polypeptide and proteolysis of long-lived (FIG. 16A) or short-lived (FIG. 16B) was determined by radioactive pulse-chase.
Figure 16B:
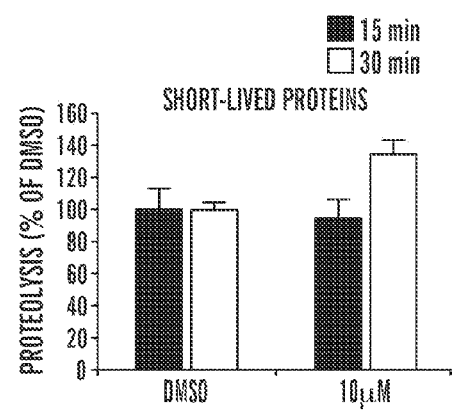

The discussion above showed that modulation of GCase polypeptide activity by IFG augmented lysosomal proteolysis. In this Example, it was further determined if the effects discussed above could also be replicated with non-native site binding compounds that can act as allosteric activators of GCase polypeptide, and therefore unlike IFG, would not require a washout to activate GCase polypeptide. Such a compound from a recently identified series of allosteric GCase polypeptide activators (Goldin et. al., PLoS One 7: e29861, 2012) was tested and a significant enhancement of lysosomal degradation capacity was observed after compound treatment (FIGS. 16A-16B).

Further in this Example, it was assessed whether GCase polypeptide overexpression had the ability to directly enhance lysosomal proteolysis in a non-neuronal cell line. Hela cells were transfected with a myc-tagged GCase polypeptide expression construct and lysosomal proteolysis was assessed by radioactive pulse-chase (FIG. 17A). GCase polypeptide overexpression resulted in a 40% increase in proteolysis compared to GFP control transfected cells (FIG. 17B). This effect was completely reversed by the addition of the well-established lysosomal inhibitors, leupeptin and ammonium chloride. This indicated that GCase polypeptide overexpression resulted in augmentation of primarily a lysosomal mediated degradation pathway. This effect was also confirmed through a different assay, by measuring the effect of GCase polypeptide overexpression on the activity of the lysosomal protease cathepsin B. A cell-permeable fluorescent-tagged cathepsin B substrate (MAGIC RED cathepsin detection kit, Immunochemistry Technologies)

was added to transfected Hela cells, and degradation of this substrate was determined in living cells after substrate wash-out. This revealed increased cathepsin B activity in GCase polypeptide transfected cells compared to those expressing GFP (FIG. 17C).

Example 9: Stimulation of the Secretory Pathway as a Treatment for Neuronal and Non-Neuronal Proteinopathies Experiments in this Example demonstrate that enhancement of the secretory pathway through Rab1a polypeptide overexpression enhanced lysosomal function and importantly, reduced α-synuclein levels in human midbrain dopamine neurons. Data in this Example illustrated that Rab1a polypeptide has the ability to stimulate lysosomal proteolysis in a general way, similar to the effects of GCase polypeptide overexpression. Therefore, data in this Example suggests that stimulation of Rab1a polypeptide activity would also provide therapeutic benefit in other diseases characterized by protein accumulation. Also as both Rab1a and GCase polypeptides are ubiquitously expressed, this effect should be apparent in both neuronal and non-neuronal tissues.

As discussed above, protein accumulation disrupted the lysosomal trafficking of GCase polypeptide, which led to decreased GCase polypeptide activity and thus resulted in compromised lysosomal proteolysis. In this Example, it was investigated whether enhancement of lysosomal enzyme trafficking through stimulation of the secretory pathway would result in increased lysosomal function and reduction of α-synuclein. Therefore, in this Example the small GTPase Rab1a polypeptide was overexpressed by lentiviral infection in iPS neurons to stimulate enzyme trafficking. Rab1a polypeptide has been established to function specifically at the ER-Golgi step of the secretory pathway (Duvernay et al., Cell Signal 17: 1457, 2005). The effect of Rab1a polypeptide was determined in human iPS dopamine neurons derived from reprogrammed fibroblasts of a PD patient (Coriell line ND27760). These cells harbor a triplication mutation in the genomic region containing SNCA which encodes for α-synuclein, leading to overexpression of the protein and lysosomal trafficking deficits. Overexpression of Rab1a polypeptide in human PD dopamine neurons resulted in a dramatic reduction of α-synuclein levels when infected at a multiplicity of infection (moi) of 5 (FIG. 18A). Further in this Example, it was determined if Rab1a polypeptide enhances lysosomal function by monitoring cathepsin B activity. The activity of cathepsin B was determined in transfected Hela cells as described above, which revealed an increase in cathepsin B activity suggesting enhanced lysosomal function by Rab1a polypeptide (FIG. 18B).

Example 10: Lysosomal GCase Polypeptide Activation by Allosteric Binding Compounds Reduces α-Synuclein Levels in Human Midbrain Neurons from a PD Patient Experiments in this Example demonstrate that allosteric binding compounds results in GCase polypeptide activation and reduced α-synuclein levels. Data in this Example therefore suggests that allosteric compounds that do not interfere with the GCase enzyme active site represent a novel therapeutic strategy for the treatment of synucleinopathies and other neurodegenerative diseases characterized by the accumulation of protein aggregates.

Figure 19A:
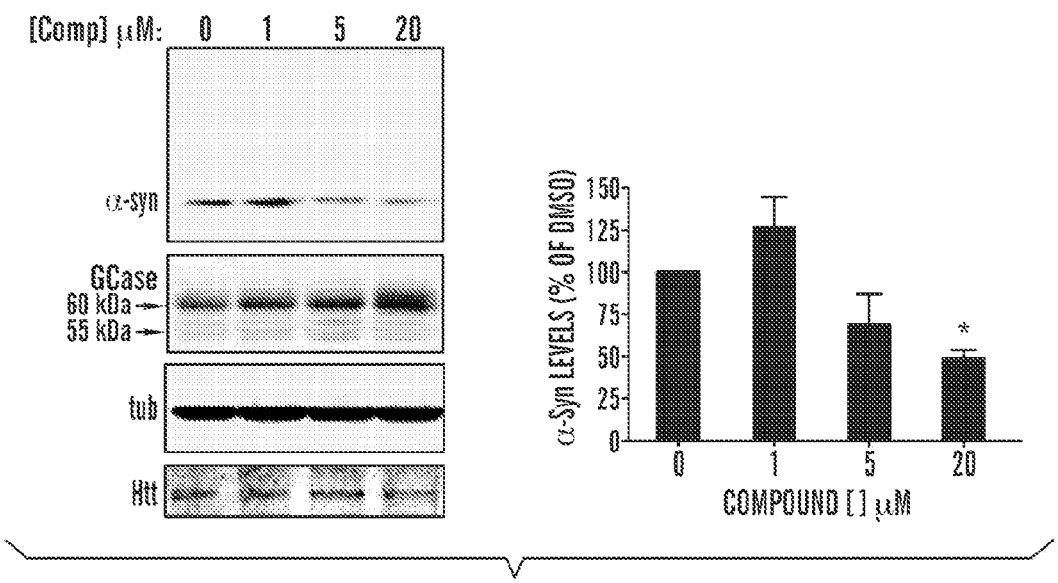
FIGS. 19A-19B demonstrate the reduction of α-synuclein by allosteric activation of GCase polypeptide in human midbrain dopamine neurons.
Figure 19B:
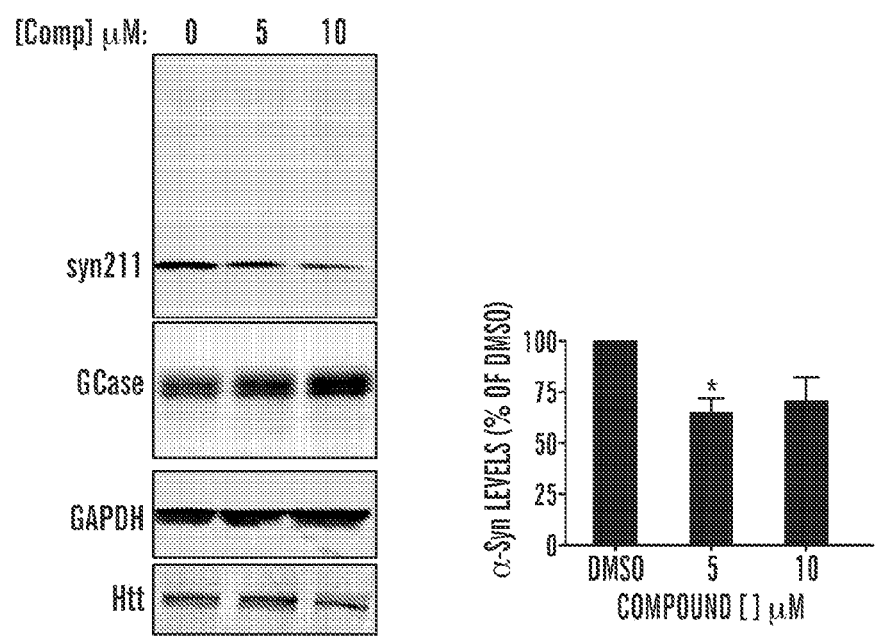

In this Example, human midbrain iPS dopamine neurons were generated from both healthy controls as well as from a PD patient harboring triplication of the SNCA genomic region, and cultured in the presence of the GCase polypeptide allosteric activator NCGC00188758 as discussed in this invention. α-synuclein levels were determined by western blot analysis and demonstrated a dose-dependent decrease in α-synuclein protein in both neurons from healthy unaffected controls as well as with neurons generated from a PD patient (FIG. 19A). It was also shown in this Example that treatment with the GCase polypeptide activator increased the levels of total GCase protein and increased the post-ER forms, indicating enhancement of flux to the lysosome (FIG. 19B).

Example 11: Treatment of Neurons with a Combination of Chaperones of GCase Polypeptide and Antioxidants Enhance Post ER Forms of GCase Experiments in this Example illustrate that combining compounds which stabilize and activate GCase polypeptide with antioxidants leads to a more efficient disruption of the pathogenic feedback loop initiated by α-synuclein accumulation as described above. Data in this Example also suggest that combination therapies targeting three critical pathways in neurons including, GCase polypeptide activation, enhancement of the secretory pathway, and antioxidant function would provide greater benefit compared to therapies that target any of these pathways individually.

Figure 20B:
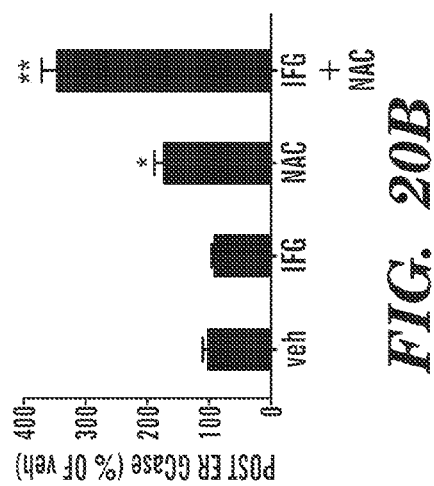
FIGS. 20A-20B show that combination of GCase chaperone IFG and antioxidants enhance post-ER GCase polypeptide in PD iPS midbrain dopamine neurons.
Figure 20A:
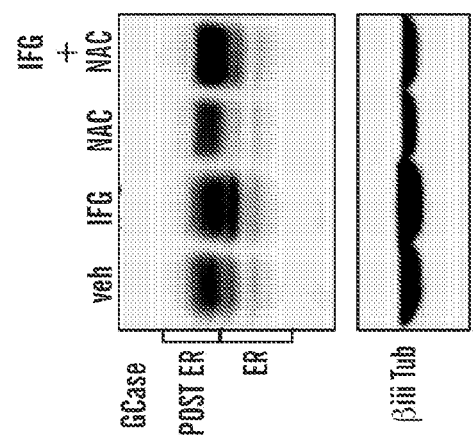

In this Example, the effect of combining the GCase polypeptide pharmacological chaperone IFG with the antioxidant n-acetyl-cysteine (NAC) on GCase polypeptide maturation in PD iPS neurons was tested. Neurons were treated with either IFG, NAC, or IFG and NAC together, and GCase polypeptide maturation was analyzed by western blot. This showed that treatment of both IFG and NAC together caused a 3-fold increase in the amount of post ER (mature) GCase polypeptide compared to either treatment alone (FIGS. 20A-20B).

Example 12: Gangliosides Influence α-Synuclein Aggregation

Experiments in this Example demonstrate that sphingolipids, namely gangliosides stabilize and enhance soluble α-synuclein oligomers.

Figure 21:
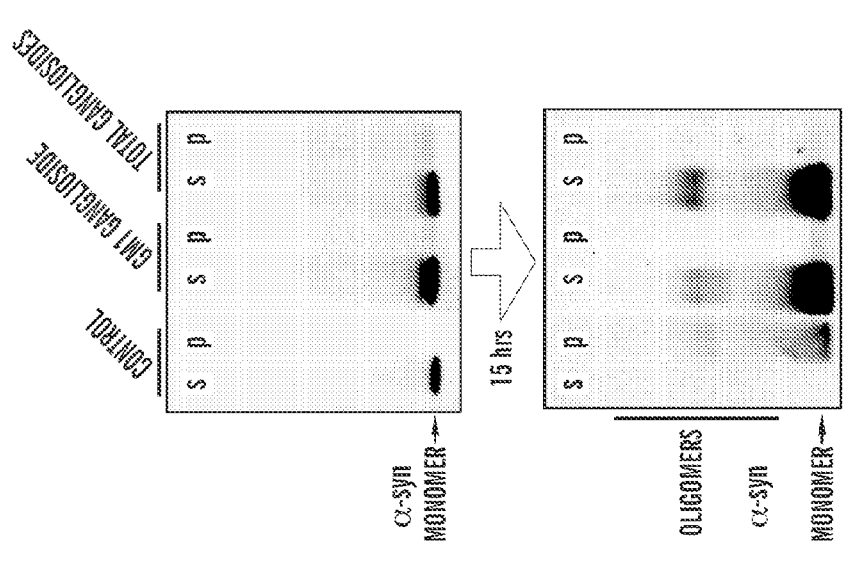
FIG. 21 shows the sedimentation analysis of α-synucleic at pH 5.0 in the presence of GM1 ganglioside or total brain gangliosides. Samples were incubated for 0 or 15 hrs, centrifuged at 100,000 g for 30 min to sediment α-synuclein aggregates, and analyzed by SDS-PAGE/western blot using syn211. The monomeric form migrates at 18 kDa and oligomeric forms migrate above 19 kDa. s, supernatant fraction; p, pellet fraction.

A 15 hr incubation of α-synuclein with either ganglioside GM1 or total brain gangliosides using a 10:1 lipid:protein ratio resulted in a dramatic stabilization and elevation of soluble α-synuclein oligomers, compared to α-synuclein alone controls (FIG. 21).

The data in this Example, in addition to documentation of α-synuclein accumulation in brains of patients with gangliosidosis (Suzuki et al., Acta Neuropathol 114: 481, 2007) suggests that lowering ganglioside levels by enhancing ganglioside metabolizing enzymes will provide benefit in Parkinson's disease and other synucleinopathies. These enzymes include, but are not limited to lysosomal β-hexosaminidase A/B/S, and β-galactosidase isoform 1.

Example 13: Exemplary Assays to Monitor Modulation of Lysosomal Enzyme Activity by Lysosomal Activating Agent High Performance Liquid Chromatography-Mass Spectroscopy (LC-MS) Hydrolysis Assay:

This assay uses liquid chromatography linked to a mass spectrometer to assess the ability of a lysosomal enzyme (e.g., GCase) in a sample (spleen homogenate) to cleave the pro-fluorescent substrates 4-methylumbelliferyl-β-d-glucopyranoside (4MU-Glc, a blue fluorogenic substrate) or C12-BODIPY-GlcCer. Chromatography is then performed using HPLC on stopped enzymatic reactions. Activity of the lysosomal activating agents can be analyzed using this assay by monitoring the dose-dependent activation of substrate turnover.

Microscale Thermophoresis (MST) Assay:

MST is a recently developed technology that measures molecule movements under a controlled temperature gradient. This assay can be applied to determine if a lysosomal activating agent physically interacts with GCase polypeptide. MST uses fluorescently labeled polypeptide targets that, on binding to ligands, can show changes in the movement of the polypeptide molecule along the temperature gradient. This technique is best suited for binding analysis due to its low protein requirements and its sensitivity.

Absorption, Distribution, Metabolism and Excretion (ADME) Assays and Pharmokinetics (PK):

Selection of possible lysosomal activating agent candidates for in vivo evaluation can be done by performing ADME studies on these agents. The stability of representative lysosomal activating agents can be examined in mouse liver microsomes. The permeability of the most potent lysosomal activating agent can be analyzed in a standard caco-2 permeability assay. For example, the efflux ratio of 0.3 suggests that the compound is not recognized by the ABC transporters expressed in the caco-2 monolayer, and therefore is expected to have reasonable good oral absorption and perhaps penetration through the blood brain barrier.

Based on the potency of the lysosomal activating agents from the ADME studies, a mouse PK study can be initiated for in vivo proof-of-principle studies.

Materials and Methods:

Antibodies

The following anti-α-synuclein antibodies were used: Syn202 (mAb, Covance, # MMS-529R, 1:1000 western blot [WB]), Syn505 (mAb, Invitrogen, #35-8300, 1:500 WB), SNL-1 (pAb, gift of Benoit I. Giasson, University of Pennsylvania, 1:1000 WB), syn211 (mAb, Sigma-Aldrich, # S_5566, 1:1000 WB, 1:400 immunocytochemistry (ICC)), LB509 (mAb, Invitrogen #18-0215, 1:500 WB, 1:100 ICC), Syn303 (mAb, gift of Harry Ischiropoulos, The Children's Hospital of Philadelphia, 1:500 WB), anti-α-synuclein C-terminal (pAb, Abcam, #ab85862, 1:200 IHC in FIG. 10B), anti-α-synuclein (pAb, Abcam, #ad52168, 1:250 IHC, in FIG. 10C).

Other antibodies: anti-neural specific enolase (pAb, Polysciences, #16625, 1:2000 WB, 47 kDa), anti-vimentin (mAb, BD PharMingen, #550513, 1:500 WB, 57 kDa), anti-glucocerebrosidase (pAb, Sigma-Aldrich, # G4171, 1:1000 WB, 55-70 kDa in Tris Glycine, 51-70 kDa in MOPS/Bis-Tris), anti-alpha-tubulin (mAb, Sigma-Aldrich, # T-6074, 1:5000 WB, 50 kDa), anti-LC3 (pAb, Abgent, # AP 1802a, 1:500 WB, 14-16 kDa), anti-LC3 (pAb, Cell Signaling, #2775, 1:50 ICC), anti-neurofilament (mAb, Developmental Studies Hybridoma Bank, University of Iowa, #2H3, 1:1000 ICC), anti-LAMP 2 (pAb, Invitrogen, #51-2200 (Igp96), 1:500 WB, 90-100 kDa Tris glycine, 70-95 kDa MOPS/Bis-Tris), anti-LAMP 1 (rat mAb, Developmental Studies Hybridoma Bank, University of Iowa, #ID4B, 1:50 ICC), anti-LAMP1 (mAb, Santa Cruz Biotechnology, #sc-20011, 1:500 WB, 110 kDa), anti-cathepsin D (goat pAb, Santa Cruz Biotechnology, #sc-6487, 1:500 WB, 50, 44, 28 kDa), anti-acid ceramidase (goat pAb, Santa Cruz Biotechnology, #sc-28486, 1:500 WB, 60 kDa). Anti-glucosylceramide (pAb, Glycobiotech, #RAS_0011, 1:50 ICC), anti-Oct4 (pAb, Abcam, #ab19857, 1:400 ICC), anti-Tra-1-60 (mAb, Millipore, #MAB4360, 1:400 ICC), anti-SSEA-4 (mAb, Millipore, #MAB4304, 1:200 ICC), anti-Nanog (pAb, Abcam, #ab21624, 1:200 ICC), anti-Neuronal class III β-tubulin (TUJ1), Covance, #MMS-435P, 1:2000 ICC). anti-tyrosine hydroxylase (pAb, EMD chemicals, #657012, 1:1000 ICC), anti-NeuN (mAb, Millipore, #MAB377, 1:100 IHC), anti-GRP78 BiP (4E3) (mAb, Abcam, #ab96483, 1:500 WB, 66 kDa), anti-calnexin (pAb, Enzo Life Sciences, #ADI-SPA-865, 1:500, WB, 90 kDa), anti-Tau, (pAb, Dako, # A0024, 1:1000 WB), anti-huntingtin (mAb, Millipore, #MAB5490, 1:1000 WB).

Plasmids

Lentiviral plasmids expressing shRNA against mouse GCase polypeptide or scrambled sequence control are in the pLKO.1 vector backbone and were obtained from Open Biosystems (item # RMM3981-98834484, mouse: 5'-cga ctt cca gtt atc caa ctt-3') and propagated in DH5-α competent cells with 100 µg/ml carbenicillin (Sigma-Aldrich # C-9231). pCDNA plasmids expressing human WT and mutant α-synuclein's were previously described (Mazzulli et al., J. Biol. Chem. 282: 31621, 2007). The α-synuclein coding sequence was subcloned into pENTR1A (Invitrogen # A10462) at the Kpnl/Xhol sites and propagated in One Shot TOP10 competent cells (Invitrogen # C4040-10) with 25 µg/ml kanamycin (Fisher Scientific, # BP906-5). The α-synuclein coding sequence from pENTR1A-α-synuclein constructs was transferred via recombination into the SIN-W-PGK lentiviral vector backbone containing the mouse phosphoglycerate kinase promoter (Deglon et al., Hum. Gen Ther. 11:179, 2000) using the gateway cloning system (Invitrogen, LR recombination reaction, #11791-020), followed by digestion with Psil to reduce pENTR1A background. SIN-W-PGK-α-synuclein constructs were propagated in TOP10 cells with 100 µg/ml carbenicillin.

Primary Cortical Cultures, Lentiviral Infection, and Leupeptin Treatment

Primary cortical culture procedures have been described in detail previously (Tsika et al., J. Neurosci. 30: 3409, 2010). Cells were infected at a multiplicity of infection (moi) of 3 for both GCase polypeptide shRNA and α-synuclein-expressing lentivirus. For leupeptin treatment, cells were infected with α-synuclein-expressing lentivirus at days in vitro (DIV) 5, then treated with 50 µM leupeptin (EMD chemicals) at DIV 8, and harvested at DIV 12 (or dpi 7).

Neurotoxicity Assessment

Cortical cells were seeded in 96-well plates at 50,000 cells/well, infected at DIV 5, and fixed in 4% paraformaldehyde at the indicated time points. The staining and analysis procedures have been described (Tsika et al., J. Neurosci. 30: 3409, 2010).

Sequential Biochemical Extraction of Cell Cultures and Tissues

Cells were harvested in Triton X-100 lysis buffer. The extracts were centrifuged at 100,000×g for 30 min. The pellets were extracted in 2% SDS buffer. Similar procedures were utilized for mouse and human brain tissues, using 20 volumes of Triton X-100 lysis buffer. Samples were loaded onto SDS-PAGE gels or subjected to native SEC followed by western blot analysis as described below (Mazzulli et al., J. Neurosci. 26:10068, 2006).

Native SEC

Infected cortical cells (8,000,000 cells/10 cm plate) were harvested in Triton X-100 lysis buffer and 100,000×g Triton X-100 soluble lysate was loaded onto a Superdex 200 HR 10/300 column (GE healthcare) as described previously (Mazzulli et al., J. Neurosci. 26:10068, 2006). Quantification of α-synuclein oligomers has been described in detail previously (Tsika et al., J. Neurosci. 30: 3409, 2010).

α-Synuclein Protein Purification and Amyloid Measurements

Recombinant human α-synuclein was purified from BL21 CodonPlus (DE3)-RIL competent *E. coli* (Agilent) as described previously (Mazzulli et al., J. Biol. Chem. 282: 31621, 2007). Purified α-synuclein was mixed with lipid dispersions and amyloid formation was determined by thioflavin T binding as described below.

Subcellular Fractionation

Infected cortical cells (8,000,000 cells/10 cm plate) were harvested in 0.25 M sucrose buffer containing 10 mM HEPES (pH 7.4) and 0.1M EDTA (SHB), homogenized, and centrifuged at 6,800×g, 4° C., for 5 min. The remaining pellet was saved (P1). The supernatant was centrifuged at 17,000×g, 4° C., for 10 min, supernatant removed (S), and the remaining pellet (P2) enriched in lysosomes was saved. Fraction S was centrifuged at 100,000×g for 1 hr to obtain P3. Pellets were extracted in 1% Triton X-100 lysis buffer, then 2% SDS buffer as described above. Fractions were analyzed by western blot analysis or by measuring GCase polypeptide activity as described below.

Statistical Analysis

One-way ANOVA with Tukey's post-hoc test was used in proteolysis, neurotoxicity, immunostaining quantifications of LC3 and α-synuclein, P2 and P3 GCase polypeptide activity assays, ANS, and thioflavin T determinations. One-way ANOVA with Dunnet's post-hoc test was used for post-ER/ER GCase polypeptide ratios of cortical neurons. Two-tailed Student's t test was utilized for biochemical analyses, quantification of α-synuclein and GCase protein levels, BODIPY 493 fluorescence analysis, and lipidomic analysis. p values less than 0.05 were considered significant. Statistical calculations were performed with GraphPad Prism Software, Version 4.0.

Histological Analysis of Gaucher Disease Mouse Models

The homozygous point-mutated gba1 mice expressing V394L (4L) crossed to the hypomorphic prosaposin mutant mice (PS-NA) have been previously described (Sun et al., 2005). For histological analysis, brains of 12 week old 4L/PS-NA mice were perfused and fixed in 4% paraformaldehyde and 8 μm sections of the substantia nigra (SN) and cortex (Ctx) were analyzed for neurodegeneration by hermatoxylin and eosin staining. For α-synuclein immunofluorescence analysis, sections were blocked in 10% goat serum/PBS with 0.4% Triton X-100, and incubated with anti-α-synuclein antibodies (1:200, abcam #ab85862), followed by anti-goat conjugated Alexa610 secondary antibodies. Images were captured with a Zeiss Apotome AxioV 200 microscope (400×). For NeuN/α-synuclein colocalization, primary antibodies were diluted in 1×PBS (rabbit anti-α-synuclein [Abcam, ad52168], 1: 250 and mouse anti-NeuN [Millipore, MAB377], 1:100) and applied to the brain section over night at 4° C. After washing with 1×PBS-0.2% Triton X-100 (10 min 3 times), the sections were incubated with the corresponding secondary antibodies in blocking solution [biotinylated goat anti-rabbit (Vector Labs, #BA-1000), 1:1000 and goat anti-mouse-Alexa488 (Invitrogen, #A11001), 1:1000], respectively. After washing with 1×PBS-0.2% Triton X-100, streptavidin-Alexa610 (1: 1500 in 1×PBS) was added and incubated to develop α-synuclein signals.

Quantification of α-Synuclein Aggregates and Eosinophilic Spheroids in 4L/PS-NA Brain Twelve-week-old 4L/PS-NA mice were analyzed for neurodegeneration by H & E staining in sections from the substantia nigra (SN) and cortex (Ctx). The arrows in FIG. 10A indicate the presence of eosinphilic spheroids, which represent axonal swelling and indicate degenerating neurons. The number of spheroids were counted in 3 brain coronal sections from 4L/PS-NA (n=3) and WT (n=2) mice. The sections (4 μm) were consecutive and every $3^{rd}$ section was used in the experiment. Images were taken from left and right hemispheres for SN (4 fields/section) and for Ctx (20 fields/section).

Sequential Biochemical Extraction of Mouse Brain

Cortex from symptomatic 4L/PS-NA (12- to 14-week-old) or 42 week D409H homozygous mice were used. Brain samples were homogenized in 10 volumes of 1% Triton X-100 buffer (1% Triton X-100, 20 mM HEPES pH 7.4, 150 mM NaCl, 10% glycerol, 1 mM EDTA, 1.5 mM $MgCl_2$, 1 mM phenylmethanesulfonyl fluoride (PMSF), 50 mM NaF, 2 mM Na orthovanadate, and a protease inhibitor cocktail (Roche diagnostics, #11-836-170-001) with a Teflon pestle and centrifuged at 100,000×g, 30 min, at 4° C. The pellet was re-extracted in another 10 volumes of Triton X-100 buffer, centrifuged as before, and the supernatants were combined for Triton-soluble fractions. The Triton-soluble fractions were subjected to 4 freeze/thaw cycles to disrupt potential protein-lipid interactions. The remaining pellet was extracted in 5 volumes of 2% SDS, 50 mM Tris-Cl, pH 7.4 by boiling for 10 min, sonication with a probe sonicator at 50% power (4×3 s pulses), then boiling for another 10 min. The SDS extraction was centrifuged at 20,000×g, 20 min, at 25° C. Protein concentration of the Triton X-100 soluble fractions was determined by the BCA micro assay (Pierce, www.piercenet.com, #23235).

*C. elegans* Experiments

Nematodes were maintained following standard procedures (Brenner, 1974). RNAi and fluorescent microscopy were conducted as described (Hamamichi et al., 2008) by feeding UA50 [balnl3; $P_{unc-54}$::α-synulcein::gfp, $P_{unc-54}$::tor-2, rol-6 (sul006)] worms with bacteria that express dsRNA (Geneservice) targeting the worm ortholog of GBA (C33C12.8) with the following modification. Worms were grown on RNAi bacteria for an extra generation, and then scored at the L4 stage for misfolding. Analysis of α-synuclein accumulation was performed in duplicate, and candidates were scored as positive if RNAi treatment significantly enhanced puncta (80% of worms exhibited increased quantity and size of α-synuclein aggregates).

Generation of Lentivirus

These procedures have been described in detail previously (Mazzulli et al., 2006). Supernatant from transfected HEK-FT cells was concentrated 500 times in neurobasal medium containing 10% fetal bovine serum. Viral titers were determined using a p24 ELISA kit (Zeptometrix, #801111).

Generation of Induced Pluripotent Stem Cells and Neuronal Differentiation

Dermal fibroblasts from a GD patient (GM00852) were reprogrammed by infection with OCT4, SOX2, cMTC, and KLF4 as previously described (Seibler et al., J. Neurosci. 31:5970, 2011). iPS cell colonies were picked and expanded on MEF feeder cells after 1-2 months. Pluripotency was determined by the expression of OCT4, Tra-1-60, SSEA4, and Nanog. Karyotype analysis by G-banding was performed by Cell Line Genetics. Neuronal differentiation was performed as described previously (Seibler et al., J. Neurosci. 31:5970, 2011). Differentiation was initiated by the addition of brain-derived neurotrophic factor (BDNF), ascorbic acid, sonic hedge hog (SHH), and fibroblast growth factor 8 (FGF8). After 10 days, cells were differentiated by the addition of BDNF, ascorbic acid, glial derived neurotrophic factor (GDNF), transforming growth factor β-3 (TGF β-3), and cyclic-AMP for 5 weeks. iPS neurons were fixed in 4% PFA and analyzed for neuronal and catecholaminergic markers, as well as α-synuclein levels, by immunfluorescence and western blot of Triton soluble fractions.

Genotyping of Patients and Cell Lines

The Sequenom MassARRAY method was used for genotyping iPS neurons, controls, or PD brain (in Table 14, Table 17, and Table 18). Genomic material from was extracted using the DNeasy kit (QIAGEN). DNA samples were genotyped using the sequenom method using MALDI-TOF mass spectrometry as a service provided by the Harvard Partners Center for Genetics and Genomics. Genotyping analysis for GBA1 mutations of samples presented in Table 15 was performed by gene sequencing as previously described (Stone et al., Hum. Mutat. 15:181, 2000).

Measurement of mRNA from Neuronal Cultures

Total RNA was extracted from $6.6 \times 10^5$ neurons at 7 dpi after infection at moi 3 with the appropriate lentiviral constructs, using 1 ml of Trizol/chloroform (Invitrogen) followed by the RNeasy mini kit (QIAGEN). cDNA was generated by reverse transcription using SuperScript III First-Strand synthesis SuperMix (Invitrogen #11752-050). The amount of cDNA was quantified by real-time PCR using the following primer sets (mouse SNCA: FW 5'-ggc agc tgg aaa gac aaa ag-3', REV 5'-cag ctc cct cca ctg tct tc-3'; mouse GBA1: FW 5'-gcc agg ctc atc gga ttc ttc-3', REV 5'-cac ggg gtc aag aga gtc ac-3'). Primers were selected based on their ability to amplify the target sequence at the same rate as the normalizing gene, actin (mouse actin primers: FW 5'-agc cat gta cgt agc cat cc-3', REV 5'-ctc tca gct gtg gtg gtg aa-3'). Real-time PCR was performed using 500 nM of each primer, 1:100 dilution of the cDNA reaction, and 2×SYBR Green PCR Master Mix (Applied Biosystems #4309159). Cycle threshold (Ct) values of the target transcript were normalized to actin Ct values and plotted as % of control.

Western Blot Analysis

Most materials for SDS-PAGE were obtained from Invitrogen (NuPAGE system). Protein lysates were boiled in sample buffer (20 mM Tris, 1% (v/v) glycerol, 180 mM β-mercaptoethanol, 0.003% (w/v) bromophenol blue, 2% (w/v) SDS, pH 6.8), resolved on 4%-12% Bis-Tris polyacrylamide precast gels in a MOPS-SDS running buffer, or 4%-12% Tris-Glycine gels. 10% Tris-Glycine gels were utilized for some GCase polypeptide western blot's (FIGS. 13B, 13D, and 13E, and FIGS. 14C and 14F). For most analyses, 50 μg/lane were used for Triton X-100 soluble fractions, while SDS fractions were loaded according the amount found in Triton X-100 soluble fractions (10-20 μl/lane). Gels were transferred onto polyvinylidene difluoride membranes (0.45 mM-pore immobilon FL; Millipore, #IPFL 000 10) in transfer buffer containing 20% methanol (Boston Bioproducts, #BP-190) for 12-16 hr at 4° C. Blots were blocked in Odyssey blocking buffer (Li-Cor biosciences) containing 0.05% Tween, or 5% non-fat dry milk in TBS-T 0.2%, followed by incubation with primary antibodies (see above for dilutions), and detected with anti-mouse or -rabbit IgG conjugated to IRDye 680 or 800 (1:10,000, Li-Cor biosciences). For controls, blots were scanned after the blocking step to determine autofluorescent bands, and also after the addition of secondary Ab alone. Any nonspecific bands detected were not included in densitometric analyses. Densitometric and MW analyses were performed using Odyssey Software v 2.1, Li-Cor biosciences).

Glycosidase Treatment 30-50 μg of T-sol lysates were denatured in 10 μl of Glycoprotein Denaturing Buffer and digested for 1 hr with 500 U of Endo H or PNGase F according to the manufacturer's instructions (New England Biolabs, #P0702S [endo H], #P0704S [PNGase F]). Control reactions were incubated in parallel without glycosidase. 30-50 μg of sample was loaded onto either 4%-12% MOPS NuPAGE gels with a bis-tris buffer (FIG. 2) or 10% Tris-Glycine gels (FIG. 14).

Immunostaining Analysis of Cultured Cells

Cortical cells grown on poly-D-lysine coated coverslips in 12 well clusters were washed very briefly in warm PBS followed by rapid fixation in PBS-buffered 4% paraformaldehyde (w/v) for 15 min. Cells were incubated with PBS containing 0.3% (v/v) Triton X-100 overnight at 4° C., then blocked in 2% (w/v) bovine serum albumin (BSA) (Sigma-Aldrich, # A-7906) and 10% normal goat serum (Jackson Immunoresearch Laboratories, #005-000-121) in PBS-Triton X-100 for 1 hr. Primary antibodies were diluted into blocking buffer (see above for dilutions), incubated overnight at 4° C., and washed extensively in PBS-Triton X-100. Secondary antibodies (anti-mouse or rabbit-conjugated Alexa 488 (1:400) or Alexa 568 [1:200], Invitrogen) were diluted in blocking buffer and incubated for 1 hr, followed by extensive washing in PBS-Triton X-100. Coverslips were mounted onto glass slides with 10 μl of 4,6-diamidino-2-phenylindole dihydrochloride (DAPI)-containing Fluoromount G (Southern Biotech, #0100-20) and visualized with a fluorescence microscope. For quantification of α-synuclein and LC3 immunostaining, pixels from equal-time exposed images were quantified using Adobe Photoshop software CS2 (Adobe Systems), and normalized to DAPI.

Quantification of Ganglioside GM1 and LAMP1 Immunofluorescent Puncta

Infected neuronal cultures were fixed and stained with either cholera toxin subunit B conjugated to AlexaFluor 488 for GM1 analysis (Invitrogen #34775), or anti-LAW1 antibodies (1 D4B-c) followed by anti-rat IgG conjugated AlexaFluor 488. Images from 20× and 100× objectives were captured with equal exposure times, and particle size and number was determined in threshold-matched images using Image J software. DAPI staining was also quantified and used to determine the total cell number/field. 3-10 fields of view were assessed for each replicate, and three replicates were performed per condition.

Quantification of Neutral Lipids by Fluorescence Staining

Intracellular neutral lipids were quantified by incorporation of 4,4-difluoro-1,3,5,7,8-pentamethyl-4-bora-3a,4α-diaza-s-indacene (BODIPY 493/503) dye, a fluorescent dye that detects neutral lipids (Invitrogen # D-3922) in living cultures. Cortical cells were grown on poly-D-lysine coated coverslips and infected with lentivirus expressing shRNA against GCase polypeptide as described above. On dpi 6.5, BODIPY 493 (1 mg/ml stock, in ethanol) was added to live cultures in complete neurobasal media at a final concentration of 10 μg/ml and incubated for 30 min at 37° C., 5% $CO_2$. Cells were then washed with warm PBS, fixed in PBS-buffered 4% paraformaldyhide (w/v), and visualized under a fluorescent microscope. Total pixels from BODIPY fluorescence in the images were quantified using Adobe Photoshop software CS2 (Adobe Systems), and normalized to a nuclear stain.

Quantification of GlcCer by SFC/MS/MS Analysis

Cortical cells grown in 6 well clusters were infected with lentiviral vectors expressing GCase polypeptide shRNA as described and harvested at dpi 6.5 in PBS. Cells were harvested by centrifugation at 200×g for 5 min and cell pellets were rapidly stored at −80° C. until analysis. Quantification of lipids was performed as a service provided by the lipidomics core facility at the Medical University of South Carolina Glycosylceramide was analyzed by supercritical fluid chromatography/mass spectrometry (SFC/MS/MS). The samples (n of 3 for each condition) were normalized to total cellular phosphate levels (P) and expressed as femtomoles/nanomole Pi.

Cellular Proteolysis Determination by Radioactive Pulse-Chase

Proteolysis of long-lived proteins was determined by radioactive pulse-chase using $^3$H-leucine. This procedure was performed as described previously (Kaushik et al. Methods Enzymol. 452: 297, 2009). Briefly, cortical cells were grown in 24 well clusters seeded at 33000 cells/well and infected at moi 3 with scrb or GCase polypeptide shRNA expressing lentiviral vectors. On dpi 4, $^3$H-leucine (PerkinElmer, # NET460A001 MC, final 5 µCi/ml) was added in standard neurobasal medium containing B27 for 2 days to trace label proteins. On dpi 6, cells were washed with conditioned neurobasal medium containing excess cold leucine (2.8 mM final) 2 times for 10 min, followed by 1 time for 2 hr to remove free amino acids released from short-lived proteins. Cells were incubated in cold media and 50 µl of media was removed at 0 and 8 hr after the washing was completed, and placed into 100 µl of 20% trichloroacetic acid. BSA was added (0.5 mg/ml, final) to facilitate the precipitation of proteins from the media and samples were incubated at 4° C. for 8-16 hr. Samples were centrifuged at 20,000×g for 20 min, 4° C., and the radioactivity was measured in 5 ml of scintillation cocktail using a Beckman LS 1701 liquid scintillation counter (Beckman Instruments). Precipitated protein pellets were extracted in 200 µl of Na deoxycholate, 0.1 M NaOH, and radioactivity was determined. Percent proteolysis was calculated as described in detail elsewhere (Kaushik et al. Methods Enzymol. 452: 297, 2009).

For leupeptin/NH$_4$Cl treatments, cells were infected as described above, then 50 µM leupeptin was added on dpi 2, followed by the addition of $^3$H-leucine on dpi 4. NH$_4$Cl (5 mM final) was added on dpi 5, and cells were chased in cold medium as described above. Proteolysis analysis of iPS neurons was performed as described above, after 2.5 weeks of growth factor (BAGTC) treatment.

Formulations of Lipid Dispersions

Purified lipids were obtained from Avanti Polar lipids including brain phosphotidylcholines (PC, #840053P), Glucosyl (β) Ceramide (18:1, GlcCer, #860547), lactosylceramide (#86057P), galactosylceramide (#860521), and glucosylsphingosine (#860535). PC was dissolved in HPLC grade chloroform containing 1% ethanol stabilizer at 25 mg/ml, and stored in glass Teflon capped vials with a nitrogen gas overlay at −20° C. GlcCer and other sphingolipids were dissolved in chloroform:methanol:—water (80:20:2, v:v) at 10 mg/ml, and used immediately. Lipids were aliquoted and mixed thoroughly (either 90:10, or 25:75 molar ratio of PC:GlcCer mixtures) in glass test tubes, followed by drying under a nitrogen stream. The mixing in of PC was found to be required for solubility and stabilization of the sphingolipid dispersions in aqueous solution. The lipid film was hydrated in PBS, transferred to a polypropylene microcentrifuge tube, and sonicated in an ultrasonic cleaner bath (Cole-Parmer Instruments, #EW-08895-04) for 30 min at 25° C. The samples were then subjected to 2 freeze/thaw cycles, followed by 10-60 min of additional sonication until the solution was clear (unclear solutions gave variable results). The lipid dispersions were added directly to purified α-synuclein and incubated as described below. The lipid dispersions were made fresh for each individual experiment.

In Vitro Assessment of α-Synuclein Aggregation in the Presence of Lipid Dispersions α-synuclein was expressed in *E. coli* and purified by boiling followed by HPLC as described previously (Mazzulli et al 2007). Purified α-synuclein was diluted in either 0.1 M sodium acetate buffer, pH 5.0, or 0.1 M sodium phosphate buffer, pH 7.4, to 138 µM (2 mg/ml). Lipids at 1.38 mM were added to equal volumes of diluted α-synuclein for final concentrations of 69 µM α-synuclein and 690 µM liposomes (10:1 final lipid:protein ratio). The pH was then determined, and it was found that the addition of lipid dispersions did not alter the final pH of the samples. Evaporation was controlled with a mineral oil overlay, and samples were incubated at 37° C. with constant shaking at 1000 rpm using an Eppendorf thermomixer compact. Samples were incubated for various times and aliquots were removed for kinetic analysis by thioflavin T. Ten microliters of sample was mixed with 190 µl of 10 µM of thioflavin T (Sigma-Aldrich, # T-3516) in 100 mM Glycine buffer, pH 8.5 and incubated at 25° C. for 5 min. Fluorescence (ex=430 nm, em=510, 0.1 s) was determined in a Wallac Victor$^2$ plate reader (Perkin Elmer) in black FluorNunc Maxisorp 96 well plates (Nunc, #475515). The assay was repeated with three separate liposome preparations, with n of 3-4 reactions each time.

Assessment of Oligomeric α-synuclein by 8-anilino-1-napthalene Sulfonate Fluorescence Oligomers were also detected by 8-anilino-1-napthalene sulfonate (ANS) (Acros #401220050). After 1 hr incubation, 2 µl of the α-synuclein-lipid reaction mixture was incubated with 100 µM ANS diluted in water in 100 µl final volume. The sample was incubated for 15 min in a white Fuor Nunc Maxicorp 96 (Nunc, #437591) and relative fluorescence units were determined in a Wallace Victor$^2$ plate reader (ex=355, em=460, 1.0 s). The contribution of ANS signal observed from lipid dispersions alone was determined by control reactions which only contained lipids, and then subtracted from the α-synuclei/lipid reactions. Additional controls included α-synuclein alone and buffer alone, which were all subjected to the same incubation times and conditions as the experimental reactions.

Sedimentation Analysis of In Vitro Formed α-Synuclein Aggregates

Reactions from 28 hr incubations were centrifuged at 100,000×g for 20 min, supernatant removed, and the pellet was dissolved in the same volume of PBS. 5 µl of each fraction was analyzed by SDS-PAGE and stained with CBB. The gels were scanned on an Odyssey infrared imager and quantified with Odyssey software V 2.1 (Li-Cor). Percent pelletable protein was calculated from n=3 experiments.

Native Gel Electrophoresis of Soluble α-Synuclein Aggregates Formed In Vitro

Recombinant α-synuclein/lipid mixtures were removed at the indicated time points and 200 ng was analyzed by native gel electrophoresis using the NativePAGE Novex Bis-Tris gel system (Invitrogen). Gels were transferred to PVDF membranes and incubated with mAb syn 211, followed by horse radish peroxidase (HRP)-conjugated secondary antibodies. HRP was detected by enhanced chemiluminescence (Pierce #32106) and exposed to film.

Negative Staining Immunoelectron Microscopy Analysis

α-synuclein/lipid incubations were absorbed onto 300 mesh carbon-coated copper grids, washed with PBS, and blocked with 1% BSA/PBS for 10 min. Syn505 (1:100) was added to the grids in blocking solution for 30 min, followed by extensive washing with PBS. 15 nm gold-conjugated secondary antibodies were added for 30 min in block solution, followed by extensive washing in PBS. The samples were stained with 1% uranyl acetate and visualized with a JEOL 1011 transmission electron microscope located at the Program in Membrane Biology at the Massachusetts General Hospital.

Glucocerebrosidase Polypeptide and Other Lysosomal Activity Assays

The assay for GCase polypeptide was performed as described (Marshall et al., 2002). Cortical cells from 12 well cultures were infected with scrb or GCase polypeptide shRNA as described above, and harvested at dpi 6.5 in 50 µl of activity assay buffer (0.25% (v/v) Triton X-100 (Sigma-Aldrich # T-8787), 0.25% (w/v) Taurocholic acid (Sigma-Aldrich, # T9034), 1 mM EDTA, in citrate/phosphate buffer, pH 5.4) freeze/thawed twice, and incubated on ice for 30 min. The samples were centrifuged at 20,000×g for 20 min and 10 µl of the supernatant was used to determine GCase polypeptide activity in 1% BSA, with 1 mM 4-Methylumbelliferyl β-glucophyranoside (4-MU, Sigma-Aldrich, # M3633) in 50 µl total volume. After 40 min incubation at 37° C. (the assay was determined to be linear through 90 min), the reaction was stopped by the addition of equi-volume 1M glycine, pH 12.5. 100 µl reactions were loaded into white 96-well plates for fluorescence (Nunc, #136101) and fluorescence (ex=355 nm, em=460, 0.1 s) was determined in a Wallac Victor$^2$ plate reader (Perkin Elmer). Analysis of GCase polypeptide activity from P2 and P3 fractions of neuronal cultures and human brain was done in a similar way, except that 5 µl of sample was used in a total reaction volume of 100 µl. For human PD analysis, extracts from 3 different controls and 6 different PD samples were tested.

For GCase polypeptide activity measurements in GD brain (Table 15) and lentiviral infected primary cultures (FIG. 13C), the nonlysosomal GCase polypeptide activity (GBA2) was subtracted from the total activity by determining the amount of activity that was not inhibited by conduritol-b-epoxide (CBE).

The following assays were done using the P2 fraction of primary neuronal cultures in the same way as GCase polypeptide: Hexosaminidase A/B/S activity assay was performed as described previously (Tropak et al., J. Biol. Chem. 279:13478, 2004) using 4-MU-N-acetyl-D-glucosaminide (Sigma # M2133). β-glucuronidase (GUSB) activity was determined with 4-MU-D-glucuronide (Sigma #M9130). Lysosomal acid phosphate activity was determined with 4-MU-phosphate (Sigma #M8168).

LC-MS Hydrolysis Assay

An Agilent 1200 LC equipped with a quaternary pump, a G1315 diode array detector, and a G1321 fluorescent detector can be used. A 4.6 mm×250 mm Agilent Eclipse Plus $C_{18}$ (5 µm) at ambient temperature can be used at a flow rate of 1.8 mL/min with a gradient of 85/15 (methanol/0.1% formic acid in water) to 100% methanol over 10 min. Lysosomal activating agents can be monitored using fluorescence detection with Ex=365 nm; Em=440 nm for 4 MU or Ex=506 nm; Em=540 nm for C12-BODIPY. The mass of the fluorescent peaks can be verified by matching with the expected peaks for the substrate and product of the reaction. Different concentrations of the lysosomal activating agents can be used (e.g., from 0, 20 nM-50 µM, 1:2 dilutions from 50 µM, 9 concentrations). Human spleen tissue can be homogenized using a food blender at the maximal speed for 5 min, followed by 10 passes in a motor-driven 50 mL glass-Teflon homogenizer. The homogenate can be centrifuged at 1000 g for 10 min. The supernatant can then be filtered using a 40 µm filter, and aliquots of resultant spleen homogenate can be stored frozen at −80° C. until use. 140 µg/well of spleen homogenate can be used for the assay. The assay buffer for the spleen homogenate is 50 mM citric acid, 115 mM $K_2HPO_4$, 110 mM KCl, 10 mM NaCl, 1 mM $MgCl_2$, and 0.01% Tween-20 at pH 5 The buffer for the purified enzyme is 50 mM citric acid, $KH_2PO_4$ (titrated to pH 5.9 for recombinant wild-type enzyme and pH 7 for N370S mutant) and 0.01% Tween-20. An automated pin-tool station (Kalypsys, San Diego, Calif.) can be used to transfer 23 nL/well of compound to the assay plate. After 5 min of incubation at room temperature, the enzyme reaction is initiated by the addition of 2 µL/well substrate. Final concentrations of 2 mM for the 4-MU-Glc and 25 µM for C12-BODIPY-Cer can be used. The enzyme and the substrate can be incubated for 30-45 min at 37° C., and the reaction can then be terminated by the addition of 2 µL/well of stop solution (1 M NaOH and 1 M Glycine mixture, pH 10).

Microsome Stability

The test lysosomal activating agent can be incubated in duplicate with CD-1 mouse liver microsomes at 37° C. The reaction would contain microsomal protein in 100 mM potassium phosphate, 2 mM NADPH, 3 mM $MgCl_2$, pH 7.4. A control can be run for each test agent omitting NADPH to detect NADPH-free degradation. At indicated times, an aliquot should be removed from each experimental and control reaction and mixed with an equal volume of ice-cold Stop Solution (0.3% AcOH in MeCN containing haloperidol, diclofenac, or other internal standard). Stopped reactions are then incubated at least ten minutes at −20° C., and an additional volume of water is added. The samples are centrifuged to remove precipitated protein, and the supernatants are analyzed by LC/MS/MS to quantitate the remaining protein. Data are reported as % remaining by dividing by the time zero concentration value.

Caco-2 Permeability

CaCo-2 cells grown in tissue culture flasks are trypsinized, suspended in medium, and the suspensions applied to wells of a collagen-coated BioCoat Cell Environment in 24-well format (BD Biosciences) at 24,500 cells per well. The cells are allowed to grow and differentiate for 3 weeks, feeding at 2-day intervals. To verify that CaCo-2 cell monolayers are properly formed, aliquots of the cell buffers can be analyzed by fluorescence to determine the transport of the impermeable dye Lucifer Yellow. For permeability, the test agent is added either to the apical (A) or basolateral (B) side and amount of permeation to the other side is determined by LC/MS/MS. The A-side buffer contains 100 µM Lucifer yellow dye, in Transport Buffer (1.98 g/L glucose in 10 mM HEPES, 1× Hank's Balanced Salt Solution) pH 6.5, and the B-side buffer is Transport Buffer, pH 7.4. CaCo-2 cells are incubated with these buffers for 2 h. Data is expressed as permeability (Papp): where dQ/dt is the rate of permeation. In bidirectional permeability studies, the asymmetry index (AI) or efflux ratio is also calculated: An AI>1 indicates a potential substrate for PGP or other active transport.

Pharmacokinetics

C57BL/6 mice, 18-26 g, male, N=36, cab be used with free access to food and water. The IP dosing solution can be prepared in 20% PEG 400+80% (20% HP-β-CD). Brain, liver samples can be homogenized with 3 volumes of PBS (pH 7.4) before sample extraction. The final concentration can be adjusted with a dilution factor of 4, assuming 1 g wet brain equals to 1 mL. LC-MS/MS analysis of samples can then be done with a Acquity UPLC BEH C18 column, flow rate 0.6 mL/min, with a mobile phase consisting of solvent A: $H_2O$—0.2% FA, 10 mM $NH_4OAC$, solvent B: MeOH—0.2% FA, 10 mM $NH_4OAC$.

```
                       SEQUENCE LISTING

GLUCAN 1, 4-ALPHA-GLUCOSIDASE
MGVRHPPCSH  RLLAVCALVS  LATAALLGHI  LLHDFLLVPR  ELSGSSPVLE  ETHPAHQQGA
SRPGPRDAQA  HPGRPRAVPT  QCDVPPNSRF  DCAPDKAITQ  EQCEARGCCY  IPAKQGLQGA
QMGQPWCFFP  PSYPSYKLEN  LSSSEMGYTA  TLTRTTPTFF  PKDILTLRLD  VMMETENRLH
FTIKDPANRR  YEVPLETPRV  HSRAPSPLYS  VEFSEEPFGV  IVHRQLDGRV  LLNTTVAPLF
FADQFLQLST  SLPSQYITGL  AEHLSPLMLS  TSWTRITLWN  RDLAPTPGAN  LYGSHPFYLA
LEDGGSAHGV  FLLNSNAMDV  VLQPSPALSW  RSTGGILDVY  IFLGPEPKSV  VQQYLDVVGY
PFMPPYWGLG  FHLCRWGYSS  TAITRQVVEN  MTRAHFPLDV  QWNDLDYMDS  RRDFTFNKDG
FRDFPAMVQE  LHQGGRRYMM  IVDPAISSSG  PAGSYRPYDE  GLRRGVFITN  ETGQPLIGKV
WPGSTAFPDF  TNPTALAWWE  DMVAEFHDQV  PFDGMWIDMN  EPSNFIRGSE  DGCPNNELEN
PPYVPGVVGG  TLQAATICAS  SHQFLSTHYN  LHNLYGLTEA  IASHRALVKA  RGTRPFVISR
STFAGHGRYA  GHWTGDVWSS  WEQLASSVPE  ILQFNLLGVP  LVGADVCGFL  GNTSEELCVR
WTQLGAFYPF  MRNHNSLLSL  PQEPYSFSEP  AQQAMRKALT  LRYALLPHLY  TLFHQAHVAG
ETVARPLFLE  FPKDSSTWTV  DHQLLWGEAL  LITPVLQAGK  AEVTGYFPLG  TWYDLQTVPI
EALGSLPPPP  AAPREPAIHS  EGQWVTLPAP  LDTINVHLRA  GYIIPLQGPG  LTTTESRQQP
MALAVALTKG  GEARGELFWD  DGESLEVLER  GAYTQVIFLA  RNNTIVNELV  RVTSEGAGLQ
LQKVTVLGVA  TAPQQVLSNG  VPVSNFTYSP  DTKVLDICVS  LLMGEQFLVS  WC
(SEQ ID NO. 25)

70 kD ALPHA-GLUCOSIDASE
APSPLYSVEF  SEEPFGVIVH  RQLDGRVLLN  TTVAPLFFAD  QFLQLSTSLP  SQYITGLAEH
LSPLMLSTSW  TRITLWNRDL  APTPGANLYG  SHPFYLALED  GGSAHGVFLL  NSNAMDVVLQ
PSPALSWRST  GGILDVYIFL  GPEPKSVVQQ  YLDVVGYPFM  PPYWGLGFHL  CRWGYSSTAI
TRQVVENMTR  AHFPLDVQWN  DLDYMDSRRD  FTFNKDGFRD  FPAMVQELHQ  GGRRYMMIVD
PAISSSGPAG  SYRPYDEGLR  RGVFITNETG  QPLIGKVWPG  STAFPDFTNP  TALAWWEDMV
AEFHDQVPFD  GMWIDMNEPS  NFIRGSEDGC  PNNELENPPY  VPGVVGGTLQ  AATICASSHQ
FLSTHYNLHN  LYGLTEAIAS  HRALVKARGT  RPFVISRSTF  AGHGRYAGHW  TGDVWSSWEQ
LASSVPEILQ  FNLLGVPLVG  ADVCGFLGNT  SEELCVRWTQ  LGAFYPFMRN  HNSLLSLPQE
PYSFSEPAQQ  AMRKALTLRY  ALLPHLYTLF  HQAHVAGETV  ARPLFLEFPK  DSSTWTVDHQ
LLWGEALLIT  PVLQAGKAEV  TGYFPLGTWY  DLQTVPIEAL  GSLPPPPAAP  REPAIHSEGQ
WVTLPAPLDT  INVHLRAGYI  IPLQGPGLTT  TESRQQPMAL  AVALTKGGEA  RGELFWDDGE
SLEVLERGAY  TQVIFLARNN  TIVNELVRVT  SEGAGLQLQK  VTVLGVATAP  QQVLSNGVPV
SNFTYSPDTK  VLDICVSLLM  GEQFLVSWC  (SEQ ID NO. 26)

GLUCOCEREBROSIDASE
MEFSSPSREE  CPKPLSRVSI  MAGSLTGLLL  LQAVSWASGA  RPCIPKSFGY  SSVVCVCNAT
YCDSFDPPTF  PALGTFSRYE  STRSGRRMEL  SMGPIQANHT  GTGLLLTLQP  EQKFQKVKGF
GGAMTDAAAL  NILALSPPAQ  NLLLKSYFSE  EGIGYNIIRV  PMASCDFSIR  TYTYADTPDD
FQLHNFSLPE  EDTKLKIPLI  HRALQLAQRP  VSLLASPWTS  PTWLKTNGAV  NGKGSLKGQP
GDIYHQTWAR  YFVKFLDAYA  EHKLQFWAVT  AENEPSAGLL  SGYPFQCLGF  TPEHQRDFIA
RDLGPTLANS  THHNVRLLML  DDQRLLLPHW  AKVVLTDPEA  AKYVHGIAVH  WYLDFLAPAK
ATLGETHRLF  PNTMLFASEA  CVGSKFWEQS  VRLGSWDRGM  QYSHSIITNL  LYHVVGWTDW
NLALNPEGGP  NWVRNFVDSP  IIVDITKDTF  YKQPMFYHLG  HFSKFIPEGS  QRVGLVASQK
NDLDAVALMH  PDGSAVVVVL  NRSSKDVPLT  IKDPAVGFLE  TISPGYSIHT  YLWRRQ
(SEQ ID NO. 27)

ALPHA-GALACTOSIDASE A PRECURSOR
MQLRNPELHL  GCALALRFLA  LVSWDIPGAR  ALDNGLARTP  TMGWLHWERF  MCNLDCQEEP
DSCISEKLFM  EMAELMVSEG  WKDAGYEYLC  IDDCWMAPQR  DSEGRLQADP  QRFPHGIRQL
ANYVHSKGLK  LGIYADVGNK  TCAGFPGSFG  YYDIDAQTFA  DWGVDLLKFD  GCYCDSLENL
ADGYKHMSLA  LNRTGRSIVY  SCEWPLYMWP  FQKPNYTEIR  QYCNHWRNFA  DIDDSWKSIK
SILDWTSFNQ  ERIVDVAGPG  GWNDPDMLVI  GNFGLSWNQQ  VTQMALWAIM  AAPLFMSNDL
RHISPQAKAL  LQDKDVIAIN  QDPLGKQGYQ  LRQGDNFEVW  ERPLSGLAWA  VAMINRQEIG
GPRSYTIAVA  SLGKGVACNP  ACFITQLLPV  KRKLGFYEWT  SRLRSHINPT  GTVLLQLENT
MQMSLKDLL  (SEQ ID NO. 28)

BETA-GALACTOSIDASE PRECURSOR
MPGFLVRILL  LLLVLLLLGP  TRGLRNATQR  MFEIDYSRDS  FLKDGQPFRY  ISGSIHYSRV
PRFYWKDRLL  KMKMAGLNAI  QTYVPWNFHE  PWPGQYQFSE  DHDGVEYFLRL  AHELGLLVIL
RPGPYICAEW  EMGGLPAWLL  EKESILLRSS  DPDYLAAVDK  WLGVLLPKMK  PLLYQNGGPV
ITVQVENEYG  SYFACDFDYL  RFLQKRFRHH  LGDDVVLFTT  DGAHKTFLKC  GALQGLYTTV
DFGTGSNITD  AFLSQRKCEP  KGPLINSEFY  TGWLDHWGQP  HSTIKTEAVA  SSLYDILARG
ASVNLYMFIG  GTNFAYWNGA  NSPYAAQPTS  YDYDAPLSEA  GDLTEKYFAL  RNIIQKFEKV
PEGPIPPSTP  KFAYGKVTLE  KLKTVGAALD  ILCPSGPIKS  LYPLTFIQVK  QHYGFVLYRT
TLPQDCSNPA  PLSSPLNGVH  DRAYVAVDGI  PQGVLERNNV  ITLNITGKAG  ATLDLLVENM
GRVNYGAYIN  DFKGLVSNLT  LSSNILTDWT  IFPPLDTEDAV  RSHLGGWGHR  DSGHHDEAWA
```

SEQUENCE LISTING

```
HNSSNYTLPA FYMGNFSIPS GIPDLPQDTF IQFPGWTKGQ VWINGFNLGR YWPARGPQLT
LFVPQHILMT SAPNTITVLE LEWAPCSSDD PELCAVTFVD RPVIGSSVTY DHPSKPVEKR
LMPPPPQKNK DSWLDHV (SEQ ID NO. 29)

GALACTOCEREBROSIDASE
MTAAAGSAGR AAVPLLLCAL LAPGGAYVLD DSDGLGREFD GIGAVSGGGA TSRLLVNYPE
PYRSQILDYL FKPNFGASLH ILKVEIGGDG QTTDGTEPSH MHYALDENYF RGYEWWLMKE
AKKRNPNITL IGLPWSFPGW LGKGFDWPYV NLQLTAYYVV TWIVGAKRYH DLDIDYIGIW
NERSYNANYI KILRKMLNYQ GLQRVKIIAS DNLWESISAS MLLDAELFKV VDVIGAHYPG
THSAKDAKLT GKKLWSSEDF STLNSDMGAG CWGRILNQNY INGYMTSTIA WNLVASYYEQ
LPYGRCGLMT AQEPWSGHYV VESPVWVSAH TTQFTQPGWY YLKTVGHLEK GGSYVALTDG
LGNLTIIIET MSHKHSKCIR PFLPYFNVSQ QFATFVLKGS FSEIPELQVW YTKLGKTSER
FLFKQLDSLW LLDSDGSFTL SLHEDELFTL TTLTTGRKGS YPLPPKSQPF PSTYKDDFNV
DYPFFSEAPN FADQTGVFEY FTNIEDPGEH HFTLRQVLNQ RPITWAADAS NTISIIGDYN
WTNLTIKCDV YIETPDTGGV FIAGRVNKGG ILIRSARGIF FWIFANGSYR VTGDLAGWII
YALGRVEVTA KKWYTLTLTI KGHFASGMLN DKSLWTDIPV NFPKNGWAAI GTHSFEFAQF
DNFLVEATR (SEQ ID NO. 30)

LYSOSOMAL ACID ALPHA-MANNOSIDASE
MSRALRPPLP PLCFFLLLLA AAGARAGGYE TCPTVQPNML NVHLLPHTHD DVGWLKTVDQ
YFYGIKNDIQ HAGVQYILDS VISALLADPT RRFIYVEIAF FSRWWHQQTN ATQEVVRDLV
RQGRLEFANG GWVMNDEAAT HYGAIVDQMT LGLRFLEDTF GNDGRPRVAW HIDPFGHSRE
QASLFAQMGF DGFFFGRLDY QDKWVRMQKL EMEQVWRAST SLKPPTADLF TGVLPNGYNP
PRNLCWDVLC VDQPLVEDPR SPEYNAKELV DYFLNVATAQ GRYYRTNHIV MTMGSDFQYE
NANMWFKNLD KLIQLVNAQQ AKGSSVHVLY STPACYLWEL NKANLTWSVK HDDFFPYADG
HHQFWTGYFS SRPALKRYER LSYNFLQVCN QLEALVGLAA NVGPYGSGDS APLNEAMAVL
QHHDAVSGTS RQHVANDYAR QLAAGWGPCE VLLSNALARL RGFKDHFTFC QQLNISICPL
SQTAARFQVI VYNPLGRKVN WMVRLPVSEG VFVVKDPNGR TVPSDVVIFP SSDSQAHPPE
LLFSASLPAL GFSTYSVAQV PRWKPQARAP QPIPRRSWSP ALTIENEHIR ATFDPDTGLL
MEIMNMNQQL LLPVRQTFFW YNASIGDNES DQASGAYIFR PNQQKPLPVS RWAQIHLVKT
PLVQEVHQNF SAWCSQVVRL YPGQRHLELE WSVGIPVGD TWGKEVISRF DTPLETKGRF
YTDSNGREIL ERRRDYRPTW KLNQTEPVAG NYYPVNTRIY ITDGNMQLTV LTDRSQGGSS
LRDGSLELMV HRRLLKDDGR GVSEPLMENG SGAWVRGRHL VLLDTAQAAA AGHRLLAEQE
VLAPQVVLAP GGGAAYNLGA PPRTQFSGLR RDLPPSVHLL TLASWGPEMV LLRLEHQFAV
GEDSGRNLSA PVTLNLRDLF STFTITRLQE TTLVANQLRE AASRLKWTTN TGPTPHQTPY
QLDPANITLE PMEIRTFLAS VQWKEVDG (SEQ ID NO. 31)

BETA-MANNOSIDASE
MRLHLLLLLA LCGAGTTAAE LSYSLRGNWS ICNGNGSLEL PGAVPGCVHS ALFQQGLIQD
SYYRFNDLNH RWVSLDNWTY SKEFKIPFEI SKWQKVNLIL EGVDTVSKIL FNEVTIGETD
NMFNRYSFDI TNVVRDVNSI ELRFQSAVLY AAQQSKAHTX YQVPPDCPPL VQKGECHVNF
VRKEQCSFSW DWGPSFPTQG IWKDVRIEAY NICHLNYFTF SPIYDKSAQE WNLEIESTFD
VVSSKPVGGQ VIXAIPKLQT QQTYSIELQP GKRIVELFVN ISKNITVETW WPHGHGNQTG
YNMTVLFELD GGLNIEKSAK VYFRTVELIE EPIKGSPGLS FYFKINGFPI FLKGSNWIPA
DSFQDRVTSE LLRRLLQSVV DANMNTLRVW GGGIYEQDEF YELCDELGIM VWQDFMFACA
LYPTDQGFLD SVTAEVAYQI KRLKSHPSII IWSGNNENEE ALMMNWYHIS FTDRPIYIKD
YVTLYVKNIR ELVLAGDKSR PFITSSPTNG AETVAEAWVS QNPNSNYFGD VHFYDYISDC
WNWKVFPKAR FASEYGYQSW PSFSTLEKVS STEDWSFNSK FSLHRQHHEG GNKQMLYQAG
LHFKLPQSTD PLRTFKDTIY LTQVMQAQCV KTETEFYRRS RSEIVDQQGH TMGALYWQLN
DIWQAPSWAS LEYGGKWKML HYFAQNFFAP LLPVGFENEN TFYIYGVSDL HSDYSMTLSV
RVHTWSSLEP VCSRVTERFV MKGGEAVCLY EEPVSELLRR CGNCTRESCV VSFYLSADHE
LLSPTNYHFL SSPKEAVGLC KAQITAIISQ QGDIFVFDLE TSAVAPFVWL DVGSIPGRFS
DNGFLMTEKT RTILFYPWEP TSKNELEQSF HVTSLTDIY (SEQ ID NO. 32)

ALPHA-L-FUCOSIDASE PRECURSOR
MRAPGMRSRP AGPALLLLLL FLGAAESVRR AQPPRRYTPD WPSLDSRPLP AWFDEAKFGV
FIHWGVFSVP AWGSEWFWWH WQGEGRPQYQ RFMRDNYPPG FSYADFGPQF TARFFHPEEW
ADLFQAAGAK YVVLTTKHHE GFTNWPSPVS WNWNSKDVGP HRDLVGELGT ALRKRNIRYG
LYHSLLEWFH PLYLLDKKNG FKTQHFVSAK TMPELYDLVN SYKPDLIWSD GEWECPDTYW
NSTNFLSWLY NDSPVKDEVV VNDRWGQNCS CHHGGYYNCE DKFKPQSLPD HKWEMCTSID
KFSWGYRRDM ALSDVTEESE IISELVQTVS LGGNYLLNIG PTKDGLIVPI FQERLLAVGK
WLSINGEAIY ASKPWRVQWE KNTTSVWYTS KGSAVYAIFL HWPENGVLNL ESPITTSTTK
ITMLGIQGDL KWSTDPDKGL FISLPQLPPS AVPAEFAWTI KLTGVK (SEQ ID NO. 33)

ALPHA-N-ACETYLGLUCOSAMINIDASE
MEAVAVAAAV GVLLLAGAGG AAGDEAREAA AVRALVARLL GPGPAADFSV SVERALAAKP
GLDTYSLGGG GAARVRVRGS TGVAAAAGLH RYLRDFCGCH VAWSGSQLRL PRPLPAVPGE
LTEATPNRYR YYQNVCTQSY SFVWWDWARW EREIDWMALN GINLALAWSG QEAIWQRVYL
ALGLTQAEIN EFFTGPAFLA WGRMGNLHTW DGPLPPSWHI KQLYLQHRVL DQMRSFGMTP
VLPAFAGHVP EAVTRVFPQV NVTKMGSWGH FNCSYSCSFL LAPEDPIFPI IGSLFLRELI
KEFGTDHIYG ADTFNEMQPP SSEPSYLAAA TTAVYEAMTA VDTEAVWLLQ GWLFQHQPQF
WGPAQIRAVL GAVPRGRLLV LDLFAESQPV YTRTASFQGQ PFIWCMLHNF GGNHGLFGAL
EAVNGGPEAA RLFPNSTMVG TGMAPEGISQ NEVVYSLMAE LGWRKDPVPD LAAWVTSFAA
RRYGVSHPDA GAAWRLLLRS VYNCSGEACR GHNRSPLVRR PSLQMNTSIW YNRSDVFEAW
RLLLTSAPSL ATSPAFRYDL LDLTRQAVQE LVSLYYEEAR SAYLSKELAS LLRAGGVLAY
ELLPALDEVL ASDSRFLLGS WLEQARAAAV SEAEADFYEQ NSRYQLTLWG PEGNILDYAN
KQLAGLVANY YTPRWRLFLE ALVDSVAQGI PFQQHQFDKN VFQLEQAFVL SKQRYPSQPR
```

GDTVDLAKKI FLKYYPGWVA GSW (SEQ ID NO. 34)

ALPHA-N-ACETYLGALACTOSAMINIDASE
MLLKTVLLLG HVAQVLMLDN GLLQTPPMGW LAWERFRCNI NCDEDPKNCI SEQLFMEMAD
RMAQDGWRDM GYTYLNIDDC WIGGRDASGR LMPDPKRFPH GIPFLADYVH SLGLKLGIYA
DMGNFTCMGY PGTTLDKVVQ DAQTFAEWKV DMLKLDGCFS TPEERAQGYP KMAAALNATG
RPIAFSCSWP AYEGGLPPRV NYSLLADICN LWRNYDDIQD SWWSVLSILN WFVEHQDILQ
PVAGPGHWND PDMLLIGNFG LSLEQSRAQM ALWTVLAAPL LMSTDLRTIS AQNMDILQNP
LMIKINQDPL GIQGRRIHKE KSLIEVYMRP LSNKASALVF FSCRTDMPYR YHSSLGQLNF
TGSVIYEAQD VYSGDIISGL RDETNFTVII NPSGVVMWYL YPIKNLEMSQ Q
(SEQ ID NO. 35)

BETA-HEXOSAMINIDASE SUBUNIT ALPHA PREPROPROTEIN
MTSSRLWFSL LLAAAFAGRA TALWPWPQNF QTSDQRYVLY PNNFQFQYDV SSAAQPGCSV
LDEAFQRYRD LLFGSGSWPR PYLTGKRHTL EKNVLVVSVV TPGCNQLPTL ESVENYTLTI
NDDQCLLLSE TVWGALRGLE TFSQLVWKSA EGTFFINKTE IEDFPRFPHR GLLLDTSRHY
LPLSSILDTL DVMAYNKLNV FHWHLVDDPS FPYESFTFPE LMRKGSYNPV THIYTAQDVK
EVIEYARLRG IRVLAEFDTP GHTLSWGPGI PGLLTPCYSG SEPSGTFGPV NPSLNNTYEF
MSTFFLEVSS VFPDFYLHLG GDEVDFTCWK SNPEIQDFMR KKGFGEDFKQ LESFYIQTLL
DIVSSYGKGY VVWQEVFDNK VKIQPDTIIQ VWREDIPVNY MKELELVTKA GFRALLSAPW
YLNRISYGPD WKDFYIVEPL AFEGTPEQKA LVIGGEACMW GEYVDNTNLV PRLWPRAGAV
AERLWSNKLT SDLTFAYERL SHFRCELLRR GVQAQPLNVG FCEQEFEQT (SEQ ID NO. 36)

BETA-HEXOSAMINIDASE SUBUNIT BETA PREPROPROTEIN
MELCGLGLPR PPMLLALLLA TLLAAMLALL TQVALVVQVA EAARAPSVSA KPGPALWPLP
LSVKMTPNLL HLAPENFYIS HSPNSTAGPS CTLLEEAFRR YHGYIFGFYK WHHEPAEFQA
KTQVQQLLVS ITLQSECDAF PNISSDESYT LLVKEPVAVL KANRVWGALR GLETFSQLVY
QDSYGTFTIN ESTIIDSPRF SHRGILIDTS RHYLPVKIIL KTLDAMAFNK FNVLHWHIVD
DQSFPYQSIT FPELSNKGSY SLSHVYTPND VRMVIEYARL RGIRVLPEFD TPGHTLSWGK
GQKDLLTPCY SRQNKLDSFG PINPTLNTTY SFLTTFFKEI SEVFPDQPIH LGGDEVEFKC
WESNPKIQDF MRQKGFGTDF KKLESFYIQK VLDIIATINK GSIVWQEVFD DKAKLAPGTI
VEVWKDSAYP EELSRVTASG FPVILSAPWY LDLISYGQDW RKYYKVEPLD FGGTQKQKQL
FIGGEACLWG EYVDATNLTP RLWPRASAVG ERLWSSKDVR DMDDAYDRLT RHRCRMVERG
IAAQPLYAGY CNHENM (SEQ ID NO. 37)

ALPHA-L-IDURONIDASE PRECURSOR
MRPLRPRAAL LALLASLLAA PPVAPAEAPH LVHVDAARAL WPLRRFWRST GFCPPLPHSQ
ADQYVLSWDQ QLNLAYVGAV PHRGIKQVRT HWLLELVTTR GSTGRGLSYN FTHLDGYLDL
LRENQLLPGF ELMGSASGHF TDFEDKQQVF EWKDLVSSLA RRYIGRYGLA HVSKWNFETW
NEPDHHDFDN VSMTMQGFLN YYDACSEGLR AASPALRLGG PGDSFHTPPR SPLSWGLLRH
CHDGTNFFTG EAGVRLDYIS LHRKGARSSI SILEQEKVVA QQIRQLFPKF ADTPIYNDEA
DPLVGWSLPQ PWRADVTYAA MVVKVIAQHQ NLLLANTTSA FPYALLSNDN AFLSYHPHPF
AQRTLTARFQ VNNTRPPHVQ LLRKPVLTAM GLLALLDEEQ LWAEVSQAGT VLDSNHTVGV
LASAHRPQGP ADAWRAAVLI YASDDTRAHP NRSVAVTLRL RGVPPGPGLV YVTRYLDNGL
CSPDGEWRRL GRPVFPTAEQ FRRMRAAEDP VAAAPRPLPA GGRLTLRPAL RLPSLLLVHV
CARPEKPPGQ VTRLRALPLT QGQLVLVWSD EHVGSKCLWT YEIQFSQDGK AYTPVSRKPS
TFNLFVFSPD TGAVSGSYRV RALDYWARPG PFSDPVPYLE VPVPRGPPSP GNP
(SEQ ID NO. 38)

BETA-GLUCURONIDASE PRECURSOR
MARGSAVAWA ALGPLLWGCA LGLQGGMLYP QESPSRECKE LDGLWSFRAD FSDNRRRGFE
EQWYRRPLWE SGPTVDMPVP SSFNDISQDW RLRHFVGWVW YEREVILPER WTQDLRTRVV
LRIGSAHSYA IVWVNGVDTL EHEGGYLPFE ADISNLVQVG PLPSRLRITI AINNTLTPTT
LPPGTIQYLT DTSKYPKGYF VQNTYFDFFN YAGLQRSVLL YTTPPTTYIDD ITVTTSVEQD
SGLVNYQISV KGSNLFKLEV RLLDAENKVV ANGTGTQGQL KVPGVSLWWP YLMHERPAYL
YSLEVQLTAQ TSLGPVSDFY TLPVGIRTVA VTKSQFLING KPFYFHGVNK HEDADIRGKG
FDWPLLVKDF NLLRWLGANA FRTSHYPYAE EVMQMCDRYG IVVIDECPGV GLALPQFFNN
VSLHHHMQVM EEVVRRDKNH PAVVMWSVAN EPASHLESAG YYLKMVIAHT KSLDPSRPVT
FVSNSNYAAD KGAPYVDVIC LNSYYSWYHD YGHLELIQLQ LATQFENWYK KYQKPIIQSE
YGAETIAGFH QDPPLMFTEE YQKSLLEQYH LGLDQKRRKY VVGELIWNFA DFMTEQSPTR
VLGNKKGIFT RQRQPKSAAF LLRERYWKIA NETRYPHSVA KSQCLENSLF T
(SEQ ID NO. 39)

LYSOSOMAL SIALIDASE
MTGERPSTAL PDRRWGPRIL GFWGGCRVWV FAAIFLLLSL AASWSKAEND FGLVQPLVTM
EQLLWVSGRQ IGSVDTFRIP LITATPRGTL LAPAEARKMS SSDEGAKFIA LRRSMDQGST
WSPTAFIVND GDVPDGLNLG AVVSDVETGV VFLFYSLCAH KAGCQVASTM LVWSKDDGVS
WSTPRNLSLD IGTEVFAPGP GSGIQKQREP RKGRLIVCGH GTLERDGVFC LLSDDHGASW
RYGSGVSGIP YGQPKQENDF NPDECQPYEL PDGSVVINAR NQNNYHCHCR IVLRSYDACD
TLRPRDVTFD PELVDPVVAA GAVVTSSGIV FFSNPAHPEF RVNLTLRWSF SNGTSWRKET
VQLWPGPSGY SSLATLEGSM DGEEQAPQLY VLYEKGRNHY TESISVAKIS VYGTL
(SEQ ID NO. 40)

IDURONATE 2-SULFATASE
MPPPRTGRGL LWLGLVLSSV CVALGSETQA NSTTDALNVL LIIVDDLRPS LGCYGDKLVR
SPNIDQLASH SLLFQNAFAQ QAVCAPSRVS FLTGRRPDTT RLYDFNSYWR VHAGNFSTIP
QYFKENGYVT MSVGKVFHPG ISSNHTDDSP YSWSFPPYHP SSEKYENTKT CRGPDGELHA

SEQUENCE LISTING

```
NLLCPVDVLD VPEGTLPDKQ STEQAIQLLE KMKTSASPFF LAVGYHKPHI PFRYPKEFQK
LYPLENITLA PDPEVPDGLP PVAYNPWMDI RQREDVQALN ISVPYGPIPV DFQRKIRQSY
FASVSYLDTQ VGRLLSALDD LQLANSTIIA FTSDHGWALG EHGEWAKYSN FDVATHVPLI
FYVPGRTASL PEAGEKLFPY LDPFDSASQL MEPGRQSMDL VELVSLFPTL AGLAGLQVPP
RCPVPSFHVE LCREGKNLLK HFRFRDLEED PYLPGNPREL IAYSQYPRPS DIPQWNSDKP
SLKDIKIMGY SIRTIDYRYT VWVGFNPDEF LANFSDIHAG ELYFVDSDPL QDHNMYNDSQ
GGDLFQLLMP (SEQ ID NO. 41)

ACID SPHINGOMYELINASE
MPRYGASLRQ SCPRSGREQG QDGTAGAPGL LWMGLVLALA LALALALSDS RVLWAPAEAH
PLSPQGHPAR LHRIVPRLRD VFGWGNLTCP ICKGLFTAIN LGLKKEPNVA RVGSVAIKLC
NLLKIAPPAV CQSIVHLFED DMVEVWRRSV LSPSEACGLL LGSTCGHWDI FSSWNISLPT
VPKPPPKPPS PPAPGAPVSR ILFLTDLHWD HDYLEGTDPD CADPLCCRRG SGLPPASRPG
AGYWGEYSKC DLPLRTLESL LSGLGPAGPF DMVYWTGDIP AHDVWHQTRQ DQLRALTTVT
ALVRKFLGPV PVYPAVGNHE SIPVNSFPPP FIEGNHSSRW LYEAMAKAWE PWLPAEALRT
LRIGGFYALS PYPGLRLISL NMNFCSRENF WLLINSTDPA GQLQWLVGEL QAAEDRGDKV
HIIGHIPPGH CLKSWSWNYY RIVARYENTL AAQFFGHTHV DEFEVFYDEE TLSRPLAVAF
LAPSATTYIG LNPGYRVYQI DGNYSRSSHV VLDHETYILN LTQANIPGAI PHWQLLYRAR
ETYGLPNTLP TAWHNLVYRM RGDMQLFQTF WFLYHKGHPP SEPCGTPCRL ATLCAQLSAR
ADSPALCRHL MPDGSLPEAQ SLWPRPLFC (SEQ ID NO. 42)
```

What is claimed is:

1. A method of treating a neurodegenerative proteinopathic disease in a subject in need thereof, the method comprising:
   administering to the subject a therapeutically effective amount of the compound NCGC00188758 having the structure of Formula I:

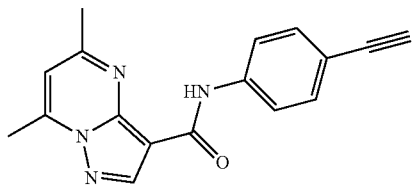 [SMILES: C#Cc1ccc(NC(=O)c2cnn3c(C)cc(C)nc23)cc1]

(Formula I), or a salt thereof, thereby to treat the neurodegenerative proteinopathic disease in the subject.

2. The method of claim 1, wherein the disease is Parkinson's disease.

* * * * *